US012622978B2

(12) United States Patent
Stice et al.

(10) Patent No.: US 12,622,978 B2
(45) Date of Patent: May 12, 2026

(54) BINDING AGENTS AND USES THEREOF FOR CENTRAL NERVOUS SYSTEM DELIVERY

(71) Applicant: Aruna Bio, Inc., Athens, GA (US)

(72) Inventors: Steven L. Stice, Athens, GA (US); Raymond Swetenburg, Athens, GA (US)

( * ) Notice: Subject to any disclaimer, the term of this patent is extended or adjusted under 35 U.S.C. 154(b) by 486 days.

(21) Appl. No.: 17/997,346

(22) PCT Filed: Apr. 27, 2021

(86) PCT No.: PCT/US2021/029455
§ 371 (c)(1),
(2) Date: Oct. 27, 2022

(87) PCT Pub. No.: WO2021/222295
PCT Pub. Date: Nov. 4, 2021

(65) Prior Publication Data
US 2023/0173094 A1      Jun. 8, 2023

Related U.S. Application Data

(60) Provisional application No. 63/015,936, filed on Apr. 27, 2020.

(51) Int. Cl.
*A61K 47/69* (2017.01)
*A61K 47/54* (2017.01)
*A61K 47/68* (2017.01)

(52) U.S. Cl.
CPC ........ *A61K 47/6901* (2017.08); *A61K 47/549* (2017.08); *A61K 47/68* (2017.08)

(58) Field of Classification Search
CPC ...... A61K 9/127–1273; A61K 31/7105; A61K 2300/00; A61K 31/713
See application file for complete search history.

(56) References Cited

U.S. PATENT DOCUMENTS

| | | | |
|---|---|---|---|
| 6,372,250 | B1 | 4/2002 | Pardridge |
| 8,846,670 | B2 | 9/2014 | Bacque et al. |
| 2009/0098118 | A1 | 4/2009 | Friess et al. |
| 2009/0269346 | A1* | 10/2009 | Starr .................... C07K 14/705 424/179.1 |
| 2011/0065645 | A1 | 3/2011 | Zou |
| 2015/0376237 | A1 | 12/2015 | Borros Gomez et al. |
| 2018/0066307 | A1 | 3/2018 | Ter-Ovanesyan et al. |

FOREIGN PATENT DOCUMENTS

| | | |
|---|---|---|
| WO | 2014071531 A1 | 5/2014 |
| WO | 2018007950 A1 | 1/2018 |

OTHER PUBLICATIONS

Extended European Search Report for corresponding EP4142737 mailed May 6, 2024, 22 pages.
Alvarez-Erviti, Lydia, et al., "Delivery of siRNA to the mouse brain by systemic injection of targeted exosomes", Nature Biotechnology, vol. 29(4): 341-345, XP055554900 (2011).
Wei, Xiaoli, et al., "A D-Peptide Ligan of Nicotine Acetylcholine Receptors for Brain-Targeted Drug Delivery", Angewandte Chemie International Edition, Verlag Chemie, Hoboken, USA, vol. 54(10): 3023-3027, XP072069800 (2015).
Kumar, Priti, et al., "Transvascular delivery of small interfering RNA to the central nervous system", Nature, Springer Nature Publishing AG, London, vol. 448(7149):39-43, XP008138068 (2007).
Anonymous: "Anti-CELSR3 ABT267", pp. 1-2, retrieved from the internet: URL:https://www.merckmillipore.com/DE/de/product/Anti-CELSR3-Antibody, MM_NF-ABT267?, XP093124731 (2013).
International Search Report and Written Opinion issued in PCT/US21/29455 mailed Sep. 2, 2021, 11 pages.

* cited by examiner

*Primary Examiner* — Thane Underdahl
(74) *Attorney, Agent, or Firm* — WOMBLE BOND DICKINSON (US) LLP; Danielle L. Herritt; Seiko Okada

(57) ABSTRACT
Disclosed herein are binding agents, conjugates, and extracellular vesicles that enhance penetration of the blood brain barrier. Uses thereof for delivery of agents, e.g., therapeutic agents, to the central nervous system are also provided.

10 Claims, 4 Drawing Sheets

Specification includes a Sequence Listing.

BINDING AGENTS AND USES THEREOF FOR CENTRAL NERVOUS SYSTEM DELIVERY

RELATED APPLICATION

This application claims the benefit of priority to U.S. Provisional Application No. 63/015,936, filed on Apr. 27, 2020, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 20, 2021, is named A106525_1050WO_SL.txt and is 621,333 bytes in size.

BACKGROUND

Macromolecules can cross the blood-brain barrier (BBB) by exploiting a small number of known pathways (see, e.g., Abbott, N. J., et al., Astrocyte-endothelial interactions at the blood-brain barrier. Nature Reviews, Neuroscience, 7(1):41-53, 2006)). It is largely accepted that extracellular vesicles (EVs) cross the blood-brain barrier (BBB) via receptor mediated transcytosis (RMT) (Morad, G., et al., Tumor-Derived Extracellular Vesicles Breach the Intact Blood-Brain Barrier via Transcytosis. ACS Nano, 2019), as other known pathways are not feasible given inherent size and charge limitations. However, only a handful of RMT pathways and/or receptors have been identified, including the insulin receptor, transferrin receptor, and low density lipoprotein receptor, and none has been shown to be involved in EV RMT. Co-opting these pathways for drug delivery is generally regarded as high risk, given the key roles these proteins play in the brain. Accordingly, there is a need for improved methods of delivering EVs across the BBB. Little is known regarding the molecular underpinnings of EV RMT. Understanding the molecules and pathways involved in EV RMT can be beneficial for, e.g., increased drug delivery to the CNS, lowered effective dose, decreased manufacturing demands, and decreased off-target effects.

SUMMARY OF THE INVENTION

In various aspects, the invention provides novel targets and binding agents that facilitate passage of associated molecules across the blood brain barrier (BBB). For example, to improve the delivery of extracellular vesicles across the blood brain barrier of a subject (e.g., to the brain or central nervous system of the subject), provided herein are extracellular vesicles (EVs) comprising one or more binding agents that specifically bind to one or more proteins (e.g., receptors) expressed by brain endothelial cells, allowing enhanced uptake across the BBB. In one aspect, provided herein is an extracellular vesicle composition that comprises a binding agent (e.g., ligand, antibody, aptamer) that binds to a receptor expressed by brain endothelial cells. In another aspect, provided herein is a method of delivering EVs (e.g., EVs comprising a therapeutic agent) across the blood brain barrier of a subject, comprising administering to the subject an EV of the present disclosure. In some embodiments, the extracellular vesicle is derived from a neural cell.

In one aspect, provided herein is an extracellular vesicle (EV) comprising an exogenous binding agent that specifically binds to a protein expressed by a brain endothelial cell. In some embodiments, the exogenous binding agent enhances transport of the EV across the blood brain barrier. In certain embodiments, the exogenous binding agent specifically binds to a target protein set forth in Table 1. In some embodiments, the exogenous binding agent comprises all or a portion of a binding agent set forth in Table 1. For example, the exogenous binding agent can comprise a binding agent set forth in Table 1, or a fragment or portion thereof that retains the ability to bind to a target protein described herein. In some embodiments, the exogenous binding agent specifically binds to a target protein set forth in Table 2.

In some embodiments, the EV comprises a plurality of exogenous binding agents, each of which specifically binds to a target protein set forth in Table 1. For example, the EV can comprise two, three, four, five, six, seven, eight, nine, or ten exogenous binding agents.

In certain embodiments, the exogenous binding agent specifically binds to a target protein set forth in Table 2. In some embodiments, the EV comprises a plurality of exogenous binding agents, each of which specifically binds to a target protein set forth in Table 2. For example, the EV can comprise two, three, four, five, six, seven, eight, nine, or ten exogenous binding agents.

In some embodiments, the exogenous binding agent specifically binds to an endothelial cell protein selected from ARHGEF18, ASB12, BAD, CD74, CD164, DCAF12L1, ECHS1, GORASP2, GPHA2, GRID2IP, HLA-DOA, HOXD4, IFNLR1, GPR37L1, HTR6, KCNT2, LIPJ, MCHR2, MESDC2, MTHFS, OCM, OR4X2, SCLT1, SERAC1, SFTD2, SHOC2, SPRYD3, STAG1, TMED10, TRIM67, TTLL7, VLDLR or ZP2, a B3GAT1-modified protein, a ST8SIA3-modified protein, or a combination thereof.

In some embodiments, the exogenous binding agent specifically binds to one or more endothelial cell proteins selected from ARHGEF18, ASB12, BAD, CD74, CD164, DCAF12L1, ECHS1, GORASP2, GPHA2, GRID2IP, HLA-DOA, HOXD4, IFNLR1, GPR37L1, HTR6, KCNT2, LIPJ, MCHR2, MESDC2, MTHFS, OCM, OR4X2, SCLT1, SERAC1, SFTD2, SHOC2, SPRYD3, STAG1, TMED10, TRIM67, TTLL7, VLDLR or ZP2, a B3GAT1-modified protein, or a ST8SIA3-modified protein. In some embodiments, the exogenous binding agent specifically binds to one, two, three, four, five, six, seven, eight, nine, ten or more endothelial cell proteins selected from ARHGEF18, ASB12, BAD, CD74, CD164, DCAF12L1, ECHS1, GORASP2, GPHA2, GRID2IP, HLA-DOA, HOXD4, IFNLR1, GPR37L1, HTR6, KCNT2, LIPJ, MCHR2, MESDC2, MTHFS, OCM, OR4X2, SCLT1, SERAC1, SFTD2, SHOC2, SPRYD3, STAG1, TMED10, TRIM67, TTLL7, VLDLR or ZP2, a B3GAT1-modified protein, or a ST8SIA3-modified protein. In some embodiments, the exogenous binding agent specifically binds to an endothelial cell protein selected from the group consisting of ARHGEF18, ASB12, BAD, DCAF12L1, ECHS1, GORASP2, GPHA2, GRID2IP, HOXD4, KCNT2, LIPJ, MESDC2, MTHFS, OCM, OR4X2, SCLT1, SERAC1, SFTD2, SHOC2, SPRYD3, STAG1, TMED10, TRIM67, TTLL7, and VLDLR. In certain embodiments, the exogenous binding agent specifically binds to an endothelial cell protein selected from the group consisting of KCNT2, OR4X2, SERAC1, SFT2D2, TMED10, and VLDLR.

In some embodiments, the exogenous binding agent specifically binds to an endothelial cell protein selected from the group consisting of CD74, HLA-DOA, VLDLR, ZP2, IFNLR1, HTR6, GPR37L1, MCHR2, CD164, a B3GAT1-modified protein, and a ST8SIA3-modified protein.

In one embodiment, the exogenous binding agent is an antibody, or an antigen binding portion thereof that specifically binds a target protein set forth in Table 1 or Table 2. In exemplary embodiments, the antibody, or antigen-binding portion thereof, is an antibody fragment selected from the group consisting of a Fab, a F(ab')$_2$, an scFv, a tandem scFv, a diabody, a minibody, and a single domain antibody. In certain embodiments, the antibody, or antigen binding portion thereof, is a humanized antibody, or antigen binding portion thereof. In some embodiments, the antibody, or antigen binding portion thereof, is a fully human antibody, or antigen binding portion thereof.

In one embodiment, the exogenous binding agent is a polypeptide ligand of a target protein set forth in Table 1 or Table 2.

In some embodiments, the polypeptide ligand comprises one or more of the binding agents set forth in Table 1, or a fragment or portion thereof that retains the ability to bind to a target protein described herein. In some embodiments, the EVs can comprise one or more (e.g., one, two, three, four, five, six, seven, eight, nine, ten or more) binding agents set forth in Table 1. In some embodiments, the EVs can comprise one or more (e.g., one, two, three, four, five, six, seven, eight, nine, ten or more) proteins selected from A2B5 antibody as described herein (Abcam Catalog #ab53521, Cambridge, Mass.; ThermoFisher Scientific Catalog #433110, Grand Island, NY), ACR, ADAM2, ADRBK1, AP2M1, APOE, APP, AR, CD1D, CD44, CD74, CLU, CTSB, CTSD, CTSF, CTSH, CTSL, CTSS, CTSV, CXCR-4 type 4 isoform a, CXCR-4 type 4 isoform b, CXCR-4 type 4 isoform c, CXCR-4 type 4 isoform d, CXCR-4 type 4 isoform e, DQB1, DRB3, ERBB4, E-selectin, HLA-DOB, HLA-DPA1, HLA-DQA1, HLA-DQA2, HLA-DQB1, HLA-DQB2, HLA-DRA, HLA-DRB1, HLA-DRB3, IFNL2, IFNLR1, IL10RB, ITGA2, ITGA3, ITGB1, Laminin (Laminin subunit gamma-1), Laminin (Laminin subunit beta-2), Laminin (Laminin subunit beta-1), Laminin (Laminin subunit alpha-2), Laminin (Laminin subunit alpha-1), Laminin (Laminin subunit alpha-5), Laminin (Laminin subunit alpha-3), Laminin (Laminin subunit gamma-3), Laminin (Laminin subunit alpha-4), Laminin (Laminin subunit gamma-2), Laminin (Laminin subunit beta-3), Laminin (Laminin subunit beta-4), LGMN, LPL, LRPAP1, MIF, MMP1, OVGP1, PLAU, PLAUR, PNP, PPARA, Pro-MCH, PSAP, P-selectin, RELN, SERPINE1, ZP1, ZP3, ZP4, ZPBP, or fragments or portions thereof that retain the ability to bind to a target protein described herein.

In some embodiments, the exogenous binding agent is an aptamer that specifically binds a target protein set forth in Table 1 or Table 2.

In various embodiments, the EV is about 20 nm to about 250 nm in size. In certain embodiments, the EV is an exosome. In some embodiments, the EV is a microvesicle.

In other embodiments, the EV is derived from a primary cell, a transformed cell, or a stem/progenitor cell. In some embodiments, the EV is derived from a neural cell, a muscle cell, an immune cell, an adipose cell, or a tumor cell. In some embodiments, the EV is derived from a neural cell, e.g., an astrocyte, an oligodendrocyte, a neuron, or a glial cell. In other embodiments, the EV is derived from an immune cell, e.g., a microglial cell or a dendritic cell. In other embodiments, the EV is derived from a stem/progenitor cell. In various embodiments, the EV is derived from an embryonic stem cell or an induced pluripotent stem cell. In other embodiments, the EV is derived from a neural progenitor cell, a neural stem cell, or a mesenchymal stem cell.

In further embodiments, the EV is derived from a cultured cell line, e.g., a CHO cell line, a HEK293 cell line, or a Vero cell line. In some embodiments, the EV is derived from cells that recombinantly express the exogenous binding agent.

In some embodiments, the EV further comprises a small molecule.

In some embodiments, the EV further comprises an exogenous nucleic acid. For example, the exogenous nucleic acid is a siRNA, a shRNA, an antisense RNA, a miRNA, or a combination thereof.

In certain embodiments, the EV further comprises an exogenous polypeptide.

In another aspect, the invention provides a pharmaceutical composition comprising a therapeutically effective amount of the EV of any one of the preceding claims, and a pharmaceutically acceptable carrier.

In some aspects, the invention also provides a method of delivering an EV across the blood brain barrier of a subject, comprising administering to the subject a composition comprising any of the EV described herein or a pharmaceutical composition comprising any of the EV described herein.

In certain embodiments, the composition is administered intravenously, intraarterially, or intranasally. In other embodiments, composition is administered orally, intramuscularly, intrathecally, intraocularlly, intradermally, intracranially, subcutaneously, or by inhalation.

In some embodiments, the EV is delivered to the brain of the subject. In one embodiment, the EV is delivered to the central nervous system of the subject.

In one aspect, the invention provides a conjugate comprising a binding agent that specifically binds to a protein expressed by a brain endothelial cell, coupled to a therapeutic agent. In some embodiments, the exogenous binding agent enhances transport of the therapeutic agent across the blood brain barrier.

In one embodiment, the binding agent is a polypeptide. In one embodiment, the binding agent is a polypeptide ligand of a protein expressed by a brain endothelial cell.

In other embodiments, the binding agent is an antibody, or antigen binding portion thereof, that specifically binds to a protein expressed by a brain endothelial cell. In certain embodiments, the binding agent is an antibody fragment selected from the group consisting of a Fab, a F(ab')$_2$, an scFv, a tandem scFv, a diabody, a minibody, and a single domain antibody.

In one embodiment, the binding agent is an aptamer that specifically binds to a protein expressed by a brain endothelial cell.

In some embodiments of the foregoing aspect, the binding agent specifically binds to a target protein set forth in Table 1. In other embodiments, the binding agent specifically binds to a target protein set forth in Table 2. In some embodiments, the binding agent specifically binds to an endothelial cell protein selected from ARHGEF18, ASB12, BAD, CD74, CD164, DCAF12L1, ECHS1, GORASP2, GPHA2, GRID2IP, HLA-DOA, HOXD4, IFNLR1, GPR37L1, HTR6, KCNT2, LIPJ, MCHR2, MESDC2, MTHFS, OCM, OR4X2, SCLT1, SERAC1, SFTD2, SHOC2, SPRYD3, STAG1, TMED10, TRIM67, TTLL7, VLDLR or ZP2, a B3GAT1-modified protein, a ST8SIA3-modified protein, or a combination thereof. In exemplary embodiments, the binding agent specifically binds to a target protein selected from the group consisting of ARHGEF18, ASB12, BAD, DCAF12L1, ECHS1, GORASP2, GPHA2, GRID2IP, HOXD4, KCNT2, LIPJ, MESDC2, MTHFS, OCM, OR4X2, SCLT1, SERAC1, SFTD2, SHOC2, SPRYD3, STAG1, TMED10, TRIM67, TTLL7, and VLDLR. In certain embodiments, the binding agent specifically binds to a target protein selected from the group consisting of KCNT2, OR4X2, SERAC1, SFT2D2, TMED10, and VLDLR.

In one embodiment, the binding agent is a polypeptide ligand of a target protein set forth in Table 1 or Table 2. In some embodiments, the polypeptide ligand comprises one or more of the binding agents set forth in Table 1, or a fragment or portion thereof that retains the ability to bind to a target protein described herein. In some embodiments, the binding agent comprises a protein selected from A2B5 antibody as described herein (Abcam Catalog #ab53521, Cambridge, MA; ThermoFisher Scientific Catalog #433110, Grand Island, NY), ACR, ADAM2, ADRBK1, AP2M1, APOE, APP, AR, CD1D, CD44, CD74, CLU, CTSB, CTSD, CTSF, CTSH, CTSL, CTSS, CTSV, CXCR-4 type 4 isoform a, CXCR-4 type 4 isoform b, CXCR-4 type 4 isoform c, CXCR-4 type 4 isoform d, CXCR-4 type 4 isoform e, DQB1, DRB3, ERBB4, E-selectin, HLA-DOB, HLA-DPA1, HLA-DQA1, HLA-DQA2, HLA-DQB1, HLA-DQB2, HLA-DRA, HLA-DRB1, HLA-DRB3, IFNL2, IFNLR1, IL10RB, ITGA2, ITGA3, ITGB1, Laminin (Laminin subunit gamma-1), Laminin (Laminin subunit beta-2), Laminin (Laminin subunit beta-1), Laminin (Laminin subunit alpha-2), Laminin (Laminin subunit alpha-1), Laminin (Laminin subunit alpha-5), Laminin (Laminin subunit alpha-3), Laminin (Laminin subunit gamma-3), Laminin (Laminin subunit alpha-4), Laminin (Laminin subunit gamma-2), Laminin (Laminin subunit beta-3), Laminin (Laminin subunit beta-4), LGMN, LPL, LRPAP1, MIF, MMP1, OVGP1, PLAU, PLAUR, PNP, PPARA, Pro-MCH, PSAP, P-selectin, RELN, SERPINE1, ZP1, ZP3, ZP4, ZPBP, or a fragment or portion thereof that retains the ability to bind to a target protein described herein.

In some embodiments, the binding agent is directly coupled to the therapeutic agent. In some embodiments, the binding agent is covalently coupled to the therapeutic agent by way of a linker. For example, the linker can be a peptide linker or a small molecule linker.

In certain embodiments, the therapeutic agent is a small molecule. In one embodiment, the therapeutic agent is a peptide. In one embodiment, the therapeutic agent is a polypeptide. In certain embodiments, the therapeutic agent is a nucleic acid. For example, the nucleic acid can be a cDNA, a DNA molecule, a plasmid, a cosmid, a siRNA, a shRNA, an antisense RNA, a miRNA, or a gRNA.

In certain embodiments, the binding agent is a bispecific antibody, or antigen binding portion thereof. In some embodiments, the bispecific antibody or the antigen binding portion thereof comprises a first binding site that specifically binds to a protein expressed by a brain endothelial cell, and a second binding site that specifically binds to a neurological disease antigen.

In other aspects, the invention provides a method of delivering a therapeutic agent across the blood brain barrier of a subject, comprising administering to the subject a conjugate provided herein. In some embodiments, the conjugate is administered intravenously. In some embodiments, the conjugate is administered intranasally. In some embodiments, the conjugate is administered intraarterially. In other embodiments, the conjugate is administered orally, intramuscularly, intrathecally, intraocularlly, intradermally, intracranially, subcutaneously, or by inhalation.

In one embodiment, the conjugate is delivered to the brain of the subject. In some embodiments, the conjugate is delivered to the central nervous system of the subject.

DETAILED DESCRIPTION

A. Definitions

Figure 1:
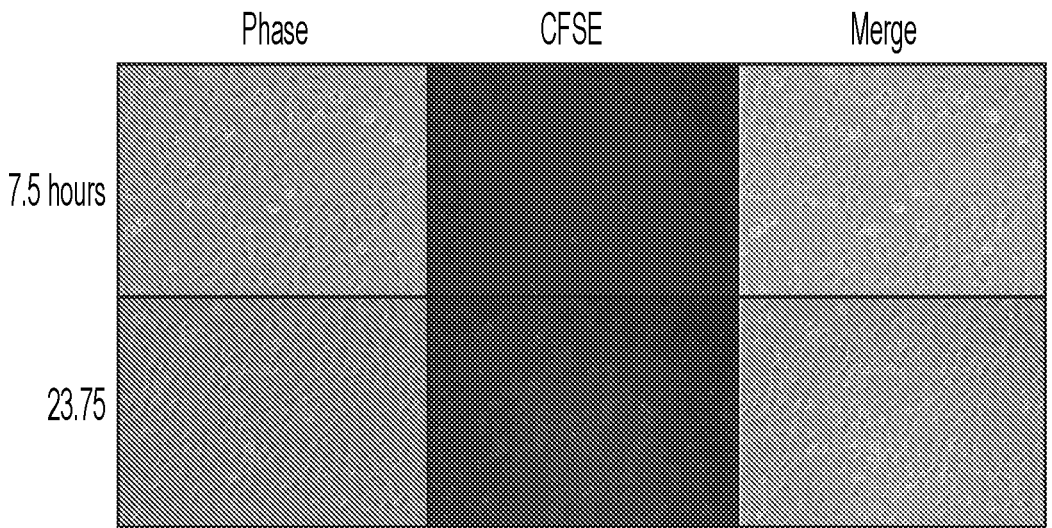
FIG. 1 shows representative images of adherent HCMEC/D3 cells treated with CFSE-labelled EVs at 7.5 and 23.75 hours. Images taken at 20×.

In order that the invention may be more readily understood, certain terms are first defined. In addition, it should be noted that whenever a value or range of values of a parameter are recited, it is intended that values and ranges intermediate to the recited values are also part of this invention.

The term "about" or "approximately" usually means within 5%, or more preferably within 1%, of a given value or range.

The term "antibody" is used herein in the broadest sense and encompasses various structures that bind a target antigen, including but not limited to monoclonal antibodies, polyclonal antibodies, multispecific antibodies (e.g., bispecific antibodies), nanobodies, monobodies, antibody mimetics, and antibody fragments so long as they exhibit the desired antigen-binding activity.

In some embodiments, an antibody includes an immunoglobulin molecule comprising four polypeptide chains, two heavy (H) chains and two light (L) chains inter-connected by disulfide bonds, as well as multimers thereof (e.g., IgM). Each heavy chain (HC) comprises a heavy chain variable region (or domain) (abbreviated herein as HCVR or VH) and a heavy chain constant region (or domain) The heavy chain constant region comprises three domains, CH1, CH2 and CH3. Each light chain (LC) comprises a light chain variable region (abbreviated herein as LCVR or VL) and a light chain constant region. The light chain constant region comprises one domain (CL1). Each VH and VL is composed of three CDRs and four FRs, arranged from amino-terminus to carboxy-terminus in the following order: FR1, CDR1, FR2, CDR2, 1-R3, CDR3, FR4 Immunoglobulin molecules can be of any type (e.g., IgG, IgE, IgM, IgD, IgA and IgY), class (e.g., IgG1, IgG2, IgG3, IgG4, IgA1 and IgA2) or subclass. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

An "antibody fragment", "antigen-binding fragment" or "antigen-binding portion" of an antibody refers to a molecule other than an intact antibody that comprises a portion of an intact antibody and that binds the antigen to which the intact antibody binds. Antibody fragments typically contain at least one or more (i.e., 1, 2, 3, 4, 5, or 6) complementary determining regions (CDRs). Examples of antibody fragments include, but are not limited to, Fv, Fab, Fab', Fab'-SH, F(ab')2; diabodies; linear antibodies; single-chain antibody molecules (e.g. scFv); and multispecific antibodies formed from antibody fragments.

The term "antibody mimetic" or "antibody mimic" refers to a molecule that is not structurally related to an antibody but is capable of specifically binding to an antigen. Examples of antibody mimetics include, but are not limited to, an adnectin (i.e., fibronectin based binding molecules), an affilin, an affimer, an affitin, an alphabody, an affibody, DARPins, an anticalin, an avimer, a fynomer, a Kunitz domain peptide, a monobody, a nanoCLAMP, a nanobody, a unibody, a versabody, an aptamer, and a peptidic molecule all of which employ binding structures that, while they mimic traditional antibody binding, are generated from and function via distinct mechanisms. The term "autologous EV" is used to describe a population of EVs which are obtained from cells from a subject or patient to whom the EVs are to be administered.

The term "aptamer" refers to oligonucleic acid or peptide molecules that bind to a specific target protein. These molecules are generally selected from a random sequence pool. The selected aptamers are capable of adapting unique tertiary structures and recognizing target molecules with high affinity and specificity. A nucleic acid aptamer is a DNA or RNA oligonucleic acid that binds to a target protein via its conformation. A nucleic acid aptamer may be constituted by DNA, RNA, or a combination thereof. A peptide aptamer is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

A "binding agent" refers to an agent that is capable of specifically binding to a protein target of interest. In exemplary embodiments, a binding agent can specifically bind to a protein expressed by an endothelial cell of the brain or CNS that comprises the blood brain barrier, also referred to herein as a "brain endothelial cell target protein" or a "blood brain barrier target protein." For example, binding agents can include any one or more of an antibody or antigen binding portion thereof, a polypeptide (e.g., ligand), an aptamer, etc. capable of specifically binding to a blood brain barrier target protein. In some embodiments, the target protein is a cell surface protein, e.g., a receptor. The term "exogenous binding agent" refers to a binding agent that is introduced into EVs by manipulation of the vesicles or the cell line from which they are derived. In some embodiments, an exogenous binding agent can be introduced into EVs by manipulation of the vesicles following their release from production cells. For example, an exogenous binding agent can refer to a binding agent that is loaded or incorporated into EVs following isolation of the EVs from a cell source. An exogenous binding agent can also be expressed from an exogenous gene in a cell from which the EV is derived, e.g., expressed from a gene that has been recombinantly introduced into the cell serving as the source of EVs. "Exogenous" refers to the manner of introduction, and does not exclude binding agents having the same or similar sequence as an agent natively expressed in a cell from which the EV is derived (e.g., in some embodiments, an EV can contain exogenous and native expression of a binding agent). An exogenous binding agent can also be incorporated into a synthetic EV. The terms "exogenous binding agent" and "binding agent" are used interchangeably.

The term "blood brain barrier (BBB)" as used herein refers to a highly selective semipermeable border of endothelial cells that prevents molecules in the circulating blood from nonselectively crossing into the extracellular fluid of the CNS. The blood brain barrier comprises endothelial cells of the capillary wall, astrocyte end-feet ensheathing the capillary, and pericytes embedded in the capillary basement membrane. The blood brain barrier prevents a variety of peripherally administered exogenous molecules from reaching the CNS to achieve a physiologically significant concentration in the CNS.

The terms "brain endothelial cell" or "blood brain barrier (BBB) endothelial cell" refer to endothelial cells present in blood vessels that vascularize the brain and central nervous system. Blood vessels that vascularize the central nervous system tightly regulate the passage of ions, cells, and other agents between the blood and the tissues of the brain and CNS. A "target protein expressed by a brain endothelial cell," also referred to herein simply as a "target protein," is a protein that localizes to the surface of a brain endothelial cell. Such cell surface proteins are described herein, and can additionally be identified using the methods described herein, as well as methods commonly known in the art. The binding agents described herein may bind to epitopes or regions of a target protein that are present, for example, on wild-type target proteins or naturally-occurring variants, e.g., splice isoforms, single nucleotide polymorphisms, fragments, glycoproteins, etc. Such epitopes may encompass regions of a target protein that include amino acids and/or amino acid modifications, e.g., carbohydrate or lipid modifications.

As used herein, the term "cargo" refers to one or more molecules that can be delivered to a target location in the body (e.g., the nervous system) by way of a binding agent disclosed herein, which facilitates delivery of the cargo across the blood brain barrier. Cargo can include, by way of example and without limitation, a small molecule (e.g., a small molecule drug), a nucleic acid (e.g., mRNA, DNA, siRNA. shRNA, antisense RNA, miRNA, etc.), a protein or peptide (e.g., a hormone, a growth factor, an enzyme, an anticoagulant, an interferon, an interleukin, an antibody, an antibody fragment, an antibody-drug conjugate, etc.), an exosome, or a liposome. In some embodiments, the cargo is a therapeutic molecule. In some embodiments, the cargo can be attached directly or indirectly to a binding agent. In other embodiments, the cargo is delivered using an EV that comprises the binding agent, as provided herein.

As used herein, the term "CDR" or "complementarity determining region" refers to the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat, based on sequence comparisons.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "central nervous system" (CNS) refers to a part of the nervous system comprising the brain and the spinal cord of organisms, e.g., subjects.

As used herein, the terms "distal" and "peripheral", in the context of administering agents "distal to the CNS" or "peripherally", "peripheral administration", and like terms, refer to administering agents to subjects at a site separated from the CNS by the blood brain barrier. When agents are administered peripherally, or at a site distal to the CNS, the agent must cross the blood brain barrier to reach the CNS. Peripheral administration or administration at a site distal to the CNS may be by numerous routes of administration, including, but not limited to, intravenous, intranasal, intraperitoneal, and oral administration.

As used herein, the term "effective amount" or "therapeutically effective amount" refers to the amount of an agent, e.g., a composition comprising EVs, e.g., exosomes, which is sufficient to reduce or ameliorate the severity and/or duration of a disorder, or one or more symptoms thereof, prevent the advancement of a disorder, cause regression of a disorder, prevent the recurrence, development, onset, or progression of one or more symptoms associated with a disorder, or enhance or improve the prophylactic or therapeutic effect(s) of another therapy.

The term "embryonic stem cell" or "ESC" refers to pluripotent cells, preferably of primates, including humans, which are isolated from the blastocyst stage embryo.

The term "enhances", "increases", "superior", and like terms, in the context of "enhances transport" refers to an increase in blood brain barrier EV transport that is at least 10%, 15%, 20%, 25%, 30%, 35%, 40%, 45%, 50%, 55%, 60%, 65%, 70%, 75%, 80%, 90%, 100%, 150%, 200%, 300%, 400%, 500%, 1000% or greater as compared to transport of EV across the blood brain barrier in the absence of the exogenous binding agent.

As used herein, the terms "extracellular vesicle" and "EV" are used herein to refer to a vesicle of about 10 nm to 10 μm in size enclosed by a lipid bilayer, e.g., a portion of a cell membrane. EVs can contain, e.g., fluid, macromolecules, solutes, and metabolites from a cell. The term "EV" encompasses vesicles that have been isolated from a recombinant cell source engineered or modified to produce/ express an exogenous agent (e.g., an exogenous polypeptide), which agent is incorporated into the EV. The term "EV" also encompasses vesicles that have been engineered (e.g., loaded) following isolation to contain an exogenous agent (e.g., an exogenous polypeptide). The term "EV" also includes artificial lipid vesicles engineered to contain bioactive molecules found in a cell-derived EVs, such as a neural EVs. The term EV encompasses both exosomes and ectosomes. EVs may be obtained from the appropriate biological source using a combination of isolation techniques, for example, centrifugation, filtration and ultracentrifugation methodologies. Exosomes are released on the exocytosis of multivesicular bodies (MVBs). Ectosomes are vesicles assembled at and released from the plasma membrane. In some cases, the EV is about 20 nm to 10 μm, 20 nm to 1 μm, 20 nm-500 nm, 30 nm-100 nm, 30 nm-160 nm, or 80 nm-160 nm in size. In some embodiments, the EVs are exosomes that are about 20 nm to 250 nm in size. EVs derived from virtually any source can be used in the compositions and methods provided herein. In exemplary embodiments, EVs can be isolated from cultured mammalian cells, including but not limited to primary cells, stem/ progenitor cells, transformed cells, and established cell lines. In some embodiments, EVs can be isolated from a neural cell (e.g., a neural progenitor cell, a neural stem cell, a glial cell, an astrocyte, an oligodendrocyte, a neuron, etc.). EVs may also be isolated from any suitable biological sample, including but not limited to, whole blood, serum, plasma, breast milk, cerebrospinal fluid, amniotic fluid, ascitic fluid, or bone marrow.

The term "Fc domain" is used to define the C-terminal region of an immunoglobulin heavy chain, which may be generated by papain digestion of an intact antibody. The Fc domain may be a native sequence Fc domain or a variant Fc domain. The Fc domain of an immunoglobulin generally comprises two constant domains, a CH2 domain and a CH3 domain, and optionally comprises a CH4 domain Replacements of amino acid residues in the Fc portion to alter antibody effector function are known in the art (Winter, et al. U.S. Pat. Nos. 5,648,260; 5,624,821). The Fc domain of an antibody mediates several important effector functions e.g. cytokine induction, ADCC, phagocytosis, complement dependent cytotoxicity (CDC) and half-life/clearance rate of antibody and antigen-antibody complexes. In certain embodiments, at least one amino acid residue is altered (e.g., deleted, inserted, or replaced) in the Fc domain of an Fc domain-containing binding protein such that effector functions of the binding protein are altered.

The term "human antibody", as used herein, refers to an antibody having variable regions in which both the framework and CDR regions are derived from human germline immunoglobulin sequences. Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "humanized antibody" is intended to refer to antibodies in which CDR sequences derived from the germline of one mammalian species, such as a mouse, have been grafted onto human framework sequences. Additional framework region modifications may be made within the human framework sequences. A "humanized form" of an antibody, e.g., a non-human antibody, refers to an antibody that has undergone humanization.

An "intact" or a "full length" antibody, as used herein, refers to an antibody comprising four polypeptide chains, two heavy (H) chains and two light (L) chains. In one embodiment, an intact antibody is an intact IgG antibody.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "multispecific antigen binding polypeptide" or "multispecific antibody" is one that targets more than one antigen or epitope. A "bispecific," "dual-specific" or "bifunctional" antigen binding polypeptide or antibody is a hybrid antigen binding polypeptide or antibody, respectively, having two different antigen binding sites. Bispecific antigen binding polypeptides and antibodies are examples of a multispecific antigen binding polypeptide or a multispecific antibody and may be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553, Brinkmann and Kontermann 2017. MABS. 9(2):182-212. The two binding sites of a bispecific antigen binding polypeptide or antibody, for example, will bind to two different epitopes, which may reside on the same or different protein targets.

The term "neural cell" refers to a cell pertaining to the nervous system. The term "neural cell" encompasses neural stem cells, e.g., neural progenitor (NP) cells, and differentiated neural cells. In some embodiments, differentiated neural cells can be derived in vitro from neural stem cells, NP cells or from pluripotent stem cells. Exemplary neural cells include a neuron, a glial cell, an astrocyte, an oligodendrocyte, or a microglial cell, a Schwann cell, or a glioma cell. In other embodiments, the neural cell can be a NP cell or a neural stem cell. The terms "neural progenitor cell" and "neural stem cell" refer to multipotent cells that have the capacity to differentiate into a restricted repertoire of neuronal and glial cell types. In some embodiments, NP cells can be derived in vitro from pluripotent stem cells, e.g., induced pluripotent stem cells (iPS cells) or embryonic stem cells (ES cells). In some embodiments, the neural cells referenced herein are human neural cells. In exemplary embodiments, the NP cells referenced herein are human NP cells. In some embodiments, the NP cells can be non-transformed. In some embodiments, the NP cells are proliferative. In some embodiments, the NP cells maintain phenotype without differentiation.

The term "neural EV" is used to refer to an EV that is derived from neural cells, for example, neural stem cells, e.g., neural progenitor cells. The term also refers to vesicles engineered to contain a sufficient number of the bioactive molecules found in cell-derived neural EV to have substantially the same bioactivity.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained. In some instances, a "pharmaceutically acceptable" refers to those compounds that are suitable for use in contact with the tissues of human beings and animals without excessive toxicity, irritation, allergic response, or complications commensurate with a reasonable benefit/risk ratio.

The term "Pluripotent Stem Cells", of which "Embryonic Stem Cells" (ESCs) and induced pluripotent stem cells (iPSCs) are a subset, are derived from pre-embryonic, embryonic, fetal tissue or adult stem cells (in the case of induced pluripotent stem cells) at any time after fertilization, and have the characteristic of being capable under appropriate conditions of producing progeny of several different cell types, especially including neuronal stem and progenitors, neural crest cells, mesenchymal stem cells (MSCs) and related proliferative and non-proliferative neural cells. The term includes both established lines of stem cells of various kinds, and cells obtained from primary tissue that are pluripotent in the manner described.

As used herein, the term "sample" refers to a specimen (e.g., cell (e.g., neural cell), tissue, blood, blood component (e.g., serum or plasma), urine, saliva, amniotic fluid, cerebrospinal fluid, pancreatic fluid, chorionic villus sample, and bone marrow) taken from a subject.

The term "specifically binds" refers to preferential binding to a target protein in a mixture of proteins that can be measured using known methods. For example, in the case of a binding agent that is an antibody, specific binding occurs on an epitope of a target protein. Typically, the antibody binds with an equilibrium dissociation constant ($K_D$) of approximately less than $10^{-6}$ M, such as approximately less than $10^{-7}$, $10^{-8}$ M, $10^{-9}$ M or $10^{-10}$ M or even lower when determined by, e.g., surface plasmon resonance (SPR) technology in a BIACORE 2000 instrument using the target protein as the analyte and the antibody as the binding agent, and binds to the target protein with an affinity that is at least two-fold greater than its affinity for binding to a non-specific target (e.g., BSA, casein). In some cases, "specifically binds" refers to binding of the binding agent to the target protein that is at least 1.5-fold, 2-fold, 2.5-fold, 3-fold, 3.5-fold, 4-fold, 4.5-fold, 5-fold, 6-fold, 7-fold, 8-fold, 9-fold, or 10-fold, 100-fold, 1000-fold or greater than its affinity for binding to a non-specific target using known methods.

As used herein, the term "subject" refers to any organism that is the target of administration or treatment. A "subject" can be an organism, for example, a mammal (e.g., a human, a non-human mammal, a non-human primate, a primate, a laboratory animal, a mouse, a rat, a hamster, a cat, or a dog). In one embodiment, a subject is a human subject. The term "patient" refers to a human subject under the treatment of a clinician, e.g., physician. A subject can be male or female.

The term "treat" and "treatment" refers to the medical management of a subject with the intent to improve, ameliorate, stabilize (i.e., not worsen), prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. Treatment does not require the complete amelioration of a symptom or disease and encompasses embodiments in which one reduces symptoms and/or underlying risk factors. "Treatment" can also mean prolonging survival as compared to expected survival if not receiving treatment. Those in need of treatment include those already with the condition or disorder, as well as those prone to have the condition or disorder or those in which the condition or disorder is to be prevented. The term "prevent" does not require the 100% elimination of the possibility of an event. Rather, it denotes that the likelihood of the occurrence of the event has been reduced in the presence of the compound or method.

In accordance with the present disclosure there may be employed conventional cell culture methods, chemical synthetic methods and other biological and pharmaceutical techniques within the skill of the art. Such techniques are well-known and are otherwise explained fully in the literature. Standard techniques for growing cells, separating cells, and where relevant, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, New York; Maniatis et al., 1982 Molecular Cloning, Cold Spring Harbor Laboratory, Plainview, New York; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, New York; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention as though explicitly stated as such. The upper and lower limits of these smaller ranges may independently be included in the ranges also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

B. Methods for Identifying Target Proteins and Binding Agents that Facilitate Traversal of the Blood Brain Barrier The present disclosure provides methods for identifying endothelial cell protein targets and binding agents that facilitate passage of agents and molecules associated therewith across the blood brain barrier (BBB). In some aspects, such methods include methods of: (i) identifying endothelial target proteins that play a role in transport of molecules across the BBB and are capable of modulating passage of exogenous agents across the BBB; and (ii) identifying agents that specifically bind to the identified endothelial cell target proteins and are capable of enhancing the transport of the agent and molecules associated therewith across the blood brain barrier, such that the binding agent and associated cargo can be delivered to the brain and/or CNS across the BBB.

(i) Method of Identifying Endothelial Target Proteins

In some aspects, the present disclosure provides methods of screening the proteins expressed in brain or CNS vascular or microvascular endothelial cells. In some embodiments, the screen is capable of and identifying endothelial target proteins that play a role in transporting molecules across the BBB and are capable of modulating passage of exogenous agents across the BBB. In some embodiments, the methods comprise: (a) introducing single gene knock-down (or knock-out) to a population of brain endothelial cells; (b) contacting the population of endothelial cells with an agent capable of traversing the BBB, e.g., neural progenitor EVs; (c) measuring the uptake of the EVs by the population of endothelial cells; (d) selecting the cells with reduced/lower uptake of the EVs than control; and (e) identifying proteins knocked down in the selected cells as candidate target proteins. Optionally, in some embodiments, the method can further comprise narrowing down a pool of candidate target proteins using an alignment and differential expression algorithm, gene expression data, and/or subcellular localization data.

In addition, in some embodiments, the method can further comprise functionally validating the candidate target proteins. For example, the candidate target proteins can be validated by knocking down each candidate target protein in brain endothelial cells, contacting the cells with the agent capable of traversing the BBB, e.g., neural progenitor EVs, and selecting target proteins that exhibit diminished uptake of the agent by the endothelial cells. In addition or alternatively, the candidate target proteins can be validated by contacting brain endothelial cells with an agent that specifically binds to a candidate target protein, and selecting target proteins that exhibit increased uptake of the agent. Exemplary binding agents can include, but are not limited to, those described herein, for example, antibodies or antigen binding portions thereof, polypeptide ligands, aptamers, etc. In some embodiments, the binding agent can be coupled to a cargo. Exemplary cargo can include, for example, a small molecule (e.g., a small molecule drug), a nucleic acid (e.g., mRNA, DNA, siRNA, shRNA, antisense RNA, miRNA, etc.), a protein or peptide (e.g., a hormone, a growth factor, an enzyme, an anticoagulant, an interferon, an interleukin, an antibody, an antibody fragment, an antibody-drug conjugate, etc.), an EV (e.g., an exosome or microvesicle), or a liposome. In some embodiments, the binding agent can be coupled to an EV In some embodiments, the methods of identifying endothelial target proteins that play a role in transport of molecules across the BBB comprise introducing single gene knock-downs (or knock-outs) to a population of brain or CNS vascular endothelial cells. In some embodiments, the brain or CNS endothelial cells are primary brain endothelial cells obtained from subjects, e.g., humans. In some embodiments, the brain or CNS endothelial cells are passaged, non-transformed, or transformed brain endothelial cells, e.g., hCMEC/D3 cells. In some embodiments, the brain or CNS endothelial cells are human cells. Transformed human brain endothelial cell cultures have been used to mimic the BBB in vitro and are sold commercially under the name HCMEC/D3 (D3) (see, e.g., Weksler, B., I. A. Romero, and P.-O. Couraud, The hCMEC/D3 cell line as a model of the human blood brain barrier. Fluids and barriers of the CNS, 2013. 10(1): p. 16-16).

In some embodiments, single-gene knock-downs or knock-outs can be generated by knocking down a single target gene in a population of cells. In other embodiments, single-gene knock-downs or knock-outs can be generated by knocking down multiple target genes in a population of cells, with approximately one gene knocked down in each cell of the population (e.g., using a library, e.g., a CRISPR-Cas9 library, a siRNA library, etc. diluted to achieve single-gene knock-down). To knock down (or knock out) genes expressed in brain or CNS endothelial cells, any method known in the art may be used, including creating a population of cells, wherein each cell comprises a single gene knock-down. In some embodiments, the CRISPR-Cas9 system is used to introduce single gene knock down (or knock out) to a population of brain or CNS endothelial cells such that each cell in a cell population has one gene knocked out (see, e.g., Horlbeck, M. A., et al., Compact and highly active next-generation libraries for CRISPR-mediated gene repression and activation. Elife, 2016. 5).

In some embodiments, the methods of identifying endothelial target proteins capable of modulating the endothelial cell function to allow an agent to cross the BBB comprise screening a population of brain or CNS endothelial cells comprising a single gene knock-down for the ability to uptake an agent of interest. Without wishing to be bound by theory, there are two general types of screens: positive and negative. In a positive screen, selection of a desired cohort of cells can be achieved by FACS based on a fluorescent phenotype, or by any other signal development methods available in the art. Positive screening has been used successfully to determine pathways of flu virus infection (Heaton, B. E., et al., A CRISPR Activation Screen Identifies a Pan-avian Influenza Virus Inhibitory Host Factor. Cell Rep, 2017. 20(7): p. 1503-1512; Han, J., et al., Genome-wide CRISPR/Cas9 Screen Identifies Host Factors Essential for Influenza Virus Replication. Cell Rep, 2018. 23(2): p.

596-607). In a negative screen, cells that do not survive the selection mechanism are identified and their genes are sequenced. Negative screens may be used to identify genes that are essential for growth/survival under certain conditions. In some embodiments, the methods for identifying endothelial target proteins comprise screening the cells using a positive screen. In some embodiments, the methods for identifying endothelial target proteins comprise screening the cells using a negative screen.

In some embodiments, the methods of screening for target proteins capable of modulating the endothelial cell function to allow an agent to cross the BBB comprise contacting the population of cells comprising a single gene knock-down (or knock-out) with molecules known to be transported, to a certain extent, across the BBB. In some embodiments, the molecules are labeled, e.g., by fluorescent tag, e.g., FITC, CFSE, for positive screening. Previous results indicate that EVs derived from neural stem cells or neural progenitor cells can cross the BBB by an unknown mechanism. Accordingly, in some embodiments, EVs derived from a neural progenitor cell line may be used to contact the population of endothelial cells comprising gene knock-down (or knock-out) and test their uptake by the endothelial cells. In some embodiments, neural progenitor EVs are fluorescently labeled such that uptake of EVs by cells is detectable on a flow cytometer. In some embodiments, cells lacking expression (via gene knock-down) of proteins involved in EV uptake have reduced fluorescence relative to cells with unperturbed uptake, thereby indicating endothelial proteins that are involved in transport of molecules across the BBB. In some embodiments, the methods of screening comprise selecting cells with lower fluorescence than control, indicating decreased EV uptake.

In some embodiments, raw data of uptake of labeled molecules into the population of cells, e.g., as measured by fluorescence intensity within the brain or CNS endothelial cells, can be analyzed using algorithms known in the art, e.g., (i) Model-based Analysis of Genome-wide CRISPR-Cas9 Knockout ("MAgeCK") (Li, W., et al., Genome Biology, 2014; 15(12):554) protocol with batch effect removal, (ii) MAgeCK gRNA alignment without batch effect removal, (iii) DESeq2 differential expression analysis, and (iv) MAgeCK alignment paired with DESeq2 differential expression analysis, to provide target protein hits. In some embodiments, initially identified candidate target proteins (identified by, e.g., number of gRNAs, p-value) are further analyzed using gene expression data and subcellular localization data, to narrow down the pool of candidate target protein.

In some embodiments, the methods of identifying target proteins further comprise validating the candidate target proteins by knocking down each candidate target protein in brain or CNS vascular endothelial cells using, e.g., CRISPR-Cas9 system, e.g., introducing into the cells CAS9 and gRNA lentiviral particles targeting each gene; contacting the knock-down cells with molecules known to be transported across the BBB, e.g., neural progenitor EVs; and screening for diminished uptake of fluorescent-labeled molecules, e.g., EVs, by the endothelial cells using flow cytometry, as provided in the present disclosure.

In some embodiments, the methods of identifying target proteins further comprise validating the candidate target proteins by treating brain or CNS vascular endothelial cells (that do not contain knock-down or knock-out of the target protein) with an agent that specifically binds to the target protein, and screening for increased uptake of the agent by the endothelial cells. In some embodiments, the binding agent is labeled with a reporter, e.g., a fluorescent label, and the screen is performed to identify increased uptake of the reporter by the endothelial cells, e.g., using flow cytometry.

Additional labels that may be used in the screen are known to persons of skill in the art, and include, e.g., radioisotope labels, the presence or absence of which can be detected in endothelial cells using known techniques.

(ii) Methods of Identifying Binding Agents

In some embodiments, candidate binding agents can be screened by contacting intact endothelial cells (in vitro or in vivo) with candidate binding agents and studying their uptake by the endothelial cells. In some embodiments, the candidate binding agents can be coupled to a reporter, e.g., a fluorescent label or a radioisotope label. In some embodiments, the candidate binding agents can be coupled to a therapeutic agent. In some embodiments, the candidate binding agents can be exogenously expressed in EVs, for example, using a fusion gene construct, conjugation, linker, covalent or non-covalent coupling, viral vectors, CRISPR-Cas9 system, or any methods available in the art. In some embodiments, the EVs can be labeled with fluorescence, e.g., CFSE. In some embodiments, the uptake of binding agent(s) is examined in vitro, e.g., by examining uptake into endothelial cells. In some embodiments, the uptake of binding agent(s) is examined in vivo, e.g., by examining uptake into the brain of subjects after one or more binding agents are peripherally administered to the subjects. In some embodiments, following peripheral administration of radio-isotope-labeled EVs to subjects, uptake of EVs is evaluated in vivo using brain and whole body single photon emission spectroscopy, measuring the relative intensity of radioactivity in the brain and throughout the body.

In some aspects, the present disclosure provides methods of identifying agents that specifically bind to the identified endothelial cell target proteins and are capable of enhancing the transport of the agent and molecules associated therewith across the BBB. In some embodiments, the methods comprise: (a) identifying, as candidate binding agents, ligands for endothelial target proteins identified to be capable of modulating transport of molecules across the BBB; (b) expressing each of the candidate binding agents in neural progenitor EVs; (c) contacting brain endothelial cells with the EVs modified to express candidate binding agents; (d) measuring uptake of the EVs by the endothelial cells; and (e) identifying the candidate binding agents which caused an enhanced uptake of EVs by the endothelial cells. In some embodiments, the methods comprise: (a) identifying, as candidate binding agents, ligands for endothelial target proteins identified to be capable of modulating transport of molecules across the BBB; (b) expressing each of the candidate binding agents in neural progenitor EVs; (c) peripherally administering the modified EVs to a subject; (d) measuring uptake of the EVs in the brain of the subject; and (e) identifying the candidate binding agents which conferred EVs an enhanced ability to cross the BBB for CNS delivery.

In some embodiments, the methods comprise identifying candidate binding agents by identifying ligands for each identified endothelial target proteins. In some embodiments, such identification is done by using known database of receptor-ligand pairs, e.g., haps://baderlab.org/CellCellInteractions.

C. Endothelial Target Proteins and Binding Agents that Facilitate Traversal of the Blood Brain Barrier The present disclosure provides binding agents capable of specifically binding to an endothelial cell protein target of interest. As exemplified herein, certain proteins expressed on the surface of endothelial cells of the brain and/or central nervous system have been identified to play a role in transport across the blood brain barrier (BBB). Agents that specifically bind to these endothelial cell proteins enhance the transport of the agent and molecules associated therewith across the blood brain barrier, thereby delivering the agent and associated cargo to the brain and/or CNS. Accordingly provided herein are binding agents designed to bind any one or more of the target proteins expressed on brain endothelial cells identified as described herein to play a role in transport across the blood brain barrier. Such binding agents can facilitate, e.g., enhance, uptake of material across the blood brain barrier (BBB).

In some aspects, the present disclosure provides certain brain endothelial cell proteins (e.g., receptors on brain endothelial cells) that were identified as described herein to facilitate the movement of material across the blood brain barrier (BBB). The brain endothelial cell proteins identified as exemplified herein are provided in Tables 1 and 2. Any one or more of these brain endothelial cell proteins can be targeted by binding agents of the present disclosure to enhance uptake of material (e.g., therapeutic compounds, extracellular vesicles, etc.) across the BBB.

In some embodiments, present disclosure provides a binding agent that specifically binds to a target protein set forth in Table 1. In other embodiments, present disclosure provides a binding agent that specifically binds to a target protein set forth in Table 2.

Binding agents useful for the compositions and methods described herein include, but are not limited to, polypeptide ligands of the target protein. Polypeptide ligands can be native ligands of the target protein, or portions thereof (e.g., fragments) that specifically bind to the target protein. Alternatively, a modified polypeptide ligand can be engineered for use in the compositions and methods described herein, which modified ligand retains the ability to specifically bind to the target protein. Exemplary polypeptide ligands of each target protein provided in Table 1 are set forth in the right-hand column. Additional binding agents include, for example, antibodies, or antigen binding portions thereof, that specifically bind to a target protein provided in Table 1, or a target protein provided in Table 2.

TABLE 1

Sequences of exemplary target proteins and associated binding agents

| Target Protein | Target Protein SEQ | Exemplary Binding Agent(s) |
|---|---|---|
| CD74 | Isoform a (SEQ ID NO: 1) | APP (SEQ ID NO: 23) |
| | mhrrrsrscr edqkpvmddq | MLPGLALLLLAAWTARALEVPTDGNAGL |
| | rdlisnneql pmlgrrpgap | LAEPQIAMFCGRLNMHMNVQNGKWDSDP |
| | eskcsrgaly tgfsilvtll | SGTKTCIDTKEGILQYCQEVYPELQITN |
| | lagqattayf lyqqqgrldk | VVEANQPVTIQNWCKRGRKQCKTHPHFV |
| | itvtsqnlql enlrmklpkp | IPYRCLVGEFVSDALLVPDKCKFLHQER |

TABLE 1-continued

Sequences of exemplary target proteins and associated binding agents

| Target Protein | Target Protein SEQ | Exemplary Binding Agent(s) |
|---|---|---|
| | pkpvskmrma tpllmqalpm | MDVCETHLHWHTVAKETCSEKSTNLHDY |
| | galpqgpmqn atkygnmted | GMLLPCGIDKFRGVEFVCCPLAEESDNV |
| | hvmhllqnad plkvypplkg | DSADAEEDDSDVWWGGADTDYADGSEDK |
| | sfpenlrhlk ntmetidwkv | VVEVAEEEEVAEVEEEEADDDEDDEDGD |
| | feswmhhwll femsrhsleq | EVEEEEAEEPYEEATERTTSIATTTTTT |
| | kptdappkvl tkcqeevshi | ESVEEVVREVCSEQAETGPCRAMISRWY |
| | pavhpgsfrp kcdengnylp | FDVTEGKCAPFFYGGCGGNRNNFDTEEY |
| | Iqcygsigyc wcvfpngtev | CMAVCGSAMSQSLLKTTQEPLARDPVKL |
| | pntrsrghhn cseslelledp | PTTAASTPDAVDKYLETPGDENEHAHFQ |
| | ssglgvtkqd lgpvpm | KAKERLEAKHRERMSQVMREWEEAERQA |
| | Isoform b (SEQ ID NO: 2) | KNLPKADKKAVIQHFQEKVESLEQEAAN |
| | mhrrrsrscr edqkpvmddq | ERQQLVETHMARVEAMLNDRRRLALENY |
| | rdlisnneql pmlgrrpgap | ITALQAVPPRPRHVFNMLKKYVRAEQKD |
| | eskcsrgaly tgfsilvtll | RQHTLKHFEHVRMVDPKKAAQIRSQVMT |
| | lagqattayf lyqqqgrldk | HLRVIYERMNQSLSLLYNVPAVAEEIQD |
| | itvtsqnlql enlrmklpkp | EVDELLQKEQNYSDDVLANMISEPRISY |
| | pkpvskmrma tpllmqalpm | GNDALMPSLTETKTTVELLPVNGEFSLD |
| | galpqgpmqn atkygnmted | DLQPWHSFGADSVPANTENEVEPVDARP |
| | hvmhllqnad plkvypplkg | AADRGLTTRPGSGLTNIKTEEISEVKMD |
| | sfpenlrhlk ntmetidwkv | AEFRHDSGYEVHHQKLVFFAEDVGSNKG |
| | feswmhhwll femsrhsleq | AIIGLMVGGVVIATVIVITLVMLKKKQY |
| | kptdappkes leledpssgl | TSIHHGVVEVDAAVTPEERHLSKMQQNG |
| | gvtkqdlgpv pm | YENPTYKFFEQMQN |
| | Isoform c (SEQ ID NO: 3) | CDID (SEQ ID NO: 24) |
| | mhrrrsrscr edqkpvmddq | MGCLLFLLLWALLQAWGSAEVPQRLFPL |
| | rdlisnneql pmlgrrpgap | RCLQISSFANSSWTRTDGLAWLGELQTH |
| | eskcsrgaly tgfsilvtll | SWSNDSDTVRSLKPWSQGTFSDQQWETL |
| | lagqattayf lyqqqgrldk | QHIFRVYRSSFTRDVKEFAKMLRLSYPL |
| | itvtsqnlql enlrmklpkp | ELQVSAGCEVHPGNASNNFFHVAFQGKD |
| | pkpvskmrma tpllmqalpm | ILSFQGTSWEPTQEAPLWVNLAIQVLNQ |
| | galpqgpmqn atkygnmted | DKWTRETVQWLLNGTCPQFVSGLLESGK |
| | hvmhllqshw nwrtrllgwv | SELKKQVKPKAWLSRGPSPGPGRLLLVC |
| | Isoform d (SEQ ID NO: 4) | HVSGFYPKPVWVKWMRGEQEQQGTQPGD |
| | mhrrrsrscr edqkpvmddq | ILPNADETWYLRATLDVVAGEAAGLSCR |
| | rdlisnneql pmlgrrpgap | VKHSSLEGQDIVLYWGGSYTSMGLIALA |
| | eskcsrgaly tgfsilvtll | VLACLLFLLIVGFTSRFKRQTSYQGVL |
| | lagqattayf lyqqqgrldk | CD74 (SEQ ID NO: 25) |
| | itvtsqnlql enlrmklpkp | MHRRRSRSCREDQKPVMDDQRDLISNNE |
| | pkpvskmrma tpllmqalpm | QLPMLGRRPGAPESKCSRGALYTGFSIL |
| | galpqgnadp ikvypplkgs | VTLLLAGQATTAYFLYQQQGRLDKLTVT |
| | fpenlrhlkn tmetidwkvf | SQNLQLENLRMKLPKPPKPVSKMRMATP |
| | eswmhhwllf emsrhsleqk | LLMQALPMGALPQGPMQNATKYGNMTED |
| | ptdappkesl eledpssglg | HVMHLLQNADPLKVYPPLKGSFPENLRH |
| | vtkqdlgpvp m | LKNTMETIDWKVFESWMHHWLLFEMSRH |
| | Isoform e (SEQ ID NO: 5) | SLEQKPTDAPPKVLTKCQEEVSHIPAVH |
| | mhrrrsrscr edqkpvmddq | PGSFRPKCDENGNYLPLQCYGSIGYCWC |
| | rdlisnneql pmlgrrpgap | VFPNGTEVPNTRSRGHHNCSESLELEDP |
| | | SSGLGVTKQDLGPVPM |
| | eskcsrgaly tgfsilvtll | CTSF (SEQ ID NO: 26) |
| | lagqattayf lyqqqgrldk | MAPWLQLLSLLGLLPGAVAAPAQPRAAS |
| | itvtsqnlql enlrmklpkp | FQAWGPPSPELLAPTRFALEMFNRGRAA |
| | pkpvskmrma tpllmqalpm | GTRAVLGLVRGRVRRAGQGSLYSLEATL |
| | galpqgpmqn atkygnmted | EEPPCNDPMVCRLPVSKKTLLCSFQVLD |
| | hvmhllqnad plkvypplkg | ELGRHVLLRKDCGPVDTKVPGAGEPKSA |
| | sfpenlrhlk ntmetidwks | FTQGSAMISSLSQNHPDNRNETFSSVIS |
| | hwnwrtrllg wv | LLNEDPLSQDLPVKMASIFKNFVITYNR |
| | | TYESKEEARWRLSVFVNNMVRAQKIQAL |
| | | DRGTAQYGVTKFSDLTEEEFRTIYLNTL |
| | | LRKEPGNKMKQAKSVGDLAPPEWDWRSK |
| | | GAVTKVKDQGMCGSCWAFSVTGNVEGQW |
| | | FLNQGTLLSLSEQELLDCDKMDKACMGG |
| | | LPSNAYSAIKNLGGLETEDDYSYQGHMQ |
| | | SCNFSAEKAKVYINDSVELSQNEQKLAA |
| | | WLAKRGPISVAINAFGMQFYRHGISRPL |
| | | RPLCSPWLIDHAVLLVGYGNRSDVPFWA |
| | | IKNSWGTDWGEKGYYYLHRGSGACGVNT |
| | | MASSAWD |
| | | CTSL (SEQ ID NO: 27) |
| | | MNPTLILAAFCLGIASATLTFDHSLEAQ |
| | | WTKWKAMHNRLYGMNEEGWRRAVWEKNM |
| | | KMIELHNQEYREGKHSFTMAMNAFGDMT |
| | | SEEFRQVMNGFQNRKPRKGKVFQEPLFY |
| | | EAPRSVDWREKGYVTPVKNQGQCGSCWA |
| | | FSATGALEGQMFRKTGRLISLSEQNLVD |
| | | CSGPQGNEGCNGGLMDYAFQYVQDNGGL |
| | | DSEESYPYEATEESCKYNPKYSVANDTG |

TABLE 1-continued

| Sequences of exemplary target proteins and associated binding agents | | |
|---|---|---|
| Target Protein | Target Protein SEQ | Exemplary Binding Agent(s) |
| | FVDIPKQEKALMKAVATVGPISVAIDAG HESFLFYKEGIYFEPDCSSEDMDHGVLV VGYGFESTESDNNKYWLVKNSWGEEWGM GGYVKMAKDRRNHCGIASAASYPTV | |
| CXCR4(isoformb)(SEQID NO:28) | MEGISIYTSDNYTEEMGSGDYDSMKEPC FREENANFNKIFLPTIYSIIFLTGIVGN GLVILVMGYQKKLRSMTDKYRLHLSVAD LLFVITLPFWAVDAVANWYFGNFLCKAV HVIYTVNLYSSVLILAFISLDRYLAIVH ATNSQRPRKLLAEKVVYVGVWIPALLLT IPDFIFANVSEADDRYICDRFYPNDLWV VVFQFQHIMVGLILPGIVILSCYCIIIS KLSHSKGHQKRKALKTTVILILAFFACW LPYYIGISIDSFILLEIIKQGCEFENTV HKWISITEALAFFHCCLNPILYAFLGAK FKTSAQHALTSVSRGSSLKILSKGKRGG HSSVSTESESSSFHSS | |
| ERBB4 (SEQ ID NO: 29) | MKPATGLWVWVSLLVAAGTVQPSDSQSV CAGTENKLSSLSDLEQQYRALRKYYENC EVVMGNLEITSIEHNRDLSFLRSVREVT GYVLVALNQFRYLPLENLRIIRGTKLYE DRYALAIFLNYRKDGNFGLQELGLKNLT EILNGGVYVDQNKFLCYADTIHWQDIVR NPWPSNLTLVSTNGSSGCGRCHKSCTGR CWGPTENHCQTLTRTVCAEQCDGRCYGP YVSDCCHRECAGGCSGPKDTDCFACMNF NDSGACVTQCPQTFVYNPTTFQLEHNFN AKYTYGAFCVKKCPHNFVVDSSSCVRAC PSSKMEVEENGIKMCKPCTDICPKACDG IGTGSLMSAQTVDSSNIDKFINCTKING NLIFLVTGIHGDPYNAIEAIDPEKLNVF RTVREITGFLNIQSWPPNMTDFSVFSNL VTIGGRVLYSGLSLLILKQQGITSLQFQ SLKEISAGNIYITDNSNLCYYHTINWTT LFSTINQRIVIRDNRKAENCTAEGMVCN HLCSSDGCWGPGPDQCLSCRRFSRGRIC IESCNLYDGEFREFENGSICVECDPQCE KMEDGLLTCHGPGPDNCTKCSHFKDGPN CVEKCPDGLQGANSFIFKYADPDRECHP CHPNCTQGCNGPTSHDCIYYPWTGHSTL PQHARTPLIAAGVIGGLFILVIVGLTFA VYVRRKSIKKKRALRRFLETELVEPLTP SGTAPNQAQLRILKETELKRVKVLGSGA FGTVYKGIWVPEGETVKIPVAIKILNET TGPKANVEFMDEALIMASMDHPHLVRLL GVCLSPTIQLVTQLMPHGCLLEYVHEHK DNIGSQLLLNWCVQIAKGMMYLEERRLV HRDLAARNVLVKSPNHVKITDFGLARLL EGDEKEYNADGGKMPIKWMALECIHYRK FTHQSDVWSYGVTIWELMTFGGKPYDGI PTREIPDLLEKGERLPQPPICTIDVYMV MVKCWMIDADSRPKFKELAAEFSRMARD PQRYLVIQGDDRMKLPSPNDSKFFQNLL DEEDLEDMMDAEEYLVPQAFNIPPPIYT SRARIDSNRSEIGHSPPPAYTPMSGNQF VYRDGGFAAEQGVSVPYRAPTSTIPEAP VAQGATAEIFDDSCCNGTLRKPVAPHVQ EDSSTQRYSADPTVFAPERSPRGELDEE GYMTPMRDKPKQEYLNPVEENPFVSRRK NGDLQALDNPEYHNASNGPPKAEDEYVN EPLYLNTFANTLGKAEYLKNNILSMPEK AKKAFDNPDYWNHSLPPRSTLQHPDYLQ EYSTKYFYKQNGRIRPIVAENPEYLSEF SLKPGTVLPPPPYRHRNTVV | |
| HLA-DPAI (SEQ ID NO: 30) | MRPEDRMFHIRAVILRALSLAFLLSLRG AGAIKADHVSTYAAFVQTHRPTGEFMFE FDEDEMFYVDLDKKETVWHLEEFGQAFS FEAQGGLANIAILNNLNTLIQRSNHTQ ATNDPPEVTVFPKEPVELGQPNTLICHI DKFFPPVLNVTWLCNGELVTEGVAESLF LPRTDYSFHKFHYLTFVPSAEDFYDCRV EHWGLDQPLLKHWEAQEPIQMPETTETV | |

TABLE 1-continued

Sequences of exemplary target proteins and associated binding agents

| Target Protein | Target Protein SEQ | Exemplary Binding Agent(s) |
|---|---|---|
| | | LCALGLVLGLVGIIVGTVLIIKSLRSGH |
| | | DPRAQGTL |
| | | HLA-DQA1 (SEQ ID NO: 31) |
| | | MILNKALMLGALALTTVMSPCGGEDIVA |
| | | DHVASYGVNLYQSYGPSGQYTHEFDGDE |
| | | QFYVDLGRKETVWCLPVLRQFRFDPQFA |
| | | LTNIAVLKHNLNSLIKRSNSTAATNEVP |
| | | EVTVFSKSPVTLGQPNILICLVDNIFPP |
| | | VVNITWLSNGHSVTEGVSETSFLSKSDH |
| | | SFFKISYLTLLPSAEESYDCKVEHWGLD |
| | | KPLLKHWEPEIPAPMSELTETVVCALGL |
| | | SVGLVGIVVGTVFIIRGLRSVGASRHQG |
| | | PL |
| | | HLA-DQA2 (SEQ ID NO: 32) |
| | | MILNKALLLGALALTAVMSPCGGEDIVA |
| | | DHVASYGVNFYQSHGPSGQYTHEFDGDE |
| | | EFYVDLETKETVWQLPMFSKFISFDPQS |
| | | ALRNMAVGKHTLEFMMRQSNSTAATNEV |
| | | PEVTVFSKFPVTLGQPNTLICLVDNIFP |
| | | PVVNITWLSNGHSVTEGVSETSFLSKSD |
| | | HSFFKISYLTFLPSADEIYDCKVEHWGL |
| | | DEPLLKHWEPEIPAPMSELTETLVCALG |
| | | LSVGLMGIVVGTVFIIQGLRSVGASRHQ |
| | | GLL |
| | | HLA-DQB1 (SEQ ID NO: 33) |
| | | MSWKKALRIPGGLRAATVTLMLAMLSTP |
| | | VAEGRDSPEDFVYQFKAMCYFTNGTERV |
| | | RYVTRYIYNREEYARFDSDVEVYRAVTP |
| | | LGPPDAEYWNSQKEVLERTRAELDTVCR |
| | | HNYQLELRTTLQRRVEPTVTISPSRTEA |
| | | LNHHNLLVCSVTDFYPAQIKVRWFRNDQ |
| | | EETTGVVSTPLIRNGDWTFQILVMLEMT |
| | | PQHGDVYTCHVEHPSLQNPITVEWRAQS |
| | | ESAQSKMLSGIGGFVLGLIFLGLGLIIH |
| | | HRSQKGLLH |
| | | HLA-DQB2 (SEQ ID NO: 34) |
| | | MSWKMALQIPGGFWAAAVTVMLVMLSTP |
| | | VAEARDFPKDFLVQFKGMCYFTNGTERV |
| | | RGVARYIYNREEYGRFDSDVGEFQAVTE |
| | | LGRSIEDWNNYKDFLEQERAAVDKVCRH |
| | | NYEAELRTTLQRQVEPTVTISPSRTEAL |
| | | NHHNLLVCSVTDFYPAQIKVRWFRNDQE |
| | | ETAGVVSTSLIRNGDWTFQILVMLEITP |
| | | QRGDIYTCQVEHPSLQSPITVEWRAQSE |
| | | SAQSKMLSGIGGFVLGLIFLGLGLIIRH |
| | | RGQKGPRGPPPAGLLH |
| | | HLADRA (SEQ ID NO: 35) |
| | | MAISGVPVLGFFIIAVLMSAQESWAIKE |
| | | EHVIIQAEFYLNPDQSGEFMFDFDGDEI |
| | | FHVDMAKKETVWRLEEFGRFASFEAQGA |
| | | LANIAVDKANLEIMTKRSNYTPITNVPP |
| | | EVTVLTNSPVELREPNVLICFIDKFTPP |
| | | VVNVTWLRNGKPVTTGVSETVFLPREDH |
| | | LFRKFHYLPFLPSTEDVYDCRVEHWGLD |
| | | EPLLKHWEFDAPSPLPETTENVVCALGL |
| | | TVGLVGIIIGTIFIIKGVRKSNAAERRG |
| | | PL |
| | | HLA-DRBI (SEQ ID NO: 36) |
| | | MVCLKLPGGSCMTALTVTLMVLSSPLAL |
| | | SGDTRPRFLWQPKRECHFFNGTERVRFL |
| | | DRYFYNQEESVRFDSDVGEFRAVTELGR |
| | | PDAEYWNSQKDILEQARAAVDTYCRHNY |
| | | GVVESFTVQRRVQPKVTVYPSKTQPLQH |
| | | HNLLVCSVSGFYPGSIEVRWFLNGQEEK |
| | | AGMVSTGLIQNGDWTFQTLVMLETVPRS |
| | | GEVYTCQVEHPSVTSPLTVEWRARSESA |
| | | QSKMLSGVGGFVLGLLFLGAGLFIYFRN |
| | | QKGHSGLQPTGFLS |
| | | HLA-DRB3 (SEQ ID NO: 37) |
| | | MVCLKLPGGSSLAALTVTLMVLSSRLAF |
| | | AGDTRPRFLELRKSECHFFNGTERVRYL |
| | | DRYFHNQEEFLRFDSDVGEYRAVTELGR |
| | | PVAESWNSQKDLLEQKRGRVDNYCRHNY |
| | | GVGESFTVQRRVHPQVTVYPAKTQPLQH |
| | | HNLLVCSVSGFYPGSIEVRWFRNGQEEK |
| | | AGVVSTGLIQNGDWTFQTLVMLETVPRS |

TABLE 1-continued

Sequences of exemplary target proteins and associated binding agents

| Target Protein Target Protein SEQ | Exemplary Binding Agent(s) |
| --- | --- |
| | GEVYTCQVEHPSVTSALTVEWRARSESA |
| | QSKMLSGVGGFVLGLLFLGAGLFIYFRN |
| | QKGHSGLQPTGFLS |
| | MIF (SEQ ID NO: 38) |
| | MPMFIVNTNVPRASVPDGFLSELTQQLA |
| | QATGKPPQYIAVHVVPDQLMAFGGSSEP |
| | CALCSLHSIGKIGGAQNRSYSKLLCGLL |
| | AERLRISPDRVYINYYDMNAANVGWNNS |
| | TFA |
| | AP2M1 (SEQ ID NO: 39) |
| | MIGGLFIYNHKGEVLISRVYRDDIGRNA |
| | VDAFRVNVIHARQQVRSPVTNIARTSFF |
| | HVKRSNIWLAAVTKQNVNAAMVFEFLYK |
| | MCDVMAAYFGKISEENIKNNFVLIYELL |
| | DEILDFGYPQNSETGALKTFITQQGIKS |
| | QHQTKEEQSQITSQVTGQIGWRREGIKY |
| | RRNELFLDVLESVNLLMSPQGQVLSAHV |
| | SGRVVMKSYLSGMPECKFGMNDKIVIEK |
| | QGKGTADETSKSGKQSIAIDDCTFHQCV |
| | RLSKFDSERSISFIPPDGEFELMRYRTT |
| | KDIILPFRVIPLVREVGRTKLEVKVVIK |
| | SNFKPSLLAQKIEVRIPTPLNTSGVQVI |
| | CMKGKAKYKASENAIVWKIKRMAGMKES |
| | QISAEIELLPTNDKKKWARPPISMNFEV |
| | PFAPSGLKVRYLKVFEPKLNYSDHDVIK |
| | WVRYIGRSGIYETRC |
| | AR (SEQ ID NO: 40) |
| | MEVQLGLGRVYPRPPSKTYRGAFQNLFQ |
| | SVREVIQNPGPRHPEAASAAPPGASLLL |
| | LQQQQQQQQQQQQQQQQQQQQQQQETSP |
| | RQQQQQQGEDGSPQAHRRGPTGYLVLDE |
| | EQQPSQPQSALECHPERGCVPEPGAAVA |
| | ASKGLPQQLPAPPDEDDSAAPSTLSLLG |
| | PTFPGLSSCSADLKDILSEASTMQLLQQ |
| | QQQEAVSEGSSSGRAREASGAPTSSKDN |
| | YLGGTSTISDNAKELCKAVSVSMGLGVE |
| | ALEHLSPGEQLRGDCMYAPLLGVPPAVR |
| | PTPCAPLAECKGSLLDDSAGKSTEDTAE |
| | YSPFKGGYTKGLEGESLGCSGSAAAGSS |
| | GTLELPSTLSLYKSGALDEAAAYQSRDY |
| | YNFPLALAGPPPPPPPPHPHARIKLENP |
| | LDYGSAWAAAAAQCRYGDLASLHGAGAA |
| | GPGSGSPSAAASSSWHTLFTAEEGQLYG |
| | PCGGGGGGGGGGGGGGGGGGGGGGGGEAG |
| | AVAPYGYTRPPQGLAGQESDFTAPDVWY |
| | PGGMVSRVPYPSPTCVKSEMGPWMDSYS |
| | GPYGDMRLETARDHVLPIDYYFPPQKTC |
| | LICGDEASGCHYGALTCGSCKVFFKRAA |
| | EGKQKYLCASRNDCTIDKFRRKNCPSCR |
| | LRKCYEAGMTLGARKLKKLGNLKLQEEG |
| | EASSTTSPTEETTQKLTVSHIEGYECQP |
| | IFLNVLEAIEPGVVCAGHDNNQPDSFAA |
| | LLSSLNELGERQLVHVVKWAKALPGFRN |
| | LHVDDQMAVIQYSWMGLMVFAMGWRSFT |
| | NVNSRMLYFAPDLVFNEYRMHKSRMYSQ |
| | CVRMRHLSQEFGWLQITPQEFLCMKALL |
| | LFSIIPVDGLKNQKFFDELRMNYIKELD |
| | RIIACKRKNPTSCSRRFYQLTKLLDSVQ |
| | PIARELHQFTFDLLIKSHMVSVDFPEMM |
| | AEIISVQVPKILSGKVKPIYFHTQ |
| | CD44 (SEQ ID NO: 41) |
| | MDKFWWHAAWGLCLVPLSLAQIDLNITC |
| | RFAGVFHVEKNGRYSISRTEAADLCKAF |
| | NSTLPTMAQMEKALSIGFETCRYGFIEG |
| | HVVIPRIHPNSICAANNTGVYILTSNTS |
| | QYDTYCFNASAPPEEDCTSVTDLPNAFD |
| | GPITITIVNRDGTRYVQKGEYRTNPEDI |
| | YPSNPTDDDVSSGSSSERSSTSGGYIFY |
| | TFSTVHPIPDEDSPWITDSTDRIPATTL |
| | MSTSATATETATKRQETWDWFSWLFLPS |
| | ESKNHLHTTTQMAGTSSNTISAGWEPNE |
| | ENEDERDRHLSFSGSGIDDDEDFISSTI |
| | STTPRAFDHTKQNQDWTQWNPSHSNPEV |
| | LLQTTTRMTDVDRNGTTAYEGNWNPEAH |
| | PPLIHHEHHEEEETPHSTSTIQATPSST |
| | TEETATQKEQWFGNRWHEGYRQTPKEDS |

TABLE 1-continued

Sequences of exemplary target proteins and associated binding agents

| Target Protein Target Protein SEQ | Exemplary Binding Agent(s) |
| --- | --- |
| | HSTTGTAAASAHTSHPMQGRTTPSPEDS |
| | SWTDFFNPISHPMGRGHQAGRRMDMDSS |
| | HSITLQPTANPNTGLVEDLDRTGPLSMT |
| | TQQSNSQSFSTSHEGLEEDKDHPTTSTL |
| | TSSNRNDVTGGRRDPNHSEGSTTLLEGY |
| | TSHYPHTKESRTFIPVTSAKTGSFGVTA |
| | VTVGDSNSNVNRSLSGDQDTFHPSGGSH |
| | TTHGSESDGHSHGSQEGGANTTSGPIRT |
| | PQIPEWLIILASLLALALILAVCIAVNS |
| | RRRCGQKKKLVINSGNGAVEDRKPSGLN |
| | GEASKSQEMVHLVNKESSETPDQFMTAD |
| | ETRNLQNVDMKIGV |
| | CTSB (SEQ ID NO: 42) |
| | MWQLWASLCCLLVLANARSRPSFHPLSD |
| | ELVNYVNKRNTTWQAGHNFYNVDMSYLK |
| | RLCGTFLGGPKPPQRVMFTEDLKLPASF |
| | DAREQWPQCPTIKEIRDQGSCGSCWAFG |
| | AVEAISDRICIHTNAHVSVEVSAEDLLT |
| | CCGSMCGDGCNGGYPAEAWNFWTRKGLV |
| | SGGLYESHVGCRPYSIPPCEHHVNGSRP |
| | PCTGEGDTPKCSKICEPGYSPTYKQDKH |
| | YGYNSYSVSNSEKDIMAEIYKNGPVEGA |
| | FSVYSDFLLYKSGVYQHVTGEMMGGHAI |
| | RILGWGVENGTPYWLVANSWNTDWGDNG |
| | FFKILRGQDHCGIESEVVAGIPRTDQYW |
| | EKI |
| | CTSD (SEQ ID NO: 43) |
| | MQPSSLLPLALCLLAAPASALVRIPLHK |
| | FTSIRRTMSEVGGSVEDLIAKGPVSKYS |
| | QAVPAVTEGPIPEVLKNYMDAQYYGEIG |
| | IGTPPQCFTVVFDTGSSNLWVPSIHCKL |
| | LDIACWIHHKYNSDKSSTYVKNGTSFDI |
| | HYGSGSLSGYLSQDTVSVPCQSASSASA |
| | LGGVKVERQVFGEATKQPGITFIAAKFD |
| | GILGMAYPRISVNNVLPVFDNLMQQKLV |
| | DQNIFSFYLSRDPDAQPGGELMLGGTDS |
| | KYYKGSLSYLNVTRKAYWQVHLDQVEVA |
| | SGLTLCKEGCEAIVDTGTSLMVGPVDEV |
| | RELQKAIGAVPLIQGEYMIPCEKVSTLP |
| | AITLKLGGKGYKLSPEDYTLKVSQAGKT |
| | LCLSGFMGMDIPPPSGPLWILGDVFIGR |
| | YYTVFDRDNNRVGFAEAARL |
| | CTSH (SEQ ID NO: 44) |
| | MWATLPLLCAGAWLLGVPVCGAAELCVN |
| | SLEKFHFKSWMSKHRKTYSTEEYHHRLQ |
| | TFASNWRKINAHNNGNHTFKMALNQFSD |
| | MSFAEIKHKYLWSEPQNCSATKSNYLRG |
| | TGPYPPSVDWRKKGNFVSPVKNQGACGS |
| | CWTFSTTGALESAIAIATGKMLSLAEQQ |
| | LVDCAQDFNNHGCQGGLPSQAFEYILYN |
| | KGIMGEDTYPYQGKDGYCKFQPGKAIGF |
| | VKDVANITIYDEEAMVEAVALYNPVSFA |
| | FEVTQDFMMYRTGIYSSTSCHKTPDKVN |
| | HAVLAVGYGEKNGIPYWIVKNSWGPQWG |
| | MNGYFLIERGKNMCGLAACASYPIPLV |
| | CTSS (SEQ ID NO: 45) |
| | MKRLVCVLLVCSSAVAQLHKDPTLDHHW |
| | HLWKKTYGKQYKEKNEEAVRRLIWEKNL |
| | KFVMLHNLEHSMGMHSYDLGMNHLGDMT |
| | SEEVMSLMSSLRVPSQWQRNITYKSNPN |
| | RILPDSVDWREKGCVTEVKYQGSCGACW |
| | AFSAVGALEAQLKLKTGKLVSLSAQNLV |
| | DCSTEKYGNKGCNGGFMTTAFQYIIDNK |
| | GIDSDASYPYKAMDQKCQYDSKYRAATC |
| | SKYTELPYGREDVLKEAVANKGPVSVGV |
| | DARHPSFFLYRSGVYYEPSCTQNVNHGV |
| | LVVGYGDLNGKEYWLVKNSWGHNFGEEG |
| | YIRMARNKGNHCGIASFPSYPEI |
| | CTSV (SEQ ID NO: 46) |
| | MNLSLVLAAFCLGIASAVPKFDQNLDTK |
| | WYQWKATHRRLYGANEEGWRRAVWEKNM |
| | KMIELHNGEYSQGKHGFTMAMNAFGDMT |
| | NEEFRQMMGCFRNQKFRKGKVFREPLFL |
| | DLPKSVDWRKKGYVTPVKNQKQCGSCWA |
| | FSATGALEGQMFRKTGKLVSLSEQNLVD |
| | CSRPQGNQGCNGGFMARAFQYVKENGGL |

TABLE 1-continued

| Sequences of exemplary target proteins and associated binding agents | | |
| --- | --- | --- |
| Target Protein | Target Protein SEQ | Exemplary Binding Agent(s) |
| | | DSEESYPYVAVDEICKYRPENSVANDTG |
| | | FTVVAPGKEKALMKAVATVGPISVAMDA |
| | | GHSSFQFYKSGIYFEPDCSSKNLDHGVL |
| | | VVGYGFEGANSNNSKYWLVKNSWGPEWG |
| | | SNGYVKIAKDKNNHCGIATAASYPNV |
| | | LGMN (SEQ ID NO: 47) |
| | | MVWKVAVFLSVALGIGAVPIDDPEDGGK |
| | | HWVVIVAGSNGWYNYRHQADACHAYQII |
| | | HRNGIPDEQIVVMMYDDIAYSEDNPTPG |
| | | IVINRPNGTDVYQGVPKDYTGEDVTPQN |
| | | FLAVLRGDAEAVKGIGSGKVLKSGPQDH |
| | | VFIYFTDHGSTGILVFPNEDLHVKDLNE |
| | | TIHYMYKHKMYRKMVFYPEACESGSMMN |
| | | HLPDNINVYATTAANPRESSYACYYDEK |
| | | RSTYLGDWYSVNWMEDSDVEDLTKETLH |
| | | KQYHLVKSHTNTSHVMQYGNKTISTMKV |
| | | MQFQGMKRKASSPVPLPPVTHLDLTPSP |
| | | DVPLTIMKRKLMNTNDLEESRQLTEEIQ |
| | | RHLDARHLIEKSVRKIVSLLAASEAEVE |
| | | QLLSERAPLTGHSCYPEALLHFRTHCFN |
| | | WHSPTYEYALRHLYVLVNLCEKPYPLHR |
| | | PKLSMDHVCLGHY |
| | | PNP (SEQ ID NO: 48) |
| | | MENGYTYEDYKNTAEWLLSHTKHRPQVA |
| | | IICGSGLGGLTDKLTQAQIFDYGEIPNF |
| | | PRSTVPGHAGRLVFGFLNGRACVMMQGR |
| | | FHMYEGYPLWKVTFPVRVFHLLGVDTLV |
| | | VTNAAGGLNPKFEVGDIMLIRDHINLPG |
| | | FSGQNPLRGPNDERFGDRFPAMSDAYDR |
| | | TMRQRALSTWKQMGEQRELQEGTYVMVA |
| | | GPSFETVAECRVLQKLGADAVGMSTVPE |
| | | VIVARHCGLRVFGFSLITNKVIMDYESL |
| | | EKANHEEVLAAGKQAAQKLEQFVSILMA |
| | | SIPLPDKAS |
| | | PPARA (SEQ ID NO: 49) |
| | | MVDTESPLCPLSPLEAGDLESPLSEEFL |
| | | QEMGNIQEISQSIGEDSSGSFGFTEYQY |
| | | LGSCPGSDGSVITDTLSPASSPSSVTYP |
| | | VVPGSVDESPSGALNIECRICGDKASGY |
| | | HYGVHACEGCKGFFRRTIRLKLVYDKCD |
| | | RSCKIQKKNRNKCQYCRFHKCLSVGMSH |
| | | NAIRFGRMPRSEKAKLKAEILTCEHDIE |
| | | DSETADLKSLAKRIYEAYLKNFNMNKVK |
| | | ARVILSGKASNNPPFVIHDMETLCMAEK |
| | | TLVAKLVANGIQNKEAEVRIFHCCQCTS |
| | | VETVTELTEFAKAIPGFANLDLNDQVTL |
| | | LKYGVYEAIFAMLSSVMNKDGMLVAYGN |
| | | GFITREFLKSLRKPFCDIMEPKFDFAMK |
| | | FNALELDDSDISLFVAAIICCGDRPGLL |
| | | NVGHIEKMQEGIVHVLRLHLQSNHPDDI |
| | | FLFPKLLQKMADLRQLVTEHAQLVQIIK |
| | | KTESDAALHPLLQEIYRDMY |
| HLA-DOA | malraglvlg fhtlmtllsp | HLADOB (SEQ ID NO: 50) |
| | qeagatkadh mgsygpafyq | MGSGWVPWVVALLVNLTRLDSSMTQGTD |
| | sygasgqfth efdeeqlfsv | SPEDFVIQAKADCYFTNGTEKVQFVVRF |
| | dlkkseavwr lpefgdfarf | IFNLEEYVRFDSDVGMFVALTKLGQPDA |
| | dpqgglagia aikahldilv | EQWNSRLDLLERSRQAVDGVCRHNYRLG |
| | ersnrsrain vpprvtvlpk | APFTVGRKVQPEVTVYPERTPLLHQHNL |
| | srvelgqpni licivdnifp | LHCSVTGFYPGDIKIKWFLNGQEERAGV |
| | pvinitwlrn gqtvtegvaq | MSTGPIRNGDWTFQTVVMLEMTPELGHV |
| | tsfysqpdhl frkfhylpfv | YTCLVDHSSLLSPVSVEWRAQSEYSWRK |
| | psaedvydcq vehwgldapl | MLSGIAAFLLGLIFLLVGIVIQLRAQKG |
| | lrhwelqvpi pppdametlv | YVRTQMSGNEVSRAVLLPQSC |
| | calglaiglv gflvgtvlii | HLA-DPAI (SEQ ID NO: 51) |
| | mgtyvssvpr (SEQ ID NO: 6) | MRPEDRMFHIRAVILRALSLAFLLSLRG |
| | | AGAIKADHVSTYAAFVQTHRPTGEFMFE |
| | | FDEDEMFYVDLDKKETVWHLEEFGQAFS |
| | | FEAQGGLANIAILNNNLNTLIQRSNHTQ |
| | | ATNDPPEVTVFPKEPVELGQPNTLICHI |
| | | DKFFPPVLNVTWLCNGELVTEGVAESLF |
| | | LPRTDYSFHKFHYLTFVPSAEDFYDCRV |
| | | EHWGLDQPLLKHWEAQEPIQMPETTETV |
| | | LCALGLVLGLVGIIVGTVLIIKSLRSGH |
| | | DPRAQGTL |
| | | HLA-DQA1 (SEQ ID NO: 52) |

TABLE 1-continued

| Sequences of exemplary target proteins and associated binding agents | | |
| --- | --- | --- |
| Target Protein | Target Protein SEQ | Exemplary Binding Agent(s) |
| | | MILNKALMLGALALTTVMSPCGGEDIVA DHVASYGVNLYQSYGPSGQYTHEFDGDE QFYVDLGRKETVWCLPVLRQFRFDPQFA LTNIAVLKHNLNSLIKRSNSTAATNEVP EVTVFSKSPVTLGQPNILICLVDNIFPP VVNITWLSNGHSVTEGVSETSFLSKSDH SFFKISYLTLLPSAEESYDCKVEHWGLD KPLLKHWEPEIPAPMSELTETVVCALGL SVGLVGIVVGTVFIIRGLRSVGASRHQG PL |
| | | HLA-DQA2 (SEQ ID NO: 53) MILNKALMLGALALTTVMSPCGGEDIVA DHVASYGVNLYQSYGPSGQYTHEFDGDE QFYVDLGRKETVWCLPVLRQFRFDPQFA LTNIAVLKHNLNSLIKRSNSTAATNEVP EVTVFSKSPVTLGQPNILICLVDNIFPP VVNITWLSNGHSVTEGVSETSFLSKSDH SFFKISYLTLLPSAEESYDCKVEHWGLD KPLLKHWEPEIPAPMSELTETVVCALGL SVGLVGIVVGTVFIIRGLRSVGASRHQG PL |
| | | HLA-DQB1 (SEQ ID NO: 54) MSWKKALRIPGGLRAATVTLMLAMLSTP VAEGRDSPEDFVYQFKAMCYFTNGTERV RYVTRYIYNREEYARFDSDVEVYRAVTP LGPPDAEYWNSQKEVLERTRAELDTVCR HNYQLELRTTLQRRVEPTVTISPSRTEA LNHHNLLVCSVTDFYPAQIKVRWFRNDQ EETTGVVSTPLIRNGDWTFQILVMLEMT PQHGDVYTCHVEHPSLQNPITVEWRAQS ESAQSKMLSGIGGFVLGLIFLGLGLIIH HRSQKGLLH |
| | | HLA-DQB2 (SEQ ID NO: 55) MSWKMALQIPGGFWAAAVTVMLVMLSTP VAEARDFPKDFLVQFKGMCYFTNGTERV RGVARYIYNREEYGRFDSDVGEFQAVTE LGRSIEDWNNYKDFLEQERAAVDKVCRH NYEAELRTTLQRQVEPTVTISPSRTEAL NHHNLLVCSVTDFYPAQIKVRWFRNDQE ETAGVVSTSLIRNGDWTFQILVMLEITP QRGDIYTCQVEHPSLQSPITVEWRAQSE SAQSKMLSGIGGFVLGLIFLGLGLIIRH RGQKGPRGPPPAGLLH |
| | | HLADRA (SEQ ID NO: 56) MAISGVPVLGFFIIAVLMSAQESWAIKE EHVIIQAEFYLNPDQSGEFMFDFDGDEI FHVDMAKKETVWRLEEFGRFASFEAQGA LANIAVDKANLEIMTKRSNYTPITNVPP EVTVLTNSPVELREPNVLICFIDKFTPP VVNVTWLRNGKPVTTGVSETVFLPREDH LFRKFHYLPFLPSTEDVYDCRVEHWGLD EPLLKHWEFDAPSPLPETTENVVCALGL TVGLVGIIIGTIFIIKGVRKSNAAERRG PL |
| | | HLA-DRBI (SEQ ID NO: 57) MAISGVPVLGFFIIAVLMSAQESWAIKE EHVIIQAEFYLNPDQSGEFMFDFDGDEI FHVDMAKKETVWRLEEFGRFASFEAQGA LANIAVDKANLEIMTKRSNYTPITNVPP EVTVLTNSPVELREPNVLICFIDKFTPP VVNVTWLRNGKPVTTGVSETVFLPREDH LFRKFHYLPFLPSTEDVYDCRVEHWGLD EPLLKHWEFDAPSPLPETTENVVCALGL TVGLVGIIIGTIFIIKGVRKSNAAERRG PL |
| | | HLA-DRB3 (SEQ ID NO: 58) MVCLKLPGGSSLAALTVTLMVLSSRLAF AGDTRPRFLELRKSECHFFNGTERVRYL DRYFHNQEEFLRFDSDVGEYRAVTELGR PVAESWNSQKDLLEQKRGRVDNYCRHNY GVGESFTVQRRVHPQVTVYPAKTQPLQH HNLLVCSVSGFYPGSIEVRWFRNGQEEK AGVVSTGLIQNGDWTFQTLVMLETVPRS GEVYTCQVEHPSVTSALTVEWRARSESA QSKMLSGVGGFVLGLLFLGAGLFIYFRN QKGHSGLQPTGFLS |

TABLE 1-continued

Sequences of exemplary target proteins and associated binding agents

| Target Protein | Target Protein SEQ | Exemplary Binding Agent(s) |
| --- | --- | --- |
| | | ITGA2 (SEQ ID NO: 59)<br>MGPERTGAAPLPLLLVLALSQGILNCCL<br>AYNVGLPEAKIFSGPSSEQFGYAVQQFI<br>NPKGNWLLVGSPWSGFPENRMGDVYKCP<br>VDLSTATCEKLNLQTSTSIPNVTEMKTN<br>MSLGLILTRNMGTGGFLTCGPLWAQQCG<br>NQYYTTGVCSDISPDFQLSASFSPATQP<br>CPSLIDVVVVCDESNSIYPWDAVKNFLE<br>KFVQGLDIGPTKTQVGLIQYANNPRVVF<br>NLNTYKTKEEMIVATSQTSQYGGDLTNT<br>FGAIQYARKYAYSAASGGRRSATKVMVV<br>VTDGESHDGSMLKAVIDQCNHDNILRFG<br>IAVLGYLNRNALDTKNLIKEIKAIASIP<br>TERYFFNVSDEAALLEKAGTLGEQIFSI<br>EGTVQGGDNFQMEMSQVGFSADYSSQND<br>ILMLGAVGAFGWSGTIVQKTSHGHLIFP<br>KQAFDQILQDRNHSSYLGYSVAAISTGE<br>STHFVAGAPRANYTGQIVLYSVNENGNI<br>TVIQAHRGDQIGSYFGSVLCSVDVDKDT<br>ITDVLLVGAPMYMSDLKKEEGRVYLFTI<br>KKGILGQHQFLEGPEGIENTRFGSAIAA<br>LSDINMDGFNDVIVGSPLENQNSGAVYI<br>YNGHQGTIRTKYSQKILGSDGAFRSHLQ<br>YFGRSLDGYGDLNGDSITDVSIGAFGQV<br>VQLWSQSIADVAIEASFTPEKITLVNKN<br>AQIILKLCFSAKFRPTKQNNQVAIVYNI<br>TLDADGFSSRVTSRGLFKENNERCLQKN<br>MVVNQAQSCPEHIIYIQEPSDVVNSLDL<br>RVDISLENPGTSPALEAYSETAKVFSIP<br>FHKDCGEDGLCISDLVLDVRQIPAAQEQ<br>PFIVSNQNKRLTFSVTLKNKRESAYNTG<br>IVVDFSENLFFASFSLPVDGTEVTCQVA<br>ASQKSVACDVGYPALKREQQVTFTINFD<br>FNLQNLQNQASLSFQALSESQEENKADN<br>LVNLKIPLLYDAEIHLTRSTNINFYEIS<br>SDGNVPSIVHSFEDVGPKFIFSLKVTTG<br>SVPVSMATVIIHIPQYTKEKNPLMYLTG<br>VQTDKAGDISCNADINPLKIGQTSSSVS<br>FKSENFRHTKELNCRTASCSNVTCWLKD<br>VHMKGEYFVNVTTRIWNGTFASSTFQTV<br>QLTAAAEINTYNPEIYVIEDNTVTIPLM<br>IMKPDEKAEVPTGVIIGSIIAGILLLLA<br>LVAILWKLGFFKRKYEKMTKNPDEIDET<br>TELSS<br>MMPI (SEQ ID NO: 60)<br>MHSFPPLLLLLFWGVVSHSFPATLETQE<br>QDVDLVQKYLEKYYNLKNDGRQVEKRRN<br>SGPVVEKLKQMQEFFGLKVTGKPDAETL<br>KVMKQPRCGVPDVAQFVLTEGNPRWEQT<br>HLTYRIENYTPDLPRADVDHAIEKAFQL<br>WSNVTPLTFTKVSEGQADIMISFVRGDH<br>RDNSPFDGPGGNLAHAFQPGPGIGGDAH<br>FDEDERWTNNFREYNLHRVAAHELGHSL<br>GLSHSTDIGALMYPSYTFSGDVQLAQDD<br>IDGIQAIYGRSQNPVQPIGPQTPKACDS<br>KLTFDAITTIRGEVMFFKDRFYMRTNPF<br>YPEVELNFISVFWPQLPNGLEAAYEFAD<br>RDEVRFFKGNKYWAVQGQNVLHGYPKDI<br>YSSFGFPRTVKHIDAALSEENTGKTYFF<br>VANKYWRYDEYKRSMDPGYPKMIAHDFP<br>GIGHKVDAVFMKDGFFYFFHGTRQYKFD<br>PKTKRILTLQKANSWFNCRKN |
| VLDLR | Isoform a (SEQ ID NO: 7)<br>mgtsalwalw lllalcwapr<br>esgatgtgrk akcepsqfqc<br>tngrcitllw kcdgdedcvd<br>gsdekncvkk tcaesdfvcn<br>ngqcvpsrwk cdgdpdcedg<br>sdespeqchm rtcriheisc<br>gahstqcipv swrcdgdendc<br>dsgedeencg nitcspdeft<br>cssgrcisrn fvcngqddcs<br>dgsdeldcap ptcgahefqc<br>stsscipisw vcdddadcsd<br>qsdesleqcg rqpvihtkcp | APOE (SEQ ID NO: 61)<br>MKVLWAALLVTFLAGCQAKVEQAVETEP<br>EPELRQQTEWQSGQRWELALGRFWDYLR<br>WVQTLSEQVQEELLSSQVTQELRALMDE<br>TMKELKAYKSELEEQLTPVAEETRARLS<br>KELQAAQARLGADMEDVCGRLVQYRGEV<br>QAMLGQSTEELRVRLASHLRKLRKRLLR<br>DADDLQKRLAVYQAGAREGAERGLSAIR<br>ERLGPLVEQGRVRAATVGSLAGQPLQER<br>AQAWGERLRARMEEMGSRTRDRLDEVKE<br>QVAEVRAKLEEQAQQIRLQAEAFQARLK<br>SWFEPLVEDMQRQWAGLVEKVQAAVGTS<br>AAPVPSDNH |

TABLE 1-continued

| Sequences of exemplary target proteins and associated binding agents | | |
|---|---|---|
| Target Protein | Target Protein SEQ | Exemplary Binding Agent(s) |

| | | |
|---|---|---|
| aseiqcgsge cihkkwrcdg | | CLU (SEQ ID NO: 62) |
| dpdckdgsde vncpsrtcrp | | MMKTLLLFVGLLLTWESGQVLGDQTVSD |
| dqfecedgsc ihgsrqcngi | | NELQEMSNQGSKYVNKEIQNAVNGVKQI |
| rdcvdgsdev ncknvnqclg | | KTLIEKTNEERKTLLSNLEEAKKKKEDA |
| pgkfkcrsge cidiskvcnq | | LNETRESETKLKELPGVCNETMMALWEE |
| eqdcrdwsde plkechinec | | CKPCLKQTCMKFYARVCRSGSGLVGRQL |
| Ivnnggcshi ckdlvigyec | | EEFLNQSSPFYFWMNGDRIDSLLENDRQ |
| dcaagfelid rktcgdidec | | QTHMLDVMQDHFSRASSIIDELFQDRFF |
| qnpgicsqic inlkggykce | | TREPQDTYHYLPFSLPHRRPHFFFPKSR |
| csrgyqmdla tgvckavgke | | IVRSLMPFSPYEPLNFHAMFQPFLEMIH |
| psliftnrrd irkiglerke | | EAQQAMDIHFHSPAFQHPPTEFIREGDD |
| yiqlveqlrn tvaldadiaa | | DRTVCREIRHNSTGCLRMKDQCDKCREI |
| qklfwadlsq kaifsasidd | | LSVDCSTNNPSQAKLRRELDESLQVAER |
| kvgrhvkmid nvynpaaiav | | LTRKYNELLKSYQWKMLNTSSLLEQLNE |
| dwvyktiywt daasktisva | | QFNWVSRLANLTQGEDQYYLRVTTVASH |
| tldgtkrkfl fnsdlrepas | | TSDSDVPSGVTEVWKLFDSDPITVTVP |
| iavdplsgfv ywsdwgepak | | VEVSRKNPKFMETVAEKALQEYRKKHRE |
| iekagmngfd rrplvtadiq | | E |
| wpngitldli ksrlywldsk | | ITGA3 (SEQ ID NO: 63) |
| ihmlssvdln gqdrrivlks | | MGPGPSRAPRAPRLMLCALALMVAAGGC |
| leflahplal tifedrvywi | | VVSAFNLDTRFLVVKEAGNPGSLFGYSV |
| dgeneavyga nkftgselat | | ALHRQTERQQRYLLLAGAPRELAVPDGY |
| Ivnnlndaqd iivyhelvqp | | TNRTGAVYLCPLTAHKDDCERMNITVKN |
| sgknwceedm enggceylcl | | DPGHHIIEDMWLGVTVASQGPAGRVLVC |
| papqindhsp kytcscpsgy | | AHRYTQVLWSGSEDQRRMVGKCYVRGND |
| nveengrdcq stattvtyse | | LELDSSDDWQTYHNEMCNSNTDYLETGM |
| tkdtntteis atsglvpggi | | CQLGTSGGFTQNTVYFGAPGAYNWKGNS |
| nvttavsevs vppkgtsaaw | | YMIQRKEWDLSEYSYKDPEDQGNLYIGY |
| ailplllvm aavggylmwr | | TMQVGSFILHPKNITIVTGAPRHRHMGA |
| nwqhknmksm nfdnpvylkt | | VFLLSQEAGGDLRRRQVLEGSQVGAYFG |
| teedlsidig rhsasvghty | | SAIALADLNNDGWQDLLVGAPYYFERKE |
| paisvvstdd dla | | EVGGAIYVFMNQAGTSFPAHPSLLLHGP |
| Isoform b (SEQ ID NO: 8) | | SGSAFGLSVASIGDINQDGFQDIAVGAP |
| mgtsalwalw lllalcwapr | | FEGLGKVYIYHSSSKGLLRQPQQVIHGE |
| esgatgtgrk akcepsqfqc | | KLGLPGLATFGYSLSGQMDVDENFYPDL |
| tngrcitllw kcdgdedcvd | | LVGSLSDHIVLLRARPVINIVHKTLVPR |
| gsdekncvkk tcaesdfvcn | | PAVLDPALCTATSCVQVELCFAYNQSAG |
| ngqcvpsrwk cdgdpdcedg | | NPNYRRNITLAYTLEADRDRRPPRLRFA |
| sdespeqchm rtcriheisc | | GSESAVFHGFFSMPEMRCQKLELLLMDN |
| gahstqcipv swrcdgendc | | LRDKLRPIIISMNYSLPLRMPDRPRLGL |
| dsgedeencg nitcspdeft | | RSLDAYPILNQAQALENHTEVQFQKECG |
| cssgrcisrn fvcnggddcs | | PDNKCESNLQMRAAFVSEQQQKLSRLQY |
| dgsdeldcap ptcgahefqc | | SRDVRKLLLSINVTNTRTSERSGEDAHE |
| stsscipisw vcdddadcsd | | ALLTLVVPPALLLSSVRPPGACQANETI |
| qsdesleqcg rqpvihtkcp | | FCELGNPFKRNQRMELLIAFEVIGVTLH |
| aseiqcgsge cihkkwrcdg | | TRDLQVQLQLSTSSHQDNLWPMILTLLV |
| dpdckdgsde vncpsrtcrp | | DYTLQTSLSMVNHRLQSFFGGTVMGESG |
| dqfecedgsc ihgsrqcngi | | MKTVEDVGSPLKYEFQVGPMGEGLVGLG |
| rdcvdgsdev ncknvnqclg | | TLVLGLEWPYEVSNGKWLLYPTEITVHG |
| pgkfkcrsge cidiskvcnq | | NGSWPCRPPGDLINPLNLTLSDPGDRPS |
| eqdcrdwsde plkechinec | | SPQRRRRQLDPGGGQGPPPVTLAAAKKA |
| Ivnnggcshi ckdlvigyec | | |
| dcaagfelid rktcgdidec | | KSETVLTCATGRAHCVWLECPIPDAPVV |
| qnpgicsqic inlkggykce | | TNVTVKARVWNSTFIEDYRDFDRVRVNG |
| csrgyqmdla tgvckavgke | | WATLFLRTSIPTINMENKTTWFSVDIDS |
| psliftnrrd irkiglerke | | ELVEELPAEIELWLVLVAVGGAGLLLLGL |
| yiqlveqlrn tvaldadiaa | | IILLLWKCGFFKRARTRALYEAKRQKAE |
| qklfwadlsq kaifsasidd | | MKSQPSETERLTDDY |
| kvgrhvkmid nvynpaaiav | | ITGBI (SEQ ID NO: 64) |
| dwvyktiywt daasktisva | | MNLQPIFWIGLISSVCCVFAQTDENRCL |
| tldgtkrkfl fnsdlrepas | | KANAKSCGECIQAGPNCGWCTNSTFLQE |
| iavdplsgfv ywsdwgepak | | GMPTSARCDDLEALKKKGCPPDDIENPR |
| iekagmngfd rrplvtadiq | | GSKDIKKNKNVTNRSKGTAEKLKPEDIT |
| wpngitldli ksrlywldsk | | QIQPQQLVLRLRSGEPQTFTLKFKRAED |
| ihmlssvdln gqdrrivlks | | YPIDLYYLMDLSYSMKDDLENVKSLGTD |
| leflahplal tifedrvywi | | LMNEMRRITSDFRIGFGSFVEKTVMPYI |
| dgeneavyga nkftgselat | | STTPAKLRNPCTSEQNCTSPFSYKNVLS |
| Ivnnlndaqd iivyhelvqp | | LTNKGEVFNELVGKQRISGNLDSPEGGF |
| sgknwceedm enggceylcl | | DAIMQVAVCGSLIGWRNVTRLLVFSTDA |
| papqindhsp kytcscpsgy | | GFHFAGDGKLGGIVLPNDGQCHLENNMY |
| nveengrdcq rinvttavse | | TMSHYYDYPSIAHLVQKLSENNIQTIFA |
| vsvppkgtsa awailpllll | | VTEEFQPVYKELKNLIPKSAVGTLSANS |
| vmaavggylm wrnwqhknmk | | SNVIQLIIDAYNSLSSEVILENGKLSEG |
| smnfdnpvyl ktteedlsid | | VTISYKSYCKNGVNGTGENGRKCSNISI |
| igrhsasvgh typaisvvst dddla | | GDEVQFEISITSNKCPKKDSDSFKIRPL |
| Isoform c (SEQ ID NO: 9) | | GFTEEVEVILQYICECECQSEGIPESPK |

TABLE 1-continued

Sequences of exemplary target proteins and associated binding agents

| Target Protein | Target Protein SEQ | Exemplary Binding Agent(s) |
|---|---|---|
| | mgtsalwalw lllalcwapr | CHEGNGTFECGACRCNEGRVGRHCECST |
| | esgatgtgrk akcepsqfqc | DEVNSEDMDAYCRKENSSEICSNNGECV |
| | tngrcitllw kcdgdedcvd | CGQCVCRKRDNTNEIYSGKFCECDNFNC |
| | gsdekncvkk tcaesdfvcn | DRSNGLICGGNGVCKCRVCECNPNYTGS |
| | ngqcvpsrwk cdgdpdcedg | ACDCSLDTSTCEASNGQICNGRGICECG |
| | sdespeqcrn itcspdeftc | VCKCTDPKFQGQTCEMCQTCLGVCAEHK |
| | ssgrcisrnf vcngqddcsd | ECVQCRAFNKGEKKDTCTQECSYFNITK |
| | gsdeldcapp tcgahefqcs | VESRDKLPQPVQPDPVSHCKEKDVDDCW |
| | tsscipiswv cdddadcsdq | FYFTYSVNGNNEVMVHVVENPECPTGPD |
| | sdesleqcgr qpvihtkcpa | IIPIVAGVVAGIVLIGLALLLIWKLLMI |
| | seiqcgsgec ihkkwrcdgd | IHDRREFAKFEKEKMNAKWDTGEN |
| | pdckdgsdev ncpsrtcrpd | PIYKSAVTTVVNPKYEGK |
| | qfecedgsci hgsrqcngir | LPL (SEQ ID NO: 65) |
| | dcvdgsdevn cknvnqclgp | MESKALLVLTLAVWLQSLTASRGGVAAA |
| | gkfkcrsgec idiskvcnqe | DQRRDFIDIESKFALRTPEDTAEDTCHL |
| | qdcrdwsdep lkechinecl | IPGVAESVATCHFNHSSKTFMVIHGWTV |
| | vnnggcshic kdlvigyecd | TGMYESWVPKLVAALYKREPDSNVIVVD |
| | caagfelidr ktcgdidecq | WLSRAQEHYPVSAGYTKLVGQDVARFIN |
| | npgicsqici nlkggykcec | WMEEEFNYPLDNVHLLGYSLGAHAAGIA |
| | srgyqmdlat gvckavgkep | GSLTNKKVNRITGLDPAGPNFEYAEAPS |
| | sliftnrrdi rkiglerkey | RLSPDDADFVDVLHFTFTRGSPGRSIGIQ |
| | iqlveqlrnt valdadiaaq | KPVGHVDIYPNGGTFQPGCNIGEAIRVI |
| | klfwadlsqk aifsasiddk | AERGLGDVDQLVKCSHERSIHLFIDSLL |
| | vgrhvkmidn vynpaaiavd | NEENPSKAYRCSSKEAFEKGLCLSCRKN |
| | wvyktiywtd aasktisvat | RCNNLGYEINKVRAKRSSKMYLKTRSQM |
| | ldgtkrkflf nsdirepasi | PYKVFHYQVKIHFSGTESETHTNQAFEI |
| | avdplsgfvy wsdwgepaki | SLYGTVAESENIPFTLPEVSTNKTYSFL |
| | ekagmngfdr rplvtadiqw | IYTEVDIGELLMLKLKWKSDSYFSWSDW |
| | pngitldlik srlywldskl | WSSPGFAIQKIRVKAGETQKKVIFCSRE |
| | hmlssvdlng qdrrivlksl | KVSHLQKGKAPAVFVKCHDKSLNKKSG |
| | eflahplalt ifedrvywid | |
| | geneavygan kftgselatl | |
| | vnnlndaqdi ivyhelvqps | LRPAP1 (SEQ ID NO: 66) |
| | gknwceedme nggceylclp | MAPRRVRSFLRGLPALLLLLLFLGPWPA |
| | apqindhspk ytcscpsgyn | ASHGGKYSREKNQPKPSPKRESGEEFRM |
| | veengrdcqs tattvtyset | EKLNQLWEKAQRLHLPPVRLAELHADLK |
| | kdtntteisa tsglvpggin | IQERDELAWKKLKLDGLDEDGEKEARLI |
| | vttavsevsv ppkgtsaawa | RNLNVILAKYGLDGKKDARQVTSNSLSG |
| | ilpllllvma avggylmwrn | TQEDGLDDPRLEKLWHKAKTSGKFSGEE |
| | wqhknmksmn fdnpvylktt | LDKLWREFLHHKEKVHEYNVLLETLSRT |
| | eedlsidigr hsasvghtyp | EEIHENVISPSDLSDIKGSVLHSRHTEL |
| | aisvvstddd la | KEKLRSINQGLDRLRRVSHQGYSTEAEF |
| | Isoform d (SEQ ID NO: 10) | EEPRVIDLWDLAQSANLTDKELEAFREE |
| | mgtsalwalw lllalcwapr | LKHFEAKIEKHNHYQKLEIAHEKLRHA |
| | esgatgtgrk akcepsqfqc | ESVGDGERVSRSREKHALLEGRTKELGY |
| | tngrcitllw kcdgdedcvd | TVKKHLQDLSGRISRARHNEL |
| | gsdekncvkk tcaesdfvcn | PLAU (SEQ ID NO: 67) |
| | ngqcvpsrwk cdgdpdcedg | MRALLARLLLCVLVVSDSKGSNELHQVP |
| | sdespeqcrn itcspdeftc | SNCDCLNGGTCVSNKYFSNIHWCNCPKK |
| | ssgrcisrnf vcngqddcsd | FGGQHCEIDKSKTCYEGNGHFYRGKAST |
| | gsdeldcapp tcgahefqcs | DTMGRPCLPWNSATVLQQTYHAHRSDAL |
| | tsscipiswv cdddadcsdq | QLGLGKHNYCRNPDNRRRPWCYVQVGLK |
| | sdesleqcgr qpvihtkcpa | PLVQECMVHDCADGKKPSSPPEELKFQC |
| | seiqcgsgec ihkkwrcdgd | GQKTLRPRFKIIGGEFTTIENQPWFAAI |
| | pdckdgsdev ncpsrtcrpd | YRRHRGGSVTYVCGGSLISPCWVISATH |
| | qfecedgsci hgsrqcngir | CFIDYPKKEDYIVYLGRSRLNSNTQGEM |
| | dcvdgsdevn cknvnqclgp | KFEVENLILHKDYSADTLAHHNDIALLK |
| | gkfkcrsgec idiskvcnqe | IRSKEGRCAQPSRTIQTICLPSMYNDPQ |
| | qdcrdwsdep lkechinecl | FGTSCEITGFGKENSTDYLYPEQLKMTV |
| | vnnggcshic kdlvigyecd | VKLISHRECQQPHYYGSEVTTKMLCAAD |
| | caagfelidr ktcgdidecq | PQWKTDSCQGDSGGPLVCSLQGRMTLTG |
| | npgicsqici nlkggykcec | IVSWGRGCALKDKPGVYTRVSHFLPWIR |
| | srgyqmdlat gvckavgkep | SHTKEENGLAL |
| | sliftnrrdi rkiglerkey | PLAUR (SEQ ID NO: 68) |
| | iqlveqlrnt valdadiaaq | MGHPPLLPLLLLLLHTCVPASWGLRCMQC |
| | klfwadlsqk aifsasiddk | KTNGDCRVEECALGQDLCRTTIVRLWEE |
| | vgrhvkmidn vynpaaiavd | GEELELVEKSCTHSEKTNRTLSYRTGLK |
| | wvyktiywtd aasktisvat | ITSLTEVVCGLDLCNQGNSGRAVTYSRS |
| | idgtkrkflf nsdirepasi | RYLECISCGSSDMSCERGRHQSLQCRSP |
| | avdplsgfvy wsdwgepaki | EEQCLDVVTHWIQEGEEGRPKDDRHLRG |
| | ekagmngfdr rplvtadiqw | CGYLPGCPGSNGFHNNDTFHFLKCCNTT |
| | pngitldlik srlywldskl | KCNEGPILELENLPQNGRQCYSCKGNST |
| | hmlssvdlng qdrrivlksl | HGCSSEETFLIDCRGPMNQCLVATGTHE |
| | eflahplalt ifedrvywid | PKNQSYMVRGCATASMCQHAHLGDAFSM |
| | geneavygan kftgselatl | NHIDVSCCTKSGCNHPDLDVQYRSGAAP |
| | vnnlndaqdi ivyhelvqps | QPGPAHLSLTITLLMTARLWGGTLLWT |

TABLE 1-continued

Sequences of exemplary target proteins and associated binding agents

| Target Protein | Target Protein SEQ | Exemplary Binding Agent(s) |
|---|---|---|
| | gknwceedme nggceylclp | RELN (SEQ ID NO: 69) |
| | apqindhspk ytcscpsgyn | MERSGWARQTFLLALLLGATLRARAAAG |
| | veengrdcqr invttavsev | YYPRFSPFFFLCTHHGELEGDGEQGEVL |
| | svppkgtsaa wailplllllv | ISLHIAGNPTYYVPGQEYHVTISTSTFF |
| | maavggylmw rnwqhknmks | DGLLVTGLYTSTSVQASQSIGGSSAFGF |
| | mnfdnpvylk tteedlsidi | GIMSDHQFGNQFMCSVVASHVSHLPTTN |
| | grhsasvght ypaisvvstd | LSFIWIAPPAGTGCVNFMATATHRGQVI |
| | ddla | FKDALAQQLCEQGAPTDVTVHPHLAEIH |
| | | SDSIILRDDFDSYHQLQLNPNIWVECNN |
| | | CETGEQCGAIMHGNAVTFCEPYGPRELI |
| | | TTGLNTTTASVLQFSIGSGSCRFSYSDP |
| | | SIIVLYAKNNSADWIQLEKIRAPSNVST |
| | | IIHILYLPEDAKGENVQFQWKQENLRVG |
| | | EVYEACWALDNILIINSAHRQVVLEDSL |
| | | DPVDTGNWLFFPGATVKHSCQSDGNSIY |
| | | FHGNEGSEFNFATTRDVDLSTEDIQEQW |
| | | SEEFESQPTGWDVLGAVIGTECGTIESG |
| | | LSMVFLKDGERKLCTPSMDTTGYGNLRF |
| | | YFVMGGICDPGNSHENDIILYAKIEGRK |
| | | EHITLDTLSYSSYKVPSLVSVVINPELQ |
| | | TPATKFCLRQKNHQGHNRNVWAVDFFHV |
| | | LPVLPSTMSHMIQFSINLGCGTHQPGNS |
| | | VSLEFSTNHGRSWSLLHTECLPEICAGP |
| | | HLPHSTVYSSENYSGWNRITIPLPNAAL |
| | | TRNTRIRWRQTGPILGNMWAIDNVYIGP |
| | | SCLKFCSGRGQCTRHGCKCDPGFSGPAC |
| | | EMASQTFPMFISESFGSSRLSSYHNFYS |
| | | IRGAEVSFGCGVLASGKALVFNKDGRRQ |
| | | LITSFLDSSQSRFLQFTLRLGSKSVLST |
| | | CRAPDQPGEGVLLHYSYDNGITWKLLEH |
| | | YSYLSYHEPRIISVELPGDAKQFGIQFR |
| | | WWQPYHSSQREDVWAIDEIIMTSVLFNS |
| | | ISLDFTNLVEVTQSLGFYLGNVQPYCGH |
| | | DWTLCFTGDSKLASSMRYVETQSMQIGA |
| | | SYMIQFSLVMGCGQKYTPHMDNQVKLEY |
| | | STNHGLTWHLVQEECLPSMPSCQEFTSA |
| | | SIYHASEFTQWRRVIVLLPQKTWSSATR |
| | | FRWSQSYYTAQDEWALDSIYIGQQCPNM |
| | | CSGHGSCDHGICRCDQGYQGTECHPEAA |
| | | LPSTIMSDFENQNGWESDWQEVIGGEIV |
| | | KPEQGCGVISSGSSLYFSKAGKRQLVSW |
| | | DLDTSWVDFVQFYIQIGGESASCNKPDS |
| | | REEGVLLQYSNNGGIQWHLLAEMYFSDF |
| | | SKPRFVYLELPAAAKTPCTRFRWWQPVF |
| | | SGEDYDQWAVDDIIILSEKQKQIIPVIN |
| | | PTLPQNFYEKPAFDYPMNQMSVWLMLAN |
| | | EGMVKNETFCAATPSAMIFGKSDGDRFA |
| | | VTRDLTLKPGYVLQFKLNIGCANQFSST |
| | | APVLLQYSHDAGMSWFLVKEGCYPASAG |
| | | KGCEGNSRELSEPTMYHTGDFEEWTRIT |
| | | IVIPRSLASSKTRFRWIQESSSQKNVPP |
| | | FGLDGVYISEPCPSYCSGHGDCISGVCF |
| | | CDLGYTAAQGTCVSNVPNHNEMFDRFEG |
| | | KLSPLWYKITGAQVGTGCGTLNDGKSLY |
| | | FNGPGKREARTVPLDTRNIRLVQFYIQI |
| | | GSKTSGITCIKPRTRNEGLIVQYSNDNG |
| | | ILWHLLRELDFMSFLEPQIISIDLPQDA |
| | | KTPATAFRWWQPQHGKHSAQWALDDVLI |
| | | GMNDSSQTGFQDKFDGSIDLQANWYRIQ |
| | | GGQVDIDCLSMDTALIFTENIGKPRYAE |
| | | TWDFHVSASTFLQFEMSMGCSKPFSNSH |
| | | SVQLQYSLNNGKDWHLVTEECVPPTIGC |
| | | LHYTESSIYTSERFQNWKRITVYLPLST |
| | | ISPRTRFRWIQANYTVGADSWAIDNVVL |
| | | ASGCPWMCSGRGICDAGRCVCDRGFGGP |
| | | YCVPVVPLPSILKDDFNGNLHPDLWPEV |
| | | YGAERGNLNGETIKSGTSLIFKGEGLRM |
| | | LISRDLDCTNTMYVQFSLRFIAKSTPER |
| | | SHSILLQFSISGGITWHLMDEFYFPQTT |
| | | NILFINVPLPYTAQTNATRFRLWQPYNN |
| | | GKKEEIWIVDDFIIDGNNVNNPVMLLDT |
| | | FDFGPREDNWFFYPGGNIGLYCPYSSKG |
| | | APEEDSAMVFVSNEVGEHSITTRDLNVN |
| | | ENTIIQFEINVGCSTDSSSADPVRLEFS |
| | | RDFGATWHLLLPLCYHSSSHVSSLCSTE |
| | | HHPSSTYYAGTMQGWRREVVHFGKLHLC |

TABLE 1-continued

| Sequences of exemplary target proteins and associated binding agents | | |
| --- | --- | --- |
| Target Protein | Target Protein SEQ | Exemplary Binding Agent(s) |
| | | GSVRFRWYQGFYPAGSQPVTWAIDNVYI |
| | | GPQCEEMCNGQGSCINGTKCICDPGYSG |
| | | PTCKISTKNPDFLKDDFEGQLESDRFLL |
| | | MSGGKPSRKCGILSSGNNLFFNEDGLRM |
| | | LMTRDLDLSHARFVQFFMRLGCGKGVPD |
| | | PRSQPVLLQYSLNGGLSWSLLQEFLFSN |
| | | SSNVGRYIALEIPLKARSGSTRLRWWQP |
| | | SENGHFYSPWVIDQILIGGNISGNTVLE |
| | | DDFTTLDSRKWLLHPGGTKMPVCGSTGD |
| | | ALVFIEKASTRYVVSTDVAVNEDSFLQI |
| | | DFAASCSVTDSCYAIELEYSVDLGLSWH |
| | | PLVRDCLPTNVECSRYHLQRILVSDTFN |
| | | KWTRITLPLPPYTRSQATRFRWHQPAPF |
| | | DKQQTWAIDNVYIGDGCIDMCSGHGRCI |
| | | QGNCVCDEQWGGLYCDDPETSLPTQLKD |
| | | NFNRAPSSQNWLTVNGGKLSTVCGAVAS |
| | | GMALHFSGGCSRLLVTVDLNLTNAEFIQ |
| | | FYFMYGCLITPNNRNQGVLLEYSVNGGI |
| | | TWNLLMEIFYDQYSKPGFVNILLPPDAK |
| | | EIATRFRWWQPRHDGLDQNDWAIDNVLI |
| | | SGSADQRTVMLDTFSSAPVPQHERSPAD |
| | | AGPVGRIAFDMFMEDKTSVNEHWLFHDD |
| | | CTVERFCDSPDGVMLCGSHDGREVYAVT |
| | | HDLTPTEGWIMQFKISVGCKVSEKIAQN |
| | | QIHVQYSTDFGVSWNYLVPQCLPADPKC |
| | | SGSVSQPSVFFPTKGWKRITYPLPESLV |
| | | GNPVRFRFYQKYSDMQWAIDNFYLGPGC |
| | | LDNCRGHGDCLREQCICDPGYSGPNCYL |
| | | THTLKTFLKERFDSEEIKPDLWMSLEGG |
| | | STCTECGILAEDTALYFGGSTVRQAVTQ |
| | | DLDLRGAKFLQYWGRIGSENNMTSCHRP |
| | | ICRKEGVLLDYSTDGGITWTLLHEMDYQ |
| | | KYISVRHDYILLPEDALTNTTRLRWWQP |
| | | FVISNGIVVSGVERAQWALDNILIGGAE |
| | | INPSQLVDTFDDEGTSHEENWSFYPNAV |
| | | RTAGFCGNPSFHLYWPNKKKDKTHNALS |
| | | SRELIIQPGYMMQFKIVVGCEATSCGDL |
| | | HSVMLEYTKDARSDSWQLVQTQCLPSSS |
| | | NSIGCSPFQFHEATIYNSVNSSSWKRIT |
| | | IQLPDHVSSSATQFRWIQKGEETEKQSW |
| | | AIDHVYIGEACPKLCSGHGYCTTGAICI |
| | | CDESFQGDDCSVFSHDLPSYIKDNFESA |
| | | RVTEANWETIQGGVIGSGCGQLAPYAHG |
| | | DSLYFNGCQIRQAATKPLDLTRASKIMF |
| | | VLQIGSMSQTDSCNSDLSGPHAVDKAVL |
| | | LQYSVNNGITWHVIAQHQPKDFTQAQRV |
| | | SYNVPLEARMKGVLLRWWQPRHNGTGHD |
| | | QWALDHVEVVLVSTRKQNYMMNFSRQHG |
| | | LRHFYNRRRRSLRRYP |
| | | SERPINEI (SEQ ID NO: 70) |
| | | MQMSPALTCLVLGLALVFGEGSAVHHPP |
| | | SYVAHLASDFGVRVFQQVAQASKDRNVV |
| | | FSPYGVASVLAMLQLTTGGETQQQIQAA |
| | | MGFKIDDKGMAPALRHLYKELMGPWNKD |
| | | EISTTDAIFVQRDLKLVQGFMPHFFRLF |
| | | RSTVKQVDFSEVERARFIINDWVKTHTK |
| | | GMISNLLGKGAVDQLTRLVLVNALYFNG |
| | | QWKTPFPDSSTHRRLFHKSDGSTVSVPM |
| | | MAQTNKFNYTEFTTPDGHYYDILELPYH |
| | | GDTLSMFIAAPYEKEVPLSALTNILSAQ |
| | | LISHWKGNMTRLPRLLVLPKFSLETEVD |
| | | LRKPLENLGMTDMFRQFQADFTSLSDQE |
| | | PLHVAQALQKVKIEVNESGTVASSSTAV |
| | | IVSARMAPEEIIMDRPFLFVVRHNPTGT |
| | | VLFMGQVMEP |
| ZP2 | Isoform 1 (SEQ ID NO: 11) | ZPI (SEQ ID NO: 71) |
| | macrqrggsw spsgwfnagw | MAGGSATTWGYPVALLLLVATLGLGRWL |
| | styrsislff alvtsgnsid | QPDPGLPGLRHSYDCGIKGMQLLVFPRP |
| | vsqlvnpafp gtvtcderei | GQTLRFKVVDEFGNRFDVNNCSICYHWV |
| | tvefpsspgt kkwhasvvdp | TSRPQEPAVFSADYRGCHVLEKDGRFHL |
| | igldmpncty ildpekltlr | RVFMEAVLPNGRVDVAQDATLICPKPDP |
| | atydnctrrv hgghqmtirv | SRTLDSQLAPPAMFSVSTPQTLSFLPTS |
| | mnnsaalrhg avmyqffcpa | GHTSQGSGHAFPSPLDPGHSSVHPTPAL |
| | mqveetqgls asticqkdfm | PSPGPGPTLATLAQPHWGTLEHWDVNKR |
| | sfslprvfsg laddskgtkv | DYIGTHLSQEQCQVASGHLPCIVRRTSK |

TABLE 1-continued

| Target Protein | Target Protein SEQ | Exemplary Binding Agent(s) |
|---|---|---|
| | | *Sequences of exemplary target proteins and associated binding agents* |

| | qmgwsievgd garaktltlp | EACQQAGCCYDNTREVPCYYGNTATVQC |
| | eamkegfsll idnhrmtfhv | FRDGYFVLVVSQEMALTHRITLANIHLA |
| | pfnatgvthy vqgnshlymv | YAPTSCSPTQHTEAFVVFYFPLTHCGTT |
| | slkltfispg qkvifssqai | MQVAGDQLIYENWLVSGIHIQKGPQGSI |
| | capdpvtcna thmtltipef | TRDSTFQLHVRCVFNASDFLPIQASIFP |
| | pgklksvsfe nqnidvsqlh | PPSPAPMTQPGPLRLELRIAKDETFSSY |
| | dngidleatn gmklhfsktl | YGEDDYPIVRLLREPVHVEVRLLQRTDP |
| | lktklsekcl ihqfylaslk | NLVLLLHQCWGAPSANPFQQPQWPILSD |
| | ltfllrpetv smviypeclc | GCPFKGDSYRTQMVALDGATPFQSHYQR |
| | espvsivtge ictqdgfmdv | FTVATFALLDSGSQRALRGLVYLFCSTS |
| | evysyqtqpa idlgtlrvgn | ACHTSGLETCSTACSTGTTRQRRSSGHR |
| | sscqpvfeaq sqglvrfhip | NDTARPQDIVSSPGPVGFEDSYGQEPTL |
| | ingcgtrykf eddkvvyene | GPTDSNGNSSLRPLLWAVLLLPAVALVL |
| | ihalwtdfpp skisrdsefr | GFGVFVGLSQTWAQKLWESNRQ |
| | mtvkcsysrn dmllninves | |
| | ltppvasvkl gpftlilqsy | ZP3 (SEQ ID NO: 72) |
| | pdnsyqqpyg eneyplvrfl | MELSYRLFICLLLWGSTELCYPQPLWLL |
| | rqpiymevrv lnrddpnikl | QGGASHPETSVQPVLVECQEATLMVMVS |
| | vlddcwatst mdpdsfpqwn | KDLFGTGKLIRAADLTLGPEACEPLVSM |
| | vvvdgcaydl dnyqttfhpv | DTEDVVRFEVGLHECGNSMQVTDDALVY |
| | gssvthpdhy qrfdmkafaf | STFLLHDPRPVGNLSIVRTNRAEIPIEC |
| | vseahvlssl vyfhcsalic | RYPRQGNVSSQAILPTWLPFRTTVFSEE |
| | nrlspdsplc svtcpvssrh | KLTFSLRLMEENWNAEKRSPTFHLGDAA |
| | rratgateae kmtvslpgpi | HLQAEIHTGSHVPLRLFVDHCVATPTPD |
| | lllsddssfr gvgssdlkas | QNASPYHTIVDFHGCLVDGLTDASSAFK |
| | gssgeksrse tgeevgsrga | VPRPGPDTLQFTVDVFHFANDSRNMIYI |
| | mdtkghktag dvgskavaav | TCHLKVTLAEQDPDELNKACSFSKPSNS |
| | aafagvvatl gfiyylyekr tvsnh | WFPVEGSADICQCCNKGDCGTPSHSRRQ |
| | Isoform 2 (SEQ ID NO: 12) | PHVMSQWSRSASRNRRHVTEEADVTVGP |
| | macrqrggsw spsgwfnagw | LIFLDRRGDHEVEQWALPSDTSVVLLGV |
| | styrsislff alvtsgnsid | GLAVVVSLTLTAVILVLTRRCRTASHPV |
| | vsqlvnpafp gtvtcderei | SASE |
| | tvefpsspgt kkwhasvvdp | ZP4 (SEQ ID NO: 73) |
| | Igldmpncty ildpekltlr | MWLLRCVLLCVSLSLAVSGQHKPEAPDY |
| | atydnctrrv hgghqmtirv | SSVLHCGPWSFQFAVNLNQEATSPPVLI |
| | mnnsaalrhg avmyqffcpa | AWDNQGLLHELQNDSDCGTWIRKGPGSS |
| | mqveetqgls asticqkdfm | WLEATYSSCYVTEWDSHYIMPVGVEGA |
| | sfslprvfsg laddskgtkv | GAAEHKVVTERKLLKCPMDLLARDAPDT |
| | qmgwsievgd garaktltlp | DWCDSIPARDRLPCAPSPISRGDCEGLG |
| | eamkegfsll idnhrmtfhv | CCYSSEEVNSCYYGNTVTLHCTREGHFS |
| | pfnatgvthy vqgnshlymv | IAVSRNVTSPPLLLDSVRLALRNDSACN |
| | slkltfispg qkvifssqai | PVMATQAFVLFQFPFTSCGTTRQITGDR |
| | capdpvtcna thmtltipef | AVYENELVATRDVKNGSRGSVTRDSIFR |
| | pgklksvsfe nqnidvsqlh | LHVSCSYSVSSNSLPINVQVFTLPPPFP |
| | dngidleatn gmklhfsktl | ETQPGPLTLELQIAKDKNYGSYYGVGDY |
| | lktklsekcl ihqfylaslk | PVVKLLRDPIYVEVSILHRTDPYLGLLL |
| | ltfllrpetv smviypeclc | QQCWATPSTDPLSQPQWPILVKGCPYIG |
| | espvsivtge ictqdgfmdv | DNYQTQLIPVQKALDLPFFPSHHQRFSIF |
| | evysyqtqpa idlgtlrvgn | TFSFVNPTVEKQALRGPVHLHCSVSVCQ |
| | sscqpvfeaq sqglvrfhip | PAETPSCVVTCPDLSRRRNFDNSSQNTT |
| | ingcgtrykf eddkvvyene | ASVSSKGPMILLQATKDPPEKLRVPVDS |
| | ihalwtdfpp skisrdsefr | KVLWVAGLSGTLILGALLVSYLAVKKQK |
| | ndmllninve sltppvasvk | SCPDQMCQ |
| | Igpftlilqs ypdnsyqqpy | ZPBP (SEQ ID NO: 74) |
| | geneyplvrf lrqpiymevr | MEAFALGPARRGRRRTRAAGSLLSRAAI |
| | vlnrddpnik lvlddcwats | LLFISAFLVRVPSSVGHLVRLPRAFRLT |
| | tmdpdsfpqw nvvvdgcayd | KDSVKIVGSTSFPVKAYVMLHQKSPHVL |
| | Idnyqttfhp vgssvthpdh | CVTQQLRNAELIDPSFQWYGPKGKVVSV |
| | yqrfdmkafa fvseahvlss | ENRTAQITSTGSLVFQNFEESMSGIYTC |
| | Ivyfhcsali cnrlspdspl | FLEYKPTVEEIVKRLQLKYAIYAYREPH |
| | csvtcpvssr hrratgatea | YYYQFTARYHAAPCNSIYNISFEKKLLQ |
| | ekmtvslpgp illlsddssf | ILSKLLLDLSCEISLLKSECHRVKMQRA |
| | rgvgssdlka sgssgeksrs | GLQNELFFAFSVSSLDTEKGPKRCTDHN |
| | etgeevgsrg amdtkghkta | CEPYKRLFKAKNLIERFFNQQVEILGRR |
| | gdvgskavaa vaafagvvat | AEQLPQIYYIEGTLQMVWINRCFPGYGM |
| | Igfiyylyek rtvsnh | NVQQHPKCPECCVICSPGSYNPRDGIHC |
| | | LQCNSSLVYGAKTCL |
| | Isoform 3 (SEQ ID NO: 13) | ACR (SEQ ID NO: 75) |
| | macrqrggsw spsgwfnagw | MVEMLPTAILLVLAVSVVAKDNATCDGP |
| | styrsislff alvtsgnsid | CGLRFRQNPQGGVRIVGGKAAQHGAWPW |
| | vsqlvnpafp gtvtcderei | MVSLQIFTYNSHRYHTCGGSLLNSRWVL |
| | tvefpsspgt kkwhasvvdp | TAAHCFVGKNNVHDWRLVFGAKEITYGN |
| | Igldmpncty ildpekltlr | NKPVKAPLQERYVEKIIIHEKYNSATEG |
| | atydnctrrv hgghqmtirv | NDIALVEITPPISCGRFIGPGCLPHFKA |
| | mnnsaalrhg avmyqffcpa | GLPRGSQSCWVAGWGYIEEKAPRPSSIL |
| | mqveetqgls asticqkdfm | MEARVDLIDLDLCNSTQWYNGRVQPTNV |

TABLE 1-continued

Sequences of exemplary target proteins and associated binding agents

| Target Protein | Target Protein SEQ | Exemplary Binding Agent(s) |
|---|---|---|
| | sfslprvfsg laddskgtkv | CAGYPVGKIDTCQGDSGGPLMCKDSKES |
| | qmgwsievgd garaktltlp | AYVVVGITSWGVGCARAKRPGIYTATWP |
| | eamkegfsll idnhrmtfhv | YLNWIASKIGSNALRMIQSATPPPPTTR |
| | pfnatgvthy vqgnshlymv | PPPIRPPFSHPISAHLPWYFQPPPRPLP |
| | slkltfispg qkvifssqai | PRPPAAQPRPPPSPPPPPPPPASPLPPP |
| | capdpvtcna thmtltipef | PPPPPPTPSSTTKLPQGLSFAKRLQQLI |
| | pgklksvsfe nqnidvsqlh | EVLKGKTYSDGKNHYDMETTELPELTST |
| | dngidleatn gmklhfsktl | S |
| | lktklsekcl ihqfylaslk | ADAM2 (SEQ ID NO: 76) |
| | ltfllrpetv smviypeclc | MWRVLFLLSGLGGLRMDSNFDSLPVQIT |
| | espvsivtge ictqdgfmdv | VPEKIRSIIKEGIESQASYKIVIEGKPY |
| | evysyqtqpa idlgtlrvgn | TVNLMQKNFLPHNFRVYSYSGTGIMKPL |
| | sscqpvfeaq sqglvrfhip | DQDFQNFCHYQGYIEGYPKSVVMVSTCT |
| | ingcgtrykf eddkvvyene | GLRGVLQFENVSYGIEPLESSVGFEHVI |
| | ihalwtdfpp skisrdsefr | YQVKHKKADVSLYNEKDIESRDLSFKLQ |
| | mtvkcsysrn dmllninves | SVEPQQDFAKYIEMHVIVEKQLYNHMGS |
| | ltppvasvkl gpftlilqsy | DTTVVAQKVFQLIGLTNAIFVSFNITII |
| | pdnsyqqpyg eneyplvrfl | LSSLELWIDENKIATTGEANELLHTFLR |
| | rqpiymevrv inrddpnikl | WKTSYLVLRPHDVAFLLVYREKSNYVGA |
| | vlddcwatst mdpdsfpqwn | TFQGKMCDANYAGGVVLHPRTISLESLA |
| | vvvdgcaydl dnyqttfhpv | VILAQLLSLSMGITYDDINKCQCSGAVC |
| | gssvthpdhy qrfdmkafaf | IMNPEAIHFSGVKIFSNCSFEDFAHFIS |
| | vseahvlssl vyfhcsalic | KQKSQCLHNQPRLDPFFKQQAVCGNAKL |
| | nrlspdsplc svtcpvssrh | EAGEECDCGTEQDCALIGETCCDIATCR |
| | rreakhkldh ispatgatea | FKAGSNCAEGPCCENCLFMSKERMCRPS |
| | ekmtvslpgp illlsddssf | FEECDLPEYCNGSSASCPENHYVQTGHP |
| | rgvgssdlka sgssgeksrs | CGLNQWICIDGVCMSGDKQCTDTFGKEV |
| | etgeevgsrg amdtkghkta | EFGPSECYSHLNSKTDVSGNCGISDSGY |
| | gdvgskavaa vaafagvvat | TQCEADNLQCGKLICKYVGKFLLQIPRA |
| | lgfiyylyek rtvsnh | TIIYANISGHLCIAVEFASDHADSQKMW |
| | | IKDGTSCGSNKVCRNQRCVSSSYLGYDC |
| | | TTDKCNDRGVCNNKKHCHCSASYLPPDC |
| | | SVQSDLWPGGSIDSGNFPPVAIPARLPE |
| | | RRYIENIYHSKPMRWPFFLFIPFFIIFC |
| | | VLIAIMVKVNFQRKKWRTEDYSSDEQPE |
| | | SESEPKG |
| | | OVGPI (SEQ ID NO: 77) |
| | | MWKLLLWVGLVLVLKHHDGAAHKLVCYF |
| | | TNWAHSRPGPASILPHDLDPFLCTHLIF |
| | | AFASMNNNQIVAKDLQDEKILYPEFNKL |
| | | KERNRELKTLLSIGGWNFGTSRFTTMLS |
| | | TFANREKFIASVISLLRTHDFDGLDLFF |
| | | LYPGLRGSPMHDRWTFLFLIEELLFAFR |
| | | DVRFLGRLLDFINVLSYDLHGSWERFTG |
| | | HNSPLFSLPEDPKSSAYAMNYWRKLGAP |
| | | SEKLIMGIPTYGRTFRLLKASKNGLQAR |
| | | AIGPASPGKYTKQEGFLAYFEICSFVWG |
| | | AKKHWIDYQYVPYANKGKEWVGYDNAIS |
| | | FSYKAWFIRREHFGGAMVWTLDMDDVRG |
| | | TFCGTGPFPLVYVLNDILVRAEFSSTSL |
| | | PQFWLSSAVNSSSTDPERLAVTTAWTTD |
| | | SKILPPGGEAGVTEIHGKCENMTITPRG |
| | | TTVTPTKETVSLGKHTVALGEKTEITGA |
| | | MTMTSVGHQSMTPGEKALTPVGHQSVTT |
| | | GQKTLTSVGYQSVTPGEKTLTPVGHQSV |
| | | TPVSHQSVSPGGTTMTPVHFQTETLRQN |
| | | TVAPRRKAVAREKVTVPSRNISVTPEGQ |
| | | TMPLRGENLTSEVGTHPRMGNLGLQMEA |
| | | ENRMMLSSSPVIQLPEQTPLAFDNRFVP |
| | | IYGNHSSVNSVTPQTSPLSLKKEIPENS |
| | | AVDEEA |
| | | PPARA (SEQ ID NO: 78) |
| | | MVDTESPLCPLSPLEAGDLESPLSEEFL |
| | | QEMGNIQEISQSIGEDSSGSFGFTEYQY |
| | | LGSCPGSDGSVITDTLSPASSPSSVTYP |
| | | VVPGSVDESPSGALNIECRICGDKASGY |
| | | HYGVHACEGCKGFFRRTIRLKLVYDKCD |
| | | RSCKIQKKNRNKCQYCRFHKCLSVGMSH |
| | | NAIRFGRMPRSEKAKLKAEILTCEHDIE |
| | | DSETADLKSLAKRIYEAYLKNFNMNKVK |
| | | ARVILSGKASNNPPFVIHDMETLCMAEK |
| | | TLVAKLVANGIQNKEAEVRIFHCCQCTS |
| | | VETVTELTEFAKAIPGFANLDLNDQVTL |
| | | LKYGVYEAIFAMLSSVMNKDGMLVAYGN |
| | | GFITREFLKSLRKPFCDIMEPKFDFAMK |
| | | FNALELDDSDISLFVAAIICCGDRPGLL |

TABLE 1-continued

Sequences of exemplary target proteins and associated binding agents

| Target Protein | Target Protein SEQ | Exemplary Binding Agent(s) |
|---|---|---|
| | | NVGHIEKMQEGIVHVLRLHLQSNHPDDI |
| | | FLFPKLLQKMADLRQLVTEHAQLVQIIK |
| | | KTESDAALHPLLQEIYRDMY |
| IFNLRI | Isoform 1 (SEQ ID NO: 14) | IFNL2 (SEQ ID NO: 79) |
| | magperwgpl llcllqaapg | MKLDMTGDCTPVLVLMAAVLTVTGAVPV |
| | rprlappqnv tllsqnfsvy | ARLHGALPDARGCHIAQFKSLSPQELQA |
| | Itwlpglgnp qdvtyfvayq | FKRAKDALEESLLLKDCRCHSRLFPRTW |
| | ssptrrrwre veecagtkel | DLRQLQVRERPMALEAELALTLKVLEAT |
| | lcsmmclkkq dlynkfkgrv | ADTDPALVDVLDQPLHTLHHILSQFRAC |
| | rtvspssksp wveseyldyl | IQPQPTAGPRTRGRLHHWLYRLQEAPKK |
| | fevepappvl vltqteeils | ESPGCLEASVTFNLFRLLTRDLNCVASG |
| | anatyqlppc mppldlkyev | DLCV |
| | afwkegagnk tlfpvtphgq | IFNLRI (SEQ ID NO: 80) |
| | pvqitlqpaa sehhclsart | MAGPERWGPLLLCLLQAAPGRPRLAPPQ |
| | iytfsvpkys kfskptcfll | NVTLLSQNFSVYLTWLPGLGNPQDVTYF |
| | evpeanwafl vlpsllilll | VAYQSSPTRRRWREVEECAGTKELLCSM |
| | viaaggviwk tlmgnpwfqr | MCLKKQDLYNKFKGRVRTVSPSSKSPWV |
| | akmpraldfs ghthpvatfq | ESEYLDYLFEVEPAPPVLVLTQTEEILS |
| | psrpesvndl flcpqkeltr | ANATYQLPPCMPPLDLKYEVAFWKEGAG |
| | gvrptprvra patqqtrwkk | NKTLFPVTPHGQPVQITLQPAASEHHCL |
| | dlaedeeeed eedtedgvsf | SARTIYTFSVPKYSKFSKPTCFLLEVPE |
| | qpyieppsfl gqehqapghs | ANWAFLVLPSLLILLLVIAAGGVIWKTL |
| | eaggvdsgrp raplvpsegs | MGNPWFQRAKMPRALDFSGHTHPVATFQ |
| | sawdssdrsw astvdsswdr | PSRPESVNDLFLCPQKELTRGVRPTPRV |
| | agsssgylaek gpgqgpggdg | RAPATQQTRWKKDLAEDEEEEDEEDTED |
| | hqeslpppef skdsgfleel | GVSFQPYIEPPSFLGQEHQAPGHSEAGG |
| | pednlsswat wgtlppepnl | VDSGRPRAPLVPSEGSSAWDSSDRSWAS |
| | vpggppvslq tltfcwessp | TVDSSWDRAGSSGYLAEKGPGQGPGGDG |
| | eeeeearese iedsdagswg | HQESLPPPEFSKDSGFLEELPEDNLSSW |
| | aestqrtedr grtlghymar | ATWGTLPPEPNLVPGGPPVSLQTLTFCW |
| | Isoform 2 (SEQ ID NO: 15) | ESSPEEEEEARESEIEDSDAGSWGAEST |
| | magperwgpl llcllqaapg | QRTEDRGRTLGHYMAR |
| | rprlappqnv tllsqnfsvy | ILIORB (SEQ ID NO: 81) |
| | Itwlpglgnp qdvtyfvayq | MAWSLGSWLGGCLLVSALGMVPPPENVR |
| | ssptrrrwre veecagtkel | MNSVNFKNILQWESPAFAKGNLTFTAQY |
| | losmmclkkq dlynkfkgrv | LSYRIFQDKCMNTTLTECDFSSLSKYGD |
| | rtvspssksp wveseyldyl | HTLRVRAEFADEHSDWVNITFCPVDDTI |
| | fevepappvl vltqteeils | IGPPGMQVEVLADSLHMRFLAPKIENEY |
| | anatyqlppc mppldlkyev | ETWTMKNVYNSWTYNVQYWKNGTDEKFQ |
| | afwkegagnk tlfpvtphgq | ITPQYDFEVLRNLEPWTTYCVQVRGFLP |
| | pvqitlqpaa sehhclsart | DRNKAGEWSEPVCEQTTHDETVPSWMVA |
| | iytfsvpkys kfskptcfll | VILMASVFMVCLALLGCFALLWCVYKKT |
| | evpeanwafl vlpsllilll | KYAFSPRNSLPQHLKEFLGHPHHNTLLF |
| | viaaggviwk tlmgnpwfqr | FSFPLSDENDVFDKLSVIAEDSESGKQN |
| | akmpralelt rgvrptprvr | PGDSCSLGTPPGQGPQS |
| | apatqqtrwk kdlaedeeee | |
| | deedtedgvs fqpyieppsf | |
| | Igqehqapgh seaggvdsgr | |
| | praplvpseg ssawdssdrs | |
| | wastvdsswd ragssgylae | |
| | kgpgqgpggd ghqeslpppe | |
| | fskdsgflee lpednlsswa | |
| | twgtlppepn ivpggppvsl | |
| | qtltfcwess peeeeeares | |
| | eiedsdagsw gaestqrted | |
| | rgrtighyma r | |
| | Isoform 3 (SEQ ID NO: 16) | |
| | magperwgpl llcllqaapg | |
| | rprlappqnv tllsqnfsvy | |
| | itwlpglgnp qdvtyfvayq | |
| | ssptrrrwre veecagtkel | |
| | icsmmclkkq dlynkfkgrv | |
| | rtvspssksp wveseyldyl | |
| | fevepappvl vltqteeils | |
| | anatyqlppc mppldlkyev | |
| | afwkegagnk tlfpvtphgq | |
| | pvqitlqpaa sehhclsart | |
| | iytfsvpkys kfskptcfll | |
| | evpglfwtht pcgnlsaqqt rvre | |
| HTR6 | mvpepgptan stpawgagpp | ADRBK1 (SEQ ID NO: 82) |
| | sapggsgwva aalcvvialt | MADLEAVLADVSYLMAMEKSKATPAARA |
| | aaansllial ictqpalrnt | SKKILLPEPSIRSVMQKYLEDRGEVTFE |
| | snfflvslft sdlmvglvvm | KIFSQKLGYLLFRDFCLNHLEEARPLVE |
| | ppamlnalyg rwvlarglcl | FYEEIKKYEKLETEEERVARSREIFDSY |

TABLE 1-continued

| Sequences of exemplary target proteins and associated binding agents | | |
|---|---|---|
| Target Protein | Target Protein SEQ | Exemplary Binding Agent(s) |
| | iwtafdvmcc sasilnlcli<br>sldryllils plryklrmtp<br>lralalvlga wslaalasfl<br>plllgwhelg harppvpgqc<br>rllaslpfvl vasgltfflp<br>sgaicftycr illaarkqav<br>qvaslttgma sqasetlqvp<br>rtprpgvesa dsrrlatkhs<br>rkalkasltl gillgmffvt<br>wlpffvaniv qavcdcispg<br>lfdvltwlgy cnstmnpiiy<br>plfmrdfkra lgrflpcprc<br>prerqaslas psirtshsgp<br>rpglslqqvl plplppdsds<br>dsdagsggss glrltaqlll<br>pgeatqdppl ptraaaavnf<br>fnidpaepel rphplgiptn<br>(SEQ ID NO: 17) | IMKELLACSHPFSKSATEHVQGHLGKKQ<br>VPPDLFQPYIEEICQNLRGDVFQKFIES<br>DKFTRFCQWKNVELNIHLTMNDFSVHRI<br>IGRGGFGEVYGCRKADTGKMYAMKCLDK<br>KRIKMKQGETLALNERIMLSLVSTGDCP<br>FIVCMSYAFHTPDKLSFILDLMNGGDLH<br>YHLSQHGVFSEADMRFYAAEIILGLEHM<br>HNRFVVYRDLKPANILLDEHGHVRISDL<br>GLACDFSKKKPHASVGTHGYMAPEVLQK<br>GVAYDSSADWFSLGCMLFKLLRGHSPFR<br>QHKTKDKHEIDRMTLTMAVELPDSFSPE<br>LRSLLEGLLQRDVNRRLGCLGRGAQEVK<br>ESPFFRSLDWQMVFLQKYPPPLIPPRGE<br>VNAADAFDIGSFDEEDTKGIKLLDSDQE<br>LYRNFPLTISERWQQEVAETVFDTINAE<br>TDRLEARKKAKNKQLGHEEDYALGKDCI<br>MHGYMSKMGNPFLTQWQRRYFYLFPNRL<br>EWRGEGEAPQSLLTMEEIQSVEETQIKE<br>RKCLLLKIRGGKQFILQCDSDPELVQWK<br>KELRDAYREAQQLVQRVPKMKNKPRSPV<br>VELSKVPLVQRGSANGL |
| GPR37L1 | mrwlwplavs lavilavgls<br>rvsggaplhl grhraetqeq<br>qsrskrgted eeakgvqqyv<br>peewaeyprp ihpaglqptk<br>plvatspnpg kdggtpdsgq<br>elrgnltgap gqrlqiqnpl<br>ypvtessysa yaimllalvv<br>favgivgnls vmcivwhsyy<br>lksawnsila slalwdflvl<br>ffclpivifn eitkqrllgd<br>vscravpfme vsslgvttfs<br>lcalgidrfh vatstlpkvr<br>piercqsila klaviwvgsm<br>tlavpelllw qlaqepaptm<br>gtldscimkp saslpeslys<br>lvmtyqnarm wwyfgcyfcl<br>pilftvtcql vtwrvrgppg<br>rksecraskh eqcesqlnst<br>vvgltvvyaf ctlpenvcni<br>vvaylstelt rqtldllgli<br>nqfstffkga itpvlllcic<br>rplgqafldc ccccceecg<br>gaseasaang sdnklktevs<br>ssiyfhkpre sppllplgtp c<br>(SEQ ID NO: 18) | PSAP (SEQ ID NO: 83)<br>MYALFLLASLLGAALAGPVLGLKECTRG<br>SAVWCQNVKTASDCGAVKHCLQTVWNKP<br>TVKSLPCDICKDVVTAAGDMLKDNATEE<br>EILVYLEKTCDWLPKPNMSASCKEIVDS<br>YLPVILDIIKGEMSRPGEVCSALNLCES<br>LQKHLAELNHQKQLESNKIPELDMTEVV<br>APFMANIPLLLYPQDGPRSKPQPKDNGD<br>VCQDCIQMVTDIQTAVRTNSTFVQALVE<br>HVKEECDRLGPGMADICKNYISQYSEIA<br>IQMMMHMQPKEICALVGFCDEVKEMPMQ<br>TLVPAKVASKNVIPALELVEPIKKHEVP<br>AKSDVYCEVCEFLVKEVTKLIDNNKTEK<br>EILDAFDKMCSKLPKSLSEECQEVVDTY<br>GSSILSILLEEVSPELVCSMLHLCSGTR<br>LPALTVHVTQPKDGGFCEVCKKLVGYLD<br>RNLEKNSTKQEILAALEKGCSFLPDPYQ<br>KQCDQFVAEYEPVLIEILVEVMDPSFVC<br>LKIGACPSAHKPLLGTEKCIWGPSYWCQ<br>NTETAAQCNAVEHCKRHVWN |
| MCHR2 | mnpfhascwn tsaellnksw<br>nkefayqtas vvdtvilpsm<br>igiicstglv gnilivftii<br>rsrkktvpdi yicnlavadl<br>vhivgmpfli hqwarggewv<br>fggplctiit sldtcnqfac<br>saimtvmsvd ryfalvqpfr<br>ltrwrtrykt irinlglwaa<br>sfilalpvwv yskvikfkdg<br>vescafdits pddvlwytly<br>itittfffpl plilvcyili<br>lcytwemyqq nkdarccnps<br>vpkqrvmklt kmvlvlvvvf<br>ilsaapyhvi qlvnlqmeqp<br>tlafyvgyyl siclsyasss<br>inpflyills gnfqkrlpqi<br>qrratekein nmgntlkshf<br>(SEQ ID NO: 19) | Pro-MCH (SEQ ID NO: 84)<br>MAKMNLSSYILILTFSLFSQGILLSASK<br>SIRNLDDDMVFNTFRLGKGFQKEDTAEK<br>SVIAPSLEQYKNDESSFMNEEENKVSKN<br>TGSKHNFLNHGLPLNLAIKPYLALKGSV<br>AFPAENGVQNTESTQEKREIGDEENSAK<br>FPIGRRDFDMLRCMLGRVYRPCWQV |
| Protein<br>containing<br>epitope<br>generated by<br>B3GAT1<br>(aB3GAT1-<br>modified<br>protein) | Isoform 1 (SEQ ID NO: 20)<br>mpkrrdilai vlivlpwtll<br>itvwhqstla pllavhkdeg<br>sdprretppg adpreyctsd<br>rdivevvrte yvytrpppws<br>dtlptihvvt ptysrpvqka<br>eltrmantll hvpnlhwlvv<br>edaprrtpit arllrdtgln<br>ythlhvetpr nykirgdard | Laminin (Laminin subunit<br>gamma-1) (SEQ ID NO: 85)<br>MRGSHRAAPALRPRGRLWPVLAVLAAAA<br>AAGCAQAAMDECTDEGGRPQRCMPEFVN<br>AAFNVTVVATNTCGTPPEEYCVQTGVTG<br>VTKSCHLCDAGQPHLQHGAAFLTDYNNQ<br>ADTTWWQSQTMLAGVQYPSSINLTLHLG<br>KAFDITYVRLKFHTSRPESFAIYKRTRE<br>DGPWIPYQYYSGSCENTYSKANRGFIRT |

TABLE 1-continued

Sequences of exemplary target proteins and associated binding agents

| Target Protein | Target Protein SEQ | Exemplary Binding Agent(s) |
|---|---|---|
| | priprgtmqr nlalrwlret | GGDEQQALCTDEFSDISPLTGGNVAFST |
| | fprnssqpgv vyfadddnty | LEGRPSAYNFDNSPVLQEWVTATDIRVT |
| | slelfeemrs trrvsvwpva | LNRLNTFGDEVFNDPKVLKSYYYAISDF |
| | fvgglryeap rvngagkvvg | AVGGRCKCNGHASECMKNEFDKLVCNCK |
| | wktvfdphrp faidmagfav | HNTYGVDCEKCLPFFNDRPWRRATAESA |
| | nlrlilqrsq ayfklrgvkg | SECLPCDCNGRSQECYFDPELYRSTGHG |
| | gyqessllre ivtlndlepk | GHCTNCQDNTDGAHCERCRENFFRLGNN |
| | aanctkilvw htrtekpvlv | EACSSCHCSPVGSLSTQCDSYGRCSCKP |
| | negkkgftdp svei | GVMGDKCDRCQPGFHSLTEAGCRPCSCD |
| | Isoform 2 (SEQ ID NO: 21) | PSGSIDECNIETGRCVCKDNVEGFNCER |
| | mgneepwvqp alempkrrdi | CKPGFFNLESSNPRGCTPCFCFGHSSVC |
| | laivlivlpw tllitvwhqs | TNAVGYSVYSISSTFQIDEDGWRAEQRD |
| | tlapllavhk degsdprret | GSEASLEWSSERQDIAVISDSYFPRYFI |
| | ppgadpreyc tsdrdivevv | APAKFLGKQVLSYGQNLSFSFRVDRRDT |
| | rteyvytrpp pwsdtlptih | RLSAEDLVLEGAGLRVSVPLIAQGNSYP |
| | vvtptysrpv qkaeltrman | SETTVKYVFRLHEATDYPWRPALTPFEF |
| | tllhvpnlhw ivvedaprrt | QKLLNNLTSIKIRGTYSERSAGYLDDVT |
| | pltarllrdt glnythlhve | LASARPGPGVPATWVESCTCPVGYGGQF |
| | tprnyklrgd ardpriprgt | CEMCLSGYRRETPNLGPYSPCVLCACNG |
| | mqrnlalrwl retfprnssq | HSETCDPETGVCNCRDNTAGPHCEKCSD |
| | pgvvyfaddd ntyslelfee | GYYGDSTAGTSSDCQPCPCPGGSSCAVV |
| | mrstrrvsvw pvafvgglry | PKTKEVVCTNCPTGTTGKRCELCDDGYF |
| | eaprvngagk vvgwktvfdp | GDPLGRNGPVRLCRLCQCSDNIDPNAVG |
| | hrpfaidmag favnlrlilq | NCNRLTGECLKCIYNTAGFYCDRCKDGF |
| | rsqayfklrg vkggyqessl | FGNPLAPNPADKCKACNCNLYGTMKQQS |
| | lrelvtlndl epkaanctki | SCNPVTGQCECLPHVTGQDCGACDPGFY |
| | lvwhtrtekp vlvnegkkgf | NLQSGQGCERCDCHALGSTNGQCDIRTG |
| | tdpsvei | QCECQPGITGQHCERCEVNHFGFGPEGC |
| | | KPCDCHPEGSLSLQCKDDGRCECREGFV |
| | | GNRCDQCEENYFYNRSWPGCQECPACYR |
| | | LVKDKVADHRVKLQELESLIANLGTGDE |
| | | MVTDQAFEDRLKEAEREVMDLLREAQDV |
| | | KDVDQNLMDRLQRVNNTLSSQISRLQNI |
| | | RNTIEETGNLAEQARAHVENTERLIEIA |
| | | SRELEKAKVAAANVSVTQPESTGDPNNM |
| | | TLLAEEARKLAERHKQEADDIVRVAKTA |
| | | NDTSTEAYNLLLRTLAGENQTAFEIEEL |
| | | NRKYEQAKNISQDLEKQAARVHEEAKRA |
| | | GDKAVEIYASVAQLSPLDSETLENEANN |
| | | IKMEAENLEQLIDQKLKDYEDLREDMRG |
| | | KELEVKNLLEKGKTEQQTADQLLARADA |
| | | AKALAEEAAKKGRDTLQEANDILNNLKD |
| | | FDRRVNDNKTAAEEALRKIPAINQTITE |
| | | ANEKTREAQQALGSAAADATEAKNKAHE |
| | | AERIASAVQKNATSTKAEAERTFAEVTD |
| | | LDNEVNNMLKQLQEAEKELKRKQDDADQ |
| | | DMMMAGMASQAAQEAEINARKAKNSVTS |
| | | LLSIINDLLEQLGQLDTVDLNKLNEIEG |
| | | TLNKAKDEMKVSDLDRKVSDLENEAKKQ |
| | | EAAIMDYNRDIEEIMKDIRNLEDIRKTL |
| | | PSGCFNTPSIEKP |
| | | Laminin (Laminin subunit |
| | | beta-2) (SEQ ID NO: 86) |
| | | MELTSRERGRGQPLPWELRLGLLLSVLA |
| | | ATLAQAPAPDVPGCSRGSCYPATGDLLV |
| | | GRADRLTASSTCGLNGPQPYCIVSHLQD |
| | | EKKCFLCDSRRPFSARDNPHSHRIQNVV |
| | | TSFAPQRRAAWWQSENGIPAVTIQLDLE |
| | | AEFHFTHLIMTFKTFRPAAMLVERSADF |
| | | GRTWHVYRYFSYDCGADFPGVPLAPPRH |
| | | WDDVVCESRYSEIEPSTEGEVIYRVLDP |
| | | AIPIPDPYSSRIQNLLKITNLRVNLTRL |
| | | HTLGDNLLDPRREIREKYYYALYELVVR |
| | | GNCFCYGHASECAPAPGAPAHAEGMVHG |
| | | ACICKHNTRGLNCEQCQDFYRDLPWRPA |
| | | EDGHSHACRKCECHGHTHSCHFDMAVYL |
| | | ASGNVSGGVCDGCQHNTAGRHCELCRPF |
| | | FYRDPTKDLRDPAVCRSCDCDPMGSQDG |
| | | GRCDSHDDPALGLVSGQCRCKEHVVGTR |
| | | CQQCRDGFFGLSISDRLGCRRCQCNARG |
| | | TVPGSTPCDPNSGSCYCKRLVTGRGCDR |
| | | CLPGHWGLSHDLLGCRPCDCDVGGALDP |
| | | QCDEGTGQCHCRQHMVGRRCEQVQPGYF |
| | | RPFLDHLIWEAEDTRGQVLDVVERLVTP |
| | | GETPSWTGSGFVRLQEGQTLEFLVASVP |
| | | KAMDYDLLLRLEPQVPEQWAELELIVQR |

TABLE 1-continued

| Sequences of exemplary target proteins and associated binding agents | | |
| --- | --- | --- |
| Target Protein | Target Protein SEQ | Exemplary Binding Agent(s) |
| | | PGPVPAHSLCGHLVPKDDRIQGTLQPHA |
| | | RYLIFPNPVCLEPGISYKLHLKLVRTGG |
| | | SAQPETPYSGPGLLIDSLVLLPRVLVLE |
| | | MFSGGDAAALERQATFERYQCHEEGLVP |
| | | SKTSPSEACAPLLISLSTLIYNGALPCQ |
| | | CNPQGSLSSECNPHGGQCLCKPGVVGRR |
| | | CDLCAPGYYGFGPTGCQACQCSHEGALS |
| | | SLCEKTSGQCLCRTGAFGLRCDRCQRGQ |
| | | WGFPSCRPCVCNGHADECNTHTGACLGC |
| | | RDHTGGEHCERCIAGFHGDPRLPYGGQC |
| | | RPCPCPEGPGSQRHFATSCHQDEYSQQI |
| | | VCHCRAGYTGLRCEACAPGHFGDPSRPG |
| | | GRCQLCECSGNIDPMDPDACDPHTGQCL |
| | | RCLHHTEGPHCAHCKPGFHGQAARQSCH |
| | | RCTCNLLGTNPQQCPSPDQCHCDPSSGQ |
| | | CPCLPNVQGPSCDRCAPNFWNLTSGHGC |
| | | QPCACHPSRARGPTCNEFTGQCHCRAGF |
| | | GGRTCSECQELHWGDPGLQCHACDCDSR |
| | | GIDTPQCHRFTGHCSCRPGVSGVRCDQC |
| | | ARGFSGIFPACHPCHACFGDWDRVVQDL |
| | | AARTQRLEQRAQELQQTGVLGAFESSFW |
| | | HMQEKLGIVQGIVGARNTSAASTAQLVE |
| | | ATEELRREIGEATEHLTQLEADLTDVQD |
| | | ENFNANHALSGLERDRLALNLTLRQLDQ |
| | | HLDLLKHSNFLGAYDSIRHAHSQSAEAE |
| | | RRANTSALAVPSPVSNSASARHRTEALM |
| | | DAQKEDFNSKHMANQRALGKLSAHTHTL |
| | | SLTDINELVCGAPGDAPCATSPCGGAGC |
| | | RDEDGQPRCGGLSCNGAAATADLALGRA |
| | | RHTQAELQRALAEGGSILSRVAETRRQA |
| | | SEAQQRAQAALDKANASRGQVEQANQEL |
| | | QELIQSVKDFLNQEGADPDSIEMVATRV |
| | | LELSIPASAEQIQHLAGAIAERVRSLAD |
| | | VDAILARTVGDVRRAEQLLQDARRARSW |
| | | AEDEKQKAETVQAALEEAQRAQGIAQGA |
| | | IRGAVADTRDTEQTLYQVQERMAGAERA |
| | | LSSAGERARQLDALLEALKLKRAGNSLA |
| | | ASTAEETAGSAQGRAQEAEQLLRGPLGD |
| | | QYQTVKALAERKAQGVLAAQARAEQLRD |
| | | EARDLLQAAQDKLQRLQELEGTYEENER |
| | | ALESKAAQLDGLEARMRSVLQAINLQVQ |
| | | IYNTCQ |
| | | Laminin (Laminin subunit |
| | | beta-1) (SEQ ID NO: 87) |
| | | MGLLQLLAFSFLALCRARVRAQEPEFSY |
| | | GCAEGSCYPATGDLLIGRAQKLSVTSTC |
| | | GLHKPEPYCIVSHLQEDKKCFICNSQDP |
| | | YHETLNPDSHLIENVVTTFAPNRLKIWW |
| | | QSENGVENVTIQLDLEAEFHFTHLIMTF |
| | | KTFRPAAMLIERSSDFGKTWGVYRYFAY |
| | | DCEASFPGISTGPMKKVDDIICDSRYSD |
| | | IEPSTEGEVIFRALDPAFKIEDPYSPRI |
| | | QNLLKITNLRIKFVKLHTLGDNLLDSRM |
| | | EIREKYYYAVYDMVVRGNCFCYGHASEC |
| | | APVDGFNEEVEGMVHGHCMCRHNTKGLN |
| | | CELCMDFYHDLPWRPAEGRNSNACKKCN |
| | | CNEHSISCHFDMAVYLATGNVSGGVCDD |
| | | CQHNTMGRNCEQCKPFYYQHPERDIRDP |
| | | NFCERCTCDPAGSQNEGICDSYTDFSTG |
| | | LIAGQCRCKLNVEGEHCDVCKEGFYDLS |
| | | SEDPFGCKSCACNPLGTIPGGNPCDSET |
| | | GHCYCKRLVTGQHCDQCLPEHWGLSNDL |
| | | DGCRPCDCDLGGALNNSCFAESGQCSCR |
| | | PHMIGRQCNEVEPGYYFATLDHYLYEAE |
| | | EANLGPGVSIVERQYIQDRIPSWTGAGF |
| | | VRVPEGAYLEFFIDNIPYSMEYDILIRY |
| | | EPQLPDHWEKAVITVQRPGRIPTSSRCG |
| | | NTIPDDDNQVVSLSPGSRYVVLPRPVCF |
| | | EKGTNYTVRLELPQYTSSDSDVESPYTL |
| | | IDSLVLMPYCKSLDIFTVGGSGDGVVTN |
| | | SAWETFQRYRCLENSRSVVKTPMTDVCR |
| | | NIIFSISALLHQTGLACECDPQGSLSSV |
| | | CDPNGGQCQCRPNVVGRTCNRCAPGTFG |
| | | FGPSGCKPCECHLQGSVNAFCNPVTGQC |
| | | HCFQGVYARQCDRCLPGHWGFPSCQPCQ |
| | | CNGHADDCDPVTGECLNCQDYTMGHNCE |

TABLE 1-continued

| Sequences of exemplary target proteins and associated binding agents | | |
| --- | --- | --- |
| Target Protein | Target Protein SEQ | Exemplary Binding Agent(s) |
| | | RCLAGYYGDPIIGSGDHCRPCPCPDGPD |
| | | SGRQFARSCYQDPVTLQLACVCDPGYIG |
| | | SRCDDCASGYFGNPSEVGGSCQPCQCHN |
| | | NIDTTDPEACDKETGRCLKCLYHTEGEH |
| | | CQFCRFGYYGDALQQDCRKCVCNYLGTV |
| | | QEHCNGSDCQCDKATGQCLCLPNVIGQN |
| | | CDRCAPNTWQLASGTGCDPCNCNAAHSF |
| | | GPSCNEFTGQCQCMPGFGGRTCSECQEL |
| | | FWGDPDVECRACDCDPRGIETPQCDQST |
| | | GQCVCVEGVEGPRCDKCTRGYSGVFPDC |
| | | TPCHQCFALWDVIIAELTNRTHRFLEKA |
| | | KALKISGVIGPYRETVDSVERKVSEIKD |
| | | ILAQSPAAEPLKNIGNLFEEAEKLIKDV |
| | | TEMMAQVEVKLSDTTSQSNSTAKELDSL |
| | | QTEAESLDNTVKELAEQLEFIKNSDIRG |
| | | ALDSITKYFQMSLEAEERVNASTTEPNS |
| | | TVEQSALMRDRVEDVMMERESQFKEKQE |
| | | EQARLLDELAGKLQSLDLSAAAEMTCGT |
| | | PPGASCSETECGGPNCRTDEGERKCGGP |
| | | GCGGLVTVAHNAWQKAMDLDQDVLSALA |
| | | EVEQLSKMVSEAKLRADEAKQSAEDILL |
| | | KTNATKEKMDKSNEELRNLIKQIRNFLT |
| | | QDSADLDSIEAVANEVLKMEMPSTPQQL |
| | | QNLTEDIRERVESLSQVEVILQHSAADI |
| | | ARAEMLLEEAKRASKSATDVKVTADMVK |
| | | EALEEAEKAQVAAEKAIKQADEDIQGTQ |
| | | NLLTSIESETAASEETLFNASQRISELE |
| | | RNVEELKRKAAQNSGEAEYIEKVVYTVK |
| | | QSAEDVKKTLDGELDEKYKKVENLIAKK |
| | | TEESADARRKAEMLQNEAKTLLAQANSK |
| | | LQLLKDLERKYEDNQRYLEDKAQELARL |
| | | EGEVRSLLKDISQKVAVYSTCL |
| | | Laminin (Laminin subunit |
| | | alpha-2) (SEQ ID NO: 88) |
| | | MPGAAGVLLLLLLSGGLGGVQAQRPQQQ |
| | | RQSQAHQQRGLFPAVLNLASNALITTNA |
| | | TCGEKGPEMYCKLVEHVPGQPVRNPQCR |
| | | ICNQNSSNPNQRHPITNAIDGKNTWWQS |
| | | PSIKNGIEYHYVTITLDLQQVFQIAYVI |
| | | VKAANSPRPGNWILERSLDDVEYKPWQY |
| | | HAVTDTECLTLYNIYPRTGPPSYAKDDE |
| | | VICTSFYSKIHPLENGEIHISLINGRPS |
| | | ADDPSPELLEFTSARYIRLRFQRIRTLN |
| | | ADLMMFAHKDPREIDPIVTRRYYYSVKD |
| | | ISVGGMCICYGHARACPLDPATNKSRCE |
| | | CEHNTCGDSCDQCCPGFHQKPWRAGTFL |
| | | TKTECEACNCHGKAEECYYDENVARRNL |
| | | SLNIRGKYIGGGVCINCTQNTAGINCET |
| | | CTDGFFRPKGVSPNYPRPCQPCHCDPIG |
| | | SLNEVCVKDEKHARRGLAPGSCHCKTGF |
| | | GGVSCDRCARGYTGYPDCKACNCSGLGS |
| | | KNEDPCFGPCICKENVEGGDCSRCKSGF |
| | | FNLQEDNWKGCDECFCSGVSNRCQSSYW |
| | | TYGKIQDMSGWYLTDLPGRIRVAPQQDD |
| | | LDSPQQISISNAEARQALPHSYYWSAPA |
| | | PYLGNKLPAVGGQLTFTISYDLEEEEED |
| | | TERVLQLMIILEGNDLSISTAQDEVYLH |
| | | PSEEHTNVLLLKEESFTIHGTHFPVRRK |
| | | EFMTVLANLKRVLLQITYSFGMDAIFRL |
| | | SSVNLESAVSYPTDGSIAAAVEVCQCPP |
| | | GYTGSSCESCWPRHRRVNGTIFGGICEP |
| | | CQCFGHAESCDDVTGECLNCKDHTGGPY |
| | | CDKCLPGFYGEPTKGTSEDCQPCACPLN |
| | | IPSNNFSPTCHLDRSLGLICDGCPVGYT |
| | | GPRCERCAEGYFGQPSVPGGSCQPCQCN |
| | | DNLDFSIPGSCDSLSGSCLICKPGTTGR |
| | | YCELCADGYFGDAVDAKNCQPCRCNAGG |
| | | SFSEVCHSQTGQCECRANVQGQRCDKCK |
| | | AGTFGLQSARGCVPCNCNSFGSKSFDCE |
| | | ESGQCWCQPGVTGKKCDRCAHGYFNFQE |
| | | GGCTACECSHLGNNCDPKTGRCICPPNT |
| | | IGEKCSKCAPNTWGHSITTGCKACNCST |
| | | VGSLDFQCNVNTGQCNCHPKFSGAKCTE |
| | | CSRGHWNYPRCNLCDCFLPGTDATTCDS |
| | | ETKKCSCSDQTGQCTCKVNVEGIHCDRC |
| | | RPGKFGLDAKNPLGCSSCYCFGTTTQCS |

TABLE 1-continued

| Sequences of exemplary target proteins and associated binding agents | | |
|---|---|---|
| Target Protein | Target Protein SEQ | Exemplary Binding Agent(s) |
| | | EAKGLIRTWVTLKAEQTILPLVDEALQH<br>TTTKGIVFQHPEIVAHMDLMREDLHLEP<br>FYWKLPEQFEGKKLMAYGGKLKYAIYFE<br>AREETGFSTYNPQVIIRGGTPTHARIIV<br>RHMAAPLIGQLTRHEIEMTEKEWKYYGD<br>DPRVHRTVTREDFLDILYDIHYILIKAT<br>YGNFMRQSRISEISMEVAEQGRGTTMTP<br>PADLIEKCDCPLGYSGLSCEACLPGFYR<br>LRSQPGGRTPGPTLGTCVPCQCNGHSSL<br>CDPETSICQNCQHHTAGDFCERCALGYY<br>GIVKGLPNDCQQCACPLISSSNNFSPSC<br>VAEGLDDYRCTACPRGYEGQYCERCAPG<br>YTGSPGNPGGSCQECECDPYGSLPVPCD<br>PVTGFCTCRPGATGRKCDGCKHWHAREG<br>WECVFCGDECTGLLLGDLARLEQMVMSI<br>NLTGPLPAPYKMLYGLENMTQELKHLLS<br>PQRAPERLIQLAEGNLNTLVTEMNELLT<br>RATKVTADGEQTGQDAERTNTRAKSLGE<br>FIKELARDAEAVNEKAIKLNETLGTRDE<br>AFERNLEGLQKEIDQMIKELRRKNLETQ<br>KEIAEDELVAAEALLKKVKKLFGESRGE<br>NEEMEKDLREKLADYKNKVDDAWDLLRE<br>ATDKIREANRLFAVNQKNMTALEKKKEA<br>VESGKRQIENTLKEGNDILDEANRLADE<br>INSIIDYVEDIQTKLPPMSEELNDKIDD<br>LSQEIKDRKLAEKVSQAESHAAQLNDSS<br>AVLDGILDEAKNISFNATAAFKAYSNIK<br>DYIDEAEKVAKEAKDLAHEATKLATGPR<br>GLLKEDAKGCLQKSFRILNEAKKLANDV<br>KENEDHLNGLKTRIENADARNGDLLRTL<br>NDTLGKLSAIPNDTAAKLQAVKDKARQA<br>NDTAKDVLAQITELHQNLDGLKKNYNKL<br>ADSVAKTNAVVKDPSKNKIIADADATVK<br>NLEQEADRLIDKLKPIKELEDNLKKNIS<br>EIKELINQARKQANSIKVSVSSGGDCIR<br>TYKPEIKKGSYNNIVVNVKTAVADNLLF<br>YLGSAKFIDFLAIEMRKGKVSFLWDVGS<br>GVGRVEYPDLTIDDSYWYRIVASRTGRN<br>GTISVRALDGPKASIVPSTHHSTSPPGY<br>TILDVDANAMLFVGGLTGKLKKADAVRV<br>ITFTGCMGETYFDNKPIGLWNFREKEGD<br>CKGCTVSPQVEDSEGTIQFDGEGYALVS<br>RPIRWYPNISTVMFKFRTFSSSALLMYL<br>ATRDLRDFMSVELTDGHIKVSYDLGSGM<br>ASVVSNQNHNDGKWKSFTLSRIQKQANI<br>SIVDIDTNQEENIATSSSGNNFGLDLKA<br>DDKIYFGGLPTLRNLSMKARPEVNLKKY<br>SGCLKDIEISRTPYNILSSPDYVGVTKG<br>CSLENVYTVSFPKPGFVELSPVPIDVGT<br>EINLSFSTKNESGIILLGSGGTPAPPRR<br>KRRQTGQAYYAILLNRGRLEVHLSTGAR<br>TMRKIVIRPEPNLFHDGREHSVHVERTR<br>GIFTVQVDENRRYMQNLTVEQPIEVKKL<br>FVGGAPPEFQPSPLRNIPPFEGCIWNLV<br>INSVPMDFARPVSFKNADIGRCAHQKLR<br>EDEDGAAPAEIVIQPEPVPTPAFPTPTP<br>VLTHGPCAAESEPALLIGSKQFGLSRNS<br>HIAIAFDDTKVKNRLTIELEVRTEAESG<br>LLFYMARINHADFATVQLRNGLPYFSYD<br>LGSGDTHTMIPTKINDGQWHKIKIMRSK<br>QEGILYVDGASNRTISPKKADILDVVGM<br>LYVGGLPINYTTRRIGPVTYSIDGCVRN<br>LHMAEAPADLEQPTSSFHVGTCFANAQR<br>GTYFDGTGFAKAVGGFKVGLDLLVEFEF<br>RTTTTTGVLLGISSQKMDGMGIEMIDEK<br>LMFHVDNGAGRFTAVYDAGVPGHLCDGQ<br>WHKVTANKIKHRIELTVDGNQVEAQSPN<br>PASTSADTNDPVFVGGFPDDLKQFGLTT<br>SIPFRGCIRSLKLTKGTGKPLEVNFAKA<br>LELRGVQPVSCPAN<br>Laminin (Laminin subunit<br>alpha-1) (SEQ ID NO: 89)<br>MRGGVLLVLLLCVAAQCRQRGLFPAILN<br>LASNAHISTNATCGEKGPEMFCKLVEHV<br>PGRPVRNPQCRICDGNSANPRERHPISH<br>AIDGTNNWWQSPSIQNGREYHWVTITLD |

TABLE 1-continued

Sequences of exemplary target proteins and associated binding agents

| Target Protein | Target Protein SEQ | Exemplary Binding Agent(s) |
|---|---|---|
| | | LRQVFQVAYVIIKAANAPRPGNWILERS |
| | | LDGTTFSPWQYYAVSDSECLSRYNITPR |
| | | RGPPTYRADDEVICTSYYSRLVPLEHGE |
| | | IHTSLINGRPSADDLSPKLLEFTSARYI |
| | | RLRLQRIRTLNADLMTLSHREPKELDPI |
| | | VTRRYYYSIKDISVGGMCICYGHASSCP |
| | | WDETTKKLQCQCEHNTCGESCNRCCPGY |
| | | HQQPWRPGTVSSGNTCEACNCHNKAKDC |
| | | YYDESVAKQKKSLNTAGQFRGGGVCINC |
| | | LQNTMGINCETCIDGYYRPHKVSPYEDE |
| | | PCRPCNCDPVGSLSSVCIKDDLHSDLHN |
| | | GKQPGQCPCKEGYTGEKCDRCQLGYKDY |
| | | PTCVSCGCNPVGSASDEPCTGPCVCKEN |
| | | VEGKACDRCKPGFYNLKEKNPRGCSECF |
| | | CFGVSDVCSSLSWPVGQVNSMSGWLVTD |
| | | LISPRKIPSQQDALGGRHQVSINNTAVM |
| | | QRLAPKYYWAAPEAYLGNKLTAFGGFLK |
| | | YTVSYDIPVETVDSNLMSHADVIIKGNG |
| | | LTLSTQAEGLSLQPYEEYLNVVRLVPEN |
| | | FQDFHSKRQIDRDQLMTVLANVTHLLIR |
| | | ANYNSAKMALYRLESVSLDIASSNAIDL |
| | | VVAADVEHCECPQGYTGTSCESCLSGYY |
| | | RVDGILFGGICQPCECHGHAAECNVHGV |
| | | CIACAHNTTGVHCEQCLPGFYGEPSRGT |
| | | PGDCQPCACPLTIASNNFSPTCHLNDGD |
| | | EVVCDWCAPGYSGAWCERCADGYYGNPT |
| | | VPGESCVPCDCSGNVDPSEAGHCDSVTG |
| | | ECLKCLGNTDGAHCERCADGFYGDAVTA |
| | | KNCRACECHVKGSHSAVCHLETGLCDCK |
| | | PNVTGQQCDQCLHGYYGLDSGHGCRPCN |
| | | CSVAGSVSDGCTDEGQCHCVPGVAGKRC |
| | | DRCAHGFYAYQDGSCTPCDCPHTQNTCD |
| | | PETGECVCPPHTQGVKCEECEDGHWGYD |
| | | AEVGCQACNCSLVGSTHHRCDVVTGHCQ |
| | | CKSKFGGRACDQCSLGYRDFPDCVPCDC |
| | | DLRGTSGDACNLEQGLCGCVEETGACPC |
| | | KENVFGPQCNECREGTFALRADNPLGCS |
| | | PCFCSGLSHLCSELEDYVRTPVTLGSDQ |
| | | PLLRVVSQSNLRGTTEGVYYQAPDFLLD |
| | | AATVRQHIRAEPFYWRLPQQFQGDQLMA |
| | | YGGKLKYSVAFYSLDGVGTSNFEPQVLI |
| | | KGGRIRKQVIYMDAPAPENGVRQEQEVA |
| | | MRENFWKYFNSVSEKPVTREDFMSVLSD |
| | | IEYILIKASYGQGLQQSRISDISMEVGR |
| | | KAEKLHPEEEVASLLENCVCPPGTVGFS |
| | | CQDCAPGYHRGKLPAGSDRGPRPLVAPC |
| | | VPCSCNNHSDTCDPNTGKCLNCGDNTAG |
| | | DHCDVCTSGYYGKVTGSASDCALCACPH |
| | | SPPASFSPTCVLEGDHDFRCDACLLGYE |
| | | GKHCERCSSSYYGNPQTPGGSCQKCDCN |
| | | PHGSVHGDCDRTSGQCVCRLGASGLRCD |
| | | ECEPRHILMETDCVSCDDECVGVLLNDL |
| | | DEIGDAVLSLNLTGIIPVPYGILSNLEN |
| | | TTKYLQESLLKENMQKDLGKIKLEGVAE |
| | | ETDNLQKKLTRMLASTQKVNRATERIFK |
| | | ESQDLAIAIERLQMSITEIMEKTTLNQT |
| | | LDEDFLLPNSTLQNMQQNGTSLLEIMQI |
| | | RDFTQLHQNATLELKAAEDLLSQIQENY |
| | | QKPLEELEVLKEAASHVLSKHNNELKAA |
| | | EALVREAEAKMQESNHLLLMVNANLREF |
| | | SDKKLHVQEEQNLTSELIVQGRGLIDAA |
| | | AAQTDAVQDALEHLEDHQDKLLLWSAKI |
| | | RHHIDDLVMHMSQRNAVDLVYRAEDHAA |
| | | EFQRLADVLYSGLENIRNVSLNATSAAY |
| | | VHYNIQSLIEESEELARDAHRTVTETSL |
| | | LSESLVSNGKAAVQRSSRFLKEGNNLSR |
| | | KLPGIALELSELRNKTNRFQENAVEITR |
| | | QTNESLLILRAIPKGIRDKGAKTKELAT |
| | | SASQSAVSTLRDVAGLSQELLNTSASLS |
| | | RVNTTLRETHQLLQDSTMATLLAGRKVK |
| | | DVEIQANLLFDRLKPLKMLEENLSRNLS |
| | | EIKLLISQARKQAASIKVAVSADRDCIR |
| | | AYQPQISSTNYNTLTLNVKTQEPDNLLF |
| | | YLGSSTASDFLAVEMRRGRVAFLWDLGS |
| | | GSTRLEFPDFPIDDNRWHSIHVARFGNI |
| | | GSLSVKEMSSNQKSPTKTSKSPGTANVL |

TABLE 1-continued

Sequences of exemplary target proteins and associated binding agents

| Target Protein | Target Protein SEQ | Exemplary Binding Agent(s) |
|---|---|---|
| | | DVNNSTLMFVGGLGGQIKKSPAVKVTHF |
| | | KGCLGEAFLNGKSIGLWNYIEREGKCRG |
| | | CFGSSQNEDPSFHFDGSGYSVVEKSLPA |
| | | TVTQIIMLFNTFSPNGLLLYLGSYGTKD |
| | | FLSIELFRGRVKVMTDLGSGPITLLTDR |
| | | RYNNGTWYKIAFQRNRKQGVLAVIDAYN |
| | | TSNKETKQGETPGASSDLNRLDKDPIYV |
| | | GGLPRSRVVRRGVTTKSFVGCIKNLEIS |
| | | RSTFDLLRNSYGVRKGCLLEPIRSVSFL |
| | | KGGYIELPPKSLSPESEWLVTFATTNSS |
| | | GIILAALGGDVEKRGDREEAHVPFFSVM |
| | | LIGGNIEVHVNPGDGTGLRKALLHAPTG |
| | | TCSDGQAHSISLVRNRRIITVQLDENNP |
| | | VEMKLGTLVESRTINVSNLYVGGIPEGE |
| | | GTSLLTMRRSFHGCIKNLIFNLELLDFN |
| | | SAVGHEQVDLDTCWLSERPKLAPDAEDS |
| | | KLLPEPRAFPEQCVVDAALEYVPGAHQF |
| | | GLTQNSHFILPFNQSAVRKKLSVELSIR |
| | | TFASSGLIYYMAHQNQADYAVLQLHGGR |
| | | LHFMFDLGKGRTKVSHPALLSDGKWHTV |
| | | KTDYVKRKGFITVDGRESPMVTVVGDGT |
| | | MLDVEGLFYLGGLPSQYQARKIGNITHS |
| | | IPACIGDVTVNSKQLDKDSPVSAFTVNR |
| | | CYAVAQEGTYFDGSGYAALVKEGYKVQS |
| | | DVNITLEFRTSSQNGVLLGISTAKVDAI |
| | | GLELVDGKVLFHVNNGAGRITAAYEPKT |
| | | ATVLCDGKWHTLQANKSKHRITLIVDGN |
| | | AVGAESPHTQSTSVDTNNPIYVGGYPAG |
| | | VKQKCLRSQTSFRGCLRKLALIKSPQVQ |
| | | SFDFSRAFELHGVFLHSCPGTES |
| | | Laminin (Laminin subunit |
| | | alpha-5) (SEQ ID NO: 90) |
| | | MAKRLCAGSALCVRGPRGPAPLLLVGLA |
| | | LLGAARAREEAGGGFSLHPPYFNLAEGA |
| | | RIAASATCGEEAPARGSPRPTEDLYCKL |
| | | VGGPVAGGDPNQTIRGQYCDICTAANSN |
| | | KAHPASNAIDGTERWWQSPPLSRGLEYN |
| | | EVNVTLDLGQVFHVAYVLIKFANSPRPD |
| | | LWVLERSMDFGRTYQPWQFFASSKRDCL |
| | | ERFGPQTLERITRDDAAICTTEYSRIVP |
| | | LENGEIVVSLVNGRPGAMNFSYSPLLRE |
| | | FTKATNVRLRFLRTNTLLGHLMGKALRD |
| | | PTVTRRYYYSIKDISIGGRCVCHGHADA |
| | | CDAKDPTDPFRLQCTCQHNTCGGTCDRC |
| | | CPGFNQQPWKPATANSANECQSCNCYGH |
| | | ATDCYYDPEVDRRRASQSLDGTYQGGGV |
| | | CIDCQHHTTGVNCERCLPGFYRSPNHPL |
| | | DSPHVCRRCNCESDFTDGTCEDLTGRCY |
| | | CRPNFSGERCDVCAEGFTGFPSCYPTPS |
| | | SSNDTREQVLPAGQIVNCDCSAAGTQGN |
| | | ACRKDPRVGRCLCKPNFQGTHCELCAPG |
| | | FYGPGCQPCQCSSPGVADDRCDPDTGQC |
| | | RCRVGFEGATCDRCAPGYFHFPLCQLCG |
| | | CSPAGTLPEGCDEAGRCLCQPEFAGPHC |
| | | DRCRPGYHGFPNCQACTCDPRGALDQLC |
| | | GAGGLCRCRPGYTGTACQECSPGFHGFP |
| | | SCVPCHCSAEGSLHAACDPRSGQCSCRP |
| | | RVTGLRCDTCVPGAYNFPYCEAGSCHPA |
| | | GLAPVDPALPEAQVPCMCRAHVEGPSCD |
| | | RCKPGFWGLSPSNPEGCTRCSCDLRGTL |
| | | GGVAECQPGTGQCFCKPHVCGQACASCK |
| | | DGFFGLDQADYFGCRSCRCDIGGALGQS |
| | | CEPRTGVCRCRPNTQGPTCSEPARDHYL |
| | | PDLHHLRLELEEAATPEGHAVRFGFNPL |
| | | EFENFSWRGYAQMAPVQPRIVARLNLTS |
| | | PDLFWLVFRYVNRGAMSVSGRVSVREEG |
| | | RSATCANCTAQSQPVAFPPSTEPAFITV |
| | | PQRGFGEPFVLNPGTWALRVEAEGVLLD |
| | | YVVLLPSAYYEAALLQLRVTEACTYRPS |
| | | AQQSGDNCLLYTHLPLDGFPSAAGLEAL |
| | | CRQDNSLPRPCPTEQLSPSHPPLITCTG |
| | | SDVDVQLQVAVPQPGRYALVVEYANEDA |
| | | RQEVGVAVHTPQRAPQQGLLSLHPCLYS |
| | | TLCRGTARDTQDHLAVFHLDSEASVRLT |
| | | AEQARFFLHGVTLVPIEEFSPEFVEPRV |
| | | SCISSHGAFGPNSAACLPSRFPKPPQPI |

TABLE 1-continued

Sequences of exemplary target proteins and associated binding agents

| Target Protein | Target Protein SEQ | Exemplary Binding Agent(s) |
| --- | --- | --- |
| | | ILRDCQVIPLPPGLPLTHAQDLTPAMSP |
| | | AGPRPRPPTAVDPDAEPTLLREPQATVV |
| | | FTTHVPTLGRYAFLLHGYQPAHPTFPVE |
| | | VLINAGRVWQGHANASFCPHGYGCRTLV |
| | | VCEGQALLDVTHSELTVTRVPKGRWLW |
| | | LDYVLVVPENVYSFGYLREEPLDKSYDF |
| | | ISHCAAQGYHISPSSSSLFCRNAAASLS |
| | | LFYNNGARPCGCHEVGATGPTCEPFGGQ |
| | | CPCHAHVIGRDCSRCATGYWGFPNCRPC |
| | | DCGARLCDELTGQCICPPRTIPPDCLLC |
| | | QPQTFGCHPLVGCEECNCSGPGIQELTD |
| | | PTCDTDSGQCKCRPNVTGRRCDTCSPGF |
| | | HGYPRCRPCDCHEAGTAPGVCDPLTGQC |
| | | YCKENVQGPKCDQCSLGTFSLDAANPKG |
| | | CTRCFCFGATERCRSSSYTRQEFVDMEG |
| | | WVLLSTDRQVVPHERQPGTEMLRADLRH |
| | | VPEAVPEAFPELYWQAPPSYLGDRVSSY |
| | | GGTLRYELHSETQRGDVFVPMESRPDVV |
| | | LQGNQMSITFLEPAYPTPGHVHRGQLQL |
| | | VEGNFRHTETRNTVSREELMMVLASLEQ |
| | | LQIRALFSQISSAVFLRRVALEVASPAG |
| | | QGALASNVELCLCPASYRGDSCQECAPG |
| | | FYRDVKGLFLGRCVPCQCHGHSDRCLPG |
| | | SGVCVDCQHNTEGAHCERCQAGFVSSRD |
| | | DPSAPCVSCPCPLSVPSNNFAEGCVLRG |
| | | GRTQCLCKPGYAGASCERCAPGFFGNPL |
| | | VLGSSCQPCDCSGNGDPNLLFSDCDPLT |
| | | GACRGCLRHTTGPRCEICAPGFYGNALL |
| | | PGNCTRCDCTPCGTEACDPHSGHCLCKA |
| | | GVTGRRCDRCQEGHFGFDGCGGCRPCAC |
| | | GPAAEGSECHPQSGQCHCRPGTMGPQCR |
| | | ECAPGYWGLPEQGCRRCQCPGGRCDPHT |
| | | GRCNCPPGLSGERCDTCSQQHQVPVPGG |
| | | PVGHSIHCEVCDHCVVLLLDDLERAGAL |
| | | LPAIHEQLRGINASSMAWARLHRLNASI |
| | | ADLQSQLRSPLGPRHETAQQLEVLEQQS |
| | | TSLGQDARRLGGQAVGTRDQASQLLAGT |
| | | EATLGHAKTLLAAIRAVDRTLSELMSQT |
| | | GHLGLANASAPSGEQLLRTLAEVERLLW |
| | | EMRARDLGAPQAAAEAELAAAQRLLARV |
| | | QEQLSSLWEENQALATQTRDRLAQHEAG |
| | | LMDLREALNRAVDATREAQELNSRNQER |
| | | LEEALQRKQELSRDNATLQATLHAARDT |
| | | LASVFRLLHSLDQAKEELERLAASLDGA |
| | | RTPLLQRMQTFSPAGSKLRLVEAAEAHA |
| | | QQLGQLALNLSSIILDVNQDRLTQRAIE |
| | | ASNAYSRILQAVQAAEDAAGQALQQADH |
| | | TWATVVRQGLVDRAQQLLANSTALEEAM |
| | | LQEQQRLGLVWAALQGARTQLRDVRAKK |
| | | DQLEAHIQAAQAMLAMDTDETSKKIAHA |
| | | KAVAAEAQDTATRVQSQLQAMQENVERW |
| | | QGQYEGLRGQDLGQAVLDAGHSVSTLEK |
| | | TLPQLLAKLSILENRGVHNASLALSASI |
| | | GRVRELIAQARGAASKVKVPMKFNGRSG |
| | | VQLRTPRDLADLAAYTALKFYLQGPEPE |
| | | PGQGTEDRFVMYMGSRQATGDYMGVSLR |
| | | DKKVHWVYQLGEAGPAVLSIDEDIGEQF |
| | | AAVSLDRTLQFGHMSVTVERQMIQETKG |
| | | DTVAPGAEGLLNLRPDDFVFYVGGYPST |
| | | FTPPPLLRFPGYRGCIEMDTLNEEVVSL |
| | | YNFERTFQLDTAVDRPCARSKSTGDPWL |
| | | TDGSYLDGTGFARISFDSQISTTKRFEQ |
| | | ELRLVSYSGVLFFLKQQSQFLCLAVQEG |
| | | SLVLLYDFGAGLKKAVPLQPPPPLTSAS |
| | | KAIQVFLLGGSRKRVLVRVERATVYSVE |
| | | QDNDLELADAYYLGGVPPDQLPPSLRRL |
| | | FPTGGSVRGCVKGIKALGKYVDLKRLNT |
| | | TGVSAGCTADLLVGRAMTFHGHGFLRLA |
| | | LSNVAPLTGNVYSGFGFHSAQDSALLYY |
| | | RASPDGLCQVSLQQGRVSLQLLRTEVKT |
| | | QAGFADGAPHYVAFYSNATGVWLYVDDQ |
| | | LQQMKPHRGPPPELQPQPEGPPRLLLGG |
| | | LPESGTIYNFSGCISNVFVQRLLGPQRV |
| | | FDLQQNLGSVNVSTGCAPALQAQTPGLG |
| | | PRGLQATARKASRRSRQPARHPACMLPP |
| | | HLRTTRDSYQFGGSLSSHLEFVGILARH |

TABLE 1-continued

| Sequences of exemplary target proteins and associated binding agents | | |
| --- | --- | --- |
| Target Protein | Target Protein SEQ | Exemplary Binding Agent(s) |
| | | RNWPSLSMHVLPRSSRGLLLFTARLRPG |
| | | SPSLALFLSNGHFVAQMEGLGTRLRAQS |
| | | RQRSRPGRWHKVSVRWEKNRILLVTDGA |
| | | RAWSQEGPHRQHQGAEHPQPHTLFVGGL |
| | | PASSHSSKLPVTVGFSGCVKRLRLHGRP |
| | | LGAPTRMAGVTPCILGPLEAGLFFPGSG |
| | | GVITLDLPGATLPDVGLELEVRPLAVTG |
| | | LIFHLGQARTPPYLQLQVTEKQVLLRAD |
| | | DGAGEFSTSVTRPSVLCDGQWHRLAVMK |
| | | SGNVLRLEVDAQSNHTVGPLLAAAAGAP |
| | | APLYLGGLPEPMAVQPWPPAYCGCMRRL |
| | | AVNRSPVAMTRSVEVHGAVGASGCPAA |
| | Laminin (Laminin subunit alpha-3) (SEQ ID NO: 91) | |
| | | MAAAARPRGRALGPVLPPTPLLLLVLRV |
| | | LPACGATARDPGAAAGLSLHPTYFNLAE |
| | | AARIWATATCGERGPGEGRPQPELYCKL |
| | | VGGPTAPGSGHTIQGQFCDYCNSEDPRK |
| | | AHPVTNAIDGSERWWQSPPLSSGTQYNR |
| | | VNLTLDLGQLFHVAYILIKFANSPRPDL |
| | | WVLERSVDFGSTYSPWQYFAHSKVDCLK |
| | | EFGREANMAVTRDDDVLCVTEYSRIVPL |
| | | ENGEVVVSLINGRPGAKNFTFSHTLREF |
| | | TKATNIRLRFLRTNTLLGHLISKAQRDP |
| | | TVTRRYYYSIKDISIGGQCVCNGHAEVC |
| | | NINNPEKLFRCECQHHTCGETCDRCCTG |
| | | YNQRRWRPAAWEQSHECEACNCHGHASN |
| | | CYYDPDVERQQASLNTQGIYAGGGVCIN |
| | | CQHNTAGVNCEQCAKGYYRPYGVPVDAP |
| | | DGCIPCSCDPEHADGCEQGSGRCHCKPN |
| | | FHGDNCEKCAIGYYNFPFCLRIPIFPVS |
| | | TPSSEDPVAGDIKGCDCNLEGVLPEICD |
| | | AHGRCLCRPGVEGPRCDTCRSGFYSFPI |
| | | CQACWCSALGSYQMPCSSVTGQCECRPG |
| | | VTGQRCDRCLSGAYDFPHCQGSSSACDP |
| | | AGTINSNLGYCQCKLHVEGPTCSRCKLL |
| | | YWNLDKENPSGCSECKCHKAGTVSGTGE |
| | | CRQGDGDCHCKSHVGGDSCDTCEDGYFA |
| | | LEKSNYFGCQGCQCDIGGALSSMCSGPS |
| | | GVCQCREHVVGKVCQRPENNYYFPDLHH |
| | | MKYEIEDGSTPNGRDLRFGFDPLAFPEF |
| | | SWRGYAQMTSVQNDVRITLNVGKSSGSL |
| | | FRVILRYVNPGTEAVSGHITIYPSWGAA |
| | | QSKEIIFLPSKEPAFVTVPGNGFADPFS |
| | | ITPGIWVACIKAEGVLLDYLVLLPRDYY |
| | | EASVLQLPVTEPCAYAGPPQENCLLYQH |
| | | LPVTRFPCTLACEARHFLLDGEPRPVAV |
| | | RQPTPAHPVMVDLSGREVELHLRLRIPQ |
| | | VGHYVVVVEYSTEAAQLFVVDVNVKSSG |
| | | SVLAGQVNIYSCNYSVLCRSAVIDHMSR |
| | | IAMYELLADADIQLKGHMARFLLHQVCI |
| | | IPIEEFSAEYVRPQVHCIASYGRFVNQS |
| | | ATCVSLAHETPPTALILDVLSGRPFPHL |
| | | PQQSSPSVDVLPGVTLKAPQNQVTLRGR |
| | | VPHLGRYVFVIHFYQAAHPTFPAQVSVD |
| | | GGWPRAGSFHASFCPHVLGCRDQVIAEG |
| | | QIEFDISEPEVAATVKVPEGKSLVLVRV |
| | | LVVPAENYDYQILHKKSMDKSLEFITNC |
| | | GKNSFYLDPQTASRFCKNSARSLVAFYH |
| | | KGALPCECHPTGATGPHCSPEGGQCPCQ |
| | | PNVIGRQCTRCATGHYGFPRCKPCSCGR |
| | | RLCEEMTGQCRCPPRTVRPQCEVCETHS |
| | | FSFHPMAGCEGCNCSRRGTIEAAMPECD |
| | | RDSGQCRCKPRITGRQCDRCASGFYRFP |
| | | ECVPCNCNRDGTEPGVCDPGTGACLCKE |
| | | NVEGTECNVCREGSFHLDPANLKGCTSC |
| | | FCFGVNNQCHSSHKRRTKFVDMLGWHLE |
| | | TADRVDIPVSFNPGSNSMVADLQELPAT |
| | | IHSASWVAPTSYLGDKVSSYGGYLTYQA |
| | | KSFGLPGDMVLLEKKPDVQLTGQHMSII |
| | | YEETNTPRPDRLHHGRVHVVEGNFRHAS |
| | | SRAPVSREELMTVLSRLADVRIQGLYFT |
| | | ETQRLTLSEVGLEEASDTGSGRIALAVE |
| | | ICACPPAYAGDSCQGCSPGYYRDHKGLY |
| | | TGRCVPCNCNGHSNQCQDGSGICVNCQH |
| | | NTAGEHCERCQEGYYGNAVHGSCRACPC |

TABLE 1-continued

Sequences of exemplary target proteins and associated binding agents

| Target Protein | Target Protein SEQ | Exemplary Binding Agent(s) |
|---|---|---|
| | | PHTNSFATGCVVNGGDVRCSCKAGYTGT |
| | | QCERCAPGYFGNPQKFGGSCQPCSCNSN |
| | | GQLGSCHPLTGDCINQEPKDSSPAEECD |
| | | DCDSCVMTLLNDLATMGEQLRLVKSQLQ |
| | | GLSASAGLLEQMRHMETQAKDLRNQLLN |
| | | YRSAISNHGSKIEGLERELTDLNQEFET |
| | | LQEKAQVNSRKAQTLNNNVNRATQSAKE |
| | | LDVKIKNVIRNVHILLKQISGTDGEGNN |
| | | VPSGDFSREWAEAQRMMRELRNRNFGKH |
| | | LREAEADKRESQLLLNRIRTWQKTHQGE |
| | | NNGLANSIRDSLNEYEAKLSDLRARLQE |
| | | AAAQAKQANGLNQENERALGAIQRQVKE |
| | | INSLQSDFTKYLTTADSSLLQTNIALQL |
| | | MEKSQKEYEKLAASLNEARQELSDKVRE |
| | | LSRSAGKTSLVEEAEKHARSLQELAKQL |
| | | EEIKRNASGDELVRCAVDAATAYENILN |
| | | AIKAAEDAANRAASASESALQTVIKEDL |
| | | PRKAKTLSSNSDKLLNEAKMTQKKLKQE |
| | | VSPALNNLQQTLNIVTVQKEVIDTNLTT |
| | | LRDGLHGIQRGDIDAMISSAKSMVRKAN |
| | | DITDEVLDGLNPIQTDVERIKDTYGRTQ |
| | | NEDFKKALTDADNSVNKLTNKLPDLWRK |
| | | IESINQQLLPLGNISDNMDRIRELIQQA |
| | | RDAASKVAVPMRFNGKSGVEVRLPNDLE |
| | | DLKGYTSLSLFLQRPNSRENGGTENMFV |
| | | MYLGNKDASRDYIGMAVVDGQLTCVYNL |
| | | GDREAELQVDQILTKSETKEAVMDRVKF |
| | | QRIYQFARLNYTKGATSSKPETPGVYDM |
| | | DGRNSNTLLNLDPENVVFYVGGYPPDFK |
| | | LPSRLSFPPYKGCIELDDLNENVLSLYN |
| | | FKKTFNLNTTEVEPCRRRKEESDKNYFE |
| | | GTGYARVPTQPHAPIPTFGQTIQTTVDR |
| | | GLLFFAENGDRFISLNIEDGKLMVRYKL |
| | | NSELPKERGVGDAINNGRDHSIQIKIGK |
| | | LQKRMWINVDVQNTIIDGEVFDFSTYYL |
| | | GGIPIAIRERFNISTPAFRGCMKNLKKT |
| | | SGVVRLNDTVGVTKKCSEDWKLVRSASF |
| | | SRGGQLSFTDLGLPPTDHLQASFGFQTF |
| | | QPSGILLDHQTWTRNLQVTLEDGYIELS |
| | | TSDSGSPIFKSPQTYMDGLLHYVSVISD |
| | | NSGLRLLIDDQLLRNSKRLKHISSSRQS |
| | | LRLGGSNFEGCISNVFVQRLSLSPEVLD |
| | | LTSNSLKRDVSLGGCSLNKPPFLMLLKG |
| | | STRFNKTKTFRINQLLQDTPVASPRSVK |
| | | VWQDACSPLPKTQANHGALQFGDIPTSH |
| | | LLFKLPQELLKPRSQFAVDMQTTSSRGL |
| | | VFHTGTKNSFMALYLSKGRLVFALGTDG |
| | | KKLRIKSKEKCNDGKWHTVVFGHDGEKG |
| | | RLVVDGLRAREGSLPGNSTISIRAPVYL |
| | | GSPPSGKPKSLPTNSFVGCLKNFQLDSK |
| | | PLYTPSSSFGVSSCLGGPLEKGIYFSEE |
| | | GGHVVLAHSVLLGPEFKLVFSIRPRSLT |
| | | GILIHIGSQPGKHLCVYLEAGKVTASMD |
| | | SGAGGTSTSVTPKQSLCDGQWHSVAVTI |
| | | KQHILHLELDTDSSYTAGQIPFPPASTQ |
| | | EPLHLGGAPANLTTLRIPVWKSFFGCLR |
| | | NIHVNHIPVPVTEALEVQGPVSLNGCPD |
| | | Q |
| | | Laminin (Laminin subunit |
| | | gamma-3) (SEQ ID NO: 92) |
| | | MAAAALLLGLALLAPRAAGAGMGACYDG |
| | | AGRPQRCLPVFENAAFGRLAQASHTCGS |
| | | PPEDFCPHVGAAGAGAHCQRCDAADPQR |
| | | HHNASYLTDFHSQDESTWWQSPSMAFGV |
| | | QYPTSVNITLRLGKAYEITYVRLKFHTS |
| | | RPESFAIYKRSRADGPWEPYQFYSASCQ |
| | | KTYGRPEGQYLRPGEDERVAFCTSEFSD |
| | | ISPLSGGNVAFSTLEGRPSAYNFEESPG |
| | | LQEWVTSTELLISLDRLNTFGDDIFKDP |
| | | KVLQSYYYAVSDFSVGGRCKCNGHASEC |
| | | GPDVAGQLACRCQHNTTGTDCERCLPFF |
| | | QDRPWARGTAEAAHECLPCNCSGRSEEC |
| | | TFDRELFRSTGHGGRCHHCRDHTAGPHC |
| | | ERCQENFYHWDPRMPCQPCDCQSAGSLH |
| | | LQCDDTGTCACKPTVTGWKCDRCLPGFH |
| | | SLSEGGCRPCTCNPAGSLDTCDPRSGRC |

TABLE 1-continued

| Sequences of exemplary target proteins and associated binding agents | | |
|---|---|---|
| Target Protein | Target Protein SEQ | Exemplary Binding Agent(s) |
| | | PCKENVEGNLCDRCRPGTFNLQPHNPAG |
| | | CSSCFCYGHSKVCASTAQFQVHHILSDF |
| | | HQGAEGWWARSVGGSEHPPQWSPNGVLL |
| | | SPEDEEELTAPEKFLGDQRFSYGQPLIL |
| | | TFRVPPGDSPLPVQLRLEGTGLALSLRH |
| | | SSLSGPQDAGHPREVELRFHLQETSEDV |
| | | APPLPPFHFQRLLANLTSLRLRVSPGPS |
| | | PAGPVFLTEVRLTSARPGLSPPASWVEI |
| | | CSCPTGYTGQFCESCAPGYKREMPQGGP |
| | | YASCVPCTCNQHGTCDPNTGICVCSHHT |
| | | EGPSCERCLPGFYGNPFAGQADDCQPCP |
| | | CPGQSACTTIPESREVVCTHCPPGQRGR |
| | | RCEVCDDGFFGDPLGLFGHPQPCHQCQC |
| | | SGNVDPNAVGNCDPLSGHCLRCLHNTTG |
| | | DHCEHCQEGFYGSALAPRPADKCMPCSC |
| | | HPQGSVSEQMPCDPVTGQCSCLPHVTAR |
| | | DCSRCYPGFFDLQPGRGCRSCKCHPLGS |
| | | QEDQCHPKTGQCTCRPGVTGQACDRCQL |
| | | GFFGFSIKGCRACRCSPLGAASAQCHEN |
| | | GTCVCRPGFEGYKCDRCHDNFFLTADGT |
| | | HCQQCPSCYALVKEEAAKLKARLTLTEG |
| | | WLQGSDCGSPWGPLDILLGEAPRGDVYQ |
| | | GHHLLPGAREAFLEQMMSLEGAVKAARE |
| | | QLQRLNKGARCAQAGSQKTCTQLADLEA |
| | | VLESSEEEILHAAAILASLEIPQEGPSQ |
| | | PTKWSHLATEARALARSHRDTATKIAAT |
| | | AWRALLASNTSYALLWNLLEGRVALETQ |
| | | RDLEDRYQEVQAAQKALRTAVAEVLPEA |
| | | ESVLATVQQVGADTAPYLALLASPGALP |
| | | QKSRAEDLGLKAKALEKTVASWQHMATE |
| | | AARTLQTAAQATLRQTEPLTKLHQEARA |
| | | ALTQASSSVQAATVTVMGARTLLADLEG |
| | | MKLQFPRPKDQAALQRKADSVSDRLLAD |
| | | TRKKTKQAERMLGNAAPLSSSAKKKGRE |
| | | AEVLAKDSAKLAKALLRERKQAHRRASR |
| | | LTSQTQATLQQASQQVLASEARRQELEE |
| | | AERVGAGLSEMEQQIRESRISLEKDIET |
| | | LSELLARLGSLDTHQAPAQALNETQWAL |
| | | ERLRLQLGSPGSLQRKLSLLEQESQQQE |
| | | LQIQGFESDLAEIRADKQNLEAILHSLP |
| | | ENCASWQ |
| | | Laminin (Laminin subunit |
| | | alpha-4) (SEQ ID NO: 93) |
| | | MALSSAWRSVLPLWLLWSAACSRAASGD |
| | | DNAFPFDIEGSSAVGRQDPPETSEPRVA |
| | | LGRLPPAAEKCNAGFFHTLSGECVPCDC |
| | | NGNSNECLDGSGYCVHCQRNTTGEHCEK |
| | | CLDGYIGDSIRGAPQFCQPCPCPLPHLA |
| | | NFAESCYRKNGAVRCICNENYAGPNCER |
| | | CAPGYYGNPLLIGSTCKKCDCSGNSDPN |
| | | LIFEDCDEVTGQCRNCLRNTTGFKCERC |
| | | APGYYGDARIAKNCAVCNCGGGPCDSVT |
| | | GECLEEGFEPPTGMDCPTISCDKCVWDL |
| | | TDALRLAALSIEEGKSGVLSVSSGAAAH |
| | | RHVNEINATIYLLKTKLSERENQYALRK |
| | | IQINNAENTMKSLLSDVEELVEKENQAS |
| | | RKGQLVQKESMDTINHASQLVEQAHDMR |
| | | DKIQEINNKMLYYGEEHELSPKEISEKL |
| | | VLAQKMLEEIRSRQPFFTQRELVDEEAD |
| | | EAYELLSQAESWQRLHNETRTLFPVVLE |
| | | QLDDYNAKLSDLQEALDQALNYVRDAED |
| | | MNRATAARQRDHEKQQERVREQMEVVNM |
| | | SLSTSADSLTTPRLTLSELDDIIKNASG |
| | | IYAEIDGAKSELQVKLSNLSNLSHDLVQ |
| | | EAIDHAQDLQQEANELSRKLHSSDMNGL |
| | | VQKALDASNVYENIVNYVSEANETAEFA |
| | | LNTTDRIYDAVSGIDTQIIYHKDESENL |
| | | LNQARELQAKAESSSDEAVADTSRRVGG |
| | | ALARKSALKTRLSDAVKQLQAAERGDAQ |
| | | QRLGQSRLITEEANRTTMEVQQATAPMA |
| | | NNLTNWSQNLQHFDSSAYNTAVNSARDA |
| | | VRNLTEVVPQLLDQLRTVEQKRPASNVS |
| | | ASIQRIRELIAQTRSVASKIQVSMMFDG |
| | | QSAVEVHSRTSMDDLKAFTSLSLYMKPP |
| | | VKRPELTETADQFILYLGSKNAKKEYMG |
| | | LAIKNDNLVYVYNLGTKDVEIPLDSKPV |

TABLE 1-continued

<u>Sequences of exemplary target proteins and associated binding agents</u>

| Target Protein | Target Protein SEQ | Exemplary Binding Agent(s) |
|---|---|---|
| | | SSWPAYFSIVKIERVGKHGKVFLTVPSL |
| | | SSTAEEKFIKKGEFSGDDSLLDLDPEDT |
| | | VFYVGGVPSNFKLPTSLNLPGFVGCLEL |
| | | ATLNNDVISLYNFKHIYNMDPSTSVPCA |
| | | RDKLAFTQSRAASYFFDGSGYAVVRDIT |
| | | RRGKFGQVTRFDIEVRTPADNGLILLMV |
| | | NGSMFFRLEMRNGYLHVFYDFGFSGGPV |
| | | HLEDTLKKAQINDAKYHEISIIYHNDKK |
| | | MILVVDRRHVKSMDNEKMKIPFTDIYIG |
| | | GAPPEILQSRALRAHLPLDINFRGCMKG |
| | | FQFQKKDFNLLEQTETLGVGYGCPEDSL |
| | | ISRRAYFNGQSFIASIQKISFFDGFEGG |
| | | FNFRTLQPNGLLFYYASGSDVFSISLDN |
| | | GTVIMDVKGIKVQSVDKQYNDGLSHFVI |
| | | SSVSPTRYELIVDKSRVGSKNPTKGKIE |
| | | QTQASEKKFYFGGSPISAQYANFTGCIS |
| | | NAYFTRVDRDVEVEDFQRYTEKVHTSLY |
| | | ECPIESSPLFLLHKKGKNLSKPKASQNK |
| | | KGGKSKDAPSWDPVALKLPERNTPRNSH |
| | | CHLSNSPRAIEHAYQYGGTANSRQEFEH |
| | | LKGDFGAKSQFSIRLRTRSSHGMIFYVS |
| | | DQEENDFMTLFLAHGRLVYMFNVGHKKL |
| | | KIRSQEKYNDGLWHDVIFIRERSSGRLV |
| | | IDGLRVLEESLPPTEATWKIKGPIYLGG |
| | | VAPGKAVKNVQINSIYSFSGCLSNLQLN |
| | | GASITSASQTFSVTPCFEGPMETGTYFS |
| | | TEGGYVVLDESFNIGLKFEIAFEVRPRS |
| | | SSGTLVHGHSVNGEYLNVHMKNGQVIVK |
| | | VNNGIRDFSTSVTPKQSLCDGRWHRITV |
| | | IRDSNVVQLDVDSEVNHVVGPLNPKPID |
| | | HREPVFVGGVPESLLTPRLAPSKPFTGC |
| | | IRHFVIDGHPVSFSKAALVSGAVSINSC |
| | | PAA |
| | | Laminin (Laminin subunit |
| | | gamma-2) (SEQ ID NO: 94) |
| | | MPALWLGCCLCFSLLLPAARATSRREVC |
| | | DCNGKSRQCIFDRELHRQTGNGFRCLNC |
| | | NDNTDGIHCEKCKNGFYRHRERDRCLPC |
| | | NCNSKGSLSARCDNSGRCSCKPGVTGAR |
| | | CDRCLPGFHMLTDAGCTQDQRLLDSKCD |
| | | CDPAGIAGPCDAGRCVCKPAVTGERCDR |
| | | CRSGYYNLDGGNPEGCTQCFCYGHSASC |
| | | RSSAEYSVHKITSTFHQDVDGWKAVQRN |
| | | GSPAKLQWSQRHQDVFSSAQRLDPVYFV |
| | | APAKFLGNQQVSYGQSLSFDYRVDRGGR |
| | | HPSAHDVILEGAGLRITAPLMPLGKTLP |
| | | CGLTKTYTFRLNEHPSNNWSPQLSYFEY |
| | | RRLLRNLTALRIRATYGEYSTGYIDNVT |
| | | LISARPVSGAPAPWVEQCICPVGYKGQF |
| | | CQDCASGYKRDSARLGPFGTCIPCNCQG |
| | | GGACDPDTGDCYSGDENPDIECADCPIG |
| | | FYNDPHDPRSCKPCPCHNGFSCSVMPET |
| | | EEVVCNNCPPGVTGARCELCADGYFGDP |
| | | FGEHGPVRPCQPCQCNNNVDPSASGNCD |
| | | RLTGRCLKCIHNTAGIYCDQCKAGYFGD |
| | | PLAPNPADKCRACNCNPMGSEPVGCRSD |
| | | GTCVCKPGFGGPNCEHGAFSCPACYNQV |
| | | KIQMDQFMQQLQRMEALISKAQGGDGVV |
| | | PDTELEGRMQQAEQALQDILRDAQISEG |
| | | ASRSLGLQLAKVRSQENSYQSRLDDLKM |
| | | TVERVRALGSQYQNRVRDTHRLITQMQL |
| | | SLAESEASLGNTNIPASDHYVGPNGFKS |
| | | LAQEATRLAESHVESASNMEQLTRETED |
| | | YSKQALSLVRKALHEGVGSGSGSPDGAV |
| | | VQGLVEKLEKTKSLAQQLTREATQAEIE |
| | | ADRSYQHSLRLLDSVSRLQGVSDQSFQV |
| | | EEAKRIKQKADSLSSLVTRHMDEFKRTQ |
| | | KNLGNWKEEAQQLLQNGKSGREKSDQLL |
| | | SRANLAKSRAQEALSMGNATFYEVESIL |
| | | KNLREFDLQVDNRKAEAEEAMKRLSYIS |
| | | QKVSDASDKTQQAERALGSAAADAQRAK |
| | | NGAGEALEISSEIEQEIGSLNLEANVTA |
| | | DGALAMEKGLASLKSEMREVEGELERKE |
| | | LEFDTNMDAVQMVITEAQKVDTRAKNAG |
| | | VTIQDTLNTLDGLLHLMDQPLSVDEEGL |
| | | VLLEQKLSRAKTQINSQLRPMMSELEER |

TABLE 1-continued

| Sequences of exemplary target proteins and associated binding agents | | |
|---|---|---|
| Target Protein | Target Protein SEQ | Exemplary Binding Agent(s) |
| | | ARQQRGHLHLLETSIDGILADVKNLENI |
| | | RDNLPPGCYNTQALEQQ |
| | | Laminin (Laminin subunit |
| | | beta-3) (SEQ ID NO: 95) |
| | | MRPFFLLCFALPGLLHAQQACSRGACYP |
| | | PVGDLLVGRTRFLRASSTCGLTKPETYC |
| | | TQYGEWQMKCCKCDSRQPHNYYSHRVEN |
| | | VASSSGPMRWWQSQNDVNPVSLQLDLDR |
| | | RFQLQEVMMEFQGPMPAGMLIERSSDFG |
| | | KTWRVYQYLAADCTSTFPRVRQGRPQSW |
| | | QDVRCQSLPQRPNARLNGGKVQLNLMDL |
| | | VSGIPATQSQKIQEVGEITNLRVNFTRL |
| | | APVPQRGYHPPSAYYAVSQLRLQGSCFC |
| | | HGHADRCAPKPGASAGPSTAVQVHDVCV |
| | | CQHNTAGPNCERCAPFYNNRPWRPAEGQ |
| | | DAHECQRCDCNGHSETCHFDPAVFAASQ |
| | | GAYGGVCDNCRDHTEGKNCERCQLHYFR |
| | | NRRPGASIQETCISCECDPDGAVPGAPC |
| | | DPVTGQCVCKEHVQGERCDLCKPGFTGL |
| | | TYANPQGCHRCDCNILGSRRDMPCDEES |
| | | GRCLCLPNVVGPKCDQCAPYHWKLASGQ |
| | | GCEPCACDPHNSLSPQCNQFTGQCPCRE |
| | | GFGGLMCSAAAIRQCPDRTYGDVATGCR |
| | | ACDCDFRGTEGPGCDKASGRCLCRPGLT |
| | | GPRCDQCQRGYCNRYPVCVACHPCFQTY |
| | | DADLREQALRFGRLRNATASLWSGPGLE |
| | | DRGLASRILDAKSKIEQIRAVLSSPAVT |
| | | EQEVAQVASAILSLRRTLQGLQLDLPLE |
| | | EETLSLPRDLESLDRSFNGLLTMYQRKR |
| | | EQFEKISSADPSGAFRMLSTAYEQSAQA |
| | | AQQVSDSSRLLDQLRDSRREAERLVRQA |
| | | GGGGGTGSPKLVALRLEMSSLPDLTPTF |
| | | NKLCGNSRQMACTPISCPGELCPQDNGT |
| | | ACGSRCRGVLPRAGGAFLMAGQVAEQLR |
| | | GFNAQLQRTRQMIRAAEESASQIQSSAQ |
| | | RLETQVSASRSQMEEDVRRTRLLIQQVR |
| | | DFLTDPDTDAATIQEVSEAVLALWLPTD |
| | | SATVLQKMNEIQAIAARLPNVDLVLSQT |
| | | KQDIARARRLQAEAEEARSRAHAVEGQV |
| | | EDVVGNLRQGTVALQEAQDTMQGTSRSL |
| | | RLIQDRVAEVQQVLRPAEKLVTSMTKQL |
| | | GDFWTRMEELRHQARQQGAEAVQAQQLA |
| | | EGASEQALSAQEGFERIKQKYAELKDRL |
| | | GQSSMLGEQGARIQSVKTEAEELFGETM |
| | | EMMDRMKDMELELLRGSQAIMLRSADLT |
| | | GLEKRVEQIRDHINGRVLYYATCK |
| | | Laminin (Laminin subunit |
| | | beta-4) (SEQ ID NO: 96) |
| | | MQFQLTLFLHLGWLSYSKAQDDCNRGAC |
| | | HPTTGDLLVGRNTQLMASSTCGLSRAQK |
| | | YCILSYLEGEQKCFICDSRFPYDPYDQP |
| | | NSHTIENVIVSFEPDREKKWWQSENGLD |
| | | HVSIRLDLEALFRFSHLILTFKTFRPAA |
| | | MLVERSTDYGHNWKVFKYFAKDCATSFP |
| | | NITSGQAQGVGDIVCDSKYSDIEPSTGG |
| | | EVVLKVLDPSFEIENPYSPYIQDLVTLT |
| | | NLRINFTKLHTLGDALLGRRQNDSLDKY |
| | | YYALYEMIVRGSCFCNGHASECRPMQKM |
| | | RGDVFSPPGMVHGQCVCQHNTDGPNCER |
| | | CKDFFQDAPWRPAADLQDNACRSCSCNS |
| | | HSSRCHFDMTTYLASGGLSGGVCEDCQH |
| | | NTEGQHCDRCRPLFYRDPLKTISDPYAC |
| | | IPCECDPDGTISGGICVSHSDPALGSVA |
| | | GQCLCKENVEGAKCDQCKPNHYGLSATD |
| | | PLGCQPCDCNPLGSLPFLTCDVDTGQCL |
| | | CLSYVTGAHCEECTVGYWGLGNHLHGCS |
| | | PCDCDIGGAYSNVCSPKNGQCECRPHVT |
| | | GRSCSEPAPGYFFAPLNFYLYEAEEATT |
| | | LQGLAPLGSETFGQSPAVHVVLGEPVPG |
| | | NPVTWTGPGFARVLPGAGLRFAVNNIPF |
| | | PVDFTIAIHYETQSAADWTVQIVVNPPG |
| | | GSEHCIPKTLQSKPQSFALPAATRIMLL |
| | | PTPICLEPDVQYSIDVYFSQPLQGESHA |
| | | HSHVLVDSLGLIPQINSLENFCSKQDLD |
| | | EYQLHNCVEIASAMGPQVLPGACERLII |
| | | SMSAKLHDGAVACKCHPQGSVGSSCSRL |

TABLE 1-continued

Sequences of exemplary target proteins and associated binding agents

| Target Protein | Target Protein SEQ | Exemplary Binding Agent(s) |
|---|---|---|
| | | GGQCQCKPLVVGRCCDRCSTGSYDLGHH |
| | | GCHPCHCHPQGSKDTVCDQVTGQCPCHG |
| | | EVSGRRCDRCLAGYFGFPSCHPCPCNRF |
| | | AELCDPETGSCFNCGGFTTGRNCERCID |
| | | GYYGNPSSGQPCRPCLCPDDPSSNQYFA |
| | | HSCYQNLWSSDVICNCLQGYTGTQCGEC |
| | | STGFYGNPRISGAPCQPCACNNNIDVTD |
| | | PESCSRVTGECLRCLHNTQGANCQLCKP |
| | | GHYGSALNQTCRRCSCHASGVSPMECPP |
| | | GGGACLCDPVTGACPCLPNVTGLACDRC |
| | | ADGYWNLVPGRGCQSCDCDPRTSQSSHC |
| | | DQLTGQCPCKLGYGGKRCSECQENYYGD |
| | | PPGRCIPCDCNRAGTQKPICDPDTGMCR |
| | | CREGVSGQRCDRCARGHSQEFPTCLQCH |
| | | LCFDQWDHTISSLSKAVQGLMRLAANME |
| | | DKRETLPVCEADFKDLRGNVSEIERILK |
| | | HPVFPSGKFLKVKDYHDSVRRQIMQLNE |
| | | QLKAVYEFQDLKDTIERAKNEADLLLED |
| | | LQEEIDLQSSVLNASIADSSENIKKYYH |
| | | ISSSAEKKINETSSTINTSANTRNDLLT |
| | | ILDTLTSKGNLSLERLKQIKIPDIQILN |
| | | EKVCGDPGNVPCVPLPCGGALCTGRKGH |
| | | RKCRGPGCHGSLTLSTNALQKAQEAKSI |
| | | IRNLDKQVRGLKNQIESISEQAEVSKNN |
| | | ALQLREKLGNIRNQSDSEEENINLFIKK |
| | | VKNFLLEENVPPEDIEKVANGVLDIHLP |
| | | IPSQNLTDELVKIQKHMQLCEDYRTDEN |
| | | RLNEEADGAQKLLVKAKAAEKAANILLN |
| | | LDKTLNQLQQAQITQGRANSTITQLTAN |
| | | ITKIKKNVLQAENQTREMKSELELAKQR |
| | | SGLEDGLSLLQTKLQRHQDHAVNAKVQA |
| | | ESAQHQAGSLEKEFVELKKQYAILQRKT |
| | | STTGLTKETLGKVKQLKDAAEKLAGDTE |
| | | AKIRRITDLERKIQDLNLSRQAKADQLR |
| | | ILEDQVVAIKNEIVEQEKKYARCYS |
| E-selectin | (SEQ ID NO: 97) | MIASQFLSALTLVLLIKESGAWSYNTST |
| | | EAMTYDEASAYCQQRYTHLVAIQNKEEI |
| | | EYLNSILSYSPSYYWIGIRKVNNVWVWV |
| | | GTQKPLTEEAKNWAPGEPNNRQKDEDCV |
| | | EIYIKREKDVGMWNDERCSKKKLALCYT |
| | | AACTNTSCSGHGECVETINNYTCKCDPG |
| | | FSGLKCEQIVNCTALESPEHGSLVCSHP |
| | | LGNFSYNSSCSISCDRGYLPSSMETMQC |
| | | MSSGEWSAPIPACNVVECDAVTNPANGF |
| | | VECFQNPGSFPWNTTCTFDCEEGFELMG |
| | | AQSLQCTSSGNWDNEKPTCKAVTCRAVR |
| | | QPQNGSVRCSHSPAGEFTFKSSCNFTCE |
| | | EGFMLQGPAQVECTTQGQWTQQIPVCEA |
| | | FQCTALSNPERGYMNCLPSASGSFRYGS |
| | | SCEFSCEQGFVLKGSKRLQCGPTGEWDN |
| | | EKPTCEAVRCDAVHQPPKGLVRCAHSPI |
| | | GEFTYKSSCAFSCEEGFELHGSTQLECT |
| | | SQGQWTEEVPSCQVVKCSSLAVPGKINM |
| | | SCSGEPVFGTVCKFACPEGWTLNGSAAR |
| | | TCGATGHWSGLLPTCEAPTESNIPLVAG |
| | | LSAAGLSLLTLAPFLLWLRKCLRKAKKF |
| | | VPASSCQSLESDGSYQKPSYIL |
| P-selectin | (SEQ ID NO: 98) | MANCQIAILYQRFQRVVFGISQLLCFSA |
| | | LISELTNQKEVAAWTYHYSTKAYSWNIS |
| | | RKYCQNRYTDLVAIQNKNEIDYLNKVLP |
| | | YYSSYYWIGIRKNNKTWTWVGTKKALTN |
| | | EAENWADNEPNNKRNNEDCVEIYIKSPS |
| | | APGKWNDEHCLKKKHALCYTASCQDMSC |
| | | SKQGECLETIGNYTCSCYPGFYGPECEY |
| | | VRECGELELPQHVLMNCSHPLGNFSFNS |
| | | QCSFHCTDGYQVNGPSKLECLASGIWTN |
| | | KPPQCLAAQCPPLKIPERGNMTCLHSAK |
| | | AFQHQSSCSFSCEEGFALVGPEVVQCTA |
| | | SGVWTAPAPVCKAVQCQHLEAPSEGTMD |
| | | CVHPLTAFAYGSSCKFECQPGYRVRGLD |
| | | MLRCIDSGHWSAPLPTCEAISCEPLESP |
| | | VHGSMDCSPSLRAFQYDTNCSFRCAEGF |
| | | MLRGADIVRCDNLGQWTAPAPVCQALQC |
| | | QDLPVPNEARVNCSHPFGAFRYQSVCSF |

TABLE 1-continued

Sequences of exemplary target proteins and associated binding agents

| Target Protein | Target Protein SEQ | Exemplary Binding Agent(s) |
|---|---|---|
| | | TCNEGLLLVGASVLQCLATGNWNSVPPE CQAIPCTPLLSPQNGTMTCVQPLGSSSY KSTCQFICDEGYSLSGPERLDCTRSGRW TDSPPMCEAIKCPELFAPEQGSLDCSDT RGEFNVGSTCHFSCDNGFKLEGPNNVEC TTSGRWSATPPTCKGIASLPTPGLQCPA LTTPGQGTMYCRHHPGTFGFNTTCYFGC NAGFTLIGDSTLSCRPSGQWTAVTPACR AVKCSELHVNKPIAMNCSNLWGNFSYGS ICSFHCLEGQLLNGSAQTACQENGHWST TVPTCQAGPLTIQEALTYFGGAVASTIG LIMGGTLLALLRKRFRQKDDGKCPLNPH SHLGTYGVFTNAAFDPSP |
| Protein containing epitope generated by ST8SIA3 (a ST8SIA3- modified protein) | mrnckmarva svlglvmlsv allilslisy vslkkenift tpkyaspgap rmymfhagfr sqfalkfldp sfvpitnslt qelqekpskw kfnrtaflhq rqeilqhvdv iknfsltkns vrigqlmhyd ysshkyvfsi snnfrsllpd vspimnkhyn icavvgnsgi Itgsqcgqei dksdfvfrcn fapteafqrd vgrktnlttf npsilekyyn nlltiqdrnn fflslkkldg ailwipafff htsatvtrtl vdffvehrgq ikvqlawpgn imqhvnrywk nkhlspkrls tgilmytlas aiceeihlyg fwpfgfdpnt redlpyhyyd kkgtkfttkw qeshqlpaef qllyrmhgeg Itkltlshca (SEQ ID NO: 22) | A2B5 antibody as described herein (Abcam Catalog # ab53521,Cambridge, MA; ThermoFisher Scientific Catalog # 433110, Grand Island, NY) |
| CD164 | Isoform 2 msrlsrsllw aatclgvlcv Isadknttqh pnvttlapis nvtsapvtsl plvttpapet cegrnscvsc fnvsvvnttc fwieckdesy cshnstvsdc qvgnttdfcs akptvqpspst tsktvttsg ttnntvtpts qpvrkstfda asfiggivlv Igvqaviffl ykfckskernyhtl (SEQ ID NO: 99) isoform 3 msrlsrsllw aatclgvlcv Isadknttqh pnvttlapis nvtsapvtsl plvttpapet cegrnscvsc fnvsvvnttc fwieckdesy cshnstvsdc qvgnttdfcs vstatpvpta nstgttnntv tptsqpvrks tfdaasfigg ivlvlgvqav ifflykfcks kernyhtl (SEQ ID NO: 100) isoform 4 msrlsrsllw aatclgvlcv Isadknttqh pnvttlapis nvtsapvtsl plvttpapet cegrnscvsc fnvsvvnttc fwieckdesy cshnstvsdc qvgnttdfcs vstatpvpta nstakptvqp spsttsktvt tsgttnntvt ptsqpvrkst fdaasfiggi vlvleircht rnyipdlkk (SEQ ID NO: 101) isoform 5 msrlsrsllw aatclgvlcv Isadknttqh pnvttlapis nvtsapvtsl plvttpapet cegrnscvsc fnvsvvnttc | CXCR-4 type 4 isoform a (SEQ ID NO: 104)_ msiplpllqiytsdnyteemgsgdydsmkep cfreenanfnkifIptiysiifitgivgngl vilvmgyqkklrsmtdkyrlhlsvadllfvi tlpfwavdavanwyfgnfickavhviytvnl yssvlilafisldrylaivhatnsqrprkll aekvvyvgvwipalllltipdfifanvseadd ryicdrfypndlwvvvfqfqhimvglilpgi vilscyciiisklshskghqkrkalkttvil ilaffacwlpyyigisidsfilleiikqgce fentvhkwisitealaffhccinpilyafig akfktsaqhaltsvsrgssllkilskgkrggh ssvstesesssfhss CXCR-4 type 4 isoform b (SEQ ID NO: 105) Megisiytsdnyteemgsgdydsmkepcfre enanfnkifIptiysiifItgivgnglvilv mgyqkklrsmtdkyrlhlsvadllfvitlpf wavdavanwyfgnfickavhviytvnlyssv lilafisIdrylaivhatnsqrprkllaekv vyvgvwipalllltipdfifanvseaddryic drfypndlwvvvfqfqhimvglilpgiviis cyciiiskishskghqkrkalkttvililaf facwlpyyigisidsfilleiikqgcefent vhkwisitealaffhccinpilyafigakfk tsaqhaltsvsrgssllkilskgkrgghssvs tesesssfhss CXCR-4 type 4 isoform c (SEQ ID NO: 106) megisenaplpnvpnapsdkhedgkrpthrr sarlgeevpfvhfitlppnipqapkglrfkt afslpttsclkprmiytsdnyteemgsgdyd smkepcfreenanfnkifIptiysiifItgi vgnglvilvmgyqkklrsmtdkyrlhlsvad llfvitlpfwavdavanwyfgnfickavhvi ytvnlyssvlilafisldrylaivhatnsqr prkllaekvvyvgvwipalllltipdfifanv seaddryicdrfypndlwvvvfqfqhimvgl ilpgivilscyciiisklshskghqkrkalk ttvililaffacwlpyyigisidsfilleii |

TABLE 1-continued

| Sequences of exemplary target proteins and associated binding agents | | |
|---|---|---|
| Target Protein | Target Protein SEQ | Exemplary Binding Agent(s) |
| | fwieckdesy cshnstvsdc<br>qvgnttdfcs vstatpvpta<br>nstakptvqp spsttsktvt<br>tseirchtrn yipdlkk<br>(SEQ ID NO: 102)<br>isoform 6<br>mrkgrkvpmy vpgvlrtypk<br>akleetcegr nscvscfnvs<br>vvnttcfwie ckdesycshn<br>stvsdcqvgn ttdfcsvsta<br>tpvptansta kptvqpspst<br>tsktvttsgt tnntvtptsq<br>pvrkstfdaa sfiggivlvl<br>gvqaviffly kfckskerny htl<br>(SEQ ID NO: 103) | kqgcefentvhkwisitealaffhcclnpil<br>yafIgakfktsaqhaltsvsrgssIkiIskg<br>krgghssvstesesssfhss<br>CXCR-4 type 4 isoform d<br>(SEQ ID NO: 107)<br>megisenaplpnvpnapsdkhedgkrpthrr<br>sarigeeiytsdnyteemgsgdydsmkepcf<br>reenanfnkifIptiysiifitgivgnglvi<br>ivmgyqkklrsmtdkyrlhlsvadllfvitl<br>pfwavdavanwyfgnfickavhviytvnlys<br>svlilafisIdrylaivhatnsqrprkllae<br>kvvyvgvwipallltipdfifanvseaddry<br>icdrfypndlwvvvfqfqhimvglilpgivi<br>lscycillsklshskghqkrkalkttvilli<br>affacwlpyyigisidsfilleiikqgcefe<br>ntvhkwisitealaffhccinpilyafigak<br>fktsaqhaltsvsrgssIkiiskgkrgghss<br>vstesesssfhss<br>CXCR-4 type 4 isoform e<br>(SEQ ID NO: 108)<br>mgsgdydsmkepcfreenanfnkifIptiys<br>iifItgivgnglviivmgyqkklrsmtdkyr<br>Ihlsvadllfvitlpfwavdavanwyfgnfl<br>ckavhviytvnlyssvlilafisIdrylaiv<br>hatnsqrprkllaekvvyvgvwipallltip<br>dfifanvseaddryicdrfypndlwvvvfqf<br>qhimvglilpgivilscycliiskishskgh<br>qkrkalkttvililaffacwlpyyigisids<br>filleiikqgcefentvhkwisitealaffh<br>cclnpilyafIgakfktsaqhaltsvsrgss<br>Ikilskgkrgghssvstesesssfhss |

In some embodiments, the binding agent specifically binds to one or more target proteins selected from B3GAT1, CD74, GPR37L1, HLA-DOA, HTR6, IFNLR1, MCHR2, ST8SIA3, CD164, VLDLR, and ZP2. In other embodiments, the binding agent specifically binds to one or more target proteins selected from ARHGEF18, ASB12, BAD, DCAF12L1, ECHS1, GORASP2, GPHA2, GRID2IP, HOXD4, KCNT2, LIPJ, MESDC2, MTHFS, OCM, OR4X2, SCLT1, SERAC1, SFTD2, SHOC2, SPRYD3, STAG1, TMED10, TRIM67, TTLL7, or VLDLR. In other embodiments, the binding agent specifically binds to one or more target proteins selected from KCNT2, OR4X2, SERAC1, SFT2D2, TMED10, or VLDLR. In certain embodiments, the binding agent specifically binds to one or more target proteins selected from GPR37L1, ST8SIA3, ZP2 and VLDLR.

In some embodiments, a binding agent for use in the compositions and methods described herein specifically binds to CD74 (HLA class II histocompatibility antigen gamma chain—also known as DHLAG, HLADG, II, Ia-GAMMA, or p33), including any known isoforms of CD74 as provided in Table 1. CD74 associates with class II major histocompatibility complex (MHC) and is chaperone that regulates antigen presentation for immune response. It also serves as cell surface receptor for the cytokine macrophage migration inhibitory factor (MIF) which, when bound to the encoded protein, initiates survival pathways and cell proliferation. CD74 also interacts with amyloid precursor protein (APP) and suppresses the production of amyloid beta (Abeta). In some embodiments, the binding agent as described herein that binds CD74 is a ligand of CD74 (or has been shown to interact with CD74), including, for example, any one or more of the ligands selected from APP, CD1D, CD74, CTSF, CTSL, CXCR4, ERBB4, HLA-DPA1, HLA- DQA1, HLA-DQA2, HLA-DQB1, HLA-DQB2, HLA-DRA, HLA-DRB1, HLA-DRB3, MIF, AP2M1, AR, CD44, CTSB, CTSD, CTSH, CTSS, CTSV, LGMN, PNP, and PPARA. In some embodiments, the binding agent that binds CD74 is an antibody or antigen-binding fragment thereof that specifically binds CD74. Antibodies that bind CD74 are known in the art, including, e.g., milatuzumab.

In some embodiments, a binding agent for use in the compositions and methods described herein specifically binds to HLA-DOA (HLA class II histocompatibility antigen, DO alpha chain—also known as HLA-DNA, HLA-DZA, or HLADZ). An exemplary amino acid sequence of HLA-DOA is provided in Table 1. HLA-DOA belongs to the HLA class II alpha chain paralogues. HLA-DOA forms a heterodimer with HLA-DOB. The heterodimer, HLA-DO, is found in lysosomes in B cells and regulates HLA-DM-mediated peptide loading on MHC class II molecules. In some embodiments, the binding agent that binds HLA-DOA is a ligand of HLA-DOA (or has been shown to interact with HLA-DOA), including, for example, HLA-DOB, HLA-DPA1, HLA-DQA1, HLA-DQA2, HLA-DQB1, HLA-DQB2, HLA-DRA, HLA-DRB1, HLA-DRB3, ITGA2, and MMP1. In some embodiments, the binding agent that binds HLA-DOA is an antibody or antigen-binding fragment thereof that specifically binds HLA-DOA. Antibodies or antigen-binding fragments thereof against HLA-DOA can be readily generated using methods available to those of skill in the art, such as by immunization, computational modeling techniques, and in vitro selection methods (e.g., phage display and cell-based display platforms) as described herein.

In some embodiments, a binding agent for use in the compositions and methods described herein specifically binds to VLDLR (very low density lipoprotein receptor— also known as CAMRQ1, CARMQ1, CHRMQ1, VLDL-R, and VLDLRCH), and includes any of the known isoforms of VLDLR as provided in Table 1. VLDLR is a lipoprotein receptor that is a member of the low density lipoprotein receptor family and is involved in VLDL-triglyceride metabolism and the reelin signaling pathway. Mutations in this gene cause VLDLR-associated cerebellar hypoplasia. In some embodiments, the binding agent as described herein that binds VLDLR is a ligand of VLDLR (or has been shown to interact with VLDLR), including, for example, any one or more of the ligands selected from APOE, CLU, ITGA3, ITGB1, LPL, LRPAP1, PLAU, PLAUR, RELN, and SER-PINE1. In some embodiments, the binding agent that binds VLDLR is an antibody or antigen-binding fragment thereof that specifically binds VLDLR. Antibodies or antigen-binding fragments thereof against VLDLR can be readily generated using methods available to those of skill in the art, such as by immunization, computational modeling techniques, and in vitro selection methods (e.g., phage display and cell-based display platforms) as described herein.

In some embodiments, a binding agent for use in the compositions and methods described herein specifically binds to ZP2 (zona pellucida glycoprotein 2—also known as OOMD6, ZPA, and Zp-2), and includes any of the known isoforms of ZP2 as provided in Table 1. ZP2 is an extracellular matrix that surrounds the oocyte and early embryo. It is composed of three glycoproteins with various functions during fertilization and preimplantation development. The glycosylated mature peptide is one of the structural components of the zona pellucida and functions in secondary binding and penetration of acrosome-reacted spermatozoa. In some embodiments, the binding agent as described herein that binds ZP2 is a ligand of ZP2 (or has been shown to interact with ZP2), including, for example, any one or more of the ligands selected from ZP1, ZP3, ZP4, ZPBP, ACR, ADAM2, OVGP1, and PPARA. In some embodiments, the binding agent that binds ZP2 is an antibody or antigen-binding fragment thereof that specifically binds ZP2. Antibodies or antigen-binding fragments thereof against ZP2 can be readily generated using methods available to those of skill in the art, such as by immunization, computational modeling techniques, and in vitro selection methods (e.g., phage display and cell-based display platforms) as described herein.

In some embodiments, a binding agent for use in the compositions and methods described herein specifically binds to IFNLR1 (interferon lambda receptor 1—also known as CRF2/12, IFNLR, IL-28R1, IL28RA, and LICR2), or to any known isoforms of IFNLR1 as provided in Table 1. IFNLR1, which belongs to the class II cytokine receptor family, forms a receptor complex with interleukin 10 receptor, beta (IL10RB). The receptor complex has been shown to interact with three closely related cytokines, including interleukin 28A (IL28A), interleukin 28B (IL28B), and interleukin 29 (IL29), which are related to type I interferons. The interaction with these cytokines have been shown to play an important role in response to microbial challenge and activate the JAK signaling system. In some embodiments, the binding agent as described herein that binds IFNLR1 is a ligand of IFNLR1 (or has been shown to interact with IFNLR1), including, for example, any one or more of the ligands selected from IFNL2, IFNLR1, and IL10RB. In some embodiments, the binding agent that binds IFNLR1 is an antibody or antigen-binding fragment thereof that specifically binds IFNLR1. Antibodies or antigen-binding fragments thereof against IFNLR1 can be readily generated using methods available to those of skill in the art, such as by immunization, computational modeling techniques, and in vitro selection methods (e.g., phage display and cell-based display platforms) as described herein.

In some embodiments, a binding agent for use in the compositions and methods described herein specifically binds to HTR6 (5-hydroxytryptamine receptor 6—also known as 5-HT6 or 5-HT6R). An exemplary amino acid sequence of HTR6 is provided in Table 1. HTR6, which belongs to the seven-transmembrane G protein-coupled receptor family of proteins, couples with the Gs alpha subunit and stimulates adenylate cyclase to activate the cyclic AMP-dependent signaling pathway. HTR6 is thought to regulate cholinergic neuronal transmission in the brain. Several antidepressants and antipsychotic drugs have been shown to have a high affinity for HTR6. In some embodiments, the binding agent as described herein that binds HTR6 is a ligand of HTR6 (or has been shown to interact with HTR6), including, for example ADRBK1. In some embodiments, the binding agent that binds IFNLR1 is an antibody or antigen-binding fragment thereof that specifically binds IFNLR1. Antibodies or antigen-binding fragments thereof against HTR6 can be readily generated using methods available to those of skill in the art, such as by immunization, computational modeling techniques, and in vitro selection methods (e.g., phage display and cell-based display platforms) as described herein.

In some embodiments, a binding agent for use in the compositions and methods described herein specifically binds to GPR37L1 (G protein-coupled receptor 37 like 1—also known as ET(B)R-LP-2, ETBR-LP-2, ETBRLP2). An exemplary amino acid sequence of GPR37L1 is provided in Table 1. GPR37L1 been shown to bind the neuroprotective and glioprotective factor prosaposin (PSAP), leading to endocytosis followed by an ERK phosphorylation cascade. It has been suggested that GPR37L1 is a constitutively active receptor which signals through the guanine nucleotide-binding protein G(s) subunit alpha, participates in the regulation of postnatal cerebellar development by modulating the Shh pathway, regulates baseline blood pressure in females, and protects against cardiovascular stress in males. GPR37L1 has been shown to mediate inhibition of astrocyte glutamate transporters and reduction in neuronal N-methyl-D-aspartate receptor activity. In some embodiments, the binding agent as described herein that binds GPR37L1 is a ligand of GPR37L1 (or has been shown to interact with GPR37L1), including, for example PSAP. In some embodiments, the binding agent that binds GPR37L1 is an antibody or antigen-binding fragment thereof that specifically binds GPR37L1. Antibodies or antigen-binding fragments thereof against GPR37L1 can be readily generated using methods available to those of skill in the art, such as by immunization, computational modeling techniques, and in vitro selection methods (e.g., phage display and cell-based display platforms) as described herein.

In some embodiments, a binding agent for use in the compositions and methods described herein specifically binds to MCHR2 (melanin concentrating hormone receptor 2—also known as GPR145, GPRv17, MCH-2R, MCH-R2, MCH2, MCHR-2, and SLT). An exemplary amino acid sequence of MCHR2 is provided in Table 1. MCHR2 is a G protein-coupled receptor for melanin-concentrating hormone (MCH), a neuropeptide that plays an important role in the control of feeding behaviors and energy metabolism. In some embodiments, the binding agent as described herein that binds MCHR2 is a ligand of MCHR2 (or has been shown to interact with MCHR2), including, for example pro-MCH. In some embodiments, the binding agent that binds MCHR2 is an antibody or antigen-binding fragment thereof that specifically binds MCHR2. Antibodies or antigen-binding fragments thereof against MCHR2 can be readily generated using methods available to those of skill in the art, such as by immunization, computational modeling techniques, and in vitro selection methods (e.g., phage display and cell-based display platforms) as described herein.

In some embodiments, a binding agent for use in the compositions and methods described herein specifically binds to an epitope generated by B3GAT1 (beta-1,3-glucuronyltransferase 1, also known as CD57, GLCATP, GLCUATP, HNK1, LEU7, NK-1, and NK1). Thus, a binding agent for use in the compositions and methods described herein specifically binds to a B3GAT1-modified protein (that comprises the epitope generated by B3GAT1). Known isoforms of B3GAT1 are provided in Table 1. B3GAT1, which is a member of the glucuronyltransferase gene family, functions as the key enzyme in a glucuronyl transfer reaction during the biosynthesis of the carbohydrate epitope HNK-1 (human natural killer-1, also known as CD57 and LEU7), a neuronally expressed carbohydrate epitope that contains a sulfoglucuronyl residue. B3GAT1 has also been shown to be involved in glycosaminoglycan biosynthesis. B3GAT1 encodes a glucuronyltransferase enzyme that places the HNK-1 epitope on extracellular proteins. Accordingly, in some embodiments, a binding agent for use in the compositions and methods described herein can specifically bind to the HNK-1 epitope, or to proteins containing the HNK-1 epitope. In some embodiments, a binding agent that specifically binds to the HNK-1 epitope is laminin, E-selectin, or P-selectin, or fragments thereof than can specifically interact with HNK-1. In some embodiments, the binding agent that binds the HNK-1 epitope is an antibody or antigen-binding fragment thereof that specifically binds the HNK-1 epitope. Antibodies or antigen-binding fragments thereof against the HNK-1 epitope can be readily generated using methods available to those of skill in the art, such as by immunization, computational modeling techniques, and in vitro selection methods (e.g., phage display and cell-based display platforms) as described herein.

In some embodiments, a binding agent for use in the compositions and methods described herein specifically binds to an epitope generated by ST8SIA3 (ST8 alpha-N-acetyl-neuraminide alpha-2,8-sialyltransferase 3—also known as SIAT8C and ST8SiaIII). Thus, a binding agent for use in the compositions and methods described herein specifically binds to a ST8SIA3-modified protein (that comprises the epitope generated by ST8SIA3). An exemplary amino acid sequence of ST8SIA3 is provided in Table 1. ST8SIA3 belongs to a family of sialyltransferases that form sialyl-alpha-2,8-sialyl-R linkages at the non-reducing termini of glycoconjugates by catalyzing the transfer of sialic acid from a CMP-linked sialic acid donor onto the terminal sialic acid of an acceptor through alpha-2,8-linkages. ST8SIA3 is a sialyltransferase which can alter the glycosylation signature of extracellular proteins. Accordingly, in some embodiments, a binding agent for use in the compositions and methods described herein can specifically bind to the glycosylation signature characteristic of ST8SIA3, e.g., sialyl-alpha-2,8-sialyl-R linkages. ST8SIA3 places the A2B5 epitope on proteins. Accordingly, in some embodiments, a binding agent for use in the compositions and methods described herein can specifically bind to the A2B5 epitope, or to proteins containing the A2B5 epitope. In some embodiments, the antibody is an A2B5 antibody as exemplified herein.

In some embodiments, a binding agent for use in the compositions and methods described herein specifically binds to CD164 (sialomucin core protein 24, also known as endolyn, MGC-24, MUC-24), including known isoforms of CD164 as provided in Table 1. CD164 is a sialomucin, which are secreted or membrane-associated mucins that appear to play a role as a cytoprotective or antiadhesive agent, and as adhesion receptors. CD164 has been shown to regulate the proliferation, adhesion and migration of hematopoietic progenitor cells. In some embodiments, the binding agent as described herein that binds CD164 is a ligand of CD164 (or has been shown to interact with CD164), including, for example, CXC chemokine receptor type 4 isoforms a through e as provided herein. In some embodiments, the binding agent that binds CD164 is an antibody or antigen-binding fragment thereof that specifically binds CD164. Antibodies or antigen-binding fragments thereof against CD164 can be readily generated using methods available to those of skill in the art, such as by immunization, computational modeling techniques, and in vitro selection methods (e.g., phage display and cell-based display platforms) as described herein.

Exemplary binding agents based on native ligands of the indicated target proteins are provided in Table 1. In other embodiments, the binding agent can be an aptamer that is capable of specifically binding to a target protein on a brain endothelial cell, e.g., a target protein set forth in Table 1, or a target protein set forth in Table 2. In other embodiments, the binding agent can be an antibody, or antigen-binding portion thereof, that is capable of specifically binding to a target protein on a brain endothelial cell, e.g., a target protein set forth in Table 1, or a target protein set forth in Table 2. In some embodiments, the antibody, or antigen binding portion thereof, is a Fab, a F(ab')$_2$, an scFv, a tandem scFv, a diabody, a minibody, or a single domain antibody.

In other embodiments, the binding agent can be a bispecific antibody or multispecific antibody, or antigen-binding portion thereof, wherein a first binding site present on the antibody or antigen-binding portion thereof are capable of specifically binding to a target protein on a brain endothelial cell, e.g., a target protein set forth in Table 1, or a target protein set forth in Table 2. In some embodiments, the bispecific antibody or multispecific antibody can further comprise a second binding site capable of specifically binding a neurological disease antigen. In exemplary embodiments, the bispecific antibody or multispecific antibody comprises a binding site for human amyloid beta (e.g., an antigen binding portion of solanezumab, an antigen binding portion of aducanumab, an antigen binding portion of gantenerumab, an antigen binding portion of lecanemab), a binding site for human programmed death 1 (PD-1) (e.g., an antigen binding portion of nivolumab), a binding site for human vascular endothelial growth factor (VEGF) (e.g., an antigen binding portion of bevacizumab), a binding site for human CD20 (e.g., an antigen binding portion of ocrelizumab, an antigen binding portion of ublituximab), a binding site for human alpha-4-integrin (e.g., an antigen binding portion of natalizumab), or a binding site for human GD2 ganglioside protein (e.g., an antigen binding portion of dinutuximab).

Antibodies that can be used in the compositions and methods described herein can be identified using techniques known in the art, such as hybridoma production. Hybridomas can be prepared using, e.g., a murine system. Protocols for immunization and subsequent isolation of splenocytes for fusion are known in the art. Fusion partners and procedures for hybridoma generation are also known. In making a desired antibody, a target protein (antigen) of choice (whole protein or fragments thereof) is isolated and/or purified Immunization of animals can be performed by any method known in the art. See, e.g., Harlow and Lane, Antibodies: A Laboratory Manual, New York: Cold Spring Harbor Press, 1990. Methods for immunizing animals such as mice, rats, sheep, goats, pigs, cattle and horses are well known in the art. See, e.g., Harlow and Lane, supra, and U.S. Pat. No. 5,994,619. A desired antigen may be administered with an adjuvant to stimulate the immune response. Adjuvants known in the art include complete or incomplete Freund's adjuvant, RIBI (muramyl dipeptides) or ISCOM (immunostimulating complexes). After immunization of an animal with a desired antigen, antibody-producing immortalized cell lines are prepared from cells isolated from the immunized animal After immunization, the animal is sacrificed and lymph node and/or splenic B cells are immortalized by methods known in the art (e.g., oncogene transfer, oncogenic virus transduction, exposure to carcinogenic or mutating compounds, fusion with an immortalized cell, e.g., a myeloma cell, and inactivating a tumor suppressor gene. See, e.g., Harlow and Lane, supra. Hybridomas can be selected, cloned and further screened for desirable characteristics, including robust growth, high antibody production and desirable antibody characteristics. Human anti-PCDH17 antibodies can also be generated in mice, such as in the HuMAb-Mouse® or XenoMouse™.

Methods for high throughput screening of antibody, or antibody fragment, libraries for molecules capable of binding a target protein (antigen) can be used to identify and affinity mature antibodies useful for the methods of the present disclosure. Such methods include in vitro display techniques known in the art, such as phage display, bacterial display, yeast display, mammalian cell display, ribosome display, mRNA display, and cDNA display, among others. The use of phage display to isolate ligands that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules). In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). These techniques, among others, can be used to identify and improve the affinity of antibodies that bind to a target protein.

In addition to in vitro display techniques, computational modeling techniques can be used to design and identify antibodies, or antibody fragments, in silico that bind a target protein. For example, using computational modeling techniques, one of skill in the art can screen libraries of antibodies, or antibody fragments, in silico for molecules capable of binding specific epitopes, such as extracellular epitopes of the target protein.

By specifically binding to the blood-brain barrier endothelial cell target proteins described herein, the binding agents and any associated cargo are able to traverse the blood-brain barrier. Accordingly, coupling the binding agents described herein to a therapeutic agent can deliver the binding agent and the therapeutic agent to the brain and central nervous system of a subject, as described below.

D. Conjugates of Binding Agent and Therapeutic Agent

In some aspects, the present disclosure is directed to conjugates comprising (i) a binding agent that specifically binds to a blood-brain barrier endothelial cell target protein provided herein (e.g., in Table 1 and/or Table 2), and (ii) a therapeutic agent. In some embodiments, the binding agent enhances transport of the therapeutic agent across the BBB. In some embodiments, the conjugate is transported across the BBB at a rate at least 10% greater, 15% greater, 20% greater, 25% greater, 30% greater, 35% greater, 40% greater, 45% greater, 50% greater, 55% greater, 60% greater, 65% greater, 70% greater, 75% greater, 80% greater, 90% greater, 100% greater, 150% greater, 200% greater, 300% greater, 400% greater, 500% greater, 1000% greater, or more than 1000% greater as compared to transport or delivery of the therapeutic agent without the binding agent.

In some embodiments, the binding agent is covalently coupled to the therapeutic agent. In some embodiments, the binding agent is non-covalently coupled to the therapeutic agent. In some embodiments, the binding agent and the therapeutic agent are directly coupled. In other embodiments, the binding agent and the therapeutic agent can be coupled by way of a linker. For example, the linker can be a peptide linker or a small molecule linker. In some embodiments, the linker is cleavable. In some other embodiments, the linker is non-cleavable. Any suitable method for covalent or non-covalently coupling of biomolecules can be used to couple a binding agent provided herein to a therapeutic agent.

In some aspects, a conjugate of the present disclosure may comprise any binding agent in accordance of the present disclosure. In one embodiment, the binding agent is a polypeptide, e.g., a polypeptide ligand of a protein expressed by a brain endothelial cell, e.g., as set forth in Table 1 or Table 2. In other embodiments, the binding agent is an antibody, or antigen binding portion thereof, that specifically binds to a protein expressed by a brain endothelial cell, e.g., as set forth in Table 1 or Table 2. In certain embodiments, the binding agent is an antibody fragment selected from the group consisting of a Fab, a F(ab')$_2$, an scFv, a tandem scFv, a diabody, a minibody, and a single domain antibody.

In one embodiment, the binding agent is an aptamer that specifically binds to a protein expressed by a brain endothelial cell.

In certain embodiments, the binding agent is a bispecific antibody, or antigen binding portion thereof. In some embodiments, the bispecific antibody comprises a first binding site that specifically binds to a protein expressed by a brain endothelial cell, and a second binding site that specifically binds to a neurological disease antigen.

In some embodiments of the foregoing aspect, the binding agent specifically binds to a target protein set forth in Table 1. In other embodiments, the binding agent specifically binds to a target protein set forth in Table 2. In some embodiments, the binding agent specifically binds to an endothelial cell protein selected from ARHGEF18, ASB12, BAD, CD74, CD164, DCAF12L1, ECHS1, GORASP2, GPHA2, GRID2IP, HLA-DOA, HOXD4, IFNLR1, GPR37L1, HTR6, KCNT2, LIPJ, MCHR2, MESDC2, MTHFS, OCM, OR4X2, SCLT1, SERAC1, SFTD2, SHOC2, SPRYD3, STAG1, TMED10, TRIM67, TTLL7, VLDLR or ZP2, a B3GAT1-modified protein, a ST8SIA3-modified protein, or a combination thereof. In exemplary embodiments, the binding agent specifically binds to a target protein selected from the group consisting of ARHGEF18, ASB12, BAD, DCAF12L1, ECHS1, GORASP2, GPHA2, GRID2IP, HOXD4, KCNT2, LIPJ, MESDC2, MTHFS, OCM, OR4X2, SCLT1, SERAC1, SFTD2, SHOC2, SPRYD3, STAG1, TMED10, TRIM67, TTLL7, and VLDLR. In certain embodiments, the binding agent specifically binds to a target protein selected from the group consisting of KCNT2, OR4X2, SERAC1, SFT2D2, TMED10, and VLDLR.

In one embodiment, the binding agent is a polypeptide ligand of a target protein set forth in Table 1 or Table 2. In some embodiments, the polypeptide ligand comprises one or more of the binding agents set forth in Table 1, or a fragment or portion thereof that retains the ability to bind to a target protein described herein. In some embodiments, the binding agent comprises a protein selected from A2B5 antibody as described herein (Abcam Catalog #ab53521, Cambridge, MA; ThermoFisher Scientific Catalog #433110, Grand Island, NY), ACR, ADAM2, ADRBK1, AP2M1, APOE, APP, AR, CD1D, CD44, CD74, CLU, CTSB, CTSD, CTSF, CTSH, CTSL, CTSS, CTSV, CXCR-4 type 4 isoform a, CXCR-4 type 4 isoform b, CXCR-4 type 4 isoform c, CXCR-4 type 4 isoform d, CXCR-4 type 4 isoform e, DQB1, DRB3, ERBB4, E-selectin, HLA-DOB, HLA-DPA1, HLA-DQA1, HLA-DQA2, HLA-DQB1, HLA-DQB2, HLA-DRA, HLA-DRB1, HLA-DRB3, IFNL2, IFNLR1, IL10RB, ITGA2, ITGA3, ITGB1, Laminin (Laminin subunit gamma-1), Laminin (Laminin subunit beta-2), Laminin (Laminin subunit beta-1), Laminin (Laminin subunit alpha-2), Laminin (Laminin subunit alpha-1), Laminin (Laminin subunit alpha-5), Laminin (Laminin subunit alpha-3), Laminin (Laminin subunit gamma-3), Laminin (Laminin subunit alpha-4), Laminin (Laminin subunit gamma-2), Laminin (Laminin subunit beta-3), Laminin (Laminin subunit beta-4), LGMN, LPL, LRPAP1, MIF, MMP1, OVGP1, PLAU, PLAUR, PNP, PPARA, Pro-MCH, PSAP, P-selectin, RELN, SERPINE1, ZP1, ZP3, ZP4, ZPBP, or a fragment or portion thereof that retains the ability to bind to a target protein described herein.

In some aspects, conjugates of the present disclosure can comprise one or more therapeutic agents coupled to a binding agent described herein. Exemplary therapeutic agents include, but are not limited to, polypeptides, small molecules, or nucleic acids.

In some embodiments, the therapeutic agent is a therapeutic peptide. In such embodiments, the binding agent and the therapeutic peptide can optionally be expressed as a fusion protein. In some embodiments, the therapeutic agent is an antibody, or an antigen binding portion thereof. In some embodiments, the therapeutic agent is a small molecule. In some embodiments, the therapeutic agent is a nucleic acid, e.g., a cDNA, a DNA molecule, a plasmid, a cosmid, a siRNA, a shRNA, an antisense RNA, a gRNA, or an miRNA. In some embodiments, the therapeutic agent is an aptamer.

The conjugates may comprise any one or a plurality of the binding agents of the present disclosure coupled to any one or a plurality of the therapeutic agents of the present disclosure. The binding agent(s) and the therapeutic agent(s) may be linked, attached, directly bound, covalently coupled, non-covalently coupled, or conjugated by any suitable method to conjugate the binding agent(s) and the therapeutic agents(s).

In exemplary embodiments, a binding agent provided herein can be coupled to an extracellular vesicle (EV), such as an exosome, to facilitate delivery of the EV across the blood brain barrier, as described below.

E. Extracellular Vesicles (EVs) Comprising a Binding Agent

In certain aspects, the present disclosure is directed to extracellular vesicle (EV) compositions, e.g., exosome and/or microvesicle compositions, that enhance delivery of the EV across the blood brain barrier of a subject (e.g., to the brain or central nervous system of a subject). In exemplary embodiments, the EVs comprise one or more exogenous binding agents that specifically bind to a protein expressed by a brain endothelial cell. The interaction between the binding agent and a protein (e.g., a receptor) expressed by brain endothelial cells facilitates transport of the EV across the blood brain barrier (BBB). In some embodiments, the binding agents enables transport of the EVs across the BBB at a rate at least 10% greater, 15% greater, 20% greater, 25% greater, 30% greater, 35% greater, 40% greater, 45% greater, 50% greater, 55% greater, 60% greater, 65% greater, 70% greater, 75% greater, 80% greater, 90% greater, 100% greater, 150% greater, 200% greater, 300% greater, 400% greater, 500% greater, 1000% greater, or more than 1000% greater as compared to transport or delivery of the EVs without the binding agent.

In some embodiments, the EVs can further comprise a cargo, e.g., a therapeutic cargo. EV cargo can include, by way of example and without limitation, a small molecule (e.g., a small molecule drug), a nucleic acid (e.g., mRNA, DNA, siRNA. shRNA, antisense RNA, miRNA, etc.), and/or a protein or peptide (e.g., a hormone, a growth factor, an enzyme, an anticoagulant, an interferon, an interleukin, an antibody, an antibody fragment, an antibody-drug conjugate, etc.). Also provided are methods of delivering the EVs across the blood brain barrier of a subject. Further provided are methods of using the EV compositions in various applications relating to the treatment of neurological disorders, including but not limited to Alzheimer's Disease, Huntington's Disease, Parkinson's Disease, or neurological cancer, e.g., glioblastoma.

Extracellular vesicles (EVs) comprise a heterogeneous group of small structures enclosed by a lipid bilayer, for example, a portion of a cellular plasma membrane. EVs can range in size from about 10 nm to 10 μm in diameter, and most commonly fall within the range of about 25-500 nm. EVs can broadly be divided into two classes, exosomes and ectosomes. Exosomes can be formed by cells through the inward budding of the endosomal membrane during the maturation of multivesicular bodies (MVBs). Exosomes can then be released to the extracellular space by fusion of MVBs with the cell surface. Exosomes are typically 25-500 nm in diameter, and in some embodiments can be within the range of about 25-250 nm, about 50-150 nm, or about 50-200 nm. Ectosomes, also known as microvesicles, can be formed by cells through budding of the plasma membrane. Ectosomes can vary in size from about 10 nm to 10 μm, and in some embodiments can be within the range of about 10-1000 nm, or about 50-500 nm.

EVs suitable for use in the compositions and methods described herein include any type of vesicle that is obtainable from a cell in any form, for instance a microvesicle, which are shed from the plasma membrane of a cell, an exosome, which are generally derived from the endo-lysosomal pathway, an apoptotic body (e.g. obtainable from apoptotic cells), a microparticle (which may be derived from e.g. platelets), an ectosome (derivable from e.g. neutrophils and monocytes in serum), prostatosome (e.g. obtainable from prostate cancer cells), or a cardiosome (e.g. derivable from cardiac cells), etc. Other suitable EVs for use in the compositions and methods disclosed herein extracellular vesicle mimics, cell and/or cell membrane-based vesicles obtained through cell extrusion, membrane extrusion, vesicle extrusion, or other techniques (e.g., synthetic EVs), etc. Suitable EVs include any type of lipid-based structure (with vesicular morphology or with any other type of suitable morphology) that can act as a delivery or transport vehicle for therapeutic agents of interest.

EVs suitable for use in the compositions and methods of the present disclosure can be derived from any suitable source. In some embodiments, EVs can be derived from neural cells, such as neural stem cells, neural progenitor cells, or differentiated neural cells, such as neurons, glial cells, or astrocytes. In exemplary embodiments, EVs comprising one or more binding agents described herein are derived from neural progenitor cells and/or neural stem cells. In some embodiments, the EVs comprising one or more binding agents described herein are derived from non-transformed cells. Essentially any type of cell capable of producing EVs can be used as a source of EVs for the compositions and methods described herein. Other suitable cell types include, for example, mesenchymal stem cells (MSCs), stromal cells, fibroblasts, endothelial cells, adipose cells, myeloid cells, B cells, T cells, NK cells, dendritic cells, monocytes, macrophages, and hepatocytes. Other cell types include established cell lines, such as those from human umbilical cord endothelial cells (HUVECs), human embryonic kidney cells (HEK cells, e.g., HEK-293 cells), or transformed neural stem cells (e.g., CTX0E03). In other embodiments, EVs suitable for use in the compositions and methods described herein can be produced synthetically. In some embodiments, the EVs are derived from cells that have been transformed or immortalized by the introduction of exogenous proliferation factors or oncogenes, such as c-myc. In other embodiments, the EVs are derived from cells that have not been transformed or immortalized, e.g., by introduction of oncogenes or oncogenic mutations.

In one embodiment, the compositions and methods described herein are implemented using an isolated population of EVs comprising exosomes and/or microvesicles. In exemplary embodiments, the isolated population of EVs is derived from neural cells, such as neural progenitor cells, neural stem cells, or astrocytes, such as neural progenitor cells, neural stem cells, or astrocytes. In some embodiments, the neural cells, e.g., neural progenitor cells, neural stem cells, or astrocytes, are non-transformed cells.

EVs, e.g., exosomes, derived from cells comprise a variety of biological molecules that reflect their cellular origin. EVs can carry these biological molecules inside the EV lumen, and/or embedded in or attached to the lipid bilayer.

This native cargo can include proteins, lipids, and/or nucleic acids, for example, mRNA or miRNA. In cases where EVs are produced by cells, the composition of the cargo is highly dependent on cell type. For example, it has been shown that EVs derived from astrocytes, neural progenitor cells, and mesenchymal stem cells each contain a distinct complement of protein cargo (see, e.g., U.S. Patent Application Publication No. US2018/0327714A1, the entire contents of which are incorporated herein by reference). EVs derived from these different cell types also contain a distinct profile of nucleic acid molecules, including mRNA and/or miRNA. In embodiments where EVs are obtained from cells, the EVs contain native cargo that reflects the contents of EVs produced by the cells from which the EVs are derived. In one embodiment, the present disclosure provides a population of EVs derived from neural cells, e.g., neural progenitor cells. Such neural EVs contain a milieu of different proteins, including cytokines and growth factors, and coding and noncoding RNA molecules, derived from neural cells. The native cargo contained in neural EVs can impact neural and vascular function by providing neuroprotection, reducing inflammation, reducing oxidative stress, improving vascular integrity, impacting metabolic activity, and inducing a neuroregenerative effect via an increase neurogenesis and differentiation.

EVs are involved in intercellular communication, allowing for the transfer of material from EVs to cells by fusion with the cell membrane. EVs have been reported to be involved in numerous physiological processes, including immune modulation, angiogenesis, migration of endothelial cells in connection with tumor growth, or reducing damage in ischemia reperfusion injury. Many of these functions are mediated by proteins, nucleic acids, or lipids contained in or on the vesicles.

EVs can also be loaded with exogenous cargo, either on the EV membrane, or in the EV lumen. EVs for use in the compositions and methods described herein are modified to contain a binding agent identified herein on the EV surface. Coupling an EV to a binding agent described herein facilitates transport of the EV and its contents across the blood-brain barrier, for delivery to the brain and CNS. In some embodiments, EVs coupled to a binding agent described herein can be loaded with exogenous cargo (e.g., small molecules, proteins, antibodies, nucleic acids, etc.), to enhance delivery of the cargo to the brain and CNS.

(i) Coupling EVs to a Binding Agent

Various methods of loading a protein of interest (e.g., binding agent), alone or in combination with cargo, into EVs are known in the art, as described herein. For example, any of the cell sources described herein from which EVs of the present disclosure are derived can be recombinantly modified using known methods to express the exogenous binding agent, which is packaged (transported, trafficked, or shuttled) into EVs, e.g., exosomes, and released from the cells. For example, various sorting domains or sorting sequence motifs may be fused (via recombinant expression) to a binding agent to transport, traffic, or shuttle the fusion polypeptide construct (comprising, e.g., a binding agent fused to a sorting domain) to a suitable vesicular structure, i.e., to a suitable EV such as an exosome. Examples of such exosomal sorting domains include, but are not limited to, the following proteins, or fragments derived therefrom (e.g., fragments comprising an exosomal sorting domain) CD9, CD53, CD63, CD81, CD54, CD50, FLOT1, FLOT2, CD49d, CD71, CD133, CD138, CD235a, ALIX, Syntenin-1, Syntenin-2, Lamp2b, TSPAN8, TSPAN14, CD37, CD82, CD151, CD231, CD102, NOTCH1, NOTCH2, NOTCH3, NOTCH4, DLL1, DLL4, JAG1, JAG2, CD49d/ITGA4, ITGB5, ITGB6, ITGB7, CD11a, CD11b, CD11c, CD18/ ITGB2, CD41, CD49b, CD49c, CD49e, CD51, CD61, CD104, Fc receptors, interleukin receptors, immunoglobulins, MHC-I or MHC-II components, CD2, CD3 epsilon, CD3 zeta, CD13, CD18, CD19, CD30, CD34, CD36, CD40, CD40L, CD44, CD45, CD45RA, CD47, CD86, CD110, CD111, CD115, CD117, CD125, CD135, CD184, CD200, CD279, CD273, CD274, CD362, COL6A1, AGRN, EGFR, GAPDH, GLUR2, GLUR3, HLA-DM, HSPG2, L1CAM, LAMB1, LAMC1, LFA-1, LGALS3BP, Mac-1 alpha, Mac-1 beta, MFGE8, SLIT2, STX3, TCRA, TCRB, TCRD, TCRG, VTI1A, VTI1B, and any combinations thereof. Numerous other polypeptides capable of transporting a polypeptide construct to an EV can be used in the methods of the present disclosure. Fusion of a sorting domain with a binding agent can, e.g., enhance the surface display of the binding agent, increase avidity, or enable interaction with a target protein (e.g., protein expressed on brain endothelial cells). The sorting domains can be found in various publicly available databases such as Uniprot or RCSB and the like.

Fusion (e.g., by recombinant expression) of a binding agent described herein to an exosomal sorting domain of a tetraspanin exosomal sorting protein or other EV membrane protein allows the binding agent to be enriched on the EV surface. In one embodiment, the binding agent is fused to the exosomal sorting domain of CD9. In another embodiment, the binding agent is fused to the exosomal sorting domain of CD63. In another embodiment, the binding agent is fused to the exosomal sorting domain of CD81. In another embodiment, the binding agent is fused to the exosomal sorting domain of Lamp2b.

Additional peptide-based sequence motifs that control the loading of cargo into exosomes have been described (see, e.g., Villarroya-Beltra, C. et al., Nat. Communications 4:2980, 2013, incorporated herein by reference in its entirety). Additionally, tags such as, e.g., ubiquitin tags, myristoylation tag, phosphatidylinositol-(4,5)-bisphosphate (PIP$_2$)-binding domain, phosphatidylinositol-(3,4,5)-trisphosphate-binding domain, and type-1 plasma membrane protein, CD43 have been shown to target proteins into extracellular vesicles (see, e.g., Shen, B., et al., JBC 286 (16):14383-95, 2011; Smith, V L et al., J. Immunology 195(6):2722-2730, 2015; Cheng, Y. et al., Biotech. Bioeng. 113(6):1315-1324, 2016, incorporated herein by reference in their entireties). Further, certain sequence motifs can be engineered to a target binding protein for incorporation into EVs (e.g., exosomes). For example, the motif EKPPHY (SEQ ID NO: 109) at the C-terminus of insulin degrading enzyme (IDE) has been shown to target the enzyme to exosomes (see, Glebov et al., JBC 286:22711-715, 2011; see also Muphy et al., Exp. & Mol. Med. 51:32, 2019, incorporated herein by reference in their entireties). See also Liu and Su (Theranostics 9(4):1015-1028, 2019) for a review on design considerations and strategies for loading a protein of interest into exosomes.

Alternatively, or in addition, one or more exogenous binding agents can be incorporated into or onto EVs by manipulation of the vesicles following their release from a cell source into the extracellular space. Such methods include, e.g., electroporation, sonication, and lipofection. Alternatively, the binding agent can be coupled to a hydrophobic moiety (e.g., cholesterol, vitamin E, etc.) and mixed with a preparation of EVs, to allow the biding agent to intercalate into the vesicle membrane. Further, one or more exogenous binding agents can be conjugated on the surface of the EV using known methods. In some embodiments, the exogenous binding agent is conjugated to the vesicle surface using click chemistry. In such embodiments, the exogenous binding agent can be coupled to the vesicle by way of a linker generated from a reaction between two complementary click chemistry functional groups. Accordingly, one or more binding agents can be conjugated to the surface of the EV using "click chemistry" (see, e.g., Kolb, H. C.; Finn, M. G.; Sharpless, K. B. Angewandte Chemie, International Edition 2001, 40, 2004-2021; Kolb, H. C.; Sharpless, K. B. Drug Discovery Today 2003, 8, 1128-1137; the disclosures of which are incorporated herein by reference in their entirety). Any suitable click reaction can be used to link the binding agent to the EV surface. Click chemistry reactions are advantageous as they are typically fast, modular, efficient, often do not produce toxic waste products, can be done with water as a solvent, and can be set up to be stereospecific.

The term "click functional group", is used interchangeably with the terms "click chemistry reagent" or "click reagent" to refer to a reagent that can rapidly and selectively react ("click", e.g., via a cycloaddition reaction) with its counterpart click reagent under mild conditions in aqueous solution. Mild conditions can include neutral pH, aqueous solution and ambient temperature, with low reactant concentrations. Examples of click functional groups include azide, alkene, alkyne, dibenzocyclooctyne (DBCO), trans-cyclooctene, nitrone, nitrilimine, nitrile oxide, isonitrile, tetrazole and tetrazine groups. Exemplary click reactions include but are not limited to Cu-azide-alkyne, strain-promoted-azide-alkyne, staudinger ligation, tetrazine ligation, photo-induced tetrazole-alkene, thiol-ene, NHS esters, epoxides, isocyanates, and aldehyde-aminooxy. In some embodiments, the linker that couples the binding agent to the EV is generated from a reaction between two complementary click functional groups ("click linker"). An EV-binding protein conjugate is prepared by reacting a binding protein comprising a first click functional group with an EV comprising a second click functional group that are known to undergo a click chemistry reaction. Exemplary pairs of click reagents that are well known to persons of skill in the art include, but are not limited to, alkyne and azide; azide (strain-promoted) and alkyne; alkyne (strain-promoted) and nitrone; alkene and azide; tetrazine and alkene; alkene and tetrazole; azide and dibenzocyclooctyne (DBCO, also known as DIBO); tetrazine and transcyclooctene; and tetrazine and norbornene.

In embodiments where EVs are produced synthetically, as described above, one or more exogenous binding agents can be introduced into the EVs by manipulation of the vesicles following manufacture of the synthetic vesicles using known methods.

In some embodiments, 1, 2, 3, 4, 5, 6, 7, 8, 9, 10, 11, 12, 13, 14, 15, or more exogenous binding agents that bind to a target protein provided in Table 1 or Table 2 can be incorporated into the EVs of the present disclosure. In some embodiments, the exogenous binding agent specifically binds to any one or more target proteins provided in Table 1. In some embodiments, the exogenous binding agent specifically binds to any one or more target proteins provided in Table 2. In some embodiments, 1, 2, 3, 4, 5, 6, 7, 8, 9, 10, 11, 12, 13, 14, 15, or more exogenous binding agents that bind to a target protein product of the genes provided in Table 2 can be incorporated into the EVs of the present disclosure. In some embodiments, 1, 2, 3, 4, 5, 6, 7, 8, 9, 10, 11, 12, 13, 14, 15, or more exogenous binding agents that bind to a target protein product of the genes provided in Tables 1 and 2 can be incorporated in the EVs of the present disclosure.

Exogenous binding agents that specifically bind a target protein on a blood-brain barrier endothelial cell are described in detail above, and can include, e.g., a polypeptide, an antibody, an aptamer, or a small molecule. In some embodiments, the exogenous binding agent that binds to the target protein is a known polypeptide ligand, or a functional fragment and/or variant thereof, of the target protein. Examples of known polypeptide ligands to a protein product of one or more of the genes provided in Tables 1 and 2 are described herein. In some embodiments, the exogenous binding agent that binds to the target protein is an antibody, or an antigen-binding fragment thereof, that specifically binds to the target protein. Examples of antibodies that bind to protein product of one or more of the genes provided in Tables 1 and 2 are described herein. In some embodiments, the exogenous binding agent is an aptamer. Methods of designing and testing the various binding agents for specific binding to a target protein are known and available to those in the art (see, e.g., U.S. Pat. No. 5,756,291).

The exogenous binding agent can be expressed in the EV in an amount that is sufficient to facilitate binding of the EV to a brain endothelial cell target protein. In some embodiments, the binding agent can be expressed in an amount sufficient to enhance passage of EVs across the blood brain barrier. In other embodiments, the binding agent can be expressed in an amount sufficient to enhance delivery of EVs to the brain and central nervous system (CNS). The concentration of the exogenous binding agent in the EV can be controlled and varied depending on the context—e.g., the nature and abundance of the target protein. In some embodiments, the exogenous binding agent is present in the EV at a concentration that is 10%, 15%, 20%, 25%, 30%, 35%, 40%, 45%, 50%, 55%, 60%, 65%, 70%, 75%, 80%, 85%, 90%, 95%, 100%, or greater than a concentration of the binding agent present in an EV derived from a cell source that does not recombinantly express the exogenous binding agent. In some embodiments, the exogenous binding agent is present in the EV at a concentration that is 10%, 15%, 20%, 25%, 30%, 35%, 40%, 45%, 50%, 55%, 60%, 65%, 70%, 75%, 80%, 85%, 90%, 95%, 100%, or greater than an average concentration of common protein factors found in an EV derived from an equivalent cell source.

(ii) EV Production

EVs suitable for use in compositions and methods disclosed herein can be produced by a variety of cell types, or can be produced synthetically. EVs can be purified from any cell source, as described above (e.g., cultured mammalian cells, including but not limited to primary cells, stem/progenitor cells, transformed cells, and established cell lines) using known methods. For example, EVs can be purified through a procedure selected from the group of techniques comprising liquid chromatography (LC), high-performance liquid chromatography (HPLC), spin filtration, tangential flow filtration, hollow fiber filtration, centrifugation, immunoprecipitation, flow field fractionation, dialysis, microfluidic-based separation, etc., or any combination thereof. In one embodiment, the purification of the EVs is carried out using a sequential combination of filtration (preferably ultrafiltration (UF), tangential flow filtration or hollow fiber filtration) and size exclusion liquid chromatography (LC). This combination of purification steps results in optimized purification, which in turn leads to superior therapeutic activity. Further, as compared to ultracentrifugation (UC), which is routinely employed for purifying EVs such as exosomes, sequential filtration-chromatography is considerably faster and possible to scale to higher manufacturing volumes, which is a significant drawback of the current UC methodology more commonly used. Another purification methodology is tangential flow filtration (TFF), which offers scalability and purity, and may be combined with others types of purification techniques such as filtration.

In some embodiments, EVs can be purified from, e.g., mesenchymal stem or stromal cells or fibroblasts (obtainable from e.g. bone marrow, adipose tissue, Wharton's jelly, perinatal tissue, tooth buds, umbilical cord blood, skin tissue, etc), amnion cells and more specifically amnion epithelial cells optionally expressing various early markers, myeloid suppressor cells, M2 polarized macrophages, adipocytes, endothelial cells, fibroblasts, etc. Cell lines include human umbilical cord endothelial cells (HUVECs), human embryonic kidney (HEK) cells, endothelial cell lines such as microvascular or lymphatic endothelial cells, chondrocytes, MSCs of different origin, airway or alveolar epithelial cells, fibroblasts, endothelial cells, etc. Also, immune cells such as B cells, T cells, NK cells, macrophages, monocytes, dendritic cells (DCs) are suitable sources from which EVs can be purified. Any type of cell which is capable of producing EVs is also encompassed herein.

In one embodiment, EVs can be derived from neural cells, such as neural progenitor cells, neurons, oligodendrocytes, microglia, Schwann cells or astrocytes. In other embodiments, EVs can be produced by one or more cell types including, but not limited to, glioma cells, platelets, reticulocytes, neurons, immune cells, intestinal epithelial cells, tumor cells, HELA cells, mesenchymal stem cells, and human embryonic kidney cells (HEK cells). In one embodiment, the EVs are exosomes. Exosomes can be derived from any of the foregoing cell types. For example, exosomes suitable for use in the compositions and methods disclosed herein can be neural exosomes. Neural exosomes can be derived from neural cells, such as neural progenitor cells, neurons, or astrocytes. In other embodiments, the exosomes can be produced by one or more cell types including, but not limited to, glioma cells, platelets, reticulocytes, neurons, immune cells, intestinal epithelial cells, tumor cells, HELA cells, mesenchymal stem cells, and human embryonic kidney cells (HEK cells). In another embodiment, the exosomes are produced synthetically. In another embodiment, the EVs are ectosomes, also known as microvesicles. Microvesicles can be derived from any of the foregoing cell types. For example, microvesicles suitable for use in the compositions and methods disclosed herein can be neural microvesicles. Neural microvesicles can be derived from neural cells, such as neural progenitor cells, neurons, or astrocytes. In other embodiments, the microvesicles can be produced by one or more cell types including, but not limited to, glioma cells, platelets, reticulocytes, neurons, immune cells, intestinal epithelial cells, tumor cells, HELA cells, mesenchymal stem cells, and human embryonic kidney cells (HEK cells). In another embodiment, the microvesicles are produced synthetically.

In some instances, the disclosed EVs can be obtained by culturing cells, such as neural cells, for a time sufficient for the cells to produce EVs. Cells used to produce EVs can be obtained, in some embodiments, from pluripotent stem cells, for example, human embryonic stem cells (hESCs) or induced pluripotent stem cells (iPSCs).

In some embodiments, EVs are isolated from neural cells or MSCs that have been differentiated from pluripotent stem cells. Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

The types of pluripotent stem cells that may be used include established lines of pluripotent cells derived from tissue formed after fertilization, including pre-embryonic tissue (such as, for example, a blastocyst), embryonic tissue, or fetal tissue taken any time during gestation, typically but not necessarily before approximately 10-12 weeks gestation. Non-limiting examples are established ethical lines of human embryonic stem cells or human embryonic germ cells, such as, for example the human embryonic stem cell lines WA01, WA07, and WA09 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (ViaCyte, San Diego, CA), as well as normal human embryonic stem cell lines such as WA01, WA07, WA09 (WiCell, Madison, WI) and BG01, BG02 (ViaCyte, San Diego, CA).

Human embryonic stem cells (hESCs) may be prepared by methods which are described in the in the art as described for example, by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995). Alternatively, they may be obtained commercially.

Epiblast stem cells (EpiScs) and induced pluripotent stem cells (iPSCs) isolated from early post-implantation stage embryos. They express OCT4 and are pluripotent. iPSCs are made by dedifferentiating adult somatic cells back to a pluripotent state by retroviral transduction of four genes (c-myc, Klf4, SOX2, OCT4).

Methods for the production of human neural progenitor (hNP) cells from human embryonic stem cells (ESCs) are described, for example, in U.S. Pat. No. 7,531,354, which is hereby incorporated by reference in its entirety. Human neuroprogenitor cells (hNPs) are known to express markers associated with the earliest multipotent neural stem cells, including Nestin, Musashi-1, SOX1, SOX2 and SOX3. In one instance, the hNPs express SOX1 (SOX1+). In another instance, the hNPs express SOX2 (SOX2+). In some other instance, the hNPs express SOX3 (SOX3+). In some specific instances, the hNPs express at least one of Nestin, Musashi-1, SOX1, SOX2 and SOX3. In other instances, the hNPs express two or more of Nestin, Musashi-1, SOX1, SOX2 and SOX3. In yet another instance, the hNPs express three or more of Nestin, Musashi-1, SOX1, SOX2 and SOX3. In some instances, the hNPs express at least one of Nestin, Musashi-1, SOX1, SOX2 and SOX3 but do not express OCT4. In some other instances, the hNPs express at least two of Nestin, Musashi-1, SOX1, SOX2 and SOX3 but do not express OCT4. In yet another instance, the hNPs express at least three of Nestin, Musashi-1, SOX1, SOX2 and SOX3 but do not express OCT4. In a specific instance, the hNPs express SOX1, SOX2 and SOX3 but do not express OCT4.

Neural progenitor cells may be cultured with or without feeder cells. In some instances, neuroprogenitor cells produced according to the methods presented in U.S. Pat. No. 7,531,354, are feeder cell free as well as free from embryoid bodies.

The disclosed EVs can be obtained in some instances by culturing differentiated neural cells, such as glial cells, derived directly or indirectly from pluripotent stem cells in cell culture medium under conditions and for a time sufficient to produce EVs, and isolating said EVs from the culture medium. Types of glial cells include oligodendrocytes, astrocytes, ependymal cells, Schwann cells, microglia, and satellite cells. In one instance, the differentiated neural cells (e.g., glial cells) comprise astrocytes. Differentiated neural cells that can be used include hN2™ neuronal cells (Aruna Bio Inc.), NeuroNet™ neurons, and AstroPro™ astrocytes (Aruna Bio Inc.).

EVs can be isolated from cell culture medium or tissue culture supernatant. EVs produced from cells can be collected from the culture medium by any suitable method. Typically, an isolated population of EVs can be prepared from cell culture or tissue supernatant by centrifugation, size exclusion columns, microfluidic devices, polymer precipitation, filtration or combinations of these methods. For example, the EVs can be prepared as described in U.S. Patent Application Document No. 20140356382, which is hereby incorporated by reference in its entirety. For example, EVs can be prepared by differential centrifugation, that is low speed (<2,0000 g) centrifugation to pellet larger particles followed by high speed (>100,000 g) centrifugation to pellet EVs, size filtration with appropriate filters (for example, 0.22 μm filter), gradient ultracentrifugation (for example, with sucrose gradient) or a combination of these methods.

In some embodiments, the EV-producing NP cells and/or neural cells disclosed herein are cultured for about 1, 2, 3, 4, 5, 6, 7, 8, 9, 10, 11, 12, 13 or 14 days or for as long as about 1, 2, 3, 4, 5, 6, 7, 8 weeks or about 1, 2, 3, 4, 5, or 6 months, depending on the cell and its ability to produce EVs. The EV-producing cells may be cultured in suitable media and grown under conditions that are readily determined by one of ordinary skill in the art. Cell culture conditions may vary with cell type and the examples presented hereinafter illustrate suitable media and conditions. For example, CMRL 1066 medium (from Invitrogen) with fetal bovine serum (e.g., at 10%) and optionally supplemented with glutamine or glutamine-containing mixtures and antibiotics could be used. Cells can be grown adhering on a surface in some embodiments, e.g. they can be grown as a monolayer to multilayers on the surface (feeder cell free) and may be grown until 30, 40, 50, 60, 70, 80, 90, 95 or 100% confluent. In other embodiments, the cells can be grown as cell aggregates in suspension cultures.

Cell growth media are well known in the art and comprise at least a minimum essential medium plus one or more optional components such as growth factors, ascorbic acid, glucose, non-essential amino acids, salts (including trace elements), glutamine, insulin (where indicated and not excluded), Activin A, transferrin, beta mercaptoethanol, and other agents well known in the art and as otherwise described herein. A preferred media is a low protein, serum-free based growth medium that supports neural cells. The growth factor used can be fibroblast growth factor 2 (FGF2), alone or preferably in combination with leukemia inhibitor factor (LIF). Depending on the NP or neural cells to be grown in the growth media, the inclusion of LIF is preferred but may not be required. Additional media includes basal cell media which may contain serum, for example, between about 0.1% and 20% (preferably, about 2-10%) fetal calf serum, or for defined medium, an absence of fetal calf serum and KSR, and optionally including bovine serum albumin (about 1-5%, preferably about 2%). In some instances, the medium is defined and is serum-free and has low protein content. In other instances, the media is media and supplement from Aruna Bio, Inc. which allow neural cultures to maintain a stable karyotype over multiple passages without the need for feeder cells, making them an excellent choice for a wide variety of research applications including early stage drug discovery. The components of the growth media depend on the type of neural cell to be grown, all of which are well known in the art. In one instance, a AB2™ Neural Cell Culture Media Kit is used and it contains AB2™ Basal Neural Medium and ANS™ Neural Medium Supplement. In a specific instance, the medium and supplement described in the instance above are specifically engineered for versatility to meet all neural cell culture needs. The AB2™ Basal Neural Medium and ANS™ Neural Medium Supplement can be used as the base for specialized mediums to direct differentiation of the hNP1™ line toward various neural phenotypes. Each lot of medium and supplement is pre-qualified for use by testing for cell growth, sterility, pH, osmolarity, and endotoxins.

Other agents which optionally may be added to the medium include, depending on the cell type grown in the media, for example, any one or more of nicotinamide, members of TGF-β family, including TGF-β 1, 2, and 3, Activin A, nodal, Bone Morphogen Proteins (BMP 2 to 7) serum albumin, members of the fibroblast growth factor (FGF) family, platelet-derived growth factor-AA, and -BB, platelet rich plasma, insulin growth factor (IGF-I, II, LR-IGF), growth differentiation factor (GDF-5, -6, -8, -10, 11), glucagon like peptide-I and II (GLP-I and II), GLP-1 and GLP-2 mimetobody, Exendin-4, parathyroid hormone, insulin, progesterone, aprotinin, hydrocortisone, ethanolamine, epidermal growth factor (EGF), gastrin I and II, copper chelators such as, for example, triethylene pentamine, forskolin, Na-Butyrate, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, heregulin, or combinations thereof, among a number of other components. Each of these components, when included, are included in effective amounts.

In some instances, suitable media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Cell media are commercially available and can be supplemented with commercially available components, including defined xeno-free components, such as those available from Invitrogen Corp. (GIBCO), Cell Applications, Inc., Biological Industries, Beth HaEmek, Israel, and Calbiochem. One of ordinary skill in the art will be able to readily modify the cell media to produce any one or more of the target cells pursuant to the present disclosure.

The disclosed EV-producing cells may be cultured on a layer of feeder cells that support the cells in various ways. Approaches for culturing cells on a layer of feeder cells are well known in the art. The cells may be grown on a cellular support or matrix, as adherent monolayers, or cell aggregates in suspension. In some instances, the use of a cellular support may be preferred, depending upon the cells used to produce the EVs. When used, cellular supports preferably comprise at least one substrate protein. Substrate proteins include, for example, an extracellular matrix protein, which is a protein found in the extracellular matrix, such as laminin, tenascin, thrombospondin, and mixtures thereof, which exhibit growth promoting and contain domains with homology to epidermal growth factor (EGF) and exhibit growth promoting activity. Other substrate proteins which may be used include for example, collagen, fibronectin, vibronectin, polylysine, polyornithine and mixtures thereof. In addition, gels and other materials such as methylcellulose of other gels which contain effective concentrations of one or more of these embryonic stem cell differentiation proteins may also be used. Exemplary differentiation proteins or materials which include these differentiation proteins include, for example, recombinant laminin, BD Cell-Tak™ Cell and Tissue Adhesive, BD™ FIBROGEN Human Recombinant Collagen I, BD™ FIBROGEN Human Recombinant Collagen III, BD Matrigel™ Basement Membrane Matrix, BD Matrigel™ Basement Membrane Matrix High Concentration (HC), BD™ PuraMatrix™ Peptide Hydrogel, Collagen I, Collagen I High Concentration (HC), Collagen II (Bovine), Collagen III, Collagen IV, Collagen V, and Collagen VI, among others.

Alternatively, these cells may be cultured in a culture system that is free of feeder cells, or essentially free of feeder cells, but nonetheless supports proliferation of the cells to produce EVs. The growth of cells in feeder-free culture can be supported using a medium conditioned by culturing previously with another cell type. Alternatively, the growth of EV-producing cells in feeder-free culture without differentiation can be supported using a chemically defined medium. These approaches are well known in the art. In certain embodiments, the cells are grown in feeder cell free medium.

EVs can be harvested at various time intervals (e.g. at about 1, 2, 4, 6, 8 or 3, 6, 9, 12 day or longer intervals, depending upon the rate of production of EVs). Exemplary yields of EVs can range from at least about 1 ng EVs/1 million cells, at least about 10 ng EVs/1 million cells, at least about 50 ng EVs/1 million cells, at least about 100 ng EVs/1 million cells, at least about 500 ng EVs/1 million cells, at least about 750 ng EVs/1 million cells, at least about 800 ng EVs/1 million cells, at least about 900 ng EVs/1 million cells, at least about 1.0 µg EVs/1 million cells, at least about 1.5 µg EVs/1 million cells, at least about 2.0 µg EVs/1 million cells, at least about 2.5 µg EVs/1 million cells, at least e.g. about 3.0 µg EVs/1 million cells, at least about 5.0 µg EVs/1 million cells, and at least about 10.0 µg EVs/1 million cells, during a time period of about 24 hours to seven days of culture of proliferative and non-proliferative neural cells as otherwise described herein.

In many instances, EVs are harvested and collected by ultracentrifugation or differential centrifugation or any combination thereof, pelleted EVs are collected, and, optionally, collected pelleted EVs are washed with a suitable medium. For example, a preparation of EVs can be prepared from cell culture or tissue supernatant by centrifugation, filtration or combinations of these methods. In some embodiments, the EVs can be prepared by differential centrifugation, that is low speed (<2,0000 g) centrifugation to pellet larger particles followed by high speed (>100,000 g) centrifugation to pellet EVs, size filtration with appropriate filters (for example, 0.22 μm filter), gradient ultracentrifugation (for example, with sucrose gradient) or a combination of these methods. EVs may be purified by differential centrifugation, micro and ultra-filtration, polymeric precipitation, microfluidic separation, immunocapture and size-exclusion chromatography. These and/or related methods for isolating and purifying EVs are described by Thery, et al., Current Protocols in Cell Biology, (2006) 3.221-3.22.29, copyright 2006 by John Wiley & Sons, Inc.; Sokolova, et al., Colloids and Surfaces B: Biointerfaces, 2011, 87, 146-150; Wiklander, et al., Journal of Extracellular Vesicles, 2015, 4, 26316, pp. 1-13; and Boing, et al., Journal of Extracellular Vesicles, 2014, 3, 23430, pp. 1-11. Other methods for isolation may be developed such as electrical field radiofrequency and acoustics.

Methods of manufacturing synthetic vesicles, such as synthetic exosomes, are known in the art. Such methods may be used to produce synthetic vesicles suitable for use in the compositions and methods provided herein. It is noted that the contents of EVs, i.e., EVs in which the lipid bilayer has been removed or eliminated and the contents obtained, may also be used to engineer artificial EVs.

(iii) Cargo to be Delivered Across the Blood Brain Barrier

In some aspects, provided herein are EVs comprising one or more exogenous binding agents, as described above, wherein the EVs further comprise cargo, e.g., one or more therapeutic agents, for delivery to the brain and CNS. In some embodiments, the cargo is exogenous cargo, which can be introduced into EVs by recombinant expression of the cargo in cells from which the EVs are derived, or introduced into EVs after the EVs are isolated from cells. In some embodiments, the exogenous cargo can include one more therapeutic agents. Virtually any molecular agent which may be used for the therapeutic management or treatment of a disease and/or disorder can be loaded into EVs. Therapeutic agents suitable for delivery via EVs encompass a wide variety of active agents, including (i) small molecule therapeutic agents synthesized via chemical synthesis, (ii) naturally derived compounds which may, e.g., be obtained via purification from natural sources, (iii) nucleic acid-based compounds of various kinds, e.g., oligonucleotides such as siRNA, splice-switching RNA, CRISPR guide strands, short hairpin RNA (shRNA), antisense oligonucleotides, polynucleotides such as mRNA, and nucleic acids which are chemically synthesized and/or which comprise chemically modified nucleotides such as 2'-O-Me, 2'-O-Allyl, 2'-O-MOE, 2'-F, 2'-CE, 2'-EA 2'-FANA, LNA, CLNA, ENA, PNA, phosphorothioates, tricyclo-DNA, etc., and (iv) peptides and polypeptides (i.e., proteins or antibodies) of any kind, including those obtained via peptide synthesis or via recombinant protein production.

Therapeutic agents can be obtained from essentially the entire space of pharmaceutically and/or pharmacologically and/or diagnostically relevant agents, for instance anticancer agents, cytostatic agents, tyrosine kinase inhibitors, statins, NSAIDs, antibiotics, antifungal agents, antibacterial agents, anti-inflammatory agents, anti-fibrotics, antihypertensives, aromatase or esterase inhibitors, an anticholinergics, SSRIs, BKT inhibitors, PPAR agonists, HER inhibitors, AKT inhibitors, BCR-ABL inhibitors, signal transduction inhibitors, angiogenesis inhibitors, synthase inhibitors, ALK inhibitors, BRAF inhibitors, MEK inhibitors, PI3K inhibitors, neprilysin inhibitors, beta2-agonists, CRTH2 antagonists, FXR agonists, BACE inhibitors, sphingosine-1-phosphate receptor modulators, MAPK inhibitors, Hedgehog signaling inhibitors, MDM2 antagonists, LSD1 inhibitors, lactamase inhibitors, TLR agonists, TLR antagonists, IDO inhibitors, ERK inhibitors, Chk1 inhibitors, splicing modulatory, DNA or RNA intercalators, etc. Other non-limiting examples of pharmacological agents as per the present invention includes for instance everolimus, trabectedin, abraxane, pazopanib, enzastaurin, vandetanib, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase (mek) inhibitor, pemetrexed, erlotinib, dasatanib, nilotinib, decatanib, panitumumab, amrubicin, oregovomab, nolatrexed, batabulin, ofatumumab, zanolimumab, edotecarin, tetrandrine, rubitecan, tesmilifene, oblimersen, ticilimumab, ipilimumab, gossypol, cilengitide, gimatecan, lucanthone, neuradiab, vitespan, talampanel, atrasentan, romidepsin, sunitinib, 5-fluorouracil, vorinostat, etoposide, gemcitabine, doxorubicin, 5'-deoxy-5-fluorouridine, vincristine, temozolomide, seliciclib, capecitabine, camptothecin, PEG-labeled irinotecan, tamoxifen, toremifene citrate, anastrazole, exemestane, letrozole, vatalanib, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, erlotinib, lapatanib, canertinib, lonafarnib, tipifarnib, amifostine, suberoyl analide hydroxamic acid, valproic acid, trichostatin sorafenib, arnsacrine, anagrelide, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, squalamine, endostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, droloxifene, 4-hydroxytamoxifen, pipendoxifene, arzoxifene, fulvestrant, acolbifene, lasofoxifene, idoxifene, topotecan, rapamycin, temsirolimus, zolendronate, prednisone, lenalidomide, gemtuzumab, hydrocortisone, dexrazoxane, alemtuzumab, all-transretinoic acid, ketoconazole, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methyl-prednisolone, prochlorperazine, granisetron, ondansetron, dolasetron, tropisetron, pegfilgrastim, erythropoietin, epoetin alfa and darbepoetin alfa, efavirinz among others. Furthermore, therapeutic agents also include naturally-derived compounds which may for instance be obtained via purification from natural sources, any type of nucleic acid-based compounds, for instance oligonucleotides such as siRNA, splice-switching RNA, CRISPR guide strands, short hairpin RNA, antisense oligonucleotides, mRNA, and in particular nucleic acid-based agents which are chemically synthesized and/or which comprise chemically modified nucleotides such as 2'-O-Me, 2'-O-Allyl, 2'-O-MOE, 2'-F, 2'-CE, 2'-EA 2'-FANA, LNA, CLNA, ENA, PNA, phosphorothioates, tricyclo-DNA, etc. Furthermore, peptides and polypeptides, and not only peptides and/or proteins obtainable via peptide synthesis but also peptides and proteins obtainable through recombinant protein production, are also contemplated as therapeutic agents suitable for use in the compositions and methods of the present disclosure.

In some embodiments, the EVs can comprise one or more inhibitory nucleic acids. For example, in some embodiments, the EVs can comprise one or more inhibitory nucleic acids selected from short interfering RNAs (siRNAs), short hairpin RNAs (shRNA), micro RNAs (miRNAs), antisense oligonucleotides (ASOs), and double-strand RNAs (dsRNA).

In some embodiments, the EVs can comprise one or more therapeutic antibody or antigen-binding portion thereof, including an antibody fragment selected from the group consisting of a Fab, a F(ab')$_2$, an scFv, a tandem scFv, a diabody, a minibody, and a single domain antibody. In some embodiments, the antibody, or antigen binding portion thereof, is a humanized antibody, or antigen binding portion thereof. In some embodiments, the antibody, or antigen binding portion thereof, is a fully human antibody, or antigen binding portion thereof.

In some embodiments, the EVs can comprise one more neurotrophic agents. In some embodiments, the EVs can comprise one or more agents selected from leukemia inhibitory factor (LIF), brain-derived neurotrophic factor (BDNF), epidermal growth factor receptor (EGF), basic fibroblast growth factor (bFGF), FGF-6, glial-derived neurotrophic factor (GDNF), granulocyte colony-stimulating factor (GCSF), hepatocyte growth factor (HGF), IFN-γ, insulin-like growth factor binding protein (IGFBP-2), IGFBP-6, IL-lra, IL-6, IL-8, monocyte chemotactic protein (MCP-1), mononuclear phagocyte colony-stimulating factor (M-CSF), neurotrophic factors (NT3), tissue inhibitor of metalloproteinases (TIMP-1), TIMP-2, tumor necrosis factor (TNF-β), vascular endothelial growth factor (VEGF), VEGF-D, urokinase plasminogen activator receptor (uPAR), bone morphogenetic protein 4 (BMP4), IL1-a, IL-3, leptin, stem cell factor (SCF), stromal cell-derived factor-1 (SDF-1), platelet derived growth factor-BB (PDGFBB), transforming growth factors beta (TGFβ-1) and TGFβ-3.

The foregoing therapeutic agents and other cargo can be loaded into EVs using art-recognized methods, including those described above as useful for coupling a binding agent to EVs. Such methods include, but are not limited to, lipofection, transfection, electroporation, click chemistry, conjugation to a hydrophobic moiety, or recombinant expression (for peptide or protein based therapeutics) of the therapeutic agent as a fusion protein with an exosomal sorting domain, such as the exosomal sorting domain of CD9, CD63, CD81, or Lamp2b, or any of the additional exosomal sorting domains described herein. Peptide or protein therapeutic agents can also be recombinantly expressed as a fusion protein with an exosomal protein (or an exosomal sorting domain thereof) typically found in the EV lumen, such as ALIX or syntenin. In other embodiments, the therapeutic agent can be loaded into EVs by coupling the agent to a cell penetrating peptide, such as, for example, transportan, penetratin, CADY-1, or VP22. Additional cell penetrating peptides are described, for example, in US20109/0388347A1, the entire contents of which are incorporated herein by reference.

Any of the foregoing agents, or combinations thereof, can be loaded into EVs comprising one or more binding agents as described herein, for delivery across the blood-brain barrier, to the brain and/or CNS.

F. Formulation, Delivery, and Administration

The EVs comprising one or more exogenous binding agents provided herein can be formulated in a pharmaceutical composition for delivery to a subject. Pharmaceutical compositions can comprise a therapeutically effective amount of the present EVs (e.g., comprising neural cell derived EVs) and a pharmaceutically acceptable carrier. For example, a therapeutically effective amount of the EVs if the present disclosure can be provided in sterile phosphate-buffered saline. Other suitable carriers are known in the art, and are described, for example, in Remington's Pharmaceutical Sciences, 18th ed. (1990). It will be understood by those skilled in the art that any mode of administration, vehicle or carrier conventionally employed and which is inert with respect to the active agent may be utilized for preparing and administering the pharmaceutical modified EVs of the present disclosure. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the disclosure, will experience no difficulty in determining suitable and appropriate vehicles, excipients and carriers or in compounding the active ingredients therewith to form the pharmaceutical compositions of the disclosure.

Formulations containing the EVs of the present disclosure (e.g., comprising neural cell derived EVs) may take the form of a liquid, solid or semi-solid, such as, for example, solutions, suspensions, emulsions, sustained-release formulations, lotions, aerosols, or the like, optionally in unit dosage forms suitable for simple administration of precise dosages. Pharmaceutical compositions typically include a conventional pharmaceutical carrier and/or excipient and may additionally include other medicinal agents, carriers, adjuvants, additives and the like. The weight percentage ratio of the EVs to the one or more excipients can be between about 20:1 to about 1:60, or between about 15:1 to about 1:45, or between about 10:1 to about 1:40, or between about 9:1, 8:1, 7:1, 6:1, 5:1, 4:1, 3:1, 2:1 or 1:1 to about 1:2, 1:3, 1:4, 1:5, 1:6, 1:7, 1:8, 1:9, 1:10, 1:15, 1:20, 1:25, 1:30, or 1:35, and preferably is about 20:1, 19:1, 18:1, 17:1, 16:1, 15:1, 14:1, 13:1, 12:1, 11:1, 10:1, 9:1, 8:1, 7:1, 6:1 or 5:1. In some embodiments, the disclosed composition comprises between about 1 μg to about 1 g or more of total EVs, for example, about 1 μg to about 100 μg, about 100 μg to about 200 μg, about 200 μg to about 300 μg, about 300 μg to about 400 μg, about 500 μg to about 600 μg, about 700 μg to about 800 μg, about 900 μg to about 1 mg, about 100 μg to about 500 μg, about 1 mg to about 500 mg, about 5 mg to about 500 mg, about 10 mg to about 500 mg, about 25 mg to about 500 mg, about 50 mg to about 350 mg, about 75 mg to about 450 mg, about 50 mg to about 450 mg, about 75 mg to about 325 mg, about 100 mg to about 650 mg, or about 500 mg to about 1 g of total EVs, and may optionally contain one or more suitable pharmaceutical carriers, additives and/or excipients.

In various instances, the pharmaceutical compositions described herein (e.g., pharmaceutical composition comprising the EVs of the present disclosure) can be formulated for delivery to a cell and/or to a subject via any route of administration know to a person of skill in the art. Modes of administration are commonly known or are apparent to those skilled in the art; for example, see Remington's Pharmaceutical Sciences (17th Ed., Mack Pub. Co. 1985).

Compositions comprising the EVs provided herein, and/ or conjugates comprising one or more binding agents and one or more therapeutic agents provided herein, can delivered to a subject by any suitable route, including but not limited to for instance auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated.

Administration of EVs coupled to a binding agent as described herein, or conjugates comprising one or more binding agents and one or more therapeutic agents described herein, is suitable for delivering the EVs to the brain or central nervous system, and in particular embodiments, across the blood-brain barrier. In some embodiments, administration is at the site of diseased and/or dysfunctional tissue (e.g., brain). In other embodiments, the site of administration is distal to the site of diseased and/or dysfunctional tissue (e.g., in the case of intravenous or intranasal delivery). In one embodiment, the EV composition described herein is administered to a subject parenterally. In one embodiment, the EV composition described herein is administered to a subject intravenously. In another embodiment, the EV composition described herein is administered to a subject intranasally. In some embodiments, the EVs coupled to the binding agents, or the therapeutic agents coupled to the binding agents, are transported across the BBB and reach the brain or the CNS at a rate at least 10% greater, 15% greater, 20% greater, 25% greater, 30% greater, 35% greater, 40% greater, 45% greater, 50% greater, 55% greater, 60% greater, 65% greater, 70% greater, 75% greater, 80% greater, 90% greater, 100% greater, 150% greater, 200% greater, 300% greater, 400% greater, 500% greater, 1000% greater, or more than 1000% greater as compared to transport or delivery of the EVs or the therapeutic agents without the binding agent, when administered at a site distal to the brain or the CNS.

An injectable composition for parenteral administration (e.g. intravenous, intramuscular, intrathecal intracerebrospinal fluid, or intranasal), can contain the EVs or the binding agent-therapeutic agent conjugates of the present disclosure and optionally additional components in a suitable i.v. solution, such as sterile physiological salt solution. In other embodiments, the composition is formulated as a suspension in an aqueous emulsion.

Liquid pharmaceutical compositions can be prepared by dissolving or dispersing a population of the EVs or the binding agent-therapeutic agent conjugates described herein, and optional pharmaceutical adjuvants, in a carrier, such as, for example, aqueous saline, aqueous dextrose, glycerol, or ethanol, to form a solution or suspension.

Intravenous formulations can comprise the EVs described herein (e.g., comprising neural cell derived EVs) or the binding agent-therapeutic agent conjugates described herein, an isotonic medium and one or more substances preventing aggregation of the EVs or the conjugates. Example intravenous/intrathecal/intracerebrospinal fluid formulations may contain saline solutions (e.g. normal saline (NS); about 0.91% w/v of NaCl, about 300 mOsm/L) and/or dextrose 4% in 0.18% saline, and optionally 1%, 2% or 3% human serum albumin. In addition, the EVs or the binding agent-therapeutic agent conjugates of the present disclosure may be disrupted to obtain the contents and the contents used in compositions according to the present disclosure.

For use in an oral liquid preparation, the composition may be prepared as a solution, suspension, emulsion, or syrup, being supplied either in liquid form or a dried form suitable for hydration in water or normal saline. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

In the case of intranasal, intratracheal or intrapulmonary administration, the compositions may be provided in a liquid formulation which can be sprayed into the nose, trachea and/or lungs.

When the composition is employed in the form of a solid preparation for oral administration, the preparation may be a tablet, granule, powder, capsule or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

The pharmaceutical compositions provided herein (e.g., pharmaceutical compositions comprising the EVs described herein, comprising neural cell derived EVs), or the binding agent-therapeutic agent conjugates may be administered once to the subject or, alternatively, multiple administrations may be performed over a period of time. For example, two, three, four, five, or more administrations may be given to the subject during one treatment, or over a set period of time. In some instances, six, eight, ten, 12, 15 or 20 or more administrations may be given to the subject during one treatment or over a period of time as a treatment regimen. In other instances, administrations may be given as needed, e.g., for as long as symptoms associated with a neurological disorder persist. In some embodiments, repeated administrations may be indicated for the remainder of the subject's life. Exemplary dosing schedules include administration of a pharmaceutical composition comprising the EVs described herein once per day, once every two days, once every three days, once per week, once every two weeks, once every month, once every two months, once every three months, six months, 12 months, or longer.

Pharmaceutical compositions comprising the EVs or the binding agent-therapeutic agent conjugates as described herein may be administered to a subject as a monotherapy (a single agent) or in a combination therapy where the subject is administered a pharmaceutical composition comprising the EVs or the binding agent-therapeutic agent conjugates in combination with one or more additional agents. A pharmaceutical composition comprising the EVs or the binding agent-therapeutic agent conjugates of the present disclosure, and one or more additional agents, can be administrated to a subject simultaneously, sequentially or temporally.

In one embodiment, the disclosure provides a pharmaceutical composition comprising the EVs as described herein (e.g., a pharmaceutical composition comprising neural cell derived EVs, e.g., comprising neural derived EVs) or the binding agent-therapeutic agent conjugates described herein for use in treating a subject having a neurological disorder, for example, Alzheimer's Disease, Huntington's Disease, Parkinson's Disease, or neurological cancer, e.g., glioblastoma. In another embodiment, the disclosure provides a pharmaceutical composition comprising the EVs as described herein (e.g., a pharmaceutical composition comprising the EVs, e.g., comprising neural derived EVs) or the binding agent-therapeutic agent conjugates for use in the manufacture of a medicament for treating a subject having a neurological disorder, for example, Alzheimer's Disease, Huntington's Disease, Parkinson's Disease, or neurological cancer, e.g., glioblastoma.

In some instances, pharmaceutical formulations may comprise about 50 ng EVs/ml fluid medium, or more. Exemplary pharmaceutical formulations can comprise about 100 ng, 200 ng, 300 ng, 400 ng, 500 ng, 600 ng, 700 ng, 800 ng, 900 ng, 1.0 µg, 1.5 µg, 2.0 µg, 2.5 µg, 3.0 µg, 5.0 µg, 10.0, 15.0 µg, 20.0 µg, 100 µg, or more EVs/ml fluid medium.

In other embodiments, pharmaceutical formulations may comprise about 0.1 µg EVs/ml medium, about 0.2 µg EVs/ml intravenous medium, about 0.3 µg EVs/ml intravenous medium, about 0.4 µg EVs/ml intravenous medium, about 0.5 µg EVs/ml intravenous medium, about 0.6 µg EVs/ml intravenous medium, about 0.7 µg EVs/ml intravenous medium, about 0.8 µg EVs/ml intravenous medium, about 0.9 µg EVs/ml intravenous medium, about 1.0 µg EVs/ml intravenous medium, about 1.5 µg EVs/ml intravenous medium, about 2.0 µg EVs/ml intravenous medium, about 2.5 µg EVs/ml intravenous medium, such as at least e.g. about 3.0 µg EVs/ml intravenous medium, such as e.g. at least about 5.0 µg EVs/ml intravenous medium, about 10.0 µg EVs/ml intravenous medium, 15.0 µg EVs/ml intravenous medium or about 20.0 µg or more EVs/ml intravenous medium.

In some instances, administering a composition includes $1 \times 10^8$ or more EVs described herein per kilogram in a single dose. In other instances, administering an EV composition includes a dosage of $1 \times 10^8$, $1 \times 10^8$ to $1 \times 10^9$, $1 \times 10^9$ to $1 \times 10^{10}$, $1 \times 10^{10}$ to $1 \times 10^{11}$, $1 \times 10^{11}$ to $1 \times 10^{12}$, $1 \times 10^{12}$ or more EVs described herein per kilogram. In some instances, a single dose is administered multiple times to the subject. In certain other instances, the multiple administrations to the subject include two or more of intravenous, intracerebrospinal, intravenous infusion, and injection.

In some instances, the pharmaceutical composition is in a dosage form comprising at least 1 mg of EVs, at least 5 mg of EVs, at least 10 mg of EVs, at least 20 mg of EVs, at least 25 mg of EVs, at least 50 mg of EVs, at least 60 mg of EVs, at least 75 mg of EVs, at least 100 mg of EVs, at least 150 mg of EVs, at least 200 mg of EVs, at least 250 mg of EVs, at least 300 mg of Ab-EVs, about 350 mg of EVs, about 400 mg of EVs, about 500 mg of EVs, about 750 mg of EVs, about 1 g (1,000 mg) or more of EVs described herein, alone or in combination with a therapeutically effective amount of at least one additional agent. In some embodiments, the pharmaceutical composition comprises between about 10 mg to about 750 mg, about 25 mg to about 650 mg, or between about 30 mg to about 500 mg, or about 35 mg to about 450 mg, most often about 50 to about 500 mg of the EVs described herein.

A therapeutically effective amount of a pharmaceutical composition comprising the EVs of the present disclosure, e.g., comprising neural derived EVs, or the binding agent-therapeutic agent conjugates of the present disclosure is an amount of sufficient to treat or ameliorate one or more symptoms of the condition being treated (e.g., a neurological disorder, for example, Alzheimer's Disease, Huntington's Disease, Parkinson's Disease, or neurological cancer, e.g., glioblastoma), while not exceeding an amount which may cause significant adverse effects. Dosages that are therapeutically effective can depend on many factors including the nature of the condition to be treated as well as the particular individual being treated.

G. Methods of Treatment

In some aspects, the present disclosure provides a method of treating a subject using compositions comprising the EVs or the binding agent-therapeutic agent conjugates described herein. Any of the compositions or pharmaceutical compositions comprising the EVs or the binding agent-therapeutic agent conjugates described herein are suitable for use in any of the methods provided herein. In exemplary embodiments, the EVs of the present disclosure are derived from neural cells, e.g., neural progenitor cells, neurons, or astrocytes. In other exemplary embodiments, the EVs are produced synthetically, and contain one or more markers characteristic of neural EVs, e.g., one or more proteins or nucleic acids present in neural EVs that are absent in EVs derived from MSCs. In other exemplary embodiments, the EVs contain one or more additional therapeutic agents, for example, one or more AED, including but not limited to those selected from carbamazepine, valproic acid, lamotrigine, oxycarbamazepine, pregabalin, gabapentin, and topiramate, and combinations thereof.

In some aspects, the present disclosure provides a method of treating (e.g., curing, suppressing, ameliorating associated symptoms of, delaying or preventing the progression of, delaying or preventing onset of, or preventing recurrence or relapse of) a neurological disorder, for example, Alzheimer's Disease, Huntington's Disease, Parkinson's Disease, or neurological cancer, e.g., glioblastoma, in a subject, comprising administering to the subject a composition comprising an EV as described herein, or the binding agent-therapeutic agent conjugates as described herein, in an amount sufficient to treat the disease or disorder in the subject. The amount sufficient to treat the disease or disorder is preferably an effective amount, e.g., a therapeutically effective amount, as provided herein.

Alteration of symptoms as a result of treatment can be measured relative to any suitable control. For example, alteration of symptoms can be measured relative to the frequency, severity, or duration, or number of symptoms experienced by the same subject prior to initiating treatment. In other embodiments, alteration of symptoms can be measured relative to the frequency, severity, duration, or number of symptoms experienced by a different subject, or group of subjects, with like symptoms who do not receive the treatment, i.e., who do not receive a composition comprising the EVs of the present disclosure or the binding agent-therapeutic agent conjugates of the present disclosure. In some embodiments, the degree of improvement is at least 5%, i.e., at least 5%, 10%, 20%, 30%, 40%, 50%, 60%, 70%, 80%, 90%, 95%, 99% or more, as determined relative to a suitable control.

In some embodiments, a composition comprising the EV or a binding agent-therapeutic agent conjugates described herein is administered to a subject as a single dose. In some embodiments, a composition comprising the EV or a binding agent-therapeutic agent conjugates described herein is administered in multiple doses. For example, the composition can be administered, in some embodiments, once every day, once every 2 days, once every 3 days, once every 4 days, once every 5 days, once every 6 days, once every 7 days, once every 2 weeks, once every 3 weeks, once every 4 weeks, once every 8 weeks, or once every 12 weeks.

It will be readily apparent to those skilled in the art that other suitable modifications and adaptations of the methods described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

The Examples below are merely illustrative, and are not intended to limit the scope of the disclosure provided herein in any way.

Example 1: Identification of Endothelial Cell Markers and Pathways for Enhanced EV Uptake Overview In vitro systems in which each cell in a cell population has one gene knocked out using the CRISPR/Cas9 system are available for genetic screens (Horlbeck, M. A., et al., Compact and highly active next-generation libraries for CRISPR-mediated gene repression and activation. Elife, 2016. 5).

The following experiments describe a genetic screen designed to identify pathways involved in EV uptake. Previous results indicate that EVs derived from neural stem cells/neural progenitor cells can cross the BBB by an unknown mechanism. Transformed human brain endothelial cell cultures have been used to mimic the BBB in vitro and are sold commercially under the name HCMEC/D3 (D3) (Weksler, B., I. A. Romero, and P.-O. Couraud, The hCMEC/D3 cell line as a model of the human blood brain barrier. Fluids and barriers of the CNS, 2013. 10(1): p. 16-16). The following study makes use of D3 cells and EVs derived from a neural progenitor cell line (AB126), which can be fluorescently labeled such that uptake of EVs by cells is detectable on a flow cytometer. D3 cells underwent Cas9 and library transduction to generate single gene knockouts, followed by treatment with fluorescently labeled EVs (AB126). Cells lacking expression (via gene knockout) of proteins involved in EV uptake have reduced fluorescence relative to cells with unperturbed uptake, thereby identifying endothelial genes and pathways that are critical or involved in EV uptake.

Preliminary Experiments

To ensure efficacy, feasibility, and reproducibility of the uptake studies described herein, preliminary experiments were necessary to optimize various parameters including, e.g., cell doubling time, EV labeling specificity, uptake time course, fluorescence maximization, antibiotic resistance profiles, and toxicity profiles. For example, it was determined that Cas9-transduced culture of 1e5 cells could feasibly increase to 8e7 cells in 4 passages, well within the 10 passage limit recommended by the D3 cell line manufacturer. In addition, ExoGlow™ Protein EV Labeling reagent was chosen for future studies, as the balance between fluorescence intensity and covalent mechanism of labeling made it more appealing than reagents that label RNA or membranes. To maximize the difference in fluorescence in high uptake versus low uptake cells, the timepoint of maximum cellular uptake of EVs was also determined. In general, there was an upward trend over the course of 24 hours that appears to plateau near the 16-24 hour mark. Given that the cells double every 1+ days, it was decided to use 24 hours as the final time point. Further, cells selected from the screen are those with lower fluorescence than control, indicating decreased EV uptake. Therefore, the higher the fluorescence in the positive control cells, the easier it is to distinguish the cells with affected uptake. Taking this into consideration, adjustments were made to, e.g., staining protocols and gating during flow cytometry. Other optimization procedures important to the feasibility of the experimental system were performed as necessary.

Cell Line Generation

Cellecta CRISPR Cas9 pRCCB-CMV-Cas9-2A-Blast (viral prep, 4.6e6 to/900 μL) was purchased from Cellecta. Cells were plated according to the table below for inoculation at 1, 3 and 10 MOI, as well as an untreated control. Doubling time was calculated using the previously determined rate of 1.31 days/doubling. Seeding density was adjusted to 30,000 cells/cm$^2$ for viral inoculation. The number of cells required per treatment (3.29E+05) was back calculated from doubling time and viral titer, in accordance with typical cell densities 1-2 days post plating.

TABLE 3

Cell culture conditions for viral inoculation with CRISPR Cas9 pRCCB-CMV-Cas9-2A-Blast. Cell number determination and viral inoculation time from plating.

| | | |
|---|---|---|
| Surface area | 3.8 | cm2 |
| Cell seeding density | 30,000 | cells/cm2 |
| Total cells | 114,000 | cells |
| Doubling time average | 1.31 | days |
| time post plate (day) | 2.00 | days |
| time posts plate (hr) | 48.01 | hours |

TABLE 4

| Amount of virus (TU) applied to each well 48 hours post-plating. | |
| --- | --- |
| MOIs needed | Virus needed (TU) |
| 0 | 0 |
| 1 | 3.29E+05 |
| 3 | 9.86E+05 |
| 10 | 3.29E+06 |
| Total virus: | 4.60E+06 |

Cells were transduced in the presence of 1 μL/mL LentiTrans with the appropriate amount of virus per MOI approximately 48 hours post-seeding. Cells were allowed to grow for 72 hours prior to 10 μg/mL blasticidin supplementation. Cells underwent two weeks of blasticidin selection and were passaged as needed. Eleven days after selection began, cells were split into 2/12 wells per MOI to perform the CRISPRuTest (Cellecta). At the end of 2 weeks in blasticidin at 10 μg/mL, cells were split into 3 groups per MOI and subjected to 1×, 2× and 4× blasticidin concentrations (10, 20, 40 μg/mL). MOI 10 was chosen as the best MOI. MOIs 1 and 3 were frozen "as is", after 5 days in higher selection. All 3 MOI 10 were passaged to 3×T225s to prepare for viral transduction as described below.

1. CRISPR Efficacy Test

The CRISPRuTest for Cas9/CRISPR-KO was purchased from Cellecta and performed per manufacturer instructions. Briefly, all three MOIs (1, 3 and 10) were split into 2 wells of a 12 well plate and treated with 20 μL of virus (either CT-A or CT-B, day 0). Cells were passaged after 3 days. On day 5, cells were dissociated and flow cytometry was performed. Flow cytometry showed that all 3 MOIs were effective in knocking out most of the GFP expression. MOI 10 was most effective and chosen for next steps, followed by MOI 1 and MOI 3 (data not shown).

2. gRNA Test Transduction/Puromycin Concentration Determination

A test transduction using the gRNA library followed by puromycin selection was performed to determine the optimal concentration to select for 1 gRNA/cell, as needed for the screen setup. Cells were plated at 50 K/cm² and transduced 24 hours later at an MOI of ~0.5. Three days later, cells were split into 6 groups and replated in the following concentrations of puromycin: 0, 0.5, 1, 2, 4 and 8 μg/mL. Cells were passaged as needed. On day 10 post-selection (day 13 post-transduction), cells were passaged, and extra cells not needed for plating were retained for flow cytometry. Here, the goal was to establish a baseline selection at 10 days. The goal of puromycin selection is to select for cells with 1 gRNA. This is accomplished by comparing selected cells (0.5, 1, 2, 4, 8 μg/mL) to unselected cells (0 μg/mL). The ideal result is a population that is 90% positive for RFP yet is not shifted higher than control. Higher RFP may indicate >1 gRNA/cell, which impact the screening process. Flow data was gated by +/−RFP and the percent GFP+/− and mode of each population was reported (data not shown).

Based on these results, 2 μg/mL is optimal, as it comes the closest to 90% RFP+ while retaining a similar mode at lesser concentrations. Although the mode (and most other measured metrics, data not shown) is above that of unselected (0 μg/mL), the manufacturer recommends selecting the concentration that affects the RFP+ fluorescence intensity the least, rather than not at all. From these results, it was decided to continue puromycin selection for two weeks post-transduction for best results. At least 10 days is recommended to allow for complete gene knockout.

3. gRNA Transduction

MOI 10 at 40 μg/mL blasticidin (10/40) was chosen as the best cell line for the screen. Four days post-plating, cells were dissociated and counted with the TC-10 cell counter. A final cell number of 1.22e8 cells was obtained. This was then combined with 32 μL of virus at 1.25e6 TU/μL, resulting in a total of 4e7 virus particles mixed with cells in suspension. The final MOI was 0.33 with 500 copies per unique gRNA, both of which were within recommended ranges. Cells were plated with 1 μL LentiTrans per mL of media in 14×T225 flasks containing ~30 mL media each at a final density of ~38 K/cm². The remainder of MOI 10/10 was frozen (10 vials at ~3.3e6 per vial) for future use.

4. Maintenance and Selection of gRNA+ Cells

On day 3 post-passaging (~72 hours), media was changed to fresh media with puromycin at 2 μg/mL. At each passage, cells were resuspended, counted, and replated in 2 μg/mL puromycin. Passages on day 3 and 8 post-puromycin included test runs on the Astrios cell sorter.

Uptake Experiment

1. EV Preparation

EVs were isolated from a final volume of 20 mL cell culture supernatant obtained from neural progenitor cell cultures. Approximately ~5e13 EVs as determined by Nanosight were generated. EVs were stored at 4° C. overnight. The following day, the EVs were split into ~10 mL fractions and loaded into 2× qEV10 35 nm Size Exclusion Chromatography (SEC) columns for purification of EVs. The three EV-containing fractions were collected (~30 mL) and reacted and labeled with 40 μM Carboxyfluorescein succinimidyl ester (CFSE) for 60 minutes at 37 C. All 30 mL was put through Zeba desalting columns in 4 mL aliquots (10 mL column, 7 kDa MWCO) per manufacturer instructions. EVs were protected from light and placed at 4° C. overnight. Nanosight indicated final EV recovery post-SEC was 3.8e12 particles.

2. Uptake Experiment

The 30 mL of EVs were applied to 7 of the 14 T225 flasks described above during a media change (30 mL media plus ~4.4 mL EV per flask) and co-incubated for 24 hours. Control dishes received a media change with an equal volume of PBS++. Images were taken at 7.5 hours post-treatment and 23.75 hours post-treatment (FIG. 1) indicating time-dependent uptake of fluorescent EVs. Treated cells were dissociated and counted, split into 3 equivalent groups and put on ice at 30e6 cells/mL for sorting. In all, about 250 million and 280 million cells were retrieved from the EV-treated and PBS-treated groups, respectively, prior to being split 3 ways into technical replicates.

3. Fluorescence Activated Cell Sorting

Figure 2:
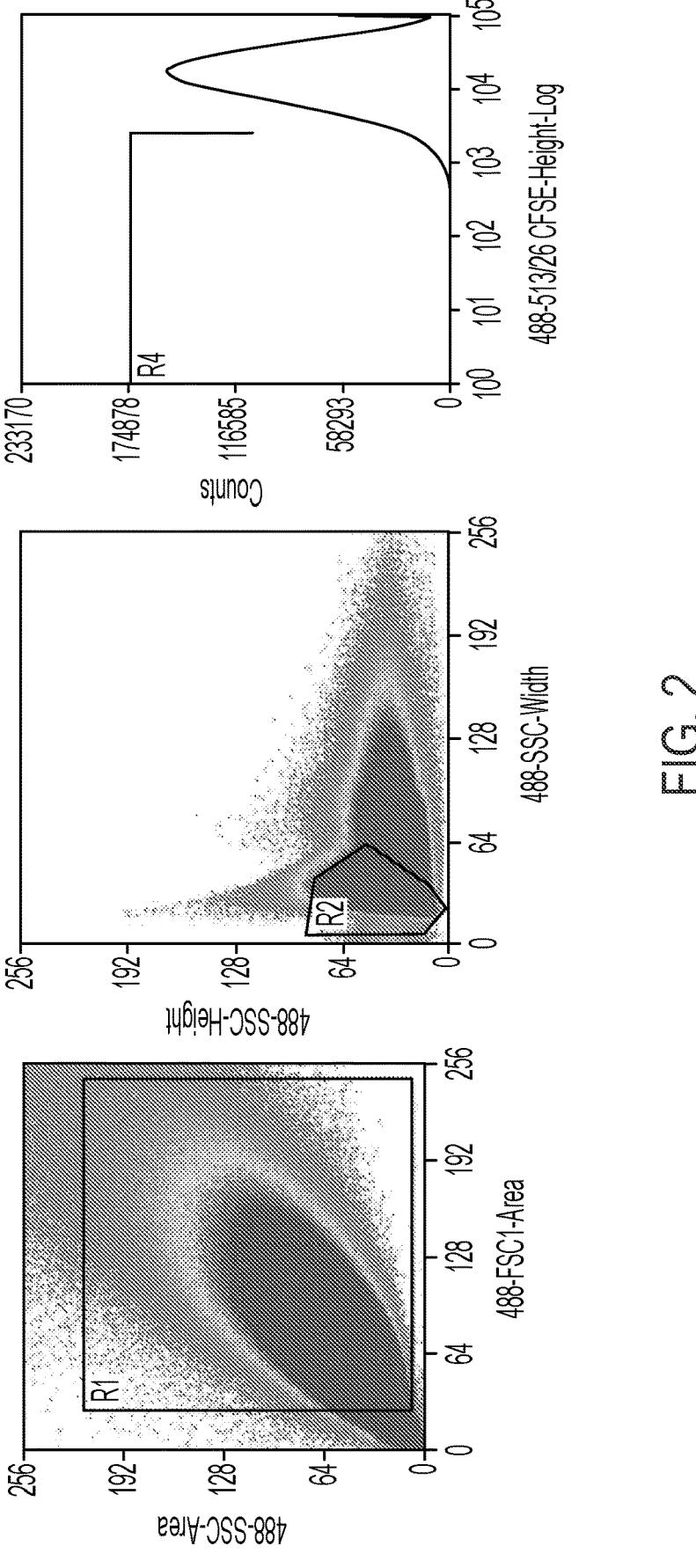
FIG. 2 shows the gating strategy for cell sorting. Events were gated based on 3 sequential gates. First, cells were separated from debris using FSC-Area vs SSC-Area (R1, left). Second, single cells were separated from doublets using SSC-Width vs SSC-Height (R2, middle). Finally, the 3-4 percent of cells with the lowest 488-Height values (R4, right) were retained for sequencing.

Cells were sorted based on a series of 3 gates using the Beckman Coulter MoFlo Astios EQ. The gating strategy used first delineated between cells and debris, then single cells, followed by retaining the bottom 3-4% of cells based on the CFSE signal (FIG. 2). Based on the flow cytometer's real time data, about 900,000 events were captured from gate R4 for each condition.

4. Cell Freezing and Shipping

During the cell sort, the remaining PBS-treated cells were dissociated, split into 3 equal groups and pelleted. Sorted cells were kept on ice in 50 mL tubes and pelleted as they came off the cell sorter. All cells pellets were resuspended in PBS+/+ and transferred to 1.8 mL Cryovials (Nunc). Cells were re-pelleted, as much PBS as possible was aspirated, and Cryovials were snap-frozen in liquid nitrogen prior to storage at −80 C until shipping. The six cell pellets were then shipped to Cellecta on dry ice for sequencing.

Results and Hit Determination

Figure 3:
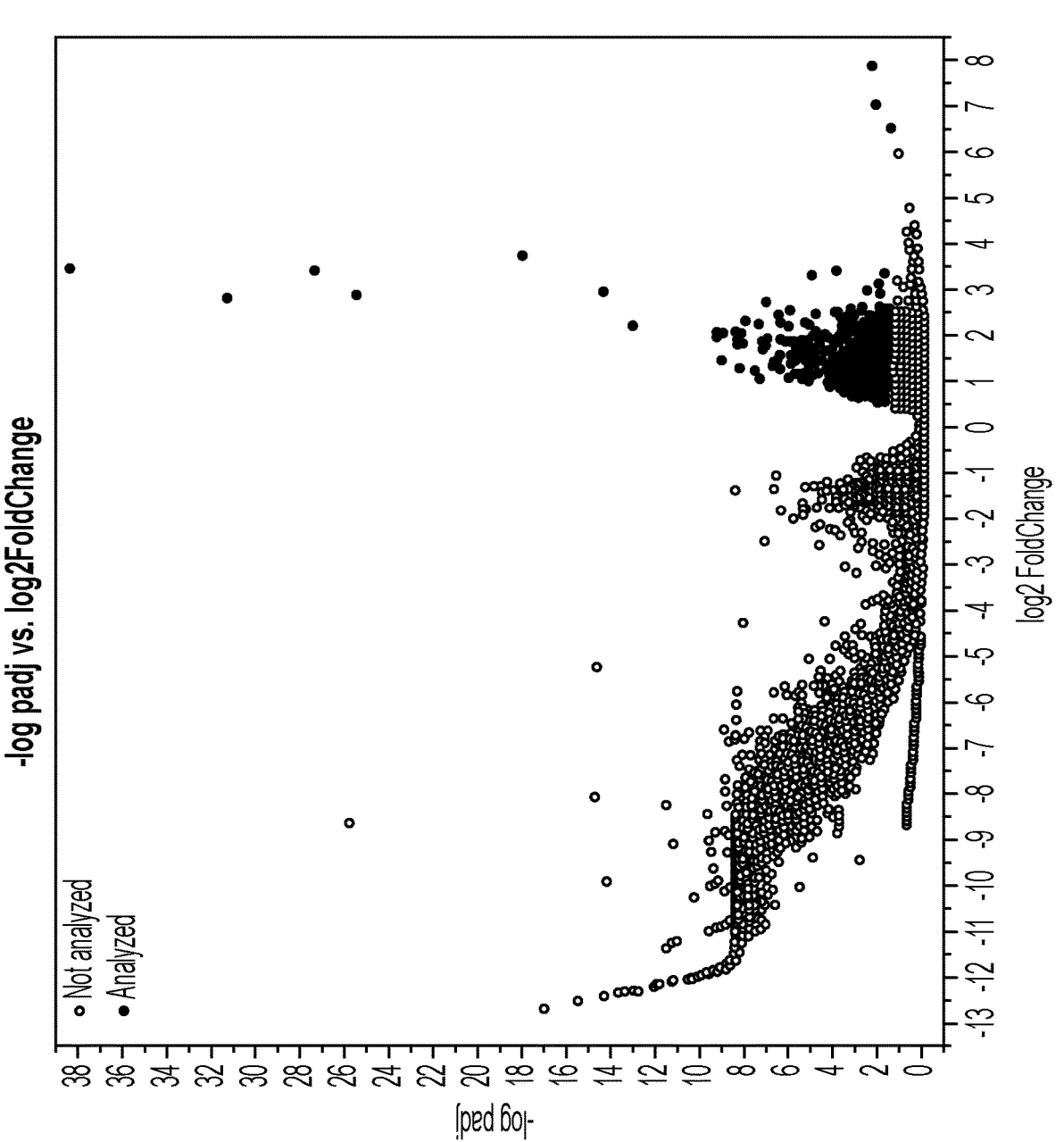
FIG. 3 is a volcano plot of gRNA sequencing alignment, plotting the negative $\log_{10}$ of the adjusted p-value and the $\log_2$ fold change. Those showing a positive fold change with a p-value less than 0.05 (red circles) were selected for further analysis.

Cellecta provided raw sequencing data (fastq files) and an excel file with reads for each of the 6 samples, annotated by each of the 80,000 sgRNA's. Using guide RNA alignments, the sequences were re-aligned and three types of analyses were performed: (i) MAgeCK (Li, W., et al., MAGeCK enables robust identification of essential genes from genome-scale CRISPR/Cas9 knockout screens. Genome Biology, 2014. 15(12): p. 554) protocol with batch effect removal, (ii) MAgeCK without batch effect removal, and (iii) MAgeCK alignment paired with DESeq2 differential expression analysis. Neither MAgeCK analyses provided high confidence hits alone. However, MAgeCK combined with DESeq2 provided robust results. Of the total gene set, 6,442 gRNAs had an adjusted p-value ($p_{adj}$) of less than 0.05 corresponding to 5,125 unique genes. Of interest were those genes enriched in the experimental condition (as opposed to those depleted), so all genes with an adjusted p-value (padj) less than 0.05 with a positive $log_2$ fold change ($log_2$FC) were further separated from the list. FIG. 3. This narrowed the list to 976 gRNAs representing 951 unique genes, with 25 genes having 2 gRNA hits.

The 951 unique genes were then cross-referenced with a list of receptor-ligand pairs (from https://baderlab.org/Cell-CellInteractions) yielding 132 unique proteins (Table 2).

TABLE 2

| Target Proteins Facilitating Traversal of the Blood Brain Barrier | | |
|---|---|---|
| Target Protein (Abbreviated) | Target Protein | Reference No. |
| 1. ACVR2B | Activin receptor type-2B | UniProt Identifier: Q13705 |
| 2. ADAMTS15 | A disintegrin and metalloproteinase with thrombospondin motifs 15 | UniProtKB Identifier: Q8TE58 |
| 3. ADIPOR2 | Adiponectin receptor protein 2 | UniProtKB Identifier: Q86V24 |
| 4. ADRA1A | Alpha-1A adrenergic receptor | UniProtKB Identifier: P35348 |
| 5. AGR2 | Anterior gradient protein 2 homolog | UniProtKB Identifier: O95994 |
| 6. ALCAM | CD166 antigen (encoded by ALCAM) | UniProtKB Identifier: Q13740 |
| 7. AMN | Protein amnionless | UniProtKB Identifier: Q9BXJ7 |
| 8. ANGPT2 | Angiopoietin-2 | UniProtKB Identifier: O15123 |
| 9. BCHE | Cholinesterase (encoded by BCHE) | UniProtKB Identifier: P06276 |
| 10. BDH2 | 3-hydroxybutyrate dehydrogenase type 2 | UniProtKB Identifier: Q9BUT1 |
| 11. BMP15 | Bone morphogenetic protein 15 | UniProtKB Identifier: O95972 |
| 12. C2orf69 | UPF0565 protein C2orf69 | UniProtKB Identifier: Q8N8R5 |
| 13. C4BPB | C4b-binding protein beta chain | UniProtKB Identifier: P20851 |
| 14. CA6 | Carbonic anhydrase 6 | UniProtKB Identifier: P23280 |
| 15. CBLN1 | Cerebellin-1 | UniProtKB Identifier: P23435 |
| 16. CD74 | HLA class II histocompatibility antigen gamma chain | UniProtKB Identifier: P04233 |
| 17. CD84 | SLAM family member 5 | UniProtKB Identifier: Q9UIB8 |
| 18. CD86 | T-lymphocyte activation antigen CD86 | UniProtKB Identifier: P42081 |
| 19. CDH1 | Cadherin-1 | UniProtKB Identifier: P12830 |
| 20. CELSR3 | Cadherin EGF LAG seven-pass G-type receptor 3 | UniProtKB Identifier: Q9NYQ7 |
| 21. CER1 | Cerberus | UniProtKB Identifier: O95813 |
| 22. CHIT1 | Chitotriosidase-1 | UniProtKB Identifier: Q13231 |
| 23. CHRNA2 | Neuronal acetylcholine receptor subunit alpha-2 | UniProtKB Identifier: Q15822 |
| 24. CLEC1B | C-type lectin domain family 1 member B | UniProtKB Identifier: Q9P126 |
| 25. COL4A6 | Collagen alpha-6(IV) chain | UniProtKB Identifier: Q14031 |
| 26. COL8A2 | Collagen alpha-2(VIII) chain | UniProtKB Identifier: P25067 |
| 27. COMP | Cartilage oligomeric matrix protein | UniProtKB Identifier: P49747 |
| 28. CRELD2 | Protein disulfide isomerase CRELD2 | UniProtKB Identifier: Q6UXH1 |
| 29. CRTAP | Cartilage-associated protein | UniProtKB Identifier: O75718 |
| 30. CTSZ | Cathepsin Z | UniProtKB Identifier: Q9UBR2 |
| 31. CXCL2 | C-X-C motif chemokine 2 | UniProtKB Identifier: P19875 |
| 32. DKK3 | Dickkopf-related protein 3 | UniProtKB Identifier: Q9UBP4 |
| 33. EXTL2 | Exostosin-like 2 | UniProtKB Identifier: Q9UBQ6 |
| 34. F7 | Coagulation factor VII | UniProtKB Identifier: P08709 |
| 35. FCGBP | IgGFc-binding protein; Fcgamma-binding protein antigen | UniProtKB Identifier: Q9Y6R7 |
| 36. FREM2 | FRAS1-related extracellular matrix protein 2 | UniProtKB Identifier: Q5SZK8 |
| 37. GC | Vitamin D-binding protein | UniProtKB Identifier: P02774 |
| 38. GDF2 | Growth/differentiation factor 2 | UniProtKB Identifier: Q9UK05 |
| 39. GLRB | Glycine receptor subunit beta | UniProtKB Identifier: P48167 |
| 40. GPHA2 | Glycoprotein hormone alpha-2 | UniProtKB Identifier: Q96T91 |
| 41. GPR37L1 | G-protein coupled receptor 37-like 1 | UniProtKB Identifier: O60883 |
| 42. GSN | Gelsolin | UniProtKB Identifier: P06396 |
| 43. GZMM | Granzyme M | UniProtKB Identifier: P51124 |
| 44. HCRTR2 | Orexin receptor type 2 | UniProtKB Identifier: O43614 |
| 45. HLA-DOA | HLA class II histocompatibility antigen, DO alpha chain | UniProtKB Identifier: P06340 |
| 46. HLA-DPA1 | HLA class II histocompatibility antigen, DP alpha 1 chain | UniProtKB Identifier: P20036 |
| 47. HNF4A | Hepatocyte nuclear factor 4-alpha | UniProtKB Identifier: P41235 |
| 48. HTR6 | 5-hydroxytryptamine receptor 6 | UniProtKB Identifier: P50406 |
| 49. IFNLR1 | Interferon lambda receptor 1 | UniProtKB Identifier: Q8IU57 |
| 50. IL11 | Interleukin-11 | UniProtKB Identifier: P20809 |
| 51. IL15 | Interleukin-15 | UniProtKB Identifier: P40933 |

TABLE 2-continued

Target Proteins Facilitating Traversal of the Blood Brain Barrier

| Target Protein (Abbreviated) | Target Protein | Reference No. |
|---|---|---|
| 52. IL17B | Interleukin-17B | UniProtKB Identifier: Q9UHF5 |
| 53. IL1RL1 | Interleukin-1 receptor-like 1 | UniProtKB Identifier: Q01638 |
| 54. IL23R | Interleukin-23 receptor | UniProtKB Identifier: Q5VWK5 |
| 55. IMPG1 | Interphotoreceptor matrix proteoglycan 1 | UniProtKB Identifier: Q17R60 |
| 56. INSL3 | Insulin-like 3 | UniProtKB Identifier: P51460 |
| 57. ITIH1 | Inter-alpha-trypsin inhibitor heavy chain H1 | UniProtKB Identifier: P19827 |
| 58. IZUMO1 | Izumo sperm-egg fusion protein 1 | UniProtKB Identifier: Q8IYV9 |
| 59. JAG1 | Protein jagged-1 | UniProtKB Identifier: P78504 |
| 60. JAG2 | Protein jagged-2 | UniProtKB Identifier: Q9Y219 |
| 61. KCNJ10 | ATP-sensitive inward rectifier potassium channel 10 | UniProtKB Identifier: P78508 |
| 62. KERA | Keratocan | UniProtKB Identifier: O60938 |
| 63. KLK10 | Glandular kallikrein-10 | UniProtKB Identifier: P36375 |
| 64. KLK11 | Kallikrein-11 | UniProtKB Identifier: Q9UBX7 |
| 65. LAMB3 | Laminin subunit beta-3 | UniProtKB Identifier: Q13751 |
| 66. LCN12 | Epididymal-specific lipocalin-12 | UniProtKB Identifier: Q6JVE5 |
| 67. LEP | Leptin | UniProtKB Identifier: P41159 |
| 68. LFNG | Beta-1,3-N-acetylglucosaminyltransferase lunatic fringe | UniProtKB Identifier: Q8NES3 |
| 69. LGMN | Legumain | UniProtKB Identifier: Q99538 |
| 70. LILRB1 | Leukocyte immunoglobulin-like receptor subfamily B member 1 | UniProtKB Identifier: Q8NHL6 |
| 71. LILRB3 | Leukocyte immunoglobulin-like receptor subfamily B member 3 | UniProtKB Identifier: O75022 |
| 72. LIPF | Gastric triacylglycerol lipase | UniProtKB Identifier: P07098 |
| 73. LPAR1 | Lysophosphatidic acid receptor 1 | UniProtKB Identifier: Q92633 |
| 74. LRP12 | Low-density lipoprotein receptor-related protein 12 | UniProtKB Identifier: Q9Y561 |
| 75. LUZP2 | Leucine zipper protein 2 | UniProtKB Identifier: Q86TE4 |
| 76. MATN3 | Matrilin-3 | UniProtKB Identifier: O15232 |
| 77. MCHR2 | Melanin-concentrating hormone receptor 2 | UniProtKB Identifier: Q969V1 |
| 78. MET | Hepatocyte growth factor receptor | UniProtKB Identifier: P08581 |
| 79. MFNG | Beta-1,3-N-acetylglucosaminyltransferase manic fringe | UniProtKB Identifier: O00587 |
| 80. MGP | Matrix Gla protein | UniProtKB Identifier: P08493 |
| 81. MMP7 | Matrilysin | UniProtKB Identifier: P09237 |
| 82. MMP11 | Stromelysin-3 | UniProtKB Identifier: P24347 |
| 83. MMP26 | Matrix metalloproteinase-26 | UniProtKB Identifier: Q9NRE1 |
| 84. MSMB | Beta-microseminoprotein | UniProtKB Identifier: P08118 |
| 85. MUC20 | Mucin-20 | UniProtKB Identifier: Q8N307 |
| 86. NAMPT | Nicotinamide phosphoribosyltransferase | UniProtKB Identifier: P43490 |
| 87. NMU | Neuromedin-U | UniProtKB Identifier: P48645 |
| 88. NOTUM | Palmitoleoyl-protein carboxylesterase NOTUM | UniProtKB Identifier: Q6P988 |
| 89. NPR2 | Atrial natriuretic peptide receptor 2 | UniProtKB Identifier: P20594 |
| 90. NPY4R | Neuropeptide Y receptor type 4 | UniProtKB Identifier: P50391 |
| 91. NR0B2 | Nuclear receptor subfamily 0 group B member 2 | UniProtKB Identifier: Q15466 |
| 92. NR2F2 | COUP transcription factor 2 | UniProtKB Identifier: P24468 |
| 93. NR6A1 | Nuclear receptor subfamily 6 group A member 1 | UniProtKB Identifier: Q15406 |
| 94. OBP2B | Odorant-binding protein 2b | UniProtKB Identifier: Q9NPH6 |
| 95. OSCAR | Osteoclast-associated immunoglobulin-like receptor | UniProtKB Identifier: Q8IYS5 |
| 96. P2RY6 | P2Y purinoceptor 6 | UniProtKB Identifier: Q15077 |
| 97. P2RY14 | P2Y purinoceptor 14 | UniProtKB Identifier: Q15391 |
| 98. P3H1 | Prolyl 3-hydroxylase 1 | UniProtKB Identifier: Q32P28 |
| 99. PDGFB | Platelet-derived growth factor subunit B | UniProtKB Identifier: P01127 |
| 100. PGA5 | Pepsin A-5 | UniProtKB Identifier: P0DJD9 |
| 101. PNP | Purine nucleoside phosphorylase | UniProtKB Identifier: P00491 |
| 102. PRL | Prolactin | UniProtKB Identifier: P01236 |
| 103. PROCR | Endothelial protein C receptor | UniProtKB Identifier: Q9UNN8 |
| 104. PROL1 | Opiorphin prepropeptide | UniProtKB Identifier: Q99935 |
| 105. PRSS12 | Neurotrypsin | UniProtKB Identifier: P56730 |
| 106. PSG6 | Pregnancy-specific beta-1-glycoprotein 6 | UniProtKB Identifier: Q00889 |
| 107. PTCH1 | Protein patched homolog 1 | UniProtKB Identifier: Q13635 |
| 108. PTGER1 | Prostaglandin E2 receptor EP1 subtype | UniProtKB Identifier: P34995 |
| 109. PTGER3 | Prostaglandin E2 receptor EP3 subtype | UniProtKB Identifier: P43115 |
| 110. PVRL1 | Poliovirus receptor-related 1 alpha isoform | UniProtKB Identifier: Q6SYC1 |
| 111. RDH8 | Retinol dehydrogenase 8 | UniProtKB Identifier: Q9NYR8 |
| 112. RNASE11 | Probable ribonuclease 11 | UniProtKB Identifier: Q8TAA1 |
| 113. RSPO1 | R-spondin-1 | UniProtKB Identifier: Q2MKA7 |
| 114. SAR1A | GTP-binding protein SAR1a | UniProtKB Identifier: Q9NR31 |
| 115. SCARB1 | Scavenger receptor class B member 1 | UniProtKB Identifier: Q8WTV0 |
| 116. SCGB2A1 | Mammaglobin-B | UniProtKB Identifier: O75556 |

TABLE 2-continued

Target Proteins Facilitating Traversal of the Blood Brain Barrier

| Target Protein (Abbreviated) | Target Protein | Reference No. |
|---|---|---|
| 117. SCGB2A2 | Mammaglobin-A | UniProtKB Identifier: Q13296 |
| 118. SERAC1 | Protein SERAC1; Serine Active Site Containing 1 | UniProtKB Identifier: Q96JX3 |
| 119. SERPINB2 | Plasminogen activator inhibitor 2 | UniProtKB Identifier: P05120 |
| 120. SFTPD | Pulmonary surfactant-associated protein D | UniProtKB Identifier: P35247 |
| 121. SLC1A5 | Neutral amino acid transporter B(0) | UniProtKB Identifier: Q15758 |
| 122. SNX2 | Sorting nexin-2 | UniProtKB Identifier: O60749 |
| 123. SPINK5 | Serine protease inhibitor Kazal-type 5 | UniProtKB Identifier: Q9NQ38 |
| 124. STRA6 | Receptor for retinol uptake STRA6 | UniProtKB Identifier: Q9BX79 |
| 125. TCN2 | Transcobalamin-2 | UniProtKB Identifier: P20062 |
| 126. TFR2 | Transferrin receptor protein 2 | UniProtKB Identifier: Q9UP52 |
| 127. THBD | Thrombomodulin | UniProtKB Identifier: P07204 |
| 128. TIMP4 | Metalloproteinase inhibitor 4 | UniProtKB Identifier: Q99727 |
| 129. VLDLR | Very low-density lipoprotein receptor | UniProtKB Identifier: P98155 |
| 130. WNT5B | Protein Wnt-5b; Wingless-Type MMTV Integration Site Family, Member 5B | UniProtKB Identifier: Q9H1J7 |
| 131. XPNPEP2 | Xaa-Pro aminopeptidase 2 | UniProtKB Identifier: O43895 |
| 132. ZP2 | Zona pellucida sperm-binding protein 2 | UniProtKB Identifier: Q05996 |

In addition to the proteins set forth in Table 2, the uptake experiment identified CD164, B3GAT1, and ST8SIA3 as targets of interest. CD164 plays a role in CD133+ cell migration. B3GAT1 and ST8SIA3 are enzymes that place particular epitopes on certain proteins, which epitopes can be targeted according to the methods of the invention. Accordingly, the epitopes generated by B3GAT1 and ST8SIA3 were also included as targets of interest.

Example 2. Validation of Genome-Wide Screen

In the earlier phase of the study, ~1,000 genes potentially involved in EV uptake and/or adherence to the HCMEC/D3 endothelial cell line were identified. This large set of genes was analyzed using gene expression data, and subcellular localization data, in addition to methods inherent to the analysis (number of gRNAs, p-value). Several targets were chosen for further validation including CD74, GPR37L1, HLA-DOA, HTR6, IFNLR1, MCHR2, VLDLR, ZP2, B3GAT1, ST8SIA3 and CD164. Two unique Cas9 lentiviral particles targeting each gene were ordered from Millipore Sigma.

Cell Line Transduction

HCMEC/D3 cells (D3) were ordered from Millipore Sigma and thawed (p0). D3 cells were cultured as described previously. On day 3, cells were split and ~1e$^5$ cells were plated onto a 12-well dish in the presence of 1 μL/mL LentiTrans reagent (Cellecta) and 5 MOI per clone of the gRNA lentiviral particles targeting each gene. 72 hours post-transduction, media was changed and supplemented with puromycin at 8 μg/mL. 3 days after initial selection, wells received a full media change supplemented with 5 μg/mL puromycin. Cells were split as needed in the presence of puromycin for a total of 14 days.

Uptake Experiment

At the end of puromycin selection for round 1, cells were passaged to 12-well dishes at 150K cells/cm2, 75K cells/cm$^2$, and 37.5K cells/cm$^2$. One day post-passage, conditioned media was enriched using a sucrose gradient protocol, labelled with CFSE as described, and free dye was removed with 5 mL 7K MWCO Zeba columns per manufacturer's instructions. Final volume was brought to 1.8 mL and split into 3, 0.6 mL aliquots and kept at 4 C. The following day (2 days post-passage) the 150 K/cm$^2$ group was treated with CFSE-labelled EVs in a complete media change. Cells were 100% confluent at the time of treatment. After 6 hours, cells were dissociated with Accumax, fixed for 10 minutes in 4% PFA and transferred to a 96-well plate for flow cytometry. This process was repeated on consecutive days for the 75 K/cm2 and 37.5 K/cm$^2$ dishes. Additionally, a HCMEC/D3 maintenance plate was dissociated and fixed to act as a "cells only" control.

Figure 4:
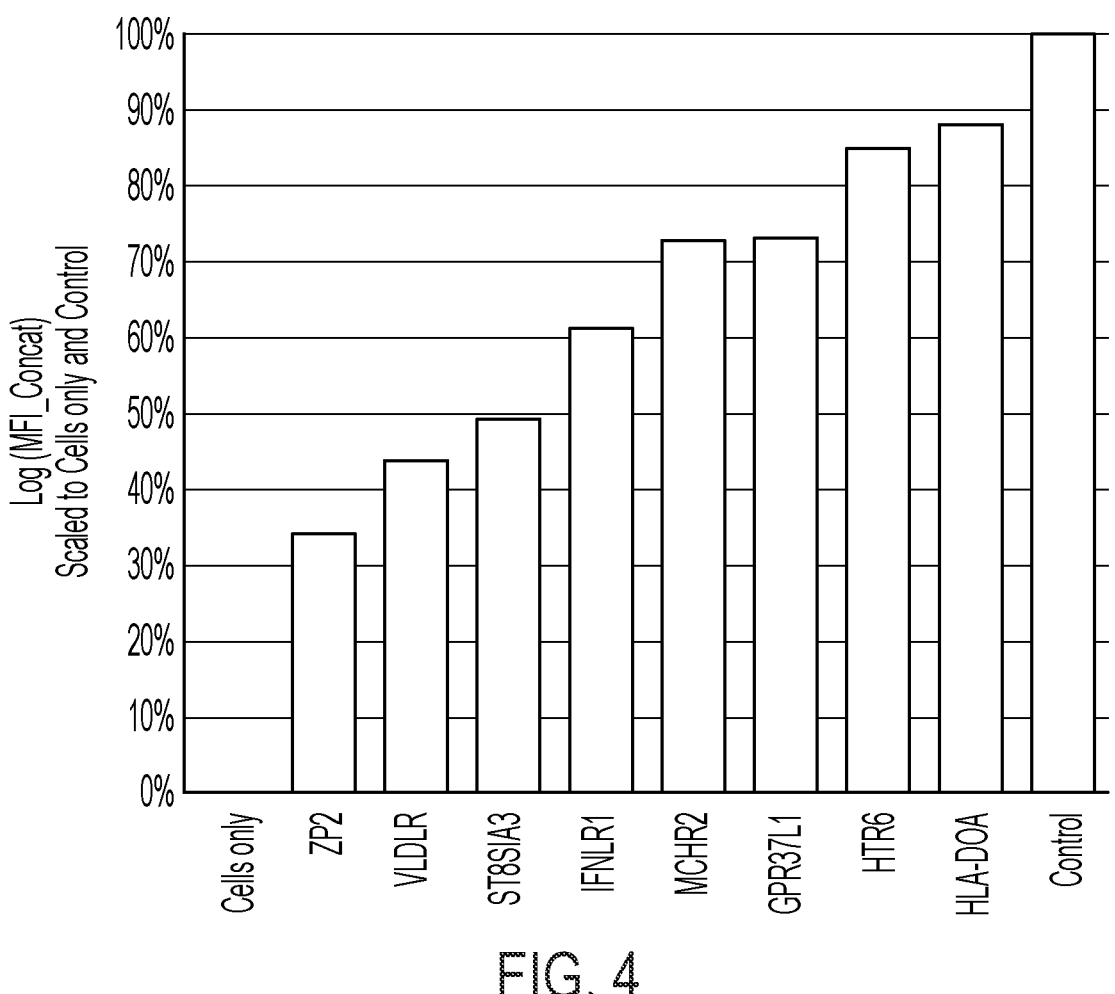
FIG. 4 shows that decreases in knockdown ranged from about 34% to about 88% in the validation study. Mean fluorescence intensity of 8 knock-out cell lines scaled to cells only and control are shown. Log-transformed median fluorescent intensity values from concatenated biological replicates were scaled to cells only (set to 0%) and CRISPR control (set to 100%).

Samples were analyzed on a Beckman Coulter CytoFlex S. Analysis was performed using FlowJo software. Briefly, single cells were gated and replicates were concatenated. Median fluorescent intensities (MFI) of the 488-525 Area (FL1-A) channel were log transformed and scaled based on "Cells only" and "CRISPR control" groups (FIG. 4). Log-transformed median fluorescent intensity values from concatenated biological replicates were scaled to cells only (set to 0%) and CRISPR control (set to 100%). Decreases in fluorescence intensity ranged from about 34% to 88%. Overall, 8 of the 11 cell lines were validated indicating their suitability as targets for enhanced EV uptake in the human brain microvascular endothelial cells.

EV Modification

Of the 8 hits, 4 were selected for proof of concept studies for modifying EVs to enhance BBB uptake: GPR37L1, ST8SIA3, ZP2 and VLDLR.

Example 3: In Vitro Penetration of Brain Endothelial Cells by Modified Exosomes

EVs derived from neural progenitor cells are modified using a Lamp2b-PSAP fusion gene construct to express PSAP, which specifically binds to GPR37L1 identified in the screen. Separately, post-isolation EVs were modified by conjugating the A2B5 antibody to EVs, which specifically binds the A2B5 epitope encoded by the ST8SIA3 enzyme. Both sets of modified EVs are labeled with CFSE for visualization. Unmodified EVs are also labeled with CFSE, and will serve as a control.

Unmodified D3 brain endothelial cells are plated in 6-well dishes and grown under standard conditions. Modified and unmodified EVs labeled with CFSE are added to 6 well dishes as follows (3 replicates per group):

Group 1: Unmodified EVs, low dose 200 EV/cell

Group 2: Unmodified EVs, intermediate dose 1000 EV/cell

Group 3: Unmodified EVs, high dose 5000 EV/cell

Group 4: EVs modified to express PSAP, low dose 200 EV/cell

Group 5: EVs modified to express PSAP, intermediate dose 1000 EV/cell

Group 6: EVs modified to express PSAP, high dose 5000 EV/cell

Group 7: EVs modified to express A2B5 antibody, low dose 200 EV/cell

Group 8: EVs modified to express A2B5 antibody, intermediate dose 1000 EV/cell

Group 9: EVs modified to express A2B5 antibody, high dose 5000 EV/cell

Uptake of the EVs by D3 brain endothelial cells is monitored over time. At 24 hours, cells are dissociated and washed, and fluorescence is quantitated using FACS.

Example 4: In Vivo Delivery of Modified Exosomes to the Brain and CNS

EVs derived from neural progenitor cells are modified as described above to express either PSAP or the A2B5 antibody, and labeled with 1.5-2 mCi of Indium-111-oxine. Unmodified EVs are also labeled with indium-111 to serve as a control. EVs are injected intravenously into the tail vein of mice as follows (3 replicates per group):

Group 1: Unmodified EVs, low dose 2.7e9 EV/kg

Group 2: Unmodified EVs, intermediate dose 2.7e10 EV/kg

Group 3: Unmodified EVs, high dose 2.7e11 EV/kg

Group 4: EVs modified to express PSAP, low dose 2.7e9 EV/kg

Group 5: EVs modified to express PSAP, intermediate dose 2.7e10 EV/kg

Group 6: EVs modified to express PSAP, high dose 2.7e11 EV/kg

Group 7: EVs modified to express A2B5 antibody, low dose 2.7e9 EV/kg

Group 8: EVs modified to express A2B5 antibody, intermediate dose 2.7e10 EV/kg

Group 9: EVs modified to express A2B5 antibody, high dose 2.7e11 EV/kg

Group 10: Free indium-111-oxine

Uptake of EVs is determined by head and whole body single photon emission spectroscopy imaging 1, 12, and 24 hours after injection, and the relative intensity of radioactivity in the brain and throughout the body is determined.

INCORPORATION BY REFERENCE

The contents of all references, patents, pending patent applications, and publications cited throughout this application are hereby expressly incorporated by reference herein in their entirety.

EQUIVALENTS

Those skilled in the art will recognize, or be able to ascertain using no more than routine experimentation, many equivalents to the specific embodiments described herein. Such equivalents are intended to be encompassed by the following claims.

What is claimed is:

1. An extracellular vesicle (EV) comprising a first exogenous binding agent that specifically binds to Cadherin EGF LAG seven-pass G-type receptor 3 (CELSR3).

2. The EV of claim 1, wherein:

the first exogenous binding agent enhances transport of the EV across the blood brain barrier; and/or the EV comprises one or more further exogenous binding agents.

3. The EV of claim 1, wherein the EV comprises a second the exogenous binding agent specifically binds to an endothelial cell protein selected from the group consisting of ARHGEF18, ASB12, BAD, DCAF12L1, ECHS1, GORASP2, GPHA2, GRID2IP, HOXD4, KCNT2, LIPJ, MESDC2, MTHFS, OCM, OR4X2, SCLT1, SERAC1, SHOC2, SPRYD3, STAG1, TMED10, TRIM67, TTLL7, VLDLR, SFT2D2, CD74, HLA-DOA, ZP2, IFNLR1, HTR6, GPR37L1, MCHR2, CD164, B3GAT1-modified protein, and ST8SIA3-modified protein.

4. The EV of claim 1, wherein the exogenous binding agent is an antibody, or an antigen binding portion thereof, optionally wherein the antibody, or antigen-binding portion thereof, is:

an antibody fragment selected from the group consisting of a Fab, a F(ab')2, an scFv, a tandem scFv, a diabody, a minibody, and a single domain antibody;

a humanized antibody, or an antigen binding portion thereof; and/or a fully human antibody, or an antigen binding portion thereof.

5. The EV of claim 1, wherein the exogenous binding agent is a polypeptide ligand or an aptamer.

6. The EV of claim 1, wherein the EV:

is about 20 nm to about 250 nm in size;

is an exosome;

is a microvesicle;

is derived from a primary cell, a transformed cell, a stem/progenitor cell, a neural cell, a muscle cell, an immune cell, an adipose cell, or a tumor cell, optionally wherein:

the neural cell is an astrocyte, an oligodendrocyte, a neuron, or a glial cell;

the immune cell is a microglial cell or a dendritic cell; or the stem/progenitor cell is an embryonic stem cell or an induced pluripotent stem cell, a neural progenitor cell, a neural stem cell, or a mesenchymal stem cell;

is derived from a cultured cell line, optionally wherein the cultured cell line is a CHO cell line, a HEK293 cell line, or a Vero cell line; and/or is derived from cells that recombinantly express the exogenous binding agent.

7. The EV of claim 1, wherein the EV further comprises a small molecule, an exogenous nucleic acid, and/or an exogenous polypeptide, optionally wherein the exogenous nucleic acid is a siRNA, a shRNA, an antisense RNA, a miRNA, or a combination thereof.

8. A pharmaceutical composition comprising a therapeutically effective amount of the EV of claim 1, and a pharmaceutically acceptable carrier.

9. A method of delivering an EV across the blood brain barrier of a subject, comprising administering to the subject a composition comprising the EV of claim 1, or a pharmaceutical composition comprising a therapeutically effective amount of the EV of claim 1.

10. The method of claim 9, wherein:

the composition is administered intravenously, intraarterially, intranasally, orally, intramuscularly, intrathecally, intraocularly, intradermally, intracranially, subcutaneously, or by inhalation; and/or the EV is delivered to the brain or the central nervous system of the subject.

* * * * *

```
                          SEQUENCE LISTING

<160> NUMBER OF SEQ ID NOS: 109

<210> SEQ ID NO 1
<211> LENGTH: 296
<212> TYPE: PRT
<213> ORGANISM: Homo sapiens

<400> SEQUENCE: 1

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140
```

-continued

```
Leu Leu Gln Asn Ala Asp Pro Leu Lys Val Tyr Pro Pro Leu Lys Gly
145             150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
                180                 185                 190

Met Ser Arg His Ser Leu Glu Gln Lys Pro Thr Asp Ala Pro Pro Lys
                195                 200                 205

Val Leu Thr Lys Cys Gln Glu Glu Val Ser His Ile Pro Ala Val His
        210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
                260                 265                 270

Glu Ser Leu Glu Leu Glu Asp Pro Ser Ser Gly Leu Gly Val Thr Lys
        275                 280                 285

Gln Asp Leu Gly Pro Val Pro Met
        290                 295

<210> SEQ ID NO 2
<211> LENGTH: 232
<212> TYPE: PRT
<213> ORGANISM: Homo sapiens

<400> SEQUENCE: 2

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
                20                  25                  30

Leu Gly Arg Arg Pro Gly Ala Pro Glu Ser Lys Cys Ser Arg Gly Ala
            35                  40                  45

Leu Tyr Thr Gly Phe Ser Ile Leu Val Thr Leu Leu Leu Ala Gly Gln
        50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
                100                 105                 110

Leu Leu Met Gln Ala Leu Pro Met Gly Ala Leu Pro Gln Gly Pro Met
            115                 120                 125

Gln Asn Ala Thr Lys Tyr Gly Asn Met Thr Glu Asp His Val Met His
        130                 135                 140

Leu Leu Gln Asn Ala Asp Pro Leu Lys Val Tyr Pro Pro Leu Lys Gly
145             150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
                180                 185                 190

Met Ser Arg His Ser Leu Glu Gln Lys Pro Thr Asp Ala Pro Pro Lys
                195                 200                 205

Glu Ser Leu Glu Leu Glu Asp Pro Ser Ser Gly Leu Gly Val Thr Lys
        210                 215                 220
```

-continued

```
Gln Asp Leu Gly Pro Val Pro Met
225             230

<210> SEQ ID NO 3
<211> LENGTH: 160
<212> TYPE: PRT
<213> ORGANISM: Homo sapiens

<400> SEQUENCE: 3

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Ser His Trp Asn Trp Arg Thr Arg Leu Leu Gly Trp Val
145                 150                 155                 160

<210> SEQ ID NO 4
<211> LENGTH: 211
<212> TYPE: PRT
<213> ORGANISM: Homo sapiens

<400> SEQUENCE: 4

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Asn Ala
        115                 120                 125

Asp Pro Leu Lys Val Tyr Pro Pro Leu Lys Gly Ser Phe Pro Glu Asn
    130                 135                 140

Leu Arg His Leu Lys Asn Thr Met Glu Thr Ile Asp Trp Lys Val Phe
145                 150                 155                 160
```

```
Glu Ser Trp Met His His Trp Leu Leu Phe Glu Met Ser Arg His Ser
                165                 170                 175

Leu Glu Gln Lys Pro Thr Asp Ala Pro Pro Lys Glu Ser Leu Glu Leu
                180                 185                 190

Glu Asp Pro Ser Ser Gly Leu Gly Val Thr Lys Gln Asp Leu Gly Pro
            195                 200                 205

Val Pro Met
        210

<210> SEQ ID NO 5
<211> LENGTH: 192
<212> TYPE: PRT
<213> ORGANISM: Homo sapiens

<400> SEQUENCE: 5

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
                20                  25                  30

Leu Gly Arg Arg Pro Gly Ala Pro Glu Ser Lys Cys Ser Arg Gly Ala
            35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
                100                 105                 110

Leu Leu Met Gln Ala Leu Pro Met Gly Ala Leu Pro Gln Gly Pro Met
            115                 120                 125

Gln Asn Ala Thr Lys Tyr Gly Asn Met Thr Glu Asp His Val Met His
        130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Ser His Trp Asn Trp Arg Thr Arg Leu Leu Gly Trp Val
                180                 185                 190

<210> SEQ ID NO 6
<211> LENGTH: 250
<212> TYPE: PRT
<213> ORGANISM: Homo sapiens

<400> SEQUENCE: 6

Met Ala Leu Arg Ala Gly Leu Val Leu Gly Phe His Thr Leu Met Thr
1               5                   10                  15

Leu Leu Ser Pro Gln Glu Ala Gly Ala Thr Lys Ala Asp His Met Gly
                20                  25                  30

Ser Tyr Gly Pro Ala Phe Tyr Gln Ser Tyr Gly Ala Ser Gly Gln Phe
            35                  40                  45

Thr His Glu Phe Asp Glu Glu Gln Leu Phe Ser Val Asp Leu Lys Lys
        50                  55                  60

Ser Glu Ala Val Trp Arg Leu Pro Glu Phe Gly Asp Phe Ala Arg Phe
65                  70                  75                  80
```

```
Asp Pro Gln Gly Gly Leu Ala Gly Ile Ala Ala Ile Lys Ala His Leu
                85                  90                  95

Asp Ile Leu Val Glu Arg Ser Asn Arg Ser Arg Ala Ile Asn Val Pro
                100                 105                 110

Pro Arg Val Thr Val Leu Pro Lys Ser Arg Val Glu Leu Gly Gln Pro
                115                 120                 125

Asn Ile Leu Ile Cys Ile Val Asp Asn Ile Phe Pro Pro Val Ile Asn
        130                 135                 140

Ile Thr Trp Leu Arg Asn Gly Gln Thr Val Thr Glu Gly Val Ala Gln
145                 150                 155                 160

Thr Ser Phe Tyr Ser Gln Pro Asp His Leu Phe Arg Lys Phe His Tyr
                165                 170                 175

Leu Pro Phe Val Pro Ser Ala Glu Asp Val Tyr Asp Cys Gln Val Glu
                180                 185                 190

His Trp Gly Leu Asp Ala Pro Leu Leu Arg His Trp Glu Leu Gln Val
                195                 200                 205

Pro Ile Pro Pro Pro Asp Ala Met Glu Thr Leu Val Cys Ala Leu Gly
        210                 215                 220

Leu Ala Ile Gly Leu Val Gly Phe Leu Val Gly Thr Val Leu Ile Ile
225                 230                 235                 240

Met Gly Thr Tyr Val Ser Ser Val Pro Arg
                245                 250

<210> SEQ ID NO 7
<211> LENGTH: 873
<212> TYPE: PRT
<213> ORGANISM: Homo sapiens

<400> SEQUENCE: 7

Met Gly Thr Ser Ala Leu Trp Ala Leu Trp Leu Leu Leu Ala Leu Cys
1               5                   10                  15

Trp Ala Pro Arg Glu Ser Gly Ala Thr Gly Thr Gly Arg Lys Ala Lys
                20                  25                  30

Cys Glu Pro Ser Gln Phe Gln Cys Thr Asn Gly Arg Cys Ile Thr Leu
                35                  40                  45

Leu Trp Lys Cys Asp Gly Asp Glu Asp Cys Val Asp Gly Ser Asp Glu
        50                  55                  60

Lys Asn Cys Val Lys Lys Thr Cys Ala Glu Ser Asp Phe Val Cys Asn
65                  70                  75                  80

Asn Gly Gln Cys Val Pro Ser Arg Trp Lys Cys Asp Gly Asp Pro Asp
                85                  90                  95

Cys Glu Asp Gly Ser Asp Glu Ser Pro Glu Gln Cys His Met Arg Thr
                100                 105                 110

Cys Arg Ile His Glu Ile Ser Cys Gly Ala His Ser Thr Gln Cys Ile
        115                 120                 125

Pro Val Ser Trp Arg Cys Asp Gly Glu Asn Asp Cys Asp Ser Gly Glu
        130                 135                 140

Asp Glu Glu Asn Cys Gly Asn Ile Thr Cys Ser Pro Asp Glu Phe Thr
145                 150                 155                 160

Cys Ser Ser Gly Arg Cys Ile Ser Arg Asn Phe Val Cys Asn Gly Gln
                165                 170                 175

Asp Asp Cys Ser Asp Gly Ser Asp Glu Leu Asp Cys Ala Pro Pro Thr
                180                 185                 190

Cys Gly Ala His Glu Phe Gln Cys Ser Thr Ser Ser Cys Ile Pro Ile
```

```
          195               200               205

Ser Trp Val Cys Asp Asp Asp Ala Asp Cys Ser Asp Gln Ser Asp Glu
    210               215               220

Ser Leu Glu Gln Cys Gly Arg Gln Pro Val Ile His Thr Lys Cys Pro
225               230               235               240

Ala Ser Glu Ile Gln Cys Gly Ser Gly Glu Cys Ile His Lys Lys Trp
                  245               250               255

Arg Cys Asp Gly Asp Pro Asp Cys Lys Asp Gly Ser Asp Glu Val Asn
                  260               265               270

Cys Pro Ser Arg Thr Cys Arg Pro Asp Gln Phe Glu Cys Glu Asp Gly
              275               280               285

Ser Cys Ile His Gly Ser Arg Gln Cys Asn Gly Ile Arg Asp Cys Val
    290               295               300

Asp Gly Ser Asp Glu Val Asn Cys Lys Asn Val Asn Gln Cys Leu Gly
305               310               315               320

Pro Gly Lys Phe Lys Cys Arg Ser Gly Glu Cys Ile Asp Ile Ser Lys
                  325               330               335

Val Cys Asn Gln Glu Gln Asp Cys Arg Asp Trp Ser Asp Glu Pro Leu
              340               345               350

Lys Glu Cys His Ile Asn Glu Cys Leu Val Asn Asn Gly Gly Cys Ser
              355               360               365

His Ile Cys Lys Asp Leu Val Ile Gly Tyr Glu Cys Asp Cys Ala Ala
    370               375               380

Gly Phe Glu Leu Ile Asp Arg Lys Thr Cys Gly Asp Ile Asp Glu Cys
385               390               395               400

Gln Asn Pro Gly Ile Cys Ser Gln Ile Cys Ile Asn Leu Lys Gly Gly
                  405               410               415

Tyr Lys Cys Glu Cys Ser Arg Gly Tyr Gln Met Asp Leu Ala Thr Gly
              420               425               430

Val Cys Lys Ala Val Gly Lys Glu Pro Ser Leu Ile Phe Thr Asn Arg
              435               440               445

Arg Asp Ile Arg Lys Ile Gly Leu Glu Arg Lys Glu Tyr Ile Gln Leu
    450               455               460

Val Glu Gln Leu Arg Asn Thr Val Ala Leu Asp Ala Asp Ile Ala Ala
465               470               475               480

Gln Lys Leu Phe Trp Ala Asp Leu Ser Gln Lys Ala Ile Phe Ser Ala
                  485               490               495

Ser Ile Asp Asp Lys Val Gly Arg His Val Lys Met Ile Asp Asn Val
              500               505               510

Tyr Asn Pro Ala Ala Ile Ala Val Asp Trp Val Tyr Lys Thr Ile Tyr
              515               520               525

Trp Thr Asp Ala Ala Ser Lys Thr Ile Ser Val Ala Thr Leu Asp Gly
    530               535               540

Thr Lys Arg Lys Phe Leu Phe Asn Ser Asp Leu Arg Glu Pro Ala Ser
545               550               555               560

Ile Ala Val Asp Pro Leu Ser Gly Phe Val Tyr Trp Ser Asp Trp Gly
                  565               570               575

Glu Pro Ala Lys Ile Glu Lys Ala Gly Met Asn Gly Phe Asp Arg Arg
              580               585               590

Pro Leu Val Thr Ala Asp Ile Gln Trp Pro Asn Gly Ile Thr Leu Asp
              595               600               605

Leu Ile Lys Ser Arg Leu Tyr Trp Leu Asp Ser Lys Leu His Met Leu
    610               615               620
```

```
Ser Ser Val Asp Leu Asn Gly Gln Asp Arg Arg Ile Val Leu Lys Ser
625             630             635             640

Leu Glu Phe Leu Ala His Pro Leu Ala Leu Thr Ile Phe Glu Asp Arg
            645             650             655

Val Tyr Trp Ile Asp Gly Glu Asn Glu Ala Val Tyr Gly Ala Asn Lys
            660             665             670

Phe Thr Gly Ser Glu Leu Ala Thr Leu Val Asn Asn Leu Asn Asp Ala
            675             680             685

Gln Asp Ile Ile Val Tyr His Glu Leu Val Gln Pro Ser Gly Lys Asn
        690             695             700

Trp Cys Glu Glu Asp Met Glu Asn Gly Gly Cys Glu Tyr Leu Cys Leu
705             710             715             720

Pro Ala Pro Gln Ile Asn Asp His Ser Pro Lys Tyr Thr Cys Ser Cys
            725             730             735

Pro Ser Gly Tyr Asn Val Glu Glu Asn Gly Arg Asp Cys Gln Ser Thr
            740             745             750

Ala Thr Thr Val Thr Tyr Ser Glu Thr Lys Asp Thr Asn Thr Thr Glu
            755             760             765

Ile Ser Ala Thr Ser Gly Leu Val Pro Gly Gly Ile Asn Val Thr Thr
        770             775             780

Ala Val Ser Glu Val Ser Val Pro Pro Lys Gly Thr Ser Ala Ala Trp
785             790             795             800

Ala Ile Leu Pro Leu Leu Leu Leu Val Met Ala Ala Val Gly Gly Tyr
            805             810             815

Leu Met Trp Arg Asn Trp Gln His Lys Asn Met Lys Ser Met Asn Phe
            820             825             830

Asp Asn Pro Val Tyr Leu Lys Thr Thr Glu Glu Asp Leu Ser Ile Asp
            835             840             845

Ile Gly Arg His Ser Ala Ser Val Gly His Thr Tyr Pro Ala Ile Ser
        850             855             860

Val Val Ser Thr Asp Asp Asp Leu Ala
865             870
```

<210> SEQ ID NO 8
<211> LENGTH: 845
<212> TYPE: PRT
<213> ORGANISM: Homo sapiens

<400> SEQUENCE: 8

```
Met Gly Thr Ser Ala Leu Trp Ala Leu Trp Leu Leu Leu Ala Leu Cys
1               5               10              15

Trp Ala Pro Arg Glu Ser Gly Ala Thr Gly Thr Gly Arg Lys Ala Lys
            20              25              30

Cys Glu Pro Ser Gln Phe Gln Cys Thr Asn Gly Arg Cys Ile Thr Leu
            35              40              45

Leu Trp Lys Cys Asp Gly Asp Glu Asp Cys Val Asp Gly Ser Asp Glu
        50              55              60

Lys Asn Cys Val Lys Lys Thr Cys Ala Glu Ser Asp Phe Val Cys Asn
65              70              75              80

Asn Gly Gln Cys Val Pro Ser Arg Trp Lys Cys Asp Gly Asp Pro Asp
            85              90              95

Cys Glu Asp Gly Ser Asp Glu Ser Pro Glu Gln Cys His Met Arg Thr
            100             105             110

Cys Arg Ile His Glu Ile Ser Cys Gly Ala His Ser Thr Gln Cys Ile
```

-continued

```
              115                 120                 125
Pro Val Ser Trp Arg Cys Asp Gly Glu Asn Asp Cys Asp Ser Gly Glu
    130                 135                 140

Asp Glu Glu Asn Cys Gly Asn Ile Thr Cys Ser Pro Asp Glu Phe Thr
145                 150                 155                 160

Cys Ser Ser Gly Arg Cys Ile Ser Arg Asn Phe Val Cys Asn Gly Gln
                165                 170                 175

Asp Asp Cys Ser Asp Gly Ser Asp Glu Leu Asp Cys Ala Pro Pro Thr
                180                 185                 190

Cys Gly Ala His Glu Phe Gln Cys Ser Thr Ser Cys Ile Pro Ile
                195                 200                 205

Ser Trp Val Cys Asp Asp Asp Ala Asp Cys Ser Asp Gln Ser Asp Glu
    210                 215                 220

Ser Leu Glu Gln Cys Gly Arg Gln Pro Val Ile His Thr Lys Cys Pro
225                 230                 235                 240

Ala Ser Glu Ile Gln Cys Gly Ser Gly Glu Cys Ile His Lys Lys Trp
                245                 250                 255

Arg Cys Asp Gly Asp Pro Asp Cys Lys Asp Gly Ser Asp Glu Val Asn
                260                 265                 270

Cys Pro Ser Arg Thr Cys Arg Pro Asp Gln Phe Glu Cys Glu Asp Gly
                275                 280                 285

Ser Cys Ile His Gly Ser Arg Gln Cys Asn Gly Ile Arg Asp Cys Val
    290                 295                 300

Asp Gly Ser Asp Glu Val Asn Cys Lys Asn Val Asn Gln Cys Leu Gly
305                 310                 315                 320

Pro Gly Lys Phe Lys Cys Arg Ser Gly Glu Cys Ile Asp Ile Ser Lys
                325                 330                 335

Val Cys Asn Gln Glu Gln Asp Cys Arg Asp Trp Ser Asp Glu Pro Leu
                340                 345                 350

Lys Glu Cys His Ile Asn Glu Cys Leu Val Asn Asn Gly Gly Cys Ser
                355                 360                 365

His Ile Cys Lys Asp Leu Val Ile Gly Tyr Glu Cys Asp Cys Ala Ala
    370                 375                 380

Gly Phe Glu Leu Ile Asp Arg Lys Thr Cys Gly Asp Ile Asp Glu Cys
385                 390                 395                 400

Gln Asn Pro Gly Ile Cys Ser Gln Ile Cys Ile Asn Leu Lys Gly Gly
                405                 410                 415

Tyr Lys Cys Glu Cys Ser Arg Gly Tyr Gln Met Asp Leu Ala Thr Gly
                420                 425                 430

Val Cys Lys Ala Val Gly Lys Glu Pro Ser Leu Ile Phe Thr Asn Arg
                435                 440                 445

Arg Asp Ile Arg Lys Ile Gly Leu Glu Arg Lys Glu Tyr Ile Gln Leu
    450                 455                 460

Val Glu Gln Leu Arg Asn Thr Val Ala Leu Asp Ala Asp Ile Ala Ala
465                 470                 475                 480

Gln Lys Leu Phe Trp Ala Asp Leu Ser Gln Lys Ala Ile Phe Ser Ala
                485                 490                 495

Ser Ile Asp Asp Lys Val Gly Arg His Val Lys Met Ile Asp Asn Val
                500                 505                 510

Tyr Asn Pro Ala Ala Ile Ala Val Asp Trp Val Tyr Lys Thr Ile Tyr
                515                 520                 525

Trp Thr Asp Ala Ala Ser Lys Thr Ile Ser Val Ala Thr Leu Asp Gly
    530                 535                 540
```

-continued

```
Thr Lys Arg Lys Phe Leu Phe Asn Ser Asp Leu Arg Glu Pro Ala Ser
545                 550                 555                 560

Ile Ala Val Asp Pro Leu Ser Gly Phe Val Tyr Trp Ser Asp Trp Gly
                565                 570                 575

Glu Pro Ala Lys Ile Glu Lys Ala Gly Met Asn Gly Phe Asp Arg Arg
                580                 585                 590

Pro Leu Val Thr Ala Asp Ile Gln Trp Pro Asn Gly Ile Thr Leu Asp
            595                 600                 605

Leu Ile Lys Ser Arg Leu Tyr Trp Leu Asp Ser Lys Leu His Met Leu
        610                 615                 620

Ser Ser Val Asp Leu Asn Gly Gln Asp Arg Arg Ile Val Leu Lys Ser
625                 630                 635                 640

Leu Glu Phe Leu Ala His Pro Leu Ala Leu Thr Ile Phe Glu Asp Arg
                645                 650                 655

Val Tyr Trp Ile Asp Gly Glu Asn Glu Ala Val Tyr Gly Ala Asn Lys
                660                 665                 670

Phe Thr Gly Ser Glu Leu Ala Thr Leu Val Asn Asn Leu Asn Asp Ala
            675                 680                 685

Gln Asp Ile Ile Val Tyr His Glu Leu Val Gln Pro Ser Gly Lys Asn
        690                 695                 700

Trp Cys Glu Glu Asp Met Glu Asn Gly Gly Cys Glu Tyr Leu Cys Leu
705                 710                 715                 720

Pro Ala Pro Gln Ile Asn Asp His Ser Pro Lys Tyr Thr Cys Ser Cys
                725                 730                 735

Pro Ser Gly Tyr Asn Val Glu Glu Asn Gly Arg Asp Cys Gln Arg Ile
            740                 745                 750

Asn Val Thr Thr Ala Val Ser Glu Val Ser Val Pro Pro Lys Gly Thr
            755                 760                 765

Ser Ala Ala Trp Ala Ile Leu Pro Leu Leu Leu Leu Val Met Ala Ala
        770                 775                 780

Val Gly Gly Tyr Leu Met Trp Arg Asn Trp Gln His Lys Asn Met Lys
785                 790                 795                 800

Ser Met Asn Phe Asp Asn Pro Val Tyr Leu Lys Thr Thr Glu Glu Asp
                805                 810                 815

Leu Ser Ile Asp Ile Gly Arg His Ser Ala Ser Val Gly His Thr Tyr
            820                 825                 830

Pro Ala Ile Ser Val Val Ser Thr Asp Asp Asp Leu Ala
        835                 840                 845
```

```
<210> SEQ ID NO 9
<211> LENGTH: 832
<212> TYPE: PRT
<213> ORGANISM: Homo sapiens

<400> SEQUENCE: 9
```

```
Met Gly Thr Ser Ala Leu Trp Ala Leu Trp Leu Leu Leu Ala Leu Cys
1                 5                   10                  15

Trp Ala Pro Arg Glu Ser Gly Ala Thr Gly Thr Gly Arg Lys Ala Lys
                20                  25                  30

Cys Glu Pro Ser Gln Phe Gln Cys Thr Asn Gly Arg Cys Ile Thr Leu
            35                  40                  45

Leu Trp Lys Cys Asp Gly Asp Glu Asp Cys Val Asp Gly Ser Asp Glu
        50                  55                  60

Lys Asn Cys Val Lys Lys Thr Cys Ala Glu Ser Asp Phe Val Cys Asn
```

-continued

```
65                    70                    75                    80

Asn Gly Gln Cys Val Pro Ser Arg Trp Lys Cys Asp Gly Asp Pro Asp
              85                    90                    95

Cys Glu Asp Gly Ser Asp Glu Ser Pro Glu Gln Cys Arg Asn Ile Thr
             100                   105                   110

Cys Ser Pro Asp Glu Phe Thr Cys Ser Ser Gly Arg Cys Ile Ser Arg
             115                   120                   125

Asn Phe Val Cys Asn Gly Gln Asp Asp Cys Ser Asp Gly Ser Asp Glu
         130                   135                   140

Leu Asp Cys Ala Pro Pro Thr Cys Gly Ala His Glu Phe Gln Cys Ser
145                   150                   155                   160

Thr Ser Ser Cys Ile Pro Ile Ser Trp Val Cys Asp Asp Asp Ala Asp
                 165                   170                   175

Cys Ser Asp Gln Ser Asp Glu Ser Leu Glu Gln Cys Gly Arg Gln Pro
             180                   185                   190

Val Ile His Thr Lys Cys Pro Ala Ser Glu Ile Gln Cys Gly Ser Gly
             195                   200                   205

Glu Cys Ile His Lys Lys Trp Arg Cys Asp Gly Asp Pro Asp Cys Lys
         210                   215                   220

Asp Gly Ser Asp Glu Val Asn Cys Pro Ser Arg Thr Cys Arg Pro Asp
225                   230                   235                   240

Gln Phe Glu Cys Glu Asp Gly Ser Cys Ile His Gly Ser Arg Gln Cys
             245                   250                   255

Asn Gly Ile Arg Asp Cys Val Asp Gly Ser Asp Glu Val Asn Cys Lys
             260                   265                   270

Asn Val Asn Gln Cys Leu Gly Pro Gly Lys Phe Lys Cys Arg Ser Gly
         275                   280                   285

Glu Cys Ile Asp Ile Ser Lys Val Cys Asn Gln Glu Gln Asp Cys Arg
         290                   295                   300

Asp Trp Ser Asp Glu Pro Leu Lys Glu Cys His Ile Asn Glu Cys Leu
305                   310                   315                   320

Val Asn Asn Gly Gly Cys Ser His Ile Cys Lys Asp Leu Val Ile Gly
             325                   330                   335

Tyr Glu Cys Asp Cys Ala Ala Gly Phe Glu Leu Ile Asp Arg Lys Thr
             340                   345                   350

Cys Gly Asp Ile Asp Glu Cys Gln Asn Pro Gly Ile Cys Ser Gln Ile
         355                   360                   365

Cys Ile Asn Leu Lys Gly Gly Tyr Lys Cys Glu Cys Ser Arg Gly Tyr
         370                   375                   380

Gln Met Asp Leu Ala Thr Gly Val Cys Lys Ala Val Gly Lys Glu Pro
385                   390                   395                   400

Ser Leu Ile Phe Thr Asn Arg Arg Asp Ile Arg Lys Ile Gly Leu Glu
                 405                   410                   415

Arg Lys Glu Tyr Ile Gln Leu Val Glu Gln Leu Arg Asn Thr Val Ala
             420                   425                   430

Leu Asp Ala Asp Ile Ala Ala Gln Lys Leu Phe Trp Ala Asp Leu Ser
         435                   440                   445

Gln Lys Ala Ile Phe Ser Ala Ser Ile Asp Asp Lys Val Gly Arg His
         450                   455                   460

Val Lys Met Ile Asp Asn Val Tyr Asn Pro Ala Ala Ile Ala Val Asp
465                   470                   475                   480

Trp Val Tyr Lys Thr Ile Tyr Trp Thr Asp Ala Ala Ser Lys Thr Ile
                 485                   490                   495
```

```
Ser Val Ala Thr Leu Asp Gly Thr Lys Arg Lys Phe Leu Phe Asn Ser
        500             505             510

Asp Leu Arg Glu Pro Ala Ser Ile Ala Val Asp Pro Leu Ser Gly Phe
        515             520             525

Val Tyr Trp Ser Asp Trp Gly Glu Pro Ala Lys Ile Glu Lys Ala Gly
        530             535             540

Met Asn Gly Phe Asp Arg Arg Pro Leu Val Thr Ala Asp Ile Gln Trp
545             550             555             560

Pro Asn Gly Ile Thr Leu Asp Leu Ile Lys Ser Arg Leu Tyr Trp Leu
        565             570             575

Asp Ser Lys Leu His Met Leu Ser Ser Val Asp Leu Asn Gly Gln Asp
        580             585             590

Arg Arg Ile Val Leu Lys Ser Leu Glu Phe Leu Ala His Pro Leu Ala
        595             600             605

Leu Thr Ile Phe Glu Asp Arg Val Tyr Trp Ile Asp Gly Glu Asn Glu
        610             615             620

Ala Val Tyr Gly Ala Asn Lys Phe Thr Gly Ser Glu Leu Ala Thr Leu
625             630             635             640

Val Asn Asn Leu Asn Asp Ala Gln Asp Ile Ile Val Tyr His Glu Leu
        645             650             655

Val Gln Pro Ser Gly Lys Asn Trp Cys Glu Glu Asp Met Glu Asn Gly
        660             665             670

Gly Cys Glu Tyr Leu Cys Leu Pro Ala Pro Gln Ile Asn Asp His Ser
        675             680             685

Pro Lys Tyr Thr Cys Ser Cys Pro Ser Gly Tyr Asn Val Glu Glu Asn
        690             695             700

Gly Arg Asp Cys Gln Ser Thr Ala Thr Thr Val Thr Tyr Ser Glu Thr
705             710             715             720

Lys Asp Thr Asn Thr Thr Glu Ile Ser Ala Thr Ser Gly Leu Val Pro
        725             730             735

Gly Gly Ile Asn Val Thr Thr Ala Val Ser Glu Val Ser Val Pro Pro
        740             745             750

Lys Gly Thr Ser Ala Ala Trp Ala Ile Leu Pro Leu Leu Leu Leu Val
        755             760             765

Met Ala Ala Val Gly Gly Tyr Leu Met Trp Arg Asn Trp Gln His Lys
770             775             780

Asn Met Lys Ser Met Asn Phe Asp Asn Pro Val Tyr Leu Lys Thr Thr
785             790             795             800

Glu Glu Asp Leu Ser Ile Asp Ile Gly Arg His Ser Ala Ser Val Gly
        805             810             815

His Thr Tyr Pro Ala Ile Ser Val Val Ser Thr Asp Asp Asp Leu Ala
        820             825             830
```

```
<210> SEQ ID NO 10
<211> LENGTH: 804
<212> TYPE: PRT
<213> ORGANISM: Homo sapiens

<400> SEQUENCE: 10
```

```
Met Gly Thr Ser Ala Leu Trp Ala Leu Trp Leu Leu Leu Ala Leu Cys
1               5               10              15

Trp Ala Pro Arg Glu Ser Gly Ala Thr Gly Thr Gly Arg Lys Ala Lys
        20              25              30

Cys Glu Pro Ser Gln Phe Gln Cys Thr Asn Gly Arg Cys Ile Thr Leu
```

-continued

```
              35                  40                  45

Leu Trp Lys Cys Asp Gly Asp Glu Asp Cys Val Asp Gly Ser Asp Glu
    50                  55                  60

Lys Asn Cys Val Lys Lys Thr Cys Ala Glu Ser Asp Phe Val Cys Asn
65                  70                  75                  80

Asn Gly Gln Cys Val Pro Ser Arg Trp Lys Cys Asp Gly Asp Pro Asp
                85                  90                  95

Cys Glu Asp Gly Ser Asp Glu Ser Pro Glu Gln Cys Arg Asn Ile Thr
            100                 105                 110

Cys Ser Pro Asp Glu Phe Thr Cys Ser Ser Gly Arg Cys Ile Ser Arg
            115                 120                 125

Asn Phe Val Cys Asn Gly Gln Asp Asp Cys Ser Asp Gly Ser Asp Glu
    130                 135                 140

Leu Asp Cys Ala Pro Pro Thr Cys Gly Ala His Glu Phe Gln Cys Ser
145                 150                 155                 160

Thr Ser Ser Cys Ile Pro Ile Ser Trp Val Cys Asp Asp Asp Ala Asp
            165                 170                 175

Cys Ser Asp Gln Ser Asp Glu Ser Leu Glu Gln Cys Gly Arg Gln Pro
            180                 185                 190

Val Ile His Thr Lys Cys Pro Ala Ser Glu Ile Gln Cys Gly Ser Gly
            195                 200                 205

Glu Cys Ile His Lys Lys Trp Arg Cys Asp Gly Asp Pro Asp Cys Lys
    210                 215                 220

Asp Gly Ser Asp Glu Val Asn Cys Pro Ser Arg Thr Cys Arg Pro Asp
225                 230                 235                 240

Gln Phe Glu Cys Glu Asp Gly Ser Cys Ile His Gly Ser Arg Gln Cys
            245                 250                 255

Asn Gly Ile Arg Asp Cys Val Asp Gly Ser Asp Glu Val Asn Cys Lys
            260                 265                 270

Asn Val Asn Gln Cys Leu Gly Pro Gly Lys Phe Lys Cys Arg Ser Gly
            275                 280                 285

Glu Cys Ile Asp Ile Ser Lys Val Cys Asn Gln Glu Gln Asp Cys Arg
    290                 295                 300

Asp Trp Ser Asp Glu Pro Leu Lys Glu Cys His Ile Asn Glu Cys Leu
305                 310                 315                 320

Val Asn Asn Gly Gly Cys Ser His Ile Cys Lys Asp Leu Val Ile Gly
            325                 330                 335

Tyr Glu Cys Asp Cys Ala Ala Gly Phe Glu Leu Ile Asp Arg Lys Thr
            340                 345                 350

Cys Gly Asp Ile Asp Glu Cys Gln Asn Pro Gly Ile Cys Ser Gln Ile
            355                 360                 365

Cys Ile Asn Leu Lys Gly Gly Tyr Lys Cys Glu Cys Ser Arg Gly Tyr
    370                 375                 380

Gln Met Asp Leu Ala Thr Gly Val Cys Lys Ala Val Gly Lys Glu Pro
385                 390                 395                 400

Ser Leu Ile Phe Thr Asn Arg Arg Asp Ile Arg Lys Ile Gly Leu Glu
                405                 410                 415

Arg Lys Glu Tyr Ile Gln Leu Val Glu Gln Leu Arg Asn Thr Val Ala
            420                 425                 430

Leu Asp Ala Asp Ile Ala Ala Gln Lys Leu Phe Trp Ala Asp Leu Ser
            435                 440                 445

Gln Lys Ala Ile Phe Ser Ala Ser Ile Asp Asp Lys Val Gly Arg His
    450                 455                 460
```

-continued

```
Val Lys Met Ile Asp Asn Val Tyr Asn Pro Ala Ala Ile Ala Val Asp
465                 470                 475                 480

Trp Val Tyr Lys Thr Ile Tyr Trp Thr Asp Ala Ala Ser Lys Thr Ile
                485                 490                 495

Ser Val Ala Thr Leu Asp Gly Thr Lys Arg Lys Phe Leu Phe Asn Ser
                500                 505                 510

Asp Leu Arg Glu Pro Ala Ser Ile Ala Val Asp Pro Leu Ser Gly Phe
            515                 520                 525

Val Tyr Trp Ser Asp Trp Gly Glu Pro Ala Lys Ile Glu Lys Ala Gly
        530                 535                 540

Met Asn Gly Phe Asp Arg Arg Pro Leu Val Thr Ala Asp Ile Gln Trp
545                 550                 555                 560

Pro Asn Gly Ile Thr Leu Asp Leu Ile Lys Ser Arg Leu Tyr Trp Leu
                565                 570                 575

Asp Ser Lys Leu His Met Leu Ser Ser Val Asp Leu Asn Gly Gln Asp
            580                 585                 590

Arg Arg Ile Val Leu Lys Ser Leu Glu Phe Leu Ala His Pro Leu Ala
            595                 600                 605

Leu Thr Ile Phe Glu Asp Arg Val Tyr Trp Ile Asp Gly Glu Asn Glu
        610                 615                 620

Ala Val Tyr Gly Ala Asn Lys Phe Thr Gly Ser Glu Leu Ala Thr Leu
625                 630                 635                 640

Val Asn Asn Leu Asn Asp Ala Gln Asp Ile Ile Val Tyr His Glu Leu
                645                 650                 655

Val Gln Pro Ser Gly Lys Asn Trp Cys Glu Glu Asp Met Glu Asn Gly
            660                 665                 670

Gly Cys Glu Tyr Leu Cys Leu Pro Ala Pro Gln Ile Asn Asp His Ser
        675                 680                 685

Pro Lys Tyr Thr Cys Ser Cys Pro Ser Gly Tyr Asn Val Glu Glu Asn
        690                 695                 700

Gly Arg Asp Cys Gln Arg Ile Asn Val Thr Thr Ala Val Ser Glu Val
705                 710                 715                 720

Ser Val Pro Pro Lys Gly Thr Ser Ala Ala Trp Ala Ile Leu Pro Leu
                725                 730                 735

Leu Leu Leu Val Met Ala Ala Val Gly Gly Tyr Leu Met Trp Arg Asn
                740                 745                 750

Trp Gln His Lys Asn Met Lys Ser Met Asn Phe Asp Asn Pro Val Tyr
            755                 760                 765

Leu Lys Thr Thr Glu Glu Asp Leu Ser Ile Asp Ile Gly Arg His Ser
            770                 775                 780

Ala Ser Val Gly His Thr Tyr Pro Ala Ile Ser Val Val Ser Thr Asp
785                 790                 795                 800

Asp Asp Leu Ala
```

```
<210> SEQ ID NO 11
<211> LENGTH: 745
<212> TYPE: PRT
<213> ORGANISM: Homo sapiens

<400> SEQUENCE: 11
```

```
Met Ala Cys Arg Gln Arg Gly Gly Ser Trp Ser Pro Ser Gly Trp Phe
1                   5                   10                  15

Asn Ala Gly Trp Ser Thr Tyr Arg Ser Ile Ser Leu Phe Phe Ala Leu
                20                  25                  30
```

-continued

```
Val Thr Ser Gly Asn Ser Ile Asp Val Ser Gln Leu Val Asn Pro Ala
        35              40              45

Phe Pro Gly Thr Val Thr Cys Asp Glu Arg Glu Ile Thr Val Glu Phe
    50              55              60

Pro Ser Ser Pro Gly Thr Lys Lys Trp His Ala Ser Val Val Asp Pro
65              70              75              80

Leu Gly Leu Asp Met Pro Asn Cys Thr Tyr Ile Leu Asp Pro Glu Lys
                85              90              95

Leu Thr Leu Arg Ala Thr Tyr Asp Asn Cys Thr Arg Arg Val His Gly
            100             105             110

Gly His Gln Met Thr Ile Arg Val Met Asn Asn Ser Ala Ala Leu Arg
            115             120             125

His Gly Ala Val Met Tyr Gln Phe Phe Cys Pro Ala Met Gln Val Glu
        130             135             140

Glu Thr Gln Gly Leu Ser Ala Ser Thr Ile Cys Gln Lys Asp Phe Met
145             150             155             160

Ser Phe Ser Leu Pro Arg Val Phe Ser Gly Leu Ala Asp Asp Ser Lys
                165             170             175

Gly Thr Lys Val Gln Met Gly Trp Ser Ile Glu Val Gly Asp Gly Ala
            180             185             190

Arg Ala Lys Thr Leu Thr Leu Pro Glu Ala Met Lys Glu Gly Phe Ser
            195             200             205

Leu Leu Ile Asp Asn His Arg Met Thr Phe His Val Pro Phe Asn Ala
        210             215             220

Thr Gly Val Thr His Tyr Val Gln Gly Asn Ser His Leu Tyr Met Val
225             230             235             240

Ser Leu Lys Leu Thr Phe Ile Ser Pro Gly Gln Lys Val Ile Phe Ser
                245             250             255

Ser Gln Ala Ile Cys Ala Pro Asp Pro Val Thr Cys Asn Ala Thr His
            260             265             270

Met Thr Leu Thr Ile Pro Glu Phe Pro Gly Lys Leu Lys Ser Val Ser
            275             280             285

Phe Glu Asn Gln Asn Ile Asp Val Ser Gln Leu His Asp Asn Gly Ile
        290             295             300

Asp Leu Glu Ala Thr Asn Gly Met Lys Leu His Phe Ser Lys Thr Leu
305             310             315             320

Leu Lys Thr Lys Leu Ser Glu Lys Cys Leu Leu His Gln Phe Tyr Leu
                325             330             335

Ala Ser Leu Lys Leu Thr Phe Leu Leu Arg Pro Glu Thr Val Ser Met
            340             345             350

Val Ile Tyr Pro Glu Cys Leu Cys Glu Ser Pro Val Ser Ile Val Thr
            355             360             365

Gly Glu Leu Cys Thr Gln Asp Gly Phe Met Asp Val Glu Val Tyr Ser
    370             375             380

Tyr Gln Thr Gln Pro Ala Leu Asp Leu Gly Thr Leu Arg Val Gly Asn
385             390             395             400

Ser Ser Cys Gln Pro Val Phe Glu Ala Gln Ser Gln Gly Leu Val Arg
            405             410             415

Phe His Ile Pro Leu Asn Gly Cys Gly Thr Arg Tyr Lys Phe Glu Asp
            420             425             430

Asp Lys Val Val Tyr Glu Asn Glu Ile His Ala Leu Trp Thr Asp Phe
        435             440             445
```

```
Pro Pro Ser Lys Ile Ser Arg Asp Ser Glu Phe Arg Met Thr Val Lys
    450             455             460

Cys Ser Tyr Ser Arg Asn Asp Met Leu Leu Asn Ile Asn Val Glu Ser
465             470             475             480

Leu Thr Pro Pro Val Ala Ser Val Lys Leu Gly Pro Phe Thr Leu Ile
            485             490             495

Leu Gln Ser Tyr Pro Asp Asn Ser Tyr Gln Gln Pro Tyr Gly Glu Asn
            500             505             510

Glu Tyr Pro Leu Val Arg Phe Leu Arg Gln Pro Ile Tyr Met Glu Val
            515             520             525

Arg Val Leu Asn Arg Asp Asp Pro Asn Ile Lys Leu Val Leu Asp Asp
    530             535             540

Cys Trp Ala Thr Ser Thr Met Asp Pro Asp Ser Phe Pro Gln Trp Asn
545             550             555             560

Val Val Val Asp Gly Cys Ala Tyr Asp Leu Asp Asn Tyr Gln Thr Thr
            565             570             575

Phe His Pro Val Gly Ser Ser Val Thr His Pro Asp His Tyr Gln Arg
            580             585             590

Phe Asp Met Lys Ala Phe Ala Phe Val Ser Glu Ala His Val Leu Ser
            595             600             605

Ser Leu Val Tyr Phe His Cys Ser Ala Leu Ile Cys Asn Arg Leu Ser
    610             615             620

Pro Asp Ser Pro Leu Cys Ser Val Thr Cys Pro Val Ser Ser Arg His
625             630             635             640

Arg Arg Ala Thr Gly Ala Thr Glu Ala Glu Lys Met Thr Val Ser Leu
            645             650             655

Pro Gly Pro Ile Leu Leu Leu Ser Asp Asp Ser Ser Phe Arg Gly Val
            660             665             670

Gly Ser Ser Asp Leu Lys Ala Ser Gly Ser Ser Gly Glu Lys Ser Arg
            675             680             685

Ser Glu Thr Gly Glu Glu Val Gly Ser Arg Gly Ala Met Asp Thr Lys
            690             695             700

Gly His Lys Thr Ala Gly Asp Val Gly Ser Lys Ala Val Ala Ala Val
705             710             715             720

Ala Ala Phe Ala Gly Val Val Ala Thr Leu Gly Phe Ile Tyr Tyr Leu
            725             730             735

Tyr Glu Lys Arg Thr Val Ser Asn His
            740             745
```

```
<210> SEQ ID NO 12
<211> LENGTH: 736
<212> TYPE: PRT
<213> ORGANISM: Homo sapiens

<400> SEQUENCE: 12

Met Ala Cys Arg Gln Arg Gly Gly Ser Trp Ser Pro Ser Gly Trp Phe
1               5               10              15

Asn Ala Gly Trp Ser Thr Tyr Arg Ser Ile Ser Leu Phe Phe Ala Leu
                20              25              30

Val Thr Ser Gly Asn Ser Ile Asp Val Ser Gln Leu Val Asn Pro Ala
            35              40              45

Phe Pro Gly Thr Val Thr Cys Asp Glu Arg Glu Ile Thr Val Glu Phe
    50              55              60

Pro Ser Ser Pro Gly Thr Lys Lys Trp His Ala Ser Val Val Asp Pro
65              70              75              80
```

-continued

```
Leu Gly Leu Asp Met Pro Asn Cys Thr Tyr Ile Leu Asp Pro Glu Lys
              85                  90                  95

Leu Thr Leu Arg Ala Thr Tyr Asp Asn Cys Thr Arg Arg Val His Gly
             100                 105                 110

Gly His Gln Met Thr Ile Arg Val Met Asn Asn Ser Ala Ala Leu Arg
             115                 120                 125

His Gly Ala Val Met Tyr Gln Phe Phe Cys Pro Ala Met Gln Val Glu
         130                 135                 140

Glu Thr Gln Gly Leu Ser Ala Ser Thr Ile Cys Gln Lys Asp Phe Met
145                 150                 155                 160

Ser Phe Ser Leu Pro Arg Val Phe Ser Gly Leu Ala Asp Asp Ser Lys
                 165                 170                 175

Gly Thr Lys Val Gln Met Gly Trp Ser Ile Glu Val Gly Asp Gly Ala
             180                 185                 190

Arg Ala Lys Thr Leu Thr Leu Pro Glu Ala Met Lys Glu Gly Phe Ser
             195                 200                 205

Leu Leu Ile Asp Asn His Arg Met Thr Phe His Val Pro Phe Asn Ala
         210                 215                 220

Thr Gly Val Thr His Tyr Val Gln Gly Asn Ser His Leu Tyr Met Val
225                 230                 235                 240

Ser Leu Lys Leu Thr Phe Ile Ser Pro Gly Gln Lys Val Ile Phe Ser
                 245                 250                 255

Ser Gln Ala Ile Cys Ala Pro Asp Pro Val Thr Cys Asn Ala Thr His
             260                 265                 270

Met Thr Leu Thr Ile Pro Glu Phe Pro Gly Lys Leu Lys Ser Val Ser
             275                 280                 285

Phe Glu Asn Gln Asn Ile Asp Val Ser Gln Leu His Asp Asn Gly Ile
         290                 295                 300

Asp Leu Glu Ala Thr Asn Gly Met Lys Leu His Phe Ser Lys Thr Leu
305                 310                 315                 320

Leu Lys Thr Lys Leu Ser Glu Lys Cys Leu Leu His Gln Phe Tyr Leu
                 325                 330                 335

Ala Ser Leu Lys Leu Thr Phe Leu Leu Arg Pro Glu Thr Val Ser Met
             340                 345                 350

Val Ile Tyr Pro Glu Cys Leu Cys Glu Ser Pro Val Ser Ile Val Thr
             355                 360                 365

Gly Glu Leu Cys Thr Gln Asp Gly Phe Met Asp Val Glu Val Tyr Ser
         370                 375                 380

Tyr Gln Thr Gln Pro Ala Leu Asp Leu Gly Thr Leu Arg Val Gly Asn
385                 390                 395                 400

Ser Ser Cys Gln Pro Val Phe Glu Ala Gln Ser Gln Gly Leu Val Arg
             405                 410                 415

Phe His Ile Pro Leu Asn Gly Cys Gly Thr Arg Tyr Lys Phe Glu Asp
             420                 425                 430

Asp Lys Val Val Tyr Glu Asn Glu Ile His Ala Leu Trp Thr Asp Phe
         435                 440                 445

Pro Pro Ser Lys Ile Ser Arg Asp Ser Glu Phe Arg Asn Asp Met Leu
     450                 455                 460

Leu Asn Ile Asn Val Glu Ser Leu Thr Pro Pro Val Ala Ser Val Lys
465                 470                 475                 480

Leu Gly Pro Phe Thr Leu Ile Leu Gln Ser Tyr Pro Asp Asn Ser Tyr
                 485                 490                 495
```

-continued

```
Gln Gln Pro Tyr Gly Glu Asn Glu Tyr Pro Leu Val Arg Phe Leu Arg
            500                 505                 510

Gln Pro Ile Tyr Met Glu Val Arg Val Leu Asn Arg Asp Asp Pro Asn
            515                 520                 525

Ile Lys Leu Val Leu Asp Asp Cys Trp Ala Thr Ser Thr Met Asp Pro
            530                 535                 540

Asp Ser Phe Pro Gln Trp Asn Val Val Val Asp Gly Cys Ala Tyr Asp
545                 550                 555                 560

Leu Asp Asn Tyr Gln Thr Thr Phe His Pro Val Gly Ser Ser Val Thr
                565                 570                 575

His Pro Asp His Tyr Gln Arg Phe Asp Met Lys Ala Phe Ala Phe Val
                580                 585                 590

Ser Glu Ala His Val Leu Ser Ser Leu Val Tyr Phe His Cys Ser Ala
            595                 600                 605

Leu Ile Cys Asn Arg Leu Ser Pro Asp Ser Pro Leu Cys Ser Val Thr
            610                 615                 620

Cys Pro Val Ser Ser Arg His Arg Arg Ala Thr Gly Ala Thr Glu Ala
625                 630                 635                 640

Glu Lys Met Thr Val Ser Leu Pro Gly Pro Ile Leu Leu Leu Ser Asp
                645                 650                 655

Asp Ser Ser Phe Arg Gly Val Gly Ser Ser Asp Leu Lys Ala Ser Gly
            660                 665                 670

Ser Ser Gly Glu Lys Ser Arg Ser Glu Thr Gly Glu Glu Val Gly Ser
            675                 680                 685

Arg Gly Ala Met Asp Thr Lys Gly His Lys Thr Ala Gly Asp Val Gly
            690                 695                 700

Ser Lys Ala Val Ala Ala Val Ala Ala Phe Ala Gly Val Val Ala Thr
705                 710                 715                 720

Leu Gly Phe Ile Tyr Tyr Leu Tyr Glu Lys Arg Thr Val Ser Asn His
                725                 730                 735
```

<210> SEQ ID NO 13
<211> LENGTH: 756
<212> TYPE: PRT
<213> ORGANISM: Homo sapiens

<400> SEQUENCE: 13

```
Met Ala Cys Arg Gln Arg Gly Gly Ser Trp Ser Pro Ser Gly Trp Phe
1               5                   10                  15

Asn Ala Gly Trp Ser Thr Tyr Arg Ser Ile Ser Leu Phe Phe Ala Leu
                20                  25                  30

Val Thr Ser Gly Asn Ser Ile Asp Val Ser Gln Leu Val Asn Pro Ala
            35                  40                  45

Phe Pro Gly Thr Val Thr Cys Asp Glu Arg Glu Ile Thr Val Glu Phe
            50                  55                  60

Pro Ser Ser Pro Gly Thr Lys Lys Trp His Ala Ser Val Val Asp Pro
65                  70                  75                  80

Leu Gly Leu Asp Met Pro Asn Cys Thr Tyr Ile Leu Asp Pro Glu Lys
                85                  90                  95

Leu Thr Leu Arg Ala Thr Tyr Asp Asn Cys Thr Arg Arg Val His Gly
            100                 105                 110

Gly His Gln Met Thr Ile Arg Val Met Asn Asn Ser Ala Ala Leu Arg
            115                 120                 125

His Gly Ala Val Met Tyr Gln Phe Phe Cys Pro Ala Met Gln Val Glu
            130                 135                 140
```

```
Glu Thr Gln Gly Leu Ser Ala Ser Thr Ile Cys Gln Lys Asp Phe Met
145             150             155             160

Ser Phe Ser Leu Pro Arg Val Phe Ser Gly Leu Ala Asp Asp Ser Lys
                165             170             175

Gly Thr Lys Val Gln Met Gly Trp Ser Ile Glu Val Gly Asp Gly Ala
            180             185             190

Arg Ala Lys Thr Leu Thr Leu Pro Glu Ala Met Lys Glu Gly Phe Ser
        195             200             205

Leu Leu Ile Asp Asn His Arg Met Thr Phe His Val Pro Phe Asn Ala
    210             215             220

Thr Gly Val Thr His Tyr Val Gln Gly Asn Ser His Leu Tyr Met Val
225             230             235             240

Ser Leu Lys Leu Thr Phe Ile Ser Pro Gly Gln Lys Val Ile Phe Ser
            245             250             255

Ser Gln Ala Ile Cys Ala Pro Asp Pro Val Thr Cys Asn Ala Thr His
            260             265             270

Met Thr Leu Thr Ile Pro Glu Phe Pro Gly Lys Leu Lys Ser Val Ser
        275             280             285

Phe Glu Asn Gln Asn Ile Asp Val Ser Gln Leu His Asp Asn Gly Ile
    290             295             300

Asp Leu Glu Ala Thr Asn Gly Met Lys Leu His Phe Ser Lys Thr Leu
305             310             315             320

Leu Lys Thr Lys Leu Ser Glu Lys Cys Leu Leu His Gln Phe Tyr Leu
            325             330             335

Ala Ser Leu Lys Leu Thr Phe Leu Leu Arg Pro Glu Thr Val Ser Met
            340             345             350

Val Ile Tyr Pro Glu Cys Leu Cys Glu Ser Pro Val Ser Ile Val Thr
            355             360             365

Gly Glu Leu Cys Thr Gln Asp Gly Phe Met Asp Val Glu Val Tyr Ser
    370             375             380

Tyr Gln Thr Gln Pro Ala Leu Asp Leu Gly Thr Leu Arg Val Gly Asn
385             390             395             400

Ser Ser Cys Gln Pro Val Phe Glu Ala Gln Ser Gln Gly Leu Val Arg
            405             410             415

Phe His Ile Pro Leu Asn Gly Cys Gly Thr Arg Tyr Lys Phe Glu Asp
            420             425             430

Asp Lys Val Val Tyr Glu Asn Glu Ile His Ala Leu Trp Thr Asp Phe
        435             440             445

Pro Pro Ser Lys Ile Ser Arg Asp Ser Glu Phe Arg Met Thr Val Lys
    450             455             460

Cys Ser Tyr Ser Arg Asn Asp Met Leu Leu Asn Ile Asn Val Glu Ser
465             470             475             480

Leu Thr Pro Pro Val Ala Ser Val Lys Leu Gly Pro Phe Thr Leu Ile
            485             490             495

Leu Gln Ser Tyr Pro Asp Asn Ser Tyr Gln Gln Pro Tyr Gly Glu Asn
            500             505             510

Glu Tyr Pro Leu Val Arg Phe Leu Arg Gln Pro Ile Tyr Met Glu Val
        515             520             525

Arg Val Leu Asn Arg Asp Asp Pro Asn Ile Lys Leu Val Leu Asp Asp
    530             535             540

Cys Trp Ala Thr Ser Thr Met Asp Pro Asp Ser Phe Pro Gln Trp Asn
545             550             555             560
```

```
Val Val Val Asp Gly Cys Ala Tyr Asp Leu Asp Asn Tyr Gln Thr Thr
            565             570             575

Phe His Pro Val Gly Ser Ser Val Thr His Pro Asp His Tyr Gln Arg
            580             585             590

Phe Asp Met Lys Ala Phe Ala Phe Val Ser Glu Ala His Val Leu Ser
        595             600             605

Ser Leu Val Tyr Phe His Cys Ser Ala Leu Ile Cys Asn Arg Leu Ser
    610             615             620

Pro Asp Ser Pro Leu Cys Ser Val Thr Cys Pro Val Ser Ser Arg His
625             630             635             640

Arg Arg Glu Ala Lys His Lys Leu Asp His Leu Ser Pro Ala Thr Gly
            645             650             655

Ala Thr Glu Ala Glu Lys Met Thr Val Ser Leu Pro Gly Pro Ile Leu
            660             665             670

Leu Leu Ser Asp Asp Ser Ser Phe Arg Gly Val Gly Ser Ser Asp Leu
        675             680             685

Lys Ala Ser Gly Ser Ser Gly Glu Lys Ser Arg Ser Glu Thr Gly Glu
    690             695             700

Glu Val Gly Ser Arg Gly Ala Met Asp Thr Lys Gly His Lys Thr Ala
705             710             715             720

Gly Asp Val Gly Ser Lys Ala Val Ala Ala Val Ala Ala Phe Ala Gly
            725             730             735

Val Val Ala Thr Leu Gly Phe Ile Tyr Tyr Leu Tyr Glu Lys Arg Thr
            740             745             750

Val Ser Asn His
        755
```

```
<210> SEQ ID NO 14
<211> LENGTH: 520
<212> TYPE: PRT
<213> ORGANISM: Homo sapiens

<400> SEQUENCE: 14

Met Ala Gly Pro Glu Arg Trp Gly Pro Leu Leu Leu Cys Leu Leu Gln
1               5               10              15

Ala Ala Pro Gly Arg Pro Arg Leu Ala Pro Pro Gln Asn Val Thr Leu
            20              25              30

Leu Ser Gln Asn Phe Ser Val Tyr Leu Thr Trp Leu Pro Gly Leu Gly
        35              40              45

Asn Pro Gln Asp Val Thr Tyr Phe Val Ala Tyr Gln Ser Ser Pro Thr
    50              55              60

Arg Arg Arg Trp Arg Glu Val Glu Glu Cys Ala Gly Thr Lys Glu Leu
65              70              75              80

Leu Cys Ser Met Met Cys Leu Lys Lys Gln Asp Leu Tyr Asn Lys Phe
            85              90              95

Lys Gly Arg Val Arg Thr Val Ser Pro Ser Ser Lys Ser Pro Trp Val
            100             105             110

Glu Ser Glu Tyr Leu Asp Tyr Leu Phe Glu Val Glu Pro Ala Pro Pro
        115             120             125

Val Leu Val Leu Thr Gln Thr Glu Glu Ile Leu Ser Ala Asn Ala Thr
    130             135             140

Tyr Gln Leu Pro Pro Cys Met Pro Pro Leu Asp Leu Lys Tyr Glu Val
145             150             155             160

Ala Phe Trp Lys Glu Gly Ala Gly Asn Lys Thr Leu Phe Pro Val Thr
            165             170             175
```

```
Pro His Gly Gln Pro Val Gln Ile Thr Leu Gln Pro Ala Ala Ser Glu
         180                 185                 190

His His Cys Leu Ser Ala Arg Thr Ile Tyr Thr Phe Ser Val Pro Lys
         195                 200                 205

Tyr Ser Lys Phe Ser Lys Pro Thr Cys Phe Leu Leu Glu Val Pro Glu
         210                 215                 220

Ala Asn Trp Ala Phe Leu Val Leu Pro Ser Leu Leu Ile Leu Leu Leu
225                 230                 235                 240

Val Ile Ala Ala Gly Gly Val Ile Trp Lys Thr Leu Met Gly Asn Pro
                 245                 250                 255

Trp Phe Gln Arg Ala Lys Met Pro Arg Ala Leu Asp Phe Ser Gly His
         260                 265                 270

Thr His Pro Val Ala Thr Phe Gln Pro Ser Arg Pro Glu Ser Val Asn
         275                 280                 285

Asp Leu Phe Leu Cys Pro Gln Lys Glu Leu Thr Arg Gly Val Arg Pro
         290                 295                 300

Thr Pro Arg Val Arg Ala Pro Ala Thr Gln Gln Thr Arg Trp Lys Lys
305                 310                 315                 320

Asp Leu Ala Glu Asp Glu Glu Glu Asp Glu Glu Asp Thr Glu Asp
                 325                 330                 335

Gly Val Ser Phe Gln Pro Tyr Ile Glu Pro Pro Ser Phe Leu Gly Gln
                 340                 345                 350

Glu His Gln Ala Pro Gly His Ser Glu Ala Gly Gly Val Asp Ser Gly
         355                 360                 365

Arg Pro Arg Ala Pro Leu Val Pro Ser Glu Gly Ser Ser Ala Trp Asp
370                 375                 380

Ser Ser Asp Arg Ser Trp Ala Ser Thr Val Asp Ser Ser Trp Asp Arg
385                 390                 395                 400

Ala Gly Ser Ser Gly Tyr Leu Ala Glu Lys Gly Pro Gly Gln Gly Pro
                 405                 410                 415

Gly Gly Asp Gly His Gln Glu Ser Leu Pro Pro Pro Glu Phe Ser Lys
                 420                 425                 430

Asp Ser Gly Phe Leu Glu Glu Leu Pro Glu Asp Asn Leu Ser Ser Trp
         435                 440                 445

Ala Thr Trp Gly Thr Leu Pro Pro Glu Pro Asn Leu Val Pro Gly Gly
         450                 455                 460

Pro Pro Val Ser Leu Gln Thr Leu Thr Phe Cys Trp Glu Ser Ser Pro
465                 470                 475                 480

Glu Glu Glu Glu Glu Ala Arg Glu Ser Glu Ile Glu Asp Ser Asp Ala
                 485                 490                 495

Gly Ser Trp Gly Ala Glu Ser Thr Gln Arg Thr Glu Asp Arg Gly Arg
         500                 505                 510

Thr Leu Gly His Tyr Met Ala Arg
         515                 520
```

```
<210> SEQ ID NO 15
<211> LENGTH: 491
<212> TYPE: PRT
<213> ORGANISM: Homo sapiens

<400> SEQUENCE: 15

Met Ala Gly Pro Glu Arg Trp Gly Pro Leu Leu Leu Cys Leu Leu Gln
1               5                   10                  15

Ala Ala Pro Gly Arg Pro Arg Leu Ala Pro Pro Gln Asn Val Thr Leu
```

-continued

```
               20                  25                  30

Leu Ser Gln Asn Phe Ser Val Tyr Leu Thr Trp Leu Pro Gly Leu Gly
            35                  40                  45

Asn Pro Gln Asp Val Thr Tyr Phe Val Ala Tyr Gln Ser Ser Pro Thr
        50                  55                  60

Arg Arg Arg Trp Arg Glu Val Glu Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
            100                 105                 110

Glu Ser Glu Tyr Leu Asp Tyr Leu Phe Glu Val Glu Pro Ala Pro Pro
        115                 120                 125

Val Leu Val Leu Thr Gln Thr Glu Glu Ile Leu Ser Ala Asn Ala Thr
        130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Thr Leu Phe Pro Val Thr
                165                 170                 175

Pro His Gly Gln Pro Val Gln Ile Thr Leu Gln Pro Ala Ala Ser Glu
            180                 185                 190

His His Cys Leu Ser Ala Arg Thr Ile Tyr Thr Phe Ser Val Pro Lys
            195                 200                 205

Tyr Ser Lys Phe Ser Lys Pro Thr Cys Phe Leu Leu Glu Val Pro Glu
        210                 215                 220

Ala Asn Trp Ala Phe Leu Val Leu Pro Ser Leu Leu Ile Leu Leu Leu
225                 230                 235                 240

Val Ile Ala Ala Gly Gly Val Ile Trp Lys Thr Leu Met Gly Asn Pro
            245                 250                 255

Trp Phe Gln Arg Ala Lys Met Pro Arg Ala Leu Glu Leu Thr Arg Gly
            260                 265                 270

Val Arg Pro Thr Pro Arg Val Arg Ala Pro Ala Thr Gln Gln Thr Arg
        275                 280                 285

Trp Lys Lys Asp Leu Ala Glu Asp Glu Glu Glu Asp Glu Glu Asp
        290                 295                 300

Thr Glu Asp Gly Val Ser Phe Gln Pro Tyr Ile Glu Pro Pro Ser Phe
305                 310                 315                 320

Leu Gly Gln Glu His Gln Ala Pro Gly His Ser Glu Ala Gly Gly Val
                325                 330                 335

Asp Ser Gly Arg Pro Arg Ala Pro Leu Val Pro Ser Glu Gly Ser Ser
            340                 345                 350

Ala Trp Asp Ser Ser Asp Arg Ser Trp Ala Ser Thr Val Asp Ser Ser
            355                 360                 365

Trp Asp Arg Ala Gly Ser Ser Gly Tyr Leu Ala Glu Lys Gly Pro Gly
        370                 375                 380

Gln Gly Pro Gly Gly Asp Gly His Gln Glu Ser Leu Pro Pro Pro Glu
385                 390                 395                 400

Phe Ser Lys Asp Ser Gly Phe Leu Glu Glu Leu Pro Glu Asp Asn Leu
            405                 410                 415

Ser Ser Trp Ala Thr Trp Gly Thr Leu Pro Pro Glu Pro Asn Leu Val
            420                 425                 430

Pro Gly Gly Pro Pro Val Ser Leu Gln Thr Leu Thr Phe Cys Trp Glu
            435                 440                 445
```

```
Ser Ser Pro Glu Glu Glu Glu Ala Arg Glu Ser Glu Ile Glu Asp
    450             455             460

Ser Asp Ala Gly Ser Trp Gly Ala Glu Ser Thr Gln Arg Thr Glu Asp
465             470             475             480

Arg Gly Arg Thr Leu Gly His Tyr Met Ala Arg
                485             490
```

```
<210> SEQ ID NO 16
<211> LENGTH: 244
<212> TYPE: PRT
<213> ORGANISM: Homo sapiens

<400> SEQUENCE: 16

Met Ala Gly Pro Glu Arg Trp Gly Pro Leu Leu Leu Cys Leu Leu Gln
1               5               10              15

Ala Ala Pro Gly Arg Pro Arg Leu Ala Pro Pro Gln Asn Val Thr Leu
                20              25              30

Leu Ser Gln Asn Phe Ser Val Tyr Leu Thr Trp Leu Pro Gly Leu Gly
            35              40              45

Asn Pro Gln Asp Val Thr Tyr Phe Val Ala Tyr Gln Ser Ser Pro Thr
        50              55              60

Arg Arg Arg Trp Arg Glu Val Glu Glu Cys Ala Gly Thr Lys Glu Leu
65              70              75              80

Leu Cys Ser Met Met Cys Leu Lys Lys Gln Asp Leu Tyr Asn Lys Phe
                85              90              95

Lys Gly Arg Val Arg Thr Val Ser Pro Ser Ser Lys Ser Pro Trp Val
            100             105             110

Glu Ser Glu Tyr Leu Asp Tyr Leu Phe Glu Val Glu Pro Ala Pro Pro
        115             120             125

Val Leu Val Leu Thr Gln Thr Glu Glu Ile Leu Ser Ala Asn Ala Thr
    130             135             140

Tyr Gln Leu Pro Pro Cys Met Pro Pro Leu Asp Leu Lys Tyr Glu Val
145             150             155             160

Ala Phe Trp Lys Glu Gly Ala Gly Asn Lys Thr Leu Phe Pro Val Thr
                165             170             175

Pro His Gly Gln Pro Val Gln Ile Thr Leu Gln Pro Ala Ala Ser Glu
            180             185             190

His His Cys Leu Ser Ala Arg Thr Ile Tyr Thr Phe Ser Val Pro Lys
        195             200             205

Tyr Ser Lys Phe Ser Lys Pro Thr Cys Phe Leu Leu Glu Val Pro Gly
    210             215             220

Leu Phe Trp Thr His Thr Pro Cys Gly Asn Leu Ser Ala Gln Gln Thr
225             230             235             240

Arg Val Arg Glu
```

```
<210> SEQ ID NO 17
<211> LENGTH: 440
<212> TYPE: PRT
<213> ORGANISM: Homo sapiens

<400> SEQUENCE: 17

Met Val Pro Glu Pro Gly Pro Thr Ala Asn Ser Thr Pro Ala Trp Gly
1               5               10              15

Ala Gly Pro Pro Ser Ala Pro Gly Gly Ser Gly Trp Val Ala Ala Ala
                20              25              30
```

-continued

```
Leu Cys Val Val Ile Ala Leu Thr Ala Ala Ala Asn Ser Leu Leu Ile
        35              40              45

Ala Leu Ile Cys Thr Gln Pro Ala Leu Arg Asn Thr Ser Asn Phe Phe
    50              55              60

Leu Val Ser Leu Phe Thr Ser Asp Leu Met Val Gly Leu Val Val Met
65              70              75              80

Pro Pro Ala Met Leu Asn Ala Leu Tyr Gly Arg Trp Val Leu Ala Arg
            85              90              95

Gly Leu Cys Leu Leu Trp Thr Ala Phe Asp Val Met Cys Cys Ser Ala
            100             105             110

Ser Ile Leu Asn Leu Cys Leu Ile Ser Leu Asp Arg Tyr Leu Leu Ile
            115             120             125

Leu Ser Pro Leu Arg Tyr Lys Leu Arg Met Thr Pro Leu Arg Ala Leu
        130             135             140

Ala Leu Val Leu Gly Ala Trp Ser Leu Ala Ala Leu Ala Ser Phe Leu
145             150             155             160

Pro Leu Leu Leu Gly Trp His Glu Leu Gly His Ala Arg Pro Pro Val
            165             170             175

Pro Gly Gln Cys Arg Leu Leu Ala Ser Leu Pro Phe Val Leu Val Ala
            180             185             190

Ser Gly Leu Thr Phe Phe Leu Pro Ser Gly Ala Ile Cys Phe Thr Tyr
            195             200             205

Cys Arg Ile Leu Leu Ala Ala Arg Lys Gln Ala Val Gln Val Ala Ser
        210             215             220

Leu Thr Thr Gly Met Ala Ser Gln Ala Ser Glu Thr Leu Gln Val Pro
225             230             235             240

Arg Thr Pro Arg Pro Gly Val Glu Ser Ala Asp Ser Arg Arg Leu Ala
            245             250             255

Thr Lys His Ser Arg Lys Ala Leu Lys Ala Ser Leu Thr Leu Gly Ile
            260             265             270

Leu Leu Gly Met Phe Phe Val Thr Trp Leu Pro Phe Phe Val Ala Asn
            275             280             285

Ile Val Gln Ala Val Cys Asp Cys Ile Ser Pro Gly Leu Phe Asp Val
    290             295             300

Leu Thr Trp Leu Gly Tyr Cys Asn Ser Thr Met Asn Pro Ile Ile Tyr
305             310             315             320

Pro Leu Phe Met Arg Asp Phe Lys Arg Ala Leu Gly Arg Phe Leu Pro
            325             330             335

Cys Pro Arg Cys Pro Arg Glu Arg Gln Ala Ser Leu Ala Ser Pro Ser
            340             345             350

Leu Arg Thr Ser His Ser Gly Pro Arg Pro Gly Leu Ser Leu Gln Gln
            355             360             365

Val Leu Pro Leu Pro Leu Pro Pro Asp Ser Asp Ser Asp Ser Asp Ala
        370             375             380

Gly Ser Gly Gly Ser Ser Gly Leu Arg Leu Thr Ala Gln Leu Leu Leu
385             390             395             400

Pro Gly Glu Ala Thr Gln Asp Pro Pro Leu Pro Thr Arg Ala Ala Ala
            405             410             415

Ala Val Asn Phe Phe Asn Ile Asp Pro Ala Glu Pro Glu Leu Arg Pro
            420             425             430

His Pro Leu Gly Ile Pro Thr Asn
            435             440
```

-continued

```
<210> SEQ ID NO 18
<211> LENGTH: 481
<212> TYPE: PRT
<213> ORGANISM: Homo sapiens

<400> SEQUENCE: 18

Met Arg Trp Leu Trp Pro Leu Ala Val Ser Leu Ala Val Ile Leu Ala
1               5                   10                  15

Val Gly Leu Ser Arg Val Ser Gly Gly Ala Pro Leu His Leu Gly Arg
            20                  25                  30

His Arg Ala Glu Thr Gln Glu Gln Gln Ser Arg Ser Lys Arg Gly Thr
        35                  40                  45

Glu Asp Glu Glu Ala Lys Gly Val Gln Gln Tyr Val Pro Glu Glu Trp
    50                  55                  60

Ala Glu Tyr Pro Arg Pro Ile His Pro Ala Gly Leu Gln Pro Thr Lys
65                  70                  75                  80

Pro Leu Val Ala Thr Ser Pro Asn Pro Gly Lys Asp Gly Gly Thr Pro
                85                  90                  95

Asp Ser Gly Gln Glu Leu Arg Gly Asn Leu Thr Gly Ala Pro Gly Gln
            100                 105                 110

Arg Leu Gln Ile Gln Asn Pro Leu Tyr Pro Val Thr Glu Ser Ser Tyr
            115                 120                 125

Ser Ala Tyr Ala Ile Met Leu Leu Ala Leu Val Val Phe Ala Val Gly
    130                 135                 140

Ile Val Gly Asn Leu Ser Val Met Cys Ile Val Trp His Ser Tyr Tyr
145                 150                 155                 160

Leu Lys Ser Ala Trp Asn Ser Ile Leu Ala Ser Leu Ala Leu Trp Asp
                165                 170                 175

Phe Leu Val Leu Phe Phe Cys Leu Pro Ile Val Ile Phe Asn Glu Ile
            180                 185                 190

Thr Lys Gln Arg Leu Leu Gly Asp Val Ser Cys Arg Ala Val Pro Phe
            195                 200                 205

Met Glu Val Ser Ser Leu Gly Val Thr Thr Phe Ser Leu Cys Ala Leu
    210                 215                 220

Gly Ile Asp Arg Phe His Val Ala Thr Ser Thr Leu Pro Lys Val Arg
225                 230                 235                 240

Pro Ile Glu Arg Cys Gln Ser Ile Leu Ala Lys Leu Ala Val Ile Trp
                245                 250                 255

Val Gly Ser Met Thr Leu Ala Val Pro Glu Leu Leu Leu Trp Gln Leu
            260                 265                 270

Ala Gln Glu Pro Ala Pro Thr Met Gly Thr Leu Asp Ser Cys Ile Met
    275                 280                 285

Lys Pro Ser Ala Ser Leu Pro Glu Ser Leu Tyr Ser Leu Val Met Thr
    290                 295                 300

Tyr Gln Asn Ala Arg Met Trp Trp Tyr Phe Gly Cys Tyr Phe Cys Leu
305                 310                 315                 320

Pro Ile Leu Phe Thr Val Thr Cys Gln Leu Val Thr Trp Arg Val Arg
                325                 330                 335

Gly Pro Pro Gly Arg Lys Ser Glu Cys Arg Ala Ser Lys His Glu Gln
            340                 345                 350

Cys Glu Ser Gln Leu Asn Ser Thr Val Val Gly Leu Thr Val Val Tyr
            355                 360                 365

Ala Phe Cys Thr Leu Pro Glu Asn Val Cys Asn Ile Val Val Ala Tyr
    370                 375                 380
```

```
Leu Ser Thr Glu Leu Thr Arg Gln Thr Leu Asp Leu Leu Gly Leu Ile
385                 390                 395                 400

Asn Gln Phe Ser Thr Phe Phe Lys Gly Ala Ile Thr Pro Val Leu Leu
                405                 410                 415

Leu Cys Ile Cys Arg Pro Leu Gly Gln Ala Phe Leu Asp Cys Cys Cys
            420                 425                 430

Cys Cys Cys Cys Glu Glu Cys Gly Gly Ala Ser Glu Ala Ser Ala Ala
        435                 440                 445

Asn Gly Ser Asp Asn Lys Leu Lys Thr Glu Val Ser Ser Ser Ile Tyr
    450                 455                 460

Phe His Lys Pro Arg Glu Ser Pro Pro Leu Leu Pro Leu Gly Thr Pro
465                 470                 475                 480

Cys
```

```
<210> SEQ ID NO 19
<211> LENGTH: 340
<212> TYPE: PRT
<213> ORGANISM: Homo sapiens

<400> SEQUENCE: 19
```

```
Met Asn Pro Phe His Ala Ser Cys Trp Asn Thr Ser Ala Glu Leu Leu
1               5               10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
            35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
            85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
            115                 120                 125

Val Asp Arg Tyr Phe Ala Leu Val Gln Pro Phe Arg Leu Thr Arg Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
            165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
            195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
            245                 250                 255

Val Val Val Phe Ile Leu Ser Ala Ala Pro Tyr His Val Ile Gln Leu
            260                 265                 270
```

```
Val Asn Leu Gln Met Glu Gln Pro Thr Leu Ala Phe Tyr Val Gly Tyr
    275                 280                 285

Tyr Leu Ser Ile Cys Leu Ser Tyr Ala Ser Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Ala Thr Glu Lys Glu Ile Asn Asn Met Gly Asn Thr Leu
                325                 330                 335

Lys Ser His Phe
            340

<210> SEQ ID NO 20
<211> LENGTH: 334
<212> TYPE: PRT
<213> ORGANISM: Homo sapiens

<400> SEQUENCE: 20

Met Pro Lys Arg Arg Asp Ile Leu Ala Ile Val Leu Ile Val Leu Pro
1               5                   10                  15

Trp Thr Leu Leu Ile Thr Val Trp His Gln Ser Thr Leu Ala Pro Leu
                20                  25                  30

Leu Ala Val His Lys Asp Glu Gly Ser Asp Pro Arg Arg Glu Thr Pro
            35                  40                  45

Pro Gly Ala Asp Pro Arg Glu Tyr Cys Thr Ser Asp Arg Asp Ile Val
        50                  55                  60

Glu Val Val Arg Thr Glu Tyr Val Tyr Thr Arg Pro Pro Pro Trp Ser
65                  70                  75                  80

Asp Thr Leu Pro Thr Ile His Val Val Thr Pro Thr Tyr Ser Arg Pro
                85                  90                  95

Val Gln Lys Ala Glu Leu Thr Arg Met Ala Asn Thr Leu Leu His Val
            100                 105                 110

Pro Asn Leu His Trp Leu Val Val Glu Asp Ala Pro Arg Arg Thr Pro
            115                 120                 125

Leu Thr Ala Arg Leu Leu Arg Asp Thr Gly Leu Asn Tyr Thr His Leu
    130                 135                 140

His Val Glu Thr Pro Arg Asn Tyr Lys Leu Arg Gly Asp Ala Arg Asp
145                 150                 155                 160

Pro Arg Ile Pro Arg Gly Thr Met Gln Arg Asn Leu Ala Leu Arg Trp
                165                 170                 175

Leu Arg Glu Thr Phe Pro Arg Asn Ser Ser Gln Pro Gly Val Val Tyr
                180                 185                 190

Phe Ala Asp Asp Asp Asn Thr Tyr Ser Leu Glu Leu Phe Glu Glu Met
            195                 200                 205

Arg Ser Thr Arg Arg Val Ser Val Trp Pro Val Ala Phe Val Gly Gly
    210                 215                 220

Leu Arg Tyr Glu Ala Pro Arg Val Asn Gly Ala Gly Lys Val Val Gly
225                 230                 235                 240

Trp Lys Thr Val Phe Asp Pro His Arg Pro Phe Ala Ile Asp Met Ala
                245                 250                 255

Gly Phe Ala Val Asn Leu Arg Leu Ile Leu Gln Arg Ser Gln Ala Tyr
            260                 265                 270

Phe Lys Leu Arg Gly Val Lys Gly Gly Tyr Gln Glu Ser Ser Leu Leu
    275                 280                 285

Arg Glu Leu Val Thr Leu Asn Asp Leu Glu Pro Lys Ala Ala Asn Cys
    290                 295                 300
```

```
Thr Lys Ile Leu Val Trp His Thr Arg Thr Glu Lys Pro Val Leu Val
305             310             315             320

Asn Glu Gly Lys Lys Gly Phe Thr Asp Pro Ser Val Glu Ile
                325             330

<210> SEQ ID NO 21
<211> LENGTH: 347
<212> TYPE: PRT
<213> ORGANISM: Homo sapiens

<400> SEQUENCE: 21

Met Gly Asn Glu Glu Pro Trp Val Gln Pro Ala Leu Glu Met Pro Lys
1               5               10              15

Arg Arg Asp Ile Leu Ala Ile Val Leu Ile Val Leu Pro Trp Thr Leu
                20              25              30

Leu Ile Thr Val Trp His Gln Ser Thr Leu Ala Pro Leu Leu Ala Val
                35              40              45

His Lys Asp Glu Gly Ser Asp Pro Arg Arg Glu Thr Pro Pro Gly Ala
    50              55              60

Asp Pro Arg Glu Tyr Cys Thr Ser Asp Arg Asp Ile Val Glu Val Val
65              70              75              80

Arg Thr Glu Tyr Val Tyr Thr Arg Pro Pro Pro Trp Ser Asp Thr Leu
                85              90              95

Pro Thr Ile His Val Val Thr Pro Thr Tyr Ser Arg Pro Val Gln Lys
                100             105             110

Ala Glu Leu Thr Arg Met Ala Asn Thr Leu Leu His Val Pro Asn Leu
                115             120             125

His Trp Leu Val Val Glu Asp Ala Pro Arg Arg Thr Pro Leu Thr Ala
    130             135             140

Arg Leu Leu Arg Asp Thr Gly Leu Asn Tyr Thr His Leu His Val Glu
145             150             155             160

Thr Pro Arg Asn Tyr Lys Leu Arg Gly Asp Ala Arg Asp Pro Arg Ile
                165             170             175

Pro Arg Gly Thr Met Gln Arg Asn Leu Ala Leu Arg Trp Leu Arg Glu
                180             185             190

Thr Phe Pro Arg Asn Ser Ser Gln Pro Gly Val Val Tyr Phe Ala Asp
                195             200             205

Asp Asp Asn Thr Tyr Ser Leu Glu Leu Phe Glu Glu Met Arg Ser Thr
    210             215             220

Arg Arg Val Ser Val Trp Pro Val Ala Phe Val Gly Gly Leu Arg Tyr
225             230             235             240

Glu Ala Pro Arg Val Asn Gly Ala Gly Lys Val Val Gly Trp Lys Thr
                245             250             255

Val Phe Asp Pro His Arg Pro Phe Ala Ile Asp Met Ala Gly Phe Ala
                260             265             270

Val Asn Leu Arg Leu Ile Leu Gln Arg Ser Gln Ala Tyr Phe Lys Leu
                275             280             285

Arg Gly Val Lys Gly Gly Tyr Gln Glu Ser Ser Leu Leu Arg Glu Leu
    290             295             300

Val Thr Leu Asn Asp Leu Glu Pro Lys Ala Ala Asn Cys Thr Lys Ile
305             310             315             320

Leu Val Trp His Thr Arg Thr Glu Lys Pro Val Leu Val Asn Glu Gly
                325             330             335

Lys Lys Gly Phe Thr Asp Pro Ser Val Glu Ile
```

```
                340                345
```

<210> SEQ ID NO 22
<211> LENGTH: 380
<212> TYPE: PRT
<213> ORGANISM: Homo sapiens

<400> SEQUENCE: 22

```
Met Arg Asn Cys Lys Met Ala Arg Val Ala Ser Val Leu Gly Leu Val
1               5                   10                  15

Met Leu Ser Val Ala Leu Leu Ile Leu Ser Leu Ile Ser Tyr Val Ser
                20                  25                  30

Leu Lys Lys Glu Asn Ile Phe Thr Thr Pro Lys Tyr Ala Ser Pro Gly
            35                  40                  45

Ala Pro Arg Met Tyr Met Phe His Ala Gly Phe Arg Ser Gln Phe Ala
        50                  55                  60

Leu Lys Phe Leu Asp Pro Ser Phe Val Pro Ile Thr Asn Ser Leu Thr
65                  70                  75                  80

Gln Glu Leu Gln Glu Lys Pro Ser Lys Trp Lys Phe Asn Arg Thr Ala
                85                  90                  95

Phe Leu His Gln Arg Gln Glu Ile Leu Gln His Val Asp Val Ile Lys
            100                 105                 110

Asn Phe Ser Leu Thr Lys Asn Ser Val Arg Ile Gly Gln Leu Met His
            115                 120                 125

Tyr Asp Tyr Ser Ser His Lys Tyr Val Phe Ser Ile Ser Asn Asn Phe
        130                 135                 140

Arg Ser Leu Leu Pro Asp Val Ser Pro Ile Met Asn Lys His Tyr Asn
145                 150                 155                 160

Ile Cys Ala Val Val Gly Asn Ser Gly Ile Leu Thr Gly Ser Gln Cys
                165                 170                 175

Gly Gln Glu Ile Asp Lys Ser Asp Phe Val Phe Arg Cys Asn Phe Ala
            180                 185                 190

Pro Thr Glu Ala Phe Gln Arg Asp Val Gly Arg Lys Thr Asn Leu Thr
            195                 200                 205

Thr Phe Asn Pro Ser Ile Leu Glu Lys Tyr Tyr Asn Asn Leu Leu Thr
        210                 215                 220

Ile Gln Asp Arg Asn Asn Phe Phe Leu Ser Leu Lys Lys Leu Asp Gly
225                 230                 235                 240

Ala Ile Leu Trp Ile Pro Ala Phe Phe Phe His Thr Ser Ala Thr Val
                245                 250                 255

Thr Arg Thr Leu Val Asp Phe Phe Val Glu His Arg Gly Gln Leu Lys
            260                 265                 270

Val Gln Leu Ala Trp Pro Gly Asn Ile Met Gln His Val Asn Arg Tyr
        275                 280                 285

Trp Lys Asn Lys His Leu Ser Pro Lys Arg Leu Ser Thr Gly Ile Leu
        290                 295                 300

Met Tyr Thr Leu Ala Ser Ala Ile Cys Glu Glu Ile His Leu Tyr Gly
305                 310                 315                 320

Phe Trp Pro Phe Gly Phe Asp Pro Asn Thr Arg Glu Asp Leu Pro Tyr
                325                 330                 335

His Tyr Tyr Asp Lys Lys Gly Thr Lys Phe Thr Thr Lys Trp Gln Glu
            340                 345                 350

Ser His Gln Leu Pro Ala Glu Phe Gln Leu Leu Tyr Arg Met His Gly
        355                 360                 365
```

```
Glu Gly Leu Thr Lys Leu Thr Leu Ser His Cys Ala
    370                 375                 380

<210> SEQ ID NO 23
<211> LENGTH: 770
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Met Ser Gln Ser Leu Leu Lys Thr
            340                 345                 350
```

```
Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
                420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
                500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
        740                 745                 750

Gln Gln Asn Gly Tyr Glu Asn Pro Thr Tyr Lys Phe Phe Glu Gln Met
    755                 760                 765
```

Gln Asn
    770

<210> SEQ ID NO 24
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Cys Leu Leu Phe Leu Leu Leu Trp Ala Leu Leu Gln Ala Trp
1               5                   10                  15

Gly Ser Ala Glu Val Pro Gln Arg Leu Phe Pro Leu Arg Cys Leu Gln
            20                  25                  30

Ile Ser Ser Phe Ala Asn Ser Ser Trp Thr Arg Thr Asp Gly Leu Ala
            35                  40                  45

Trp Leu Gly Glu Leu Gln Thr His Ser Trp Ser Asn Asp Ser Asp Thr
    50                  55                  60

Val Arg Ser Leu Lys Pro Trp Ser Gln Gly Thr Phe Ser Asp Gln Gln
65                  70                  75                  80

Trp Glu Thr Leu Gln His Ile Phe Arg Val Tyr Arg Ser Ser Phe Thr
                85                  90                  95

Arg Asp Val Lys Glu Phe Ala Lys Met Leu Arg Leu Ser Tyr Pro Leu
            100                 105                 110

Glu Leu Gln Val Ser Ala Gly Cys Glu Val His Pro Gly Asn Ala Ser
            115                 120                 125

Asn Asn Phe Phe His Val Ala Phe Gln Gly Lys Asp Ile Leu Ser Phe
    130                 135                 140

Gln Gly Thr Ser Trp Glu Pro Thr Gln Glu Ala Pro Leu Trp Val Asn
145                 150                 155                 160

Leu Ala Ile Gln Val Leu Asn Gln Asp Lys Trp Thr Arg Glu Thr Val
                165                 170                 175

Gln Trp Leu Leu Asn Gly Thr Cys Pro Gln Phe Val Ser Gly Leu Leu
            180                 185                 190

Glu Ser Gly Lys Ser Glu Leu Lys Lys Gln Val Lys Pro Lys Ala Trp
            195                 200                 205

Leu Ser Arg Gly Pro Ser Pro Gly Pro Gly Arg Leu Leu Leu Val Cys
    210                 215                 220

His Val Ser Gly Phe Tyr Pro Lys Pro Val Trp Val Lys Trp Met Arg
225                 230                 235                 240

Gly Glu Gln Glu Gln Gln Gly Thr Gln Pro Gly Asp Ile Leu Pro Asn
                245                 250                 255

Ala Asp Glu Thr Trp Tyr Leu Arg Ala Thr Leu Asp Val Val Ala Gly
            260                 265                 270

Glu Ala Ala Gly Leu Ser Cys Arg Val Lys His Ser Ser Leu Glu Gly
            275                 280                 285

Gln Asp Ile Val Leu Tyr Trp Gly Gly Ser Tyr Thr Ser Met Gly Leu
    290                 295                 300

Ile Ala Leu Ala Val Leu Ala Cys Leu Leu Phe Leu Leu Ile Val Gly
305                 310                 315                 320

Phe Thr Ser Arg Phe Lys Arg Gln Thr Ser Tyr Gln Gly Val Leu
                325                 330                 335

<210> SEQ ID NO 25

```
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
                20                  25                  30

Leu Gly Arg Arg Pro Gly Ala Pro Glu Ser Lys Cys Ser Arg Gly Ala
            35                  40                  45

Leu Tyr Thr Gly Phe Ser Ile Leu Val Thr Leu Leu Leu Ala Gly Gln
        50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
                100                 105                 110

Leu Leu Met Gln Ala Leu Pro Met Gly Ala Leu Pro Gln Gly Pro Met
            115                 120                 125

Gln Asn Ala Thr Lys Tyr Gly Asn Met Thr Glu Asp His Val Met His
        130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
                180                 185                 190

Met Ser Arg His Ser Leu Glu Gln Lys Pro Thr Asp Ala Pro Pro Lys
            195                 200                 205

Val Leu Thr Lys Cys Gln Glu Glu Val Ser His Ile Pro Ala Val His
        210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
        275                 280                 285

Gln Asp Leu Gly Pro Val Pro Met
    290                 295

<210> SEQ ID NO 26
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Pro Trp Leu Gln Leu Leu Ser Leu Leu Gly Leu Leu Pro Gly
1               5                   10                  15
```

-continued

```
Ala Val Ala Ala Pro Ala Gln Pro Arg Ala Ala Ser Phe Gln Ala Trp
         20                  25                  30

Gly Pro Pro Ser Pro Glu Leu Leu Ala Pro Thr Arg Phe Ala Leu Glu
         35                  40                  45

Met Phe Asn Arg Gly Arg Ala Ala Gly Thr Arg Ala Val Leu Gly Leu
         50                  55                  60

Val Arg Gly Arg Val Arg Arg Ala Gly Gln Gly Ser Leu Tyr Ser Leu
65                  70                  75                  80

Glu Ala Thr Leu Glu Glu Pro Pro Cys Asn Asp Pro Met Val Cys Arg
                 85                  90                  95

Leu Pro Val Ser Lys Lys Thr Leu Leu Cys Ser Phe Gln Val Leu Asp
                100                 105                 110

Glu Leu Gly Arg His Val Leu Leu Arg Lys Asp Cys Gly Pro Val Asp
                115                 120                 125

Thr Lys Val Pro Gly Ala Gly Glu Pro Lys Ser Ala Phe Thr Gln Gly
         130                 135                 140

Ser Ala Met Ile Ser Ser Leu Ser Gln Asn His Pro Asp Asn Arg Asn
145                 150                 155                 160

Glu Thr Phe Ser Ser Val Ile Ser Leu Leu Asn Glu Asp Pro Leu Ser
                165                 170                 175

Gln Asp Leu Pro Val Lys Met Ala Ser Ile Phe Lys Asn Phe Val Ile
                180                 185                 190

Thr Tyr Asn Arg Thr Tyr Glu Ser Lys Glu Glu Ala Arg Trp Arg Leu
         195                 200                 205

Ser Val Phe Val Asn Asn Met Val Arg Ala Gln Lys Ile Gln Ala Leu
         210                 215                 220

Asp Arg Gly Thr Ala Gln Tyr Gly Val Thr Lys Phe Ser Asp Leu Thr
225                 230                 235                 240

Glu Glu Glu Phe Arg Thr Ile Tyr Leu Asn Thr Leu Leu Arg Lys Glu
                245                 250                 255

Pro Gly Asn Lys Met Lys Gln Ala Lys Ser Val Gly Asp Leu Ala Pro
         260                 265                 270

Pro Glu Trp Asp Trp Arg Ser Lys Gly Ala Val Thr Lys Val Lys Asp
         275                 280                 285

Gln Gly Met Cys Gly Ser Cys Trp Ala Phe Ser Val Thr Gly Asn Val
         290                 295                 300

Glu Gly Gln Trp Phe Leu Asn Gln Gly Thr Leu Leu Ser Leu Ser Glu
305                 310                 315                 320

Gln Glu Leu Leu Asp Cys Asp Lys Met Asp Lys Ala Cys Met Gly Gly
                325                 330                 335

Leu Pro Ser Asn Ala Tyr Ser Ala Ile Lys Asn Leu Gly Gly Leu Glu
         340                 345                 350

Thr Glu Asp Asp Tyr Ser Tyr Gln Gly His Met Gln Ser Cys Asn Phe
         355                 360                 365

Ser Ala Glu Lys Ala Lys Val Tyr Ile Asn Asp Ser Val Glu Leu Ser
         370                 375                 380

Gln Asn Glu Gln Lys Leu Ala Ala Trp Leu Ala Lys Arg Gly Pro Ile
385                 390                 395                 400

Ser Val Ala Ile Asn Ala Phe Gly Met Gln Phe Tyr Arg His Gly Ile
                405                 410                 415

Ser Arg Pro Leu Arg Pro Leu Cys Ser Pro Trp Leu Ile Asp His Ala
         420                 425                 430
```

-continued

```
Val Leu Leu Val Gly Tyr Gly Asn Arg Ser Asp Val Pro Phe Trp Ala
        435                 440                 445

Ile Lys Asn Ser Trp Gly Thr Asp Trp Gly Glu Lys Gly Tyr Tyr Tyr
    450                 455                 460

Leu His Arg Gly Ser Gly Ala Cys Gly Val Asn Thr Met Ala Ser Ser
465                 470                 475                 480

Ala Val Val Asp

<210> SEQ ID NO 27
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Asn Pro Thr Leu Ile Leu Ala Ala Phe Cys Leu Gly Ile Ala Ser
1               5                   10                  15

Ala Thr Leu Thr Phe Asp His Ser Leu Glu Ala Gln Trp Thr Lys Trp
            20                  25                  30

Lys Ala Met His Asn Arg Leu Tyr Gly Met Asn Glu Glu Gly Trp Arg
        35                  40                  45

Arg Ala Val Trp Glu Lys Asn Met Lys Met Ile Glu Leu His Asn Gln
    50                  55                  60

Glu Tyr Arg Glu Gly Lys His Ser Phe Thr Met Ala Met Asn Ala Phe
65                  70                  75                  80

Gly Asp Met Thr Ser Glu Glu Phe Arg Gln Val Met Asn Gly Phe Gln
            85                  90                  95

Asn Arg Lys Pro Arg Lys Gly Lys Val Phe Gln Glu Pro Leu Phe Tyr
            100                 105                 110

Glu Ala Pro Arg Ser Val Asp Trp Arg Glu Lys Gly Tyr Val Thr Pro
        115                 120                 125

Val Lys Asn Gln Gly Gln Cys Gly Ser Cys Trp Ala Phe Ser Ala Thr
    130                 135                 140

Gly Ala Leu Glu Gly Gln Met Phe Arg Lys Thr Gly Arg Leu Ile Ser
145                 150                 155                 160

Leu Ser Glu Gln Asn Leu Val Asp Cys Ser Gly Pro Gln Gly Asn Glu
            165                 170                 175

Gly Cys Asn Gly Gly Leu Met Asp Tyr Ala Phe Gln Tyr Val Gln Asp
            180                 185                 190

Asn Gly Gly Leu Asp Ser Glu Glu Ser Tyr Pro Tyr Glu Ala Thr Glu
        195                 200                 205

Glu Ser Cys Lys Tyr Asn Pro Lys Tyr Ser Val Ala Asn Asp Thr Gly
    210                 215                 220

Phe Val Asp Ile Pro Lys Gln Glu Lys Ala Leu Met Lys Ala Val Ala
225                 230                 235                 240

Thr Val Gly Pro Ile Ser Val Ala Ile Asp Ala Gly His Glu Ser Phe
            245                 250                 255

Leu Phe Tyr Lys Glu Gly Ile Tyr Phe Glu Pro Asp Cys Ser Ser Glu
            260                 265                 270

Asp Met Asp His Gly Val Leu Val Val Gly Tyr Gly Phe Glu Ser Thr
        275                 280                 285

Glu Ser Asp Asn Asn Lys Tyr Trp Leu Val Lys Asn Ser Trp Gly Glu
    290                 295                 300
```

-continued

Glu Trp Gly Met Gly Gly Tyr Val Lys Met Ala Lys Asp Arg Arg Asn
305                 310                 315                 320

His Cys Gly Ile Ala Ser Ala Ala Ser Tyr Pro Thr Val
                325                 330

<210> SEQ ID NO 28
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Glu Gly Ile Ser Ile Tyr Thr Ser Asp Asn Tyr Thr Glu Glu Met
1                   5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
        50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Val Phe Gln Phe Gln His Ile Met Val Gly Leu
            195                 200                 205

Ile Leu Pro Gly Ile Val Ile Leu Ser Cys Tyr Cys Ile Ile Ile Ser
        210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
                260                 265                 270

Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
        290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
        340                     345                 350

<210> SEQ ID NO 29
<211> LENGTH: 1308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45

Leu Arg Lys Tyr Tyr Glu Asn Cys Glu Val Val Met Gly Asn Leu Glu
    50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
            85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
            165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
            245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
    290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
            325                 330                 335

Ile Gly Thr Gly Ser Leu Met Ser Ala Gln Thr Val Asp Ser Ser Asn

-continued

```
                340                 345                 350

Ile Asp Lys Phe Ile Asn Cys Thr Lys Ile Asn Gly Asn Leu Ile Phe
        355                 360                 365

Leu Val Thr Gly Ile His Gly Asp Pro Tyr Asn Ala Ile Glu Ala Ile
        370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
                420                 425                 430

Ser Leu Leu Ile Leu Lys Gln Gln Gly Ile Thr Ser Leu Gln Phe Gln
        435                 440                 445

Ser Leu Lys Glu Ile Ser Ala Gly Asn Ile Tyr Ile Thr Asp Asn Ser
        450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
                500                 505                 510

Trp Gly Pro Gly Pro Asp Gln Cys Leu Ser Cys Arg Arg Phe Ser Arg
        515                 520                 525

Gly Arg Ile Cys Ile Glu Ser Cys Asn Leu Tyr Asp Gly Glu Phe Arg
        530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
                580                 585                 590

Cys Pro Asp Gly Leu Gln Gly Ala Asn Ser Phe Ile Phe Lys Tyr Ala
        595                 600                 605

Asp Pro Asp Arg Glu Cys His Pro Cys His Pro Asn Cys Thr Gln Gly
        610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
                645                 650                 655

Val Ile Gly Gly Leu Phe Ile Leu Val Ile Val Gly Leu Thr Phe Ala
                660                 665                 670

Val Tyr Val Arg Arg Lys Ser Ile Lys Lys Arg Ala Leu Arg Arg
        675                 680                 685

Phe Leu Glu Thr Glu Leu Val Glu Pro Leu Thr Pro Ser Gly Thr Ala
        690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
                725                 730                 735

Trp Val Pro Glu Gly Glu Thr Val Lys Ile Pro Val Ala Ile Lys Ile
                740                 745                 750

Leu Asn Glu Thr Thr Gly Pro Lys Ala Asn Val Glu Phe Met Asp Glu
        755                 760                 765
```

Ala Leu Ile Met Ala Ser Met Asp His Pro His Leu Val Arg Leu Leu
        770             775             780

Gly Val Cys Leu Ser Pro Thr Ile Gln Leu Val Thr Gln Leu Met Pro
785             790             795             800

His Gly Cys Leu Leu Glu Tyr Val His Glu His Lys Asp Asn Ile Gly
            805             810             815

Ser Gln Leu Leu Leu Asn Trp Cys Val Gln Ile Ala Lys Gly Met Met
            820             825             830

Tyr Leu Glu Glu Arg Arg Leu Val His Arg Asp Leu Ala Ala Arg Asn
        835             840             845

Val Leu Val Lys Ser Pro Asn His Val Lys Ile Thr Asp Phe Gly Leu
    850             855             860

Ala Arg Leu Leu Glu Gly Asp Glu Lys Glu Tyr Asn Ala Asp Gly Gly
865             870             875             880

Lys Met Pro Ile Lys Trp Met Ala Leu Glu Cys Ile His Tyr Arg Lys
            885             890             895

Phe Thr His Gln Ser Asp Val Trp Ser Tyr Gly Val Thr Ile Trp Glu
            900             905             910

Leu Met Thr Phe Gly Gly Lys Pro Tyr Asp Gly Ile Pro Thr Arg Glu
            915             920             925

Ile Pro Asp Leu Leu Glu Lys Gly Glu Arg Leu Pro Gln Pro Pro Ile
    930             935             940

Cys Thr Ile Asp Val Tyr Met Val Met Val Lys Cys Trp Met Ile Asp
945             950             955             960

Ala Asp Ser Arg Pro Lys Phe Lys Glu Leu Ala Ala Glu Phe Ser Arg
            965             970             975

Met Ala Arg Asp Pro Gln Arg Tyr Leu Val Ile Gln Gly Asp Asp Arg
            980             985             990

Met Lys Leu Pro Ser Pro Asn Asp  Ser Lys Phe Phe Gln  Asn Leu Leu
        995             1000            1005

Asp Glu  Glu Asp Leu Glu Asp  Met Met Asp Ala Glu  Glu Tyr Leu
    1010            1015            1020

Val Pro  Gln Ala Phe Asn Ile  Pro Pro Pro Ile Tyr  Thr Ser Arg
    1025            1030            1035

Ala Arg  Ile Asp Ser Asn Arg  Ser Glu Ile Gly His  Ser Pro Pro
    1040            1045            1050

Pro Ala  Tyr Thr Pro Met Ser  Gly Asn Gln Phe Val  Tyr Arg Asp
    1055            1060            1065

Gly Gly  Phe Ala Ala Glu Gln  Gly Val Ser Val Pro  Tyr Arg Ala
    1070            1075            1080

Pro Thr  Ser Thr Ile Pro Glu  Ala Pro Val Ala Gln  Gly Ala Thr
    1085            1090            1095

Ala Glu  Ile Phe Asp Asp Ser  Cys Cys Asn Gly Thr  Leu Arg Lys
    1100            1105            1110

Pro Val  Ala Pro His Val Gln  Glu Asp Ser Ser Thr  Gln Arg Tyr
    1115            1120            1125

Ser Ala  Asp Pro Thr Val Phe  Ala Pro Glu Arg Ser  Pro Arg Gly
    1130            1135            1140

Glu Leu  Asp Glu Glu Gly Tyr  Met Thr Pro Met Arg  Asp Lys Pro
    1145            1150            1155

Lys Gln  Glu Tyr Leu Asn Pro  Val Glu Glu Asn Pro  Phe Val Ser
    1160            1165            1170

```
Arg Arg Lys Asn Gly Asp Leu  Gln Ala Leu Asp Asn  Pro Glu Tyr
    1175             1180             1185

His Asn  Ala Ser Asn Gly Pro  Pro Lys Ala Glu Asp  Glu Tyr Val
    1190             1195             1200

Asn Glu  Pro Leu Tyr Leu Asn  Thr Phe Ala Asn Thr  Leu Gly Lys
    1205             1210             1215

Ala Glu  Tyr Leu Lys Asn Asn  Ile Leu Ser Met Pro  Glu Lys Ala
    1220             1225             1230

Lys Lys  Ala Phe Asp Asn Pro  Asp Tyr Trp Asn His  Ser Leu Pro
    1235             1240             1245

Pro Arg  Ser Thr Leu Gln His  Pro Asp Tyr Leu Gln  Glu Tyr Ser
    1250             1255             1260

Thr Lys  Tyr Phe Tyr Lys Gln  Asn Gly Arg Ile Arg  Pro Ile Val
    1265             1270             1275

Ala Glu  Asn Pro Glu Tyr Leu  Ser Glu Phe Ser Leu  Lys Pro Gly
    1280             1285             1290

Thr Val  Leu Pro Pro Pro Pro  Tyr Arg His Arg Asn  Thr Val Val
    1295             1300             1305

<210> SEQ ID NO 30
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Arg Pro Glu Asp Arg Met Phe His Ile Arg Ala Val Ile Leu Arg
1               5               10              15

Ala Leu Ser Leu Ala Phe Leu Leu Ser Leu Arg Gly Ala Gly Ala Ile
            20              25              30

Lys Ala Asp His Val Ser Thr Tyr Ala Ala Phe Val Gln Thr His Arg
        35              40              45

Pro Thr Gly Glu Phe Met Phe Glu Phe Asp Glu Asp Glu Met Phe Tyr
    50              55              60

Val Asp Leu Asp Lys Lys Glu Thr Val Trp His Leu Glu Glu Phe Gly
65              70              75              80

Gln Ala Phe Ser Phe Glu Ala Gln Gly Gly Leu Ala Asn Ile Ala Ile
            85              90              95

Leu Asn Asn Asn Leu Asn Thr Leu Ile Gln Arg Ser Asn His Thr Gln
            100             105             110

Ala Thr Asn Asp Pro Pro Glu Val Thr Val Phe Pro Lys Glu Pro Val
        115             120             125

Glu Leu Gly Gln Pro Asn Thr Leu Ile Cys His Ile Asp Lys Phe Phe
    130             135             140

Pro Pro Val Leu Asn Val Thr Trp Leu Cys Asn Gly Glu Leu Val Thr
145             150             155             160

Glu Gly Val Ala Glu Ser Leu Phe Leu Pro Arg Thr Asp Tyr Ser Phe
            165             170             175

His Lys Phe His Tyr Leu Thr Phe Val Pro Ser Ala Glu Asp Phe Tyr
            180             185             190

Asp Cys Arg Val Glu His Trp Gly Leu Asp Gln Pro Leu Leu Lys His
        195             200             205

Trp Glu Ala Gln Glu Pro Ile Gln Met Pro Glu Thr Thr Glu Thr Val
    210             215             220
```

-continued

```
Leu Cys Ala Leu Gly Leu Val Leu Gly Leu Val Gly Ile Ile Val Gly
225                 230                 235                 240

Thr Val Leu Ile Ile Lys Ser Leu Arg Ser Gly His Asp Pro Arg Ala
                245                 250                 255

Gln Gly Thr Leu
            260

<210> SEQ ID NO 31
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Ile Leu Asn Lys Ala Leu Met Leu Gly Ala Leu Ala Leu Thr Thr
1               5                   10                  15

Val Met Ser Pro Cys Gly Gly Glu Asp Ile Val Ala Asp His Val Ala
                20                  25                  30

Ser Tyr Gly Val Asn Leu Tyr Gln Ser Tyr Gly Pro Ser Gly Gln Tyr
            35                  40                  45

Thr His Glu Phe Asp Gly Asp Glu Gln Phe Tyr Val Asp Leu Gly Arg
        50                  55                  60

Lys Glu Thr Val Trp Cys Leu Pro Val Leu Arg Gln Phe Arg Phe Asp
65                  70                  75                  80

Pro Gln Phe Ala Leu Thr Asn Ile Ala Val Leu Lys His Asn Leu Asn
                85                  90                  95

Ser Leu Ile Lys Arg Ser Asn Ser Thr Ala Ala Thr Asn Glu Val Pro
                100                 105                 110

Glu Val Thr Val Phe Ser Lys Ser Pro Val Thr Leu Gly Gln Pro Asn
            115                 120                 125

Ile Leu Ile Cys Leu Val Asp Asn Ile Phe Pro Pro Val Val Asn Ile
            130                 135                 140

Thr Trp Leu Ser Asn Gly His Ser Val Thr Glu Gly Val Ser Glu Thr
145                 150                 155                 160

Ser Phe Leu Ser Lys Ser Asp His Ser Phe Phe Lys Ile Ser Tyr Leu
                165                 170                 175

Thr Leu Leu Pro Ser Ala Glu Glu Ser Tyr Asp Cys Lys Val Glu His
                180                 185                 190

Trp Gly Leu Asp Lys Pro Leu Leu Lys His Trp Glu Pro Glu Ile Pro
            195                 200                 205

Ala Pro Met Ser Glu Leu Thr Glu Thr Val Val Cys Ala Leu Gly Leu
            210                 215                 220

Ser Val Gly Leu Val Gly Ile Val Val Gly Thr Val Phe Ile Ile Arg
225                 230                 235                 240

Gly Leu Arg Ser Val Gly Ala Ser Arg His Gln Gly Pro Leu
                245                 250

<210> SEQ ID NO 32
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32
```

-continued

```
Met Ile Leu Asn Lys Ala Leu Leu Leu Gly Ala Leu Ala Leu Thr Ala
1               5                   10                  15

Val Met Ser Pro Cys Gly Gly Glu Asp Ile Val Ala Asp His Val Ala
            20                  25                  30

Ser Tyr Gly Val Asn Phe Tyr Gln Ser His Gly Pro Ser Gly Gln Tyr
        35                  40                  45

Thr His Glu Phe Asp Gly Asp Glu Glu Phe Tyr Val Asp Leu Glu Thr
    50                  55                  60

Lys Glu Thr Val Trp Gln Leu Pro Met Phe Ser Lys Phe Ile Ser Phe
65                  70                  75                  80

Asp Pro Gln Ser Ala Leu Arg Asn Met Ala Val Gly Lys His Thr Leu
                85                  90                  95

Glu Phe Met Met Arg Gln Ser Asn Ser Thr Ala Ala Thr Asn Glu Val
            100                 105                 110

Pro Glu Val Thr Val Phe Ser Lys Phe Pro Val Thr Leu Gly Gln Pro
            115                 120                 125

Asn Thr Leu Ile Cys Leu Val Asp Asn Ile Phe Pro Pro Val Val Asn
    130                 135                 140

Ile Thr Trp Leu Ser Asn Gly His Ser Val Thr Glu Gly Val Ser Glu
145                 150                 155                 160

Thr Ser Phe Leu Ser Lys Ser Asp His Ser Phe Phe Lys Ile Ser Tyr
                165                 170                 175

Leu Thr Phe Leu Pro Ser Ala Asp Glu Ile Tyr Asp Cys Lys Val Glu
            180                 185                 190

His Trp Gly Leu Asp Glu Pro Leu Leu Lys His Trp Glu Pro Glu Ile
            195                 200                 205

Pro Ala Pro Met Ser Glu Leu Thr Glu Thr Leu Val Cys Ala Leu Gly
    210                 215                 220

Leu Ser Val Gly Leu Met Gly Ile Val Val Gly Thr Val Phe Ile Ile
225                 230                 235                 240

Gln Gly Leu Arg Ser Val Gly Ala Ser Arg His Gln Gly Leu Leu
                245                 250                 255

<210> SEQ ID NO 33
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ser Trp Lys Lys Ala Leu Arg Ile Pro Gly Gly Leu Arg Ala Ala
1               5                   10                  15

Thr Val Thr Leu Met Leu Ala Met Leu Ser Thr Pro Val Ala Glu Gly
            20                  25                  30

Arg Asp Ser Pro Glu Asp Phe Val Tyr Gln Phe Lys Ala Met Cys Tyr
        35                  40                  45

Phe Thr Asn Gly Thr Glu Arg Val Arg Tyr Val Thr Arg Tyr Ile Tyr
    50                  55                  60

Asn Arg Glu Glu Tyr Ala Arg Phe Asp Ser Asp Val Glu Val Tyr Arg
65                  70                  75                  80

Ala Val Thr Pro Leu Gly Pro Pro Asp Ala Glu Tyr Trp Asn Ser Gln
                85                  90                  95

Lys Glu Val Leu Glu Arg Thr Arg Ala Glu Leu Asp Thr Val Cys Arg
```

-continued

```
            100             105             110

His Asn Tyr Gln Leu Glu Leu Arg Thr Thr Leu Gln Arg Arg Val Glu
            115             120             125

Pro Thr Val Thr Ile Ser Pro Ser Arg Thr Glu Ala Leu Asn His His
    130             135             140

Asn Leu Leu Val Cys Ser Val Thr Asp Phe Tyr Pro Ala Gln Ile Lys
145             150             155             160

Val Arg Trp Phe Arg Asn Asp Gln Glu Glu Thr Thr Gly Val Val Ser
            165             170             175

Thr Pro Leu Ile Arg Asn Gly Asp Trp Thr Phe Gln Ile Leu Val Met
            180             185             190

Leu Glu Met Thr Pro Gln His Gly Asp Val Tyr Thr Cys His Val Glu
            195             200             205

His Pro Ser Leu Gln Asn Pro Ile Thr Val Glu Trp Arg Ala Gln Ser
            210             215             220

Glu Ser Ala Gln Ser Lys Met Leu Ser Gly Ile Gly Gly Phe Val Leu
225             230             235             240

Gly Leu Ile Phe Leu Gly Leu Gly Leu Ile Ile His His Arg Ser Gln
            245             250             255

Lys Gly Leu Leu His
            260

<210> SEQ ID NO 34
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ser Trp Lys Met Ala Leu Gln Ile Pro Gly Gly Phe Trp Ala Ala
1               5               10              15

Ala Val Thr Val Met Leu Val Met Leu Ser Thr Pro Val Ala Glu Ala
            20              25              30

Arg Asp Phe Pro Lys Asp Phe Leu Val Gln Phe Lys Gly Met Cys Tyr
            35              40              45

Phe Thr Asn Gly Thr Glu Arg Val Arg Gly Val Ala Arg Tyr Ile Tyr
    50              55              60

Asn Arg Glu Glu Tyr Gly Arg Phe Asp Ser Asp Val Gly Glu Phe Gln
65              70              75              80

Ala Val Thr Glu Leu Gly Arg Ser Ile Glu Asp Trp Asn Asn Tyr Lys
            85              90              95

Asp Phe Leu Glu Gln Glu Arg Ala Ala Val Asp Lys Val Cys Arg His
            100             105             110

Asn Tyr Glu Ala Glu Leu Arg Thr Thr Leu Gln Arg Gln Val Glu Pro
            115             120             125

Thr Val Thr Ile Ser Pro Ser Arg Thr Glu Ala Leu Asn His His Asn
    130             135             140

Leu Leu Val Cys Ser Val Thr Asp Phe Tyr Pro Ala Gln Ile Lys Val
145             150             155             160

Arg Trp Phe Arg Asn Asp Gln Glu Glu Thr Ala Gly Val Val Ser Thr
            165             170             175

Ser Leu Ile Arg Asn Gly Asp Trp Thr Phe Gln Ile Leu Val Met Leu
            180             185             190
```

```
Glu Ile Thr Pro Gln Arg Gly Asp Ile Tyr Thr Cys Gln Val Glu His
        195                 200                 205

Pro Ser Leu Gln Ser Pro Ile Thr Val Glu Trp Arg Ala Gln Ser Glu
    210                 215                 220

Ser Ala Gln Ser Lys Met Leu Ser Gly Ile Gly Gly Phe Val Leu Gly
225                 230                 235                 240

Leu Ile Phe Leu Gly Leu Gly Leu Ile Ile Arg His Arg Gly Gln Lys
            245                 250                 255

Gly Pro Arg Gly Pro Pro Ala Gly Leu Leu His
        260                 265
```

<210> SEQ ID NO 35
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
            85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
            165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
            195                 200                 205

Ser Pro Leu Pro Glu Thr Thr Glu Asn Val Val Cys Ala Leu Gly Leu
    210                 215                 220

Thr Val Gly Leu Val Gly Ile Ile Ile Gly Thr Ile Phe Ile Ile Lys
225                 230                 235                 240

Gly Val Arg Lys Ser Asn Ala Ala Glu Arg Arg Gly Pro Leu
            245                 250
```

<210> SEQ ID NO 36
<211> LENGTH: 266
<212> TYPE: PRT
<213> ORGANISM: Artificial Sequence -continued
<220> FEATURE:
<223> OTHER INFORMATION: Description of Artificial Sequence: Synthetic
     polypeptide

<400> SEQUENCE: 36

Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ser Gly Asp Thr
                20                  25                  30

Arg Pro Arg Phe Leu Trp Gln Pro Lys Arg Glu Cys His Phe Phe Asn
            35                  40                  45

Gly Thr Glu Arg Val Arg Phe Leu Asp Arg Tyr Phe Tyr Asn Gln Glu
        50                  55                  60

Glu Ser Val Arg Phe Asp Ser Asp Val Gly Glu Phe Arg Ala Val Thr
65                  70                  75                  80

Glu Leu Gly Arg Pro Asp Ala Glu Tyr Trp Asn Ser Gln Lys Asp Ile
                85                  90                  95

Leu Glu Gln Ala Arg Ala Ala Val Asp Thr Tyr Cys Arg His Asn Tyr
            100                 105                 110

Gly Val Val Glu Ser Phe Thr Val Gln Arg Arg Val Gln Pro Lys Val
            115                 120                 125

Thr Val Tyr Pro Ser Lys Thr Gln Pro Leu Gln His His Asn Leu Leu
        130                 135                 140

Val Cys Ser Val Ser Gly Phe Tyr Pro Gly Ser Ile Glu Val Arg Trp
145                 150                 155                 160

Phe Leu Asn Gly Gln Glu Glu Lys Ala Gly Met Val Ser Thr Gly Leu
                165                 170                 175

Ile Gln Asn Gly Asp Trp Thr Phe Gln Thr Leu Val Met Leu Glu Thr
                180                 185                 190

Val Pro Arg Ser Gly Glu Val Tyr Thr Cys Gln Val Glu His Pro Ser
            195                 200                 205

Val Thr Ser Pro Leu Thr Val Glu Trp Arg Ala Arg Ser Glu Ser Ala
        210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
            260                 265

<210> SEQ ID NO 37
<211> LENGTH: 266
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 37

Met Val Cys Leu Lys Leu Pro Gly Gly Ser Ser Leu Ala Ala Leu Thr
1               5                   10                  15

Val Thr Leu Met Val Leu Ser Ser Arg Leu Ala Phe Ala Gly Asp Thr
                20                  25                  30

Arg Pro Arg Phe Leu Glu Leu Arg Lys Ser Glu Cys His Phe Phe Asn
            35                  40                  45

Gly Thr Glu Arg Val Arg Tyr Leu Asp Arg Tyr Phe His Asn Gln Glu
        50                  55                  60

Glu Phe Leu Arg Phe Asp Ser Asp Val Gly Glu Tyr Arg Ala Val Thr
65                  70                  75                  80

Glu Leu Gly Arg Pro Val Ala Glu Ser Trp Asn Ser Gln Lys Asp Leu
                85                  90                  95

Leu Glu Gln Lys Arg Gly Arg Val Asp Asn Tyr Cys Arg His Asn Tyr
                100                 105                 110

Gly Val Gly Glu Ser Phe Thr Val Gln Arg Arg Val His Pro Gln Val
        115                 120                 125

Thr Val Tyr Pro Ala Lys Thr Gln Pro Leu Gln His His Asn Leu Leu
    130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
                180                 185                 190

Val Pro Arg Ser Gly Glu Val Tyr Thr Cys Gln Val Glu His Pro Ser
        195                 200                 205

Val Thr Ser Ala Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
        260                 265

<210> SEQ ID NO 38
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
                20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
                100                 105                 110

Thr Phe Ala
        115

<210> SEQ ID NO 39
<211> LENGTH: 435
<212> TYPE: PRT

-continued

<213> ORGANISM: Artificial Sequence
<220> FEATURE:
<223> OTHER INFORMATION: Description of Artificial Sequence: Synthetic
      polypeptide

<400> SEQUENCE: 39

Met Ile Gly Gly Leu Phe Ile Tyr Asn His Lys Gly Glu Val Leu Ile
1               5                   10                  15

Ser Arg Val Tyr Arg Asp Asp Ile Gly Arg Asn Ala Val Asp Ala Phe
                20                  25                  30

Arg Val Asn Val Ile His Ala Arg Gln Gln Val Arg Ser Pro Val Thr
            35                  40                  45

Asn Ile Ala Arg Thr Ser Phe Phe His Val Lys Arg Ser Asn Ile Trp
        50                  55                  60

Leu Ala Ala Val Thr Lys Gln Asn Val Asn Ala Ala Met Val Phe Glu
65                  70                  75                  80

Phe Leu Tyr Lys Met Cys Asp Val Met Ala Ala Tyr Phe Gly Lys Ile
                85                  90                  95

Ser Glu Glu Asn Ile Lys Asn Asn Phe Val Leu Ile Tyr Glu Leu Leu
                100                 105                 110

Asp Glu Ile Leu Asp Phe Gly Tyr Pro Gln Asn Ser Glu Thr Gly Ala
            115                 120                 125

Leu Lys Thr Phe Ile Thr Gln Gln Gly Ile Lys Ser Gln His Gln Thr
        130                 135                 140

Lys Glu Glu Gln Ser Gln Ile Thr Ser Gln Val Thr Gly Gln Ile Gly
145                 150                 155                 160

Trp Arg Arg Glu Gly Ile Lys Tyr Arg Arg Asn Glu Leu Phe Leu Asp
                165                 170                 175

Val Leu Glu Ser Val Asn Leu Leu Met Ser Pro Gln Gly Gln Val Leu
                180                 185                 190

Ser Ala His Val Ser Gly Arg Val Val Met Lys Ser Tyr Leu Ser Gly
            195                 200                 205

Met Pro Glu Cys Lys Phe Gly Met Asn Asp Lys Ile Val Ile Glu Lys
        210                 215                 220

Gln Gly Lys Gly Thr Ala Asp Glu Thr Ser Lys Ser Gly Lys Gln Ser
225                 230                 235                 240

Ile Ala Ile Asp Asp Cys Thr Phe His Gln Cys Val Arg Leu Ser Lys
                245                 250                 255

Phe Asp Ser Glu Arg Ser Ile Ser Phe Ile Pro Pro Asp Gly Glu Phe
                260                 265                 270

Glu Leu Met Arg Tyr Arg Thr Thr Lys Asp Ile Ile Leu Pro Phe Arg
                275                 280                 285

Val Ile Pro Leu Val Arg Glu Val Gly Arg Thr Lys Leu Glu Val Lys
        290                 295                 300

Val Val Ile Lys Ser Asn Phe Lys Pro Ser Leu Leu Ala Gln Lys Ile
305                 310                 315                 320

Glu Val Arg Ile Pro Thr Pro Leu Asn Thr Ser Gly Val Gln Val Ile
            325                 330                 335

Cys Met Lys Gly Lys Ala Lys Tyr Lys Ala Ser Glu Asn Ala Ile Val
            340                 345                 350

Trp Lys Ile Lys Arg Met Ala Gly Met Lys Glu Ser Gln Ile Ser Ala
        355                 360                 365

Glu Ile Glu Leu Leu Pro Thr Asn Asp Lys Lys Lys Trp Ala Arg Pro
        370                 375                 380

```
Pro Ile Ser Met Asn Phe Glu Val Pro Phe Ala Pro Ser Gly Leu Lys
385                 390             395             400

Val Arg Tyr Leu Lys Val Phe Glu Pro Lys Leu Asn Tyr Ser Asp His
            405             410             415

Asp Val Ile Lys Trp Val Arg Tyr Ile Gly Arg Ser Gly Ile Tyr Glu
            420             425             430

Thr Arg Cys
        435

<210> SEQ ID NO 40
<211> LENGTH: 920
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Glu Val Gln Leu Gly Leu Gly Arg Val Tyr Pro Arg Pro Pro Ser
1               5               10              15

Lys Thr Tyr Arg Gly Ala Phe Gln Asn Leu Phe Gln Ser Val Arg Glu
            20              25              30

Val Ile Gln Asn Pro Gly Pro Arg His Pro Glu Ala Ala Ser Ala Ala
        35              40              45

Pro Pro Gly Ala Ser Leu Leu Leu Leu Gln Gln Gln Gln Gln Gln Gln
    50              55              60

Gln Gln Gln Gln Gln Gln Gln Gln Gln Gln Gln Gln Gln Gln Gln Gln
65              70              75              80

Glu Thr Ser Pro Arg Gln Gln Gln Gln Gln Gly Glu Asp Gly Ser
            85              90              95

Pro Gln Ala His Arg Arg Gly Pro Thr Gly Tyr Leu Val Leu Asp Glu
            100             105             110

Glu Gln Gln Pro Ser Gln Pro Gln Ser Ala Leu Glu Cys His Pro Glu
            115             120             125

Arg Gly Cys Val Pro Glu Pro Gly Ala Ala Val Ala Ala Ser Lys Gly
        130             135             140

Leu Pro Gln Gln Leu Pro Ala Pro Pro Asp Glu Asp Asp Ser Ala Ala
145             150             155             160

Pro Ser Thr Leu Ser Leu Leu Gly Pro Thr Phe Pro Gly Leu Ser Ser
            165             170             175

Cys Ser Ala Asp Leu Lys Asp Ile Leu Ser Glu Ala Ser Thr Met Gln
            180             185             190

Leu Leu Gln Gln Gln Gln Glu Ala Val Ser Glu Gly Ser Ser Ser
            195             200             205

Gly Arg Ala Arg Glu Ala Ser Gly Ala Pro Thr Ser Ser Lys Asp Asn
    210             215             220

Tyr Leu Gly Gly Thr Ser Thr Ile Ser Asp Asn Ala Lys Glu Leu Cys
225             230             235             240

Lys Ala Val Ser Val Ser Met Gly Leu Gly Val Glu Ala Leu Glu His
            245             250             255

Leu Ser Pro Gly Glu Gln Leu Arg Gly Asp Cys Met Tyr Ala Pro Leu
            260             265             270

Leu Gly Val Pro Pro Ala Val Arg Pro Thr Pro Cys Ala Pro Leu Ala
            275             280             285

Glu Cys Lys Gly Ser Leu Leu Asp Asp Ser Ala Gly Lys Ser Thr Glu
    290             295             300
```

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
                340                 345                 350

Leu Asp Glu Ala Ala Ala Tyr Gln Ser Arg Asp Tyr Tyr Asn Phe Pro
                355                 360                 365

Leu Ala Leu Ala Gly Pro Pro Pro Pro Pro Pro Pro His Pro His
        370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
                420                 425                 430

Ser Ser Trp His Thr Leu Phe Thr Ala Glu Glu Gly Gln Leu Tyr Gly
                435                 440                 445

Pro Cys Gly Gly Gly Gly Gly Gly Gly Gly Gly Gly Gly Gly Gly Gly
        450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
                500                 505                 510

Pro Tyr Pro Ser Pro Thr Cys Val Lys Ser Glu Met Gly Pro Trp Met
                515                 520                 525

Asp Ser Tyr Ser Gly Pro Tyr Gly Asp Met Arg Leu Glu Thr Ala Arg
                530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
                580                 585                 590

Lys Tyr Leu Cys Ala Ser Arg Asn Asp Cys Thr Ile Asp Lys Phe Arg
                595                 600                 605

Arg Lys Asn Cys Pro Ser Cys Arg Leu Arg Lys Cys Tyr Glu Ala Gly
                610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
                660                 665                 670

Ile Phe Leu Asn Val Leu Glu Ala Ile Glu Pro Gly Val Val Cys Ala
                675                 680                 685

Gly His Asp Asn Asn Gln Pro Asp Ser Phe Ala Ala Leu Leu Ser Ser
        690                 695                 700

Leu Asn Glu Leu Gly Glu Arg Gln Leu Val His Val Val Lys Trp Ala
705                 710                 715                 720

-continued

```
Lys Ala Leu Pro Gly Phe Arg Asn Leu His Val Asp Asp Gln Met Ala
            725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
            755                 760                 765

Leu Val Phe Asn Glu Tyr Arg Met His Lys Ser Arg Met Tyr Ser Gln
        770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
                820                 825                 830

Met Asn Tyr Ile Lys Glu Leu Asp Arg Ile Ile Ala Cys Lys Arg Lys
            835                 840                 845

Asn Pro Thr Ser Cys Ser Arg Arg Phe Tyr Gln Leu Thr Lys Leu Leu
        850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920

<210> SEQ ID NO 41
<211> LENGTH: 742
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160
```

-continued

```
Tyr Arg Thr Asn Pro Glu Asp Ile Tyr Pro Ser Asn Pro Thr Asp Asp
            165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
            195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
                260                 265                 270

Ser Ala Gly Trp Glu Pro Asn Glu Glu Asn Glu Asp Glu Arg Asp Arg
                275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
                340                 345                 350

Thr Ala Tyr Glu Gly Asn Trp Asn Pro Glu Ala His Pro Pro Leu Ile
                355                 360                 365

His His Glu His His Glu Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
                420                 425                 430

Thr Ser His Pro Met Gln Gly Arg Thr Thr Pro Ser Pro Glu Asp Ser
                435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
                500                 505                 510

Phe Ser Thr Ser His Glu Gly Leu Glu Glu Asp Lys Asp His Pro Thr
                515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575
```

-continued

```
Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
            595                 600                 605

Phe His Pro Ser Gly Gly Ser His Thr Thr His Gly Ser Glu Ser Asp
            610                 615                 620

Gly His Ser His Gly Ser Gln Glu Gly Gly Ala Asn Thr Thr Ser Gly
        625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
            675                 680                 685

Gly Ala Val Glu Asp Arg Lys Pro Ser Gly Leu Asn Gly Glu Ala Ser
        690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 42
<211> LENGTH: 339
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Trp Gln Leu Trp Ala Ser Leu Cys Cys Leu Leu Val Leu Ala Asn
1                 5                 10                 15

Ala Arg Ser Arg Pro Ser Phe His Pro Leu Ser Asp Glu Leu Val Asn
            20                 25                 30

Tyr Val Asn Lys Arg Asn Thr Thr Trp Gln Ala Gly His Asn Phe Tyr
            35                 40                 45

Asn Val Asp Met Ser Tyr Leu Lys Arg Leu Cys Gly Thr Phe Leu Gly
        50                 55                 60

Gly Pro Lys Pro Pro Gln Arg Val Met Phe Thr Glu Asp Leu Lys Leu
65                 70                 75                 80

Pro Ala Ser Phe Asp Ala Arg Glu Gln Trp Pro Gln Cys Pro Thr Ile
                85                 90                 95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
            115                 120                 125

Val Ser Val Glu Val Ser Ala Glu Asp Leu Leu Thr Cys Cys Gly Ser
        130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190
```

Gly Ser Arg Pro Pro Cys Thr Gly Glu Gly Asp Thr Pro Lys Cys Ser
        195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
            275                 280                 285

Asn Gly Thr Pro Tyr Trp Leu Val Ala Asn Ser Trp Asn Thr Asp Trp
        290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 43
<211> LENGTH: 412
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gln Pro Ser Ser Leu Leu Pro Leu Ala Leu Cys Leu Leu Ala Ala
1                   5                   10                  15

Pro Ala Ser Ala Leu Val Arg Ile Pro Leu His Lys Phe Thr Ser Ile
            20                  25                  30

Arg Arg Thr Met Ser Glu Val Gly Gly Ser Val Glu Asp Leu Ile Ala
        35                  40                  45

Lys Gly Pro Val Ser Lys Tyr Ser Gln Ala Val Pro Ala Val Thr Glu
    50                  55                  60

Gly Pro Ile Pro Glu Val Leu Lys Asn Tyr Met Asp Ala Gln Tyr Tyr
65                  70                  75                  80

Gly Glu Ile Gly Ile Gly Thr Pro Pro Gln Cys Phe Thr Val Val Phe
                85                  90                  95

Asp Thr Gly Ser Ser Asn Leu Trp Val Pro Ser Ile His Cys Lys Leu
            100                 105                 110

Leu Asp Ile Ala Cys Trp Ile His His Lys Tyr Asn Ser Asp Lys Ser
            115                 120                 125

Ser Thr Tyr Val Lys Asn Gly Thr Ser Phe Asp Ile His Tyr Gly Ser
        130                 135                 140

Gly Ser Leu Ser Gly Tyr Leu Ser Gln Asp Thr Val Ser Val Pro Cys
145                 150                 155                 160

Gln Ser Ala Ser Ser Ala Ser Ala Leu Gly Gly Val Lys Val Glu Arg
                165                 170                 175

Gln Val Phe Gly Glu Ala Thr Lys Gln Pro Gly Ile Thr Phe Ile Ala
            180                 185                 190

Ala Lys Phe Asp Gly Ile Leu Gly Met Ala Tyr Pro Arg Ile Ser Val
        195                 200                 205

-continued

```
Asn Asn Val Leu Pro Val Phe Asp Asn Leu Met Gln Gln Lys Leu Val
    210             215             220

Asp Gln Asn Ile Phe Ser Phe Tyr Leu Ser Arg Asp Pro Asp Ala Gln
225             230             235             240

Pro Gly Gly Glu Leu Met Leu Gly Gly Thr Asp Ser Lys Tyr Tyr Lys
            245             250             255

Gly Ser Leu Ser Tyr Leu Asn Val Thr Arg Lys Ala Tyr Trp Gln Val
            260             265             270

His Leu Asp Gln Val Glu Val Ala Ser Gly Leu Thr Leu Cys Lys Glu
            275             280             285

Gly Cys Glu Ala Ile Val Asp Thr Gly Thr Ser Leu Met Val Gly Pro
    290             295             300

Val Asp Glu Val Arg Glu Leu Gln Lys Ala Ile Gly Ala Val Pro Leu
305             310             315             320

Ile Gln Gly Glu Tyr Met Ile Pro Cys Glu Lys Val Ser Thr Leu Pro
            325             330             335

Ala Ile Thr Leu Lys Leu Gly Gly Lys Gly Tyr Lys Leu Ser Pro Glu
            340             345             350

Asp Tyr Thr Leu Lys Val Ser Gln Ala Gly Lys Thr Leu Cys Leu Ser
            355             360             365

Gly Phe Met Gly Met Asp Ile Pro Pro Pro Ser Gly Pro Leu Trp Ile
    370             375             380

Leu Gly Asp Val Phe Ile Gly Arg Tyr Tyr Thr Val Phe Asp Arg Asp
385             390             395             400

Asn Asn Arg Val Gly Phe Ala Glu Ala Ala Arg Leu
            405             410
```

<210> SEQ ID NO 44
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Trp Ala Thr Leu Pro Leu Leu Cys Ala Gly Ala Trp Leu Leu Gly
1               5               10              15

Val Pro Val Cys Gly Ala Ala Glu Leu Cys Val Asn Ser Leu Glu Lys
                20              25              30

Phe His Phe Lys Ser Trp Met Ser Lys His Arg Lys Thr Tyr Ser Thr
            35              40              45

Glu Glu Tyr His His Arg Leu Gln Thr Phe Ala Ser Asn Trp Arg Lys
    50              55              60

Ile Asn Ala His Asn Asn Gly Asn His Thr Phe Lys Met Ala Leu Asn
65              70              75              80

Gln Phe Ser Asp Met Ser Phe Ala Glu Ile Lys His Lys Tyr Leu Trp
            85              90              95

Ser Glu Pro Gln Asn Cys Ser Ala Thr Lys Ser Asn Tyr Leu Arg Gly
            100             105             110

Thr Gly Pro Tyr Pro Pro Ser Val Asp Trp Arg Lys Lys Gly Asn Phe
            115             120             125

Val Ser Pro Val Lys Asn Gln Gly Ala Cys Gly Ser Cys Trp Thr Phe
    130             135             140

Ser Thr Thr Gly Ala Leu Glu Ser Ala Ile Ala Ile Ala Thr Gly Lys
```

-continued

```
145              150              155              160

Met Leu Ser Leu Ala Glu Gln Gln Leu Val Asp Cys Ala Gln Asp Phe
                165              170              175

Asn Asn His Gly Cys Gln Gly Gly Leu Pro Ser Gln Ala Phe Glu Tyr
            180              185              190

Ile Leu Tyr Asn Lys Gly Ile Met Gly Glu Asp Thr Tyr Pro Tyr Gln
            195              200              205

Gly Lys Asp Gly Tyr Cys Lys Phe Gln Pro Gly Lys Ala Ile Gly Phe
            210              215              220

Val Lys Asp Val Ala Asn Ile Thr Ile Tyr Asp Glu Glu Ala Met Val
225              230              235              240

Glu Ala Val Ala Leu Tyr Asn Pro Val Ser Phe Ala Phe Glu Val Thr
                245              250              255

Gln Asp Phe Met Met Tyr Arg Thr Gly Ile Tyr Ser Ser Thr Ser Cys
                260              265              270

His Lys Thr Pro Asp Lys Val Asn His Ala Val Leu Ala Val Gly Tyr
                275              280              285

Gly Glu Lys Asn Gly Ile Pro Tyr Trp Ile Val Lys Asn Ser Trp Gly
            290              295              300

Pro Gln Trp Gly Met Asn Gly Tyr Phe Leu Ile Glu Arg Gly Lys Asn
305              310              315              320

Met Cys Gly Leu Ala Ala Cys Ala Ser Tyr Pro Ile Pro Leu Val
                325              330              335
```

```
<210> SEQ ID NO 45
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Lys Arg Leu Val Cys Val Leu Leu Val Cys Ser Ser Ala Val Ala
1               5               10              15

Gln Leu His Lys Asp Pro Thr Leu Asp His His Trp His Leu Trp Lys
            20              25              30

Lys Thr Tyr Gly Lys Gln Tyr Lys Glu Lys Asn Glu Glu Ala Val Arg
        35              40              45

Arg Leu Ile Trp Glu Lys Asn Leu Lys Phe Val Met Leu His Asn Leu
    50              55              60

Glu His Ser Met Gly Met His Ser Tyr Asp Leu Gly Met Asn His Leu
65              70              75              80

Gly Asp Met Thr Ser Glu Glu Val Met Ser Leu Met Ser Ser Leu Arg
                85              90              95

Val Pro Ser Gln Trp Gln Arg Asn Ile Thr Tyr Lys Ser Asn Pro Asn
            100             105             110

Arg Ile Leu Pro Asp Ser Val Asp Trp Arg Glu Lys Gly Cys Val Thr
        115             120             125

Glu Val Lys Tyr Gln Gly Ser Cys Gly Ala Cys Trp Ala Phe Ser Ala
    130             135             140

Val Gly Ala Leu Glu Ala Gln Leu Lys Leu Lys Thr Gly Lys Leu Val
145             150             155             160

Ser Leu Ser Ala Gln Asn Leu Val Asp Cys Ser Thr Glu Lys Tyr Gly
            165             170             175
```

```
Asn Lys Gly Cys Asn Gly Gly Phe Met Thr Thr Ala Phe Gln Tyr Ile
            180                 185                 190

Ile Asp Asn Lys Gly Ile Asp Ser Asp Ala Ser Tyr Pro Tyr Lys Ala
            195                 200                 205

Met Asp Gln Lys Cys Gln Tyr Asp Ser Lys Tyr Arg Ala Ala Thr Cys
    210                 215                 220

Ser Lys Tyr Thr Glu Leu Pro Tyr Gly Arg Glu Asp Val Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
            260                 265                 270

Thr Gln Asn Val Asn His Gly Val Leu Val Val Gly Tyr Gly Asp Leu
            275                 280                 285

Asn Gly Lys Glu Tyr Trp Leu Val Lys Asn Ser Trp Gly His Asn Phe
    290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
            325                 330
```

```
<210> SEQ ID NO 46
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asn Leu Ser Leu Val Leu Ala Ala Phe Cys Leu Gly Ile Ala Ser
1                   5                   10                  15

Ala Val Pro Lys Phe Asp Gln Asn Leu Asp Thr Lys Trp Tyr Gln Trp
                20                  25                  30

Lys Ala Thr His Arg Arg Leu Tyr Gly Ala Asn Glu Glu Gly Trp Arg
            35                  40                  45

Arg Ala Val Trp Glu Lys Asn Met Lys Met Ile Glu Leu His Asn Gly
    50                  55                  60

Glu Tyr Ser Gln Gly Lys His Gly Phe Thr Met Ala Met Asn Ala Phe
65                  70                  75                  80

Gly Asp Met Thr Asn Glu Glu Phe Arg Gln Met Met Gly Cys Phe Arg
                85                  90                  95

Asn Gln Lys Phe Arg Lys Gly Lys Val Phe Arg Glu Pro Leu Phe Leu
            100                 105                 110

Asp Leu Pro Lys Ser Val Asp Trp Arg Lys Lys Gly Tyr Val Thr Pro
            115                 120                 125

Val Lys Asn Gln Lys Gln Cys Gly Ser Cys Trp Ala Phe Ser Ala Thr
    130                 135                 140

Gly Ala Leu Glu Gly Gln Met Phe Arg Lys Thr Gly Lys Leu Val Ser
145                 150                 155                 160

Leu Ser Glu Gln Asn Leu Val Asp Cys Ser Arg Pro Gln Gly Asn Gln
                165                 170                 175

Gly Cys Asn Gly Gly Phe Met Ala Arg Ala Phe Gln Tyr Val Lys Glu
            180                 185                 190

Asn Gly Gly Leu Asp Ser Glu Glu Ser Tyr Pro Tyr Val Ala Val Asp
            195                 200                 205
```

```
Glu Ile Cys Lys Tyr Arg Pro Glu Asn Ser Val Ala Asn Asp Thr Gly
    210                 215                 220

Phe Thr Val Val Ala Pro Gly Lys Glu Lys Ala Leu Met Lys Ala Val
225                 230                 235                 240

Ala Thr Val Gly Pro Ile Ser Val Ala Met Asp Ala Gly His Ser Ser
                245                 250                 255

Phe Gln Phe Tyr Lys Ser Gly Ile Tyr Phe Glu Pro Asp Cys Ser Ser
                260                 265                 270

Lys Asn Leu Asp His Gly Val Leu Val Val Gly Tyr Gly Phe Glu Gly
            275                 280                 285

Ala Asn Ser Asn Asn Ser Lys Tyr Trp Leu Val Lys Asn Ser Trp Gly
    290                 295                 300

Pro Glu Trp Gly Ser Asn Gly Tyr Val Lys Ile Ala Lys Asp Lys Asn
305                 310                 315                 320

Asn His Cys Gly Ile Ala Thr Ala Ala Ser Tyr Pro Asn Val
                325                 330

<210> SEQ ID NO 47
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Val Trp Lys Val Ala Val Phe Leu Ser Val Ala Leu Gly Ile Gly
1               5                   10                  15

Ala Val Pro Ile Asp Asp Pro Glu Asp Gly Gly Lys His Trp Val Val
                20                  25                  30

Ile Val Ala Gly Ser Asn Gly Trp Tyr Asn Tyr Arg His Gln Ala Asp
            35                  40                  45

Ala Cys His Ala Tyr Gln Ile Ile His Arg Asn Gly Ile Pro Asp Glu
    50                  55                  60

Gln Ile Val Val Met Met Tyr Asp Asp Ile Ala Tyr Ser Glu Asp Asn
65                  70                  75                  80

Pro Thr Pro Gly Ile Val Ile Asn Arg Pro Asn Gly Thr Asp Val Tyr
                85                  90                  95

Gln Gly Val Pro Lys Asp Tyr Thr Gly Glu Asp Val Thr Pro Gln Asn
                100                 105                 110

Phe Leu Ala Val Leu Arg Gly Asp Ala Glu Ala Val Lys Gly Ile Gly
            115                 120                 125

Ser Gly Lys Val Leu Lys Ser Gly Pro Gln Asp His Val Phe Ile Tyr
    130                 135                 140

Phe Thr Asp His Gly Ser Thr Gly Ile Leu Val Phe Pro Asn Glu Asp
145                 150                 155                 160

Leu His Val Lys Asp Leu Asn Glu Thr Ile His Tyr Met Tyr Lys His
                165                 170                 175

Lys Met Tyr Arg Lys Met Val Phe Tyr Ile Glu Ala Cys Glu Ser Gly
                180                 185                 190

Ser Met Met Asn His Leu Pro Asp Asn Ile Asn Val Tyr Ala Thr Thr
                195                 200                 205

Ala Ala Asn Pro Arg Glu Ser Ser Tyr Ala Cys Tyr Tyr Asp Glu Lys
    210                 215                 220

Arg Ser Thr Tyr Leu Gly Asp Trp Tyr Ser Val Asn Trp Met Glu Asp
```

```
225             230             235             240

Ser Asp Val Glu Asp Leu Thr Lys Glu Thr Leu His Lys Gln Tyr His
            245             250             255

Leu Val Lys Ser His Thr Asn Thr Ser His Val Met Gln Tyr Gly Asn
            260             265             270

Lys Thr Ile Ser Thr Met Lys Val Met Gln Phe Gln Gly Met Lys Arg
            275             280             285

Lys Ala Ser Ser Pro Val Pro Leu Pro Pro Val Thr His Leu Asp Leu
            290             295             300

Thr Pro Ser Pro Asp Val Pro Leu Thr Ile Met Lys Arg Lys Leu Met
305             310             315             320

Asn Thr Asn Asp Leu Glu Glu Ser Arg Gln Leu Thr Glu Glu Ile Gln
            325             330             335

Arg His Leu Asp Ala Arg His Leu Ile Glu Lys Ser Val Arg Lys Ile
            340             345             350

Val Ser Leu Leu Ala Ala Ser Glu Ala Glu Val Glu Gln Leu Leu Ser
            355             360             365

Glu Arg Ala Pro Leu Thr Gly His Ser Cys Tyr Pro Glu Ala Leu Leu
            370             375             380

His Phe Arg Thr His Cys Phe Asn Trp His Ser Pro Thr Tyr Glu Tyr
385             390             395             400

Ala Leu Arg His Leu Tyr Val Leu Val Asn Leu Cys Glu Lys Pro Tyr
            405             410             415

Pro Leu His Arg Ile Lys Leu Ser Met Asp His Val Cys Leu Gly His
            420             425             430

Tyr
```

<210> SEQ ID NO 48
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Glu Asn Gly Tyr Thr Tyr Glu Asp Tyr Lys Asn Thr Ala Glu Trp
1               5               10              15

Leu Leu Ser His Thr Lys His Arg Pro Gln Val Ala Ile Ile Cys Gly
            20              25              30

Ser Gly Leu Gly Gly Leu Thr Asp Lys Leu Thr Gln Ala Gln Ile Phe
            35              40              45

Asp Tyr Gly Glu Ile Pro Asn Phe Pro Arg Ser Thr Val Pro Gly His
            50              55              60

Ala Gly Arg Leu Val Phe Gly Phe Leu Asn Gly Arg Ala Cys Val Met
65              70              75              80

Met Gln Gly Arg Phe His Met Tyr Glu Gly Tyr Pro Leu Trp Lys Val
            85              90              95

Thr Phe Pro Val Arg Val Phe His Leu Leu Gly Val Asp Thr Leu Val
            100             105             110

Val Thr Asn Ala Ala Gly Gly Leu Asn Pro Lys Phe Glu Val Gly Asp
            115             120             125

Ile Met Leu Ile Arg Asp His Ile Asn Leu Pro Gly Phe Ser Gly Gln
            130             135             140

Asn Pro Leu Arg Gly Pro Asn Asp Glu Arg Phe Gly Asp Arg Phe Pro
```

```
145                 150                 155                 160

Ala Met Ser Asp Ala Tyr Asp Arg Thr Met Arg Gln Arg Ala Leu Ser
                165                 170                 175

Thr Trp Lys Gln Met Gly Glu Gln Arg Glu Leu Gln Glu Gly Thr Tyr
                180                 185                 190

Val Met Val Ala Gly Pro Ser Phe Glu Thr Val Ala Glu Cys Arg Val
                195                 200                 205

Leu Gln Lys Leu Gly Ala Asp Ala Val Gly Met Ser Thr Val Pro Glu
        210                 215                 220

Val Ile Val Ala Arg His Cys Gly Leu Arg Val Phe Gly Phe Ser Leu
225                 230                 235                 240

Ile Thr Asn Lys Val Ile Met Asp Tyr Glu Ser Leu Glu Lys Ala Asn
                245                 250                 255

His Glu Glu Val Leu Ala Ala Gly Lys Gln Ala Ala Gln Lys Leu Glu
                260                 265                 270

Gln Phe Val Ser Ile Leu Met Ala Ser Ile Pro Leu Pro Asp Lys Ala
                275                 280                 285

Ser

<210> SEQ ID NO 49
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Val Asp Thr Glu Ser Pro Leu Cys Pro Leu Ser Pro Leu Glu Ala
1               5                   10                  15

Gly Asp Leu Glu Ser Pro Leu Ser Glu Glu Phe Leu Gln Glu Met Gly
                20                  25                  30

Asn Ile Gln Glu Ile Ser Gln Ser Ile Gly Glu Asp Ser Ser Gly Ser
                35                  40                  45

Phe Gly Phe Thr Glu Tyr Gln Tyr Leu Gly Ser Cys Pro Gly Ser Asp
        50                  55                  60

Gly Ser Val Ile Thr Asp Thr Leu Ser Pro Ala Ser Ser Pro Ser Ser
65                  70                  75                  80

Val Thr Tyr Pro Val Val Pro Gly Ser Val Asp Glu Ser Pro Ser Gly
                85                  90                  95

Ala Leu Asn Ile Glu Cys Arg Ile Cys Gly Asp Lys Ala Ser Gly Tyr
                100                 105                 110

His Tyr Gly Val His Ala Cys Glu Gly Cys Lys Gly Phe Phe Arg Arg
        115                 120                 125

Thr Ile Arg Leu Lys Leu Val Tyr Asp Lys Cys Asp Arg Ser Cys Lys
        130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
                180                 185                 190

His Asp Ile Glu Asp Ser Glu Thr Ala Asp Leu Lys Ser Leu Ala Lys
        195                 200                 205

Arg Ile Tyr Glu Ala Tyr Leu Lys Asn Phe Asn Met Asn Lys Val Lys
```

-continued

```
             210                 215                 220

Ala Arg Val Ile Leu Ser Gly Lys Ala Ser Asn Asn Pro Pro Phe Val
225                 230                 235                 240

Ile His Asp Met Glu Thr Leu Cys Met Ala Glu Lys Thr Leu Val Ala
                245                 250                 255

Lys Leu Val Ala Asn Gly Ile Gln Asn Lys Glu Ala Glu Val Arg Ile
                260                 265                 270

Phe His Cys Cys Gln Cys Thr Ser Val Glu Thr Val Thr Glu Leu Thr
                275                 280                 285

Glu Phe Ala Lys Ala Ile Pro Gly Phe Ala Asn Leu Asp Leu Asn Asp
        290                 295                 300

Gln Val Thr Leu Leu Lys Tyr Gly Val Tyr Glu Ala Ile Phe Ala Met
305                 310                 315                 320

Leu Ser Ser Val Met Asn Lys Asp Gly Met Leu Val Ala Tyr Gly Asn
                325                 330                 335

Gly Phe Ile Thr Arg Glu Phe Leu Lys Ser Leu Arg Lys Pro Phe Cys
                340                 345                 350

Asp Ile Met Glu Pro Lys Phe Asp Phe Ala Met Lys Phe Asn Ala Leu
                355                 360                 365

Glu Leu Asp Asp Ser Asp Ile Ser Leu Phe Val Ala Ala Ile Ile Cys
        370                 375                 380

Cys Gly Asp Arg Pro Gly Leu Leu Asn Val Gly His Ile Glu Lys Met
385                 390                 395                 400

Gln Glu Gly Ile Val His Val Leu Arg Leu His Leu Gln Ser Asn His
                405                 410                 415

Pro Asp Asp Ile Phe Leu Phe Pro Lys Leu Leu Gln Lys Met Ala Asp
                420                 425                 430

Leu Arg Gln Leu Val Thr Glu His Ala Gln Leu Val Gln Ile Ile Lys
        435                 440                 445

Lys Thr Glu Ser Asp Ala Ala Leu His Pro Leu Leu Gln Glu Ile Tyr
        450                 455                 460

Arg Asp Met Tyr
465
```

<210> SEQ ID NO 50
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Met Gly Ser Gly Trp Val Pro Trp Val Val Ala Leu Leu Val Asn Leu
1               5                   10                  15

Thr Arg Leu Asp Ser Ser Met Thr Gln Gly Thr Asp Ser Pro Glu Asp
                20                  25                  30

Phe Val Ile Gln Ala Lys Ala Asp Cys Tyr Phe Thr Asn Gly Thr Glu
            35                  40                  45

Lys Val Gln Phe Val Val Arg Phe Ile Phe Asn Leu Glu Glu Tyr Val
        50                  55                  60

Arg Phe Asp Ser Asp Val Gly Met Phe Val Ala Leu Thr Lys Leu Gly
65                  70                  75                  80

Gln Pro Asp Ala Glu Gln Trp Asn Ser Arg Leu Asp Leu Leu Glu Arg
                85                  90                  95
```

```
Ser Arg Gln Ala Val Asp Gly Val Cys Arg His Asn Tyr Arg Leu Gly
            100                 105                 110

Ala Pro Phe Thr Val Gly Arg Lys Val Gln Pro Glu Val Thr Val Tyr
            115                 120                 125

Pro Glu Arg Thr Pro Leu Leu His Gln His Asn Leu Leu His Cys Ser
            130                 135                 140

Val Thr Gly Phe Tyr Pro Gly Asp Ile Lys Ile Lys Trp Phe Leu Asn
145                 150                 155                 160

Gly Gln Glu Glu Arg Ala Gly Val Met Ser Thr Gly Pro Ile Arg Asn
                165                 170                 175

Gly Asp Trp Thr Phe Gln Thr Val Val Met Leu Glu Met Thr Pro Glu
            180                 185                 190

Leu Gly His Val Tyr Thr Cys Leu Val Asp His Ser Ser Leu Leu Ser
            195                 200                 205

Pro Val Ser Val Glu Trp Arg Ala Gln Ser Glu Tyr Ser Trp Arg Lys
            210                 215                 220

Met Leu Ser Gly Ile Ala Ala Phe Leu Leu Gly Leu Ile Phe Leu Leu
225                 230                 235                 240

Val Gly Ile Val Ile Gln Leu Arg Ala Gln Lys Gly Tyr Val Arg Thr
                245                 250                 255

Gln Met Ser Gly Asn Glu Val Ser Arg Ala Val Leu Leu Pro Gln Ser
                260                 265                 270

Cys
```

```
<210> SEQ ID NO 51
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51
```

```
Met Arg Pro Glu Asp Arg Met Phe His Ile Arg Ala Val Ile Leu Arg
1               5                   10                  15

Ala Leu Ser Leu Ala Phe Leu Leu Ser Leu Arg Gly Ala Gly Ala Ile
            20                  25                  30

Lys Ala Asp His Val Ser Thr Tyr Ala Ala Phe Val Gln Thr His Arg
            35                  40                  45

Pro Thr Gly Glu Phe Met Phe Glu Phe Asp Glu Asp Glu Met Phe Tyr
            50                  55                  60

Val Asp Leu Asp Lys Lys Glu Thr Val Trp His Leu Glu Glu Phe Gly
65                  70                  75                  80

Gln Ala Phe Ser Phe Glu Ala Gln Gly Gly Leu Ala Asn Ile Ala Ile
                85                  90                  95

Leu Asn Asn Asn Leu Asn Thr Leu Ile Gln Arg Ser Asn His Thr Gln
            100                 105                 110

Ala Thr Asn Asp Pro Pro Glu Val Thr Val Phe Pro Lys Glu Pro Val
            115                 120                 125

Glu Leu Gly Gln Pro Asn Thr Leu Ile Cys His Ile Asp Lys Phe Phe
            130                 135                 140

Pro Pro Val Leu Asn Val Thr Trp Leu Cys Asn Gly Glu Leu Val Thr
145                 150                 155                 160

Glu Gly Val Ala Glu Ser Leu Phe Leu Pro Arg Thr Asp Tyr Ser Phe
                165                 170                 175
```

-continued

```
His Lys Phe His Tyr Leu Thr Phe Val Pro Ser Ala Glu Asp Phe Tyr
            180                 185                 190

Asp Cys Arg Val Glu His Trp Gly Leu Asp Gln Pro Leu Leu Lys His
            195             200                 205

Trp Glu Ala Gln Glu Pro Ile Gln Met Pro Glu Thr Thr Glu Thr Val
    210                 215                 220

Leu Cys Ala Leu Gly Leu Val Leu Gly Leu Val Gly Ile Ile Val Gly
225                 230                 235                 240

Thr Val Leu Ile Ile Lys Ser Leu Arg Ser Gly His Asp Pro Arg Ala
                245                 250                 255

Gln Gly Thr Leu
            260

<210> SEQ ID NO 52
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Ile Leu Asn Lys Ala Leu Met Leu Gly Ala Leu Ala Leu Thr Thr
1               5                   10                  15

Val Met Ser Pro Cys Gly Gly Glu Asp Ile Val Ala Asp His Val Ala
            20                  25                  30

Ser Tyr Gly Val Asn Leu Tyr Gln Ser Tyr Gly Pro Ser Gly Gln Tyr
        35                  40                  45

Thr His Glu Phe Asp Gly Asp Glu Gln Phe Tyr Val Asp Leu Gly Arg
    50                  55                  60

Lys Glu Thr Val Trp Cys Leu Pro Val Leu Arg Gln Phe Arg Phe Asp
65                  70                  75                  80

Pro Gln Phe Ala Leu Thr Asn Ile Ala Val Leu Lys His Asn Leu Asn
                85                  90                  95

Ser Leu Ile Lys Arg Ser Asn Ser Thr Ala Ala Thr Asn Glu Val Pro
            100                 105                 110

Glu Val Thr Val Phe Ser Lys Ser Pro Val Thr Leu Gly Gln Pro Asn
            115                 120                 125

Ile Leu Ile Cys Leu Val Asp Asn Ile Phe Pro Pro Val Val Asn Ile
        130                 135                 140

Thr Trp Leu Ser Asn Gly His Ser Val Thr Glu Gly Val Ser Glu Thr
145                 150                 155                 160

Ser Phe Leu Ser Lys Ser Asp His Ser Phe Phe Lys Ile Ser Tyr Leu
                165                 170                 175

Thr Leu Leu Pro Ser Ala Glu Glu Ser Tyr Asp Cys Lys Val Glu His
            180                 185                 190

Trp Gly Leu Asp Lys Pro Leu Leu Lys His Trp Glu Pro Glu Ile Pro
            195                 200                 205

Ala Pro Met Ser Glu Leu Thr Glu Thr Val Val Cys Ala Leu Gly Leu
    210                 215                 220

Ser Val Gly Leu Val Gly Ile Val Val Gly Thr Val Phe Ile Ile Arg
225                 230                 235                 240

Gly Leu Arg Ser Val Gly Ala Ser Arg His Gln Gly Pro Leu
                245                 250

<210> SEQ ID NO 53
```

<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Ile Leu Asn Lys Ala Leu Met Leu Gly Ala Leu Ala Leu Thr Thr
1               5                   10                  15

Val Met Ser Pro Cys Gly Gly Glu Asp Ile Val Ala Asp His Val Ala
                20                  25                  30

Ser Tyr Gly Val Asn Leu Tyr Gln Ser Tyr Gly Pro Ser Gly Gln Tyr
            35                  40                  45

Thr His Glu Phe Asp Gly Asp Glu Gln Phe Tyr Val Asp Leu Gly Arg
        50                  55                  60

Lys Glu Thr Val Trp Cys Leu Pro Val Leu Arg Gln Phe Arg Phe Asp
65                  70                  75                  80

Pro Gln Phe Ala Leu Thr Asn Ile Ala Val Leu Lys His Asn Leu Asn
                85                  90                  95

Ser Leu Ile Lys Arg Ser Asn Ser Thr Ala Ala Thr Asn Glu Val Pro
            100                 105                 110

Glu Val Thr Val Phe Ser Lys Ser Pro Val Thr Leu Gly Gln Pro Asn
            115                 120                 125

Ile Leu Ile Cys Leu Val Asp Asn Ile Phe Pro Pro Val Val Asn Ile
        130                 135                 140

Thr Trp Leu Ser Asn Gly His Ser Val Thr Glu Gly Val Ser Glu Thr
145                 150                 155                 160

Ser Phe Leu Ser Lys Ser Asp His Ser Phe Phe Lys Ile Ser Tyr Leu
                165                 170                 175

Thr Leu Leu Pro Ser Ala Glu Glu Ser Tyr Asp Cys Lys Val Glu His
            180                 185                 190

Trp Gly Leu Asp Lys Pro Leu Leu Lys His Trp Glu Pro Glu Ile Pro
            195                 200                 205

Ala Pro Met Ser Glu Leu Thr Glu Thr Val Val Cys Ala Leu Gly Leu
        210                 215                 220

Ser Val Gly Leu Val Gly Ile Val Val Gly Thr Val Phe Ile Ile Arg
225                 230                 235                 240

Gly Leu Arg Ser Val Gly Ala Ser Arg His Gln Gly Pro Leu
                245                 250

<210> SEQ ID NO 54
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Ser Trp Lys Lys Ala Leu Arg Ile Pro Gly Gly Leu Arg Ala Ala
1               5                   10                  15

Thr Val Thr Leu Met Leu Ala Met Leu Ser Thr Pro Val Ala Glu Gly
                20                  25                  30

Arg Asp Ser Pro Glu Asp Phe Val Tyr Gln Phe Lys Ala Met Cys Tyr
            35                  40                  45

Phe Thr Asn Gly Thr Glu Arg Val Arg Tyr Val Thr Arg Tyr Ile Tyr
        50                  55                  60

-continued

```
Asn Arg Glu Glu Tyr Ala Arg Phe Asp Ser Asp Val Glu Val Tyr Arg
65                  70                  75                  80

Ala Val Thr Pro Leu Gly Pro Pro Asp Ala Glu Tyr Trp Asn Ser Gln
                85                  90                  95

Lys Glu Val Leu Glu Arg Thr Arg Ala Glu Leu Asp Thr Val Cys Arg
                100                 105                 110

His Asn Tyr Gln Leu Glu Leu Arg Thr Thr Leu Gln Arg Arg Val Glu
            115                 120                 125

Pro Thr Val Thr Ile Ser Pro Ser Arg Thr Glu Ala Leu Asn His His
    130                 135                 140

Asn Leu Leu Val Cys Ser Val Thr Asp Phe Tyr Pro Ala Gln Ile Lys
145                 150                 155                 160

Val Arg Trp Phe Arg Asn Asp Gln Glu Glu Thr Thr Gly Val Val Ser
                165                 170                 175

Thr Pro Leu Ile Arg Asn Gly Asp Trp Thr Phe Gln Ile Leu Val Met
                180                 185                 190

Leu Glu Met Thr Pro Gln His Gly Asp Val Tyr Thr Cys His Val Glu
            195                 200                 205

His Pro Ser Leu Gln Asn Pro Ile Thr Val Glu Trp Arg Ala Gln Ser
    210                 215                 220

Glu Ser Ala Gln Ser Lys Met Leu Ser Gly Ile Gly Gly Phe Val Leu
225                 230                 235                 240

Gly Leu Ile Phe Leu Gly Leu Gly Leu Ile Ile His His Arg Ser Gln
                245                 250                 255

Lys Gly Leu Leu His
            260
```

```
<210> SEQ ID NO 55
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55
```

```
Met Ser Trp Lys Met Ala Leu Gln Ile Pro Gly Gly Phe Trp Ala Ala
1               5                   10                  15

Ala Val Thr Val Met Leu Val Met Leu Ser Thr Pro Val Ala Glu Ala
                20                  25                  30

Arg Asp Phe Pro Lys Asp Phe Leu Val Gln Phe Lys Gly Met Cys Tyr
            35                  40                  45

Phe Thr Asn Gly Thr Glu Arg Val Arg Gly Val Ala Arg Tyr Ile Tyr
    50                  55                  60

Asn Arg Glu Glu Tyr Gly Arg Phe Asp Ser Asp Val Gly Glu Phe Gln
65                  70                  75                  80

Ala Val Thr Glu Leu Gly Arg Ser Ile Glu Asp Trp Asn Asn Tyr Lys
                85                  90                  95

Asp Phe Leu Glu Gln Glu Arg Ala Ala Val Asp Lys Val Cys Arg His
                100                 105                 110

Asn Tyr Glu Ala Glu Leu Arg Thr Thr Leu Gln Arg Gln Val Glu Pro
            115                 120                 125

Thr Val Thr Ile Ser Pro Ser Arg Thr Glu Ala Leu Asn His His Asn
    130                 135                 140

Leu Leu Val Cys Ser Val Thr Asp Phe Tyr Pro Ala Gln Ile Lys Val
```

-continued

```
145             150             155             160

Arg Trp Phe Arg Asn Asp Gln Glu Glu Thr Ala Gly Val Val Ser Thr
                165             170             175

Ser Leu Ile Arg Asn Gly Asp Trp Thr Phe Gln Ile Leu Val Met Leu
                180             185             190

Glu Ile Thr Pro Gln Arg Gly Asp Ile Tyr Thr Cys Gln Val Glu His
                195             200             205

Pro Ser Leu Gln Ser Pro Ile Thr Val Glu Trp Arg Ala Gln Ser Glu
        210             215             220

Ser Ala Gln Ser Lys Met Leu Ser Gly Ile Gly Gly Phe Val Leu Gly
225             230             235             240

Leu Ile Phe Leu Gly Leu Gly Leu Ile Ile Arg His Arg Gly Gln Lys
                245             250             255

Gly Pro Arg Gly Pro Pro Ala Gly Leu Leu His
                260             265
```

```
<210> SEQ ID NO 56
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Ala Ile Ser Gly Val Pro Val Leu Gly Phe Phe Ile Ile Ala Val
1               5               10              15

Leu Met Ser Ala Gln Glu Ser Trp Ala Ile Lys Glu Glu His Val Ile
                20              25              30

Ile Gln Ala Glu Phe Tyr Leu Asn Pro Asp Gln Ser Gly Glu Phe Met
        35              40              45

Phe Asp Phe Asp Gly Asp Glu Ile Phe His Val Asp Met Ala Lys Lys
        50              55              60

Glu Thr Val Trp Arg Leu Glu Glu Phe Gly Arg Phe Ala Ser Phe Glu
65              70              75              80

Ala Gln Gly Ala Leu Ala Asn Ile Ala Val Asp Lys Ala Asn Leu Glu
                85              90              95

Ile Met Thr Lys Arg Ser Asn Tyr Thr Pro Ile Thr Asn Val Pro Pro
                100             105             110

Glu Val Thr Val Leu Thr Asn Ser Pro Val Glu Leu Arg Glu Pro Asn
        115             120             125

Val Leu Ile Cys Phe Ile Asp Lys Phe Thr Pro Pro Val Val Asn Val
        130             135             140

Thr Trp Leu Arg Asn Gly Lys Pro Val Thr Thr Gly Val Ser Glu Thr
145             150             155             160

Val Phe Leu Pro Arg Glu Asp His Leu Phe Arg Lys Phe His Tyr Leu
                165             170             175

Pro Phe Leu Pro Ser Thr Glu Asp Val Tyr Asp Cys Arg Val Glu His
                180             185             190

Trp Gly Leu Asp Glu Pro Leu Leu Lys His Trp Glu Phe Asp Ala Pro
                195             200             205

Ser Pro Leu Pro Glu Thr Thr Glu Asn Val Val Cys Ala Leu Gly Leu
        210             215             220

Thr Val Gly Leu Val Gly Ile Ile Ile Gly Thr Ile Phe Ile Ile Lys
225             230             235             240
```

```
Gly Val Arg Lys Ser Asn Ala Ala Glu Arg Arg Gly Pro Leu
            245                 250

<210> SEQ ID NO 57
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
            115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
            195                 200                 205

Ser Pro Leu Pro Glu Thr Thr Glu Asn Val Val Cys Ala Leu Gly Leu
    210                 215                 220

Thr Val Gly Leu Val Gly Ile Ile Ile Gly Thr Ile Phe Ile Ile Lys
225                 230                 235                 240

Gly Val Arg Lys Ser Asn Ala Ala Glu Arg Arg Gly Pro Leu
            245                 250

<210> SEQ ID NO 58
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Val Cys Leu Lys Leu Pro Gly Gly Ser Ser Leu Ala Ala Leu Thr
1               5                   10                  15

Val Thr Leu Met Val Leu Ser Ser Arg Leu Ala Phe Ala Gly Asp Thr
            20                  25                  30
```

```
Arg Pro Arg Phe Leu Glu Leu Arg Lys Ser Glu Cys His Phe Phe Asn
        35              40              45
```

```
Gly Thr Glu Arg Val Arg Tyr Leu Asp Arg Tyr Phe His Asn Gln Glu
    50              55              60
```

```
Glu Phe Leu Arg Phe Asp Ser Asp Val Gly Glu Tyr Arg Ala Val Thr
65              70              75              80
```

```
Glu Leu Gly Arg Pro Val Ala Glu Ser Trp Asn Ser Gln Lys Asp Leu
                85              90              95
```

```
Leu Glu Gln Lys Arg Gly Arg Val Asp Asn Tyr Cys Arg His Asn Tyr
            100             105             110
```

```
Gly Val Gly Glu Ser Phe Thr Val Gln Arg Arg Val His Pro Gln Val
            115             120             125
```

```
Thr Val Tyr Pro Ala Lys Thr Gln Pro Leu Gln His His Asn Leu Leu
    130             135             140
```

```
Val Cys Ser Val Ser Gly Phe Tyr Pro Gly Ser Ile Glu Val Arg Trp
145             150             155             160
```

```
Phe Arg Asn Gly Gln Glu Glu Lys Ala Gly Val Val Ser Thr Gly Leu
            165             170             175
```

```
Ile Gln Asn Gly Asp Trp Thr Phe Gln Thr Leu Val Met Leu Glu Thr
            180             185             190
```

```
Val Pro Arg Ser Gly Glu Val Tyr Thr Cys Gln Val Glu His Pro Ser
            195             200             205
```

```
Val Thr Ser Ala Leu Thr Val Glu Trp Arg Ala Arg Ser Glu Ser Ala
    210             215             220
```

```
Gln Ser Lys Met Leu Ser Gly Val Gly Gly Phe Val Leu Gly Leu Leu
225             230             235             240
```

```
Phe Leu Gly Ala Gly Leu Phe Ile Tyr Phe Arg Asn Gln Lys Gly His
            245             250             255
```

```
Ser Gly Leu Gln Pro Thr Gly Phe Leu Ser
            260             265
```

<210> SEQ ID NO 59
<211> LENGTH: 1181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Met Gly Pro Glu Arg Thr Gly Ala Ala Pro Leu Pro Leu Leu Leu Val
1               5               10              15
```

```
Leu Ala Leu Ser Gln Gly Ile Leu Asn Cys Cys Leu Ala Tyr Asn Val
            20              25              30
```

```
Gly Leu Pro Glu Ala Lys Ile Phe Ser Gly Pro Ser Ser Glu Gln Phe
            35              40              45
```

```
Gly Tyr Ala Val Gln Gln Phe Ile Asn Pro Lys Gly Asn Trp Leu Leu
    50              55              60
```

```
Val Gly Ser Pro Trp Ser Gly Phe Pro Glu Asn Arg Met Gly Asp Val
65              70              75              80
```

```
Tyr Lys Cys Pro Val Asp Leu Ser Thr Ala Thr Cys Glu Lys Leu Asn
                85              90              95
```

```
Leu Gln Thr Ser Thr Ser Ile Pro Asn Val Thr Glu Met Lys Thr Asn
            100             105             110
```

```
Met Ser Leu Gly Leu Ile Leu Thr Arg Asn Met Gly Thr Gly Gly Phe
            115             120             125
```

```
Leu Thr Cys Gly Pro Leu Trp Ala Gln Gln Cys Gly Asn Gln Tyr Tyr
    130             135             140
Thr Thr Gly Val Cys Ser Asp Ile Ser Pro Asp Phe Gln Leu Ser Ala
145             150             155             160
Ser Phe Ser Pro Ala Thr Gln Pro Cys Pro Ser Leu Ile Asp Val Val
            165             170             175
Val Val Cys Asp Glu Ser Asn Ser Ile Tyr Pro Trp Asp Ala Val Lys
            180             185             190
Asn Phe Leu Glu Lys Phe Val Gln Gly Leu Asp Ile Gly Pro Thr Lys
            195             200             205
Thr Gln Val Gly Leu Ile Gln Tyr Ala Asn Asn Pro Arg Val Val Phe
    210             215             220
Asn Leu Asn Thr Tyr Lys Thr Lys Glu Glu Met Ile Val Ala Thr Ser
225             230             235             240
Gln Thr Ser Gln Tyr Gly Gly Asp Leu Thr Asn Thr Phe Gly Ala Ile
            245             250             255
Gln Tyr Ala Arg Lys Tyr Ala Tyr Ser Ala Ala Ser Gly Gly Arg Arg
            260             265             270
Ser Ala Thr Lys Val Met Val Val Val Thr Asp Gly Glu Ser His Asp
            275             280             285
Gly Ser Met Leu Lys Ala Val Ile Asp Gln Cys Asn His Asp Asn Ile
    290             295             300
Leu Arg Phe Gly Ile Ala Val Leu Gly Tyr Leu Asn Arg Asn Ala Leu
305             310             315             320
Asp Thr Lys Asn Leu Ile Lys Glu Ile Lys Ala Ile Ala Ser Ile Pro
            325             330             335
Thr Glu Arg Tyr Phe Phe Asn Val Ser Asp Glu Ala Ala Leu Leu Glu
            340             345             350
Lys Ala Gly Thr Leu Gly Glu Gln Ile Phe Ser Ile Glu Gly Thr Val
            355             360             365
Gln Gly Gly Asp Asn Phe Gln Met Glu Met Ser Gln Val Gly Phe Ser
    370             375             380
Ala Asp Tyr Ser Ser Gln Asn Asp Ile Leu Met Leu Gly Ala Val Gly
385             390             395             400
Ala Phe Gly Trp Ser Gly Thr Ile Val Gln Lys Thr Ser His Gly His
            405             410             415
Leu Ile Phe Pro Lys Gln Ala Phe Asp Gln Ile Leu Gln Asp Arg Asn
            420             425             430
His Ser Ser Tyr Leu Gly Tyr Ser Val Ala Ala Ile Ser Thr Gly Glu
            435             440             445
Ser Thr His Phe Val Ala Gly Ala Pro Arg Ala Asn Tyr Thr Gly Gln
    450             455             460
Ile Val Leu Tyr Ser Val Asn Glu Asn Gly Asn Ile Thr Val Ile Gln
465             470             475             480
Ala His Arg Gly Asp Gln Ile Gly Ser Tyr Phe Gly Ser Val Leu Cys
            485             490             495
Ser Val Asp Val Asp Lys Asp Thr Ile Thr Asp Val Leu Leu Val Gly
            500             505             510
Ala Pro Met Tyr Met Ser Asp Leu Lys Lys Glu Glu Gly Arg Val Tyr
            515             520             525
Leu Phe Thr Ile Lys Lys Gly Ile Leu Gly Gln His Gln Phe Leu Glu
    530             535             540
```

```
Gly Pro Glu Gly Ile Glu Asn Thr Arg Phe Gly Ser Ala Ile Ala Ala
545                 550                 555                 560

Leu Ser Asp Ile Asn Met Asp Gly Phe Asn Asp Val Ile Val Gly Ser
                565                 570                 575

Pro Leu Glu Asn Gln Asn Ser Gly Ala Val Tyr Ile Tyr Asn Gly His
            580                 585                 590

Gln Gly Thr Ile Arg Thr Lys Tyr Ser Gln Lys Ile Leu Gly Ser Asp
        595                 600                 605

Gly Ala Phe Arg Ser His Leu Gln Tyr Phe Gly Arg Ser Leu Asp Gly
    610                 615                 620

Tyr Gly Asp Leu Asn Gly Asp Ser Ile Thr Asp Val Ser Ile Gly Ala
625                 630                 635                 640

Phe Gly Gln Val Val Gln Leu Trp Ser Gln Ser Ile Ala Asp Val Ala
                645                 650                 655

Ile Glu Ala Ser Phe Thr Pro Glu Lys Ile Thr Leu Val Asn Lys Asn
                660                 665                 670

Ala Gln Ile Ile Leu Lys Leu Cys Phe Ser Ala Lys Phe Arg Pro Thr
            675                 680                 685

Lys Gln Asn Asn Gln Val Ala Ile Val Tyr Asn Ile Thr Leu Asp Ala
        690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
                725                 730                 735

Cys Pro Glu His Ile Ile Tyr Ile Gln Glu Pro Ser Asp Val Val Asn
            740                 745                 750

Ser Leu Asp Leu Arg Val Asp Ile Ser Leu Glu Asn Pro Gly Thr Ser
        755                 760                 765

Pro Ala Leu Glu Ala Tyr Ser Glu Thr Ala Lys Val Phe Ser Ile Pro
    770                 775                 780

Phe His Lys Asp Cys Gly Glu Asp Gly Leu Cys Ile Ser Asp Leu Val
785                 790                 795                 800

Leu Asp Val Arg Gln Ile Pro Ala Ala Gln Glu Gln Pro Phe Ile Val
                805                 810                 815

Ser Asn Gln Asn Lys Arg Leu Thr Phe Ser Val Thr Leu Lys Asn Lys
            820                 825                 830

Arg Glu Ser Ala Tyr Asn Thr Gly Ile Val Val Asp Phe Ser Glu Asn
        835                 840                 845

Leu Phe Phe Ala Ser Phe Ser Leu Pro Val Asp Gly Thr Glu Val Thr
    850                 855                 860

Cys Gln Val Ala Ala Ser Gln Lys Ser Val Ala Cys Asp Val Gly Tyr
865                 870                 875                 880

Pro Ala Leu Lys Arg Glu Gln Gln Val Thr Phe Thr Ile Asn Phe Asp
                885                 890                 895

Phe Asn Leu Gln Asn Leu Gln Asn Gln Ala Ser Leu Ser Phe Gln Ala
            900                 905                 910

Leu Ser Glu Ser Gln Glu Glu Asn Lys Ala Asp Asn Leu Val Asn Leu
        915                 920                 925

Lys Ile Pro Leu Leu Tyr Asp Ala Glu Ile His Leu Thr Arg Ser Thr
    930                 935                 940

Asn Ile Asn Phe Tyr Glu Ile Ser Ser Asp Gly Asn Val Pro Ser Ile
945                 950                 955                 960

Val His Ser Phe Glu Asp Val Gly Pro Lys Phe Ile Phe Ser Leu Lys
```

-continued

```
                  965                 970                 975
Val Thr Thr Gly Ser Val Pro Val Ser Met Ala Thr Val Ile Ile His
              980                 985                 990

Ile Pro Gln Tyr Thr Lys Glu Lys  Asn Pro Leu Met Tyr  Leu Thr Gly
          995                 1000                1005

Val Gln  Thr Asp Lys Ala Gly  Asp Ile Ser Cys Asn  Ala Asp Ile
     1010                 1015                 1020

Asn Pro  Leu Lys Ile Gly Gln  Thr Ser Ser Ser Val  Ser Phe Lys
     1025                 1030                 1035

Ser Glu  Asn Phe Arg His Thr  Lys Glu Leu Asn Cys  Arg Thr Ala
     1040                 1045                 1050

Ser Cys  Ser Asn Val Thr Cys  Trp Leu Lys Asp Val  His Met Lys
     1055                 1060                 1065

Gly Glu  Tyr Phe Val Asn Val  Thr Thr Arg Ile Trp  Asn Gly Thr
     1070                 1075                 1080

Phe Ala  Ser Ser Thr Phe Gln  Thr Val Gln Leu Thr  Ala Ala Ala
     1085                 1090                 1095

Glu Ile  Asn Thr Tyr Asn Pro  Glu Ile Tyr Val Ile  Glu Asp Asn
     1100                 1105                 1110

Thr Val  Thr Ile Pro Leu Met  Ile Met Lys Pro Asp  Glu Lys Ala
     1115                 1120                 1125

Glu Val  Pro Thr Gly Val Ile  Ile Gly Ser Ile Ile  Ala Gly Ile
     1130                 1135                 1140

Leu Leu  Leu Leu Ala Leu Val  Ala Ile Leu Trp Lys  Leu Gly Phe
     1145                 1150                 1155

Phe Lys  Arg Lys Tyr Glu Lys  Met Thr Lys Asn Pro  Asp Glu Ile
     1160                 1165                 1170

Asp Glu  Thr Thr Glu Leu Ser  Ser
     1175                 1180
```

```
<210> SEQ ID NO 60
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met His Ser Phe Pro Pro Leu Leu Leu Leu Leu Phe Trp Gly Val Val
1                5                  10                  15

Ser His Ser Phe Pro Ala Thr Leu Glu Thr Gln Glu Gln Asp Val Asp
              20                  25                  30

Leu Val Gln Lys Tyr Leu Glu Lys Tyr Tyr Asn Leu Lys Asn Asp Gly
          35                  40                  45

Arg Gln Val Glu Lys Arg Arg Asn Ser Gly Pro Val Val Glu Lys Leu
     50                  55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
              85                  90                  95

Val Ala Gln Phe Val Leu Thr Glu Gly Asn Pro Arg Trp Glu Gln Thr
              100                 105                 110

His Leu Thr Tyr Arg Ile Glu Asn Tyr Thr Pro Asp Leu Pro Arg Ala
          115                 120                 125
```

```
Asp Val Asp His Ala Ile Glu Lys Ala Phe Gln Leu Trp Ser Asn Val
    130             135             140

Thr Pro Leu Thr Phe Thr Lys Val Ser Glu Gly Gln Ala Asp Ile Met
145             150             155             160

Ile Ser Phe Val Arg Gly Asp His Arg Asp Asn Ser Pro Phe Asp Gly
            165             170             175

Pro Gly Gly Asn Leu Ala His Ala Phe Gln Pro Gly Pro Gly Ile Gly
            180             185             190

Gly Asp Ala His Phe Asp Glu Asp Glu Arg Trp Thr Asn Asn Phe Arg
            195             200             205

Glu Tyr Asn Leu His Arg Val Ala Ala His Glu Leu Gly His Ser Leu
    210             215             220

Gly Leu Ser His Ser Thr Asp Ile Gly Ala Leu Met Tyr Pro Ser Tyr
225             230             235             240

Thr Phe Ser Gly Asp Val Gln Leu Ala Gln Asp Asp Ile Asp Gly Ile
            245             250             255

Gln Ala Ile Tyr Gly Arg Ser Gln Asn Pro Val Gln Pro Ile Gly Pro
            260             265             270

Gln Thr Pro Lys Ala Cys Asp Ser Lys Leu Thr Phe Asp Ala Ile Thr
            275             280             285

Thr Ile Arg Gly Glu Val Met Phe Phe Lys Asp Arg Phe Tyr Met Arg
    290             295             300

Thr Asn Pro Phe Tyr Pro Glu Val Glu Leu Asn Phe Ile Ser Val Phe
305             310             315             320

Trp Pro Gln Leu Pro Asn Gly Leu Glu Ala Ala Tyr Glu Phe Ala Asp
            325             330             335

Arg Asp Glu Val Arg Phe Phe Lys Gly Asn Lys Tyr Trp Ala Val Gln
            340             345             350

Gly Gln Asn Val Leu His Gly Tyr Pro Lys Asp Ile Tyr Ser Ser Phe
            355             360             365

Gly Phe Pro Arg Thr Val Lys His Ile Asp Ala Ala Leu Ser Glu Glu
    370             375             380

Asn Thr Gly Lys Thr Tyr Phe Phe Val Ala Asn Lys Tyr Trp Arg Tyr
385             390             395             400

Asp Glu Tyr Lys Arg Ser Met Asp Pro Gly Tyr Pro Lys Met Ile Ala
            405             410             415

His Asp Phe Pro Gly Ile Gly His Lys Val Asp Ala Val Phe Met Lys
            420             425             430

Asp Gly Phe Phe Tyr Phe Phe His Gly Thr Arg Gln Tyr Lys Phe Asp
            435             440             445

Pro Lys Thr Lys Arg Ile Leu Thr Leu Gln Lys Ala Asn Ser Trp Phe
    450             455             460

Asn Cys Arg Lys Asn
465
```

```
<210> SEQ ID NO 61
<211> LENGTH: 317
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Lys Val Leu Trp Ala Ala Leu Leu Val Thr Phe Leu Ala Gly Cys
1               5               10              15
```

```
Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315
```

```
<210> SEQ ID NO 62
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
```

```
          50                55                60
Glu Glu Arg Lys Thr Leu Leu Ser Asn Leu Glu Glu Ala Lys Lys Lys
65                70                75                80

Lys Glu Asp Ala Leu Asn Glu Thr Arg Glu Ser Glu Thr Lys Leu Lys
               85                90                95

Glu Leu Pro Gly Val Cys Asn Glu Thr Met Met Ala Leu Trp Glu Glu
              100               105               110

Cys Lys Pro Cys Leu Lys Gln Thr Cys Met Lys Phe Tyr Ala Arg Val
              115               120               125

Cys Arg Ser Gly Ser Gly Leu Val Gly Arg Gln Leu Glu Glu Phe Leu
          130               135               140

Asn Gln Ser Ser Pro Phe Tyr Phe Trp Met Asn Gly Asp Arg Ile Asp
145               150               155               160

Ser Leu Leu Glu Asn Asp Arg Gln Gln Thr His Met Leu Asp Val Met
              165               170               175

Gln Asp His Phe Ser Arg Ala Ser Ser Ile Ile Asp Glu Leu Phe Gln
              180               185               190

Asp Arg Phe Phe Thr Arg Glu Pro Gln Asp Thr Tyr His Tyr Leu Pro
              195               200               205

Phe Ser Leu Pro His Arg Arg Pro His Phe Phe Phe Pro Lys Ser Arg
          210               215               220

Ile Val Arg Ser Leu Met Pro Phe Ser Pro Tyr Glu Pro Leu Asn Phe
225               230               235               240

His Ala Met Phe Gln Pro Phe Leu Glu Met Ile His Glu Ala Gln Gln
              245               250               255

Ala Met Asp Ile His Phe His Ser Pro Ala Phe Gln His Pro Pro Thr
              260               265               270

Glu Phe Ile Arg Glu Gly Asp Asp Asp Arg Thr Val Cys Arg Glu Ile
              275               280               285

Arg His Asn Ser Thr Gly Cys Leu Arg Met Lys Asp Gln Cys Asp Lys
          290               295               300

Cys Arg Glu Ile Leu Ser Val Asp Cys Ser Thr Asn Asn Pro Ser Gln
305               310               315               320

Ala Lys Leu Arg Arg Glu Leu Asp Glu Ser Leu Gln Val Ala Glu Arg
              325               330               335

Leu Thr Arg Lys Tyr Asn Glu Leu Leu Lys Ser Tyr Gln Trp Lys Met
              340               345               350

Leu Asn Thr Ser Ser Leu Leu Glu Gln Leu Asn Glu Gln Phe Asn Trp
              355               360               365

Val Ser Arg Leu Ala Asn Leu Thr Gln Gly Glu Asp Gln Tyr Tyr Leu
          370               375               380

Arg Val Thr Thr Val Ala Ser His Thr Ser Asp Ser Asp Val Pro Ser
385               390               395               400

Gly Val Thr Glu Val Val Val Lys Leu Phe Asp Ser Asp Pro Ile Thr
              405               410               415

Val Thr Val Pro Val Glu Val Ser Arg Lys Asn Pro Lys Phe Met Glu
              420               425               430

Thr Val Ala Glu Lys Ala Leu Gln Glu Tyr Arg Lys Lys His Arg Glu
          435               440               445

Glu
```

<210> SEQ ID NO 63
<211> LENGTH: 1051

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Gly Pro Gly Pro Ser Arg Ala Pro Arg Ala Pro Arg Leu Met Leu
1               5                   10                  15

Cys Ala Leu Ala Leu Met Val Ala Ala Gly Gly Cys Val Val Ser Ala
                20                  25                  30

Phe Asn Leu Asp Thr Arg Phe Leu Val Val Lys Glu Ala Gly Asn Pro
            35                  40                  45

Gly Ser Leu Phe Gly Tyr Ser Val Ala Leu His Arg Gln Thr Glu Arg
        50                  55                  60

Gln Gln Arg Tyr Leu Leu Leu Ala Gly Ala Pro Arg Glu Leu Ala Val
65                  70                  75                  80

Pro Asp Gly Tyr Thr Asn Arg Thr Gly Ala Val Tyr Leu Cys Pro Leu
                85                  90                  95

Thr Ala His Lys Asp Asp Cys Glu Arg Met Asn Ile Thr Val Lys Asn
            100                 105                 110

Asp Pro Gly His His Ile Ile Glu Asp Met Trp Leu Gly Val Thr Val
        115                 120                 125

Ala Ser Gln Gly Pro Ala Gly Arg Val Leu Val Cys Ala His Arg Tyr
        130                 135                 140

Thr Gln Val Leu Trp Ser Gly Ser Glu Asp Gln Arg Arg Met Val Gly
145                 150                 155                 160

Lys Cys Tyr Val Arg Gly Asn Asp Leu Glu Leu Asp Ser Ser Asp Asp
                165                 170                 175

Trp Gln Thr Tyr His Asn Glu Met Cys Asn Ser Asn Thr Asp Tyr Leu
            180                 185                 190

Glu Thr Gly Met Cys Gln Leu Gly Thr Ser Gly Gly Phe Thr Gln Asn
            195                 200                 205

Thr Val Tyr Phe Gly Ala Pro Gly Ala Tyr Asn Trp Lys Gly Asn Ser
        210                 215                 220

Tyr Met Ile Gln Arg Lys Glu Trp Asp Leu Ser Glu Tyr Ser Tyr Lys
225                 230                 235                 240

Asp Pro Glu Asp Gln Gly Asn Leu Tyr Ile Gly Tyr Thr Met Gln Val
                245                 250                 255

Gly Ser Phe Ile Leu His Pro Lys Asn Ile Thr Ile Val Thr Gly Ala
            260                 265                 270

Pro Arg His Arg His Met Gly Ala Val Phe Leu Leu Ser Gln Glu Ala
        275                 280                 285

Gly Gly Asp Leu Arg Arg Arg Gln Val Leu Glu Gly Ser Gln Val Gly
        290                 295                 300

Ala Tyr Phe Gly Ser Ala Ile Ala Leu Ala Asp Leu Asn Asn Asp Gly
305                 310                 315                 320

Trp Gln Asp Leu Leu Val Gly Ala Pro Tyr Tyr Phe Glu Arg Lys Glu
            325                 330                 335

Glu Val Gly Gly Ala Ile Tyr Val Phe Met Asn Gln Ala Gly Thr Ser
            340                 345                 350

Phe Pro Ala His Pro Ser Leu Leu Leu His Gly Pro Ser Gly Ser Ala
            355                 360                 365

Phe Gly Leu Ser Val Ala Ser Ile Gly Asp Ile Asn Gln Asp Gly Phe
        370                 375                 380
```

-continued

```
Gln Asp Ile Ala Val Gly Ala Pro Phe Glu Gly Leu Gly Lys Val Tyr
385                 390             395                 400

Ile Tyr His Ser Ser Ser Lys Gly Leu Leu Arg Gln Pro Gln Gln Val
            405             410             415

Ile His Gly Glu Lys Leu Gly Leu Pro Gly Leu Ala Thr Phe Gly Tyr
        420             425             430

Ser Leu Ser Gly Gln Met Asp Val Asp Glu Asn Phe Tyr Pro Asp Leu
        435             440             445

Leu Val Gly Ser Leu Ser Asp His Ile Val Leu Leu Arg Ala Arg Pro
    450             455             460

Val Ile Asn Ile Val His Lys Thr Leu Val Pro Arg Pro Ala Val Leu
465             470             475             480

Asp Pro Ala Leu Cys Thr Ala Thr Ser Cys Val Gln Val Glu Leu Cys
            485             490             495

Phe Ala Tyr Asn Gln Ser Ala Gly Asn Pro Asn Tyr Arg Arg Asn Ile
            500             505             510

Thr Leu Ala Tyr Thr Leu Glu Ala Asp Arg Asp Arg Arg Pro Pro Arg
        515             520             525

Leu Arg Phe Ala Gly Ser Glu Ser Ala Val Phe His Gly Phe Phe Ser
    530             535             540

Met Pro Glu Met Arg Cys Gln Lys Leu Glu Leu Leu Leu Met Asp Asn
545             550             555             560

Leu Arg Asp Lys Leu Arg Pro Ile Ile Ile Ser Met Asn Tyr Ser Leu
            565             570             575

Pro Leu Arg Met Pro Asp Arg Pro Arg Leu Gly Leu Arg Ser Leu Asp
            580             585             590

Ala Tyr Pro Ile Leu Asn Gln Ala Gln Ala Leu Glu Asn His Thr Glu
            595             600             605

Val Gln Phe Gln Lys Glu Cys Gly Pro Asp Asn Lys Cys Glu Ser Asn
    610             615             620

Leu Gln Met Arg Ala Ala Phe Val Ser Glu Gln Gln Gln Lys Leu Ser
625             630             635             640

Arg Leu Gln Tyr Ser Arg Asp Val Arg Lys Leu Leu Leu Ser Ile Asn
            645             650             655

Val Thr Asn Thr Arg Thr Ser Glu Arg Ser Gly Glu Asp Ala His Glu
            660             665             670

Ala Leu Leu Thr Leu Val Val Pro Pro Ala Leu Leu Leu Ser Ser Val
        675             680             685

Arg Pro Pro Gly Ala Cys Gln Ala Asn Glu Thr Ile Phe Cys Glu Leu
    690             695             700

Gly Asn Pro Phe Lys Arg Asn Gln Arg Met Glu Leu Leu Ile Ala Phe
705             710             715             720

Glu Val Ile Gly Val Thr Leu His Thr Arg Asp Leu Gln Val Gln Leu
            725             730             735

Gln Leu Ser Thr Ser Ser His Gln Asp Asn Leu Trp Pro Met Ile Leu
        740             745             750

Thr Leu Leu Val Asp Tyr Thr Leu Gln Thr Ser Leu Ser Met Val Asn
        755             760             765

His Arg Leu Gln Ser Phe Phe Gly Gly Thr Val Met Gly Glu Ser Gly
    770             775             780

Met Lys Thr Val Glu Asp Val Gly Ser Pro Leu Lys Tyr Glu Phe Gln
785             790             795             800
```

-continued

```
Val Gly Pro Met Gly Glu Gly Leu Val Gly Leu Gly Thr Leu Val Leu
            805                 810                 815

Gly Leu Glu Trp Pro Tyr Glu Val Ser Asn Gly Lys Trp Leu Leu Tyr
            820                 825                 830

Pro Thr Glu Ile Thr Val His Gly Asn Gly Ser Trp Pro Cys Arg Pro
            835                 840                 845

Pro Gly Asp Leu Ile Asn Pro Leu Asn Leu Thr Leu Ser Asp Pro Gly
        850                 855                 860

Asp Arg Pro Ser Ser Pro Gln Arg Arg Arg Gln Leu Asp Pro Gly
865                 870                 875                 880

Gly Gly Gln Gly Pro Pro Pro Val Thr Leu Ala Ala Ala Lys Lys Ala
            885                 890                 895

Lys Ser Glu Thr Val Leu Thr Cys Ala Thr Gly Arg Ala His Cys Val
            900                 905                 910

Trp Leu Glu Cys Pro Ile Pro Asp Ala Pro Val Val Thr Asn Val Thr
            915                 920                 925

Val Lys Ala Arg Val Trp Asn Ser Thr Phe Ile Glu Asp Tyr Arg Asp
        930                 935                 940

Phe Asp Arg Val Arg Val Asn Gly Trp Ala Thr Leu Phe Leu Arg Thr
945                 950                 955                 960

Ser Ile Pro Thr Ile Asn Met Glu Asn Lys Thr Thr Trp Phe Ser Val
            965                 970                 975

Asp Ile Asp Ser Glu Leu Val Glu Glu Leu Pro Ala Glu Ile Glu Leu
            980                 985                 990

Trp Leu Val Leu Val Ala Val Gly  Ala Gly Leu Leu Leu  Leu Gly Leu
        995                 1000                 1005

Ile Ile  Leu Leu Leu Trp Lys  Cys Gly Phe Phe Lys  Arg Ala Arg
    1010                 1015                 1020

Thr Arg  Ala Leu Tyr Glu Ala  Lys Arg Gln Lys Ala  Glu Met Lys
    1025                 1030                 1035

Ser Gln  Pro Ser Glu Thr Glu  Arg Leu Thr Asp Asp  Tyr
    1040                 1045                 1050

<210> SEQ ID NO 64
<211> LENGTH: 798
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110
```

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
        130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
                180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
        210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
        260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
        290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
                340                 345                 350

Pro Lys Ser Ala Val Gly Thr Leu Ser Ala Asn Ser Ser Asn Val Ile
        355                 360                 365

Gln Leu Ile Ile Asp Ala Tyr Asn Ser Leu Ser Ser Glu Val Ile Leu
        370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430

Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
        450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
        500                 505                 510

Asp Ala Tyr Cys Arg Lys Glu Asn Ser Ser Glu Ile Cys Ser Asn Asn
        515                 520                 525

-continued

```
Gly Glu Cys Val Cys Gly Gln Cys Val Cys Arg Lys Arg Asp Asn Thr
    530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
                595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
                660                 665                 670

Val Glu Ser Arg Asp Lys Leu Pro Gln Pro Val Gln Pro Asp Pro Val
                675                 680                 685

Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
                740                 745                 750

Leu Leu Met Ile Ile His Asp Arg Arg Glu Phe Ala Lys Phe Glu Lys
    755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795
```

<210> SEQ ID NO 65
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Met Glu Ser Lys Ala Leu Leu Val Leu Thr Leu Ala Val Trp Leu Gln
1                   5                   10                  15

Ser Leu Thr Ala Ser Arg Gly Gly Val Ala Ala Ala Asp Gln Arg Arg
                20                  25                  30

Asp Phe Ile Asp Ile Glu Ser Lys Phe Ala Leu Arg Thr Pro Glu Asp
                35                  40                  45

Thr Ala Glu Asp Thr Cys His Leu Ile Pro Gly Val Ala Glu Ser Val
    50                  55                  60

Ala Thr Cys His Phe Asn His Ser Ser Lys Thr Phe Met Val Ile His
65                  70                  75                  80

Gly Trp Thr Val Thr Gly Met Tyr Glu Ser Trp Val Pro Lys Leu Val
                85                  90                  95
```

-continued

```
Ala Ala Leu Tyr Lys Arg Glu Pro Asp Ser Asn Val Ile Val Val Asp
            100                 105                 110

Trp Leu Ser Arg Ala Gln Glu His Tyr Pro Val Ser Ala Gly Tyr Thr
            115                 120                 125

Lys Leu Val Gly Gln Asp Val Ala Arg Phe Ile Asn Trp Met Glu Glu
        130                 135                 140

Glu Phe Asn Tyr Pro Leu Asp Asn Val His Leu Leu Gly Tyr Ser Leu
145                 150                 155                 160

Gly Ala His Ala Ala Gly Ile Ala Gly Ser Leu Thr Asn Lys Lys Val
                165                 170                 175

Asn Arg Ile Thr Gly Leu Asp Pro Ala Gly Pro Asn Phe Glu Tyr Ala
                180                 185                 190

Glu Ala Pro Ser Arg Leu Ser Pro Asp Asp Ala Asp Phe Val Asp Val
                195                 200                 205

Leu His Thr Phe Thr Arg Gly Ser Pro Gly Arg Ser Ile Gly Ile Gln
        210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
                245                 250                 255

Leu Gly Asp Val Asp Gln Leu Val Lys Cys Ser His Glu Arg Ser Ile
                260                 265                 270

His Leu Phe Ile Asp Ser Leu Leu Asn Glu Glu Asn Pro Ser Lys Ala
        275                 280                 285

Tyr Arg Cys Ser Ser Lys Glu Ala Phe Glu Lys Gly Leu Cys Leu Ser
        290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
                325                 330                 335

Pro Tyr Lys Val Phe His Tyr Gln Val Lys Ile His Phe Ser Gly Thr
                340                 345                 350

Glu Ser Glu Thr His Thr Asn Gln Ala Phe Glu Ile Ser Leu Tyr Gly
            355                 360                 365

Thr Val Ala Glu Ser Glu Asn Ile Pro Phe Thr Leu Pro Glu Val Ser
    370                 375                 380

Thr Asn Lys Thr Tyr Ser Phe Leu Ile Tyr Thr Glu Val Asp Ile Gly
385                 390                 395                 400

Glu Leu Leu Met Leu Lys Leu Lys Trp Lys Ser Asp Ser Tyr Phe Ser
                405                 410                 415

Trp Ser Asp Trp Trp Ser Ser Pro Gly Phe Ala Ile Gln Lys Ile Arg
            420                 425                 430

Val Lys Ala Gly Glu Thr Gln Lys Lys Val Ile Phe Cys Ser Arg Glu
            435                 440                 445

Lys Val Ser His Leu Gln Lys Gly Lys Ala Pro Ala Val Phe Val Lys
        450                 455                 460

Cys His Asp Lys Ser Leu Asn Lys Lys Ser Gly
465                 470                 475
```

```
<210> SEQ ID NO 66
<211> LENGTH: 357
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 66

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
                20                  25                  30

Gly Lys Tyr Ser Arg Glu Lys Asn Gln Pro Lys Pro Ser Pro Lys Arg
            35                  40                  45

Glu Ser Gly Glu Glu Phe Arg Met Glu Lys Leu Asn Gln Leu Trp Glu
        50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
                100                 105                 110

Arg Asn Leu Asn Val Ile Leu Ala Lys Tyr Gly Leu Asp Gly Lys Lys
            115                 120                 125

Asp Ala Arg Gln Val Thr Ser Asn Ser Leu Ser Gly Thr Gln Glu Asp
        130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
                180                 185                 190

Leu Ser Arg Thr Glu Glu Ile His Glu Asn Val Ile Ser Pro Ser Asp
            195                 200                 205

Leu Ser Asp Ile Lys Gly Ser Val Leu His Ser Arg His Thr Glu Leu
        210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
                245                 250                 255

Val Ile Asp Leu Trp Asp Leu Ala Gln Ser Ala Asn Leu Thr Asp Lys
                260                 265                 270

Glu Leu Glu Ala Phe Arg Glu Glu Leu Lys His Phe Glu Ala Lys Ile
            275                 280                 285

Glu Lys His Asn His Tyr Gln Lys Gln Leu Glu Ile Ala His Glu Lys
        290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
                340                 345                 350

Arg His Asn Glu Leu
            355

<210> SEQ ID NO 67
<211> LENGTH: 431
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
            20                  25                  30

Cys Leu Asn Gly Gly Thr Cys Val Ser Asn Lys Tyr Phe Ser Asn Ile
        35                  40                  45

His Trp Cys Asn Cys Pro Lys Lys Phe Gly Gln His Cys Glu Ile
    50                  55                  60

Asp Lys Ser Lys Thr Cys Tyr Glu Gly Asn Gly His Phe Tyr Arg Gly
65                  70                  75                  80

Lys Ala Ser Thr Asp Thr Met Gly Arg Pro Cys Leu Pro Trp Asn Ser
                85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125

Arg Arg Pro Trp Cys Tyr Val Gln Val Gly Leu Lys Pro Leu Val Gln
    130                 135                 140

Glu Cys Met Val His Asp Cys Ala Asp Gly Lys Lys Pro Ser Ser Pro
145                 150                 155                 160

Pro Glu Glu Leu Lys Phe Gln Cys Gly Gln Lys Thr Leu Arg Pro Arg
                165                 170                 175

Phe Lys Ile Ile Gly Gly Glu Phe Thr Thr Ile Glu Asn Gln Pro Trp
            180                 185                 190

Phe Ala Ala Ile Tyr Arg Arg His Arg Gly Gly Ser Val Thr Tyr Val
        195                 200                 205

Cys Gly Gly Ser Leu Ile Ser Pro Cys Trp Val Ile Ser Ala Thr His
    210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                245                 250                 255

Glu Asn Leu Ile Leu His Lys Asp Tyr Ser Ala Asp Thr Leu Ala His
            260                 265                 270

His Asn Asp Ile Ala Leu Leu Lys Ile Arg Ser Lys Glu Gly Arg Cys
        275                 280                 285

Ala Gln Pro Ser Arg Thr Ile Gln Thr Ile Cys Leu Pro Ser Met Tyr
    290                 295                 300

Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
                325                 330                 335

Val Lys Leu Ile Ser His Arg Glu Cys Gln Gln Pro His Tyr Tyr Gly
            340                 345                 350

Ser Glu Val Thr Thr Lys Met Leu Cys Ala Ala Asp Pro Gln Trp Lys
        355                 360                 365

Thr Asp Ser Cys Gln Gly Asp Ser Gly Gly Pro Leu Val Cys Ser Leu
    370                 375                 380

Gln Gly Arg Met Thr Leu Thr Gly Ile Val Ser Trp Gly Arg Gly Cys

-continued

```
385              390              395              400

Ala Leu Lys Asp Lys Pro Gly Val Tyr Thr Arg Val Ser His Phe Leu
             405              410              415

Pro Trp Ile Arg Ser His Thr Lys Glu Glu Asn Gly Leu Ala Leu
             420              425              430

<210> SEQ ID NO 68
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Gly His Pro Pro Leu Leu Pro Leu Leu Leu Leu His Thr Cys
1                5                10               15

Val Pro Ala Ser Trp Gly Leu Arg Cys Met Gln Cys Lys Thr Asn Gly
             20               25               30

Asp Cys Arg Val Glu Glu Cys Ala Leu Gly Gln Asp Leu Cys Arg Thr
         35               40               45

Thr Ile Val Arg Leu Trp Glu Glu Gly Glu Glu Leu Glu Leu Val Glu
     50               55               60

Lys Ser Cys Thr His Ser Glu Lys Thr Asn Arg Thr Leu Ser Tyr Arg
65               70               75               80

Thr Gly Leu Lys Ile Thr Ser Leu Thr Glu Val Val Cys Gly Leu Asp
             85               90               95

Leu Cys Asn Gln Gly Asn Ser Gly Arg Ala Val Thr Tyr Ser Arg Ser
             100              105              110

Arg Tyr Leu Glu Cys Ile Ser Cys Gly Ser Ser Asp Met Ser Cys Glu
             115              120              125

Arg Gly Arg His Gln Ser Leu Gln Cys Arg Ser Pro Glu Glu Gln Cys
         130              135              140

Leu Asp Val Val Thr His Trp Ile Gln Glu Gly Glu Glu Gly Arg Pro
145              150              155              160

Lys Asp Asp Arg His Leu Arg Gly Cys Gly Tyr Leu Pro Gly Cys Pro
             165              170              175

Gly Ser Asn Gly Phe His Asn Asn Asp Thr Phe His Phe Leu Lys Cys
             180              185              190

Cys Asn Thr Thr Lys Cys Asn Glu Gly Pro Ile Leu Glu Leu Glu Asn
         195              200              205

Leu Pro Gln Asn Gly Arg Gln Cys Tyr Ser Cys Lys Gly Asn Ser Thr
     210              215              220

His Gly Cys Ser Ser Glu Glu Thr Phe Leu Ile Asp Cys Arg Gly Pro
225              230              235              240

Met Asn Gln Cys Leu Val Ala Thr Gly Thr His Glu Pro Lys Asn Gln
             245              250              255

Ser Tyr Met Val Arg Gly Cys Ala Thr Ala Ser Met Cys Gln His Ala
             260              265              270

His Leu Gly Asp Ala Phe Ser Met Asn His Ile Asp Val Ser Cys Cys
         275              280              285

Thr Lys Ser Gly Cys Asn His Pro Asp Leu Asp Val Gln Tyr Arg Ser
     290              295              300

Gly Ala Ala Pro Gln Pro Gly Pro Ala His Leu Ser Leu Thr Ile Thr
305              310              315              320
```

```
Leu Leu Met Thr Ala Arg Leu Trp Gly Gly Thr Leu Leu Trp Thr
            325                 330                 335

<210> SEQ ID NO 69
<211> LENGTH: 3460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Glu Arg Ser Gly Trp Ala Arg Gln Thr Phe Leu Leu Ala Leu Leu
1               5                   10                  15

Leu Gly Ala Thr Leu Arg Ala Arg Ala Ala Ala Gly Tyr Tyr Pro Arg
            20                  25                  30

Phe Ser Pro Phe Phe Phe Leu Cys Thr His His Gly Glu Leu Glu Gly
            35                  40                  45

Asp Gly Glu Gln Gly Glu Val Leu Ile Ser Leu His Ile Ala Gly Asn
    50                  55                  60

Pro Thr Tyr Tyr Val Pro Gly Gln Glu Tyr His Val Thr Ile Ser Thr
65                  70                  75                  80

Ser Thr Phe Phe Asp Gly Leu Leu Val Thr Gly Leu Tyr Thr Ser Thr
            85                  90                  95

Ser Val Gln Ala Ser Gln Ser Ile Gly Gly Ser Ser Ala Phe Gly Phe
            100                 105                 110

Gly Ile Met Ser Asp His Gln Phe Gly Asn Gln Phe Met Cys Ser Val
            115                 120                 125

Val Ala Ser His Val Ser His Leu Pro Thr Thr Asn Leu Ser Phe Ile
    130                 135                 140

Trp Ile Ala Pro Pro Ala Gly Thr Gly Cys Val Asn Phe Met Ala Thr
145                 150                 155                 160

Ala Thr His Arg Gly Gln Val Ile Phe Lys Asp Ala Leu Ala Gln Gln
            165                 170                 175

Leu Cys Glu Gln Gly Ala Pro Thr Asp Val Thr Val His Pro His Leu
            180                 185                 190

Ala Glu Ile His Ser Asp Ser Ile Ile Leu Arg Asp Asp Phe Asp Ser
            195                 200                 205

Tyr His Gln Leu Gln Leu Asn Pro Asn Ile Trp Val Glu Cys Asn Asn
    210                 215                 220

Cys Glu Thr Gly Glu Gln Cys Gly Ala Ile Met His Gly Asn Ala Val
225                 230                 235                 240

Thr Phe Cys Glu Pro Tyr Gly Pro Arg Glu Leu Ile Thr Thr Gly Leu
            245                 250                 255

Asn Thr Thr Thr Ala Ser Val Leu Gln Phe Ser Ile Gly Ser Gly Ser
            260                 265                 270

Cys Arg Phe Ser Tyr Ser Asp Pro Ser Ile Ile Val Leu Tyr Ala Lys
            275                 280                 285

Asn Asn Ser Ala Asp Trp Ile Gln Leu Glu Lys Ile Arg Ala Pro Ser
    290                 295                 300

Asn Val Ser Thr Ile Ile His Ile Leu Tyr Leu Pro Glu Asp Ala Lys
305                 310                 315                 320

Gly Glu Asn Val Gln Phe Gln Trp Lys Gln Glu Asn Leu Arg Val Gly
            325                 330                 335

Glu Val Tyr Glu Ala Cys Trp Ala Leu Asp Asn Ile Leu Ile Ile Asn
            340                 345                 350
```

Ser Ala His Arg Gln Val Val Leu Glu Asp Ser Leu Asp Pro Val Asp
        355                 360                 365

Thr Gly Asn Trp Leu Phe Phe Pro Gly Ala Thr Val Lys His Ser Cys
        370                 375                 380

Gln Ser Asp Gly Asn Ser Ile Tyr Phe His Gly Asn Glu Gly Ser Glu
385                     390                 395                 400

Phe Asn Phe Ala Thr Thr Arg Asp Val Asp Leu Ser Thr Glu Asp Ile
                405                 410                 415

Gln Glu Gln Trp Ser Glu Glu Phe Glu Ser Gln Pro Thr Gly Trp Asp
                420                 425                 430

Val Leu Gly Ala Val Ile Gly Thr Glu Cys Gly Thr Ile Glu Ser Gly
                435                 440                 445

Leu Ser Met Val Phe Leu Lys Asp Gly Glu Arg Lys Leu Cys Thr Pro
        450                 455                 460

Ser Met Asp Thr Thr Gly Tyr Gly Asn Leu Arg Phe Tyr Phe Val Met
465                     470                 475                 480

Gly Gly Ile Cys Asp Pro Gly Asn Ser His Glu Asn Asp Ile Ile Leu
                485                 490                 495

Tyr Ala Lys Ile Glu Gly Arg Lys Glu His Ile Thr Leu Asp Thr Leu
                500                 505                 510

Ser Tyr Ser Ser Tyr Lys Val Pro Ser Leu Val Ser Val Val Ile Asn
        515                 520                 525

Pro Glu Leu Gln Thr Pro Ala Thr Lys Phe Cys Leu Arg Gln Lys Asn
        530                 535                 540

His Gln Gly His Asn Arg Asn Val Trp Ala Val Asp Phe Phe His Val
545                     550                 555                 560

Leu Pro Val Leu Pro Ser Thr Met Ser His Met Ile Gln Phe Ser Ile
                565                 570                 575

Asn Leu Gly Cys Gly Thr His Gln Pro Gly Asn Ser Val Ser Leu Glu
                580                 585                 590

Phe Ser Thr Asn His Gly Arg Ser Trp Ser Leu Leu His Thr Glu Cys
        595                 600                 605

Leu Pro Glu Ile Cys Ala Gly Pro His Leu Pro His Ser Thr Val Tyr
        610                 615                 620

Ser Ser Glu Asn Tyr Ser Gly Trp Asn Arg Ile Thr Ile Pro Leu Pro
625                     630                 635                 640

Asn Ala Ala Leu Thr Arg Asn Thr Arg Ile Arg Trp Arg Gln Thr Gly
                645                 650                 655

Pro Ile Leu Gly Asn Met Trp Ala Ile Asp Asn Val Tyr Ile Gly Pro
                660                 665                 670

Ser Cys Leu Lys Phe Cys Ser Gly Arg Gly Gln Cys Thr Arg His Gly
        675                 680                 685

Cys Lys Cys Asp Pro Gly Phe Ser Gly Pro Ala Cys Glu Met Ala Ser
        690                 695                 700

Gln Thr Phe Pro Met Phe Ile Ser Glu Ser Phe Gly Ser Ser Arg Leu
705                     710                 715                 720

Ser Ser Tyr His Asn Phe Tyr Ser Ile Arg Gly Ala Glu Val Ser Phe
                725                 730                 735

Gly Cys Gly Val Leu Ala Ser Gly Lys Ala Leu Val Phe Asn Lys Asp
                740                 745                 750

Gly Arg Arg Gln Leu Ile Thr Ser Phe Leu Asp Ser Ser Gln Ser Arg
        755                 760                 765

```
Phe Leu Gln Phe Thr Leu Arg Leu Gly Ser Lys Ser Val Leu Ser Thr
    770                 775                 780

Cys Arg Ala Pro Asp Gln Pro Gly Glu Gly Val Leu Leu His Tyr Ser
785                 790                 795                 800

Tyr Asp Asn Gly Ile Thr Trp Lys Leu Leu Glu His Tyr Ser Tyr Leu
                805                 810                 815

Ser Tyr His Glu Pro Arg Ile Ile Ser Val Glu Leu Pro Gly Asp Ala
            820                 825                 830

Lys Gln Phe Gly Ile Gln Phe Arg Trp Trp Gln Pro Tyr His Ser Ser
            835                 840                 845

Gln Arg Glu Asp Val Trp Ala Ile Asp Glu Ile Ile Met Thr Ser Val
    850                 855                 860

Leu Phe Asn Ser Ile Ser Leu Asp Phe Thr Asn Leu Val Glu Val Thr
865                 870                 875                 880

Gln Ser Leu Gly Phe Tyr Leu Gly Asn Val Gln Pro Tyr Cys Gly His
                885                 890                 895

Asp Trp Thr Leu Cys Phe Thr Gly Asp Ser Lys Leu Ala Ser Ser Met
            900                 905                 910

Arg Tyr Val Glu Thr Gln Ser Met Gln Ile Gly Ala Ser Tyr Met Ile
            915                 920                 925

Gln Phe Ser Leu Val Met Gly Cys Gly Gln Lys Tyr Thr Pro His Met
    930                 935                 940

Asp Asn Gln Val Lys Leu Glu Tyr Ser Thr Asn His Gly Leu Thr Trp
945                 950                 955                 960

His Leu Val Gln Glu Glu Cys Leu Pro Ser Met Pro Ser Cys Gln Glu
                965                 970                 975

Phe Thr Ser Ala Ser Ile Tyr His Ala Ser Glu Phe Thr Gln Trp Arg
                980                 985                 990

Arg Val Ile Val Leu Leu Pro Gln Lys Thr Trp Ser Ser Ala Thr Arg
            995                 1000                1005

Phe Arg Trp Ser Gln Ser Tyr Tyr Thr Ala Gln Asp Glu Trp Ala
    1010                1015                1020

Leu Asp Ser Ile Tyr Ile Gly Gln Gln Cys Pro Asn Met Cys Ser
    1025                1030                1035

Gly His Gly Ser Cys Asp His Gly Ile Cys Arg Cys Asp Gln Gly
    1040                1045                1050

Tyr Gln Gly Thr Glu Cys His Pro Glu Ala Ala Leu Pro Ser Thr
    1055                1060                1065

Ile Met Ser Asp Phe Glu Asn Gln Asn Gly Trp Glu Ser Asp Trp
    1070                1075                1080

Gln Glu Val Ile Gly Gly Glu Ile Val Lys Pro Glu Gln Gly Cys
    1085                1090                1095

Gly Val Ile Ser Ser Gly Ser Ser Leu Tyr Phe Ser Lys Ala Gly
    1100                1105                1110

Lys Arg Gln Leu Val Ser Trp Asp Leu Asp Thr Ser Trp Val Asp
    1115                1120                1125

Phe Val Gln Phe Tyr Ile Gln Ile Gly Gly Glu Ser Ala Ser Cys
    1130                1135                1140

Asn Lys Pro Asp Ser Arg Glu Glu Gly Val Leu Leu Gln Tyr Ser
    1145                1150                1155

Asn Asn Gly Gly Ile Gln Trp His Leu Leu Ala Glu Met Tyr Phe
    1160                1165                1170

Ser Asp Phe Ser Lys Pro Arg Phe Val Tyr Leu Glu Leu Pro Ala
```

-continued

```
        1175                1180                1185

Ala Ala Lys Thr Pro Cys Thr Arg Phe Arg Trp Trp Gln Pro Val
    1190                1195                1200

Phe Ser Gly Glu Asp Tyr Asp Gln Trp Ala Val Asp Asp Ile Ile
    1205                1210                1215

Ile Leu Ser Glu Lys Gln Lys Gln Ile Ile Pro Val Ile Asn Pro
    1220                1225                1230

Thr Leu Pro Gln Asn Phe Tyr Glu Lys Pro Ala Phe Asp Tyr Pro
    1235                1240                1245

Met Asn Gln Met Ser Val Trp Leu Met Leu Ala Asn Glu Gly Met
    1250                1255                1260

Val Lys Asn Glu Thr Phe Cys Ala Ala Thr Pro Ser Ala Met Ile
    1265                1270                1275

Phe Gly Lys Ser Asp Gly Asp Arg Phe Ala Val Thr Arg Asp Leu
    1280                1285                1290

Thr Leu Lys Pro Gly Tyr Val Leu Gln Phe Lys Leu Asn Ile Gly
    1295                1300                1305

Cys Ala Asn Gln Phe Ser Ser Thr Ala Pro Val Leu Leu Gln Tyr
    1310                1315                1320

Ser His Asp Ala Gly Met Ser Trp Phe Leu Val Lys Glu Gly Cys
    1325                1330                1335

Tyr Pro Ala Ser Ala Gly Lys Gly Cys Glu Gly Asn Ser Arg Glu
    1340                1345                1350

Leu Ser Glu Pro Thr Met Tyr His Thr Gly Asp Phe Glu Glu Trp
    1355                1360                1365

Thr Arg Ile Thr Ile Val Ile Pro Arg Ser Leu Ala Ser Ser Lys
    1370                1375                1380

Thr Arg Phe Arg Trp Ile Gln Glu Ser Ser Ser Gln Lys Asn Val
    1385                1390                1395

Pro Pro Phe Gly Leu Asp Gly Val Tyr Ile Ser Glu Pro Cys Pro
    1400                1405                1410

Ser Tyr Cys Ser Gly His Gly Asp Cys Ile Ser Gly Val Cys Phe
    1415                1420                1425

Cys Asp Leu Gly Tyr Thr Ala Ala Gln Gly Thr Cys Val Ser Asn
    1430                1435                1440

Val Pro Asn His Asn Glu Met Phe Asp Arg Phe Glu Gly Lys Leu
    1445                1450                1455

Ser Pro Leu Trp Tyr Lys Ile Thr Gly Ala Gln Val Gly Thr Gly
    1460                1465                1470

Cys Gly Thr Leu Asn Asp Gly Lys Ser Leu Tyr Phe Asn Gly Pro
    1475                1480                1485

Gly Lys Arg Glu Ala Arg Thr Val Pro Leu Asp Thr Arg Asn Ile
    1490                1495                1500

Arg Leu Val Gln Phe Tyr Ile Gln Ile Gly Ser Lys Thr Ser Gly
    1505                1510                1515

Ile Thr Cys Ile Lys Pro Arg Thr Arg Asn Glu Gly Leu Ile Val
    1520                1525                1530

Gln Tyr Ser Asn Asp Asn Gly Ile Leu Trp His Leu Leu Arg Glu
    1535                1540                1545

Leu Asp Phe Met Ser Phe Leu Glu Pro Gln Ile Ile Ser Ile Asp
    1550                1555                1560

Leu Pro Gln Asp Ala Lys Thr Pro Ala Thr Ala Phe Arg Trp Trp
    1565                1570                1575
```

-continued

```
Gln Pro  Gln His Gly Lys His  Ser Ala Gln Trp Ala  Leu Asp Asp
    1580             1585             1590

Val Leu  Ile Gly Met Asn Asp  Ser Ser Gln Thr Gly  Phe Gln Asp
    1595             1600             1605

Lys Phe  Asp Gly Ser Ile Asp  Leu Gln Ala Asn Trp  Tyr Arg Ile
    1610             1615             1620

Gln Gly  Gly Gln Val Asp Ile  Asp Cys Leu Ser Met  Asp Thr Ala
    1625             1630             1635

Leu Ile  Phe Thr Glu Asn Ile  Gly Lys Pro Arg Tyr  Ala Glu Thr
    1640             1645             1650

Trp Asp  Phe His Val Ser Ala  Ser Thr Phe Leu Gln  Phe Glu Met
    1655             1660             1665

Ser Met  Gly Cys Ser Lys Pro  Phe Ser Asn Ser His  Ser Val Gln
    1670             1675             1680

Leu Gln  Tyr Ser Leu Asn Asn  Gly Lys Asp Trp His  Leu Val Thr
    1685             1690             1695

Glu Glu  Cys Val Pro Pro Thr  Ile Gly Cys Leu His  Tyr Thr Glu
    1700             1705             1710

Ser Ser  Ile Tyr Thr Ser Glu  Arg Phe Gln Asn Trp  Lys Arg Ile
    1715             1720             1725

Thr Val  Tyr Leu Pro Leu Ser  Thr Ile Ser Pro Arg  Thr Arg Phe
    1730             1735             1740

Arg Trp  Ile Gln Ala Asn Tyr  Thr Val Gly Ala Asp  Ser Trp Ala
    1745             1750             1755

Ile Asp  Asn Val Val Leu Ala  Ser Gly Cys Pro Trp  Met Cys Ser
    1760             1765             1770

Gly Arg  Gly Ile Cys Asp Ala  Gly Arg Cys Val Cys  Asp Arg Gly
    1775             1780             1785

Phe Gly  Gly Pro Tyr Cys Val  Pro Val Val Pro Leu  Pro Ser Ile
    1790             1795             1800

Leu Lys  Asp Asp Phe Asn Gly  Asn Leu His Pro Asp  Leu Trp Pro
    1805             1810             1815

Glu Val  Tyr Gly Ala Glu Arg  Gly Asn Leu Asn Gly  Glu Thr Ile
    1820             1825             1830

Lys Ser  Gly Thr Ser Leu Ile  Phe Lys Gly Glu Gly  Leu Arg Met
    1835             1840             1845

Leu Ile  Ser Arg Asp Leu Asp  Cys Thr Asn Thr Met  Tyr Val Gln
    1850             1855             1860

Phe Ser  Leu Arg Phe Ile Ala  Lys Ser Thr Pro Glu  Arg Ser His
    1865             1870             1875

Ser Ile  Leu Leu Gln Phe Ser  Ile Ser Gly Gly Ile  Thr Trp His
    1880             1885             1890

Leu Met  Asp Glu Phe Tyr Phe  Pro Gln Thr Thr Asn  Ile Leu Phe
    1895             1900             1905

Ile Asn  Val Pro Leu Pro Tyr  Thr Ala Gln Thr Asn  Ala Thr Arg
    1910             1915             1920

Phe Arg  Leu Trp Gln Pro Tyr  Asn Asn Gly Lys Lys  Glu Glu Ile
    1925             1930             1935

Trp Ile  Val Asp Asp Phe Ile  Ile Asp Gly Asn Asn  Val Asn Asn
    1940             1945             1950

Pro Val  Met Leu Leu Asp Thr  Phe Asp Phe Gly Pro  Arg Glu Asp
    1955             1960             1965
```

```
Asn Trp Phe Phe Tyr Pro Gly  Gly Asn Ile Gly Leu  Tyr Cys Pro
    1970             1975              1980

Tyr Ser Ser Lys Gly Ala Pro  Glu Glu Asp Ser Ala  Met Val Phe
    1985             1990              1995

Val Ser Asn Glu Val Gly Glu  His Ser Ile Thr Thr  Arg Asp Leu
    2000             2005              2010

Asn Val Asn Glu Asn Thr Ile  Ile Gln Phe Glu Ile  Asn Val Gly
    2015             2020              2025

Cys Ser Thr Asp Ser Ser Ser  Ala Asp Pro Val Arg  Leu Glu Phe
    2030             2035              2040

Ser Arg Asp Phe Gly Ala Thr  Trp His Leu Leu Leu  Pro Leu Cys
    2045             2050              2055

Tyr His Ser Ser Ser His Val  Ser Ser Leu Cys Ser  Thr Glu His
    2060             2065              2070

His Pro Ser Ser Thr Tyr Tyr  Ala Gly Thr Met Gln  Gly Trp Arg
    2075             2080              2085

Arg Glu Val Val His Phe Gly  Lys Leu His Leu Cys  Gly Ser Val
    2090             2095              2100

Arg Phe Arg Trp Tyr Gln Gly  Phe Tyr Pro Ala Gly  Ser Gln Pro
    2105             2110              2115

Val Thr Trp Ala Ile Asp Asn  Val Tyr Ile Gly Pro  Gln Cys Glu
    2120             2125              2130

Glu Met Cys Asn Gly Gln Gly  Ser Cys Ile Asn Gly  Thr Lys Cys
    2135             2140              2145

Ile Cys Asp Pro Gly Tyr Ser  Gly Pro Thr Cys Lys  Ile Ser Thr
    2150             2155              2160

Lys Asn Pro Asp Phe Leu Lys  Asp Asp Phe Glu Gly  Gln Leu Glu
    2165             2170              2175

Ser Asp Arg Phe Leu Leu Met  Ser Gly Gly Lys Pro  Ser Arg Lys
    2180             2185              2190

Cys Gly Ile Leu Ser Ser Gly  Asn Asn Leu Phe Phe  Asn Glu Asp
    2195             2200              2205

Gly Leu Arg Met Leu Met Thr  Arg Asp Leu Asp Leu  Ser His Ala
    2210             2215              2220

Arg Phe Val Gln Phe Phe Met  Arg Leu Gly Cys Gly  Lys Gly Val
    2225             2230              2235

Pro Asp Pro Arg Ser Gln Pro  Val Leu Leu Gln Tyr  Ser Leu Asn
    2240             2245              2250

Gly Gly Leu Ser Trp Ser Leu  Leu Gln Glu Phe Leu  Phe Ser Asn
    2255             2260              2265

Ser Ser Asn Val Gly Arg Tyr  Ile Ala Leu Glu Ile  Pro Leu Lys
    2270             2275              2280

Ala Arg Ser Gly Ser Thr Arg  Leu Arg Trp Trp Gln  Pro Ser Glu
    2285             2290              2295

Asn Gly His Phe Tyr Ser Pro  Trp Val Ile Asp Gln  Ile Leu Ile
    2300             2305              2310

Gly Gly Asn Ile Ser Gly Asn  Thr Val Leu Glu Asp  Asp Phe Thr
    2315             2320              2325

Thr Leu Asp Ser Arg Lys Trp  Leu Leu His Pro Gly  Gly Thr Lys
    2330             2335              2340

Met Pro Val Cys Gly Ser Thr  Gly Asp Ala Leu Val  Phe Ile Glu
    2345             2350              2355

Lys Ala Ser Thr Arg Tyr Val  Val Ser Thr Asp Val  Ala Val Asn
```

```
        2360              2365              2370

Glu Asp Ser Phe Leu Gln Ile Asp Phe Ala Ala Ser Cys Ser Val
    2375              2380              2385

Thr Asp Ser Cys Tyr Ala Ile Glu Leu Glu Tyr Ser Val Asp Leu
    2390              2395              2400

Gly Leu Ser Trp His Pro Leu Val Arg Asp Cys Leu Pro Thr Asn
    2405              2410              2415

Val Glu Cys Ser Arg Tyr His Leu Gln Arg Ile Leu Val Ser Asp
    2420              2425              2430

Thr Phe Asn Lys Trp Thr Arg Ile Thr Leu Pro Leu Pro Pro Tyr
    2435              2440              2445

Thr Arg Ser Gln Ala Thr Arg Phe Arg Trp His Gln Pro Ala Pro
    2450              2455              2460

Phe Asp Lys Gln Gln Thr Trp Ala Ile Asp Asn Val Tyr Ile Gly
    2465              2470              2475

Asp Gly Cys Ile Asp Met Cys Ser Gly His Gly Arg Cys Ile Gln
    2480              2485              2490

Gly Asn Cys Val Cys Asp Glu Gln Trp Gly Gly Leu Tyr Cys Asp
    2495              2500              2505

Asp Pro Glu Thr Ser Leu Pro Thr Gln Leu Lys Asp Asn Phe Asn
    2510              2515              2520

Arg Ala Pro Ser Ser Gln Asn Trp Leu Thr Val Asn Gly Gly Lys
    2525              2530              2535

Leu Ser Thr Val Cys Gly Ala Val Ala Ser Gly Met Ala Leu His
    2540              2545              2550

Phe Ser Gly Gly Cys Ser Arg Leu Leu Val Thr Val Asp Leu Asn
    2555              2560              2565

Leu Thr Asn Ala Glu Phe Ile Gln Phe Tyr Phe Met Tyr Gly Cys
    2570              2575              2580

Leu Ile Thr Pro Asn Asn Arg Asn Gln Gly Val Leu Leu Glu Tyr
    2585              2590              2595

Ser Val Asn Gly Gly Ile Thr Trp Asn Leu Leu Met Glu Ile Phe
    2600              2605              2610

Tyr Asp Gln Tyr Ser Lys Pro Gly Phe Val Asn Ile Leu Leu Pro
    2615              2620              2625

Pro Asp Ala Lys Glu Ile Ala Thr Arg Phe Arg Trp Trp Gln Pro
    2630              2635              2640

Arg His Asp Gly Leu Asp Gln Asn Asp Trp Ala Ile Asp Asn Val
    2645              2650              2655

Leu Ile Ser Gly Ser Ala Asp Gln Arg Thr Val Met Leu Asp Thr
    2660              2665              2670

Phe Ser Ser Ala Pro Val Pro Gln His Glu Arg Ser Pro Ala Asp
    2675              2680              2685

Ala Gly Pro Val Gly Arg Ile Ala Phe Asp Met Phe Met Glu Asp
    2690              2695              2700

Lys Thr Ser Val Asn Glu His Trp Leu Phe His Asp Asp Cys Thr
    2705              2710              2715

Val Glu Arg Phe Cys Asp Ser Pro Asp Gly Val Met Leu Cys Gly
    2720              2725              2730

Ser His Asp Gly Arg Glu Val Tyr Ala Val Thr His Asp Leu Thr
    2735              2740              2745

Pro Thr Glu Gly Trp Ile Met Gln Phe Lys Ile Ser Val Gly Cys
    2750              2755              2760
```

```
Lys Val Ser Glu Lys Ile Ala Gln Asn Gln Ile His Val Gln Tyr
    2765              2770              2775

Ser Thr Asp Phe Gly Val Ser Trp Asn Tyr Leu Val Pro Gln Cys
    2780              2785              2790

Leu Pro Ala Asp Pro Lys Cys Ser Gly Ser Val Ser Gln Pro Ser
    2795              2800              2805

Val Phe Phe Pro Thr Lys Gly Trp Lys Arg Ile Thr Tyr Pro Leu
    2810              2815              2820

Pro Glu Ser Leu Val Gly Asn Pro Val Arg Phe Arg Phe Tyr Gln
    2825              2830              2835

Lys Tyr Ser Asp Met Gln Trp Ala Ile Asp Asn Phe Tyr Leu Gly
    2840              2845              2850

Pro Gly Cys Leu Asp Asn Cys Arg Gly His Gly Asp Cys Leu Arg
    2855              2860              2865

Glu Gln Cys Ile Cys Asp Pro Gly Tyr Ser Gly Pro Asn Cys Tyr
    2870              2875              2880

Leu Thr His Thr Leu Lys Thr Phe Leu Lys Glu Arg Phe Asp Ser
    2885              2890              2895

Glu Glu Ile Lys Pro Asp Leu Trp Met Ser Leu Glu Gly Gly Ser
    2900              2905              2910

Thr Cys Thr Glu Cys Gly Ile Leu Ala Glu Asp Thr Ala Leu Tyr
    2915              2920              2925

Phe Gly Gly Ser Thr Val Arg Gln Ala Val Thr Gln Asp Leu Asp
    2930              2935              2940

Leu Arg Gly Ala Lys Phe Leu Gln Tyr Trp Gly Arg Ile Gly Ser
    2945              2950              2955

Glu Asn Asn Met Thr Ser Cys His Arg Pro Ile Cys Arg Lys Glu
    2960              2965              2970

Gly Val Leu Leu Asp Tyr Ser Thr Asp Gly Gly Ile Thr Trp Thr
    2975              2980              2985

Leu Leu His Glu Met Asp Tyr Gln Lys Tyr Ile Ser Val Arg His
    2990              2995              3000

Asp Tyr Ile Leu Leu Pro Glu Asp Ala Leu Thr Asn Thr Thr Arg
    3005              3010              3015

Leu Arg Trp Trp Gln Pro Phe Val Ile Ser Asn Gly Ile Val Val
    3020              3025              3030

Ser Gly Val Glu Arg Ala Gln Trp Ala Leu Asp Asn Ile Leu Ile
    3035              3040              3045

Gly Gly Ala Glu Ile Asn Pro Ser Gln Leu Val Asp Thr Phe Asp
    3050              3055              3060

Asp Glu Gly Thr Ser His Glu Glu Asn Trp Ser Phe Tyr Pro Asn
    3065              3070              3075

Ala Val Arg Thr Ala Gly Phe Cys Gly Asn Pro Ser Phe His Leu
    3080              3085              3090

Tyr Trp Pro Asn Lys Lys Lys Asp Lys Thr His Asn Ala Leu Ser
    3095              3100              3105

Ser Arg Glu Leu Ile Ile Gln Pro Gly Tyr Met Met Gln Phe Lys
    3110              3115              3120

Ile Val Val Gly Cys Glu Ala Thr Ser Cys Gly Asp Leu His Ser
    3125              3130              3135

Val Met Leu Glu Tyr Thr Lys Asp Ala Arg Ser Asp Ser Trp Gln
    3140              3145              3150
```

```
Leu Val  Gln Thr Gln Cys Leu  Pro Ser Ser Ser Asn  Ser Ile Gly
    3155            3160            3165

Cys Ser  Pro Phe Gln Phe His  Glu Ala Thr Ile Tyr  Asn Ser Val
    3170            3175            3180

Asn Ser  Ser Ser Trp Lys Arg  Ile Thr Ile Gln Leu  Pro Asp His
    3185            3190            3195

Val Ser  Ser Ser Ala Thr Gln  Phe Arg Trp Ile Gln  Lys Gly Glu
    3200            3205            3210

Glu Thr  Glu Lys Gln Ser Trp  Ala Ile Asp His Val  Tyr Ile Gly
    3215            3220            3225

Glu Ala  Cys Pro Lys Leu Cys  Ser Gly His Gly Tyr  Cys Thr Thr
    3230            3235            3240

Gly Ala  Ile Cys Ile Cys Asp  Glu Ser Phe Gln Gly  Asp Asp Cys
    3245            3250            3255

Ser Val  Phe Ser His Asp Leu  Pro Ser Tyr Ile Lys  Asp Asn Phe
    3260            3265            3270

Glu Ser  Ala Arg Val Thr Glu  Ala Asn Trp Glu Thr  Ile Gln Gly
    3275            3280            3285

Gly Val  Ile Gly Ser Gly Cys  Gly Gln Leu Ala Pro  Tyr Ala His
    3290            3295            3300

Gly Asp  Ser Leu Tyr Phe Asn  Gly Cys Gln Ile Arg  Gln Ala Ala
    3305            3310            3315

Thr Lys  Pro Leu Asp Leu Thr  Arg Ala Ser Lys Ile  Met Phe Val
    3320            3325            3330

Leu Gln  Ile Gly Ser Met Ser  Gln Thr Asp Ser Cys  Asn Ser Asp
    3335            3340            3345

Leu Ser  Gly Pro His Ala Val  Asp Lys Ala Val Leu  Leu Gln Tyr
    3350            3355            3360

Ser Val  Asn Asn Gly Ile Thr  Trp His Val Ile Ala  Gln His Gln
    3365            3370            3375

Pro Lys  Asp Phe Thr Gln Ala  Gln Arg Val Ser Tyr  Asn Val Pro
    3380            3385            3390

Leu Glu  Ala Arg Met Lys Gly  Val Leu Leu Arg Trp  Trp Gln Pro
    3395            3400            3405

Arg His  Asn Gly Thr Gly His  Asp Gln Trp Ala Leu  Asp His Val
    3410            3415            3420

Glu Val  Val Leu Val Ser Thr  Arg Lys Gln Asn Tyr  Met Met Asn
    3425            3430            3435

Phe Ser  Arg Gln His Gly Leu  Arg His Phe Tyr Asn  Arg Arg Arg
    3440            3445            3450

Arg Ser  Leu Arg Arg Tyr Pro
    3455            3460
```

<210> SEQ ID NO 70
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Met Gln Met Ser Pro Ala Leu Thr Cys Leu Val Leu Gly Leu Ala Leu
1               5                   10                  15

Val Phe Gly Glu Gly Ser Ala Val His His Pro Pro Ser Tyr Val Ala
            20                  25                  30
```

```
His Leu Ala Ser Asp Phe Gly Val Arg Val Phe Gln Gln Val Ala Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
            115                 120                 125

Val Gln Gly Phe Met Pro His Phe Phe Arg Leu Phe Arg Ser Thr Val
        130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
            195                 200                 205

Arg Arg Leu Phe His Lys Ser Asp Gly Ser Thr Val Ser Val Pro Met
        210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
                260                 265                 270

Leu Thr Asn Ile Leu Ser Ala Gln Leu Ile Ser His Trp Lys Gly Asn
            275                 280                 285

Met Thr Arg Leu Pro Arg Leu Leu Val Leu Pro Lys Phe Ser Leu Glu
        290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Ser Thr Ala Val Ile Val Ser Ala
            355                 360                 365

Arg Met Ala Pro Glu Glu Ile Ile Met Asp Arg Pro Phe Leu Phe Val
        370                 375                 380

Val Arg His Asn Pro Thr Gly Thr Val Leu Phe Met Gly Gln Val Met
385                 390                 395                 400

Glu Pro
```

```
<210> SEQ ID NO 71
<211> LENGTH: 638
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 71

Met Ala Gly Gly Ser Ala Thr Thr Trp Gly Tyr Pro Val Ala Leu Leu
1               5                   10                  15

Leu Leu Val Ala Thr Leu Gly Leu Gly Arg Trp Leu Gln Pro Asp Pro
                20                  25                  30

Gly Leu Pro Gly Leu Arg His Ser Tyr Asp Cys Gly Ile Lys Gly Met
            35                  40                  45

Gln Leu Leu Val Phe Pro Arg Pro Gly Gln Thr Leu Arg Phe Lys Val
    50                  55                  60

Val Asp Glu Phe Gly Asn Arg Phe Asp Val Asn Asn Cys Ser Ile Cys
65                  70                  75                  80

Tyr His Trp Val Thr Ser Arg Pro Gln Glu Pro Ala Val Phe Ser Ala
                85                  90                  95

Asp Tyr Arg Gly Cys His Val Leu Glu Lys Asp Gly Arg Phe His Leu
            100                 105                 110

Arg Val Phe Met Glu Ala Val Leu Pro Asn Gly Arg Val Asp Val Ala
        115                 120                 125

Gln Asp Ala Thr Leu Ile Cys Pro Lys Pro Asp Pro Ser Arg Thr Leu
    130                 135                 140

Asp Ser Gln Leu Ala Pro Pro Ala Met Phe Ser Val Ser Thr Pro Gln
145                 150                 155                 160

Thr Leu Ser Phe Leu Pro Thr Ser Gly His Thr Ser Gln Gly Ser Gly
                165                 170                 175

His Ala Phe Pro Ser Pro Leu Asp Pro Gly His Ser Ser Val His Pro
            180                 185                 190

Thr Pro Ala Leu Pro Ser Pro Gly Pro Gly Pro Thr Leu Ala Thr Leu
        195                 200                 205

Ala Gln Pro His Trp Gly Thr Leu Glu His Trp Asp Val Asn Lys Arg
    210                 215                 220

Asp Tyr Ile Gly Thr His Leu Ser Gln Glu Gln Cys Gln Val Ala Ser
225                 230                 235                 240

Gly His Leu Pro Cys Ile Val Arg Arg Thr Ser Lys Glu Ala Cys Gln
                245                 250                 255

Gln Ala Gly Cys Cys Tyr Asp Asn Thr Arg Glu Val Pro Cys Tyr Tyr
            260                 265                 270

Gly Asn Thr Ala Thr Val Gln Cys Phe Arg Asp Gly Tyr Phe Val Leu
        275                 280                 285

Val Val Ser Gln Glu Met Ala Leu Thr His Arg Ile Thr Leu Ala Asn
    290                 295                 300

Ile His Leu Ala Tyr Ala Pro Thr Ser Cys Ser Pro Thr Gln His Thr
305                 310                 315                 320

Glu Ala Phe Val Val Phe Tyr Phe Pro Leu Thr His Cys Gly Thr Thr
                325                 330                 335

Met Gln Val Ala Gly Asp Gln Leu Ile Tyr Glu Asn Trp Leu Val Ser
            340                 345                 350

Gly Ile His Ile Gln Lys Gly Pro Gln Gly Ser Ile Thr Arg Asp Ser
        355                 360                 365

Thr Phe Gln Leu His Val Arg Cys Val Phe Asn Ala Ser Asp Phe Leu
    370                 375                 380

Pro Ile Gln Ala Ser Ile Phe Pro Pro Pro Ser Pro Ala Pro Met Thr
385                 390                 395                 400

-continued

```
Gln Pro Gly Pro Leu Arg Leu Glu Leu Arg Ile Ala Lys Asp Glu Thr
                405             410             415

Phe Ser Ser Tyr Tyr Gly Glu Asp Tyr Pro Ile Val Arg Leu Leu
                420             425             430

Arg Glu Pro Val His Val Glu Val Arg Leu Leu Gln Arg Thr Asp Pro
                435             440             445

Asn Leu Val Leu Leu Leu His Gln Cys Trp Gly Ala Pro Ser Ala Asn
        450             455             460

Pro Phe Gln Gln Pro Gln Trp Pro Ile Leu Ser Asp Gly Cys Pro Phe
465             470             475             480

Lys Gly Asp Ser Tyr Arg Thr Gln Met Val Ala Leu Asp Gly Ala Thr
                485             490             495

Pro Phe Gln Ser His Tyr Gln Arg Phe Thr Val Ala Thr Phe Ala Leu
                500             505             510

Leu Asp Ser Gly Ser Gln Arg Ala Leu Arg Gly Leu Val Tyr Leu Phe
                515             520             525

Cys Ser Thr Ser Ala Cys His Thr Ser Gly Leu Glu Thr Cys Ser Thr
        530             535             540

Ala Cys Ser Thr Gly Thr Thr Arg Gln Arg Arg Ser Ser Gly His Arg
545             550             555             560

Asn Asp Thr Ala Arg Pro Gln Asp Ile Val Ser Ser Pro Gly Pro Val
                565             570             575

Gly Phe Glu Asp Ser Tyr Gly Gln Glu Pro Thr Leu Gly Pro Thr Asp
                580             585             590

Ser Asn Gly Asn Ser Ser Leu Arg Pro Leu Leu Trp Ala Val Leu Leu
        595             600             605

Leu Pro Ala Val Ala Leu Val Leu Gly Phe Gly Val Phe Val Gly Leu
    610             615             620

Ser Gln Thr Trp Ala Gln Lys Leu Trp Glu Ser Asn Arg Gln
625             630             635
```

```
<210> SEQ ID NO 72
<211> LENGTH: 424
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72
```

```
Met Glu Leu Ser Tyr Arg Leu Phe Ile Cys Leu Leu Leu Trp Gly Ser
1               5               10              15

Thr Glu Leu Cys Tyr Pro Gln Pro Leu Trp Leu Leu Gln Gly Gly Ala
                20              25              30

Ser His Pro Glu Thr Ser Val Gln Pro Val Leu Val Glu Cys Gln Glu
        35              40              45

Ala Thr Leu Met Val Met Val Ser Lys Asp Leu Phe Gly Thr Gly Lys
    50              55              60

Leu Ile Arg Ala Ala Asp Leu Thr Leu Gly Pro Glu Ala Cys Glu Pro
65              70              75              80

Leu Val Ser Met Asp Thr Glu Asp Val Val Arg Phe Glu Val Gly Leu
                85              90              95

His Glu Cys Gly Asn Ser Met Gln Val Thr Asp Asp Ala Leu Val Tyr
            100             105             110

Ser Thr Phe Leu Leu His Asp Pro Arg Pro Val Gly Asn Leu Ser Ile
        115             120             125
```

-continued

```
Val Arg Thr Asn Arg Ala Glu Ile Pro Ile Glu Cys Arg Tyr Pro Arg
    130                 135                 140

Gln Gly Asn Val Ser Ser Gln Ala Ile Leu Pro Thr Trp Leu Pro Phe
145                 150                 155                 160

Arg Thr Thr Val Phe Ser Glu Glu Lys Leu Thr Phe Ser Leu Arg Leu
                165                 170                 175

Met Glu Glu Asn Trp Asn Ala Glu Lys Arg Ser Pro Thr Phe His Leu
                180                 185                 190

Gly Asp Ala Ala His Leu Gln Ala Glu Ile His Thr Gly Ser His Val
                195                 200                 205

Pro Leu Arg Leu Phe Val Asp His Cys Val Ala Thr Pro Thr Pro Asp
    210                 215                 220

Gln Asn Ala Ser Pro Tyr His Thr Ile Val Asp Phe His Gly Cys Leu
225                 230                 235                 240

Val Asp Gly Leu Thr Asp Ala Ser Ser Ala Phe Lys Val Pro Arg Pro
                245                 250                 255

Gly Pro Asp Thr Leu Gln Phe Thr Val Asp Val Phe His Phe Ala Asn
                260                 265                 270

Asp Ser Arg Asn Met Ile Tyr Ile Thr Cys His Leu Lys Val Thr Leu
                275                 280                 285

Ala Glu Gln Asp Pro Asp Glu Leu Asn Lys Ala Cys Ser Phe Ser Lys
    290                 295                 300

Pro Ser Asn Ser Trp Phe Pro Val Glu Gly Ser Ala Asp Ile Cys Gln
305                 310                 315                 320

Cys Cys Asn Lys Gly Asp Cys Gly Thr Pro Ser His Ser Arg Arg Gln
                325                 330                 335

Pro His Val Met Ser Gln Trp Ser Arg Ser Ala Ser Arg Asn Arg Arg
                340                 345                 350

His Val Thr Glu Glu Ala Asp Val Thr Val Gly Pro Leu Ile Phe Leu
                355                 360                 365

Asp Arg Arg Gly Asp His Glu Val Glu Gln Trp Ala Leu Pro Ser Asp
    370                 375                 380

Thr Ser Val Val Leu Leu Gly Val Gly Leu Ala Val Val Val Ser Leu
385                 390                 395                 400

Thr Leu Thr Ala Val Ile Leu Val Leu Thr Arg Arg Cys Arg Thr Ala
                405                 410                 415

Ser His Pro Val Ser Ala Ser Glu
                420
```

```
<210> SEQ ID NO 73
<211> LENGTH: 540
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73
```

```
Met Trp Leu Leu Arg Cys Val Leu Leu Cys Val Ser Leu Ser Leu Ala
1               5                   10                  15

Val Ser Gly Gln His Lys Pro Glu Ala Pro Asp Tyr Ser Ser Val Leu
                20                  25                  30

His Cys Gly Pro Trp Ser Phe Gln Phe Ala Val Asn Leu Asn Gln Glu
        35                  40                  45

Ala Thr Ser Pro Pro Val Leu Ile Ala Trp Asp Asn Gln Gly Leu Leu
```

-continued

```
      50              55              60

His Glu Leu Gln Asn Asp Ser Asp Cys Gly Thr Trp Ile Arg Lys Gly
65              70              75              80

Pro Gly Ser Ser Val Val Leu Glu Ala Thr Tyr Ser Ser Cys Tyr Val
                85              90              95

Thr Glu Trp Asp Ser His Tyr Ile Met Pro Val Gly Val Glu Gly Ala
            100             105             110

Gly Ala Ala Glu His Lys Val Val Thr Glu Arg Lys Leu Leu Lys Cys
            115             120             125

Pro Met Asp Leu Leu Ala Arg Asp Ala Pro Asp Thr Asp Trp Cys Asp
        130             135             140

Ser Ile Pro Ala Arg Asp Arg Leu Pro Cys Ala Pro Ser Pro Ile Ser
145             150             155             160

Arg Gly Asp Cys Glu Gly Leu Gly Cys Cys Tyr Ser Ser Glu Glu Val
            165             170             175

Asn Ser Cys Tyr Tyr Gly Asn Thr Val Thr Leu His Cys Thr Arg Glu
            180             185             190

Gly His Phe Ser Ile Ala Val Ser Arg Asn Val Thr Ser Pro Pro Leu
            195             200             205

Leu Leu Asp Ser Val Arg Leu Ala Leu Arg Asn Asp Ser Ala Cys Asn
        210             215             220

Pro Val Met Ala Thr Gln Ala Phe Val Leu Phe Gln Phe Pro Phe Thr
225             230             235             240

Ser Cys Gly Thr Thr Arg Gln Ile Thr Gly Asp Arg Ala Val Tyr Glu
            245             250             255

Asn Glu Leu Val Ala Thr Arg Asp Val Lys Asn Gly Ser Arg Gly Ser
            260             265             270

Val Thr Arg Asp Ser Ile Phe Arg Leu His Val Ser Cys Ser Tyr Ser
        275             280             285

Val Ser Ser Asn Ser Leu Pro Ile Asn Val Gln Val Phe Thr Leu Pro
        290             295             300

Pro Pro Phe Pro Glu Thr Gln Pro Gly Pro Leu Thr Leu Glu Leu Gln
305             310             315             320

Ile Ala Lys Asp Lys Asn Tyr Gly Ser Tyr Tyr Gly Val Gly Asp Tyr
            325             330             335

Pro Val Val Lys Leu Leu Arg Asp Pro Ile Tyr Val Glu Val Ser Ile
            340             345             350

Leu His Arg Thr Asp Pro Tyr Leu Gly Leu Leu Leu Gln Gln Cys Trp
            355             360             365

Ala Thr Pro Ser Thr Asp Pro Leu Ser Gln Pro Gln Trp Pro Ile Leu
        370             375             380

Val Lys Gly Cys Pro Tyr Ile Gly Asp Asn Tyr Gln Thr Gln Leu Ile
385             390             395             400

Pro Val Gln Lys Ala Leu Asp Leu Pro Phe Pro Ser His His Gln Arg
            405             410             415

Phe Ser Ile Phe Thr Phe Ser Phe Val Asn Pro Thr Val Glu Lys Gln
            420             425             430

Ala Leu Arg Gly Pro Val His Leu His Cys Ser Val Ser Val Cys Gln
        435             440             445

Pro Ala Glu Thr Pro Ser Cys Val Val Thr Cys Pro Asp Leu Ser Arg
    450             455             460

Arg Arg Asn Phe Asp Asn Ser Ser Gln Asn Thr Thr Ala Ser Val Ser
465             470             475             480
```

-continued

Ser Lys Gly Pro Met Ile Leu Leu Gln Ala Thr Lys Asp Pro Pro Glu
                485                 490                 495

Lys Leu Arg Val Pro Val Asp Ser Lys Val Leu Trp Val Ala Gly Leu
            500                 505                 510

Ser Gly Thr Leu Ile Leu Gly Ala Leu Leu Val Ser Tyr Leu Ala Val
        515                 520                 525

Lys Lys Gln Lys Ser Cys Pro Asp Gln Met Cys Gln
    530                 535                 540

<210> SEQ ID NO 74
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Glu Ala Phe Ala Leu Gly Pro Ala Arg Arg Gly Arg Arg Arg Thr
1               5                   10                  15

Arg Ala Ala Gly Ser Leu Leu Ser Arg Ala Ala Ile Leu Leu Phe Ile
            20                  25                  30

Ser Ala Phe Leu Val Arg Val Pro Ser Ser Val Gly His Leu Val Arg
        35                  40                  45

Leu Pro Arg Ala Phe Arg Leu Thr Lys Asp Ser Val Lys Ile Val Gly
    50                  55                  60

Ser Thr Ser Phe Pro Val Lys Ala Tyr Val Met Leu His Gln Lys Ser
65                  70                  75                  80

Pro His Val Leu Cys Val Thr Gln Gln Leu Arg Asn Ala Glu Leu Ile
            85                  90                  95

Asp Pro Ser Phe Gln Trp Tyr Gly Pro Lys Gly Lys Val Val Ser Val
            100                 105                 110

Glu Asn Arg Thr Ala Gln Ile Thr Ser Thr Gly Ser Leu Val Phe Gln
        115                 120                 125

Asn Phe Glu Glu Ser Met Ser Gly Ile Tyr Thr Cys Phe Leu Glu Tyr
        130                 135                 140

Lys Pro Thr Val Glu Glu Ile Val Lys Arg Leu Gln Leu Lys Tyr Ala
145                 150                 155                 160

Ile Tyr Ala Tyr Arg Glu Pro His Tyr Tyr Tyr Gln Phe Thr Ala Arg
            165                 170                 175

Tyr His Ala Ala Pro Cys Asn Ser Ile Tyr Asn Ile Ser Phe Glu Lys
            180                 185                 190

Lys Leu Leu Gln Ile Leu Ser Lys Leu Leu Leu Asp Leu Ser Cys Glu
        195                 200                 205

Ile Ser Leu Leu Lys Ser Glu Cys His Arg Val Lys Met Gln Arg Ala
    210                 215                 220

Gly Leu Gln Asn Glu Leu Phe Phe Ala Phe Ser Val Ser Ser Leu Asp
225                 230                 235                 240

Thr Glu Lys Gly Pro Lys Arg Cys Thr Asp His Asn Cys Glu Pro Tyr
            245                 250                 255

Lys Arg Leu Phe Lys Ala Lys Asn Leu Ile Glu Arg Phe Phe Asn Gln
            260                 265                 270

Gln Val Glu Ile Leu Gly Arg Arg Ala Glu Gln Leu Pro Gln Ile Tyr
        275                 280                 285

Tyr Ile Glu Gly Thr Leu Gln Met Val Trp Ile Asn Arg Cys Phe Pro

-continued

```
        290              295              300

Gly Tyr Gly Met Asn Val Gln Gln His Pro Lys Cys Pro Glu Cys Cys
305                 310              315                 320

Val Ile Cys Ser Pro Gly Ser Tyr Asn Pro Arg Asp Gly Ile His Cys
                325              330              335

Leu Gln Cys Asn Ser Ser Leu Val Tyr Gly Ala Lys Thr Cys Leu
                340              345              350

<210> SEQ ID NO 75
<211> LENGTH: 421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Val Glu Met Leu Pro Thr Ala Ile Leu Leu Val Leu Ala Val Ser
1               5              10               15

Val Val Ala Lys Asp Asn Ala Thr Cys Asp Gly Pro Cys Gly Leu Arg
                20              25              30

Phe Arg Gln Asn Pro Gln Gly Gly Val Arg Ile Val Gly Gly Lys Ala
            35              40              45

Ala Gln His Gly Ala Trp Pro Trp Met Val Ser Leu Gln Ile Phe Thr
    50              55              60

Tyr Asn Ser His Arg Tyr His Thr Cys Gly Gly Ser Leu Leu Asn Ser
65              70              75              80

Arg Trp Val Leu Thr Ala Ala His Cys Phe Val Gly Lys Asn Asn Val
                85              90              95

His Asp Trp Arg Leu Val Phe Gly Ala Lys Glu Ile Thr Tyr Gly Asn
            100             105             110

Asn Lys Pro Val Lys Ala Pro Leu Gln Glu Arg Tyr Val Glu Lys Ile
            115             120             125

Ile Ile His Glu Lys Tyr Asn Ser Ala Thr Glu Gly Asn Asp Ile Ala
    130             135             140

Leu Val Glu Ile Thr Pro Pro Ile Ser Cys Gly Arg Phe Ile Gly Pro
145             150             155             160

Gly Cys Leu Pro His Phe Lys Ala Gly Leu Pro Arg Gly Ser Gln Ser
            165             170             175

Cys Trp Val Ala Gly Trp Gly Tyr Ile Glu Glu Lys Ala Pro Arg Pro
            180             185             190

Ser Ser Ile Leu Met Glu Ala Arg Val Asp Leu Ile Asp Leu Asp Leu
            195             200             205

Cys Asn Ser Thr Gln Trp Tyr Asn Gly Arg Val Gln Pro Thr Asn Val
    210             215             220

Cys Ala Gly Tyr Pro Val Gly Lys Ile Asp Thr Cys Gln Gly Asp Ser
225             230             235             240

Gly Gly Pro Leu Met Cys Lys Asp Ser Lys Glu Ser Ala Tyr Val Val
            245             250             255

Val Gly Ile Thr Ser Trp Gly Val Gly Cys Ala Arg Ala Lys Arg Pro
            260             265             270

Gly Ile Tyr Thr Ala Thr Trp Pro Tyr Leu Asn Trp Ile Ala Ser Lys
            275             280             285

Ile Gly Ser Asn Ala Leu Arg Met Ile Gln Ser Ala Thr Pro Pro Pro
    290             295             300
```

-continued

```
Pro Thr Thr Arg Pro Pro Pro Ile Arg Pro Pro Phe Ser His Pro Ile
305             310             315                 320

Ser Ala His Leu Pro Trp Tyr Phe Gln Pro Pro Arg Pro Leu Pro
                325             330                 335

Pro Arg Pro Pro Ala Ala Gln Pro Arg Pro Pro Pro Ser Pro Pro Pro
            340             345                 350

Pro Pro Pro Pro Pro Ala Ser Pro Leu Pro Pro Pro Pro Pro Pro
        355             360                 365

Pro Pro Thr Pro Ser Ser Thr Thr Lys Leu Pro Gln Gly Leu Ser Phe
    370             375                 380

Ala Lys Arg Leu Gln Gln Leu Ile Glu Val Leu Lys Gly Lys Thr Tyr
385             390             395                 400

Ser Asp Gly Lys Asn His Tyr Asp Met Glu Thr Thr Glu Leu Pro Glu
            405             410                 415

Leu Thr Ser Thr Ser
            420

<210> SEQ ID NO 76
<211> LENGTH: 735
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Trp Arg Val Leu Phe Leu Leu Ser Gly Leu Gly Gly Leu Arg Met
1               5               10                  15

Asp Ser Asn Phe Asp Ser Leu Pro Val Gln Ile Thr Val Pro Glu Lys
                20              25                  30

Ile Arg Ser Ile Ile Lys Glu Gly Ile Glu Ser Gln Ala Ser Tyr Lys
            35              40                  45

Ile Val Ile Glu Gly Lys Pro Tyr Thr Val Asn Leu Met Gln Lys Asn
    50              55                  60

Phe Leu Pro His Asn Phe Arg Val Tyr Ser Tyr Ser Gly Thr Gly Ile
65              70              75                  80

Met Lys Pro Leu Asp Gln Asp Phe Gln Asn Phe Cys His Tyr Gln Gly
                85              90                  95

Tyr Ile Glu Gly Tyr Pro Lys Ser Val Val Met Val Ser Thr Cys Thr
            100             105                 110

Gly Leu Arg Gly Val Leu Gln Phe Glu Asn Val Ser Tyr Gly Ile Glu
        115             120             125

Pro Leu Glu Ser Ser Val Gly Phe Glu His Val Ile Tyr Gln Val Lys
    130             135             140

His Lys Lys Ala Asp Val Ser Leu Tyr Asn Glu Lys Asp Ile Glu Ser
145             150             155                 160

Arg Asp Leu Ser Phe Lys Leu Gln Ser Val Glu Pro Gln Gln Asp Phe
                165             170                 175

Ala Lys Tyr Ile Glu Met His Val Ile Val Glu Lys Gln Leu Tyr Asn
            180             185                 190

His Met Gly Ser Asp Thr Thr Val Val Ala Gln Lys Val Phe Gln Leu
        195             200             205

Ile Gly Leu Thr Asn Ala Ile Phe Val Ser Phe Asn Ile Thr Ile Ile
    210             215             220

Leu Ser Ser Leu Glu Leu Trp Ile Asp Glu Asn Lys Ile Ala Thr Thr
225             230             235                 240
```

```
Gly Glu Ala Asn Glu Leu Leu His Thr Phe Leu Arg Trp Lys Thr Ser
            245             250             255

Tyr Leu Val Leu Arg Pro His Asp Val Ala Phe Leu Leu Val Tyr Arg
            260             265             270

Glu Lys Ser Asn Tyr Val Gly Ala Thr Phe Gln Gly Lys Met Cys Asp
            275             280             285

Ala Asn Tyr Ala Gly Gly Val Val Leu His Pro Arg Thr Ile Ser Leu
            290             295             300

Glu Ser Leu Ala Val Ile Leu Ala Gln Leu Leu Ser Leu Ser Met Gly
305             310             315             320

Ile Thr Tyr Asp Asp Ile Asn Lys Cys Gln Cys Ser Gly Ala Val Cys
            325             330             335

Ile Met Asn Pro Glu Ala Ile His Phe Ser Gly Val Lys Ile Phe Ser
            340             345             350

Asn Cys Ser Phe Glu Asp Phe Ala His Phe Ile Ser Lys Gln Lys Ser
            355             360             365

Gln Cys Leu His Asn Gln Pro Arg Leu Asp Pro Phe Phe Lys Gln Gln
            370             375             380

Ala Val Cys Gly Asn Ala Lys Leu Glu Ala Gly Glu Glu Cys Asp Cys
385             390             395             400

Gly Thr Glu Gln Asp Cys Ala Leu Ile Gly Glu Thr Cys Cys Asp Ile
            405             410             415

Ala Thr Cys Arg Phe Lys Ala Gly Ser Asn Cys Ala Glu Gly Pro Cys
            420             425             430

Cys Glu Asn Cys Leu Phe Met Ser Lys Glu Arg Met Cys Arg Pro Ser
            435             440             445

Phe Glu Glu Cys Asp Leu Pro Glu Tyr Cys Asn Gly Ser Ser Ala Ser
            450             455             460

Cys Pro Glu Asn His Tyr Val Gln Thr Gly His Pro Cys Gly Leu Asn
465             470             475             480

Gln Trp Ile Cys Ile Asp Gly Val Cys Met Ser Gly Asp Lys Gln Cys
            485             490             495

Thr Asp Thr Phe Gly Lys Glu Val Glu Phe Gly Pro Ser Glu Cys Tyr
            500             505             510

Ser His Leu Asn Ser Lys Thr Asp Val Ser Gly Asn Cys Gly Ile Ser
            515             520             525

Asp Ser Gly Tyr Thr Gln Cys Glu Ala Asp Asn Leu Gln Cys Gly Lys
            530             535             540

Leu Ile Cys Lys Tyr Val Gly Lys Phe Leu Leu Gln Ile Pro Arg Ala
545             550             555             560

Thr Ile Ile Tyr Ala Asn Ile Ser Gly His Leu Cys Ile Ala Val Glu
            565             570             575

Phe Ala Ser Asp His Ala Asp Ser Gln Lys Met Trp Ile Lys Asp Gly
            580             585             590

Thr Ser Cys Gly Ser Asn Lys Val Cys Arg Asn Gln Arg Cys Val Ser
            595             600             605

Ser Ser Tyr Leu Gly Tyr Asp Cys Thr Thr Asp Lys Cys Asn Asp Arg
            610             615             620

Gly Val Cys Asn Asn Lys Lys His Cys His Cys Ser Ala Ser Tyr Leu
625             630             635             640

Pro Pro Asp Cys Ser Val Gln Ser Asp Leu Trp Pro Gly Gly Ser Ile
            645             650             655
```

-continued

```
Asp Ser Gly Asn Phe Pro Pro Val Ala Ile Pro Ala Arg Leu Pro Glu
            660             665             670

Arg Arg Tyr Ile Glu Asn Ile Tyr His Ser Lys Pro Met Arg Trp Pro
            675             680             685

Phe Phe Leu Phe Ile Pro Phe Phe Ile Ile Phe Cys Val Leu Ile Ala
            690             695             700

Ile Met Val Lys Val Asn Phe Gln Arg Lys Lys Trp Arg Thr Glu Asp
705             710             715             720

Tyr Ser Ser Asp Glu Gln Pro Glu Ser Glu Ser Glu Pro Lys Gly
            725             730             735

<210> SEQ ID NO 77
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Trp Lys Leu Leu Leu Trp Val Gly Leu Val Leu Val Leu Lys His
1               5               10              15

His Asp Gly Ala Ala His Lys Leu Val Cys Tyr Phe Thr Asn Trp Ala
            20              25              30

His Ser Arg Pro Gly Pro Ala Ser Ile Leu Pro His Asp Leu Asp Pro
            35              40              45

Phe Leu Cys Thr His Leu Ile Phe Ala Phe Ala Ser Met Asn Asn Asn
            50              55              60

Gln Ile Val Ala Lys Asp Leu Gln Asp Glu Lys Ile Leu Tyr Pro Glu
65              70              75              80

Phe Asn Lys Leu Lys Glu Arg Asn Arg Glu Leu Lys Thr Leu Leu Ser
            85              90              95

Ile Gly Gly Trp Asn Phe Gly Thr Ser Arg Phe Thr Thr Met Leu Ser
            100             105             110

Thr Phe Ala Asn Arg Glu Lys Phe Ile Ala Ser Val Ile Ser Leu Leu
            115             120             125

Arg Thr His Asp Phe Asp Gly Leu Asp Leu Phe Phe Leu Tyr Pro Gly
            130             135             140

Leu Arg Gly Ser Pro Met His Asp Arg Trp Thr Phe Leu Phe Leu Ile
145             150             155             160

Glu Glu Leu Leu Phe Ala Phe Arg Lys Glu Ala Leu Leu Thr Met Arg
            165             170             175

Pro Arg Leu Leu Leu Ser Ala Ala Val Ser Gly Val Pro His Ile Val
            180             185             190

Gln Thr Ser Tyr Asp Val Arg Phe Leu Gly Arg Leu Leu Asp Phe Ile
            195             200             205

Asn Val Leu Ser Tyr Asp Leu His Gly Ser Trp Glu Arg Phe Thr Gly
            210             215             220

His Asn Ser Pro Leu Phe Ser Leu Pro Glu Asp Pro Lys Ser Ser Ala
225             230             235             240

Tyr Ala Met Asn Tyr Trp Arg Lys Leu Gly Ala Pro Ser Glu Lys Leu
            245             250             255

Ile Met Gly Ile Pro Thr Tyr Gly Arg Thr Phe Arg Leu Leu Lys Ala
            260             265             270

Ser Lys Asn Gly Leu Gln Ala Arg Ala Ile Gly Pro Ala Ser Pro Gly
            275             280             285
```

```
Lys Tyr Thr Lys Gln Glu Gly Phe Leu Ala Tyr Phe Glu Ile Cys Ser
    290                 295                 300

Phe Val Trp Gly Ala Lys Lys His Trp Ile Asp Tyr Gln Tyr Val Pro
305                 310                 315                 320

Tyr Ala Asn Lys Gly Lys Glu Trp Val Gly Tyr Asp Asn Ala Ile Ser
                325                 330                 335

Phe Ser Tyr Lys Ala Trp Phe Ile Arg Arg Glu His Phe Gly Gly Ala
            340                 345                 350

Met Val Trp Thr Leu Asp Met Asp Asp Val Arg Gly Thr Phe Cys Gly
            355                 360                 365

Thr Gly Pro Phe Pro Leu Val Tyr Val Leu Asn Asp Ile Leu Val Arg
    370                 375                 380

Ala Glu Phe Ser Ser Thr Ser Leu Pro Gln Phe Trp Leu Ser Ser Ala
385                 390                 395                 400

Val Asn Ser Ser Ser Thr Asp Pro Glu Arg Leu Ala Val Thr Thr Ala
                405                 410                 415

Trp Thr Thr Asp Ser Lys Ile Leu Pro Pro Gly Gly Glu Ala Gly Val
            420                 425                 430

Thr Glu Ile His Gly Lys Cys Glu Asn Met Thr Ile Thr Pro Arg Gly
            435                 440                 445

Thr Thr Val Thr Pro Thr Lys Glu Thr Val Ser Leu Gly Lys His Thr
    450                 455                 460

Val Ala Leu Gly Glu Lys Thr Glu Ile Thr Gly Ala Met Thr Met Thr
465                 470                 475                 480

Ser Val Gly His Gln Ser Met Thr Pro Gly Glu Lys Ala Leu Thr Pro
                485                 490                 495

Val Gly His Gln Ser Val Thr Thr Gly Gln Lys Thr Leu Thr Ser Val
            500                 505                 510

Gly Tyr Gln Ser Val Thr Pro Gly Glu Lys Thr Leu Thr Pro Val Gly
            515                 520                 525

His Gln Ser Val Thr Pro Val Ser His Gln Ser Val Ser Pro Gly Gly
    530                 535                 540

Thr Thr Met Thr Pro Val His Phe Gln Thr Glu Thr Leu Arg Gln Asn
545                 550                 555                 560

Thr Val Ala Pro Arg Arg Lys Ala Val Ala Arg Glu Lys Val Thr Val
                565                 570                 575

Pro Ser Arg Asn Ile Ser Val Thr Pro Glu Gly Gln Thr Met Pro Leu
                580                 585                 590

Arg Gly Glu Asn Leu Thr Ser Glu Val Gly Thr His Pro Arg Met Gly
            595                 600                 605

Asn Leu Gly Leu Gln Met Glu Ala Glu Asn Arg Met Met Leu Ser Ser
    610                 615                 620

Ser Pro Val Ile Gln Leu Pro Glu Gln Thr Pro Leu Ala Phe Asp Asn
625                 630                 635                 640

Arg Phe Val Pro Ile Tyr Gly Asn His Ser Ser Val Asn Ser Val Thr
                645                 650                 655

Pro Gln Thr Ser Pro Leu Ser Leu Lys Lys Glu Ile Pro Glu Asn Ser
            660                 665                 670

Ala Val Asp Glu Glu Ala
    675

<210> SEQ ID NO 78
<211> LENGTH: 468
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Met Val Asp Thr Glu Ser Pro Leu Cys Pro Leu Ser Pro Leu Glu Ala
1               5                   10                  15

Gly Asp Leu Glu Ser Pro Leu Ser Glu Glu Phe Leu Gln Glu Met Gly
            20                  25                  30

Asn Ile Gln Glu Ile Ser Gln Ser Ile Gly Glu Asp Ser Ser Gly Ser
            35                  40                  45

Phe Gly Phe Thr Glu Tyr Gln Tyr Leu Gly Ser Cys Pro Gly Ser Asp
    50                  55                  60

Gly Ser Val Ile Thr Asp Thr Leu Ser Pro Ala Ser Ser Pro Ser Ser
65                  70                  75                  80

Val Thr Tyr Pro Val Val Pro Gly Ser Val Asp Glu Ser Pro Ser Gly
                85                  90                  95

Ala Leu Asn Ile Glu Cys Arg Ile Cys Gly Asp Lys Ala Ser Gly Tyr
            100                 105                 110

His Tyr Gly Val His Ala Cys Glu Gly Cys Lys Gly Phe Phe Arg Arg
            115                 120                 125

Thr Ile Arg Leu Lys Leu Val Tyr Asp Lys Cys Asp Arg Ser Cys Lys
    130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Ile Glu Asp Ser Glu Thr Ala Asp Leu Lys Ser Leu Ala Lys
            195                 200                 205

Arg Ile Tyr Glu Ala Tyr Leu Lys Asn Phe Asn Met Asn Lys Val Lys
    210                 215                 220

Ala Arg Val Ile Leu Ser Gly Lys Ala Ser Asn Asn Pro Pro Phe Val
225                 230                 235                 240

Ile His Asp Met Glu Thr Leu Cys Met Ala Glu Lys Thr Leu Val Ala
                245                 250                 255

Lys Leu Val Ala Asn Gly Ile Gln Asn Lys Glu Ala Glu Val Arg Ile
            260                 265                 270

Phe His Cys Cys Gln Cys Thr Ser Val Glu Thr Val Thr Glu Leu Thr
            275                 280                 285

Glu Phe Ala Lys Ala Ile Pro Gly Phe Ala Asn Leu Asp Leu Asn Asp
    290                 295                 300

Gln Val Thr Leu Leu Lys Tyr Gly Val Tyr Glu Ala Ile Phe Ala Met
305                 310                 315                 320

Leu Ser Ser Val Met Asn Lys Asp Gly Met Leu Val Ala Tyr Gly Asn
                325                 330                 335

Gly Phe Ile Thr Arg Glu Phe Leu Lys Ser Leu Arg Lys Pro Phe Cys
            340                 345                 350

Asp Ile Met Glu Pro Lys Phe Asp Phe Ala Met Lys Phe Asn Ala Leu
            355                 360                 365

Glu Leu Asp Asp Ser Asp Ile Ser Leu Phe Val Ala Ala Ile Ile Cys
    370                 375                 380
```

-continued

```
Cys Gly Asp Arg Pro Gly Leu Leu Asn Val Gly His Ile Glu Lys Met
385                 390                 395                 400

Gln Glu Gly Ile Val His Val Leu Arg Leu His Leu Gln Ser Asn His
                405                 410                 415

Pro Asp Asp Ile Phe Leu Phe Pro Lys Leu Leu Gln Lys Met Ala Asp
                420                 425                 430

Leu Arg Gln Leu Val Thr Glu His Ala Gln Leu Val Gln Ile Ile Lys
            435                 440                 445

Lys Thr Glu Ser Asp Ala Ala Leu His Pro Leu Leu Gln Glu Ile Tyr
        450                 455                 460

Arg Asp Met Tyr
465
```

```
<210> SEQ ID NO 79
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79
```

```
Met Lys Leu Asp Met Thr Gly Asp Cys Thr Pro Val Leu Val Leu Met
1               5                   10                  15

Ala Ala Val Leu Thr Val Thr Gly Ala Val Pro Val Ala Arg Leu His
            20                  25                  30

Gly Ala Leu Pro Asp Ala Arg Gly Cys His Ile Ala Gln Phe Lys Ser
        35                  40                  45

Leu Ser Pro Gln Glu Leu Gln Ala Phe Lys Arg Ala Lys Asp Ala Leu
    50                  55                  60

Glu Glu Ser Leu Leu Leu Lys Asp Cys Arg Cys His Ser Arg Leu Phe
65                  70                  75                  80

Pro Arg Thr Trp Asp Leu Arg Gln Leu Gln Val Arg Glu Arg Pro Met
                85                  90                  95

Ala Leu Glu Ala Glu Leu Ala Leu Thr Leu Lys Val Leu Glu Ala Thr
            100                 105                 110

Ala Asp Thr Asp Pro Ala Leu Val Asp Val Leu Asp Gln Pro Leu His
        115                 120                 125

Thr Leu His His Ile Leu Ser Gln Phe Arg Ala Cys Ile Gln Pro Gln
        130                 135                 140

Pro Thr Ala Gly Pro Arg Thr Arg Gly Arg Leu His His Trp Leu Tyr
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
        195                 200
```

```
<210> SEQ ID NO 80
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80
```

```
Met Ala Gly Pro Glu Arg Trp Gly Pro Leu Leu Leu Cys Leu Leu Gln
1               5              10               15

Ala Ala Pro Gly Arg Pro Arg Leu Ala Pro Pro Gln Asn Val Thr Leu
        20              25               30

Leu Ser Gln Asn Phe Ser Val Tyr Leu Thr Trp Leu Pro Gly Leu Gly
        35              40               45

Asn Pro Gln Asp Val Thr Tyr Phe Val Ala Tyr Gln Ser Ser Pro Thr
    50              55              60

Arg Arg Arg Trp Arg Glu Val Glu Glu Cys Ala Gly Thr Lys Glu Leu
65              70              75               80

Leu Cys Ser Met Met Cys Leu Lys Lys Gln Asp Leu Tyr Asn Lys Phe
            85              90               95

Lys Gly Arg Val Arg Thr Val Ser Pro Ser Ser Lys Ser Pro Trp Val
        100             105             110

Glu Ser Glu Tyr Leu Asp Tyr Leu Phe Glu Val Glu Pro Ala Pro Pro
        115             120             125

Val Leu Val Leu Thr Gln Thr Glu Glu Ile Leu Ser Ala Asn Ala Thr
    130             135             140

Tyr Gln Leu Pro Pro Cys Met Pro Pro Leu Asp Leu Lys Tyr Glu Val
145             150             155             160

Ala Phe Trp Lys Glu Gly Ala Gly Asn Lys Thr Leu Phe Pro Val Thr
            165             170             175

Pro His Gly Gln Pro Val Gln Ile Thr Leu Gln Pro Ala Ala Ser Glu
            180             185             190

His His Cys Leu Ser Ala Arg Thr Ile Tyr Thr Phe Ser Val Pro Lys
            195             200             205

Tyr Ser Lys Phe Ser Lys Pro Thr Cys Phe Leu Leu Glu Val Pro Glu
    210             215             220

Ala Asn Trp Ala Phe Leu Val Leu Pro Ser Leu Leu Ile Leu Leu Leu
225             230             235             240

Val Ile Ala Ala Gly Gly Val Ile Trp Lys Thr Leu Met Gly Asn Pro
            245             250             255

Trp Phe Gln Arg Ala Lys Met Pro Arg Ala Leu Asp Phe Ser Gly His
            260             265             270

Thr His Pro Val Ala Thr Phe Gln Pro Ser Arg Pro Glu Ser Val Asn
            275             280             285

Asp Leu Phe Leu Cys Pro Gln Lys Glu Leu Thr Arg Gly Val Arg Pro
    290             295             300

Thr Pro Arg Val Arg Ala Pro Ala Thr Gln Gln Thr Arg Trp Lys Lys
305             310             315             320

Asp Leu Ala Glu Asp Glu Glu Glu Glu Asp Glu Glu Asp Thr Glu Asp
            325             330             335

Gly Val Ser Phe Gln Pro Tyr Ile Glu Pro Pro Ser Phe Leu Gly Gln
            340             345             350

Glu His Gln Ala Pro Gly His Ser Glu Ala Gly Gly Val Asp Ser Gly
            355             360             365

Arg Pro Arg Ala Pro Leu Val Pro Ser Glu Gly Ser Ser Ala Trp Asp
    370             375             380

Ser Ser Asp Arg Ser Trp Ala Ser Thr Val Asp Ser Ser Trp Asp Arg
385             390             395             400

Ala Gly Ser Ser Gly Tyr Leu Ala Glu Lys Gly Pro Gly Gln Gly Pro
            405             410             415
```

-continued

```
Gly Gly Asp Gly His Gln Glu Ser Leu Pro Pro Pro Glu Phe Ser Lys
            420                 425                 430

Asp Ser Gly Phe Leu Glu Glu Leu Pro Glu Asp Asn Leu Ser Ser Trp
            435                 440                 445

Ala Thr Trp Gly Thr Leu Pro Pro Glu Pro Asn Leu Val Pro Gly Gly
            450                 455                 460

Pro Pro Val Ser Leu Gln Thr Leu Thr Phe Cys Trp Glu Ser Ser Pro
465                 470                 475                 480

Glu Glu Glu Glu Glu Ala Arg Glu Ser Glu Ile Glu Asp Ser Asp Ala
                485                 490                 495

Gly Ser Trp Gly Ala Glu Ser Thr Gln Arg Thr Glu Asp Arg Gly Arg
                500                 505                 510

Thr Leu Gly His Tyr Met Ala Arg
            515                 520
```

```
<210> SEQ ID NO 81
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Ala Trp Ser Leu Gly Ser Trp Leu Gly Gly Cys Leu Leu Val Ser
1                   5                   10                  15

Ala Leu Gly Met Val Pro Pro Pro Glu Asn Val Arg Met Asn Ser Val
                20                  25                  30

Asn Phe Lys Asn Ile Leu Gln Trp Glu Ser Pro Ala Phe Ala Lys Gly
            35                  40                  45

Asn Leu Thr Phe Thr Ala Gln Tyr Leu Ser Tyr Arg Ile Phe Gln Asp
        50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
            115                 120                 125

Met Arg Phe Leu Ala Pro Lys Ile Glu Asn Glu Tyr Glu Thr Trp Thr
        130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
                180                 185                 190

Gly Phe Leu Pro Asp Arg Asn Lys Ala Gly Glu Trp Ser Glu Pro Val
            195                 200                 205

Cys Glu Gln Thr Thr His Asp Glu Thr Val Pro Ser Trp Met Val Ala
        210                 215                 220

Val Ile Leu Met Ala Ser Val Phe Met Val Cys Leu Ala Leu Leu Gly
225                 230                 235                 240

Cys Phe Ala Leu Leu Trp Cys Val Tyr Lys Lys Thr Lys Tyr Ala Phe
                245                 250                 255
```

-continued

```
Ser Pro Arg Asn Ser Leu Pro Gln His Leu Lys Glu Phe Leu Gly His
        260                 265                 270

Pro His His Asn Thr Leu Leu Phe Phe Ser Phe Pro Leu Ser Asp Glu
        275                 280                 285

Asn Asp Val Phe Asp Lys Leu Ser Val Ile Ala Glu Asp Ser Glu Ser
    290                 295                 300

Gly Lys Gln Asn Pro Gly Asp Ser Cys Ser Leu Gly Thr Pro Pro Gly
305                 310                 315                 320

Gln Gly Pro Gln Ser
                325
```

```
<210> SEQ ID NO 82
<211> LENGTH: 689
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82
```

```
Met Ala Asp Leu Glu Ala Val Leu Ala Asp Val Ser Tyr Leu Met Ala
1               5                   10                  15

Met Glu Lys Ser Lys Ala Thr Pro Ala Ala Arg Ala Ser Lys Lys Ile
            20                  25                  30

Leu Leu Pro Glu Pro Ser Ile Arg Ser Val Met Gln Lys Tyr Leu Glu
        35                  40                  45

Asp Arg Gly Glu Val Thr Phe Glu Lys Ile Phe Ser Gln Lys Leu Gly
    50                  55                  60

Tyr Leu Leu Phe Arg Asp Phe Cys Leu Asn His Leu Glu Glu Ala Arg
65                  70                  75                  80

Pro Leu Val Glu Phe Tyr Glu Glu Ile Lys Lys Tyr Glu Lys Leu Glu
                85                  90                  95

Thr Glu Glu Glu Arg Val Ala Arg Ser Arg Glu Ile Phe Asp Ser Tyr
            100                 105                 110

Ile Met Lys Glu Leu Leu Ala Cys Ser His Pro Phe Ser Lys Ser Ala
        115                 120                 125

Thr Glu His Val Gln Gly His Leu Gly Lys Lys Gln Val Pro Pro Asp
    130                 135                 140

Leu Phe Gln Pro Tyr Ile Glu Glu Ile Cys Gln Asn Leu Arg Gly Asp
145                 150                 155                 160

Val Phe Gln Lys Phe Ile Glu Ser Asp Lys Phe Thr Arg Phe Cys Gln
                165                 170                 175

Trp Lys Asn Val Glu Leu Asn Ile His Leu Thr Met Asn Asp Phe Ser
            180                 185                 190

Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
    210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Ser Tyr Ala Phe His Thr Pro Asp Lys Leu Ser Phe Ile Leu Asp
            260                 265                 270

Leu Met Asn Gly Gly Asp Leu His Tyr His Leu Ser Gln His Gly Val
```

-continued

```
                275                 280                 285

Phe Ser Glu Ala Asp Met Arg Phe Tyr Ala Ala Glu Ile Ile Leu Gly
    290                 295                 300

Leu Glu His Met His Asn Arg Phe Val Val Tyr Arg Asp Leu Lys Pro
305                 310                 315                 320

Ala Asn Ile Leu Leu Asp Glu His Gly His Val Arg Ile Ser Asp Leu
                325                 330                 335

Gly Leu Ala Cys Asp Phe Ser Lys Lys Lys Pro His Ala Ser Val Gly
                340                 345                 350

Thr His Gly Tyr Met Ala Pro Glu Val Leu Gln Lys Gly Val Ala Tyr
                355                 360                 365

Asp Ser Ser Ala Asp Trp Phe Ser Leu Gly Cys Met Leu Phe Lys Leu
    370                 375                 380

Leu Arg Gly His Ser Pro Phe Arg Gln His Lys Thr Lys Asp Lys His
385                 390                 395                 400

Glu Ile Asp Arg Met Thr Leu Thr Met Ala Val Glu Leu Pro Asp Ser
                405                 410                 415

Phe Ser Pro Glu Leu Arg Ser Leu Leu Glu Gly Leu Leu Gln Arg Asp
                420                 425                 430

Val Asn Arg Arg Leu Gly Cys Leu Gly Arg Gly Ala Gln Glu Val Lys
                435                 440                 445

Glu Ser Pro Phe Phe Arg Ser Leu Asp Trp Gln Met Val Phe Leu Gln
    450                 455                 460

Lys Tyr Pro Pro Pro Leu Ile Pro Pro Arg Gly Glu Val Asn Ala Ala
465                 470                 475                 480

Asp Ala Phe Asp Ile Gly Ser Phe Asp Glu Glu Asp Thr Lys Gly Ile
                485                 490                 495

Lys Leu Leu Asp Ser Asp Gln Glu Leu Tyr Arg Asn Phe Pro Leu Thr
                500                 505                 510

Ile Ser Glu Arg Trp Gln Gln Glu Val Ala Glu Thr Val Phe Asp Thr
                515                 520                 525

Ile Asn Ala Glu Thr Asp Arg Leu Glu Ala Arg Lys Lys Ala Lys Asn
    530                 535                 540

Lys Gln Leu Gly His Glu Glu Asp Tyr Ala Leu Gly Lys Asp Cys Ile
545                 550                 555                 560

Met His Gly Tyr Met Ser Lys Met Gly Asn Pro Phe Leu Thr Gln Trp
                565                 570                 575

Gln Arg Arg Tyr Phe Tyr Leu Phe Pro Asn Arg Leu Glu Trp Arg Gly
                580                 585                 590

Glu Gly Glu Ala Pro Gln Ser Leu Leu Thr Met Glu Glu Ile Gln Ser
                595                 600                 605

Val Glu Glu Thr Gln Ile Lys Glu Arg Lys Cys Leu Leu Leu Lys Ile
    610                 615                 620

Arg Gly Gly Lys Gln Phe Ile Leu Gln Cys Asp Ser Asp Pro Glu Leu
625                 630                 635                 640

Val Gln Trp Lys Lys Glu Leu Arg Asp Ala Tyr Arg Glu Ala Gln Gln
                645                 650                 655

Leu Val Gln Arg Val Pro Lys Met Lys Asn Lys Pro Arg Ser Pro Val
                660                 665                 670

Val Glu Leu Ser Lys Val Pro Leu Val Gln Arg Gly Ser Ala Asn Gly
                675                 680                 685

Leu
```

<210> SEQ ID NO 83
<211> LENGTH: 524
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
                20                  25                  30

Cys Gln Asn Val Lys Thr Ala Ser Asp Cys Gly Ala Val Lys His Cys
            35                  40                  45

Leu Gln Thr Val Trp Asn Lys Pro Thr Val Lys Ser Leu Pro Cys Asp
        50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
            115                 120                 125

Gly Glu Val Cys Ser Ala Leu Asn Leu Cys Glu Ser Leu Gln Lys His
        130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
            195                 200                 205

Gln Thr Ala Val Arg Thr Asn Ser Thr Phe Val Gln Ala Leu Val Glu
        210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
            275                 280                 285

Ser Lys Asn Val Ile Pro Ala Leu Glu Leu Val Glu Pro Ile Lys Lys
        290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
            355                 360                 365

-continued

```
Leu Ser Ile Leu Leu Glu Glu Val Ser Pro Glu Leu Val Cys Ser Met
    370             375             380

Leu His Leu Cys Ser Gly Thr Arg Leu Pro Ala Leu Thr Val His Val
385             390             395             400

Thr Gln Pro Lys Asp Gly Gly Phe Cys Glu Val Cys Lys Lys Leu Val
            405             410             415

Gly Tyr Leu Asp Arg Asn Leu Glu Lys Asn Ser Thr Lys Gln Glu Ile
            420             425             430

Leu Ala Ala Leu Glu Lys Gly Cys Ser Phe Leu Pro Asp Pro Tyr Gln
        435             440             445

Lys Gln Cys Asp Gln Phe Val Ala Glu Tyr Glu Pro Val Leu Ile Glu
    450             455             460

Ile Leu Val Glu Val Met Asp Pro Ser Phe Val Cys Leu Lys Ile Gly
465             470             475             480

Ala Cys Pro Ser Ala His Lys Pro Leu Leu Gly Thr Glu Lys Cys Ile
            485             490             495

Trp Gly Pro Ser Tyr Trp Cys Gln Asn Thr Glu Thr Ala Ala Gln Cys
            500             505             510

Asn Ala Val Glu His Cys Lys Arg His Val Trp Asn
        515             520
```

<210> SEQ ID NO 84
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Met Ala Lys Met Asn Leu Ser Ser Tyr Ile Leu Ile Leu Thr Phe Ser
1               5               10              15

Leu Phe Ser Gln Gly Ile Leu Leu Ser Ala Ser Lys Ser Ile Arg Asn
            20              25              30

Leu Asp Asp Asp Met Val Phe Asn Thr Phe Arg Leu Gly Lys Gly Phe
        35              40              45

Gln Lys Glu Asp Thr Ala Glu Lys Ser Val Ile Ala Pro Ser Leu Glu
    50              55              60

Gln Tyr Lys Asn Asp Glu Ser Ser Phe Met Asn Glu Glu Glu Asn Lys
65              70              75              80

Val Ser Lys Asn Thr Gly Ser Lys His Asn Phe Leu Asn His Gly Leu
            85              90              95

Pro Leu Asn Leu Ala Ile Lys Pro Tyr Leu Ala Leu Lys Gly Ser Val
            100             105             110

Ala Phe Pro Ala Glu Asn Gly Val Gln Asn Thr Glu Ser Thr Gln Glu
        115             120             125

Lys Arg Glu Ile Gly Asp Glu Glu Asn Ser Ala Lys Phe Pro Ile Gly
    130             135             140

Arg Arg Asp Phe Asp Met Leu Arg Cys Met Leu Gly Arg Val Tyr Arg
145             150             155             160

Pro Cys Trp Gln Val
                165
```

<210> SEQ ID NO 85
<211> LENGTH: 1609
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 85

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Ala Gly Cys
                20                  25                  30

Ala Gln Ala Ala Met Asp Glu Cys Thr Asp Glu Gly Gly Arg Pro Gln
            35                  40                  45

Arg Cys Met Pro Glu Phe Val Asn Ala Ala Phe Asn Val Thr Val Val
        50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
            115                 120                 125

Tyr Pro Ser Ser Ile Asn Leu Thr Leu His Leu Gly Lys Ala Phe Asp
        130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
                180                 185                 190

Phe Ile Arg Thr Gly Gly Asp Glu Gln Gln Ala Leu Cys Thr Asp Glu
            195                 200                 205

Phe Ser Asp Ile Ser Pro Leu Thr Gly Gly Asn Val Ala Phe Ser Thr
        210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
                260                 265                 270

Tyr Tyr Tyr Ala Ile Ser Asp Phe Ala Val Gly Gly Arg Cys Lys Cys
            275                 280                 285

Asn Gly His Ala Ser Glu Cys Met Lys Asn Glu Phe Asp Lys Leu Val
        290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
            340                 345                 350

Phe Asp Pro Glu Leu Tyr Arg Ser Thr Gly His Gly Gly His Cys Thr
            355                 360                 365

Asn Cys Gln Asp Asn Thr Asp Gly Ala His Cys Glu Arg Cys Arg Glu
        370                 375                 380

-continued

```
Asn Phe Phe Arg Leu Gly Asn Asn Glu Ala Cys Ser Ser Cys His Cys
385             390             395             400

Ser Pro Val Gly Ser Leu Ser Thr Gln Cys Asp Ser Tyr Gly Arg Cys
            405             410             415

Ser Cys Lys Pro Gly Val Met Gly Asp Lys Cys Asp Arg Cys Gln Pro
            420             425             430

Gly Phe His Ser Leu Thr Glu Ala Gly Cys Arg Pro Cys Ser Cys Asp
            435             440             445

Pro Ser Gly Ser Ile Asp Glu Cys Asn Ile Glu Thr Gly Arg Cys Val
    450             455             460

Cys Lys Asp Asn Val Glu Gly Phe Asn Cys Glu Arg Cys Lys Pro Gly
465             470             475             480

Phe Phe Asn Leu Glu Ser Ser Asn Pro Arg Gly Cys Thr Pro Cys Phe
            485             490             495

Cys Phe Gly His Ser Ser Val Cys Thr Asn Ala Val Gly Tyr Ser Val
            500             505             510

Tyr Ser Ile Ser Ser Thr Phe Gln Ile Asp Glu Asp Gly Trp Arg Ala
            515             520             525

Glu Gln Arg Asp Gly Ser Glu Ala Ser Leu Glu Trp Ser Ser Glu Arg
    530             535             540

Gln Asp Ile Ala Val Ile Ser Asp Ser Tyr Phe Pro Arg Tyr Phe Ile
545             550             555             560

Ala Pro Ala Lys Phe Leu Gly Lys Gln Val Leu Ser Tyr Gly Gln Asn
            565             570             575

Leu Ser Phe Ser Phe Arg Val Asp Arg Arg Asp Thr Arg Leu Ser Ala
            580             585             590

Glu Asp Leu Val Leu Glu Gly Ala Gly Leu Arg Val Ser Val Pro Leu
    595             600             605

Ile Ala Gln Gly Asn Ser Tyr Pro Ser Glu Thr Thr Val Lys Tyr Val
    610             615             620

Phe Arg Leu His Glu Ala Thr Asp Tyr Pro Trp Arg Pro Ala Leu Thr
625             630             635             640

Pro Phe Glu Phe Gln Lys Leu Leu Asn Asn Leu Thr Ser Ile Lys Ile
            645             650             655

Arg Gly Thr Tyr Ser Glu Arg Ser Ala Gly Tyr Leu Asp Asp Val Thr
            660             665             670

Leu Ala Ser Ala Arg Pro Gly Pro Gly Val Pro Ala Thr Trp Val Glu
            675             680             685

Ser Cys Thr Cys Pro Val Gly Tyr Gly Gly Gln Phe Cys Glu Met Cys
    690             695             700

Leu Ser Gly Tyr Arg Arg Glu Thr Pro Asn Leu Gly Pro Tyr Ser Pro
705             710             715             720

Cys Val Leu Cys Ala Cys Asn Gly His Ser Glu Thr Cys Asp Pro Glu
            725             730             735

Thr Gly Val Cys Asn Cys Arg Asp Asn Thr Ala Gly Pro His Cys Glu
            740             745             750

Lys Cys Ser Asp Gly Tyr Tyr Gly Asp Ser Thr Ala Gly Thr Ser Ser
            755             760             765

Asp Cys Gln Pro Cys Pro Cys Pro Gly Gly Ser Ser Cys Ala Val Val
    770             775             780

Pro Lys Thr Lys Glu Val Val Cys Thr Asn Cys Pro Thr Gly Thr Thr
785             790             795             800

Gly Lys Arg Cys Glu Leu Cys Asp Asp Gly Tyr Phe Gly Asp Pro Leu
```

-continued

```
              805                810                815

Gly Arg Asn Gly Pro Val Arg Leu Cys Arg Leu Cys Gln Cys Ser Asp
          820                825                830

Asn Ile Asp Pro Asn Ala Val Gly Asn Cys Asn Arg Leu Thr Gly Glu
      835                840                845

Cys Leu Lys Cys Ile Tyr Asn Thr Ala Gly Phe Tyr Cys Asp Arg Cys
  850                855                860

Lys Asp Gly Phe Phe Gly Asn Pro Leu Ala Pro Asn Pro Ala Asp Lys
865                870                875                880

Cys Lys Ala Cys Asn Cys Asn Leu Tyr Gly Thr Met Lys Gln Gln Ser
              885                890                895

Ser Cys Asn Pro Val Thr Gly Gln Cys Glu Cys Leu Pro His Val Thr
          900                905                910

Gly Gln Asp Cys Gly Ala Cys Asp Pro Gly Phe Tyr Asn Leu Gln Ser
          915                920                925

Gly Gln Gly Cys Glu Arg Cys Asp Cys His Ala Leu Gly Ser Thr Asn
      930                935                940

Gly Gln Cys Asp Ile Arg Thr Gly Gln Cys Glu Cys Gln Pro Gly Ile
945                950                955                960

Thr Gly Gln His Cys Glu Arg Cys Glu Val Asn His Phe Gly Phe Gly
              965                970                975

Pro Glu Gly Cys Lys Pro Cys Asp Cys His Pro Glu Gly Ser Leu Ser
          980                985                990

Leu Gln Cys Lys Asp Asp Gly Arg  Cys Glu Cys Arg Glu  Gly Phe Val
          995                1000                1005

Gly Asn  Arg Cys Asp Gln Cys  Glu Glu Asn Tyr Phe  Tyr Asn Arg
    1010                1015                1020

Ser Trp  Pro Gly Cys Gln Glu  Cys Pro Ala Cys Tyr  Arg Leu Val
    1025                1030                1035

Lys Asp  Lys Val Ala Asp His  Arg Val Lys Leu Gln  Glu Leu Glu
    1040                1045                1050

Ser Leu  Ile Ala Asn Leu Gly  Thr Gly Asp Glu Met  Val Thr Asp
    1055                1060                1065

Gln Ala  Phe Glu Asp Arg Leu  Lys Glu Ala Glu Arg  Glu Val Met
    1070                1075                1080

Asp Leu  Leu Arg Glu Ala Gln  Asp Val Lys Asp Val  Asp Gln Asn
    1085                1090                1095

Leu Met  Asp Arg Leu Gln Arg  Val Asn Asn Thr Leu  Ser Ser Gln
    1100                1105                1110

Ile Ser  Arg Leu Gln Asn Ile  Arg Asn Thr Ile Glu  Glu Thr Gly
    1115                1120                1125

Asn Leu  Ala Glu Gln Ala Arg  Ala His Val Glu Asn  Thr Glu Arg
    1130                1135                1140

Leu Ile  Glu Ile Ala Ser Arg  Glu Leu Glu Lys Ala  Lys Val Ala
    1145                1150                1155

Ala Ala  Asn Val Ser Val Thr  Gln Pro Glu Ser Thr  Gly Asp Pro
    1160                1165                1170

Asn Asn  Met Thr Leu Leu Ala  Glu Glu Ala Arg Lys  Leu Ala Glu
    1175                1180                1185

Arg His  Lys Gln Glu Ala Asp  Asp Ile Val Arg Val  Ala Lys Thr
    1190                1195                1200

Ala Asn  Asp Thr Ser Thr Glu  Ala Tyr Asn Leu Leu  Leu Arg Thr
    1205                1210                1215
```

-continued

```
Leu Ala  Gly Glu Asn Gln Thr  Ala Phe Glu Ile Glu  Glu Leu Asn
    1220             1225             1230

Arg Lys  Tyr Glu Gln Ala Lys  Asn Ile Ser Gln Asp  Leu Glu Lys
    1235             1240             1245

Gln Ala  Ala Arg Val His Glu  Glu Ala Lys Arg Ala  Gly Asp Lys
    1250             1255             1260

Ala Val  Glu Ile Tyr Ala Ser  Val Ala Gln Leu Ser  Pro Leu Asp
    1265             1270             1275

Ser Glu  Thr Leu Glu Asn Glu  Ala Asn Asn Ile Lys  Met Glu Ala
    1280             1285             1290

Glu Asn  Leu Glu Gln Leu Ile  Asp Gln Lys Leu Lys  Asp Tyr Glu
    1295             1300             1305

Asp Leu  Arg Glu Asp Met Arg  Gly Lys Glu Leu Glu  Val Lys Asn
    1310             1315             1320

Leu Leu  Glu Lys Gly Lys Thr  Glu Gln Gln Thr Ala  Asp Gln Leu
    1325             1330             1335

Leu Ala  Arg Ala Asp Ala Ala  Lys Ala Leu Ala Glu  Glu Ala Ala
    1340             1345             1350

Lys Lys  Gly Arg Asp Thr Leu  Gln Glu Ala Asn Asp  Ile Leu Asn
    1355             1360             1365

Asn Leu  Lys Asp Phe Asp Arg  Arg Val Asn Asp Asn  Lys Thr Ala
    1370             1375             1380

Ala Glu  Glu Ala Leu Arg Lys  Ile Pro Ala Ile Asn  Gln Thr Ile
    1385             1390             1395

Thr Glu  Ala Asn Glu Lys Thr  Arg Glu Ala Gln Gln  Ala Leu Gly
    1400             1405             1410

Ser Ala  Ala Ala Asp Ala Thr  Glu Ala Lys Asn Lys  Ala His Glu
    1415             1420             1425

Ala Glu  Arg Ile Ala Ser Ala  Val Gln Lys Asn Ala  Thr Ser Thr
    1430             1435             1440

Lys Ala  Glu Ala Glu Arg Thr  Phe Ala Glu Val Thr  Asp Leu Asp
    1445             1450             1455

Asn Glu  Val Asn Asn Met Leu  Lys Gln Leu Gln Glu  Ala Glu Lys
    1460             1465             1470

Glu Leu  Lys Arg Lys Gln Asp  Asp Ala Asp Gln Asp  Met Met Met
    1475             1480             1485

Ala Gly  Met Ala Ser Gln Ala  Ala Gln Glu Ala Glu  Ile Asn Ala
    1490             1495             1500

Arg Lys  Ala Lys Asn Ser Val  Thr Ser Leu Leu Ser  Ile Ile Asn
    1505             1510             1515

Asp Leu  Leu Glu Gln Leu Gly  Gln Leu Asp Thr Val  Asp Leu Asn
    1520             1525             1530

Lys Leu  Asn Glu Ile Glu Gly  Thr Leu Asn Lys Ala  Lys Asp Glu
    1535             1540             1545

Met Lys  Val Ser Asp Leu Asp  Arg Lys Val Ser Asp  Leu Glu Asn
    1550             1555             1560

Glu Ala  Lys Lys Gln Glu Ala  Ala Ile Met Asp Tyr  Asn Arg Asp
    1565             1570             1575

Ile Glu  Glu Ile Met Lys Asp  Ile Arg Asn Leu Glu  Asp Ile Arg
    1580             1585             1590

Lys Thr  Leu Pro Ser Gly Cys  Phe Asn Thr Pro Ser  Ile Glu Lys
    1595             1600             1605
```

Pro

<210> SEQ ID NO 86
<211> LENGTH: 1798
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
            20                  25                  30

Gln Ala Pro Ala Pro Asp Val Pro Gly Cys Ser Arg Gly Ser Cys Tyr
        35                  40                  45

Pro Ala Thr Gly Asp Leu Leu Val Gly Arg Ala Asp Arg Leu Thr Ala
    50                  55                  60

Ser Ser Thr Cys Gly Leu Asn Gly Pro Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Arg Ala Ala Trp Trp Gln Ser Glu Asn
            115                 120                 125

Gly Ile Pro Ala Val Thr Ile Gln Leu Asp Leu Glu Ala Glu Phe His
        130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
            180                 185                 190

Pro Pro Arg His Trp Asp Asp Val Val Cys Glu Ser Arg Tyr Ser Glu
            195                 200                 205

Ile Glu Pro Ser Thr Glu Gly Glu Val Ile Tyr Arg Val Leu Asp Pro
        210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
                245                 250                 255

Asp Asn Leu Leu Asp Pro Arg Arg Glu Ile Arg Glu Lys Tyr Tyr Tyr
            260                 265                 270

Ala Leu Tyr Glu Leu Val Val Arg Gly Asn Cys Phe Cys Tyr Gly His
        275                 280                 285

Ala Ser Glu Cys Ala Pro Ala Pro Gly Ala Pro Ala His Ala Glu Gly
        290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
                325                 330                 335

Glu Asp Gly His Ser His Ala Cys Arg Lys Cys Glu Cys His Gly His
            340                 345                 350

-continued

```
Thr His Ser Cys His Phe Asp Met Ala Val Tyr Leu Ala Ser Gly Asn
        355                 360                 365

Val Ser Gly Gly Val Cys Asp Gly Cys Gln His Asn Thr Ala Gly Arg
    370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
                405                 410                 415

Ser Gln Asp Gly Gly Arg Cys Asp Ser His Asp Asp Pro Ala Leu Gly
            420                 425                 430

Leu Val Ser Gly Gln Cys Arg Cys Lys Glu His Val Val Gly Thr Arg
            435                 440                 445

Cys Gln Gln Cys Arg Asp Gly Phe Phe Gly Leu Ser Ile Ser Asp Arg
    450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                485                 490                 495

Val Thr Gly Arg Gly Cys Asp Arg Cys Leu Pro Gly His Trp Gly Leu
            500                 505                 510

Ser His Asp Leu Leu Gly Cys Arg Pro Cys Asp Cys Asp Val Gly Gly
        515                 520                 525

Ala Leu Asp Pro Gln Cys Asp Glu Gly Thr Gly Gln Cys His Cys Arg
        530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
            580                 585                 590

Ser Trp Thr Gly Ser Gly Phe Val Arg Leu Gln Glu Gly Gln Thr Leu
        595                 600                 605

Glu Phe Leu Val Ala Ser Val Pro Lys Ala Met Asp Tyr Asp Leu Leu
    610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Lys Asp Asp Arg Ile Gln Gly Thr Leu Gln Pro His Ala
            660                 665                 670

Arg Tyr Leu Ile Phe Pro Asn Pro Val Cys Leu Glu Pro Gly Ile Ser
        675                 680                 685

Tyr Lys Leu His Leu Lys Leu Val Arg Thr Gly Gly Ser Ala Gln Pro
    690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
            740                 745                 750

Gly Leu Val Pro Ser Lys Thr Ser Pro Ser Glu Ala Cys Ala Pro Leu
        755                 760                 765

Leu Ile Ser Leu Ser Thr Leu Ile Tyr Asn Gly Ala Leu Pro Cys Gln
```

```
         770              775              780

Cys Asn Pro Gln Gly Ser Leu Ser Ser Glu Cys Asn Pro His Gly Gly
785              790              795              800

Gln Cys Leu Cys Lys Pro Gly Val Val Gly Arg Arg Cys Asp Leu Cys
                 805              810              815

Ala Pro Gly Tyr Tyr Gly Phe Gly Pro Thr Gly Cys Gln Ala Cys Gln
                 820              825              830

Cys Ser His Glu Gly Ala Leu Ser Ser Leu Cys Glu Lys Thr Ser Gly
             835              840              845

Gln Cys Leu Cys Arg Thr Gly Ala Phe Gly Leu Arg Cys Asp Arg Cys
850              855              860

Gln Arg Gly Gln Trp Gly Phe Pro Ser Cys Arg Pro Cys Val Cys Asn
865              870              875              880

Gly His Ala Asp Glu Cys Asn Thr His Thr Gly Ala Cys Leu Gly Cys
                 885              890              895

Arg Asp His Thr Gly Gly Glu His Cys Glu Arg Cys Ile Ala Gly Phe
             900              905              910

His Gly Asp Pro Arg Leu Pro Tyr Gly Gly Gln Cys Arg Pro Cys Pro
             915              920              925

Cys Pro Glu Gly Pro Gly Ser Gln Arg His Phe Ala Thr Ser Cys His
     930              935              940

Gln Asp Glu Tyr Ser Gln Gln Ile Val Cys His Cys Arg Ala Gly Tyr
945              950              955              960

Thr Gly Leu Arg Cys Glu Ala Cys Ala Pro Gly His Phe Gly Asp Pro
                 965              970              975

Ser Arg Pro Gly Gly Arg Cys Gln Leu Cys Glu Cys Ser Gly Asn Ile
             980              985              990

Asp Pro Met Asp Pro Asp Ala Cys  Asp Pro His Thr Gly  Gln Cys Leu
     995              1000              1005

Arg Cys  Leu His His Thr Glu  Gly Pro His Cys  His Cys Lys
    1010              1015              1020

Pro Gly  Phe His Gly Gln Ala  Ala Arg Gln Ser Cys  His Arg Cys
    1025              1030              1035

Thr Cys  Asn Leu Leu Gly Thr  Asn Pro Gln Gln Cys  Pro Ser Pro
    1040              1045              1050

Asp Gln  Cys His Cys Asp Pro  Ser Ser Gly Gln Cys  Pro Cys Leu
    1055              1060              1065

Pro Asn  Val Gln Gly Pro Ser  Cys Asp Arg Cys Ala  Pro Asn Phe
    1070              1075              1080

Trp Asn  Leu Thr Ser Gly His  Gly Cys Gln Pro Cys  Ala Cys His
    1085              1090              1095

Pro Ser  Arg Ala Arg Gly Pro  Thr Cys Asn Glu Phe  Thr Gly Gln
    1100              1105              1110

Cys His  Cys Arg Ala Gly Phe  Gly Gly Arg Thr Cys  Ser Glu Cys
    1115              1120              1125

Gln Glu  Leu His Trp Gly Asp  Pro Gly Leu Gln Cys  His Ala Cys
    1130              1135              1140

Asp Cys  Asp Ser Arg Gly Ile  Asp Thr Pro Gln Cys  His Arg Phe
    1145              1150              1155

Thr Gly  His Cys Ser Cys Arg  Pro Gly Val Ser Gly  Val Arg Cys
    1160              1165              1170

Asp Gln  Cys Ala Arg Gly Phe  Ser Gly Ile Phe Pro  Ala Cys His
    1175              1180              1185
```

-continued

```
Pro Cys His Ala Cys Phe Gly Asp Trp Asp Arg Val Val Gln Asp
    1190                1195                1200

Leu Ala Ala Arg Thr Gln Arg Leu Glu Gln Arg Ala Gln Glu Leu
    1205                1210                1215

Gln Gln Thr Gly Val Leu Gly Ala Phe Glu Ser Ser Phe Trp His
    1220                1225                1230

Met Gln Glu Lys Leu Gly Ile Val Gln Gly Ile Val Gly Ala Arg
    1235                1240                1245

Asn Thr Ser Ala Ala Ser Thr Ala Gln Leu Val Glu Ala Thr Glu
    1250                1255                1260

Glu Leu Arg Arg Glu Ile Gly Glu Ala Thr Glu His Leu Thr Gln
    1265                1270                1275

Leu Glu Ala Asp Leu Thr Asp Val Gln Asp Glu Asn Phe Asn Ala
    1280                1285                1290

Asn His Ala Leu Ser Gly Leu Glu Arg Asp Arg Leu Ala Leu Asn
    1295                1300                1305

Leu Thr Leu Arg Gln Leu Asp Gln His Leu Asp Leu Leu Lys His
    1310                1315                1320

Ser Asn Phe Leu Gly Ala Tyr Asp Ser Ile Arg His Ala His Ser
    1325                1330                1335

Gln Ser Ala Glu Ala Glu Arg Arg Ala Asn Thr Ser Ala Leu Ala
    1340                1345                1350

Val Pro Ser Pro Val Ser Asn Ser Ala Ser Ala Arg His Arg Thr
    1355                1360                1365

Glu Ala Leu Met Asp Ala Gln Lys Glu Asp Phe Asn Ser Lys His
    1370                1375                1380

Met Ala Asn Gln Arg Ala Leu Gly Lys Leu Ser Ala His Thr His
    1385                1390                1395

Thr Leu Ser Leu Thr Asp Ile Asn Glu Leu Val Cys Gly Ala Pro
    1400                1405                1410

Gly Asp Ala Pro Cys Ala Thr Ser Pro Cys Gly Gly Ala Gly Cys
    1415                1420                1425

Arg Asp Glu Asp Gly Gln Pro Arg Cys Gly Gly Leu Ser Cys Asn
    1430                1435                1440

Gly Ala Ala Ala Thr Ala Asp Leu Ala Leu Gly Arg Ala Arg His
    1445                1450                1455

Thr Gln Ala Glu Leu Gln Arg Ala Leu Ala Glu Gly Gly Ser Ile
    1460                1465                1470

Leu Ser Arg Val Ala Glu Thr Arg Arg Gln Ala Ser Glu Ala Gln
    1475                1480                1485

Gln Arg Ala Gln Ala Ala Leu Asp Lys Ala Asn Ala Ser Arg Gly
    1490                1495                1500

Gln Val Glu Gln Ala Asn Gln Glu Leu Gln Glu Leu Ile Gln Ser
    1505                1510                1515

Val Lys Asp Phe Leu Asn Gln Glu Gly Ala Asp Pro Asp Ser Ile
    1520                1525                1530

Glu Met Val Ala Thr Arg Val Leu Glu Leu Ser Ile Pro Ala Ser
    1535                1540                1545

Ala Glu Gln Ile Gln His Leu Ala Gly Ala Ile Ala Glu Arg Val
    1550                1555                1560

Arg Ser Leu Ala Asp Val Asp Ala Ile Leu Ala Arg Thr Val Gly
    1565                1570                1575
```

-continued

```
Asp Val  Arg Arg Ala Glu Gln  Leu Leu Gln Asp Ala  Arg Arg Ala
    1580             1585             1590

Arg Ser  Trp Ala Glu Asp Glu  Lys Gln Lys Ala Glu  Thr Val Gln
    1595             1600             1605

Ala Ala  Leu Glu Glu Ala Gln  Arg Ala Gln Gly Ile  Ala Gln Gly
    1610             1615             1620

Ala Ile  Arg Gly Ala Val Ala  Asp Thr Arg Asp Thr  Glu Gln Thr
    1625             1630             1635

Leu Tyr  Gln Val Gln Glu Arg  Met Ala Gly Ala Glu  Arg Ala Leu
    1640             1645             1650

Ser Ser  Ala Gly Glu Arg Ala  Arg Gln Leu Asp Ala  Leu Leu Glu
    1655             1660             1665

Ala Leu  Lys Leu Lys Arg Ala  Gly Asn Ser Leu Ala  Ala Ser Thr
    1670             1675             1680

Ala Glu  Glu Thr Ala Gly Ser  Ala Gln Gly Arg Ala  Gln Glu Ala
    1685             1690             1695

Glu Gln  Leu Leu Arg Gly Pro  Leu Gly Asp Gln Tyr  Gln Thr Val
    1700             1705             1710

Lys Ala  Leu Ala Glu Arg Lys  Ala Gln Gly Val Leu  Ala Ala Gln
    1715             1720             1725

Ala Arg  Ala Glu Gln Leu Arg  Asp Glu Ala Arg Asp  Leu Leu Gln
    1730             1735             1740

Ala Ala  Gln Asp Lys Leu Gln  Arg Leu Gln Glu Leu  Glu Gly Thr
    1745             1750             1755

Tyr Glu  Glu Asn Glu Arg Ala  Leu Glu Ser Lys Ala  Ala Gln Leu
    1760             1765             1770

Asp Gly  Leu Glu Ala Arg Met  Arg Ser Val Leu Gln  Ala Ile Asn
    1775             1780             1785

Leu Gln  Val Gln Ile Tyr Asn  Thr Cys Gln
    1790             1795
```

```
<210> SEQ ID NO 87
<211> LENGTH: 1786
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
    50                  55                  60

Cys Ile Val Ser His Leu Gln Glu Asp Lys Lys Cys Phe Ile Cys Asn
65                  70                  75                  80

Ser Gln Asp Pro Tyr His Glu Thr Leu Asn Pro Asp Ser His Leu Ile
                85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125
```

```
Ala Glu Phe His Phe Thr His Leu Ile Met Thr Phe Lys Thr Phe Arg
    130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
                180                 185                 190

Arg Tyr Ser Asp Ile Glu Pro Ser Thr Glu Gly Glu Val Ile Phe Arg
                195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
                260                 265                 270

Cys Tyr Gly His Ala Ser Glu Cys Ala Pro Val Asp Gly Phe Asn Glu
                275                 280                 285

Glu Val Glu Gly Met Val His Gly His Cys Met Cys Arg His Asn Thr
    290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu
                340                 345                 350

Ala Thr Gly Asn Val Ser Gly Gly Val Cys Asp Asp Cys Gln His Asn
                355                 360                 365

Thr Met Gly Arg Asn Cys Glu Gln Cys Lys Pro Phe Tyr Tyr Gln His
    370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
                420                 425                 430

Glu Gly Glu His Cys Asp Val Cys Lys Glu Gly Phe Tyr Asp Leu Ser
                435                 440                 445

Ser Glu Asp Pro Phe Gly Cys Lys Ser Cys Ala Cys Asn Pro Leu Gly
    450                 455                 460

Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                485                 490                 495

His Trp Gly Leu Ser Asn Asp Leu Asp Gly Cys Arg Pro Cys Asp Cys
                500                 505                 510

Asp Leu Gly Gly Ala Leu Asn Asn Ser Cys Phe Ala Glu Ser Gly Gln
    515                 520                 525

Cys Ser Cys Arg Pro His Met Ile Gly Arg Gln Cys Asn Glu Val Glu
    530                 535                 540
```

-continued

```
Pro Gly Tyr Tyr Phe Ala Thr Leu Asp His Tyr Leu Tyr Glu Ala Glu
545             550             555             560

Glu Ala Asn Leu Gly Pro Gly Val Ser Ile Val Glu Arg Gln Tyr Ile
                565             570             575

Gln Asp Arg Ile Pro Ser Trp Thr Gly Ala Gly Phe Val Arg Val Pro
            580             585             590

Glu Gly Ala Tyr Leu Glu Phe Phe Ile Asp Asn Ile Pro Tyr Ser Met
            595             600             605

Glu Tyr Asp Ile Leu Ile Arg Tyr Glu Pro Gln Leu Pro Asp His Trp
    610             615             620

Glu Lys Ala Val Ile Thr Val Gln Arg Pro Gly Arg Ile Pro Thr Ser
625             630             635             640

Ser Arg Cys Gly Asn Thr Ile Pro Asp Asp Asn Gln Val Val Ser
            645             650             655

Leu Ser Pro Gly Ser Arg Tyr Val Val Leu Pro Arg Pro Val Cys Phe
            660             665             670

Glu Lys Gly Thr Asn Tyr Thr Val Arg Leu Glu Leu Pro Gln Tyr Thr
            675             680             685

Ser Ser Asp Ser Asp Val Glu Ser Pro Tyr Thr Leu Ile Asp Ser Leu
    690             695             700

Val Leu Met Pro Tyr Cys Lys Ser Leu Asp Ile Phe Thr Val Gly Gly
705             710             715             720

Ser Gly Asp Gly Val Val Thr Asn Ser Ala Trp Glu Thr Phe Gln Arg
            725             730             735

Tyr Arg Cys Leu Glu Asn Ser Arg Ser Val Val Lys Thr Pro Met Thr
            740             745             750

Asp Val Cys Arg Asn Ile Ile Phe Ser Ile Ser Ala Leu Leu His Gln
            755             760             765

Thr Gly Leu Ala Cys Glu Cys Asp Pro Gln Gly Ser Leu Ser Ser Val
    770             775             780

Cys Asp Pro Asn Gly Gly Gln Cys Gln Cys Arg Pro Asn Val Val Gly
785             790             795             800

Arg Thr Cys Asn Arg Cys Ala Pro Gly Thr Phe Gly Phe Gly Pro Ser
            805             810             815

Gly Cys Lys Pro Cys Glu Cys His Leu Gln Gly Ser Val Asn Ala Phe
            820             825             830

Cys Asn Pro Val Thr Gly Gln Cys His Cys Phe Gln Gly Val Tyr Ala
            835             840             845

Arg Gln Cys Asp Arg Cys Leu Pro Gly His Trp Gly Phe Pro Ser Cys
    850             855             860

Gln Pro Cys Gln Cys Asn Gly His Ala Asp Asp Cys Asp Pro Val Thr
865             870             875             880

Gly Glu Cys Leu Asn Cys Gln Asp Tyr Thr Met Gly His Asn Cys Glu
            885             890             895

Arg Cys Leu Ala Gly Tyr Tyr Gly Asp Pro Ile Ile Gly Ser Gly Asp
            900             905             910

His Cys Arg Pro Cys Pro Cys Pro Asp Gly Pro Asp Ser Gly Arg Gln
            915             920             925

Phe Ala Arg Ser Cys Tyr Gln Asp Pro Val Thr Leu Gln Leu Ala Cys
    930             935             940

Val Cys Asp Pro Gly Tyr Ile Gly Ser Arg Cys Asp Asp Cys Ala Ser
945             950             955             960

Gly Tyr Phe Gly Asn Pro Ser Glu Val Gly Gly Ser Cys Gln Pro Cys
```

-continued

```
              965              970              975
Gln Cys His Asn Asn Ile Asp Thr Thr Asp Pro Glu Ala Cys Asp Lys
          980              985              990

Glu Thr Gly Arg Cys Leu Lys Cys  Leu Tyr His Thr Glu  Gly Glu His
      995              1000             1005

Cys Gln  Phe Cys Arg Phe Gly  Tyr Tyr Gly Asp Ala  Leu Gln Gln
    1010             1015             1020

Asp Cys  Arg Lys Cys Val Cys  Asn Tyr Leu Gly Thr  Val Gln Glu
    1025             1030             1035

His Cys  Asn Gly Ser Asp Cys  Gln Cys Asp Lys Ala  Thr Gly Gln
    1040             1045             1050

Cys Leu  Cys Leu Pro Asn Val  Ile Gly Gln Asn Cys  Asp Arg Cys
    1055             1060             1065

Ala Pro  Asn Thr Trp Gln Leu  Ala Ser Gly Thr Gly  Cys Asp Pro
    1070             1075             1080

Cys Asn  Cys Asn Ala Ala His  Ser Phe Gly Pro Ser  Cys Asn Glu
    1085             1090             1095

Phe Thr  Gly Gln Cys Gln Cys  Met Pro Gly Phe Gly  Gly Arg Thr
    1100             1105             1110

Cys Ser  Glu Cys Gln Glu Leu  Phe Trp Gly Asp Pro  Asp Val Glu
    1115             1120             1125

Cys Arg  Ala Cys Asp Cys Asp  Pro Arg Gly Ile Glu  Thr Pro Gln
    1130             1135             1140

Cys Asp  Gln Ser Thr Gly Gln  Cys Val Cys Val Glu  Gly Val Glu
    1145             1150             1155

Gly Pro  Arg Cys Asp Lys Cys  Thr Arg Gly Tyr Ser  Gly Val Phe
    1160             1165             1170

Pro Asp  Cys Thr Pro Cys His  Gln Cys Phe Ala Leu  Trp Asp Val
    1175             1180             1185

Ile Ile  Ala Glu Leu Thr Asn  Arg Thr His Arg Phe  Leu Glu Lys
    1190             1195             1200

Ala Lys  Ala Leu Lys Ile Ser  Gly Val Ile Gly Pro  Tyr Arg Glu
    1205             1210             1215

Thr Val  Asp Ser Val Glu Arg  Lys Val Ser Glu Ile  Lys Asp Ile
    1220             1225             1230

Leu Ala  Gln Ser Pro Ala Ala  Glu Pro Leu Lys Asn  Ile Gly Asn
    1235             1240             1245

Leu Phe  Glu Glu Ala Glu Lys  Leu Ile Lys Asp Val  Thr Glu Met
    1250             1255             1260

Met Ala  Gln Val Glu Val Lys  Leu Ser Asp Thr Thr  Ser Gln Ser
    1265             1270             1275

Asn Ser  Thr Ala Lys Glu Leu  Asp Ser Leu Gln Thr  Glu Ala Glu
    1280             1285             1290

Ser Leu  Asp Asn Thr Val Lys  Glu Leu Ala Glu Gln  Leu Glu Phe
    1295             1300             1305

Ile Lys  Asn Ser Asp Ile Arg  Gly Ala Leu Asp Ser  Ile Thr Lys
    1310             1315             1320

Tyr Phe  Gln Met Ser Leu Glu  Ala Glu Glu Arg Val  Asn Ala Ser
    1325             1330             1335

Thr Thr  Glu Pro Asn Ser Thr  Val Glu Gln Ser Ala  Leu Met Arg
    1340             1345             1350

Asp Arg  Val Glu Asp Val Met  Met Glu Arg Glu Ser  Gln Phe Lys
    1355             1360             1365
```

-continued

```
Glu Lys Gln Glu Glu Gln Ala  Arg Leu Leu Asp Glu  Leu Ala Gly
    1370              1375              1380

Lys Leu Gln Ser Leu Asp Leu  Ser Ala Ala Ala Glu  Met Thr Cys
    1385              1390              1395

Gly Thr Pro Pro Gly Ala Ser  Cys Ser Glu Thr Glu  Cys Gly Gly
    1400              1405              1410

Pro Asn Cys Arg Thr Asp Glu  Gly Glu Arg Lys Cys  Gly Gly Pro
    1415              1420              1425

Gly Cys Gly Gly Leu Val Thr  Val Ala His Asn Ala  Trp Gln Lys
    1430              1435              1440

Ala Met Asp Leu Asp Gln Asp  Val Leu Ser Ala Leu  Ala Glu Val
    1445              1450              1455

Glu Gln Leu Ser Lys Met Val  Ser Glu Ala Lys Leu  Arg Ala Asp
    1460              1465              1470

Glu Ala Lys Gln Ser Ala Glu  Asp Ile Leu Leu Lys  Thr Asn Ala
    1475              1480              1485

Thr Lys Glu Lys Met Asp Lys  Ser Asn Glu Glu Leu  Arg Asn Leu
    1490              1495              1500

Ile Lys Gln Ile Arg Asn Phe  Leu Thr Gln Asp Ser  Ala Asp Leu
    1505              1510              1515

Asp Ser Ile Glu Ala Val Ala  Asn Glu Val Leu Lys  Met Glu Met
    1520              1525              1530

Pro Ser Thr Pro Gln Gln Leu  Gln Asn Leu Thr Glu  Asp Ile Arg
    1535              1540              1545

Glu Arg Val Glu Ser Leu Ser  Gln Val Glu Val Ile  Leu Gln His
    1550              1555              1560

Ser Ala Ala Asp Ile Ala Arg  Ala Glu Met Leu Leu  Glu Glu Ala
    1565              1570              1575

Lys Arg Ala Ser Lys Ser Ala  Thr Asp Val Lys Val  Thr Ala Asp
    1580              1585              1590

Met Val Lys Glu Ala Leu Glu  Glu Ala Glu Lys Ala  Gln Val Ala
    1595              1600              1605

Ala Glu Lys Ala Ile Lys Gln  Ala Asp Glu Asp Ile  Gln Gly Thr
    1610              1615              1620

Gln Asn Leu Leu Thr Ser Ile  Glu Ser Glu Thr Ala  Ala Ser Glu
    1625              1630              1635

Glu Thr Leu Phe Asn Ala Ser  Gln Arg Ile Ser Glu  Leu Glu Arg
    1640              1645              1650

Asn Val Glu Glu Leu Lys Arg  Lys Ala Ala Gln Asn  Ser Gly Glu
    1655              1660              1665

Ala Glu Tyr Ile Glu Lys Val  Val Tyr Thr Val Lys  Gln Ser Ala
    1670              1675              1680

Glu Asp Val Lys Lys Thr Leu  Asp Gly Glu Leu Asp  Glu Lys Tyr
    1685              1690              1695

Lys Lys Val Glu Asn Leu Ile  Ala Lys Lys Thr Glu  Glu Ser Ala
    1700              1705              1710

Asp Ala Arg Arg Lys Ala Glu  Met Leu Gln Asn Glu  Ala Lys Thr
    1715              1720              1725

Leu Leu Ala Gln Ala Asn Ser  Lys Leu Gln Leu Leu  Lys Asp Leu
    1730              1735              1740

Glu Arg Lys Tyr Glu Asp Asn  Gln Arg Tyr Leu Glu  Asp Lys Ala
    1745              1750              1755
```

-continued

```
Gln Glu  Leu Ala Arg Leu Glu  Gly Glu Val Arg Ser  Leu Leu Lys
    1760                1765               1770

Asp Ile  Ser Gln Lys Val Ala  Val Tyr Ser Thr Cys  Leu
    1775                1780               1785

<210> SEQ ID NO 88
<211> LENGTH: 3122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Pro Gly Ala Ala Gly Val Leu Leu Leu Leu Leu Ser Gly Gly
1               5                10               15

Leu Gly Gly Val Gln Ala Gln Arg Pro Gln Gln Arg Gln Ser Gln
            20               25               30

Ala His Gln Gln Arg Gly Leu Phe Pro Ala Val Leu Asn Leu Ala Ser
        35               40               45

Asn Ala Leu Ile Thr Thr Asn Ala Thr Cys Gly Glu Lys Gly Pro Glu
    50               55               60

Met Tyr Cys Lys Leu Val Glu His Val Pro Gly Gln Pro Val Arg Asn
65               70               75               80

Pro Gln Cys Arg Ile Cys Asn Gln Asn Ser Ser Asn Pro Asn Gln Arg
            85               90               95

His Pro Ile Thr Asn Ala Ile Asp Gly Lys Asn Thr Trp Trp Gln Ser
            100              105              110

Pro Ser Ile Lys Asn Gly Ile Glu Tyr His Tyr Val Thr Ile Thr Leu
        115              120              125

Asp Leu Gln Gln Val Phe Gln Ile Ala Tyr Val Ile Val Lys Ala Ala
    130              135              140

Asn Ser Pro Arg Pro Gly Asn Trp Ile Leu Glu Arg Ser Leu Asp Asp
145              150              155              160

Val Glu Tyr Lys Pro Trp Gln Tyr His Ala Val Thr Asp Thr Glu Cys
            165              170              175

Leu Thr Leu Tyr Asn Ile Tyr Pro Arg Thr Gly Pro Pro Ser Tyr Ala
            180              185              190

Lys Asp Asp Glu Val Ile Cys Thr Ser Phe Tyr Ser Lys Ile His Pro
        195              200              205

Leu Glu Asn Gly Glu Ile His Ile Ser Leu Ile Asn Gly Arg Pro Ser
    210              215              220

Ala Asp Asp Pro Ser Pro Glu Leu Leu Glu Phe Thr Ser Ala Arg Tyr
225              230              235              240

Ile Arg Leu Arg Phe Gln Arg Ile Arg Thr Leu Asn Ala Asp Leu Met
            245              250              255

Met Phe Ala His Lys Asp Pro Arg Glu Ile Asp Pro Ile Val Thr Arg
            260              265              270

Arg Tyr Tyr Tyr Ser Val Lys Asp Ile Ser Val Gly Gly Met Cys Ile
        275              280              285

Cys Tyr Gly His Ala Arg Ala Cys Pro Leu Asp Pro Ala Thr Asn Lys
    290              295              300

Ser Arg Cys Glu Cys Glu His Asn Thr Cys Gly Asp Ser Cys Asp Gln
305              310              315              320

Cys Cys Pro Gly Phe His Gln Lys Pro Trp Arg Ala Gly Thr Phe Leu
            325              330              335
```

-continued

```
Thr Lys Thr Glu Cys Glu Ala Cys Asn Cys His Gly Lys Ala Glu Glu
            340                 345                 350

Cys Tyr Tyr Asp Glu Asn Val Ala Arg Arg Asn Leu Ser Leu Asn Ile
            355                 360                 365

Arg Gly Lys Tyr Ile Gly Gly Gly Val Cys Ile Asn Cys Thr Gln Asn
            370                 375                 380

Thr Ala Gly Ile Asn Cys Glu Thr Cys Thr Asp Gly Phe Phe Arg Pro
385                 390                 395                 400

Lys Gly Val Ser Pro Asn Tyr Pro Arg Pro Cys Gln Pro Cys His Cys
                405                 410                 415

Asp Pro Ile Gly Ser Leu Asn Glu Val Cys Val Lys Asp Glu Lys His
            420                 425                 430

Ala Arg Arg Gly Leu Ala Pro Gly Ser Cys His Cys Lys Thr Gly Phe
            435                 440                 445

Gly Gly Val Ser Cys Asp Arg Cys Ala Arg Gly Tyr Thr Gly Tyr Pro
            450                 455                 460

Asp Cys Lys Ala Cys Asn Cys Ser Gly Leu Gly Ser Lys Asn Glu Asp
465                 470                 475                 480

Pro Cys Phe Gly Pro Cys Ile Cys Lys Glu Asn Val Glu Gly Gly Asp
                485                 490                 495

Cys Ser Arg Cys Lys Ser Gly Phe Phe Asn Leu Gln Glu Asp Asn Trp
            500                 505                 510

Lys Gly Cys Asp Glu Cys Phe Cys Ser Gly Val Ser Asn Arg Cys Gln
            515                 520                 525

Ser Ser Tyr Trp Thr Tyr Gly Lys Ile Gln Asp Met Ser Gly Trp Tyr
            530                 535                 540

Leu Thr Asp Leu Pro Gly Arg Ile Arg Val Ala Pro Gln Gln Asp Asp
545                 550                 555                 560

Leu Asp Ser Pro Gln Gln Ile Ser Ile Ser Asn Ala Glu Ala Arg Gln
                565                 570                 575

Ala Leu Pro His Ser Tyr Tyr Trp Ser Ala Pro Ala Pro Tyr Leu Gly
            580                 585                 590

Asn Lys Leu Pro Ala Val Gly Gly Gln Leu Thr Phe Thr Ile Ser Tyr
            595                 600                 605

Asp Leu Glu Glu Glu Glu Glu Asp Thr Glu Arg Val Leu Gln Leu Met
            610                 615                 620

Ile Ile Leu Glu Gly Asn Asp Leu Ser Ile Ser Thr Ala Gln Asp Glu
625                 630                 635                 640

Val Tyr Leu His Pro Ser Glu Glu His Thr Asn Val Leu Leu Leu Lys
                645                 650                 655

Glu Glu Ser Phe Thr Ile His Gly Thr His Phe Pro Val Arg Arg Lys
            660                 665                 670

Glu Phe Met Thr Val Leu Ala Asn Leu Lys Arg Val Leu Leu Gln Ile
            675                 680                 685

Thr Tyr Ser Phe Gly Met Asp Ala Ile Phe Arg Leu Ser Ser Val Asn
            690                 695                 700

Leu Glu Ser Ala Val Ser Tyr Pro Thr Asp Gly Ser Ile Ala Ala Ala
705                 710                 715                 720

Val Glu Val Cys Gln Cys Pro Pro Gly Tyr Thr Gly Ser Ser Cys Glu
                725                 730                 735

Ser Cys Trp Pro Arg His Arg Arg Val Asn Gly Thr Ile Phe Gly Gly
            740                 745                 750
```

-continued

```
Ile Cys Glu Pro Cys Gln Cys Phe Gly His Ala Glu Ser Cys Asp Asp
        755             760             765

Val Thr Gly Glu Cys Leu Asn Cys Lys Asp His Thr Gly Gly Pro Tyr
    770             775             780

Cys Asp Lys Cys Leu Pro Gly Phe Tyr Gly Glu Pro Thr Lys Gly Thr
785             790             795             800

Ser Glu Asp Cys Gln Pro Cys Ala Cys Pro Leu Asn Ile Pro Ser Asn
            805             810             815

Asn Phe Ser Pro Thr Cys His Leu Asp Arg Ser Leu Gly Leu Ile Cys
            820             825             830

Asp Gly Cys Pro Val Gly Tyr Thr Gly Pro Arg Cys Glu Arg Cys Ala
            835             840             845

Glu Gly Tyr Phe Gly Gln Pro Ser Val Pro Gly Gly Ser Cys Gln Pro
    850             855             860

Cys Gln Cys Asn Asp Asn Leu Asp Phe Ser Ile Pro Gly Ser Cys Asp
865             870             875             880

Ser Leu Ser Gly Ser Cys Leu Ile Cys Lys Pro Gly Thr Thr Gly Arg
            885             890             895

Tyr Cys Glu Leu Cys Ala Asp Gly Tyr Phe Gly Asp Ala Val Asp Ala
        900             905             910

Lys Asn Cys Gln Pro Cys Arg Cys Asn Ala Gly Gly Ser Phe Ser Glu
        915             920             925

Val Cys His Ser Gln Thr Gly Gln Cys Glu Cys Arg Ala Asn Val Gln
    930             935             940

Gly Gln Arg Cys Asp Lys Cys Lys Ala Gly Thr Phe Gly Leu Gln Ser
945             950             955             960

Ala Arg Gly Cys Val Pro Cys Asn Cys Asn Ser Phe Gly Ser Lys Ser
            965             970             975

Phe Asp Cys Glu Glu Ser Gly Gln Cys Trp Cys Gln Pro Gly Val Thr
            980             985             990

Gly Lys Lys Cys Asp Arg Cys Ala  His Gly Tyr Phe Asn  Phe Gln Glu
        995             1000            1005

Gly Gly  Cys Thr Ala Cys Glu  Cys Ser His Leu Gly  Asn Asn Cys
    1010            1015            1020

Asp Pro  Lys Thr Gly Arg Cys  Ile Cys Pro Pro Asn  Thr Ile Gly
    1025            1030            1035

Glu Lys  Cys Ser Lys Cys Ala  Pro Asn Thr Trp Gly  His Ser Ile
    1040            1045            1050

Thr Thr  Gly Cys Lys Ala Cys  Asn Cys Ser Thr Val  Gly Ser Leu
    1055            1060            1065

Asp Phe  Gln Cys Asn Val Asn  Thr Gly Gln Cys Asn  Cys His Pro
    1070            1075            1080

Lys Phe  Ser Gly Ala Lys Cys  Thr Glu Cys Ser Arg  Gly His Trp
    1085            1090            1095

Asn Tyr  Pro Arg Cys Asn Leu  Cys Asp Cys Phe Leu  Pro Gly Thr
    1100            1105            1110

Asp Ala  Thr Thr Cys Asp Ser  Glu Thr Lys Lys Cys  Ser Cys Ser
    1115            1120            1125

Asp Gln  Thr Gly Gln Cys Thr  Cys Lys Val Asn Val  Glu Gly Ile
    1130            1135            1140

His Cys  Asp Arg Cys Arg Pro  Gly Lys Phe Gly Leu  Asp Ala Lys
    1145            1150            1155

Asn Pro  Leu Gly Cys Ser Ser  Cys Tyr Cys Phe Gly  Thr Thr Thr
```

-continued

```
        1160              1165              1170

Gln Cys  Ser Glu Ala Lys Gly  Leu Ile Arg Thr Trp  Val Thr Leu
    1175              1180              1185

Lys Ala  Glu Gln Thr Ile Leu  Pro Leu Val Asp Glu  Ala Leu Gln
    1190              1195              1200

His Thr  Thr Thr Lys Gly Ile  Val Phe Gln His Pro  Glu Ile Val
    1205              1210              1215

Ala His  Met Asp Leu Met Arg  Glu Asp Leu His Leu  Glu Pro Phe
    1220              1225              1230

Tyr Trp  Lys Leu Pro Glu Gln  Phe Glu Gly Lys Lys  Leu Met Ala
    1235              1240              1245

Tyr Gly  Gly Lys Leu Lys Tyr  Ala Ile Tyr Phe Glu  Ala Arg Glu
    1250              1255              1260

Glu Thr  Gly Phe Ser Thr Tyr  Asn Pro Gln Val Ile  Ile Arg Gly
    1265              1270              1275

Gly Thr  Pro Thr His Ala Arg  Ile Ile Val Arg His  Met Ala Ala
    1280              1285              1290

Pro Leu  Ile Gly Gln Leu Thr  Arg His Glu Ile Glu  Met Thr Glu
    1295              1300              1305

Lys Glu  Trp Lys Tyr Tyr Gly  Asp Asp Pro Arg Val  His Arg Thr
    1310              1315              1320

Val Thr  Arg Glu Asp Phe Leu  Asp Ile Leu Tyr Asp  Ile His Tyr
    1325              1330              1335

Ile Leu  Ile Lys Ala Thr Tyr  Gly Asn Phe Met Arg  Gln Ser Arg
    1340              1345              1350

Ile Ser  Glu Ile Ser Met Glu  Val Ala Glu Gln Gly  Arg Gly Thr
    1355              1360              1365

Thr Met  Thr Pro Pro Ala Asp  Leu Ile Glu Lys Cys  Asp Cys Pro
    1370              1375              1380

Leu Gly  Tyr Ser Gly Leu Ser  Cys Glu Ala Cys Leu  Pro Gly Phe
    1385              1390              1395

Tyr Arg  Leu Arg Ser Gln Pro  Gly Gly Arg Thr Pro  Gly Pro Thr
    1400              1405              1410

Leu Gly  Thr Cys Val Pro Cys  Gln Cys Asn Gly His  Ser Ser Leu
    1415              1420              1425

Cys Asp  Pro Glu Thr Ser Ile  Cys Gln Asn Cys Gln  His His Thr
    1430              1435              1440

Ala Gly  Asp Phe Cys Glu Arg  Cys Ala Leu Gly Tyr  Tyr Gly Ile
    1445              1450              1455

Val Lys  Gly Leu Pro Asn Asp  Cys Gln Gln Cys Ala  Cys Pro Leu
    1460              1465              1470

Ile Ser  Ser Ser Asn Asn Phe  Ser Pro Ser Cys Val  Ala Glu Gly
    1475              1480              1485

Leu Asp  Asp Tyr Arg Cys Thr  Ala Cys Pro Arg Gly  Tyr Glu Gly
    1490              1495              1500

Gln Tyr  Cys Glu Arg Cys Ala  Pro Gly Tyr Thr Gly  Ser Pro Gly
    1505              1510              1515

Asn Pro  Gly Gly Ser Cys Gln  Glu Cys Glu Cys Asp  Pro Tyr Gly
    1520              1525              1530

Ser Leu  Pro Val Pro Cys Asp  Pro Val Thr Gly Phe  Cys Thr Cys
    1535              1540              1545

Arg Pro  Gly Ala Thr Gly Arg  Lys Cys Asp Gly Cys  Lys His Trp
    1550              1555              1560
```

-continued

```
His Ala Arg Glu Gly Trp Glu  Cys Val Phe Cys Gly  Asp Glu Cys
    1565              1570              1575

Thr Gly Leu Leu Leu Gly Asp  Leu Ala Arg Leu Glu  Gln Met Val
    1580              1585              1590

Met Ser Ile Asn Leu Thr Gly  Pro Leu Pro Ala Pro  Tyr Lys Met
    1595              1600              1605

Leu Tyr Gly Leu Glu Asn Met  Thr Gln Glu Leu Lys  His Leu Leu
    1610              1615              1620

Ser Pro Gln Arg Ala Pro Glu  Arg Leu Ile Gln Leu  Ala Glu Gly
    1625              1630              1635

Asn Leu Asn Thr Leu Val Thr  Glu Met Asn Glu Leu  Leu Thr Arg
    1640              1645              1650

Ala Thr Lys Val Thr Ala Asp  Gly Glu Gln Thr Gly  Gln Asp Ala
    1655              1660              1665

Glu Arg Thr Asn Thr Arg Ala  Lys Ser Leu Gly Glu  Phe Ile Lys
    1670              1675              1680

Glu Leu Ala Arg Asp Ala Glu  Ala Val Asn Glu Lys  Ala Ile Lys
    1685              1690              1695

Leu Asn Glu Thr Leu Gly Thr  Arg Asp Glu Ala Phe  Glu Arg Asn
    1700              1705              1710

Leu Glu Gly Leu Gln Lys Glu  Ile Asp Gln Met Ile  Lys Glu Leu
    1715              1720              1725

Arg Arg Lys Asn Leu Glu Thr  Gln Lys Glu Ile Ala  Glu Asp Glu
    1730              1735              1740

Leu Val Ala Ala Glu Ala Leu  Leu Lys Lys Val Lys  Lys Leu Phe
    1745              1750              1755

Gly Glu Ser Arg Gly Glu Asn  Glu Glu Met Glu Lys  Asp Leu Arg
    1760              1765              1770

Glu Lys Leu Ala Asp Tyr Lys  Asn Lys Val Asp Asp  Ala Trp Asp
    1775              1780              1785

Leu Leu Arg Glu Ala Thr Asp  Lys Ile Arg Glu Ala  Asn Arg Leu
    1790              1795              1800

Phe Ala Val Asn Gln Lys Asn  Met Thr Ala Leu Glu  Lys Lys Lys
    1805              1810              1815

Glu Ala Val Glu Ser Gly Lys  Arg Gln Ile Glu Asn  Thr Leu Lys
    1820              1825              1830

Glu Gly Asn Asp Ile Leu Asp  Glu Ala Asn Arg Leu  Ala Asp Glu
    1835              1840              1845

Ile Asn Ser Ile Ile Asp Tyr  Val Glu Asp Ile Gln  Thr Lys Leu
    1850              1855              1860

Pro Pro Met Ser Glu Glu Leu  Asn Asp Lys Ile Asp  Asp Leu Ser
    1865              1870              1875

Gln Glu Ile Lys Asp Arg Lys  Leu Ala Glu Lys Val  Ser Gln Ala
    1880              1885              1890

Glu Ser His Ala Ala Gln Leu  Asn Asp Ser Ser Ala  Val Leu Asp
    1895              1900              1905

Gly Ile Leu Asp Glu Ala Lys  Asn Ile Ser Phe Asn  Ala Thr Ala
    1910              1915              1920

Ala Phe Lys Ala Tyr Ser Asn  Ile Lys Asp Tyr Ile  Asp Glu Ala
    1925              1930              1935

Glu Lys Val Ala Lys Glu Ala  Lys Asp Leu Ala His  Glu Ala Thr
    1940              1945              1950
```

-continued

```
Lys Leu  Ala Thr Gly Pro Arg  Gly Leu Leu Lys Glu  Asp Ala Lys
    1955             1960             1965

Gly Cys  Leu Gln Lys Ser Phe  Arg Ile Leu Asn Glu  Ala Lys Lys
    1970             1975             1980

Leu Ala  Asn Asp Val Lys Glu  Asn Glu Asp His Leu  Asn Gly Leu
    1985             1990             1995

Lys Thr  Arg Ile Glu Asn Ala  Asp Ala Arg Asn Gly  Asp Leu Leu
    2000             2005             2010

Arg Thr  Leu Asn Asp Thr Leu  Gly Lys Leu Ser Ala  Ile Pro Asn
    2015             2020             2025

Asp Thr  Ala Ala Lys Leu Gln  Ala Val Lys Asp Lys  Ala Arg Gln
    2030             2035             2040

Ala Asn  Asp Thr Ala Lys Asp  Val Leu Ala Gln Ile  Thr Glu Leu
    2045             2050             2055

His Gln  Asn Leu Asp Gly Leu  Lys Lys Asn Tyr Asn  Lys Leu Ala
    2060             2065             2070

Asp Ser  Val Ala Lys Thr Asn  Ala Val Val Lys Asp  Pro Ser Lys
    2075             2080             2085

Asn Lys  Ile Ile Ala Asp Ala  Asp Ala Thr Val Lys  Asn Leu Glu
    2090             2095             2100

Gln Glu  Ala Asp Arg Leu Ile  Asp Lys Leu Lys Pro  Ile Lys Glu
    2105             2110             2115

Leu Glu  Asp Asn Leu Lys Lys  Asn Ile Ser Glu Ile  Lys Glu Leu
    2120             2125             2130

Ile Asn  Gln Ala Arg Lys Gln  Ala Asn Ser Ile Lys  Val Ser Val
    2135             2140             2145

Ser Ser  Gly Gly Asp Cys Ile  Arg Thr Tyr Lys Pro  Glu Ile Lys
    2150             2155             2160

Lys Gly  Ser Tyr Asn Asn Ile  Val Val Asn Val Lys  Thr Ala Val
    2165             2170             2175

Ala Asp  Asn Leu Leu Phe Tyr  Leu Gly Ser Ala Lys  Phe Ile Asp
    2180             2185             2190

Phe Leu  Ala Ile Glu Met Arg  Lys Gly Lys Val Ser  Phe Leu Trp
    2195             2200             2205

Asp Val  Gly Ser Gly Val Gly  Arg Val Glu Tyr Pro  Asp Leu Thr
    2210             2215             2220

Ile Asp  Asp Ser Tyr Trp Tyr  Arg Ile Val Ala Ser  Arg Thr Gly
    2225             2230             2235

Arg Asn  Gly Thr Ile Ser Val  Arg Ala Leu Asp Gly  Pro Lys Ala
    2240             2245             2250

Ser Ile  Val Pro Ser Thr His  His Ser Thr Ser Pro  Pro Gly Tyr
    2255             2260             2265

Thr Ile  Leu Asp Val Asp Ala  Asn Ala Met Leu Phe  Val Gly Gly
    2270             2275             2280

Leu Thr  Gly Lys Leu Lys Lys  Ala Asp Ala Val Arg  Val Ile Thr
    2285             2290             2295

Phe Thr  Gly Cys Met Gly Glu  Thr Tyr Phe Asp Asn  Lys Pro Ile
    2300             2305             2310

Gly Leu  Trp Asn Phe Arg Glu  Lys Glu Gly Asp Cys  Lys Gly Cys
    2315             2320             2325

Thr Val  Ser Pro Gln Val Glu  Asp Ser Glu Gly Thr  Ile Gln Phe
    2330             2335             2340

Asp Gly  Glu Gly Tyr Ala Leu  Val Ser Arg Pro Ile  Arg Trp Tyr
```

-continued

```
                2345                 2350                 2355

Pro Asn Ile Ser Thr Val Met Phe Lys Phe Arg Thr Phe Ser Ser
    2360                 2365                 2370

Ser Ala Leu Leu Met Tyr Leu Ala Thr Arg Asp Leu Arg Asp Phe
    2375                 2380                 2385

Met Ser Val Glu Leu Thr Asp Gly His Ile Lys Val Ser Tyr Asp
    2390                 2395                 2400

Leu Gly Ser Gly Met Ala Ser Val Val Ser Asn Gln Asn His Asn
    2405                 2410                 2415

Asp Gly Lys Trp Lys Ser Phe Thr Leu Ser Arg Ile Gln Lys Gln
    2420                 2425                 2430

Ala Asn Ile Ser Ile Val Asp Ile Asp Thr Asn Gln Glu Glu Asn
    2435                 2440                 2445

Ile Ala Thr Ser Ser Ser Gly Asn Asn Phe Gly Leu Asp Leu Lys
    2450                 2455                 2460

Ala Asp Asp Lys Ile Tyr Phe Gly Gly Leu Pro Thr Leu Arg Asn
    2465                 2470                 2475

Leu Ser Met Lys Ala Arg Pro Glu Val Asn Leu Lys Lys Tyr Ser
    2480                 2485                 2490

Gly Cys Leu Lys Asp Ile Glu Ile Ser Arg Thr Pro Tyr Asn Ile
    2495                 2500                 2505

Leu Ser Ser Pro Asp Tyr Val Gly Val Thr Lys Gly Cys Ser Leu
    2510                 2515                 2520

Glu Asn Val Tyr Thr Val Ser Phe Pro Lys Pro Gly Phe Val Glu
    2525                 2530                 2535

Leu Ser Pro Val Pro Ile Asp Val Gly Thr Glu Ile Asn Leu Ser
    2540                 2545                 2550

Phe Ser Thr Lys Asn Glu Ser Gly Ile Ile Leu Leu Gly Ser Gly
    2555                 2560                 2565

Gly Thr Pro Ala Pro Pro Arg Arg Lys Arg Arg Gln Thr Gly Gln
    2570                 2575                 2580

Ala Tyr Tyr Ala Ile Leu Leu Asn Arg Gly Arg Leu Glu Val His
    2585                 2590                 2595

Leu Ser Thr Gly Ala Arg Thr Met Arg Lys Ile Val Ile Arg Pro
    2600                 2605                 2610

Glu Pro Asn Leu Phe His Asp Gly Arg Glu His Ser Val His Val
    2615                 2620                 2625

Glu Arg Thr Arg Gly Ile Phe Thr Val Gln Val Asp Glu Asn Arg
    2630                 2635                 2640

Arg Tyr Met Gln Asn Leu Thr Val Glu Gln Pro Ile Glu Val Lys
    2645                 2650                 2655

Lys Leu Phe Val Gly Gly Ala Pro Pro Glu Phe Gln Pro Ser Pro
    2660                 2665                 2670

Leu Arg Asn Ile Pro Pro Phe Glu Gly Cys Ile Trp Asn Leu Val
    2675                 2680                 2685

Ile Asn Ser Val Pro Met Asp Phe Ala Arg Pro Val Ser Phe Lys
    2690                 2695                 2700

Asn Ala Asp Ile Gly Arg Cys Ala His Gln Lys Leu Arg Glu Asp
    2705                 2710                 2715

Glu Asp Gly Ala Ala Pro Ala Glu Ile Val Ile Gln Pro Glu Pro
    2720                 2725                 2730

Val Pro Thr Pro Ala Phe Pro Thr Pro Thr Pro Val Leu Thr His
    2735                 2740                 2745
```

```
Gly Pro Cys Ala Ala Glu Ser  Glu Pro Ala Leu Leu  Ile Gly Ser
    2750              2755              2760

Lys Gln Phe Gly Leu Ser Arg  Asn Ser His Ile Ala  Ile Ala Phe
    2765              2770              2775

Asp Asp Thr Lys Val Lys Asn  Arg Leu Thr Ile Glu  Leu Glu Val
    2780              2785              2790

Arg Thr Glu Ala Glu Ser Gly  Leu Leu Phe Tyr Met  Ala Arg Ile
    2795              2800              2805

Asn His Ala Asp Phe Ala Thr  Val Gln Leu Arg Asn  Gly Leu Pro
    2810              2815              2820

Tyr Phe Ser Tyr Asp Leu Gly  Ser Gly Asp Thr His  Thr Met Ile
    2825              2830              2835

Pro Thr Lys Ile Asn Asp Gly  Gln Trp His Lys Ile  Lys Ile Met
    2840              2845              2850

Arg Ser Lys Gln Glu Gly Ile  Leu Tyr Val Asp Gly  Ala Ser Asn
    2855              2860              2865

Arg Thr Ile Ser Pro Lys Lys  Ala Asp Ile Leu Asp  Val Val Gly
    2870              2875              2880

Met Leu Tyr Val Gly Gly Leu  Pro Ile Asn Tyr Thr  Thr Arg Arg
    2885              2890              2895

Ile Gly Pro Val Thr Tyr Ser  Ile Asp Gly Cys Val  Arg Asn Leu
    2900              2905              2910

His Met Ala Glu Ala Pro Ala  Asp Leu Glu Gln Pro  Thr Ser Ser
    2915              2920              2925

Phe His Val Gly Thr Cys Phe  Ala Asn Ala Gln Arg  Gly Thr Tyr
    2930              2935              2940

Phe Asp Gly Thr Gly Phe Ala  Lys Ala Val Gly Gly  Phe Lys Val
    2945              2950              2955

Gly Leu Asp Leu Leu Val Glu  Phe Glu Phe Arg Thr  Thr Thr Thr
    2960              2965              2970

Thr Gly Val Leu Leu Gly Ile  Ser Ser Gln Lys Met  Asp Gly Met
    2975              2980              2985

Gly Ile Glu Met Ile Asp Glu  Lys Leu Met Phe His  Val Asp Asn
    2990              2995              3000

Gly Ala Gly Arg Phe Thr Ala  Val Tyr Asp Ala Gly  Val Pro Gly
    3005              3010              3015

His Leu Cys Asp Gly Gln Trp  His Lys Val Thr Ala  Asn Lys Ile
    3020              3025              3030

Lys His Arg Ile Glu Leu Thr  Val Asp Gly Asn Gln  Val Glu Ala
    3035              3040              3045

Gln Ser Pro Asn Pro Ala Ser  Thr Ser Ala Asp Thr  Asn Asp Pro
    3050              3055              3060

Val Phe Val Gly Gly Phe Pro  Asp Asp Leu Lys Gln  Phe Gly Leu
    3065              3070              3075

Thr Thr Ser Ile Pro Phe Arg  Gly Cys Ile Arg Ser  Leu Lys Leu
    3080              3085              3090

Thr Lys Gly Thr Gly Lys Pro  Leu Glu Val Asn Phe  Ala Lys Ala
    3095              3100              3105

Leu Glu Leu Arg Gly Val Gln  Pro Val Ser Cys Pro  Ala Asn
    3110              3115              3120
```

<210> SEQ ID NO 89
<211> LENGTH: 3075

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Met Arg Gly Gly Val Leu Leu Val Leu Leu Leu Cys Val Ala Ala Gln
1               5                   10                  15

Cys Arg Gln Arg Gly Leu Phe Pro Ala Ile Leu Asn Leu Ala Ser Asn
            20                  25                  30

Ala His Ile Ser Thr Asn Ala Thr Cys Gly Glu Lys Gly Pro Glu Met
        35                  40                  45

Phe Cys Lys Leu Val Glu His Val Pro Gly Arg Pro Val Arg Asn Pro
    50                  55                  60

Gln Cys Arg Ile Cys Asp Gly Asn Ser Ala Asn Pro Arg Glu Arg His
65                  70                  75                  80

Pro Ile Ser His Ala Ile Asp Gly Thr Asn Asn Trp Trp Gln Ser Pro
                85                  90                  95

Ser Ile Gln Asn Gly Arg Glu Tyr His Trp Val Thr Ile Thr Leu Asp
            100                 105                 110

Leu Arg Gln Val Phe Gln Val Ala Tyr Val Ile Ile Lys Ala Ala Asn
            115                 120                 125

Ala Pro Arg Pro Gly Asn Trp Ile Leu Glu Arg Ser Leu Asp Gly Thr
    130                 135                 140

Thr Phe Ser Pro Trp Gln Tyr Tyr Ala Val Ser Asp Ser Glu Cys Leu
145                 150                 155                 160

Ser Arg Tyr Asn Ile Thr Pro Arg Arg Gly Pro Pro Thr Tyr Arg Ala
            165                 170                 175

Asp Asp Glu Val Ile Cys Thr Ser Tyr Tyr Ser Arg Leu Val Pro Leu
            180                 185                 190

Glu His Gly Glu Ile His Thr Ser Leu Ile Asn Gly Arg Pro Ser Ala
            195                 200                 205

Asp Asp Leu Ser Pro Lys Leu Leu Glu Phe Thr Ser Ala Arg Tyr Ile
    210                 215                 220

Arg Leu Arg Leu Gln Arg Ile Arg Thr Leu Asn Ala Asp Leu Met Thr
225                 230                 235                 240

Leu Ser His Arg Glu Pro Lys Glu Leu Asp Pro Ile Val Thr Arg Arg
            245                 250                 255

Tyr Tyr Tyr Ser Ile Lys Asp Ile Ser Val Gly Gly Met Cys Ile Cys
            260                 265                 270

Tyr Gly His Ala Ser Ser Cys Pro Trp Asp Glu Thr Thr Lys Lys Leu
            275                 280                 285

Gln Cys Gln Cys Glu His Asn Thr Cys Gly Glu Ser Cys Asn Arg Cys
    290                 295                 300

Cys Pro Gly Tyr His Gln Gln Pro Trp Arg Pro Gly Thr Val Ser Ser
305                 310                 315                 320

Gly Asn Thr Cys Glu Ala Cys Asn Cys His Asn Lys Ala Lys Asp Cys
            325                 330                 335

Tyr Tyr Asp Glu Ser Val Ala Lys Gln Lys Lys Ser Leu Asn Thr Ala
            340                 345                 350

Gly Gln Phe Arg Gly Gly Gly Val Cys Ile Asn Cys Leu Gln Asn Thr
            355                 360                 365

Met Gly Ile Asn Cys Glu Thr Cys Ile Asp Gly Tyr Tyr Arg Pro His
370                 375                 380
```

-continued

```
Lys Val Ser Pro Tyr Glu Asp Glu Pro Cys Arg Pro Cys Asn Cys Asp
385             390             395             400

Pro Val Gly Ser Leu Ser Ser Val Cys Ile Lys Asp Asp Leu His Ser
            405             410             415

Asp Leu His Asn Gly Lys Gln Pro Gly Gln Cys Pro Cys Lys Glu Gly
            420             425             430

Tyr Thr Gly Glu Lys Cys Asp Arg Cys Gln Leu Gly Tyr Lys Asp Tyr
            435             440             445

Pro Thr Cys Val Ser Cys Gly Cys Asn Pro Val Gly Ser Ala Ser Asp
            450             455             460

Glu Pro Cys Thr Gly Pro Cys Val Cys Lys Glu Asn Val Glu Gly Lys
465             470             475             480

Ala Cys Asp Arg Cys Lys Pro Gly Phe Tyr Asn Leu Lys Glu Lys Asn
            485             490             495

Pro Arg Gly Cys Ser Glu Cys Phe Cys Phe Gly Val Ser Asp Val Cys
            500             505             510

Ser Ser Leu Ser Trp Pro Val Gly Gln Val Asn Ser Met Ser Gly Trp
            515             520             525

Leu Val Thr Asp Leu Ile Ser Pro Arg Lys Ile Pro Ser Gln Gln Asp
            530             535             540

Ala Leu Gly Gly Arg His Gln Val Ser Ile Asn Asn Thr Ala Val Met
545             550             555             560

Gln Arg Leu Ala Pro Lys Tyr Tyr Trp Ala Ala Pro Glu Ala Tyr Leu
            565             570             575

Gly Asn Lys Leu Thr Ala Phe Gly Gly Phe Leu Lys Tyr Thr Val Ser
            580             585             590

Tyr Asp Ile Pro Val Glu Thr Val Asp Ser Asn Leu Met Ser His Ala
            595             600             605

Asp Val Ile Ile Lys Gly Asn Gly Leu Thr Leu Ser Thr Gln Ala Glu
            610             615             620

Gly Leu Ser Leu Gln Pro Tyr Glu Glu Tyr Leu Asn Val Val Arg Leu
625             630             635             640

Val Pro Glu Asn Phe Gln Asp Phe His Ser Lys Arg Gln Ile Asp Arg
            645             650             655

Asp Gln Leu Met Thr Val Leu Ala Asn Val Thr His Leu Leu Ile Arg
            660             665             670

Ala Asn Tyr Asn Ser Ala Lys Met Ala Leu Tyr Arg Leu Glu Ser Val
            675             680             685

Ser Leu Asp Ile Ala Ser Ser Asn Ala Ile Asp Leu Val Val Ala Ala
            690             695             700

Asp Val Glu His Cys Glu Cys Pro Gln Gly Tyr Thr Gly Thr Ser Cys
705             710             715             720

Glu Ser Cys Leu Ser Gly Tyr Tyr Arg Val Asp Gly Ile Leu Phe Gly
            725             730             735

Gly Ile Cys Gln Pro Cys Glu Cys His Gly His Ala Ala Glu Cys Asn
            740             745             750

Val His Gly Val Cys Ile Ala Cys Ala His Asn Thr Thr Gly Val His
            755             760             765

Cys Glu Gln Cys Leu Pro Gly Phe Tyr Gly Glu Pro Ser Arg Gly Thr
            770             775             780

Pro Gly Asp Cys Gln Pro Cys Ala Cys Pro Leu Thr Ile Ala Ser Asn
785             790             795             800
```

-continued

```
Asn Phe Ser Pro Thr Cys His Leu Asn Asp Gly Asp Glu Val Val Cys
            805                 810                 815

Asp Trp Cys Ala Pro Gly Tyr Ser Gly Ala Trp Cys Glu Arg Cys Ala
            820                 825                 830

Asp Gly Tyr Tyr Gly Asn Pro Thr Val Pro Gly Glu Ser Cys Val Pro
        835                 840                 845

Cys Asp Cys Ser Gly Asn Val Asp Pro Ser Glu Ala Gly His Cys Asp
850                 855                 860

Ser Val Thr Gly Glu Cys Leu Lys Cys Leu Gly Asn Thr Asp Gly Ala
865                 870                 875                 880

His Cys Glu Arg Cys Ala Asp Gly Phe Tyr Gly Asp Ala Val Thr Ala
            885                 890                 895

Lys Asn Cys Arg Ala Cys Glu Cys His Val Lys Gly Ser His Ser Ala
            900                 905                 910

Val Cys His Leu Glu Thr Gly Leu Cys Asp Cys Lys Pro Asn Val Thr
            915                 920                 925

Gly Gln Gln Cys Asp Gln Cys Leu His Gly Tyr Tyr Gly Leu Asp Ser
        930                 935                 940

Gly His Gly Cys Arg Pro Cys Asn Cys Ser Val Ala Gly Ser Val Ser
945                 950                 955                 960

Asp Gly Cys Thr Asp Glu Gly Gln Cys His Cys Val Pro Gly Val Ala
            965                 970                 975

Gly Lys Arg Cys Asp Arg Cys Ala His Gly Phe Tyr Ala Tyr Gln Asp
            980                 985                 990

Gly Ser Cys Thr Pro Cys Asp Cys  Pro His Thr Gln Asn  Thr Cys Asp
        995                 1000                1005

Pro Glu  Thr Gly Glu Cys Val  Cys Pro Pro His Thr  Gln Gly Val
    1010                1015                1020

Lys Cys  Glu Glu Cys Glu Asp  Gly His Trp Gly Tyr  Asp Ala Glu
    1025                1030                1035

Val Gly  Cys Gln Ala Cys Asn  Cys Ser Leu Val Gly  Ser Thr His
    1040                1045                1050

His Arg  Cys Asp Val Val Thr  Gly His Cys Gln Cys  Lys Ser Lys
    1055                1060                1065

Phe Gly  Gly Arg Ala Cys Asp  Gln Cys Ser Leu Gly  Tyr Arg Asp
    1070                1075                1080

Phe Pro  Asp Cys Val Pro Cys  Asp Cys Asp Leu Arg  Gly Thr Ser
    1085                1090                1095

Gly Asp  Ala Cys Asn Leu Glu  Gln Gly Leu Cys Gly  Cys Val Glu
    1100                1105                1110

Glu Thr  Gly Ala Cys Pro Cys  Lys Glu Asn Val Phe  Gly Pro Gln
    1115                1120                1125

Cys Asn  Glu Cys Arg Glu Gly  Thr Phe Ala Leu Arg  Ala Asp Asn
    1130                1135                1140

Pro Leu  Gly Cys Ser Pro Cys  Phe Cys Ser Gly Leu  Ser His Leu
    1145                1150                1155

Cys Ser  Glu Leu Glu Asp Tyr  Val Arg Thr Pro Val  Thr Leu Gly
    1160                1165                1170

Ser Asp  Gln Pro Leu Leu Arg  Val Val Ser Gln Ser  Asn Leu Arg
    1175                1180                1185

Gly Thr  Thr Glu Gly Val Tyr  Tyr Gln Ala Pro Asp  Phe Leu Leu
    1190                1195                1200

Asp Ala  Ala Thr Val Arg Gln  His Ile Arg Ala Glu  Pro Phe Tyr
```

-continued

```
          1205                    1210                    1215

Trp Arg  Leu Pro Gln Gln Phe  Gln Gly Asp Gln Leu  Met Ala Tyr
     1220                 1225                 1230

Gly Gly  Lys Leu Lys Tyr Ser  Val Ala Phe Tyr Ser  Leu Asp Gly
     1235                 1240                 1245

Val Gly  Thr Ser Asn Phe Glu  Pro Gln Val Leu Ile  Lys Gly Gly
     1250                 1255                 1260

Arg Ile  Arg Lys Gln Val Ile  Tyr Met Asp Ala Pro  Ala Pro Glu
     1265                 1270                 1275

Asn Gly  Val Arg Gln Glu Gln  Glu Val Ala Met Arg  Glu Asn Phe
     1280                 1285                 1290

Trp Lys  Tyr Phe Asn Ser Val  Ser Glu Lys Pro Val  Thr Arg Glu
     1295                 1300                 1305

Asp Phe  Met Ser Val Leu Ser  Asp Ile Glu Tyr Ile  Leu Ile Lys
     1310                 1315                 1320

Ala Ser  Tyr Gly Gln Gly Leu  Gln Gln Ser Arg Ile  Ser Asp Ile
     1325                 1330                 1335

Ser Met  Glu Val Gly Arg Lys  Ala Glu Lys Leu His  Pro Glu Glu
     1340                 1345                 1350

Glu Val  Ala Ser Leu Leu Glu  Asn Cys Val Cys Pro  Pro Gly Thr
     1355                 1360                 1365

Val Gly  Phe Ser Cys Gln Asp  Cys Ala Pro Gly Tyr  His Arg Gly
     1370                 1375                 1380

Lys Leu  Pro Ala Gly Ser Asp  Arg Gly Pro Arg Pro  Leu Val Ala
     1385                 1390                 1395

Pro Cys  Val Pro Cys Ser Cys  Asn Asn His Ser Asp  Thr Cys Asp
     1400                 1405                 1410

Pro Asn  Thr Gly Lys Cys Leu  Asn Cys Gly Asp Asn  Thr Ala Gly
     1415                 1420                 1425

Asp His  Cys Asp Val Cys Thr  Ser Gly Tyr Tyr Gly  Lys Val Thr
     1430                 1435                 1440

Gly Ser  Ala Ser Asp Cys Ala  Leu Cys Ala Cys Pro  His Ser Pro
     1445                 1450                 1455

Pro Ala  Ser Phe Ser Pro Thr  Cys Val Leu Glu Gly  Asp His Asp
     1460                 1465                 1470

Phe Arg  Cys Asp Ala Cys Leu  Leu Gly Tyr Glu Gly  Lys His Cys
     1475                 1480                 1485

Glu Arg  Cys Ser Ser Ser Tyr  Tyr Gly Asn Pro Gln  Thr Pro Gly
     1490                 1495                 1500

Gly Ser  Cys Gln Lys Cys Asp  Cys Asn Pro His Gly  Ser Val His
     1505                 1510                 1515

Gly Asp  Cys Asp Arg Thr Ser  Gly Gln Cys Val Cys  Arg Leu Gly
     1520                 1525                 1530

Ala Ser  Gly Leu Arg Cys Asp  Glu Cys Glu Pro Arg  His Ile Leu
     1535                 1540                 1545

Met Glu  Thr Asp Cys Val Ser  Cys Asp Asp Glu Cys  Val Gly Val
     1550                 1555                 1560

Leu Leu  Asn Asp Leu Asp Glu  Ile Gly Asp Ala Val  Leu Ser Leu
     1565                 1570                 1575

Asn Leu  Thr Gly Ile Ile Pro  Val Pro Tyr Gly Ile  Leu Ser Asn
     1580                 1585                 1590

Leu Glu  Asn Thr Thr Lys Tyr  Leu Gln Glu Ser Leu  Leu Lys Glu
     1595                 1600                 1605
```

-continued

```
Asn Met  Gln Lys Asp Leu Gly  Lys Ile Lys Leu Glu  Gly Val Ala
    1610             1615             1620

Glu Glu  Thr Asp Asn Leu Gln  Lys Lys Leu Thr Arg  Met Leu Ala
    1625             1630             1635

Ser Thr  Gln Lys Val Asn Arg  Ala Thr Glu Arg Ile  Phe Lys Glu
    1640             1645             1650

Ser Gln  Asp Leu Ala Ile Ala  Ile Glu Arg Leu Gln  Met Ser Ile
    1655             1660             1665

Thr Glu  Ile Met Glu Lys Thr  Thr Leu Asn Gln Thr  Leu Asp Glu
    1670             1675             1680

Asp Phe  Leu Leu Pro Asn Ser  Thr Leu Gln Asn Met  Gln Gln Asn
    1685             1690             1695

Gly Thr  Ser Leu Leu Glu Ile  Met Gln Ile Arg Asp  Phe Thr Gln
    1700             1705             1710

Leu His  Gln Asn Ala Thr Leu  Glu Leu Lys Ala Ala  Glu Asp Leu
    1715             1720             1725

Leu Ser  Gln Ile Gln Glu Asn  Tyr Gln Lys Pro Leu  Glu Glu Leu
    1730             1735             1740

Glu Val  Leu Lys Glu Ala Ala  Ser His Val Leu Ser  Lys His Asn
    1745             1750             1755

Asn Glu  Leu Lys Ala Ala Glu  Ala Leu Val Arg Glu  Ala Glu Ala
    1760             1765             1770

Lys Met  Gln Glu Ser Asn His  Leu Leu Leu Met Val  Asn Ala Asn
    1775             1780             1785

Leu Arg  Glu Phe Ser Asp Lys  Lys Leu His Val Gln  Glu Glu Gln
    1790             1795             1800

Asn Leu  Thr Ser Glu Leu Ile  Val Gln Gly Arg Gly  Leu Ile Asp
    1805             1810             1815

Ala Ala  Ala Ala Gln Thr Asp  Ala Val Gln Asp Ala  Leu Glu His
    1820             1825             1830

Leu Glu  Asp His Gln Asp Lys  Leu Leu Leu Trp Ser  Ala Lys Ile
    1835             1840             1845

Arg His  His Ile Asp Asp Leu  Val Met His Met Ser  Gln Arg Asn
    1850             1855             1860

Ala Val  Asp Leu Val Tyr Arg  Ala Glu Asp His Ala  Ala Glu Phe
    1865             1870             1875

Gln Arg  Leu Ala Asp Val Leu  Tyr Ser Gly Leu Glu  Asn Ile Arg
    1880             1885             1890

Asn Val  Ser Leu Asn Ala Thr  Ser Ala Ala Tyr Val  His Tyr Asn
    1895             1900             1905

Ile Gln  Ser Leu Ile Glu Glu  Ser Glu Glu Leu Ala  Arg Asp Ala
    1910             1915             1920

His Arg  Thr Val Thr Glu Thr  Ser Leu Leu Ser Glu  Ser Leu Val
    1925             1930             1935

Ser Asn  Gly Lys Ala Ala Val  Gln Arg Ser Ser Arg  Phe Leu Lys
    1940             1945             1950

Glu Gly  Asn Asn Leu Ser Arg  Lys Leu Pro Gly Ile  Ala Leu Glu
    1955             1960             1965

Leu Ser  Glu Leu Arg Asn Lys  Thr Asn Arg Phe Gln  Glu Asn Ala
    1970             1975             1980

Val Glu  Ile Thr Arg Gln Thr  Asn Glu Ser Leu Leu  Ile Leu Arg
    1985             1990             1995
```

-continued

```
Ala Ile Pro Lys Gly Ile Arg  Asp Lys Gly Ala Lys  Thr Lys Glu
    2000             2005              2010

Leu Ala Thr Ser Ala Ser Gln  Ser Ala Val Ser Thr  Leu Arg Asp
    2015             2020              2025

Val Ala Gly Leu Ser Gln Glu  Leu Leu Asn Thr Ser  Ala Ser Leu
    2030             2035              2040

Ser Arg Val Asn Thr Thr Leu  Arg Glu Thr His Gln  Leu Leu Gln
    2045             2050              2055

Asp Ser Thr Met Ala Thr Leu  Leu Ala Gly Arg Lys  Val Lys Asp
    2060             2065              2070

Val Glu Ile Gln Ala Asn Leu  Leu Phe Asp Arg Leu  Lys Pro Leu
    2075             2080              2085

Lys Met Leu Glu Glu Asn Leu  Ser Arg Asn Leu Ser  Glu Ile Lys
    2090             2095              2100

Leu Leu Ile Ser Gln Ala Arg  Lys Gln Ala Ala Ser  Ile Lys Val
    2105             2110              2115

Ala Val Ser Ala Asp Arg Asp  Cys Ile Arg Ala Tyr  Gln Pro Gln
    2120             2125              2130

Ile Ser Ser Thr Asn Tyr Asn  Thr Leu Thr Leu Asn  Val Lys Thr
    2135             2140              2145

Gln Glu Pro Asp Asn Leu Leu  Phe Tyr Leu Gly Ser  Ser Thr Ala
    2150             2155              2160

Ser Asp Phe Leu Ala Val Glu  Met Arg Arg Gly Arg  Val Ala Phe
    2165             2170              2175

Leu Trp Asp Leu Gly Ser Gly  Ser Thr Arg Leu Glu  Phe Pro Asp
    2180             2185              2190

Phe Pro Ile Asp Asp Asn Arg  Trp His Ser Ile His  Val Ala Arg
    2195             2200              2205

Phe Gly Asn Ile Gly Ser Leu  Ser Val Lys Glu Met  Ser Ser Asn
    2210             2215              2220

Gln Lys Ser Pro Thr Lys Thr  Ser Lys Ser Pro Gly  Thr Ala Asn
    2225             2230              2235

Val Leu Asp Val Asn Asn Ser  Thr Leu Met Phe Val  Gly Gly Leu
    2240             2245              2250

Gly Gly Gln Ile Lys Lys Ser  Pro Ala Val Lys Val  Thr His Phe
    2255             2260              2265

Lys Gly Cys Leu Gly Glu Ala  Phe Leu Asn Gly Lys  Ser Ile Gly
    2270             2275              2280

Leu Trp Asn Tyr Ile Glu Arg  Glu Gly Lys Cys Arg  Gly Cys Phe
    2285             2290              2295

Gly Ser Ser Gln Asn Glu Asp  Pro Ser Phe His Phe  Asp Gly Ser
    2300             2305              2310

Gly Tyr Ser Val Val Glu Lys  Ser Leu Pro Ala Thr  Val Thr Gln
    2315             2320              2325

Ile Ile Met Leu Phe Asn Thr  Phe Ser Pro Asn Gly  Leu Leu Leu
    2330             2335              2340

Tyr Leu Gly Ser Tyr Gly Thr  Lys Asp Phe Leu Ser  Ile Glu Leu
    2345             2350              2355

Phe Arg Gly Arg Val Lys Val  Met Thr Asp Leu Gly  Ser Gly Pro
    2360             2365              2370

Ile Thr Leu Leu Thr Asp Arg  Arg Tyr Asn Asn Gly  Thr Trp Tyr
    2375             2380              2385

Lys Ile Ala Phe Gln Arg Asn  Arg Lys Gln Gly Val  Leu Ala Val
```

-continued

```
          2390                    2395                    2400

Ile Asp  Ala Tyr Asn Thr Ser  Asn Lys Glu Thr Lys  Gln Gly Glu
    2405                    2410                    2415

Thr Pro  Gly Ala Ser Ser Asp  Leu Asn Arg Leu Asp  Lys Asp Pro
    2420                    2425                    2430

Ile Tyr  Val Gly Gly Leu Pro  Arg Ser Arg Val Val  Arg Arg Gly
    2435                    2440                    2445

Val Thr  Thr Lys Ser Phe Val  Gly Cys Ile Lys Asn  Leu Glu Ile
    2450                    2455                    2460

Ser Arg  Ser Thr Phe Asp Leu  Leu Arg Asn Ser Tyr  Gly Val Arg
    2465                    2470                    2475

Lys Gly  Cys Leu Leu Glu Pro  Ile Arg Ser Val Ser  Phe Leu Lys
    2480                    2485                    2490

Gly Gly  Tyr Ile Glu Leu Pro  Pro Lys Ser Leu Ser  Pro Glu Ser
    2495                    2500                    2505

Glu Trp  Leu Val Thr Phe Ala  Thr Thr Asn Ser Ser  Gly Ile Ile
    2510                    2515                    2520

Leu Ala  Ala Leu Gly Gly Asp  Val Glu Lys Arg Gly  Asp Arg Glu
    2525                    2530                    2535

Glu Ala  His Val Pro Phe Phe  Ser Val Met Leu Ile  Gly Gly Asn
    2540                    2545                    2550

Ile Glu  Val His Val Asn Pro  Gly Asp Gly Thr Gly  Leu Arg Lys
    2555                    2560                    2565

Ala Leu  Leu His Ala Pro Thr  Gly Thr Cys Ser Asp  Gly Gln Ala
    2570                    2575                    2580

His Ser  Ile Ser Leu Val Arg  Asn Arg Arg Ile Ile  Thr Val Gln
    2585                    2590                    2595

Leu Asp  Glu Asn Asn Pro Val  Glu Met Lys Leu Gly  Thr Leu Val
    2600                    2605                    2610

Glu Ser  Arg Thr Ile Asn Val  Ser Asn Leu Tyr Val  Gly Gly Ile
    2615                    2620                    2625

Pro Glu  Gly Glu Gly Thr Ser  Leu Leu Thr Met Arg  Arg Ser Phe
    2630                    2635                    2640

His Gly  Cys Ile Lys Asn Leu  Ile Phe Asn Leu Glu  Leu Leu Asp
    2645                    2650                    2655

Phe Asn  Ser Ala Val Gly His  Glu Gln Val Asp Leu  Asp Thr Cys
    2660                    2665                    2670

Trp Leu  Ser Glu Arg Pro Lys  Leu Ala Pro Asp Ala  Glu Asp Ser
    2675                    2680                    2685

Lys Leu  Leu Pro Glu Pro Arg  Ala Phe Pro Glu Gln  Cys Val Val
    2690                    2695                    2700

Asp Ala  Ala Leu Glu Tyr Val  Pro Gly Ala His Gln  Phe Gly Leu
    2705                    2710                    2715

Thr Gln  Asn Ser His Phe Ile  Leu Pro Phe Asn Gln  Ser Ala Val
    2720                    2725                    2730

Arg Lys  Lys Leu Ser Val Glu  Leu Ser Ile Arg Thr  Phe Ala Ser
    2735                    2740                    2745

Ser Gly  Leu Ile Tyr Tyr Met  Ala His Gln Asn Gln  Ala Asp Tyr
    2750                    2755                    2760

Ala Val  Leu Gln Leu His Gly  Gly Arg Leu His Phe  Met Phe Asp
    2765                    2770                    2775

Leu Gly  Lys Gly Arg Thr Lys  Val Ser His Pro Ala  Leu Leu Ser
    2780                    2785                    2790
```

Asp Gly Lys Trp His Thr Val  Lys Thr Asp Tyr Val  Lys Arg Lys
    2795                2800                2805

Gly Phe Ile Thr Val Asp Gly  Arg Glu Ser Pro Met  Val Thr Val
    2810                2815                2820

Val Gly Asp Gly Thr Met Leu  Asp Val Glu Gly Leu  Phe Tyr Leu
    2825                2830                2835

Gly Gly Leu Pro Ser Gln Tyr  Gln Ala Arg Lys Ile  Gly Asn Ile
    2840                2845                2850

Thr His Ser Ile Pro Ala Cys  Ile Gly Asp Val Thr  Val Asn Ser
    2855                2860                2865

Lys Gln Leu Asp Lys Asp Ser  Pro Val Ser Ala Phe  Thr Val Asn
    2870                2875                2880

Arg Cys Tyr Ala Val Ala Gln  Glu Gly Thr Tyr Phe  Asp Gly Ser
    2885                2890                2895

Gly Tyr Ala Ala Leu Val Lys  Glu Gly Tyr Lys Val  Gln Ser Asp
    2900                2905                2910

Val Asn Ile Thr Leu Glu Phe  Arg Thr Ser Ser Gln  Asn Gly Val
    2915                2920                2925

Leu Leu Gly Ile Ser Thr Ala  Lys Val Asp Ala Ile  Gly Leu Glu
    2930                2935                2940

Leu Val Asp Gly Lys Val Leu  Phe His Val Asn Asn  Gly Ala Gly
    2945                2950                2955

Arg Ile Thr Ala Ala Tyr Glu  Pro Lys Thr Ala Thr  Val Leu Cys
    2960                2965                2970

Asp Gly Lys Trp His Thr Leu  Gln Ala Asn Lys Ser  Lys His Arg
    2975                2980                2985

Ile Thr Leu Ile Val Asp Gly  Asn Ala Val Gly Ala  Glu Ser Pro
    2990                2995                3000

His Thr Gln Ser Thr Ser Val  Asp Thr Asn Asn Pro  Ile Tyr Val
    3005                3010                3015

Gly Gly Tyr Pro Ala Gly Val  Lys Gln Lys Cys Leu  Arg Ser Gln
    3020                3025                3030

Thr Ser Phe Arg Gly Cys Leu  Arg Lys Leu Ala Leu  Ile Lys Ser
    3035                3040                3045

Pro Gln Val Gln Ser Phe Asp  Phe Ser Arg Ala Phe  Glu Leu His
    3050                3055                3060

Gly Val Phe Leu His Ser Cys  Pro Gly Thr Glu Ser
    3065                3070                3075

<210> SEQ ID NO 90
<211> LENGTH: 3695
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Ala Lys Arg Leu Cys Ala Gly Ser Ala Leu Cys Val Arg Gly Pro
1               5                   10                  15

Arg Gly Pro Ala Pro Leu Leu Leu Val Gly Leu Ala Leu Leu Gly Ala
            20                  25                  30

Ala Arg Ala Arg Glu Glu Ala Gly Gly Gly Phe Ser Leu His Pro Pro
        35                  40                  45

Tyr Phe Asn Leu Ala Glu Gly Ala Arg Ile Ala Ala Ser Ala Thr Cys

-continued

```
         50                  55                  60

Gly Glu Glu Ala Pro Ala Arg Gly Ser Pro Arg Pro Thr Glu Asp Leu
65                  70                  75                  80

Tyr Cys Lys Leu Val Gly Gly Pro Val Ala Gly Gly Asp Pro Asn Gln
                85                  90                  95

Thr Ile Arg Gly Gln Tyr Cys Asp Ile Cys Thr Ala Ala Asn Ser Asn
                100                 105                 110

Lys Ala His Pro Ala Ser Asn Ala Ile Asp Gly Thr Glu Arg Trp Trp
            115                 120                 125

Gln Ser Pro Pro Leu Ser Arg Gly Leu Glu Tyr Asn Glu Val Asn Val
        130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Phe Ala Ser Ser Lys
            180                 185                 190

Arg Asp Cys Leu Glu Arg Phe Gly Pro Gln Thr Leu Glu Arg Ile Thr
            195                 200                 205

Arg Asp Asp Ala Ala Ile Cys Thr Thr Glu Tyr Ser Arg Ile Val Pro
        210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
        275                 280                 285

Tyr Ser Ile Lys Asp Ile Ser Ile Gly Gly Arg Cys Val Cys His Gly
        290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
                325                 330                 335

Cys Pro Gly Phe Asn Gln Gln Pro Trp Lys Pro Ala Thr Ala Asn Ser
            340                 345                 350

Ala Asn Glu Cys Gln Ser Cys Asn Cys Tyr Gly His Ala Thr Asp Cys
        355                 360                 365

Tyr Tyr Asp Pro Glu Val Asp Arg Arg Arg Ala Ser Gln Ser Leu Asp
        370                 375                 380

Gly Thr Tyr Gln Gly Gly Gly Val Cys Ile Asp Cys Gln His His Thr
385                 390                 395                 400

Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
            420                 425                 430

Ser Asp Phe Thr Asp Gly Thr Cys Glu Asp Leu Thr Gly Arg Cys Tyr
            435                 440                 445

Cys Arg Pro Asn Phe Ser Gly Glu Arg Cys Asp Val Cys Ala Glu Gly
        450                 455                 460

Phe Thr Gly Phe Pro Ser Cys Tyr Pro Thr Pro Ser Ser Ser Asn Asp
465                 470                 475                 480
```

-continued

```
Thr Arg Glu Gln Val Leu Pro Ala Gly Gln Ile Val Asn Cys Asp Cys
            485             490             495

Ser Ala Ala Gly Thr Gln Gly Asn Ala Cys Arg Lys Asp Pro Arg Val
            500             505             510

Gly Arg Cys Leu Cys Lys Pro Asn Phe Gln Gly Thr His Cys Glu Leu
            515             520             525

Cys Ala Pro Gly Phe Tyr Gly Pro Gly Cys Gln Pro Cys Gln Cys Ser
    530             535             540

Ser Pro Gly Val Ala Asp Asp Arg Cys Asp Pro Asp Thr Gly Gln Cys
545             550             555             560

Arg Cys Arg Val Gly Phe Glu Gly Ala Thr Cys Asp Arg Cys Ala Pro
            565             570             575

Gly Tyr Phe His Phe Pro Leu Cys Gln Leu Cys Gly Cys Ser Pro Ala
            580             585             590

Gly Thr Leu Pro Glu Gly Cys Asp Glu Ala Gly Arg Cys Leu Cys Gln
            595             600             605

Pro Glu Phe Ala Gly Pro His Cys Asp Arg Cys Arg Pro Gly Tyr His
    610             615             620

Gly Phe Pro Asn Cys Gln Ala Cys Thr Cys Asp Pro Arg Gly Ala Leu
625             630             635             640

Asp Gln Leu Cys Gly Ala Gly Gly Leu Cys Arg Cys Arg Pro Gly Tyr
            645             650             655

Thr Gly Thr Ala Cys Gln Glu Cys Ser Pro Gly Phe His Gly Phe Pro
            660             665             670

Ser Cys Val Pro Cys His Cys Ser Ala Glu Gly Ser Leu His Ala Ala
            675             680             685

Cys Asp Pro Arg Ser Gly Gln Cys Ser Cys Arg Pro Arg Val Thr Gly
    690             695             700

Leu Arg Cys Asp Thr Cys Val Pro Gly Ala Tyr Asn Phe Pro Tyr Cys
705             710             715             720

Glu Ala Gly Ser Cys His Pro Ala Gly Leu Ala Pro Val Asp Pro Ala
            725             730             735

Leu Pro Glu Ala Gln Val Pro Cys Met Cys Arg Ala His Val Glu Gly
            740             745             750

Pro Ser Cys Asp Arg Cys Lys Pro Gly Phe Trp Gly Leu Ser Pro Ser
            755             760             765

Asn Pro Glu Gly Cys Thr Arg Cys Ser Cys Asp Leu Arg Gly Thr Leu
    770             775             780

Gly Gly Val Ala Glu Cys Gln Pro Gly Thr Gly Gln Cys Phe Cys Lys
785             790             795             800

Pro His Val Cys Gly Gln Ala Cys Ala Ser Cys Lys Asp Gly Phe Phe
            805             810             815

Gly Leu Asp Gln Ala Asp Tyr Phe Gly Cys Arg Ser Cys Arg Cys Asp
            820             825             830

Ile Gly Gly Ala Leu Gly Gln Ser Cys Glu Pro Arg Thr Gly Val Cys
            835             840             845

Arg Cys Arg Pro Asn Thr Gln Gly Pro Thr Cys Ser Glu Pro Ala Arg
    850             855             860

Asp His Tyr Leu Pro Asp Leu His His Leu Arg Leu Glu Leu Glu Glu
865             870             875             880

Ala Ala Thr Pro Glu Gly His Ala Val Arg Phe Gly Phe Asn Pro Leu
            885             890             895
```

Glu Phe Glu Asn Phe Ser Trp Arg Gly Tyr Ala Gln Met Ala Pro Val
            900                 905                 910

Gln Pro Arg Ile Val Ala Arg Leu Asn Leu Thr Ser Pro Asp Leu Phe
        915                 920                 925

Trp Leu Val Phe Arg Tyr Val Asn Arg Gly Ala Met Ser Val Ser Gly
    930                 935                 940

Arg Val Ser Val Arg Glu Glu Gly Arg Ser Ala Thr Cys Ala Asn Cys
945                 950                 955                 960

Thr Ala Gln Ser Gln Pro Val Ala Phe Pro Pro Ser Thr Glu Pro Ala
                965                 970                 975

Phe Ile Thr Val Pro Gln Arg Gly Phe Gly Glu Pro Phe Val Leu Asn
                980                 985                 990

Pro Gly Thr Trp Ala Leu Arg Val  Glu Ala Glu Gly Val  Leu Leu Asp
        995                 1000                1005

Tyr Val  Val Leu Leu Pro Ser  Ala Tyr Tyr Glu Ala  Ala Leu Leu
    1010                1015                1020

Gln Leu  Arg Val Thr Glu Ala  Cys Thr Tyr Arg Pro  Ser Ala Gln
    1025                1030                1035

Gln Ser  Gly Asp Asn Cys Leu  Leu Tyr Thr His Leu  Pro Leu Asp
    1040                1045                1050

Gly Phe  Pro Ser Ala Ala Gly  Leu Glu Ala Leu Cys  Arg Gln Asp
    1055                1060                1065

Asn Ser  Leu Pro Arg Pro Cys  Pro Thr Glu Gln Leu  Ser Pro Ser
    1070                1075                1080

His Pro  Pro Leu Ile Thr Cys  Thr Gly Ser Asp Val  Asp Val Gln
    1085                1090                1095

Leu Gln  Val Ala Val Pro Gln  Pro Gly Arg Tyr Ala  Leu Val Val
    1100                1105                1110

Glu Tyr  Ala Asn Glu Asp Ala  Arg Gln Glu Val Gly  Val Ala Val
    1115                1120                1125

His Thr  Pro Gln Arg Ala Pro  Gln Gln Gly Leu Leu  Ser Leu His
    1130                1135                1140

Pro Cys  Leu Tyr Ser Thr Leu  Cys Arg Gly Thr Ala  Arg Asp Thr
    1145                1150                1155

Gln Asp  His Leu Ala Val Phe  His Leu Asp Ser Glu  Ala Ser Val
    1160                1165                1170

Arg Leu  Thr Ala Glu Gln Ala  Arg Phe Phe Leu His  Gly Val Thr
    1175                1180                1185

Leu Val  Pro Ile Glu Glu Phe  Ser Pro Glu Phe Val  Glu Pro Arg
    1190                1195                1200

Val Ser  Cys Ile Ser Ser His  Gly Ala Phe Gly Pro  Asn Ser Ala
    1205                1210                1215

Ala Cys  Leu Pro Ser Arg Phe  Pro Lys Pro Pro Gln  Pro Ile Ile
    1220                1225                1230

Leu Arg  Asp Cys Gln Val Ile  Pro Leu Pro Pro Gly  Leu Pro Leu
    1235                1240                1245

Thr His  Ala Gln Asp Leu Thr  Pro Ala Met Ser Pro  Ala Gly Pro
    1250                1255                1260

Arg Pro  Arg Pro Pro Thr Ala  Val Asp Pro Asp Ala  Glu Pro Thr
    1265                1270                1275

Leu Leu  Arg Glu Pro Gln Ala  Thr Val Val Phe Thr  Thr His Val
    1280                1285                1290

Pro Thr  Leu Gly Arg Tyr Ala  Phe Leu Leu His Gly  Tyr Gln Pro

-continued

```
        1295              1300                1305

Ala His  Pro Thr Phe Pro Val  Glu Val Leu Ile Asn  Ala Gly Arg
    1310             1315                1320

Val Trp  Gln Gly His Ala Asn  Ala Ser Phe Cys Pro  His Gly Tyr
    1325             1330                1335

Gly Cys  Arg Thr Leu Val Val  Cys Glu Gly Gln Ala  Leu Leu Asp
    1340             1345                1350

Val Thr  His Ser Glu Leu Thr  Val Thr Val Arg Val  Pro Lys Gly
    1355             1360                1365

Arg Trp  Leu Trp Leu Asp Tyr  Val Leu Val Val Pro  Glu Asn Val
    1370             1375                1380

Tyr Ser  Phe Gly Tyr Leu Arg  Glu Glu Pro Leu Asp  Lys Ser Tyr
    1385             1390                1395

Asp Phe  Ile Ser His Cys Ala  Ala Gln Gly Tyr His  Ile Ser Pro
    1400             1405                1410

Ser Ser  Ser Ser Leu Phe Cys  Arg Asn Ala Ala Ala  Ser Leu Ser
    1415             1420                1425

Leu Phe  Tyr Asn Asn Gly Ala  Arg Pro Cys Gly Cys  His Glu Val
    1430             1435                1440

Gly Ala  Thr Gly Pro Thr Cys  Glu Pro Phe Gly Gly  Gln Cys Pro
    1445             1450                1455

Cys His  Ala His Val Ile Gly  Arg Asp Cys Ser Arg  Cys Ala Thr
    1460             1465                1470

Gly Tyr  Trp Gly Phe Pro Asn  Cys Arg Pro Cys Asp  Cys Gly Ala
    1475             1480                1485

Arg Leu  Cys Asp Glu Leu Thr  Gly Gln Cys Ile Cys  Pro Pro Arg
    1490             1495                1500

Thr Ile  Pro Pro Asp Cys Leu  Leu Cys Gln Pro Gln  Thr Phe Gly
    1505             1510                1515

Cys His  Pro Leu Val Gly Cys  Glu Glu Cys Asn Cys  Ser Gly Pro
    1520             1525                1530

Gly Ile  Gln Glu Leu Thr Asp  Pro Thr Cys Asp Thr  Asp Ser Gly
    1535             1540                1545

Gln Cys  Lys Cys Arg Pro Asn  Val Thr Gly Arg Arg  Cys Asp Thr
    1550             1555                1560

Cys Ser  Pro Gly Phe His Gly  Tyr Pro Arg Cys Arg  Pro Cys Asp
    1565             1570                1575

Cys His  Glu Ala Gly Thr Ala  Pro Gly Val Cys Asp  Pro Leu Thr
    1580             1585                1590

Gly Gln  Cys Tyr Cys Lys Glu  Asn Val Gln Gly Pro  Lys Cys Asp
    1595             1600                1605

Gln Cys  Ser Leu Gly Thr Phe  Ser Leu Asp Ala Ala  Asn Pro Lys
    1610             1615                1620

Gly Cys  Thr Arg Cys Phe Cys  Phe Gly Ala Thr Glu  Arg Cys Arg
    1625             1630                1635

Ser Ser  Ser Tyr Thr Arg Gln  Glu Phe Val Asp Met  Glu Gly Trp
    1640             1645                1650

Val Leu  Leu Ser Thr Asp Arg  Gln Val Val Pro His  Glu Arg Gln
    1655             1660                1665

Pro Gly  Thr Glu Met Leu Arg  Ala Asp Leu Arg His  Val Pro Glu
    1670             1675                1680

Ala Val  Pro Glu Ala Phe Pro  Glu Leu Tyr Trp Gln  Ala Pro Pro
    1685             1690                1695
```

-continued

```
Ser Tyr  Leu Gly Asp Arg Val  Ser Ser Tyr Gly Gly  Thr Leu Arg
    1700              1705              1710

Tyr Glu  Leu His Ser Glu Thr  Gln Arg Gly Asp Val  Phe Val Pro
    1715              1720              1725

Met Glu  Ser Arg Pro Asp Val  Val Leu Gln Gly Asn  Gln Met Ser
    1730              1735              1740

Ile Thr  Phe Leu Glu Pro Ala  Tyr Pro Thr Pro Gly  His Val His
    1745              1750              1755

Arg Gly  Gln Leu Gln Leu Val  Glu Gly Asn Phe Arg  His Thr Glu
    1760              1765              1770

Thr Arg  Asn Thr Val Ser Arg  Glu Glu Leu Met Met  Val Leu Ala
    1775              1780              1785

Ser Leu  Glu Gln Leu Gln Ile  Arg Ala Leu Phe Ser  Gln Ile Ser
    1790              1795              1800

Ser Ala  Val Phe Leu Arg Arg  Val Ala Leu Glu Val  Ala Ser Pro
    1805              1810              1815

Ala Gly  Gln Gly Ala Leu Ala  Ser Asn Val Glu Leu  Cys Leu Cys
    1820              1825              1830

Pro Ala  Ser Tyr Arg Gly Asp  Ser Cys Gln Glu Cys  Ala Pro Gly
    1835              1840              1845

Phe Tyr  Arg Asp Val Lys Gly  Leu Phe Leu Gly Arg  Cys Val Pro
    1850              1855              1860

Cys Gln  Cys His Gly His Ser  Asp Arg Cys Leu Pro  Gly Ser Gly
    1865              1870              1875

Val Cys  Val Asp Cys Gln His  Asn Thr Glu Gly Ala  His Cys Glu
    1880              1885              1890

Arg Cys  Gln Ala Gly Phe Val  Ser Ser Arg Asp Asp  Pro Ser Ala
    1895              1900              1905

Pro Cys  Val Ser Cys Pro Cys  Pro Leu Ser Val Pro  Ser Asn Asn
    1910              1915              1920

Phe Ala  Glu Gly Cys Val Leu  Arg Gly Gly Arg Thr  Gln Cys Leu
    1925              1930              1935

Cys Lys  Pro Gly Tyr Ala Gly  Ala Ser Cys Glu Arg  Cys Ala Pro
    1940              1945              1950

Gly Phe  Phe Gly Asn Pro Leu  Val Leu Gly Ser Ser  Cys Gln Pro
    1955              1960              1965

Cys Asp  Cys Ser Gly Asn Gly  Asp Pro Asn Leu Leu  Phe Ser Asp
    1970              1975              1980

Cys Asp  Pro Leu Thr Gly Ala  Cys Arg Gly Cys Leu  Arg His Thr
    1985              1990              1995

Thr Gly  Pro Arg Cys Glu Ile  Cys Ala Pro Gly Phe  Tyr Gly Asn
    2000              2005              2010

Ala Leu  Leu Pro Gly Asn Cys  Thr Arg Cys Asp Cys  Thr Pro Cys
    2015              2020              2025

Gly Thr  Glu Ala Cys Asp Pro  His Ser Gly His Cys  Leu Cys Lys
    2030              2035              2040

Ala Gly  Val Thr Gly Arg Arg  Cys Asp Arg Cys Gln  Glu Gly His
    2045              2050              2055

Phe Gly  Phe Asp Gly Cys Gly  Gly Cys Arg Pro Cys  Ala Cys Gly
    2060              2065              2070

Pro Ala  Ala Glu Gly Ser Glu  Cys His Pro Gln Ser  Gly Gln Cys
    2075              2080              2085
```

-continued

```
His Cys Arg Pro Gly Thr Met  Gly Pro Gln Cys Arg  Glu Cys Ala
    2090             2095              2100

Pro Gly Tyr Trp Gly Leu Pro  Glu Gln Gly Cys Arg  Arg Cys Gln
    2105             2110              2115

Cys Pro Gly Gly Arg Cys Asp  Pro His Thr Gly Arg  Cys Asn Cys
    2120             2125              2130

Pro Pro Gly Leu Ser Gly Glu  Arg Cys Asp Thr Cys  Ser Gln Gln
    2135             2140              2145

His Gln Val Pro Val Pro Gly  Gly Pro Val Gly His  Ser Ile His
    2150             2155              2160

Cys Glu Val Cys Asp His Cys  Val Val Leu Leu Leu  Asp Asp Leu
    2165             2170              2175

Glu Arg Ala Gly Ala Leu Leu  Pro Ala Ile His Glu  Gln Leu Arg
    2180             2185              2190

Gly Ile Asn Ala Ser Ser Met  Ala Trp Ala Arg Leu  His Arg Leu
    2195             2200              2205

Asn Ala Ser Ile Ala Asp Leu  Gln Ser Gln Leu Arg  Ser Pro Leu
    2210             2215              2220

Gly Pro Arg His Glu Thr Ala  Gln Gln Leu Glu Val  Leu Glu Gln
    2225             2230              2235

Gln Ser Thr Ser Leu Gly Gln  Asp Ala Arg Arg Leu  Gly Gly Gln
    2240             2245              2250

Ala Val Gly Thr Arg Asp Gln  Ala Ser Gln Leu Leu  Ala Gly Thr
    2255             2260              2265

Glu Ala Thr Leu Gly His Ala  Lys Thr Leu Leu Ala  Ala Ile Arg
    2270             2275              2280

Ala Val Asp Arg Thr Leu Ser  Glu Leu Met Ser Gln  Thr Gly His
    2285             2290              2295

Leu Gly Leu Ala Asn Ala Ser  Ala Pro Ser Gly Glu  Gln Leu Leu
    2300             2305              2310

Arg Thr Leu Ala Glu Val Glu  Arg Leu Leu Trp Glu  Met Arg Ala
    2315             2320              2325

Arg Asp Leu Gly Ala Pro Gln  Ala Ala Ala Glu Ala  Glu Leu Ala
    2330             2335              2340

Ala Ala Gln Arg Leu Leu Ala  Arg Val Gln Glu Gln  Leu Ser Ser
    2345             2350              2355

Leu Trp Glu Glu Asn Gln Ala  Leu Ala Thr Gln Thr  Arg Asp Arg
    2360             2365              2370

Leu Ala Gln His Glu Ala Gly  Leu Met Asp Leu Arg  Glu Ala Leu
    2375             2380              2385

Asn Arg Ala Val Asp Ala Thr  Arg Glu Ala Gln Glu  Leu Asn Ser
    2390             2395              2400

Arg Asn Gln Glu Arg Leu Glu  Glu Ala Leu Gln Arg  Lys Gln Glu
    2405             2410              2415

Leu Ser Arg Asp Asn Ala Thr  Leu Gln Ala Thr Leu  His Ala Ala
    2420             2425              2430

Arg Asp Thr Leu Ala Ser Val  Phe Arg Leu Leu His  Ser Leu Asp
    2435             2440              2445

Gln Ala Lys Glu Glu Leu Glu  Arg Leu Ala Ala Ser  Leu Asp Gly
    2450             2455              2460

Ala Arg Thr Pro Leu Leu Gln  Arg Met Gln Thr Phe  Ser Pro Ala
    2465             2470              2475

Gly Ser Lys Leu Arg Leu Val  Glu Ala Ala Glu Ala  His Ala Gln
```

-continued

```
       2480                2485                2490

Gln Leu  Gly Gln Leu Ala Leu  Asn Leu Ser Ser Ile  Ile Leu Asp
   2495                2500                2505

Val Asn  Gln Asp Arg Leu Thr  Gln Arg Ala Ile Glu  Ala Ser Asn
   2510                2515                2520

Ala Tyr  Ser Arg Ile Leu Gln  Ala Val Gln Ala Ala  Glu Asp Ala
   2525                2530                2535

Ala Gly  Gln Ala Leu Gln Gln  Ala Asp His Thr Trp  Ala Thr Val
   2540                2545                2550

Val Arg  Gln Gly Leu Val Asp  Arg Ala Gln Gln Leu  Leu Ala Asn
   2555                2560                2565

Ser Thr  Ala Leu Glu Glu Ala  Met Leu Gln Glu Gln  Gln Arg Leu
   2570                2575                2580

Gly Leu  Val Trp Ala Ala Leu  Gln Gly Ala Arg Thr  Gln Leu Arg
   2585                2590                2595

Asp Val  Arg Ala Lys Lys Asp  Gln Leu Glu Ala His  Ile Gln Ala
   2600                2605                2610

Ala Gln  Ala Met Leu Ala Met  Asp Thr Asp Glu Thr  Ser Lys Lys
   2615                2620                2625

Ile Ala  His Ala Lys Ala Val  Ala Ala Glu Ala Gln  Asp Thr Ala
   2630                2635                2640

Thr Arg  Val Gln Ser Gln Leu  Gln Ala Met Gln Glu  Asn Val Glu
   2645                2650                2655

Arg Trp  Gln Gly Gln Tyr Glu  Gly Leu Arg Gly Gln  Asp Leu Gly
   2660                2665                2670

Gln Ala  Val Leu Asp Ala Gly  His Ser Val Ser Thr  Leu Glu Lys
   2675                2680                2685

Thr Leu  Pro Gln Leu Leu Ala  Lys Leu Ser Ile Leu  Glu Asn Arg
   2690                2695                2700

Gly Val  His Asn Ala Ser Leu  Ala Leu Ser Ala Ser  Ile Gly Arg
   2705                2710                2715

Val Arg  Glu Leu Ile Ala Gln  Ala Arg Gly Ala Ala  Ser Lys Val
   2720                2725                2730

Lys Val  Pro Met Lys Phe Asn  Gly Arg Ser Gly Val  Gln Leu Arg
   2735                2740                2745

Thr Pro  Arg Asp Leu Ala Asp  Leu Ala Ala Tyr Thr  Ala Leu Lys
   2750                2755                2760

Phe Tyr  Leu Gln Gly Pro Glu  Pro Glu Pro Gly Gln  Gly Thr Glu
   2765                2770                2775

Asp Arg  Phe Val Met Tyr Met  Gly Ser Arg Gln Ala  Thr Gly Asp
   2780                2785                2790

Tyr Met  Gly Val Ser Leu Arg  Asp Lys Lys Val His  Trp Val Tyr
   2795                2800                2805

Gln Leu  Gly Glu Ala Gly Pro  Ala Val Leu Ser Ile  Asp Glu Asp
   2810                2815                2820

Ile Gly  Glu Gln Phe Ala Ala  Val Ser Leu Asp Arg  Thr Leu Gln
   2825                2830                2835

Phe Gly  His Met Ser Val Thr  Val Glu Arg Gln Met  Ile Gln Glu
   2840                2845                2850

Thr Lys  Gly Asp Thr Val Ala  Pro Gly Ala Glu Gly  Leu Leu Asn
   2855                2860                2865

Leu Arg  Pro Asp Asp Phe Val  Phe Tyr Val Gly Gly  Tyr Pro Ser
   2870                2875                2880
```

-continued

```
Thr Phe Thr Pro Pro Pro Leu  Leu Arg Phe Pro Gly  Tyr Arg Gly
    2885             2890             2895

Cys Ile Glu Met Asp Thr Leu  Asn Glu Glu Val Val  Ser Leu Tyr
    2900             2905             2910

Asn Phe Glu Arg Thr Phe Gln  Leu Asp Thr Ala Val  Asp Arg Pro
    2915             2920             2925

Cys Ala Arg Ser Lys Ser Thr  Gly Asp Pro Trp Leu  Thr Asp Gly
    2930             2935             2940

Ser Tyr Leu Asp Gly Thr Gly  Phe Ala Arg Ile Ser  Phe Asp Ser
    2945             2950             2955

Gln Ile Ser Thr Thr Lys Arg  Phe Glu Gln Glu Leu  Arg Leu Val
    2960             2965             2970

Ser Tyr Ser Gly Val Leu Phe  Phe Leu Lys Gln Gln  Ser Gln Phe
    2975             2980             2985

Leu Cys Leu Ala Val Gln Glu  Gly Ser Leu Val Leu  Leu Tyr Asp
    2990             2995             3000

Phe Gly Ala Gly Leu Lys Lys  Ala Val Pro Leu Gln  Pro Pro Pro
    3005             3010             3015

Pro Leu Thr Ser Ala Ser Lys  Ala Ile Gln Val Phe  Leu Leu Gly
    3020             3025             3030

Gly Ser Arg Lys Arg Val Leu  Val Arg Val Glu Arg  Ala Thr Val
    3035             3040             3045

Tyr Ser Val Glu Gln Asp Asn  Asp Leu Glu Leu Ala  Asp Ala Tyr
    3050             3055             3060

Tyr Leu Gly Gly Val Pro Pro  Asp Gln Leu Pro Pro  Ser Leu Arg
    3065             3070             3075

Arg Leu Phe Pro Thr Gly Gly  Ser Val Arg Gly Cys  Val Lys Gly
    3080             3085             3090

Ile Lys Ala Leu Gly Lys Tyr  Val Asp Leu Lys Arg  Leu Asn Thr
    3095             3100             3105

Thr Gly Val Ser Ala Gly Cys  Thr Ala Asp Leu Leu  Val Gly Arg
    3110             3115             3120

Ala Met Thr Phe His Gly His  Gly Phe Leu Arg Leu  Ala Leu Ser
    3125             3130             3135

Asn Val Ala Pro Leu Thr Gly  Asn Val Tyr Ser Gly  Phe Gly Phe
    3140             3145             3150

His Ser Ala Gln Asp Ser Ala  Leu Leu Tyr Tyr Arg  Ala Ser Pro
    3155             3160             3165

Asp Gly Leu Cys Gln Val Ser  Leu Gln Gln Gly Arg  Val Ser Leu
    3170             3175             3180

Gln Leu Leu Arg Thr Glu Val  Lys Thr Gln Ala Gly  Phe Ala Asp
    3185             3190             3195

Gly Ala Pro His Tyr Val Ala  Phe Tyr Ser Asn Ala  Thr Gly Val
    3200             3205             3210

Trp Leu Tyr Val Asp Asp Gln  Leu Gln Gln Met Lys  Pro His Arg
    3215             3220             3225

Gly Pro Pro Pro Glu Leu Gln  Pro Gln Pro Glu Gly  Pro Pro Arg
    3230             3235             3240

Leu Leu Leu Gly Gly Leu Pro  Glu Ser Gly Thr Ile  Tyr Asn Phe
    3245             3250             3255

Ser Gly Cys Ile Ser Asn Val  Phe Val Gln Arg Leu  Leu Gly Pro
    3260             3265             3270
```

-continued

```
Gln Arg  Val Phe Asp Leu Gln  Gln Asn Leu Gly Ser  Val Asn Val
    3275                3280              3285

Ser Thr  Gly Cys Ala Pro Ala  Leu Gln Ala Gln Thr  Pro Gly Leu
    3290                3295              3300

Gly Pro  Arg Gly Leu Gln Ala  Thr Ala Arg Lys Ala  Ser Arg Arg
    3305                3310              3315

Ser Arg  Gln Pro Ala Arg His  Pro Ala Cys Met Leu  Pro Pro His
    3320                3325              3330

Leu Arg  Thr Thr Arg Asp Ser  Tyr Gln Phe Gly Gly  Ser Leu Ser
    3335                3340              3345

Ser His  Leu Glu Phe Val Gly  Ile Leu Ala Arg His  Arg Asn Trp
    3350                3355              3360

Pro Ser  Leu Ser Met His Val  Leu Pro Arg Ser Ser  Arg Gly Leu
    3365                3370              3375

Leu Leu  Phe Thr Ala Arg Leu  Arg Pro Gly Ser Pro  Ser Leu Ala
    3380                3385              3390

Leu Phe  Leu Ser Asn Gly His  Phe Val Ala Gln Met  Glu Gly Leu
    3395                3400              3405

Gly Thr  Arg Leu Arg Ala Gln  Ser Arg Gln Arg Ser  Arg Pro Gly
    3410                3415              3420

Arg Trp  His Lys Val Ser Val  Arg Trp Glu Lys Asn  Arg Ile Leu
    3425                3430              3435

Leu Val  Thr Asp Gly Ala Arg  Ala Trp Ser Gln Glu  Gly Pro His
    3440                3445              3450

Arg Gln  His Gln Gly Ala Glu  His Pro Gln Pro His  Thr Leu Phe
    3455                3460              3465

Val Gly  Gly Leu Pro Ala Ser  Ser His Ser Ser Lys  Leu Pro Val
    3470                3475              3480

Thr Val  Gly Phe Ser Gly Cys  Val Lys Arg Leu Arg  Leu His Gly
    3485                3490              3495

Arg Pro  Leu Gly Ala Pro Thr  Arg Met Ala Gly Val  Thr Pro Cys
    3500                3505              3510

Ile Leu  Gly Pro Leu Glu Ala  Gly Leu Phe Phe Pro  Gly Ser Gly
    3515                3520              3525

Gly Val  Ile Thr Leu Asp Leu  Pro Gly Ala Thr Leu  Pro Asp Val
    3530                3535              3540

Gly Leu  Glu Leu Glu Val Arg  Pro Leu Ala Val Thr  Gly Leu Ile
    3545                3550              3555

Phe His  Leu Gly Gln Ala Arg  Thr Pro Pro Tyr Leu  Gln Leu Gln
    3560                3565              3570

Val Thr  Glu Lys Gln Val Leu  Leu Arg Ala Asp Asp  Gly Ala Gly
    3575                3580              3585

Glu Phe  Ser Thr Ser Val Thr  Arg Pro Ser Val Leu  Cys Asp Gly
    3590                3595              3600

Gln Trp  His Arg Leu Ala Val  Met Lys Ser Gly Asn  Val Leu Arg
    3605                3610              3615

Leu Glu  Val Asp Ala Gln Ser  Asn His Thr Val Gly  Pro Leu Leu
    3620                3625              3630

Ala Ala  Ala Ala Gly Ala Pro  Ala Pro Leu Tyr Leu  Gly Gly Leu
    3635                3640              3645

Pro Glu  Pro Met Ala Val Gln  Pro Trp Pro Pro Ala  Tyr Cys Gly
    3650                3655              3660

Cys Met  Arg Arg Leu Ala Val  Asn Arg Ser Pro Val  Ala Met Thr
```

```
              3665                3670                3675

Arg Ser  Val Glu Val His Gly  Ala Val Gly Ala Ser  Gly Cys Pro
    3680                3685                3690

Ala Ala
    3695

<210> SEQ ID NO 91
<211> LENGTH: 3333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Ala Ala Ala Arg Pro Arg Gly Arg Ala Leu Gly Pro Val Leu
1               5                   10                  15

Pro Pro Thr Pro Leu Leu Leu Leu Val Leu Arg Val Leu Pro Ala Cys
              20                  25                  30

Gly Ala Thr Ala Arg Asp Pro Gly Ala Ala Ala Gly Leu Ser Leu His
          35                  40                  45

Pro Thr Tyr Phe Asn Leu Ala Glu Ala Ala Arg Ile Trp Ala Thr Ala
    50                  55                  60

Thr Cys Gly Glu Arg Gly Pro Gly Glu Gly Arg Pro Gln Pro Glu Leu
65                  70                  75                  80

Tyr Cys Lys Leu Val Gly Gly Pro Thr Ala Pro Gly Ser Gly His Thr
              85                  90                  95

Ile Gln Gly Gln Phe Cys Asp Tyr Cys Asn Ser Glu Asp Pro Arg Lys
              100                 105                 110

Ala His Pro Val Thr Asn Ala Ile Asp Gly Ser Glu Arg Trp Trp Gln
          115                 120                 125

Ser Pro Pro Leu Ser Ser Gly Thr Gln Tyr Asn Arg Val Asn Leu Thr
    130                 135                 140

Leu Asp Leu Gly Gln Leu Phe His Val Ala Tyr Ile Leu Ile Lys Phe
145                 150                 155                 160

Ala Asn Ser Pro Arg Pro Asp Leu Trp Val Leu Glu Arg Ser Val Asp
              165                 170                 175

Phe Gly Ser Thr Tyr Ser Pro Trp Gln Tyr Phe Ala His Ser Lys Val
              180                 185                 190

Asp Cys Leu Lys Glu Phe Gly Arg Glu Ala Asn Met Ala Val Thr Arg
          195                 200                 205

Asp Asp Asp Val Leu Cys Val Thr Glu Tyr Ser Arg Ile Val Pro Leu
    210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala Thr
              245                 250                 255

Asn Ile Arg Leu Arg Phe Leu Arg Thr Asn Thr Leu Leu Gly His Leu
              260                 265                 270

Ile Ser Lys Ala Gln Arg Asp Pro Thr Val Thr Arg Arg Tyr Tyr Tyr
          275                 280                 285

Ser Ile Lys Asp Ile Ser Ile Gly Gly Gln Cys Val Cys Asn Gly His
    290                 295                 300

Ala Glu Val Cys Asn Ile Asn Asn Pro Glu Lys Leu Phe Arg Cys Glu
305                 310                 315                 320
```

413 414

-continued

```
Cys Gln His His Thr Cys Gly Glu Thr Cys Asp Arg Cys Cys Thr Gly
            325             330             335

Tyr Asn Gln Arg Arg Trp Arg Pro Ala Ala Trp Glu Gln Ser His Glu
        340             345             350

Cys Glu Ala Cys Asn Cys His Gly His Ala Ser Asn Cys Tyr Tyr Asp
        355             360             365

Pro Asp Val Glu Arg Gln Gln Ala Ser Leu Asn Thr Gln Gly Ile Tyr
    370             375             380

Ala Gly Gly Gly Val Cys Ile Asn Cys Gln His Asn Thr Ala Gly Val
385             390             395             400

Asn Cys Glu Gln Cys Ala Lys Gly Tyr Tyr Arg Pro Tyr Gly Val Pro
        405             410             415

Val Asp Ala Pro Asp Gly Cys Ile Pro Cys Ser Cys Asp Pro Glu His
        420             425             430

Ala Asp Gly Cys Glu Gln Gly Ser Gly Arg Cys His Cys Lys Pro Asn
        435             440             445

Phe His Gly Asp Asn Cys Glu Lys Cys Ala Ile Gly Tyr Tyr Asn Phe
    450             455             460

Pro Phe Cys Leu Arg Ile Pro Ile Phe Pro Val Ser Thr Pro Ser Ser
465             470             475             480

Glu Asp Pro Val Ala Gly Asp Ile Lys Gly Cys Asp Cys Asn Leu Glu
        485             490             495

Gly Val Leu Pro Glu Ile Cys Asp Ala His Gly Arg Cys Leu Cys Arg
        500             505             510

Pro Gly Val Glu Gly Pro Arg Cys Asp Thr Cys Arg Ser Gly Phe Tyr
        515             520             525

Ser Phe Pro Ile Cys Gln Ala Cys Trp Cys Ser Ala Leu Gly Ser Tyr
    530             535             540

Gln Met Pro Cys Ser Ser Val Thr Gly Gln Cys Glu Cys Arg Pro Gly
545             550             555             560

Val Thr Gly Gln Arg Cys Asp Arg Cys Leu Ser Gly Ala Tyr Asp Phe
        565             570             575

Pro His Cys Gln Gly Ser Ser Ser Ala Cys Asp Pro Ala Gly Thr Ile
        580             585             590

Asn Ser Asn Leu Gly Tyr Cys Gln Cys Lys Leu His Val Glu Gly Pro
        595             600             605

Thr Cys Ser Arg Cys Lys Leu Leu Tyr Trp Asn Leu Asp Lys Glu Asn
    610             615             620

Pro Ser Gly Cys Ser Glu Cys Lys Cys His Lys Ala Gly Thr Val Ser
625             630             635             640

Gly Thr Gly Glu Cys Arg Gln Gly Asp Gly Asp Cys His Cys Lys Ser
        645             650             655

His Val Gly Gly Asp Ser Cys Asp Thr Cys Glu Asp Gly Tyr Phe Ala
        660             665             670

Leu Glu Lys Ser Asn Tyr Phe Gly Cys Gln Gly Cys Gln Cys Asp Ile
        675             680             685

Gly Gly Ala Leu Ser Ser Met Cys Ser Gly Pro Ser Gly Val Cys Gln
    690             695             700

Cys Arg Glu His Val Val Gly Lys Val Cys Gln Arg Pro Glu Asn Asn
705             710             715             720

Tyr Tyr Phe Pro Asp Leu His His Met Lys Tyr Glu Ile Glu Asp Gly
        725             730             735

Ser Thr Pro Asn Gly Arg Asp Leu Arg Phe Gly Phe Asp Pro Leu Ala
```

-continued

```
                740               745               750

Phe Pro Glu Phe Ser Trp Arg Gly Tyr Ala Gln Met Thr Ser Val Gln
        755               760               765

Asn Asp Val Arg Ile Thr Leu Asn Val Gly Lys Ser Ser Gly Ser Leu
    770               775               780

Phe Arg Val Ile Leu Arg Tyr Val Asn Pro Gly Thr Glu Ala Val Ser
785               790               795               800

Gly His Ile Thr Ile Tyr Pro Ser Trp Gly Ala Ala Gln Ser Lys Glu
            805               810               815

Ile Ile Phe Leu Pro Ser Lys Glu Pro Ala Phe Val Thr Val Pro Gly
            820               825               830

Asn Gly Phe Ala Asp Pro Phe Ser Ile Thr Pro Gly Ile Trp Val Ala
        835               840               845

Cys Ile Lys Ala Glu Gly Val Leu Leu Asp Tyr Leu Val Leu Leu Pro
    850               855               860

Arg Asp Tyr Tyr Glu Ala Ser Val Leu Gln Leu Pro Val Thr Glu Pro
865               870               875               880

Cys Ala Tyr Ala Gly Pro Pro Gln Glu Asn Cys Leu Leu Tyr Gln His
            885               890               895

Leu Pro Val Thr Arg Phe Pro Cys Thr Leu Ala Cys Glu Ala Arg His
            900               905               910

Phe Leu Leu Asp Gly Glu Pro Arg Pro Val Ala Val Arg Gln Pro Thr
        915               920               925

Pro Ala His Pro Val Met Val Asp Leu Ser Gly Arg Glu Val Glu Leu
    930               935               940

His Leu Arg Leu Arg Ile Pro Gln Val Gly His Tyr Val Val Val Val
945               950               955               960

Glu Tyr Ser Thr Glu Ala Ala Gln Leu Phe Val Val Asp Val Asn Val
            965               970               975

Lys Ser Ser Gly Ser Val Leu Ala Gly Gln Val Asn Ile Tyr Ser Cys
        980               985               990

Asn Tyr Ser Val Leu Cys Arg Ser  Ala Val Ile Asp His  Met Ser Arg
        995               1000               1005

Ile Ala  Met Tyr Glu Leu Leu  Ala Asp Ala Asp Ile  Gln Leu Lys
    1010               1015               1020

Gly His  Met Ala Arg Phe Leu  Leu His Gln Val Cys  Ile Ile Pro
    1025               1030               1035

Ile Glu  Glu Phe Ser Ala Glu  Tyr Val Arg Pro Gln  Val His Cys
    1040               1045               1050

Ile Ala  Ser Tyr Gly Arg Phe  Val Asn Gln Ser Ala  Thr Cys Val
    1055               1060               1065

Ser Leu  Ala His Glu Thr Pro  Pro Thr Ala Leu Ile  Leu Asp Val
    1070               1075               1080

Leu Ser  Gly Arg Pro Phe Pro  His Leu Pro Gln Gln  Ser Ser Pro
    1085               1090               1095

Ser Val  Asp Val Leu Pro Gly  Val Thr Leu Lys Ala  Pro Gln Asn
    1100               1105               1110

Gln Val  Thr Leu Arg Gly Arg  Val Pro His Leu Gly  Arg Tyr Val
    1115               1120               1125

Phe Val  Ile His Phe Tyr Gln  Ala Ala His Pro Thr  Phe Pro Ala
    1130               1135               1140

Gln Val  Ser Val Asp Gly Gly  Trp Pro Arg Ala Gly  Ser Phe His
    1145               1150               1155
```

-continued

```
Ala Ser Phe Cys Pro His Val Leu Gly Cys Arg Asp Gln Val Ile
    1160             1165             1170

Ala Glu Gly Gln Ile Glu Phe Asp Ile Ser Glu Pro Glu Val Ala
    1175             1180             1185

Ala Thr Val Lys Val Pro Glu Gly Lys Ser Leu Val Leu Val Arg
    1190             1195             1200

Val Leu Val Val Pro Ala Glu Asn Tyr Asp Tyr Gln Ile Leu His
    1205             1210             1215

Lys Lys Ser Met Asp Lys Ser Leu Glu Phe Ile Thr Asn Cys Gly
    1220             1225             1230

Lys Asn Ser Phe Tyr Leu Asp Pro Gln Thr Ala Ser Arg Phe Cys
    1235             1240             1245

Lys Asn Ser Ala Arg Ser Leu Val Ala Phe Tyr His Lys Gly Ala
    1250             1255             1260

Leu Pro Cys Glu Cys His Pro Thr Gly Ala Thr Gly Pro His Cys
    1265             1270             1275

Ser Pro Glu Gly Gly Gln Cys Pro Cys Gln Pro Asn Val Ile Gly
    1280             1285             1290

Arg Gln Cys Thr Arg Cys Ala Thr Gly His Tyr Gly Phe Pro Arg
    1295             1300             1305

Cys Lys Pro Cys Ser Cys Gly Arg Arg Leu Cys Glu Glu Met Thr
    1310             1315             1320

Gly Gln Cys Arg Cys Pro Pro Arg Thr Val Arg Pro Gln Cys Glu
    1325             1330             1335

Val Cys Glu Thr His Ser Phe Ser Phe His Pro Met Ala Gly Cys
    1340             1345             1350

Glu Gly Cys Asn Cys Ser Arg Arg Gly Thr Ile Glu Ala Ala Met
    1355             1360             1365

Pro Glu Cys Asp Arg Asp Ser Gly Gln Cys Arg Cys Lys Pro Arg
    1370             1375             1380

Ile Thr Gly Arg Gln Cys Asp Arg Cys Ala Ser Gly Phe Tyr Arg
    1385             1390             1395

Phe Pro Glu Cys Val Pro Cys Asn Cys Asn Arg Asp Gly Thr Glu
    1400             1405             1410

Pro Gly Val Cys Asp Pro Gly Thr Gly Ala Cys Leu Cys Lys Glu
    1415             1420             1425

Asn Val Glu Gly Thr Glu Cys Asn Val Cys Arg Glu Gly Ser Phe
    1430             1435             1440

His Leu Asp Pro Ala Asn Leu Lys Gly Cys Thr Ser Cys Phe Cys
    1445             1450             1455

Phe Gly Val Asn Asn Gln Cys His Ser Ser His Lys Arg Arg Thr
    1460             1465             1470

Lys Phe Val Asp Met Leu Gly Trp His Leu Glu Thr Ala Asp Arg
    1475             1480             1485

Val Asp Ile Pro Val Ser Phe Asn Pro Gly Ser Asn Ser Met Val
    1490             1495             1500

Ala Asp Leu Gln Glu Leu Pro Ala Thr Ile His Ser Ala Ser Trp
    1505             1510             1515

Val Ala Pro Thr Ser Tyr Leu Gly Asp Lys Val Ser Ser Tyr Gly
    1520             1525             1530

Gly Tyr Leu Thr Tyr Gln Ala Lys Ser Phe Gly Leu Pro Gly Asp
    1535             1540             1545
```

-continued

Met Val Leu Leu Glu Lys Lys Pro Asp Val Gln Leu Thr Gly Gln
    1550         1555             1560

His Met Ser Ile Ile Tyr Glu Glu Thr Asn Thr Pro Arg Pro Asp
    1565         1570             1575

Arg Leu His His Gly Arg Val His Val Val Glu Gly Asn Phe Arg
    1580         1585             1590

His Ala Ser Ser Arg Ala Pro Val Ser Arg Glu Glu Leu Met Thr
    1595         1600             1605

Val Leu Ser Arg Leu Ala Asp Val Arg Ile Gln Gly Leu Tyr Phe
    1610         1615             1620

Thr Glu Thr Gln Arg Leu Thr Leu Ser Glu Val Gly Leu Glu Glu
    1625         1630             1635

Ala Ser Asp Thr Gly Ser Gly Arg Ile Ala Leu Ala Val Glu Ile
    1640         1645             1650

Cys Ala Cys Pro Pro Ala Tyr Ala Gly Asp Ser Cys Gln Gly Cys
    1655         1660             1665

Ser Pro Gly Tyr Tyr Arg Asp His Lys Gly Leu Tyr Thr Gly Arg
    1670         1675             1680

Cys Val Pro Cys Asn Cys Asn Gly His Ser Asn Gln Cys Gln Asp
    1685         1690             1695

Gly Ser Gly Ile Cys Val Asn Cys Gln His Asn Thr Ala Gly Glu
    1700         1705             1710

His Cys Glu Arg Cys Gln Glu Gly Tyr Tyr Gly Asn Ala Val His
    1715         1720             1725

Gly Ser Cys Arg Ala Cys Pro Cys Pro His Thr Asn Ser Phe Ala
    1730         1735             1740

Thr Gly Cys Val Val Asn Gly Gly Asp Val Arg Cys Ser Cys Lys
    1745         1750             1755

Ala Gly Tyr Thr Gly Thr Gln Cys Glu Arg Cys Ala Pro Gly Tyr
    1760         1765             1770

Phe Gly Asn Pro Gln Lys Phe Gly Gly Ser Cys Gln Pro Cys Ser
    1775         1780             1785

Cys Asn Ser Asn Gly Gln Leu Gly Ser Cys His Pro Leu Thr Gly
    1790         1795             1800

Asp Cys Ile Asn Gln Glu Pro Lys Asp Ser Ser Pro Ala Glu Glu
    1805         1810             1815

Cys Asp Asp Cys Asp Ser Cys Val Met Thr Leu Leu Asn Asp Leu
    1820         1825             1830

Ala Thr Met Gly Glu Gln Leu Arg Leu Val Lys Ser Gln Leu Gln
    1835         1840             1845

Gly Leu Ser Ala Ser Ala Gly Leu Leu Glu Gln Met Arg His Met
    1850         1855             1860

Glu Thr Gln Ala Lys Asp Leu Arg Asn Gln Leu Leu Asn Tyr Arg
    1865         1870             1875

Ser Ala Ile Ser Asn His Gly Ser Lys Ile Glu Gly Leu Glu Arg
    1880         1885             1890

Glu Leu Thr Asp Leu Asn Gln Glu Phe Glu Thr Leu Gln Glu Lys
    1895         1900             1905

Ala Gln Val Asn Ser Arg Lys Ala Gln Thr Leu Asn Asn Asn Val
    1910         1915             1920

Asn Arg Ala Thr Gln Ser Ala Lys Glu Leu Asp Val Lys Ile Lys
    1925         1930             1935

Asn Val Ile Arg Asn Val His Ile Leu Leu Lys Gln Ile Ser Gly

-continued

```
    1940            1945            1950

Thr Asp Gly Glu Gly Asn Asn  Val Pro Ser Gly Asp  Phe Ser Arg
    1955            1960            1965

Glu Trp Ala Glu Ala Gln Arg  Met Met Arg Glu Leu  Arg Asn Arg
    1970            1975            1980

Asn Phe Gly Lys His Leu Arg  Glu Ala Glu Ala Asp  Lys Arg Glu
    1985            1990            1995

Ser Gln Leu Leu Leu Asn Arg  Ile Arg Thr Trp Gln  Lys Thr His
    2000            2005            2010

Gln Gly Glu Asn Asn Gly Leu  Ala Asn Ser Ile Arg  Asp Ser Leu
    2015            2020            2025

Asn Glu Tyr Glu Ala Lys Leu  Ser Asp Leu Arg Ala  Arg Leu Gln
    2030            2035            2040

Glu Ala Ala Ala Gln Ala Lys  Gln Ala Asn Gly Leu  Asn Gln Glu
    2045            2050            2055

Asn Glu Arg Ala Leu Gly Ala  Ile Gln Arg Gln Val  Lys Glu Ile
    2060            2065            2070

Asn Ser Leu Gln Ser Asp Phe  Thr Lys Tyr Leu Thr  Thr Ala Asp
    2075            2080            2085

Ser Ser Leu Leu Gln Thr Asn  Ile Ala Leu Gln Leu  Met Glu Lys
    2090            2095            2100

Ser Gln Lys Glu Tyr Glu Lys  Leu Ala Ala Ser Leu  Asn Glu Ala
    2105            2110            2115

Arg Gln Glu Leu Ser Asp Lys  Val Arg Glu Leu Ser  Arg Ser Ala
    2120            2125            2130

Gly Lys Thr Ser Leu Val Glu  Glu Ala Glu Lys His  Ala Arg Ser
    2135            2140            2145

Leu Gln Glu Leu Ala Lys Gln  Leu Glu Glu Ile Lys  Arg Asn Ala
    2150            2155            2160

Ser Gly Asp Glu Leu Val Arg  Cys Ala Val Asp Ala  Ala Thr Ala
    2165            2170            2175

Tyr Glu Asn Ile Leu Asn Ala  Ile Lys Ala Ala Glu  Asp Ala Ala
    2180            2185            2190

Asn Arg Ala Ala Ser Ala Ser  Glu Ser Ala Leu Gln  Thr Val Ile
    2195            2200            2205

Lys Glu Asp Leu Pro Arg Lys  Ala Lys Thr Leu Ser  Ser Asn Ser
    2210            2215            2220

Asp Lys Leu Leu Asn Glu Ala  Lys Met Thr Gln Lys  Lys Leu Lys
    2225            2230            2235

Gln Glu Val Ser Pro Ala Leu  Asn Asn Leu Gln Gln  Thr Leu Asn
    2240            2245            2250

Ile Val Thr Val Gln Lys Glu  Val Ile Asp Thr Asn  Leu Thr Thr
    2255            2260            2265

Leu Arg Asp Gly Leu His Gly  Ile Gln Arg Gly Asp  Ile Asp Ala
    2270            2275            2280

Met Ile Ser Ser Ala Lys Ser  Met Val Arg Lys Ala  Asn Asp Ile
    2285            2290            2295

Thr Asp Glu Val Leu Asp Gly  Leu Asn Pro Ile Gln  Thr Asp Val
    2300            2305            2310

Glu Arg Ile Lys Asp Thr Tyr  Gly Arg Thr Gln Asn  Glu Asp Phe
    2315            2320            2325

Lys Lys Ala Leu Thr Asp Ala  Asp Asn Ser Val Asn  Lys Leu Thr
    2330            2335            2340
```

-continued

```
Asn Lys Leu Pro Asp Leu Trp  Arg Lys Ile Glu Ser  Ile Asn Gln
    2345             2350                2355

Gln Leu Leu Pro Leu Gly Asn  Ile Ser Asp Asn Met  Asp Arg Ile
    2360             2365                2370

Arg Glu Leu Ile Gln Gln Ala  Arg Asp Ala Ala Ser  Lys Val Ala
    2375             2380                2385

Val Pro Met Arg Phe Asn Gly  Lys Ser Gly Val Glu  Val Arg Leu
    2390             2395                2400

Pro Asn Asp Leu Glu Asp Leu  Lys Gly Tyr Thr Ser  Leu Ser Leu
    2405             2410                2415

Phe Leu Gln Arg Pro Asn Ser  Arg Glu Asn Gly Gly  Thr Glu Asn
    2420             2425                2430

Met Phe Val Met Tyr Leu Gly  Asn Lys Asp Ala Ser  Arg Asp Tyr
    2435             2440                2445

Ile Gly Met Ala Val Val Asp  Gly Gln Leu Thr Cys  Val Tyr Asn
    2450             2455                2460

Leu Gly Asp Arg Glu Ala Glu  Leu Gln Val Asp Gln  Ile Leu Thr
    2465             2470                2475

Lys Ser Glu Thr Lys Glu Ala  Val Met Asp Arg Val  Lys Phe Gln
    2480             2485                2490

Arg Ile Tyr Gln Phe Ala Arg  Leu Asn Tyr Thr Lys  Gly Ala Thr
    2495             2500                2505

Ser Ser Lys Pro Glu Thr Pro  Gly Val Tyr Asp Met  Asp Gly Arg
    2510             2515                2520

Asn Ser Asn Thr Leu Leu Asn  Leu Asp Pro Glu Asn  Val Val Phe
    2525             2530                2535

Tyr Val Gly Gly Tyr Pro Pro  Asp Phe Lys Leu Pro  Ser Arg Leu
    2540             2545                2550

Ser Phe Pro Pro Tyr Lys Gly  Cys Ile Glu Leu Asp  Asp Leu Asn
    2555             2560                2565

Glu Asn Val Leu Ser Leu Tyr  Asn Phe Lys Lys Thr  Phe Asn Leu
    2570             2575                2580

Asn Thr Thr Glu Val Glu Pro  Cys Arg Arg Arg Lys  Glu Glu Ser
    2585             2590                2595

Asp Lys Asn Tyr Phe Glu Gly  Thr Gly Tyr Ala Arg  Val Pro Thr
    2600             2605                2610

Gln Pro His Ala Pro Ile Pro  Thr Phe Gly Gln Thr  Ile Gln Thr
    2615             2620                2625

Thr Val Asp Arg Gly Leu Leu  Phe Phe Ala Glu Asn  Gly Asp Arg
    2630             2635                2640

Phe Ile Ser Leu Asn Ile Glu  Asp Gly Lys Leu Met  Val Arg Tyr
    2645             2650                2655

Lys Leu Asn Ser Glu Leu Pro  Lys Glu Arg Gly Val  Gly Asp Ala
    2660             2665                2670

Ile Asn Asn Gly Arg Asp His  Ser Ile Gln Ile Lys  Ile Gly Lys
    2675             2680                2685

Leu Gln Lys Arg Met Trp Ile  Asn Val Asp Val Gln  Asn Thr Ile
    2690             2695                2700

Ile Asp Gly Glu Val Phe Asp  Phe Ser Thr Tyr Tyr  Leu Gly Gly
    2705             2710                2715

Ile Pro Ile Ala Ile Arg Glu  Arg Phe Asn Ile Ser  Thr Pro Ala
    2720             2725                2730
```

-continued

```
Phe Arg Gly Cys Met Lys Asn  Leu Lys Lys Thr Ser  Gly Val Val
    2735                2740                2745

Arg Leu Asn Asp Thr Val Gly  Val Thr Lys Lys Cys  Ser Glu Asp
    2750                2755                2760

Trp Lys Leu Val Arg Ser Ala  Ser Phe Ser Arg Gly  Gly Gln Leu
    2765                2770                2775

Ser Phe Thr Asp Leu Gly Leu  Pro Pro Thr Asp His  Leu Gln Ala
    2780                2785                2790

Ser Phe Gly Phe Gln Thr Phe  Gln Pro Ser Gly Ile  Leu Leu Asp
    2795                2800                2805

His Gln Thr Trp Thr Arg Asn  Leu Gln Val Thr Leu  Glu Asp Gly
    2810                2815                2820

Tyr Ile Glu Leu Ser Thr Ser  Asp Ser Gly Ser Pro  Ile Phe Lys
    2825                2830                2835

Ser Pro Gln Thr Tyr Met Asp  Gly Leu Leu His Tyr  Val Ser Val
    2840                2845                2850

Ile Ser Asp Asn Ser Gly Leu  Arg Leu Leu Ile Asp  Asp Gln Leu
    2855                2860                2865

Leu Arg Asn Ser Lys Arg Leu  Lys His Ile Ser Ser  Ser Arg Gln
    2870                2875                2880

Ser Leu Arg Leu Gly Gly Ser  Asn Phe Glu Gly Cys  Ile Ser Asn
    2885                2890                2895

Val Phe Val Gln Arg Leu Ser  Leu Ser Pro Glu Val  Leu Asp Leu
    2900                2905                2910

Thr Ser Asn Ser Leu Lys Arg  Asp Val Ser Leu Gly  Gly Cys Ser
    2915                2920                2925

Leu Asn Lys Pro Pro Phe Leu  Met Leu Leu Lys Gly  Ser Thr Arg
    2930                2935                2940

Phe Asn Lys Thr Lys Thr Phe  Arg Ile Asn Gln Leu  Leu Gln Asp
    2945                2950                2955

Thr Pro Val Ala Ser Pro Arg  Ser Val Lys Val Trp  Gln Asp Ala
    2960                2965                2970

Cys Ser Pro Leu Pro Lys Thr  Gln Ala Asn His Gly  Ala Leu Gln
    2975                2980                2985

Phe Gly Asp Ile Pro Thr Ser  His Leu Leu Phe Lys  Leu Pro Gln
    2990                2995                3000

Glu Leu Leu Lys Pro Arg Ser  Gln Phe Ala Val Asp  Met Gln Thr
    3005                3010                3015

Thr Ser Ser Arg Gly Leu Val  Phe His Thr Gly Thr  Lys Asn Ser
    3020                3025                3030

Phe Met Ala Leu Tyr Leu Ser  Lys Gly Arg Leu Val  Phe Ala Leu
    3035                3040                3045

Gly Thr Asp Gly Lys Lys Leu  Arg Ile Lys Ser Lys  Glu Lys Cys
    3050                3055                3060

Asn Asp Gly Lys Trp His Thr  Val Val Phe Gly His  Asp Gly Glu
    3065                3070                3075

Lys Gly Arg Leu Val Val Asp  Gly Leu Arg Ala Arg  Glu Gly Ser
    3080                3085                3090

Leu Pro Gly Asn Ser Thr Ile  Ser Ile Arg Ala Pro  Val Tyr Leu
    3095                3100                3105

Gly Ser Pro Pro Ser Gly Lys  Pro Lys Ser Leu Pro  Thr Asn Ser
    3110                3115                3120

Phe Val Gly Cys Leu Lys Asn  Phe Gln Leu Asp Ser  Lys Pro Leu
```

-continued

```
         3125              3130              3135

Tyr Thr  Pro Ser Ser Ser Phe  Gly Val Ser Ser Cys  Leu Gly Gly
    3140              3145              3150

Pro Leu  Glu Lys Gly Ile Tyr  Phe Ser Glu Glu Gly  Gly His Val
    3155              3160              3165

Val Leu  Ala His Ser Val Leu  Leu Gly Pro Glu Phe  Lys Leu Val
    3170              3175              3180

Phe Ser  Ile Arg Pro Arg Ser  Leu Thr Gly Ile Leu  Ile His Ile
    3185              3190              3195

Gly Ser  Gln Pro Gly Lys His  Leu Cys Val Tyr Leu  Glu Ala Gly
    3200              3205              3210

Lys Val  Thr Ala Ser Met Asp  Ser Gly Ala Gly Gly  Thr Ser Thr
    3215              3220              3225

Ser Val  Thr Pro Lys Gln Ser  Leu Cys Asp Gly Gln  Trp His Ser
    3230              3235              3240

Val Ala  Val Thr Ile Lys Gln  His Ile Leu His Leu  Glu Leu Asp
    3245              3250              3255

Thr Asp  Ser Ser Tyr Thr Ala  Gly Gln Ile Pro Phe  Pro Pro Ala
    3260              3265              3270

Ser Thr  Gln Glu Pro Leu His  Leu Gly Gly Ala Pro  Ala Asn Leu
    3275              3280              3285

Thr Thr  Leu Arg Ile Pro Val  Trp Lys Ser Phe Phe  Gly Cys Leu
    3290              3295              3300

Arg Asn  Ile His Val Asn His  Ile Pro Val Pro Val  Thr Glu Ala
    3305              3310              3315

Leu Glu  Val Gln Gly Pro Val  Ser Leu Asn Gly Cys  Pro Asp Gln
    3320              3325              3330

<210> SEQ ID NO 92
<211> LENGTH: 1575
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Ala Ala Ala Ala Leu Leu Leu Gly Leu Ala Leu Leu Ala Pro Arg
1               5                   10                  15

Ala Ala Gly Ala Gly Met Gly Ala Cys Tyr Asp Gly Ala Gly Arg Pro
                20                  25                  30

Gln Arg Cys Leu Pro Val Phe Glu Asn Ala Ala Phe Gly Arg Leu Ala
        35                  40                  45

Gln Ala Ser His Thr Cys Gly Ser Pro Pro Glu Asp Phe Cys Pro His
    50                  55                  60

Val Gly Ala Ala Gly Ala Gly Ala His Cys Gln Arg Cys Asp Ala Ala
65                  70                  75                  80

Asp Pro Gln Arg His His Asn Ala Ser Tyr Leu Thr Asp Phe His Ser
                85                  90                  95

Gln Asp Glu Ser Thr Trp Trp Gln Ser Pro Ser Met Ala Phe Gly Val
            100                 105                 110

Gln Tyr Pro Thr Ser Val Asn Ile Thr Leu Arg Leu Gly Lys Ala Tyr
        115                 120                 125

Glu Ile Thr Tyr Val Arg Leu Lys Phe His Thr Ser Arg Pro Glu Ser
    130                 135                 140
```

-continued

```
Phe Ala Ile Tyr Lys Arg Ser Arg Ala Asp Gly Pro Trp Glu Pro Tyr
145             150             155             160

Gln Phe Tyr Ser Ala Ser Cys Gln Lys Thr Tyr Gly Arg Pro Glu Gly
                165             170             175

Gln Tyr Leu Arg Pro Gly Glu Asp Glu Arg Val Ala Phe Cys Thr Ser
            180             185             190

Glu Phe Ser Asp Ile Ser Pro Leu Ser Gly Gly Asn Val Ala Phe Ser
            195             200             205

Thr Leu Glu Gly Arg Pro Ser Ala Tyr Asn Phe Glu Glu Ser Pro Gly
    210             215             220

Leu Gln Glu Trp Val Thr Ser Thr Glu Leu Leu Ile Ser Leu Asp Arg
225             230             235             240

Leu Asn Thr Phe Gly Asp Asp Ile Phe Lys Asp Pro Lys Val Leu Gln
            245             250             255

Ser Tyr Tyr Tyr Ala Val Ser Asp Phe Ser Val Gly Gly Arg Cys Lys
            260             265             270

Cys Asn Gly His Ala Ser Glu Cys Gly Pro Asp Val Ala Gly Gln Leu
    275             280             285

Ala Cys Arg Cys Gln His Asn Thr Thr Gly Thr Asp Cys Glu Arg Cys
    290             295             300

Leu Pro Phe Phe Gln Asp Arg Pro Trp Ala Arg Gly Thr Ala Glu Ala
305             310             315             320

Ala His Glu Cys Leu Pro Cys Asn Cys Ser Gly Arg Ser Glu Glu Cys
            325             330             335

Thr Phe Asp Arg Glu Leu Phe Arg Ser Thr Gly His Gly Gly Arg Cys
            340             345             350

His His Cys Arg Asp His Thr Ala Gly Pro His Cys Glu Arg Cys Gln
    355             360             365

Glu Asn Phe Tyr His Trp Asp Pro Arg Met Pro Cys Gln Pro Cys Asp
    370             375             380

Cys Gln Ser Ala Gly Ser Leu His Leu Gln Cys Asp Asp Thr Gly Thr
385             390             395             400

Cys Ala Cys Lys Pro Thr Val Thr Gly Trp Lys Cys Asp Arg Cys Leu
            405             410             415

Pro Gly Phe His Ser Leu Ser Glu Gly Gly Cys Arg Pro Cys Thr Cys
            420             425             430

Asn Pro Ala Gly Ser Leu Asp Thr Cys Asp Pro Arg Ser Gly Arg Cys
    435             440             445

Pro Cys Lys Glu Asn Val Glu Gly Asn Leu Cys Asp Arg Cys Arg Pro
    450             455             460

Gly Thr Phe Asn Leu Gln Pro His Asn Pro Ala Gly Cys Ser Ser Cys
465             470             475             480

Phe Cys Tyr Gly His Ser Lys Val Cys Ala Ser Thr Ala Gln Phe Gln
            485             490             495

Val His His Ile Leu Ser Asp Phe His Gln Gly Ala Glu Gly Trp Trp
            500             505             510

Ala Arg Ser Val Gly Gly Ser Glu His Pro Pro Gln Trp Ser Pro Asn
            515             520             525

Gly Val Leu Leu Ser Pro Glu Asp Glu Glu Leu Thr Ala Pro Glu
    530             535             540

Lys Phe Leu Gly Asp Gln Arg Phe Ser Tyr Gly Gln Pro Leu Ile Leu
545             550             555             560

Thr Phe Arg Val Pro Pro Gly Asp Ser Pro Leu Pro Val Gln Leu Arg
```

-continued

```
                 565               570               575
Leu Glu Gly Thr Gly Leu Ala Leu Ser Leu Arg His Ser Ser Leu Ser
                 580               585               590

Gly Pro Gln Asp Ala Gly His Pro Arg Glu Val Glu Leu Arg Phe His
             595               600               605

Leu Gln Glu Thr Ser Glu Asp Val Ala Pro Pro Leu Pro Pro Phe His
         610               615               620

Phe Gln Arg Leu Leu Ala Asn Leu Thr Ser Leu Arg Leu Arg Val Ser
625               630               635               640

Pro Gly Pro Ser Pro Ala Gly Pro Val Phe Leu Thr Glu Val Arg Leu
             645               650               655

Thr Ser Ala Arg Pro Gly Leu Ser Pro Pro Ala Ser Trp Val Glu Ile
             660               665               670

Cys Ser Cys Pro Thr Gly Tyr Thr Gly Gln Phe Cys Glu Ser Cys Ala
             675               680               685

Pro Gly Tyr Lys Arg Glu Met Pro Gln Gly Gly Pro Tyr Ala Ser Cys
         690               695               700

Val Pro Cys Thr Cys Asn Gln His Gly Thr Cys Asp Pro Asn Thr Gly
705               710               715               720

Ile Cys Val Cys Ser His His Thr Glu Gly Pro Ser Cys Glu Arg Cys
             725               730               735

Leu Pro Gly Phe Tyr Gly Asn Pro Phe Ala Gly Gln Ala Asp Asp Cys
             740               745               750

Gln Pro Cys Pro Cys Pro Gly Gln Ser Ala Cys Thr Thr Ile Pro Glu
             755               760               765

Ser Arg Glu Val Val Cys Thr His Cys Pro Pro Gly Gln Arg Gly Arg
         770               775               780

Arg Cys Glu Val Cys Asp Asp Gly Phe Phe Gly Asp Pro Leu Gly Leu
785               790               795               800

Phe Gly His Pro Gln Pro Cys His Gln Cys Gln Cys Ser Gly Asn Val
             805               810               815

Asp Pro Asn Ala Val Gly Asn Cys Asp Pro Leu Ser Gly His Cys Leu
             820               825               830

Arg Cys Leu His Asn Thr Thr Gly Asp His Cys Glu His Cys Gln Glu
             835               840               845

Gly Phe Tyr Gly Ser Ala Leu Ala Pro Arg Pro Ala Asp Lys Cys Met
         850               855               860

Pro Cys Ser Cys His Pro Gln Gly Ser Val Ser Glu Gln Met Pro Cys
865               870               875               880

Asp Pro Val Thr Gly Gln Cys Ser Cys Leu Pro His Val Thr Ala Arg
             885               890               895

Asp Cys Ser Arg Cys Tyr Pro Gly Phe Phe Asp Leu Gln Pro Gly Arg
             900               905               910

Gly Cys Arg Ser Cys Lys Cys His Pro Leu Gly Ser Gln Glu Asp Gln
             915               920               925

Cys His Pro Lys Thr Gly Gln Cys Thr Cys Arg Pro Gly Val Thr Gly
         930               935               940

Gln Ala Cys Asp Arg Cys Gln Leu Gly Phe Phe Gly Phe Ser Ile Lys
945               950               955               960

Gly Cys Arg Ala Cys Arg Cys Ser Pro Leu Gly Ala Ala Ser Ala Gln
             965               970               975

Cys His Glu Asn Gly Thr Cys Val Cys Arg Pro Gly Phe Glu Gly Tyr
         980               985               990
```

-continued

```
Lys Cys Asp Arg Cys His Asp Asn  Phe Phe Leu Thr Ala  Asp Gly Thr
    995                1000                 1005

His Cys  Gln Gln Cys Pro Ser  Cys Tyr Ala Leu Val  Lys Glu Glu
    1010                1015                1020

Ala Ala  Lys Leu Lys Ala Arg  Leu Thr Leu Thr Glu  Gly Trp Leu
    1025                1030                1035

Gln Gly  Ser Asp Cys Gly Ser  Pro Trp Gly Pro Leu  Asp Ile Leu
    1040                1045                1050

Leu Gly  Glu Ala Pro Arg Gly  Asp Val Tyr Gln Gly  His His Leu
    1055                1060                1065

Leu Pro  Gly Ala Arg Glu Ala  Phe Leu Glu Gln Met  Met Ser Leu
    1070                1075                1080

Glu Gly  Ala Val Lys Ala Ala  Arg Glu Gln Leu Gln  Arg Leu Asn
    1085                1090                1095

Lys Gly  Ala Arg Cys Ala Gln  Ala Gly Ser Gln Lys  Thr Cys Thr
    1100                1105                1110

Gln Leu  Ala Asp Leu Glu Ala  Val Leu Glu Ser Ser  Glu Glu Glu
    1115                1120                1125

Ile Leu  His Ala Ala Ala Ile  Leu Ala Ser Leu Glu  Ile Pro Gln
    1130                1135                1140

Glu Gly  Pro Ser Gln Pro Thr  Lys Trp Ser His Leu  Ala Thr Glu
    1145                1150                1155

Ala Arg  Ala Leu Ala Arg Ser  His Arg Asp Thr Ala  Thr Lys Ile
    1160                1165                1170

Ala Ala  Thr Ala Trp Arg Ala  Leu Leu Ala Ser Asn  Thr Ser Tyr
    1175                1180                1185

Ala Leu  Leu Trp Asn Leu Leu  Glu Gly Arg Val Ala  Leu Glu Thr
    1190                1195                1200

Gln Arg  Asp Leu Glu Asp Arg  Tyr Gln Glu Val Gln  Ala Ala Gln
    1205                1210                1215

Lys Ala  Leu Arg Thr Ala Val  Ala Glu Val Leu Pro  Glu Ala Glu
    1220                1225                1230

Ser Val  Leu Ala Thr Val Gln  Gln Val Gly Ala Asp  Thr Ala Pro
    1235                1240                1245

Tyr Leu  Ala Leu Leu Ala Ser  Pro Gly Ala Leu Pro  Gln Lys Ser
    1250                1255                1260

Arg Ala  Glu Asp Leu Gly Leu  Lys Ala Lys Ala Leu  Glu Lys Thr
    1265                1270                1275

Val Ala  Ser Trp Gln His Met  Ala Thr Glu Ala Ala  Arg Thr Leu
    1280                1285                1290

Gln Thr  Ala Ala Gln Ala Thr  Leu Arg Gln Thr Glu  Pro Leu Thr
    1295                1300                1305

Lys Leu  His Gln Glu Ala Arg  Ala Ala Leu Thr Gln  Ala Ser Ser
    1310                1315                1320

Ser Val  Gln Ala Ala Thr Val  Thr Val Met Gly Ala  Arg Thr Leu
    1325                1330                1335

Leu Ala  Asp Leu Glu Gly Met  Lys Leu Gln Phe Pro  Arg Pro Lys
    1340                1345                1350

Asp Gln  Ala Ala Leu Gln Arg  Lys Ala Asp Ser Val  Ser Asp Arg
    1355                1360                1365

Leu Leu  Ala Asp Thr Arg Lys  Lys Thr Lys Gln Ala  Glu Arg Met
    1370                1375                1380
```

-continued

```
Leu Gly  Asn Ala Ala Pro Leu  Ser Ser Ser Ala Lys  Lys Lys Gly
    1385                 1390                 1395

Arg Glu  Ala Glu Val Leu Ala  Lys Asp Ser Ala Lys  Leu Ala Lys
    1400                 1405                 1410

Ala Leu  Leu Arg Glu Arg Lys  Gln Ala His Arg Arg  Ala Ser Arg
    1415                 1420                 1425

Leu Thr  Ser Gln Thr Gln Ala  Thr Leu Gln Gln Ala  Ser Gln Gln
    1430                 1435                 1440

Val Leu  Ala Ser Glu Ala Arg  Arg Gln Glu Leu Glu  Glu Ala Glu
    1445                 1450                 1455

Arg Val  Gly Ala Gly Leu Ser  Glu Met Glu Gln Gln  Ile Arg Glu
    1460                 1465                 1470

Ser Arg  Ile Ser Leu Glu Lys  Asp Ile Glu Thr Leu  Ser Glu Leu
    1475                 1480                 1485

Leu Ala  Arg Leu Gly Ser Leu  Asp Thr His Gln Ala  Pro Ala Gln
    1490                 1495                 1500

Ala Leu  Asn Glu Thr Gln Trp  Ala Leu Glu Arg Leu  Arg Leu Gln
    1505                 1510                 1515

Leu Gly  Ser Pro Gly Ser Leu  Gln Arg Lys Leu Ser  Leu Leu Glu
    1520                 1525                 1530

Gln Glu  Ser Gln Gln Gln Glu  Leu Gln Ile Gln Gly  Phe Glu Ser
    1535                 1540                 1545

Asp Leu  Ala Glu Ile Arg Ala  Asp Lys Gln Asn Leu  Glu Ala Ile
    1550                 1555                 1560

Leu His  Ser Leu Pro Glu Asn  Cys Ala Ser Trp Gln
    1565                 1570                 1575

<210> SEQ ID NO 93
<211> LENGTH: 1823
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
    50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160
```

-continued

```
Tyr Ala Gly Pro Asn Cys Glu Arg Cys Ala Pro Gly Tyr Tyr Gly Asn
            165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
            195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Met Asp Cys Pro Thr Ile Ser
                260                 265                 270

Cys Asp Lys Cys Val Trp Asp Leu Thr Asp Ala Leu Arg Leu Ala Ala
            275                 280                 285

Leu Ser Ile Glu Glu Gly Lys Ser Gly Val Leu Ser Val Ser Ser Gly
    290                 295                 300

Ala Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
                325                 330                 335

Ile Gln Ile Asn Asn Ala Glu Asn Thr Met Lys Ser Leu Leu Ser Asp
            340                 345                 350

Val Glu Glu Leu Val Glu Lys Glu Asn Gln Ala Ser Arg Lys Gly Gln
            355                 360                 365

Leu Val Gln Lys Glu Ser Met Asp Thr Ile Asn His Ala Ser Gln Leu
    370                 375                 380

Val Glu Gln Ala His Asp Met Arg Asp Lys Ile Gln Glu Ile Asn Asn
385                 390                 395                 400

Lys Met Leu Tyr Tyr Gly Glu Glu His Glu Leu Ser Pro Lys Glu Ile
                405                 410                 415

Ser Glu Lys Leu Val Leu Ala Gln Lys Met Leu Glu Glu Ile Arg Ser
            420                 425                 430

Arg Gln Pro Phe Phe Thr Gln Arg Glu Leu Val Asp Glu Glu Ala Asp
            435                 440                 445

Glu Ala Tyr Glu Leu Leu Ser Gln Ala Glu Ser Trp Gln Arg Leu His
    450                 455                 460

Asn Glu Thr Arg Thr Leu Phe Pro Val Val Leu Glu Gln Leu Asp Asp
465                 470                 475                 480

Tyr Asn Ala Lys Leu Ser Asp Leu Gln Glu Ala Leu Asp Gln Ala Leu
                485                 490                 495

Asn Tyr Val Arg Asp Ala Glu Asp Met Asn Arg Ala Thr Ala Ala Arg
            500                 505                 510

Gln Arg Asp His Glu Lys Gln Gln Glu Arg Val Arg Glu Gln Met Glu
            515                 520                 525

Val Val Asn Met Ser Leu Ser Thr Ser Ala Asp Ser Leu Thr Thr Pro
    530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
                565                 570                 575
```

```
Ser Asn Leu Ser Asn Leu Ser His Asp Leu Val Gln Glu Ala Ile Asp
            580             585                 590

His Ala Gln Asp Leu Gln Gln Glu Ala Asn Glu Leu Ser Arg Lys Leu
        595             600             605

His Ser Ser Asp Met Asn Gly Leu Val Gln Lys Ala Leu Asp Ala Ser
        610             615             620

Asn Val Tyr Glu Asn Ile Val Asn Tyr Val Ser Glu Ala Asn Glu Thr
625             630             635                 640

Ala Glu Phe Ala Leu Asn Thr Thr Asp Arg Ile Tyr Asp Ala Val Ser
            645             650                 655

Gly Ile Asp Thr Gln Ile Ile Tyr His Lys Asp Glu Ser Glu Asn Leu
            660             665             670

Leu Asn Gln Ala Arg Glu Leu Gln Ala Lys Ala Glu Ser Ser Ser Asp
        675             680             685

Glu Ala Val Ala Asp Thr Ser Arg Arg Val Gly Gly Ala Leu Ala Arg
        690             695             700

Lys Ser Ala Leu Lys Thr Arg Leu Ser Asp Ala Val Lys Gln Leu Gln
705             710             715                 720

Ala Ala Glu Arg Gly Asp Ala Gln Gln Arg Leu Gly Gln Ser Arg Leu
            725             730             735

Ile Thr Glu Glu Ala Asn Arg Thr Thr Met Glu Val Gln Gln Ala Thr
            740             745             750

Ala Pro Met Ala Asn Asn Leu Thr Asn Trp Ser Gln Asn Leu Gln His
            755             760             765

Phe Asp Ser Ser Ala Tyr Asn Thr Ala Val Asn Ser Ala Arg Asp Ala
        770             775             780

Val Arg Asn Leu Thr Glu Val Val Pro Gln Leu Leu Asp Gln Leu Arg
785             790             795                 800

Thr Val Glu Gln Lys Arg Pro Ala Ser Asn Val Ser Ala Ser Ile Gln
            805             810             815

Arg Ile Arg Glu Leu Ile Ala Gln Thr Arg Ser Val Ala Ser Lys Ile
            820             825             830

Gln Val Ser Met Met Phe Asp Gly Gln Ser Ala Val Glu Val His Ser
            835             840             845

Arg Thr Ser Met Asp Asp Leu Lys Ala Phe Thr Ser Leu Ser Leu Tyr
        850             855             860

Met Lys Pro Pro Val Lys Arg Pro Glu Leu Thr Glu Thr Ala Asp Gln
865             870             875                 880

Phe Ile Leu Tyr Leu Gly Ser Lys Asn Ala Lys Lys Glu Tyr Met Gly
            885             890             895

Leu Ala Ile Lys Asn Asp Asn Leu Val Tyr Val Tyr Asn Leu Gly Thr
            900             905             910

Lys Asp Val Glu Ile Pro Leu Asp Ser Lys Pro Val Ser Ser Trp Pro
        915             920             925

Ala Tyr Phe Ser Ile Val Lys Ile Glu Arg Val Gly Lys His Gly Lys
        930             935             940

Val Phe Leu Thr Val Pro Ser Leu Ser Ser Thr Ala Glu Glu Lys Phe
945             950             955                 960

Ile Lys Lys Gly Glu Phe Ser Gly Asp Asp Ser Leu Leu Asp Leu Asp
            965             970             975

Pro Glu Asp Thr Val Phe Tyr Val Gly Gly Val Pro Ser Asn Phe Lys
            980             985             990

Leu Pro Thr Ser Leu Asn Leu Pro  Gly Phe Val Gly Cys  Leu Glu Leu
```

-continued

```
        995              1000              1005

Ala Thr  Leu Asn Asn Asp Val  Ile Ser Leu Tyr Asn  Phe Lys His
    1010             1015             1020

Ile Tyr  Asn Met Asp Pro Ser  Thr Ser Val Pro Cys  Ala Arg Asp
    1025             1030             1035

Lys Leu  Ala Phe Thr Gln Ser  Arg Ala Ala Ser Tyr  Phe Phe Asp
    1040             1045             1050

Gly Ser  Gly Tyr Ala Val Val  Arg Asp Ile Thr Arg  Arg Gly Lys
    1055             1060             1065

Phe Gly  Gln Val Thr Arg Phe  Asp Ile Glu Val Arg  Thr Pro Ala
    1070             1075             1080

Asp Asn  Gly Leu Ile Leu Leu  Met Val Asn Gly Ser  Met Phe Phe
    1085             1090             1095

Arg Leu  Glu Met Arg Asn Gly  Tyr Leu His Val Phe  Tyr Asp Phe
    1100             1105             1110

Gly Phe  Ser Gly Gly Pro Val  His Leu Glu Asp Thr  Leu Lys Lys
    1115             1120             1125

Ala Gln  Ile Asn Asp Ala Lys  Tyr His Glu Ile Ser  Ile Ile Tyr
    1130             1135             1140

His Asn  Asp Lys Lys Met Ile  Leu Val Val Asp Arg  Arg His Val
    1145             1150             1155

Lys Ser  Met Asp Asn Glu Lys  Met Lys Ile Pro Phe  Thr Asp Ile
    1160             1165             1170

Tyr Ile  Gly Gly Ala Pro Pro  Glu Ile Leu Gln Ser  Arg Ala Leu
    1175             1180             1185

Arg Ala  His Leu Pro Leu Asp  Ile Asn Phe Arg Gly  Cys Met Lys
    1190             1195             1200

Gly Phe  Gln Phe Gln Lys Lys  Asp Phe Asn Leu Leu  Glu Gln Thr
    1205             1210             1215

Glu Thr  Leu Gly Val Gly Tyr  Gly Cys Pro Glu Asp  Ser Leu Ile
    1220             1225             1230

Ser Arg  Arg Ala Tyr Phe Asn  Gly Gln Ser Phe Ile  Ala Ser Ile
    1235             1240             1245

Gln Lys  Ile Ser Phe Phe Asp  Gly Phe Glu Gly Gly  Phe Asn Phe
    1250             1255             1260

Arg Thr  Leu Gln Pro Asn Gly  Leu Leu Phe Tyr Tyr  Ala Ser Gly
    1265             1270             1275

Ser Asp  Val Phe Ser Ile Ser  Leu Asp Asn Gly Thr  Val Ile Met
    1280             1285             1290

Asp Val  Lys Gly Ile Lys Val  Gln Ser Val Asp Lys  Gln Tyr Asn
    1295             1300             1305

Asp Gly  Leu Ser His Phe Val  Ile Ser Ser Val Ser  Pro Thr Arg
    1310             1315             1320

Tyr Glu  Leu Ile Val Asp Lys  Ser Arg Val Gly Ser  Lys Asn Pro
    1325             1330             1335

Thr Lys  Gly Lys Ile Glu Gln  Thr Gln Ala Ser Glu  Lys Lys Phe
    1340             1345             1350

Tyr Phe  Gly Gly Ser Pro Ile  Ser Ala Gln Tyr Ala  Asn Phe Thr
    1355             1360             1365

Gly Cys  Ile Ser Asn Ala Tyr  Phe Thr Arg Val Asp  Arg Asp Val
    1370             1375             1380

Glu Val  Glu Asp Phe Gln Arg  Tyr Thr Glu Lys Val  His Thr Ser
    1385             1390             1395
```

```
Leu Tyr  Glu Cys Pro Ile Glu  Ser Ser Pro Leu Phe  Leu Leu His
    1400             1405              1410

Lys Lys  Gly Lys Asn Leu Ser  Lys Pro Lys Ala Ser  Gln Asn Lys
    1415             1420              1425

Lys Gly  Gly Lys Ser Lys Asp  Ala Pro Ser Trp Asp  Pro Val Ala
    1430             1435              1440

Leu Lys  Leu Pro Glu Arg Asn  Thr Pro Arg Asn Ser  His Cys His
    1445             1450              1455

Leu Ser  Asn Ser Pro Arg Ala  Ile Glu His Ala Tyr  Gln Tyr Gly
    1460             1465              1470

Gly Thr  Ala Asn Ser Arg Gln  Glu Phe Glu His Leu  Lys Gly Asp
    1475             1480              1485

Phe Gly  Ala Lys Ser Gln Phe  Ser Ile Arg Leu Arg  Thr Arg Ser
    1490             1495              1500

Ser His  Gly Met Ile Phe Tyr  Val Ser Asp Gln Glu  Glu Asn Asp
    1505             1510              1515

Phe Met  Thr Leu Phe Leu Ala  His Gly Arg Leu Val  Tyr Met Phe
    1520             1525              1530

Asn Val  Gly His Lys Lys Leu  Lys Ile Arg Ser Gln  Glu Lys Tyr
    1535             1540              1545

Asn Asp  Gly Leu Trp His Asp  Val Ile Phe Ile Arg  Glu Arg Ser
    1550             1555              1560

Ser Gly  Arg Leu Val Ile Asp  Gly Leu Arg Val Leu  Glu Glu Ser
    1565             1570              1575

Leu Pro  Pro Thr Glu Ala Thr  Trp Lys Ile Lys Gly  Pro Ile Tyr
    1580             1585              1590

Leu Gly  Gly Val Ala Pro Gly  Lys Ala Val Lys Asn  Val Gln Ile
    1595             1600              1605

Asn Ser  Ile Tyr Ser Phe Ser  Gly Cys Leu Ser Asn  Leu Gln Leu
    1610             1615              1620

Asn Gly  Ala Ser Ile Thr Ser  Ala Ser Gln Thr Phe  Ser Val Thr
    1625             1630              1635

Pro Cys  Phe Glu Gly Pro Met  Glu Thr Gly Thr Tyr  Phe Ser Thr
    1640             1645              1650

Glu Gly  Gly Tyr Val Val Leu  Asp Glu Ser Phe Asn  Ile Gly Leu
    1655             1660              1665

Lys Phe  Glu Ile Ala Phe Glu  Val Arg Pro Arg Ser  Ser Ser Gly
    1670             1675              1680

Thr Leu  Val His Gly His Ser  Val Asn Gly Glu Tyr  Leu Asn Val
    1685             1690              1695

His Met  Lys Asn Gly Gln Val  Ile Val Lys Val Asn  Asn Gly Ile
    1700             1705              1710

Arg Asp  Phe Ser Thr Ser Val  Thr Pro Lys Gln Ser  Leu Cys Asp
    1715             1720              1725

Gly Arg  Trp His Arg Ile Thr  Val Ile Arg Asp Ser  Asn Val Val
    1730             1735              1740

Gln Leu  Asp Val Asp Ser Glu  Val Asn His Val Val  Gly Pro Leu
    1745             1750              1755

Asn Pro  Lys Pro Ile Asp His  Arg Glu Pro Val Phe  Val Gly Gly
    1760             1765              1770

Val Pro  Glu Ser Leu Leu Thr  Pro Arg Leu Ala Pro  Ser Lys Pro
    1775             1780              1785
```

-continued

```
Phe Thr  Gly Cys Ile Arg His  Phe Val Ile Asp Gly  His Pro Val
    1790              1795              1800

Ser Phe  Ser Lys Ala Ala Leu  Val Ser Gly Ala Val  Ser Ile Asn
    1805              1810              1815

Ser Cys  Pro Ala Ala
    1820

<210> SEQ ID NO 94
<211> LENGTH: 1193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
            20              25              30

Lys Ser Arg Gln Cys Ile Phe Asp Arg Glu Leu His Arg Gln Thr Gly
        35              40              45

Asn Gly Phe Arg Cys Leu Asn Cys Asn Asp Asn Thr Asp Gly Ile His
    50              55              60

Cys Glu Lys Cys Lys Asn Gly Phe Tyr Arg His Arg Glu Arg Asp Arg
65              70              75              80

Cys Leu Pro Cys Asn Cys Asn Ser Lys Gly Ser Leu Ser Ala Arg Cys
            85              90              95

Asp Asn Ser Gly Arg Cys Ser Cys Lys Pro Gly Val Thr Gly Ala Arg
            100             105             110

Cys Asp Arg Cys Leu Pro Gly Phe His Met Leu Thr Asp Ala Gly Cys
            115             120             125

Thr Gln Asp Gln Arg Leu Leu Asp Ser Lys Cys Asp Cys Asp Pro Ala
    130             135             140

Gly Ile Ala Gly Pro Cys Asp Ala Gly Arg Cys Val Cys Lys Pro Ala
145             150             155             160

Val Thr Gly Glu Arg Cys Asp Arg Cys Arg Ser Gly Tyr Tyr Asn Leu
            165             170             175

Asp Gly Gly Asn Pro Glu Gly Cys Thr Gln Cys Phe Cys Tyr Gly His
            180             185             190

Ser Ala Ser Cys Arg Ser Ser Ala Glu Tyr Ser Val His Lys Ile Thr
        195             200             205

Ser Thr Phe His Gln Asp Val Asp Gly Trp Lys Ala Val Gln Arg Asn
    210             215             220

Gly Ser Pro Ala Lys Leu Gln Trp Ser Gln Arg His Gln Asp Val Phe
225             230             235             240

Ser Ser Ala Gln Arg Leu Asp Pro Val Tyr Phe Val Ala Pro Ala Lys
            245             250             255

Phe Leu Gly Asn Gln Gln Val Ser Tyr Gly Gln Ser Leu Ser Phe Asp
            260             265             270

Tyr Arg Val Asp Arg Gly Gly Arg His Pro Ser Ala His Asp Val Ile
        275             280             285

Leu Glu Gly Ala Gly Leu Arg Ile Thr Ala Pro Leu Met Pro Leu Gly
    290             295             300

Lys Thr Leu Pro Cys Gly Leu Thr Lys Thr Tyr Thr Phe Arg Leu Asn
305             310             315             320
```

-continued

```
Glu His Pro Ser Asn Asn Trp Ser Pro Gln Leu Ser Tyr Phe Glu Tyr
            325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
            355                 360                 365

Arg Pro Val Ser Gly Ala Pro Ala Pro Trp Val Glu Gln Cys Ile Cys
    370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
                405                 410                 415

Asn Cys Gln Gly Gly Gly Ala Cys Asp Pro Asp Thr Gly Asp Cys Tyr
                420                 425                 430

Ser Gly Asp Glu Asn Pro Asp Ile Glu Cys Ala Asp Cys Pro Ile Gly
            435                 440                 445

Phe Tyr Asn Asp Pro His Asp Pro Arg Ser Cys Lys Pro Cys Pro Cys
    450                 455                 460

His Asn Gly Phe Ser Cys Ser Val Met Pro Glu Thr Glu Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
                500                 505                 510

Pro Cys Gln Pro Cys Gln Cys Asn Asn Asn Val Asp Pro Ser Ala Ser
            515                 520                 525

Gly Asn Cys Asp Arg Leu Thr Gly Arg Cys Leu Lys Cys Ile His Asn
    530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
                580                 585                 590

Cys Lys Pro Gly Phe Gly Gly Pro Asn Cys Glu His Gly Ala Phe Ser
            595                 600                 605

Cys Pro Ala Cys Tyr Asn Gln Val Lys Ile Gln Met Asp Gln Phe Met
    610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
            660                 665                 670

Ala Ser Arg Ser Leu Gly Leu Gln Leu Ala Lys Val Arg Ser Gln Glu
            675                 680                 685

Asn Ser Tyr Gln Ser Arg Leu Asp Asp Leu Lys Met Thr Val Glu Arg
    690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735
```

```
Leu Gly Asn Thr Asn Ile Pro Ala Ser Asp His Tyr Val Gly Pro Asn
            740                 745                 750

Gly Phe Lys Ser Leu Ala Gln Glu Ala Thr Arg Leu Ala Glu Ser His
            755                 760                 765

Val Glu Ser Ala Ser Asn Met Glu Gln Leu Thr Arg Glu Thr Glu Asp
    770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
            835                 840                 845

Leu Arg Leu Leu Asp Ser Val Ser Arg Leu Gln Gly Val Ser Asp Gln
    850                 855                 860

Ser Phe Gln Val Glu Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
            900                 905                 910

Gly Lys Ser Gly Arg Glu Lys Ser Asp Gln Leu Leu Ser Arg Ala Asn
            915                 920                 925

Leu Ala Lys Ser Arg Ala Gln Glu Ala Leu Ser Met Gly Asn Ala Thr
    930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Glu Ala Met Lys Arg Leu
                965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala  Ala Ala Asp Ala Gln  Arg Ala Lys
            995                 1000                1005

Asn Gly  Ala Gly Glu Ala Leu  Glu Ile Ser Ser Glu  Ile Glu Gln
    1010                1015                1020

Glu Ile  Gly Ser Leu Asn Leu  Glu Ala Asn Val Thr  Ala Asp Gly
    1025                1030                1035

Ala Leu  Ala Met Glu Lys Gly  Leu Ala Ser Leu Lys  Ser Glu Met
    1040                1045                1050

Arg Glu  Val Glu Gly Glu Leu  Glu Arg Lys Glu Leu  Glu Phe Asp
    1055                1060                1065

Thr Asn  Met Asp Ala Val Gln  Met Val Ile Thr Glu  Ala Gln Lys
    1070                1075                1080

Val Asp  Thr Arg Ala Lys Asn  Ala Gly Val Thr Ile  Gln Asp Thr
    1085                1090                1095

Leu Asn  Thr Leu Asp Gly Leu  Leu His Leu Met Asp  Gln Pro Leu
    1100                1105                1110

Ser Val  Asp Glu Glu Gly Leu  Val Leu Leu Glu Gln  Lys Leu Ser
    1115                1120                1125

Arg Ala  Lys Thr Gln Ile Asn  Ser Gln Leu Arg Pro  Met Met Ser
    1130                1135                1140

Glu Leu  Glu Glu Arg Ala Arg  Gln Gln Arg Gly His  Leu His Leu
```

-continued

```
            1145                1150                1155

Leu Glu  Thr Ser Ile Asp Gly  Ile Leu Ala Asp Val  Lys Asn Leu
    1160                1165                1170

Glu Asn  Ile Arg Asp Asn Leu  Pro Pro Gly Cys Tyr  Asn Thr Gln
    1175                1180                1185

Ala Leu  Glu Gln Gln
    1190

<210> SEQ ID NO 95
<211> LENGTH: 1172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Arg Pro Phe Phe Leu Leu Cys Phe Ala Leu Pro Gly Leu Leu His
1               5                   10                  15

Ala Gln Gln Ala Cys Ser Arg Gly Ala Cys Tyr Pro Pro Val Gly Asp
                20                  25                  30

Leu Leu Val Gly Arg Thr Arg Phe Leu Arg Ala Ser Ser Thr Cys Gly
            35                  40                  45

Leu Thr Lys Pro Glu Thr Tyr Cys Thr Gln Tyr Gly Glu Trp Gln Met
    50                  55                  60

Lys Cys Cys Lys Cys Asp Ser Arg Gln Pro His Asn Tyr Tyr Ser His
65              70                  75                  80

Arg Val Glu Asn Val Ala Ser Ser Ser Gly Pro Met Arg Trp Trp Gln
                85                  90                  95

Ser Gln Asn Asp Val Asn Pro Val Ser Leu Gln Leu Asp Leu Asp Arg
                100                 105                 110

Arg Phe Gln Leu Gln Glu Val Met Met Glu Phe Gln Gly Pro Met Pro
            115                 120                 125

Ala Gly Met Leu Ile Glu Arg Ser Ser Asp Phe Gly Lys Thr Trp Arg
    130                 135                 140

Val Tyr Gln Tyr Leu Ala Ala Asp Cys Thr Ser Thr Phe Pro Arg Val
145                 150                 155                 160

Arg Gln Gly Arg Pro Gln Ser Trp Gln Asp Val Arg Cys Gln Ser Leu
                165                 170                 175

Pro Gln Arg Pro Asn Ala Arg Leu Asn Gly Gly Lys Val Gln Leu Asn
            180                 185                 190

Leu Met Asp Leu Val Ser Gly Ile Pro Ala Thr Gln Ser Gln Lys Ile
            195                 200                 205

Gln Glu Val Gly Glu Ile Thr Asn Leu Arg Val Asn Phe Thr Arg Leu
    210                 215                 220

Ala Pro Val Pro Gln Arg Gly Tyr His Pro Pro Ser Ala Tyr Tyr Ala
225                 230                 235                 240

Val Ser Gln Leu Arg Leu Gln Gly Ser Cys Phe Cys His Gly His Ala
                245                 250                 255

Asp Arg Cys Ala Pro Lys Pro Gly Ala Ser Ala Gly Pro Ser Thr Ala
            260                 265                 270

Val Gln Val His Asp Val Cys Val Cys Gln His Asn Thr Ala Gly Pro
            275                 280                 285

Asn Cys Glu Arg Cys Ala Pro Phe Tyr Asn Asn Arg Pro Trp Arg Pro
    290                 295                 300
```

-continued

```
Ala Glu Gly Gln Asp Ala His Glu Cys Gln Arg Cys Asp Cys Asn Gly
305             310             315             320

His Ser Glu Thr Cys His Phe Asp Pro Ala Val Phe Ala Ala Ser Gln
            325             330             335

Gly Ala Tyr Gly Gly Val Cys Asp Asn Cys Arg Asp His Thr Glu Gly
            340             345             350

Lys Asn Cys Glu Arg Cys Gln Leu His Tyr Phe Arg Asn Arg Arg Pro
            355             360             365

Gly Ala Ser Ile Gln Glu Thr Cys Ile Ser Cys Glu Cys Asp Pro Asp
            370             375             380

Gly Ala Val Pro Gly Ala Pro Cys Asp Pro Val Thr Gly Gln Cys Val
385             390             395             400

Cys Lys Glu His Val Gln Gly Glu Arg Cys Asp Leu Cys Lys Pro Gly
            405             410             415

Phe Thr Gly Leu Thr Tyr Ala Asn Pro Gln Gly Cys His Arg Cys Asp
            420             425             430

Cys Asn Ile Leu Gly Ser Arg Arg Asp Met Pro Cys Asp Glu Glu Ser
            435             440             445

Gly Arg Cys Leu Cys Leu Pro Asn Val Val Gly Pro Lys Cys Asp Gln
            450             455             460

Cys Ala Pro Tyr His Trp Lys Leu Ala Ser Gly Gln Gly Cys Glu Pro
465             470             475             480

Cys Ala Cys Asp Pro His Asn Ser Leu Ser Pro Gln Cys Asn Gln Phe
            485             490             495

Thr Gly Gln Cys Pro Cys Arg Glu Gly Phe Gly Gly Leu Met Cys Ser
            500             505             510

Ala Ala Ala Ile Arg Gln Cys Pro Asp Arg Thr Tyr Gly Asp Val Ala
            515             520             525

Thr Gly Cys Arg Ala Cys Asp Cys Asp Phe Arg Gly Thr Glu Gly Pro
            530             535             540

Gly Cys Asp Lys Ala Ser Gly Arg Cys Leu Cys Arg Pro Gly Leu Thr
545             550             555             560

Gly Pro Arg Cys Asp Gln Cys Gln Arg Gly Tyr Cys Asn Arg Tyr Pro
            565             570             575

Val Cys Val Ala Cys His Pro Cys Phe Gln Thr Tyr Asp Ala Asp Leu
            580             585             590

Arg Glu Gln Ala Leu Arg Phe Gly Arg Leu Arg Asn Ala Thr Ala Ser
            595             600             605

Leu Trp Ser Gly Pro Gly Leu Glu Asp Arg Gly Leu Ala Ser Arg Ile
            610             615             620

Leu Asp Ala Lys Ser Lys Ile Glu Gln Ile Arg Ala Val Leu Ser Ser
625             630             635             640

Pro Ala Val Thr Glu Gln Glu Val Ala Gln Val Ala Ser Ala Ile Leu
            645             650             655

Ser Leu Arg Arg Thr Leu Gln Gly Leu Gln Leu Asp Leu Pro Leu Glu
            660             665             670

Glu Glu Thr Leu Ser Leu Pro Arg Asp Leu Glu Ser Leu Asp Arg Ser
            675             680             685

Phe Asn Gly Leu Leu Thr Met Tyr Gln Arg Lys Arg Glu Gln Phe Glu
            690             695             700

Lys Ile Ser Ser Ala Asp Pro Ser Gly Ala Phe Arg Met Leu Ser Thr
705             710             715             720

Ala Tyr Glu Gln Ser Ala Gln Ala Ala Gln Gln Val Ser Asp Ser Ser
```

-continued

```
                    725                   730                   735
Arg Leu Leu Asp Gln Leu Arg Asp Ser Arg Arg Glu Ala Glu Arg Leu
              740                   745                   750

Val Arg Gln Ala Gly Gly Gly Gly Thr Gly Ser Pro Lys Leu Val
              755                   760                   765

Ala Leu Arg Leu Glu Met Ser Ser Leu Pro Asp Leu Thr Pro Thr Phe
          770                   775                   780

Asn Lys Leu Cys Gly Asn Ser Arg Gln Met Ala Cys Thr Pro Ile Ser
      785                   790                   795                   800

Cys Pro Gly Glu Leu Cys Pro Gln Asp Asn Gly Thr Ala Cys Gly Ser
              805                   810                   815

Arg Cys Arg Gly Val Leu Pro Arg Ala Gly Gly Ala Phe Leu Met Ala
              820                   825                   830

Gly Gln Val Ala Glu Gln Leu Arg Gly Phe Asn Ala Gln Leu Gln Arg
              835                   840                   845

Thr Arg Gln Met Ile Arg Ala Ala Glu Glu Ser Ala Ser Gln Ile Gln
          850                   855                   860

Ser Ser Ala Gln Arg Leu Glu Thr Gln Val Ser Ala Ser Arg Ser Gln
      865                   870                   875                   880

Met Glu Glu Asp Val Arg Arg Thr Arg Leu Leu Ile Gln Gln Val Arg
              885                   890                   895

Asp Phe Leu Thr Asp Pro Asp Thr Asp Ala Ala Thr Ile Gln Glu Val
              900                   905                   910

Ser Glu Ala Val Leu Ala Leu Trp Leu Pro Thr Asp Ser Ala Thr Val
              915                   920                   925

Leu Gln Lys Met Asn Glu Ile Gln Ala Ile Ala Ala Arg Leu Pro Asn
          930                   935                   940

Val Asp Leu Val Leu Ser Gln Thr Lys Gln Asp Ile Ala Arg Ala Arg
      945                   950                   955                   960

Arg Leu Gln Ala Glu Ala Glu Glu Ala Arg Ser Arg Ala His Ala Val
              965                   970                   975

Glu Gly Gln Val Glu Asp Val Val Gly Asn Leu Arg Gln Gly Thr Val
              980                   985                   990

Ala Leu Gln Glu Ala Gln Asp Thr  Met Gln Gly Thr Ser  Arg Ser Leu
          995                   1000                  1005

Arg Leu  Ile Gln Asp Arg Val  Ala Glu Val Gln Gln  Val Leu Arg
      1010                  1015                  1020

Pro Ala  Glu Lys Leu Val Thr  Ser Met Thr Lys Gln  Leu Gly Asp
      1025                  1030                  1035

Phe Trp  Thr Arg Met Glu Glu  Leu Arg His Gln Ala  Arg Gln Gln
      1040                  1045                  1050

Gly Ala  Glu Ala Val Gln Ala  Gln Gln Leu Ala Glu  Gly Ala Ser
      1055                  1060                  1065

Glu Gln  Ala Leu Ser Ala Gln  Glu Gly Phe Glu Arg  Ile Lys Gln
      1070                  1075                  1080

Lys Tyr  Ala Glu Leu Lys Asp  Arg Leu Gly Gln Ser  Ser Met Leu
      1085                  1090                  1095

Gly Glu  Gln Gly Ala Arg Ile  Gln Ser Val Lys Thr  Glu Ala Glu
      1100                  1105                  1110

Glu Leu  Phe Gly Glu Thr Met  Glu Met Met Asp Arg  Met Lys Asp
      1115                  1120                  1125

Met Glu  Leu Glu Leu Leu Arg  Gly Ser Gln Ala Ile  Met Leu Arg
      1130                  1135                  1140
```

```
Ser Ala  Asp Leu Thr Gly Leu  Glu Lys Arg Val Glu  Gln Ile Arg
    1145             1150             1155

Asp His  Ile Asn Gly Arg Val  Leu Tyr Tyr Ala Thr  Cys Lys
    1160             1165             1170

<210> SEQ ID NO 96
<211> LENGTH: 1761
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Gln Phe Gln Leu Thr Leu Phe Leu His Leu Gly Trp Leu Ser Tyr
1               5                   10                  15

Ser Lys Ala Gln Asp Asp Cys Asn Arg Gly Ala Cys His Pro Thr Thr
                20                  25                  30

Gly Asp Leu Leu Val Gly Arg Asn Thr Gln Leu Met Ala Ser Ser Thr
        35                  40                  45

Cys Gly Leu Ser Arg Ala Gln Lys Tyr Cys Ile Leu Ser Tyr Leu Glu
    50                  55                  60

Gly Glu Gln Lys Cys Phe Ile Cys Asp Ser Arg Phe Pro Tyr Asp Pro
65                  70                  75                  80

Tyr Asp Gln Pro Asn Ser His Thr Ile Glu Asn Val Ile Val Ser Phe
                85                  90                  95

Glu Pro Asp Arg Glu Lys Lys Trp Trp Gln Ser Glu Asn Gly Leu Asp
                100                 105                 110

His Val Ser Ile Arg Leu Asp Leu Glu Ala Leu Phe Arg Phe Ser His
        115                 120                 125

Leu Ile Leu Thr Phe Lys Thr Phe Arg Pro Ala Ala Met Leu Val Glu
    130                 135                 140

Arg Ser Thr Asp Tyr Gly His Asn Trp Lys Val Phe Lys Tyr Phe Ala
145                 150                 155                 160

Lys Asp Cys Ala Thr Ser Phe Pro Asn Ile Thr Ser Gly Gln Ala Gln
                165                 170                 175

Gly Val Gly Asp Ile Val Cys Asp Ser Lys Tyr Ser Asp Ile Glu Pro
                180                 185                 190

Ser Thr Gly Gly Glu Val Val Leu Lys Val Leu Asp Pro Ser Phe Glu
        195                 200                 205

Ile Glu Asn Pro Tyr Ser Pro Tyr Ile Gln Asp Leu Val Thr Leu Thr
    210                 215                 220

Asn Leu Arg Ile Asn Phe Thr Lys Leu His Thr Leu Gly Asp Ala Leu
225                 230                 235                 240

Leu Gly Arg Arg Gln Asn Asp Ser Leu Asp Lys Tyr Tyr Tyr Ala Leu
                245                 250                 255

Tyr Glu Met Ile Val Arg Gly Ser Cys Phe Cys Asn Gly His Ala Ser
                260                 265                 270

Glu Cys Arg Pro Met Gln Lys Met Arg Gly Asp Val Phe Ser Pro Pro
        275                 280                 285

Gly Met Val His Gly Gln Cys Val Cys Gln His Asn Thr Asp Gly Pro
    290                 295                 300

Asn Cys Glu Arg Cys Lys Asp Phe Phe Gln Asp Ala Pro Trp Arg Pro
305                 310                 315                 320

Ala Ala Asp Leu Gln Asp Asn Ala Cys Arg Ser Cys Ser Cys Asn Ser
```

-continued

```
                    325                 330                 335

His Ser Ser Arg Cys His Phe Asp Met Thr Thr Tyr Leu Ala Ser Gly
            340                 345                 350

Gly Leu Ser Gly Gly Val Cys Glu Asp Cys Gln His Asn Thr Glu Gly
            355                 360                 365

Gln His Cys Asp Arg Cys Arg Pro Leu Phe Tyr Arg Asp Pro Leu Lys
    370                 375                 380

Thr Ile Ser Asp Pro Tyr Ala Cys Ile Pro Cys Glu Cys Asp Pro Asp
385                 390                 395                 400

Gly Thr Ile Ser Gly Gly Ile Cys Val Ser His Ser Asp Pro Ala Leu
            405                 410                 415

Gly Ser Val Ala Gly Gln Cys Leu Cys Lys Glu Asn Val Glu Gly Ala
            420                 425                 430

Lys Cys Asp Gln Cys Lys Pro Asn His Tyr Gly Leu Ser Ala Thr Asp
            435                 440                 445

Pro Leu Gly Cys Gln Pro Cys Asp Cys Asn Pro Leu Gly Ser Leu Pro
    450                 455                 460

Phe Leu Thr Cys Asp Val Asp Thr Gly Gln Cys Leu Cys Leu Ser Tyr
465                 470                 475                 480

Val Thr Gly Ala His Cys Glu Glu Cys Thr Val Gly Tyr Trp Gly Leu
            485                 490                 495

Gly Asn His Leu His Gly Cys Ser Pro Cys Asp Cys Asp Ile Gly Gly
            500                 505                 510

Ala Tyr Ser Asn Val Cys Ser Pro Lys Asn Gly Gln Cys Glu Cys Arg
            515                 520                 525

Pro His Val Thr Gly Arg Ser Cys Ser Glu Pro Ala Pro Gly Tyr Phe
    530                 535                 540

Phe Ala Pro Leu Asn Phe Tyr Leu Tyr Glu Ala Glu Glu Ala Thr Thr
545                 550                 555                 560

Leu Gln Gly Leu Ala Pro Leu Gly Ser Glu Thr Phe Gly Gln Ser Pro
            565                 570                 575

Ala Val His Val Val Leu Gly Glu Pro Val Pro Gly Asn Pro Val Thr
            580                 585                 590

Trp Thr Gly Pro Gly Phe Ala Arg Val Leu Pro Gly Ala Gly Leu Arg
            595                 600                 605

Phe Ala Val Asn Asn Ile Pro Phe Pro Val Asp Phe Thr Ile Ala Ile
    610                 615                 620

His Tyr Glu Thr Gln Ser Ala Ala Asp Trp Thr Val Gln Ile Val Val
625                 630                 635                 640

Asn Pro Pro Gly Gly Ser Glu His Cys Ile Pro Lys Thr Leu Gln Ser
            645                 650                 655

Lys Pro Gln Ser Phe Ala Leu Pro Ala Ala Thr Arg Ile Met Leu Leu
            660                 665                 670

Pro Thr Pro Ile Cys Leu Glu Pro Asp Val Gln Tyr Ser Ile Asp Val
            675                 680                 685

Tyr Phe Ser Gln Pro Leu Gln Gly Glu Ser His Ala His Ser His Val
            690                 695                 700

Leu Val Asp Ser Leu Gly Leu Ile Pro Gln Ile Asn Ser Leu Glu Asn
705                 710                 715                 720

Phe Cys Ser Lys Gln Asp Leu Asp Glu Tyr Gln Leu His Asn Cys Val
            725                 730                 735

Glu Ile Ala Ser Ala Met Gly Pro Gln Val Leu Pro Gly Ala Cys Glu
            740                 745                 750
```

```
Arg Leu Ile Ile Ser Met Ser Ala Lys Leu His Asp Gly Ala Val Ala
        755                 760                 765

Cys Lys Cys His Pro Gln Gly Ser Val Gly Ser Ser Cys Ser Arg Leu
        770                 775                 780

Gly Gly Gln Cys Gln Cys Lys Pro Leu Val Val Gly Arg Cys Cys Asp
785                 790                 795                 800

Arg Cys Ser Thr Gly Ser Tyr Asp Leu Gly His His Gly Cys His Pro
                805                 810                 815

Cys His Cys His Pro Gln Gly Ser Lys Asp Thr Val Cys Asp Gln Val
                820                 825                 830

Thr Gly Gln Cys Pro Cys His Gly Glu Val Ser Gly Arg Arg Cys Asp
        835                 840                 845

Arg Cys Leu Ala Gly Tyr Phe Gly Phe Pro Ser Cys His Pro Cys Pro
        850                 855                 860

Cys Asn Arg Phe Ala Glu Leu Cys Asp Pro Glu Thr Gly Ser Cys Phe
865                 870                 875                 880

Asn Cys Gly Gly Phe Thr Thr Gly Arg Asn Cys Glu Arg Cys Ile Asp
                885                 890                 895

Gly Tyr Tyr Gly Asn Pro Ser Ser Gly Gln Pro Cys Arg Pro Cys Leu
                900                 905                 910

Cys Pro Asp Asp Pro Ser Ser Asn Gln Tyr Phe Ala His Ser Cys Tyr
                915                 920                 925

Gln Asn Leu Trp Ser Ser Asp Val Ile Cys Asn Cys Leu Gln Gly Tyr
        930                 935                 940

Thr Gly Thr Gln Cys Gly Glu Cys Ser Thr Gly Phe Tyr Gly Asn Pro
945                 950                 955                 960

Arg Ile Ser Gly Ala Pro Cys Gln Pro Cys Ala Cys Asn Asn Asn Ile
                965                 970                 975

Asp Val Thr Asp Pro Glu Ser Cys Ser Arg Val Thr Gly Glu Cys Leu
                980                 985                 990

Arg Cys Leu His Asn Thr Gln Gly  Ala Asn Cys Gln Leu  Cys Lys Pro
        995                 1000                 1005

Gly His  Tyr Gly Ser Ala Leu  Asn Gln Thr Cys Arg  Arg Cys Ser
        1010                 1015                 1020

Cys His  Ala Ser Gly Val Ser  Pro Met Glu Cys Pro  Pro Gly Gly
        1025                 1030                 1035

Gly Ala  Cys Leu Cys Asp Pro  Val Thr Gly Ala Cys  Pro Cys Leu
        1040                 1045                 1050

Pro Asn  Val Thr Gly Leu Ala  Cys Asp Arg Cys Ala  Asp Gly Tyr
        1055                 1060                 1065

Trp Asn  Leu Val Pro Gly Arg  Gly Cys Gln Ser Cys  Asp Cys Asp
        1070                 1075                 1080

Pro Arg  Thr Ser Gln Ser Ser  His Cys Asp Gln Leu  Thr Gly Gln
        1085                 1090                 1095

Cys Pro  Cys Lys Leu Gly Tyr  Gly Gly Lys Arg Cys  Ser Glu Cys
        1100                 1105                 1110

Gln Glu  Asn Tyr Tyr Gly Asp  Pro Pro Gly Arg Cys  Ile Pro Cys
        1115                 1120                 1125

Asp Cys  Asn Arg Ala Gly Thr  Gln Lys Pro Ile Cys  Asp Pro Asp
        1130                 1135                 1140

Thr Gly  Met Cys Arg Cys Arg  Glu Gly Val Ser Gly  Gln Arg Cys
        1145                 1150                 1155
```

```
Asp Arg Cys Ala Arg Gly His  Ser Gln Glu Phe Pro  Thr Cys Leu
    1160             1165             1170

Gln Cys His Leu Cys Phe Asp  Gln Trp Asp His Thr  Ile Ser Ser
    1175             1180             1185

Leu Ser Lys Ala Val Gln Gly  Leu Met Arg Leu Ala  Ala Asn Met
    1190             1195             1200

Glu Asp Lys Arg Glu Thr Leu  Pro Val Cys Glu Ala  Asp Phe Lys
    1205             1210             1215

Asp Leu Arg Gly Asn Val Ser  Glu Ile Glu Arg Ile  Leu Lys His
    1220             1225             1230

Pro Val Phe Pro Ser Gly Lys  Phe Leu Lys Val Lys  Asp Tyr His
    1235             1240             1245

Asp Ser Val Arg Arg Gln Ile  Met Gln Leu Asn Glu  Gln Leu Lys
    1250             1255             1260

Ala Val Tyr Glu Phe Gln Asp  Leu Lys Asp Thr Ile  Glu Arg Ala
    1265             1270             1275

Lys Asn Glu Ala Asp Leu Leu  Leu Glu Asp Leu Gln  Glu Glu Ile
    1280             1285             1290

Asp Leu Gln Ser Ser Val Leu  Asn Ala Ser Ile Ala  Asp Ser Ser
    1295             1300             1305

Glu Asn Ile Lys Lys Tyr Tyr  His Ile Ser Ser Ser  Ala Glu Lys
    1310             1315             1320

Lys Ile Asn Glu Thr Ser Ser  Thr Ile Asn Thr Ser  Ala Asn Thr
    1325             1330             1335

Arg Asn Asp Leu Leu Thr Ile  Leu Asp Thr Leu Thr  Ser Lys Gly
    1340             1345             1350

Asn Leu Ser Leu Glu Arg Leu  Lys Gln Ile Lys Ile  Pro Asp Ile
    1355             1360             1365

Gln Ile Leu Asn Glu Lys Val  Cys Gly Asp Pro Gly  Asn Val Pro
    1370             1375             1380

Cys Val Pro Leu Pro Cys Gly  Gly Ala Leu Cys Thr  Gly Arg Lys
    1385             1390             1395

Gly His Arg Lys Cys Arg Gly  Pro Gly Cys His Gly  Ser Leu Thr
    1400             1405             1410

Leu Ser Thr Asn Ala Leu Gln  Lys Ala Gln Glu Ala  Lys Ser Ile
    1415             1420             1425

Ile Arg Asn Leu Asp Lys Gln  Val Arg Gly Leu Lys  Asn Gln Ile
    1430             1435             1440

Glu Ser Ile Ser Glu Gln Ala  Glu Val Ser Lys Asn  Asn Ala Leu
    1445             1450             1455

Gln Leu Arg Glu Lys Leu Gly  Asn Ile Arg Asn Gln  Ser Asp Ser
    1460             1465             1470

Glu Glu Glu Asn Ile Asn Leu  Phe Ile Lys Lys Val  Lys Asn Phe
    1475             1480             1485

Leu Leu Glu Glu Asn Val Pro  Pro Glu Asp Ile Glu  Lys Val Ala
    1490             1495             1500

Asn Gly Val Leu Asp Ile His  Leu Pro Ile Pro Ser  Gln Asn Leu
    1505             1510             1515

Thr Asp Glu Leu Val Lys Ile  Gln Lys His Met Gln  Leu Cys Glu
    1520             1525             1530

Asp Tyr Arg Thr Asp Glu Asn  Arg Leu Asn Glu Glu  Ala Asp Gly
    1535             1540             1545

Ala Gln Lys Leu Leu Val Lys  Ala Lys Ala Ala Glu  Lys Ala Ala
```

```
        1550            1555            1560

Asn Ile  Leu Leu Asn Leu Asp  Lys Thr Leu Asn Gln  Leu Gln Gln
    1565            1570            1575

Ala Gln  Ile Thr Gln Gly Arg  Ala Asn Ser Thr Ile  Thr Gln Leu
    1580            1585            1590

Thr Ala  Asn Ile Thr Lys Ile  Lys Lys Asn Val Leu  Gln Ala Glu
    1595            1600            1605

Asn Gln  Thr Arg Glu Met Lys  Ser Glu Leu Glu Leu  Ala Lys Gln
    1610            1615            1620

Arg Ser  Gly Leu Glu Asp Gly  Leu Ser Leu Leu Gln  Thr Lys Leu
    1625            1630            1635

Gln Arg  His Gln Asp His Ala  Val Asn Ala Lys Val  Gln Ala Glu
    1640            1645            1650

Ser Ala  Gln His Gln Ala Gly  Ser Leu Glu Lys Glu  Phe Val Glu
    1655            1660            1665

Leu Lys  Lys Gln Tyr Ala Ile  Leu Gln Arg Lys Thr  Ser Thr Thr
    1670            1675            1680

Gly Leu  Thr Lys Glu Thr Leu  Gly Lys Val Lys Gln  Leu Lys Asp
    1685            1690            1695

Ala Ala  Glu Lys Leu Ala Gly  Asp Thr Glu Ala Lys  Ile Arg Arg
    1700            1705            1710

Ile Thr  Asp Leu Glu Arg Lys  Ile Gln Asp Leu Asn  Leu Ser Arg
    1715            1720            1725

Gln Ala  Lys Ala Asp Gln Leu  Arg Ile Leu Glu Asp  Gln Val Val
    1730            1735            1740

Ala Ile  Lys Asn Glu Ile Val  Glu Gln Glu Lys Lys  Tyr Ala Arg
    1745            1750            1755

Cys Tyr  Ser
    1760

<210> SEQ ID NO 97
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Ile Ala Ser Gln Phe Leu Ser Ala Leu Thr Leu Val Leu Leu Ile
1               5                   10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45

Ala Ile Gln Asn Lys Glu Glu Ile Glu Tyr Leu Asn Ser Ile Leu Ser
    50                  55                  60

Tyr Ser Pro Ser Tyr Tyr Trp Ile Gly Ile Arg Lys Val Asn Asn Val
65                  70                  75                  80

Trp Val Trp Val Gly Thr Gln Lys Pro Leu Thr Glu Glu Ala Lys Asn
                85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125
```

-continued

```
Arg Cys Ser Lys Lys Lys Leu Ala Leu Cys Tyr Thr Ala Ala Cys Thr
    130             135                 140

Asn Thr Ser Cys Ser Gly His Gly Glu Cys Val Glu Thr Ile Asn Asn
145             150                 155                 160

Tyr Thr Cys Lys Cys Asp Pro Gly Phe Ser Gly Leu Lys Cys Glu Gln
            165                 170                 175

Ile Val Asn Cys Thr Ala Leu Glu Ser Pro Glu His Gly Ser Leu Val
            180                 185                 190

Cys Ser His Pro Leu Gly Asn Phe Ser Tyr Asn Ser Ser Cys Ser Ile
        195                 200                 205

Ser Cys Asp Arg Gly Tyr Leu Pro Ser Ser Met Glu Thr Met Gln Cys
    210                 215                 220

Met Ser Ser Gly Glu Trp Ser Ala Pro Ile Pro Ala Cys Asn Val Val
225             230                 235                 240

Glu Cys Asp Ala Val Thr Asn Pro Ala Asn Gly Phe Val Glu Cys Phe
            245                 250                 255

Gln Asn Pro Gly Ser Phe Pro Trp Asn Thr Thr Cys Thr Phe Asp Cys
            260                 265                 270

Glu Glu Gly Phe Glu Leu Met Gly Ala Gln Ser Leu Gln Cys Thr Ser
        275                 280                 285

Ser Gly Asn Trp Asp Asn Glu Lys Pro Thr Cys Lys Ala Val Thr Cys
    290                 295                 300

Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
            325                 330                 335

Glu Gly Phe Met Leu Gln Gly Pro Ala Gln Val Glu Cys Thr Thr Gln
            340                 345                 350

Gly Gln Trp Thr Gln Gln Ile Pro Val Cys Glu Ala Phe Gln Cys Thr
        355                 360                 365

Ala Leu Ser Asn Pro Glu Arg Gly Tyr Met Asn Cys Leu Pro Ser Ala
    370                 375                 380

Ser Gly Ser Phe Arg Tyr Gly Ser Ser Cys Glu Phe Ser Cys Glu Gln
385                 390                 395                 400

Gly Phe Val Leu Lys Gly Ser Lys Arg Leu Gln Cys Gly Pro Thr Gly
            405                 410                 415

Glu Trp Asp Asn Glu Lys Pro Thr Cys Glu Ala Val Arg Cys Asp Ala
            420                 425                 430

Val His Gln Pro Pro Lys Gly Leu Val Arg Cys Ala His Ser Pro Ile
        435                 440                 445

Gly Glu Phe Thr Tyr Lys Ser Ser Cys Ala Phe Ser Cys Glu Glu Gly
    450                 455                 460

Phe Glu Leu His Gly Ser Thr Gln Leu Glu Cys Thr Ser Gln Gly Gln
465                 470                 475                 480

Trp Thr Glu Glu Val Pro Ser Cys Gln Val Val Lys Cys Ser Ser Leu
            485                 490                 495

Ala Val Pro Gly Lys Ile Asn Met Ser Cys Ser Gly Glu Pro Val Phe
            500                 505                 510

Gly Thr Val Cys Lys Phe Ala Cys Pro Glu Gly Trp Thr Leu Asn Gly
        515                 520                 525

Ser Ala Ala Arg Thr Cys Gly Ala Thr Gly His Trp Ser Gly Leu Leu
    530                 535                 540

Pro Thr Cys Glu Ala Pro Thr Glu Ser Asn Ile Pro Leu Val Ala Gly
```

-continued

```
        545             550             555             560

Leu Ser Ala Ala Gly Leu Ser Leu Leu Thr Leu Ala Pro Phe Leu Leu
                 565             570             575

Trp Leu Arg Lys Cys Leu Arg Lys Ala Lys Lys Phe Val Pro Ala Ser
             580             585             590

Ser Cys Gln Ser Leu Glu Ser Asp Gly Ser Tyr Gln Lys Pro Ser Tyr
             595             600             605

Ile Leu
    610

<210> SEQ ID NO 98
<211> LENGTH: 830
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Ala Asn Cys Gln Ile Ala Ile Leu Tyr Gln Arg Phe Gln Arg Val
1               5               10              15

Val Phe Gly Ile Ser Gln Leu Leu Cys Phe Ser Ala Leu Ile Ser Glu
                20              25              30

Leu Thr Asn Gln Lys Glu Val Ala Ala Trp Thr Tyr His Tyr Ser Thr
             35              40              45

Lys Ala Tyr Ser Trp Asn Ile Ser Arg Lys Tyr Cys Gln Asn Arg Tyr
    50              55              60

Thr Asp Leu Val Ala Ile Gln Asn Lys Asn Glu Ile Asp Tyr Leu Asn
65              70              75              80

Lys Val Leu Pro Tyr Tyr Ser Ser Tyr Tyr Trp Ile Gly Ile Arg Lys
                85              90              95

Asn Asn Lys Thr Trp Thr Trp Val Gly Thr Lys Lys Ala Leu Thr Asn
             100             105             110

Glu Ala Glu Asn Trp Ala Asp Asn Glu Pro Asn Asn Lys Arg Asn Asn
         115             120             125

Glu Asp Cys Val Glu Ile Tyr Ile Lys Ser Pro Ser Ala Pro Gly Lys
    130             135             140

Trp Asn Asp Glu His Cys Leu Lys Lys Lys His Ala Leu Cys Tyr Thr
145             150             155             160

Ala Ser Cys Gln Asp Met Ser Cys Ser Lys Gln Gly Glu Cys Leu Glu
             165             170             175

Thr Ile Gly Asn Tyr Thr Cys Ser Cys Tyr Pro Gly Phe Tyr Gly Pro
             180             185             190

Glu Cys Glu Tyr Val Arg Glu Cys Gly Glu Leu Glu Leu Pro Gln His
         195             200             205

Val Leu Met Asn Cys Ser His Pro Leu Gly Asn Phe Ser Phe Asn Ser
    210             215             220

Gln Cys Ser Phe His Cys Thr Asp Gly Tyr Gln Val Asn Gly Pro Ser
225             230             235             240

Lys Leu Glu Cys Leu Ala Ser Gly Ile Trp Thr Asn Lys Pro Pro Gln
             245             250             255

Cys Leu Ala Ala Gln Cys Pro Pro Leu Lys Ile Pro Glu Arg Gly Asn
             260             265             270

Met Thr Cys Leu His Ser Ala Lys Ala Phe Gln His Gln Ser Ser Cys
             275             280             285
```

-continued

```
Ser Phe Ser Cys Glu Glu Gly Phe Ala Leu Val Gly Pro Glu Val Val
    290             295             300

Gln Cys Thr Ala Ser Gly Val Trp Thr Ala Pro Ala Pro Val Cys Lys
305             310             315             320

Ala Val Gln Cys Gln His Leu Glu Ala Pro Ser Glu Gly Thr Met Asp
            325             330             335

Cys Val His Pro Leu Thr Ala Phe Ala Tyr Gly Ser Ser Cys Lys Phe
            340             345             350

Glu Cys Gln Pro Gly Tyr Arg Val Arg Gly Leu Asp Met Leu Arg Cys
        355             360             365

Ile Asp Ser Gly His Trp Ser Ala Pro Leu Pro Thr Cys Glu Ala Ile
    370             375             380

Ser Cys Glu Pro Leu Glu Ser Pro Val His Gly Ser Met Asp Cys Ser
385             390             395             400

Pro Ser Leu Arg Ala Phe Gln Tyr Asp Thr Asn Cys Ser Phe Arg Cys
            405             410             415

Ala Glu Gly Phe Met Leu Arg Gly Ala Asp Ile Val Arg Cys Asp Asn
            420             425             430

Leu Gly Gln Trp Thr Ala Pro Ala Pro Val Cys Gln Ala Leu Gln Cys
        435             440             445

Gln Asp Leu Pro Val Pro Asn Glu Ala Arg Val Asn Cys Ser His Pro
    450             455             460

Phe Gly Ala Phe Arg Tyr Gln Ser Val Cys Ser Phe Thr Cys Asn Glu
465             470             475             480

Gly Leu Leu Leu Val Gly Ala Ser Val Leu Gln Cys Leu Ala Thr Gly
            485             490             495

Asn Trp Asn Ser Val Pro Pro Glu Cys Gln Ala Ile Pro Cys Thr Pro
            500             505             510

Leu Leu Ser Pro Gln Asn Gly Thr Met Thr Cys Val Gln Pro Leu Gly
            515             520             525

Ser Ser Ser Tyr Lys Ser Thr Cys Gln Phe Ile Cys Asp Glu Gly Tyr
    530             535             540

Ser Leu Ser Gly Pro Glu Arg Leu Asp Cys Thr Arg Ser Gly Arg Trp
545             550             555             560

Thr Asp Ser Pro Pro Met Cys Glu Ala Ile Lys Cys Pro Glu Leu Phe
            565             570             575

Ala Pro Glu Gln Gly Ser Leu Asp Cys Ser Asp Thr Arg Gly Glu Phe
            580             585             590

Asn Val Gly Ser Thr Cys His Phe Ser Cys Asp Asn Gly Phe Lys Leu
        595             600             605

Glu Gly Pro Asn Asn Val Glu Cys Thr Thr Ser Gly Arg Trp Ser Ala
    610             615             620

Thr Pro Pro Thr Cys Lys Gly Ile Ala Ser Leu Pro Thr Pro Gly Leu
625             630             635             640

Gln Cys Pro Ala Leu Thr Thr Pro Gly Gln Gly Thr Met Tyr Cys Arg
            645             650             655

His His Pro Gly Thr Phe Gly Phe Asn Thr Thr Cys Tyr Phe Gly Cys
            660             665             670

Asn Ala Gly Phe Thr Leu Ile Gly Asp Ser Thr Leu Ser Cys Arg Pro
            675             680             685

Ser Gly Gln Trp Thr Ala Val Thr Pro Ala Cys Arg Ala Val Lys Cys
    690             695             700

Ser Glu Leu His Val Asn Lys Pro Ile Ala Met Asn Cys Ser Asn Leu
```

```
705             710             715             720

Trp Gly Asn Phe Ser Tyr Gly Ser Ile Cys Ser Phe His Cys Leu Glu
            725             730             735

Gly Gln Leu Leu Asn Gly Ser Ala Gln Thr Ala Cys Gln Glu Asn Gly
        740             745             750

His Trp Ser Thr Thr Val Pro Thr Cys Gln Ala Gly Pro Leu Thr Ile
        755             760             765

Gln Glu Ala Leu Thr Tyr Phe Gly Gly Ala Val Ala Ser Thr Ile Gly
770             775             780

Leu Ile Met Gly Gly Thr Leu Leu Ala Leu Leu Arg Lys Arg Phe Arg
785             790             795             800

Gln Lys Asp Asp Gly Lys Cys Pro Leu Asn Pro His Ser His Leu Gly
            805             810             815

Thr Tyr Gly Val Phe Thr Asn Ala Ala Phe Asp Pro Ser Pro
            820             825             830

<210> SEQ ID NO 99
<211> LENGTH: 184
<212> TYPE: PRT
<213> ORGANISM: Homo sapiens

<400> SEQUENCE: 99

Met Ser Arg Leu Ser Arg Ser Leu Leu Trp Ala Ala Thr Cys Leu Gly
1               5               10              15

Val Leu Cys Val Leu Ser Ala Asp Lys Asn Thr Thr Gln His Pro Asn
            20              25              30

Val Thr Thr Leu Ala Pro Ile Ser Asn Val Thr Ser Ala Pro Val Thr
        35              40              45

Ser Leu Pro Leu Val Thr Thr Pro Ala Pro Glu Thr Cys Glu Gly Arg
    50              55              60

Asn Ser Cys Val Ser Cys Phe Asn Val Ser Val Val Asn Thr Thr Cys
65              70              75              80

Phe Trp Ile Glu Cys Lys Asp Glu Ser Tyr Cys Ser His Asn Ser Thr
            85              90              95

Val Ser Asp Cys Gln Val Gly Asn Thr Thr Asp Phe Cys Ser Ala Lys
            100             105             110

Pro Thr Val Gln Pro Ser Pro Ser Thr Thr Ser Lys Thr Val Thr Thr
        115             120             125

Ser Gly Thr Thr Asn Asn Thr Val Thr Pro Thr Ser Gln Pro Val Arg
    130             135             140

Lys Ser Thr Phe Asp Ala Ala Ser Phe Ile Gly Gly Ile Val Leu Val
145             150             155             160

Leu Gly Val Gln Ala Val Ile Phe Phe Leu Tyr Lys Phe Cys Lys Ser
            165             170             175

Lys Glu Arg Asn Tyr His Thr Leu
            180

<210> SEQ ID NO 100
<211> LENGTH: 178
<212> TYPE: PRT
<213> ORGANISM: Homo sapiens

<400> SEQUENCE: 100

Met Ser Arg Leu Ser Arg Ser Leu Leu Trp Ala Ala Thr Cys Leu Gly
1               5               10              15

Val Leu Cys Val Leu Ser Ala Asp Lys Asn Thr Thr Gln His Pro Asn
```

-continued

```
            20              25              30
Val Thr Thr Leu Ala Pro Ile Ser Asn Val Thr Ser Ala Pro Val Thr
        35              40              45

Ser Leu Pro Leu Val Thr Thr Pro Ala Pro Glu Thr Cys Glu Gly Arg
    50              55              60

Asn Ser Cys Val Ser Cys Phe Asn Val Ser Val Val Asn Thr Thr Cys
65              70              75              80

Phe Trp Ile Glu Cys Lys Asp Glu Ser Tyr Cys Ser His Asn Ser Thr
                85              90              95

Val Ser Asp Cys Gln Val Gly Asn Thr Thr Asp Phe Cys Ser Val Ser
                100             105             110

Thr Ala Thr Pro Val Pro Thr Ala Asn Ser Thr Gly Thr Thr Asn Asn
        115             120             125

Thr Val Thr Pro Thr Ser Gln Pro Val Arg Lys Ser Thr Phe Asp Ala
    130             135             140

Ala Ser Phe Ile Gly Gly Ile Val Leu Val Leu Gly Val Gln Ala Val
145             150             155             160

Ile Phe Phe Leu Tyr Lys Phe Cys Lys Ser Lys Glu Arg Asn Tyr His
                165             170             175

Thr Leu
```

```
<210> SEQ ID NO 101
<211> LENGTH: 189
<212> TYPE: PRT
<213> ORGANISM: Homo sapiens

<400> SEQUENCE: 101
```

```
Met Ser Arg Leu Ser Arg Ser Leu Leu Trp Ala Ala Thr Cys Leu Gly
1               5               10              15

Val Leu Cys Val Leu Ser Ala Asp Lys Asn Thr Thr Gln His Pro Asn
            20              25              30

Val Thr Thr Leu Ala Pro Ile Ser Asn Val Thr Ser Ala Pro Val Thr
        35              40              45

Ser Leu Pro Leu Val Thr Thr Pro Ala Pro Glu Thr Cys Glu Gly Arg
    50              55              60

Asn Ser Cys Val Ser Cys Phe Asn Val Ser Val Val Asn Thr Thr Cys
65              70              75              80

Phe Trp Ile Glu Cys Lys Asp Glu Ser Tyr Cys Ser His Asn Ser Thr
                85              90              95

Val Ser Asp Cys Gln Val Gly Asn Thr Thr Asp Phe Cys Ser Val Ser
                100             105             110

Thr Ala Thr Pro Val Pro Thr Ala Asn Ser Thr Ala Lys Pro Thr Val
        115             120             125

Gln Pro Ser Pro Ser Thr Thr Ser Lys Thr Val Thr Thr Ser Gly Thr
    130             135             140

Thr Asn Asn Thr Val Thr Pro Thr Ser Gln Pro Val Arg Lys Ser Thr
145             150             155             160

Phe Asp Ala Ala Ser Phe Ile Gly Gly Ile Val Leu Val Leu Glu Ile
                165             170             175

Arg Cys His Thr Arg Asn Tyr Ile Pro Asp Leu Lys Lys
            180             185
```

```
<210> SEQ ID NO 102
<211> LENGTH: 157
<212> TYPE: PRT
```

-continued

<213> ORGANISM: Homo sapiens

<400> SEQUENCE: 102

```
Met Ser Arg Leu Ser Arg Ser Leu Leu Trp Ala Ala Thr Cys Leu Gly
1               5                   10                  15

Val Leu Cys Val Leu Ser Ala Asp Lys Asn Thr Thr Gln His Pro Asn
            20                  25                  30

Val Thr Thr Leu Ala Pro Ile Ser Asn Val Thr Ser Ala Pro Val Thr
            35                  40                  45

Ser Leu Pro Leu Val Thr Thr Pro Ala Pro Glu Thr Cys Glu Gly Arg
        50                  55                  60

Asn Ser Cys Val Ser Cys Phe Asn Val Ser Val Val Asn Thr Thr Cys
65                  70                  75                  80

Phe Trp Ile Glu Cys Lys Asp Glu Ser Tyr Cys Ser His Asn Ser Thr
                85                  90                  95

Val Ser Asp Cys Gln Val Gly Asn Thr Thr Asp Phe Cys Ser Val Ser
            100                 105                 110

Thr Ala Thr Pro Val Pro Thr Ala Asn Ser Thr Ala Lys Pro Thr Val
            115                 120                 125

Gln Pro Ser Pro Ser Thr Thr Ser Lys Thr Val Thr Thr Ser Glu Ile
        130                 135                 140

Arg Cys His Thr Arg Asn Tyr Ile Pro Asp Leu Lys Lys
145                 150                 155
```

<210> SEQ ID NO 103
<211> LENGTH: 163
<212> TYPE: PRT
<213> ORGANISM: Homo sapiens

<400> SEQUENCE: 103

```
Met Arg Lys Gly Arg Lys Val Pro Met Tyr Val Pro Gly Val Leu Arg
1               5                   10                  15

Thr Tyr Pro Lys Ala Lys Leu Glu Glu Thr Cys Glu Gly Arg Asn Ser
            20                  25                  30

Cys Val Ser Cys Phe Asn Val Ser Val Val Asn Thr Thr Cys Phe Trp
            35                  40                  45

Ile Glu Cys Lys Asp Glu Ser Tyr Cys Ser His Asn Ser Thr Val Ser
        50                  55                  60

Asp Cys Gln Val Gly Asn Thr Thr Asp Phe Cys Ser Val Ser Thr Ala
65                  70                  75                  80

Thr Pro Val Pro Thr Ala Asn Ser Thr Ala Lys Pro Thr Val Gln Pro
                85                  90                  95

Ser Pro Ser Thr Thr Ser Lys Thr Val Thr Thr Ser Gly Thr Thr Asn
            100                 105                 110

Asn Thr Val Thr Pro Thr Ser Gln Pro Val Arg Lys Ser Thr Phe Asp
            115                 120                 125

Ala Ala Ser Phe Ile Gly Gly Ile Val Leu Val Leu Gly Val Gln Ala
        130                 135                 140

Val Ile Phe Phe Leu Tyr Lys Phe Cys Lys Ser Lys Glu Arg Asn Tyr
145                 150                 155                 160

His Thr Leu
```

<210> SEQ ID NO 104
<211> LENGTH: 356
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 104

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
                20                  25                  30

Phe Arg Glu Glu Asn Ala Asn Phe Asn Lys Ile Phe Leu Pro Thr Ile
            35                  40                  45

Tyr Ser Ile Ile Phe Leu Thr Gly Ile Val Gly Asn Gly Leu Val Ile
    50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
                100                 105                 110

Cys Lys Ala Val His Val Ile Tyr Thr Val Asn Leu Tyr Ser Ser Val
            115                 120                 125

Leu Ile Leu Ala Phe Ile Ser Leu Asp Arg Tyr Leu Ala Ile Val His
    130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
            180                 185                 190

Phe Tyr Pro Asn Asp Leu Trp Val Val Val Phe Gln Phe Gln His Ile
            195                 200                 205

Met Val Gly Leu Ile Leu Pro Gly Ile Val Ile Leu Ser Cys Tyr Cys
    210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
                260                 265                 270

Ile Ile Lys Gln Gly Cys Glu Phe Glu Asn Thr Val His Lys Trp Ile
            275                 280                 285

Ser Ile Thr Glu Ala Leu Ala Phe Phe His Cys Cys Leu Asn Pro Ile
    290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys Arg Gly Gly His Ser Ser Val Ser Thr Glu Ser Glu Ser Ser Ser
            340                 345                 350

Phe His Ser Ser
        355

<210> SEQ ID NO 105
<211> LENGTH: 352
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 105

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Val Phe Gln Phe Gln His Ile Met Val Gly Leu
            195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 106
<211> LENGTH: 423
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 106

Met Glu Gly Ile Ser Glu Asn Ala Pro Leu Pro Asn Val Pro Asn Ala
1               5                   10                  15

Pro Ser Asp Lys His Glu Asp Gly Lys Arg Pro Thr His Arg Arg Ser
            20                  25                  30

Ala Arg Leu Gly Glu Glu Val Pro Phe Val His Phe Leu Thr Leu Pro
        35                  40                  45

Pro Asn Ile Pro Gln Ala Pro Lys Gly Leu Arg Phe Lys Thr Ala Phe
    50                  55                  60

Ser Leu Pro Thr Thr Ser Cys Leu Lys Pro Arg Met Ile Tyr Thr Ser
65                  70                  75                  80

Asp Asn Tyr Thr Glu Glu Met Gly Ser Gly Asp Tyr Asp Ser Met Lys
                85                  90                  95

Glu Pro Cys Phe Arg Glu Glu Asn Ala Asn Phe Asn Lys Ile Phe Leu
            100                 105                 110

Pro Thr Ile Tyr Ser Ile Ile Phe Leu Thr Gly Ile Val Gly Asn Gly
        115                 120                 125

Leu Val Ile Leu Val Met Gly Tyr Gln Lys Lys Leu Arg Ser Met Thr
    130                 135                 140

Asp Lys Tyr Arg Leu His Leu Ser Val Ala Asp Leu Leu Phe Val Ile
145                 150                 155                 160

Thr Leu Pro Phe Trp Ala Val Asp Ala Val Ala Asn Trp Tyr Phe Gly
                165                 170                 175

Asn Phe Leu Cys Lys Ala Val His Val Ile Tyr Thr Val Asn Leu Tyr
            180                 185                 190

Ser Ser Val Leu Ile Leu Ala Phe Ile Ser Leu Asp Arg Tyr Leu Ala
        195                 200                 205

Ile Val His Ala Thr Asn Ser Gln Arg Pro Arg Lys Leu Leu Ala Glu
    210                 215                 220

Lys Val Val Tyr Val Gly Val Trp Ile Pro Ala Leu Leu Leu Thr Ile
225                 230                 235                 240

Pro Asp Phe Ile Phe Ala Asn Val Ser Glu Ala Asp Asp Arg Tyr Ile
                245                 250                 255

Cys Asp Arg Phe Tyr Pro Asn Asp Leu Trp Val Val Val Phe Gln Phe
            260                 265                 270

Gln His Ile Met Val Gly Leu Ile Leu Pro Gly Ile Val Ile Leu Ser
        275                 280                 285

Cys Tyr Cys Ile Ile Ile Ser Lys Leu Ser His Ser Lys Gly His Gln
    290                 295                 300

Lys Arg Lys Ala Leu Lys Thr Thr Val Ile Leu Ile Leu Ala Phe Phe
305                 310                 315                 320

Ala Cys Trp Leu Pro Tyr Tyr Ile Gly Ile Ser Ile Asp Ser Phe Ile
                325                 330                 335

Leu Leu Glu Ile Ile Lys Gln Gly Cys Glu Phe Glu Asn Thr Val His
            340                 345                 350

Lys Trp Ile Ser Ile Thr Glu Ala Leu Ala Phe Phe His Cys Cys Leu
        355                 360                 365

Asn Pro Ile Leu Tyr Ala Phe Leu Gly Ala Lys Phe Lys Thr Ser Ala
    370                 375                 380

Gln His Ala Leu Thr Ser Val Ser Arg Gly Ser Ser Leu Lys Ile Leu
385                 390                 395                 400

```
Ser Lys Gly Lys Arg Gly Gly His Ser Ser Val Ser Thr Glu Ser Glu
                405                 410                 415

Ser Ser Ser Phe His Ser Ser
            420

<210> SEQ ID NO 107
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Glu Gly Ile Ser Glu Asn Ala Pro Leu Pro Asn Val Pro Asn Ala
1               5                   10                  15

Pro Ser Asp Lys His Glu Asp Gly Lys Arg Pro Thr His Arg Arg Ser
            20                  25                  30

Ala Arg Leu Gly Glu Glu Ile Tyr Thr Ser Asp Asn Tyr Thr Glu Glu
            35                  40                  45

Met Gly Ser Gly Asp Tyr Asp Ser Met Lys Glu Pro Cys Phe Arg Glu
        50                  55                  60

Glu Asn Ala Asn Phe Asn Lys Ile Phe Leu Pro Thr Ile Tyr Ser Ile
65                  70                  75                  80

Ile Phe Leu Thr Gly Ile Val Gly Asn Gly Leu Val Ile Leu Val Met
                85                  90                  95

Gly Tyr Gln Lys Lys Leu Arg Ser Met Thr Asp Lys Tyr Arg Leu His
            100                 105                 110

Leu Ser Val Ala Asp Leu Leu Phe Val Ile Thr Leu Pro Phe Trp Ala
            115                 120                 125

Val Asp Ala Val Ala Asn Trp Tyr Phe Gly Asn Phe Leu Cys Lys Ala
        130                 135                 140

Val His Val Ile Tyr Thr Val Asn Leu Tyr Ser Ser Val Leu Ile Leu
145                 150                 155                 160

Ala Phe Ile Ser Leu Asp Arg Tyr Leu Ala Ile Val His Ala Thr Asn
                165                 170                 175

Ser Gln Arg Pro Arg Lys Leu Leu Ala Glu Lys Val Val Tyr Val Gly
            180                 185                 190

Val Trp Ile Pro Ala Leu Leu Leu Thr Ile Pro Asp Phe Ile Phe Ala
            195                 200                 205

Asn Val Ser Glu Ala Asp Asp Arg Tyr Ile Cys Asp Arg Phe Tyr Pro
        210                 215                 220

Asn Asp Leu Trp Val Val Val Phe Gln Phe Gln His Ile Met Val Gly
225                 230                 235                 240

Leu Ile Leu Pro Gly Ile Val Ile Leu Ser Cys Tyr Cys Ile Ile Ile
                245                 250                 255

Ser Lys Leu Ser His Ser Lys Gly His Gln Lys Arg Lys Ala Leu Lys
            260                 265                 270

Thr Thr Val Ile Leu Ile Leu Ala Phe Phe Ala Cys Trp Leu Pro Tyr
            275                 280                 285

Tyr Ile Gly Ile Ser Ile Asp Ser Phe Ile Leu Leu Glu Ile Ile Lys
        290                 295                 300

Gln Gly Cys Glu Phe Glu Asn Thr Val His Lys Trp Ile Ser Ile Thr
305                 310                 315                 320

Glu Ala Leu Ala Phe Phe His Cys Cys Leu Asn Pro Ile Leu Tyr Ala
```

```
              325                 330                 335
Phe Leu Gly Ala Lys Phe Lys Thr Ser Ala Gln His Ala Leu Thr Ser
          340                 345                 350

Val Ser Arg Gly Ser Ser Leu Lys Ile Leu Ser Lys Gly Lys Arg Gly
          355                 360                 365

Gly His Ser Ser Val Ser Thr Glu Ser Glu Ser Ser Ser Phe His Ser
          370                 375                 380

Ser
385
```

<210> SEQ ID NO 108
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Met Gly Ser Gly Asp Tyr Asp Ser Met Lys Glu Pro Cys Phe Arg Glu
1               5                   10                  15

Glu Asn Ala Asn Phe Asn Lys Ile Phe Leu Pro Thr Ile Tyr Ser Ile
            20                  25                  30

Ile Phe Leu Thr Gly Ile Val Gly Asn Gly Leu Val Ile Leu Val Met
            35                  40                  45

Gly Tyr Gln Lys Lys Leu Arg Ser Met Thr Asp Lys Tyr Arg Leu His
        50                  55                  60

Leu Ser Val Ala Asp Leu Leu Phe Val Ile Thr Leu Pro Phe Trp Ala
65                  70                  75                  80

Val Asp Ala Val Ala Asn Trp Tyr Phe Gly Asn Phe Leu Cys Lys Ala
                85                  90                  95

Val His Val Ile Tyr Thr Val Asn Leu Tyr Ser Ser Val Leu Ile Leu
            100                 105                 110

Ala Phe Ile Ser Leu Asp Arg Tyr Leu Ala Ile Val His Ala Thr Asn
            115                 120                 125

Ser Gln Arg Pro Arg Lys Leu Leu Ala Glu Lys Val Val Tyr Val Gly
        130                 135                 140

Val Trp Ile Pro Ala Leu Leu Leu Thr Ile Pro Asp Phe Ile Phe Ala
145                 150                 155                 160

Asn Val Ser Glu Ala Asp Asp Arg Tyr Ile Cys Asp Arg Phe Tyr Pro
                165                 170                 175

Asn Asp Leu Trp Val Val Val Phe Gln Phe Gln His Ile Met Val Gly
            180                 185                 190

Leu Ile Leu Pro Gly Ile Val Ile Leu Ser Cys Tyr Cys Ile Ile Ile
            195                 200                 205

Ser Lys Leu Ser His Ser Lys Gly His Gln Lys Arg Lys Ala Leu Lys
        210                 215                 220

Thr Thr Val Ile Leu Ile Leu Ala Phe Phe Ala Cys Trp Leu Pro Tyr
225                 230                 235                 240

Tyr Ile Gly Ile Ser Ile Asp Ser Phe Ile Leu Leu Glu Ile Ile Lys
                245                 250                 255

Gln Gly Cys Glu Phe Glu Asn Thr Val His Lys Trp Ile Ser Ile Thr
            260                 265                 270

Glu Ala Leu Ala Phe Phe His Cys Cys Leu Asn Pro Ile Leu Tyr Ala
            275                 280                 285
```

-continued

```
Phe Leu Gly Ala Lys Phe Lys Thr Ser Ala Gln His Ala Leu Thr Ser
    290                 295                 300

Val Ser Arg Gly Ser Ser Leu Lys Ile Leu Ser Lys Gly Lys Arg Gly
305                 310                 315                 320

Gly His Ser Ser Val Ser Thr Glu Ser Glu Ser Ser Ser Phe His Ser
                325                 330                 335

Ser

<210> SEQ ID NO 109
<211> LENGTH: 6
<212> TYPE: PRT
<213> ORGANISM: Unknown
<220> FEATURE:
<223> OTHER INFORMATION: Description of Unknown:
      Insulin degrading enzyme motif

<400> SEQUENCE: 109

Glu Lys Pro Pro His Tyr
1               5
```